United States Patent
Vogt et al.

(10) Patent No.: US 11,178,871 B2
(45) Date of Patent: Nov. 23, 2021

(54) HERBICIDAL PYRIMIDINE COMPOUNDS

(71) Applicant: BASF SE, Ludwigshafen am Rhein (DE)

(72) Inventors: Florian Vogt, Ludwigshafen (DE); Matthias Witschel, Ludwigshafen (DE); Tobias Seiser, Limburgerhof (DE); Veronica Lopez Carrillo, Ludwigshafen (DE); Thomas Seitz, Ludwigshafen (DE); Gerd Kraemer, Limburgerhof (DE); Klaus Kreuz, Limburgerhof (DE); Trevor William Newton, Limburgerhof (DE); Klaus Reinhard, Limburgerhof (DE); Doreen Schachtschabel, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 47 days.

(21) Appl. No.: 16/320,701

(22) PCT Filed: Jul. 10, 2017

(86) PCT No.: PCT/EP2017/067295
§ 371 (c)(1),
(2) Date: Jan. 25, 2019

(87) PCT Pub. No.: WO2018/019555
PCT Pub. Date: Feb. 1, 2018

(65) Prior Publication Data
US 2019/0159453 A1 May 30, 2019

(30) Foreign Application Priority Data
Jul. 26, 2016 (EP) .................................. 16181122

(51) Int. Cl.
| | | |
|---|---|---|
| *A01N 43/76* | (2006.01) | |
| *C07D 413/04* | (2006.01) | |
| *C07D 413/06* | (2006.01) | |
| *C07D 417/04* | (2006.01) | |
| *C07D 405/04* | (2006.01) | |
| *A01N 43/78* | (2006.01) | |
| *A01N 43/80* | (2006.01) | |
| *A01N 43/82* | (2006.01) | |
| *A01N 43/58* | (2006.01) | |
| *A01N 57/20* | (2006.01) | |
| *C07D 409/04* | (2006.01) | |
| *C07D 405/06* | (2006.01) | |
| *A01N 43/60* | (2006.01) | |
| *C07D 239/26* | (2006.01) | |
| *C07D 403/04* | (2006.01) | |
| *A01N 43/54* | (2006.01) | |

(52) U.S. Cl.
CPC ............ *A01N 43/76* (2013.01); *A01N 43/54* (2013.01); *A01N 43/58* (2013.01); *A01N 43/60* (2013.01); *A01N 43/78* (2013.01); *A01N 43/80* (2013.01); *A01N 43/82* (2013.01); *A01N 57/20* (2013.01); *C07D 239/26* (2013.01); *C07D 403/04* (2013.01); *C07D 405/04* (2013.01); *C07D 405/06* (2013.01); *C07D 409/04* (2013.01); *C07D 413/04* (2013.01); *C07D 413/06* (2013.01); *C07D 417/04* (2013.01)

(58) Field of Classification Search
CPC ............................ C07D 413/04; A01N 43/76
See application file for complete search history.

(56) References Cited

U.S. PATENT DOCUMENTS 5,385,905 A * 1/1995 Heinemann ............ A01N 43/54
514/256

FOREIGN PATENT DOCUMENTS

| EP | 0557860 B1 | 1/2001 |
|---|---|---|
| WO | 97/06150 * | 2/1997 |
| WO | 9706150 A1 | 2/1997 |
| WO | 0066565 A1 | 11/2000 |
| WO | 0073278 A2 | 12/2000 |

(Continued)

OTHER PUBLICATIONS

European Search Report for EP Patent Application No. 16181122.9, dated Oct. 7, 2016, 4 pages.

(Continued)

*Primary Examiner* — Tracy Vivlemore
*Assistant Examiner* — Ebenezer O Sackey
(74) *Attorney, Agent, or Firm* — Marshall, Gerstein & Borun LLP

(57) ABSTRACT

The present invention relates to the use of pyrimidine compounds of formula (I),

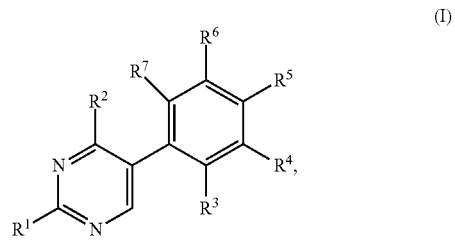

or their agriculturally acceptable salts or derivatives as herbicides, wherein the variables are defined according to the description, specific pyrimidine compounds of formula (I), compositions comprising them and their use as herbicides, i.e. for controlling harmful plants, and also a method for controlling unwanted vegetation which comprises allowing a herbicidal effective amount of at least one pyrimidine compounds of the formula (I) to act on plants, their seed and/or their habitat.

21 Claims, No Drawings

(56) References Cited

FOREIGN PATENT DOCUMENTS

| WO | 2005063721 A1 | 7/2005 |
| WO | 2016120116 A1 | 8/2016 |
| WO | 2016120355 A2 | 8/2016 |
| WO | 2018015180 A1 | 1/2018 |
| WO | 2018019552 A1 | 2/2018 |
| WO | 2018019554 A1 | 2/2018 |
| WO | 2018019574 A1 | 2/2018 |
| WO | 2018019765 A1 | 2/2018 |
| WO | 2018019860 A1 | 2/2018 |

OTHER PUBLICATIONS

International Search Report for PCT Patent Application No. PCTEP2017067295, dated Sep. 28, 2017, 3 pages.

* cited by examiner

HERBICIDAL PYRIMIDINE COMPOUNDS

This application is a National Stage application of International Application No. PCT/EP2017/067295, filed Jul. 10, 2017. This application also claims priority under 35 U.S.C. § 119 to European Patent Application No. 16181122.9, filed Jul. 26, 2016.

The present invention relates to pyrimidine compounds of the general formula (I) defined below and to their use as herbicides. Moreover, the invention relates to compositions for crop protection and to a method for controlling unwanted vegetation.

Compounds having a 5-phenyl pyrimidine moiety are known in the art. WO 2000/073278 describes such compounds being antagonists of the Neurokinin 1 receptor and thus having pharmaceutical properties.

In agriculture, there is a constant demand to develop novel active ingredients, which complement or outperform present methods of treatment regarding activity, selectivity and environmental safety.

These and further objects are achieved by pyrimidine compounds of formula (I), defined below, and by their agriculturally suitable salts.

Accordingly, the present invention provides the use of pyrimidine compounds of formula (I)

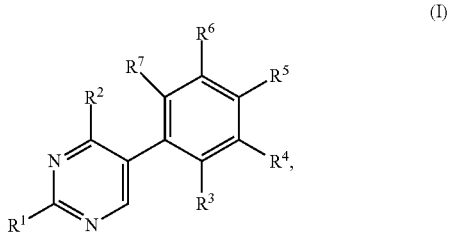

(I)

including agriculturally acceptable salts or derivatives of the pyrimidine compounds of formula (I) having an acidic functionality, as herbicides, wherein in formula (I) the variables have the following meanings:

$R^1$ $C_1$-$C_6$-alkyl, $C_1$-$C_6$-haloalkyl, HO—$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, 5-, 6- or 9-membered heteroaryl, or 3- to 6-membered heterocyclyl;
wherein the cyclic groups of $R^1$ are unsubstituted or substituted by $R^a$;

$R^2$ is $C_1$-$C_6$-alkyl, $C_1$-$C_6$-haloalkyl, $C_2$-$C_6$-alkenyl, $C_2$-$C_6$-haloalkenyl, $C_1$-$C_6$-alkoxy-$C_2$-$C_6$-alkenyl, $C_1$-$C_6$-alkoxy-$C_2$-$C_6$-haloalkenyl, $C_1$-$C_6$-haloalkoxy-$C_2$-$C_6$-alkenyl, $C_1$-$C_6$-haloalkoxy-$C_2$-$C_6$-haloalkenyl, $C_2$-$C_6$-alkynyl, $C_2$-$C_6$-haloalkynyl, $C_1$-$C_6$-alkoxy-$C_2$-$C_6$-alkynyl, $C_1$-$C_6$-alkoxy-$C_3$-$C_6$-haloalkynyl, $C_1$-$C_6$-haloalkoxy-$C_2$-$C_6$-alkynyl, $C_1$-$C_6$-haloalkoxy-$C_3$-$C_6$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-halocycloalkyl-$C_1$-$C_6$-alkyl, $C_3$-$C_6$-halocycloalkyl-$C_1$-$C_6$-haloalkyl, $C_3$-$C_6$-cycloalkenyl-$C_1$-$C_6$-alkyl, $C_3$-$C_6$-cycloalkenyl-$C_1$-$C_6$-haloalkyl, $C_3$-$C_6$-halocycloalkenyl-$C_1$-$C_6$-alkyl, $C_3$-$C_6$-halocycloalkenyl-$C_1$-$C_6$-haloalkyl, $C_3$-$C_6$-cycloalkyl-$C_2$-$C_6$-alkenyl, $C_3$-$C_6$-cycloalkyl-$C_2$-$C_6$-haloalkenyl, $C_3$-$C_6$-halocycloalkyl-$C_2$-$C_6$-alkenyl, $C_3$-$C_6$-halocycloalkyl-$C_2$-$C_6$-haloalkenyl, $C_3$-$C_6$-cycloalkenyl-$C_2$-$C_6$-alkenyl, $C_3$-$C_6$-cycloalkenyl-$C_2$-$C_6$-haloalkenyl, $C_3$-$C_6$-halocycloalkenyl-$C_2$-$C_6$-alkenyl, $C_3$-$C_6$-halocycloalkenyl-$C_2$-$C_6$-haloalkenyl, $C_3$-$C_6$-cycloalkyl-$C_2$-$C_6$-alkynyl, $C_3$-$C_6$-cycloalkyl-$C_3$-$C_6$-haloalkynyl, $C_3$-$C_6$-halocycloalkyl-$C_2$-$C_6$-alkynyl, $C_3$-$C_6$-halocycloalkyl-$C_3$-$C_6$-haloalkynyl, $C_3$-$C_6$-cycloalkenyl-$C_2$-$C_6$-alkynyl, $C_3$-$C_6$-cycloalkenyl-$C_3$-$C_6$-haloalkynyl, $C_3$-$C_6$-halocycloalkenyl-$C_2$-$C_6$-alkynyl, $C_3$-$C_6$-halocycloalkenyl-$C_3$-$C_6$-haloalkynyl, $C_3$-$C_6$-cycloalkyl-$C_1$-$C_6$-alkylidenyl, $C_3$-$C_6$-cycloalkyl-$C_2$-$C_6$-haloalkylidenyl, $C_3$-$C_6$-halocycloalkyl-$C_1$-$C_6$-alkylidenyl, $C_3$-$C_6$-halocycloalkyl-$C_2$-$C_6$-haloalkylidenyl, $C_3$-$C_6$-cycloalkenyl-$C_1$-$C_6$-alkylidenyl, $C_3$-$C_6$-cycloalkenyl-$C_2$-$C_6$-haloalkylidenyl, $C_3$-$C_6$-halocycloalkenyl-$C_1$-$C_6$-alkylidenyl, $C_3$-$C_6$-halocycloalkenyl-$C_2$-$C_6$-haloalkylidenyl, heterocyclyl-$C_1$-$C_6$-alkylidenyl, heterocyclyl-$C_2$-$C_6$-haloalkylidenyl, $C_3$-$C_6$-hydroxycycloalkyl-$C_1$-$C_6$-alkyl, $C_3$-$C_6$-hydroxycycloalkyl-$C_1$-$C_6$-haloalkyl, $C_3$-$C_6$-hydroxycycloalkenyl-$C_1$-$C_6$-alkyl, $C_3$-$C_6$-hydroxycycloalkenyl-$C_1$-$C_6$-haloalkyl, $C_1$-$C_6$-hydroxyalkyl, $C_2$-$C_6$-hydroxyhaloalkyl, $C_3$-$C_6$-hydroxyalkenyl, $C_3$-$C_6$-hydroxyhaloalkenyl, $C_3$-$C_6$-hydroxyalkynyl, $C_4$-$C_6$-hydroxyhaloalkynyl, $C_3$-$C_6$-hydroxycycloalkyl, $C_3$-$C_6$-hydroxyhalocycloalkyl, $C_3$-$C_6$-hydroxycycloalkenyl, $C_3$-$C_6$-hydroxyhalocycloalkenyl, $C_3$-$C_6$-cycloalkyl-$C_1$-$C_6$-hydroxyalkyl, $C_3$-$C_6$-cycloalkyl-$C_2$-$C_6$-hydroxyhaloalkyl, $C_3$-$C_6$-halocycloalkyl-$C_1$-$C_6$-hydroxyalkyl, $C_3$-$C_6$-halocycloalkyl-$C_2$-$C_6$-hydroxyhaloalkyl, $C_3$-$C_6$-cycloalkenyl-$C_1$-$C_6$-hydroxyalkyl, $C_3$-$C_6$-cycloalkenyl-$C_2$-$C_6$-hydroxyhaloalkyl, $C_3$-$C_6$-halocycloalkenyl-$C_1$-$C_6$-hydroxyalkyl, $C_3$-$C_6$-halocycloalkenyl-$C_2$-$C_6$-hydroxyhaloalkyl, $C_3$-$C_6$-cycloalkyl-$C_3$-$C_6$-hydroxyalkenyl, $C_3$-$C_6$-cycloalkyl-$C_3$-$C_6$-hydroxyhaloalkenyl, $C_3$-$C_6$-halocycloalkyl-$C_3$-$C_6$-hydroxyalkenyl, $C_3$-$C_6$-halocycloalkyl-$C_3$-$C_6$-hydroxyhaloalkenyl, $C_3$-$C_6$-cycloalkenyl-$C_3$-$C_6$-hydroxyalkenyl, $C_3$-$C_6$-cycloalkenyl-$C_3$-$C_6$-hydroxyhaloalkenyl, $C_3$-$C_6$-halocycloalkenyl-$C_3$-$C_6$-hydroxyalkenyl, $C_3$-$C_6$-halocycloalkenyl-$C_3$-$C_6$-hydroxyhaloalkenyl, $C_3$-$C_6$-cycloalkyl-$C_3$-$C_6$-hydroxyalkynyl, $C_3$-$C_6$-cycloalkyl-$C_3$-$C_6$-hydroxyhaloalkynyl, $C_3$-$C_6$-halocycloalkyl-$C_3$-$C_6$-hydroxyalkynyl, $C_3$-$C_6$-halocycloalkyl-$C_3$-$C_6$-hydroxyhaloalkynyl, $C_3$-$C_6$-cycloalkenyl-$C_3$-$C_6$-hydroxyalkynyl, $C_3$-$C_6$-cycloalkenyl-$C_3$-$C_6$-hydroxyhaloalkynyl, $C_3$-$C_6$-halocycloalkenyl-$C_3$-$C_6$-hydroxyalkynyl, $C_3$-$C_6$-halocycloalkenyl-$C_2$-$C_6$-hydroxyhaloalkynyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-hydroxyalkyl, $C_1$-$C_6$-haloalkoxycarbonyl-$C_1$-$C_6$-hydroxyalkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-hydroxycycloalkyl-$C_1$-$C_6$-hydroxyalkyl, $C_3$-$C_6$-hydroxycycloalkenyl-$C_1$-$C_6$-hydroxyalkyl, $C_3$-$C_6$-hydroxycycloalkyl-$C_3$-$C_6$-hydroxyalkenyl, $C_3$-$C_6$-hydroxycycloalkenyl-$C_3$-$C_6$-hydroxyalkenyl, $C_3$-$C_6$-hydroxycycloalkyl-$C_3$-$C_6$-hydroxyalkynyl, $C_3$-$C_6$-hydroxycycloalkenyl-$C_3$-$C_6$-hydroxyalkenyl, $C_2$-$C_6$-dihydroxyalkyl, $C_3$-$C_6$-dihydroxyhaloalkyl, $C_4$-$C_6$-dihydroxyalkenyl, $C_4$-$C_6$-dihydroxyhaloalkenyl, $C_4$-$C_6$-dihydroxyalkynyl, $C_5$-$C_6$-dihydroxyhaloalkynyl, $C_4$-$C_6$-dihydroxycycloalkyl, $C_4$-$C_6$-dihydroxyhalocycloalkyl, $C_4$-$C_6$-dihydroxycycloalkenyl, $C_4$-$C_6$-dihydroxyhalocycloalkenyl, $C_3$-$C_6$-cycloalkyl-$C_2$-$C_6$-dihydroxyalkyl, $C_3$-$C_6$-halocycloalkyl-$C_2$-$C_6$-dihydroxyalkyl, $C_3$-$C_6$-cycloalkenyl-$C_2$-$C_6$-dihydroxyalkyl, $C_3$-$C_6$-halocycloalkenyl-$C_2$-$C_6$-dihydroxyalkyl, $C_3$-$C_6$-cycloalkyl-$C_3$-$C_6$-dihydroxyalkenyl, $C_3$-$C_6$-halocycloalkyl-$C_3$-$C_6$-dihydroxyalkenyl, $C_3$-$C_6$-cycloalkenyl-$C_3$-$C_6$-dihydroxyalkenyl, $C_3$-$C_6$-halocycloalkenyl-$C_3$-$C_6$-dihydroxyalkenyl, $C_3$-$C_6$-cycloalkyl-$C_4$-$C_6$-dihydroxyalkynyl, $C_3$-$C_6$-halocycloalkyl-$C_4$-$C_6$-dihydroxyalkynyl, $C_3$-$C_6$-cycloalkenyl-$C_4$-$C_6$-dihydroxyalkynyl, $C_3$-$C_6$-halocycloalkyl-$C_4$-$C_6$-dihydroxyalkynyl, $C_3$-$C_6$-cycloalkyl-$C_3$-$C_6$-dihydroxyalkylidenyl, $C_3$-$C_6$-halocycloalkyl-$C_3$-$C_6$-dihydroxyalkylidenyl, heterocyclyl-$C_3$-$C_6$-dihydroxyalkylidenyl, hydroxycarbonyl-$C_2$-$C_6$-dihydroxyalkyl, hydroxycarbonyl-$C_3$-$C_6$-dihydroxyhaloalkyl, $C_1$-$C_6$-alkoxycarbonyl-$C_2$-$C_6$-dihydroxyalkyl, $C_1$-$C_6$-haloalkoxycarbonyl-$C_2$-$C_6$-dihydroxyalkyl, $C_1$-$C_6$-alkoxycarbonyl-$C_3$-$C_6$-dihydroxyhaloalkyl, $C_3$-$C_6$-dihydroxycycloalkyl-$C_1$-$C_6$-alkyl, $C_3$-$C_6$-dihydroxycycloalkyl-$C_1$-$C_6$-haloalkyl-$C_3$-$C_6$-dihydroxycycloalkyl-$C_2$-$C_6$-alkenyl, $C_3$-$C_6$-dihydroxycycloalkyl-$C_2$-$C_6$-haloalkenyl, $C_3$-$C_6$-dihydroxycycloalkyl-$C_2$-$C_6$-alkynyl, $C_3$-$C_6$-dihydroxycycloalkyl-$C_3$-$C_6$-haloalkynyl, $C_1$-$C_6$-alkylcarbonyl-$C_1$-$C_6$-alkyl, $C_1$-$C_6$-haloalkylcarbonyl-$C_1$-$C_6$-alkyl, $C_1$-$C_6$-alkylcarbonyl-$C_1$-$C_6$-haloalkyl, $C_1$-$C_6$-haloalkylcarbonyl-$C_1$-$C_6$-haloalkyl, hydroxycarbonyl-$C_2$-$C_6$-alkenyl, hydroxycarbonyl-$C_2$-$C_6$-haloalkenyl, $C_1$-$C_6$-alkoxycarbonyl-$C_2$-$C_6$-alkenyl, $C_1$-$C_6$-haloalkoxycarbonyl-$C_2$-$C_6$-alkenyl, $C_1$-$C_6$-alkoxycarbonyl-$C_2$-$C_6$-haloalkenyl, $C_1$-$C_6$-haloalkoxycarbonyl-$C_2$-$C_6$-haloalkenyl, hydroxycarbonyl-$C_2$-$C_6$-alkynyl, hydroxycarbonyl-$C_3$-$C_6$-haloalkynyl, $C_1$-$C_6$-alkoxycarbonyl-$C_2$-$C_6$-alkynyl, $C_1$-$C_6$-haloalkoxycarbonyl-$C_2$-$C_6$-alkynyl, $C_1$-$C_6$-alkoxycarbonyl-$C_3$-$C_6$-haloalkynyl, $C_1$-$C_6$-haloalkoxycarbonyl-$C_3$-$C_6$-haloalkynyl, $C_1$-$C_6$-cyanoalkyl, $C_2$-$C_6$-cyanohaloalkyl, $C_1$-$C_6$-dicyanoalkyl, $C_2$-$C_6$-dicyanohaloalkyl, di(hydroxycarbonyl)-$C_1$-$C_6$-alkyl, di(hydroxycarbonyl)-$C_1$-$C_6$-haloalkyl, di($C_1$-$C_6$-alkoxycarbonyl)-$C_1$-$C_6$-alkyl, di($C_1$-$C_6$-haloalkoxycarbonyl)-$C_1$-$C_6$-alkyl, di($C_1$-$C_6$-alkoxycarbonyl)-$C_1$-$C_6$-haloalkyl, di($C_1$-$C_6$-haloalkoxycarbonyl)$C_1$-$C_6$-haloalkyl, di($C_1$-$C_6$-alkoxyl)phosphoryl-$C_1$-$C_6$-alkyl, di($C_1$-$C_6$-haloalkoxyl)phosphoryl-$C_1$-$C_6$-alkyl, di($C_1$-$C_6$-alkoxyl)phosphoryl-$C_1$-$C_6$-haloalkyl, di($C_1$-$C_6$-haloalkoxyl)phosphoryl-$C_1$-$C_6$-haloalkyl, phosphoryl-$C_1$-$C_6$-alkyl, phosphoryl-$C_1$-$C_6$-haloalkyl, di[di($C_1$-$C_6$-alkoxyl)phosphoryl-)]$C_1$-$C_6$-alkyl, di[di($C_1$-$C_6$-haloalkoxyl)phosphoryl-)]$C_1$-$C_6$-alkyl, di[di($C_1$-$C_6$-alkoxyl)phosphoryl-)]$C_1$-$C_6$-haloalkyl, di[di($C_1$-$C_6$-haloalkoxyl)phosphoryl-)]$C_1$-$C_6$-haloalkyl, diphosphoryl-$C_1$-$C_6$-alkyl, diphosphoryl-$C_1$-$C_6$-haloalkyl, $C_1$-$C_6$-alkylthio-$C_1$-$C_6$-alkyl, $C_1$-$C_6$-haloalkylthio-$C_1$-$C_6$-alkyl, $C_1$-$C_6$-alkylthio-$C_1$-$C_6$-haloalkyl, $C_1$-$C_6$-haloalkylthio-$C_1$-$C_6$-haloalkyl, $C_1$-$C_6$-alkylsulfinyl-$C_1$-$C_6$-alkyl, $C_1$-$C_6$-haloalkylsulfinyl-$C_1$-$C_6$-alkyl, $C_1$-$C_6$-alkylsulfinyl-$C_1$-$C_6$-haloalkyl, $C_1$-$C_6$-haloalkylsulfinyl-$C_1$-$C_6$-haloalkyl, $C_1$-$C_6$-alkylsulfonyl-$C_1$-$C_6$-alkyl, $C_1$-$C_6$-haloalkylsulfonyl-$C_1$-$C_6$-alkyl, $C_1$-$C_6$-haloalkylsulfonyl-$C_1$-$C_6$-haloalkyl, phenyl, 5-, 6- or 9 membered heteroaryl, 3- to 6-membered heterocyclyl, ($C_1$-$C_6$-alkyl)carbonylaminocarbonyl, ($C_3$-$C_6$-alkenyl)carbonylaminocarbonyl, ($C_3$-$C_6$-alkynyl)carbonylaminocarbonyl, ($C_1$-$C_6$-haloalkyl)carbonylaminocarbonyl, alkynylphenylcarbonylaminocarbonyl, ($C_3$-$C_6$-cycloalkyl)carbonylaminocarbonyl, [di($C_1$-$C_6$-alkyl)amino]carbonylaminocarbonyl, heterocyclylcarbonylaminocarbonyl, heteroarylcarbonylaminocarbonyl, [($C_1$-$C_6$-alkyl)carbonyl]($C_1$-$C_6$-alkyl)aminocarbonyl, [($C_1$-$C_6$-haloalkyl)carbonyl]($C_1$-$C_6$-alkyl)aminocarbonyl, [($C_3$-$C_6$-cycloalkyl)carbonyl]($C_1$-$C_6$-alkyl)aminocarbonyl, (phenylcarbonyl)($C_1$-$C_6$-alkyl)aminocarbonyl, (heterocyclylcarbonyl)($C_1$-$C_6$-alkyl)aminocarbonyl, (heteroarylcarbonyl)($C_1$-$C_6$-alkyl)aminocarbonyl, [($C_1$-$C_6$-alkyl)carbonyl]($C_1$-$C_6$-alkoxy)aminocarbonyl, [($C_1$-$C_6$-haloalkyl)carbonyl]($C_1$-$C_6$-alkoxy)aminocarbonyl, [($C_3$-$C_6$-cycloalkyl)carbonyl]($C_1$-$C_6$-alkyloxy)aminocarbonyl, (phenylcarbonyl)($C_1$-$C_6$-alkoxy)aminocarbonyl, (heterocyclylcarbonyl)($C_1$-$C_6$-alkoxy)aminocarbonyl, (heteroarylcarbonyl)($C_1$-$C_6$-alkoxy)aminocarbonyl, [($C_1$-$C_6$-alkyl)carbonyl]($C_3$-$C_6$-alkenyl)aminocarbonyl, [($C_1$-$C_6$-haloalkyl)carbonyl]($C_2$-$C_6$-alkenyl)aminocarbonyl, [($C_3$-$C_6$-cycloalkyl)carbonyl]($C_3$-$C_6$-alkenyl)aminocarbonyl, (phenylcarbonyl)($C_3$-$C_6$-alkenyl)aminocarbonyl, (heterocyclylcarbonyl)($C_3$-$C_6$-alkenyl)aminocarbonyl, (heteroarylcarbonyl)($C_3$-$C_6$-alkenyl)aminocarbonyl, [($C_1$-$C_6$-alkyl)carbonyl]($C_3$-$C_6$-alkynyl)aminocarbonyl, [($C_1$-$C_6$-haloalkyl)carbonyl]($C_3$-$C_6$-alkynyl)aminocarbonyl, [($C_3$-$C_6$-cycloalkyl)carbonyl]($C_3$-$C_6$-alkynyl)aminocarbonyl, (phenylcarbonyl)($C_3$-$C_6$-alkynyl)aminocarbonyl, (heterocyclylcarbonyl)($C_3$-$C_6$-alkynyl)aminocarbonyl, (heteroarylcarbonyl)($C_3$-$C_6$-alkynyl)aminocarbonyl, [($C_2$-$C_6$-alkenyl)carbonyl]aminocarbonyl, [($C_2$-$C_6$-alkenyl)carbonyl]($C_1$-$C_6$-alkyl)aminocarbonyl, [($C_2$-$C_6$-alkenyl)carbonyl]($C_1$-$C_6$-alkoxy)aminocarbonyl, [($C_3$-$C_6$-alkynyl)carbonyl]aminocarbonyl, [($C_3$-$C_6$-alkynyl)carbonyl]($C_1$-$C_6$-alkyl)aminocarbonyl, [($C_3$-$C_6$-alkynyl)carbonyl]($C_1$-$C_6$-alkoxy)aminocarbonyl, [di($C_1$-$C_6$-alkyl)amino]carbonylaminocarbonyl, [di($C_1$-$C_6$-alkyl)aminocarbonyl]($C_1$-$C_6$-alkyl)aminocarbonyl, [di($C_1$-$C_6$-alkyl)aminocarbonyl]($C_1$-$C_6$-alkoxy)aminocarbonyl;

wherein OH groups of $R^2$ are unsubstituted or substituted by $R^b$;

cyclic groups of $R^2$ are unsubstituted or substituted by $R^c$; and acyclic aliphatic groups of $R^2$ are unsubstituted or substituted by $R^d$.

$R^b$ is $C_1$-$C_6$-alkyl, $C_1$-$C_6$-haloalkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-

C₆-haloalkyl, C₁-C₆-alkyloxycarbonyl, C₁-C₆-haloalkyloxycarbonyl, C₁-C₆-alkylthiocarbonyl, C₁-C₆-haloalkylthiocarbonyl, C₁-C₆-alkylaminocarbonyl, C₁-C₆-haloalkylaminocarbonyl, C₁-C₆-dialkylaminocarbonyl, C₁-C₆-dihaloalkylaminocarbonyl, C₁-C₆-alkylsulfonyl, C₁-C₆-haloalkylsulfonyl, C₁-C₆-alkoxy-C₁-C₆-alkyl, C₁-C₆-haloalkoxy-C₁-C₆-alkyl, C₁-C₆-alkoxy-C₁-C₆-haloalkyl, C₁-C₆-haloalkoxy-C₁-C₆-haloalkyl, phenyl-C₁-C₆-alkyl, or phenyl-C₁-C₆-haloalkyl;

Rᶜ is halogen, CN, NO₂, C₁-C₆-alkyl, C₁-C₆-haloalkyl, OH, C₁-C₆-alkoxy, C₁-C₆-haloalkoxy, C₁-C₆-alkylthio, C₁-C₆-alkylsulfinyl, or C₁-C₆-alkylsulfonyl;

Rᵈ is phenyl, 5- or 6-membered heteroaryl, or 3- to 6-membered heterocyclyl; wherein the substituent Rᵈ is unsubstituted or substituted by Rᵉ;

Rᵉ is halogen, CN, NO₂, C₁-C₆-alkyl, C₁-C₆-haloalkyl, OH, C₁-C₆-alkoxy, C₁-C₆-haloalkoxy, C₁-C₆-alkylsulfonyl;

R³ halogen, CN, NO₂, C₁-C₆-alkyl, C₁-C₆-haloalkyl, C₁-C₆-alkylcarbonyl, C₂-C₆-alkenyl, C₂-C₆-haloalkenyl, C₂-C₆-alkynyl, C₂-C₆-haloalkynyl, C₁-C₆-alkoxy, C₁-C₆-haloalkoxy, C₃-C₆-alkenyloxy, C₃-C₆-haloalkenyloxy, C₃-C₆-alkynyloxy, C₃-C₆-haloalkynyloxy, C₁-C₆-alkoxy-C₁-C₆-alkoxy, hydroxycarbonyl, C₁-C₆-alkoxycarbonyl, C₁-C₆-alkylthio, C₁-C₆-haloalkylthio, NH₂, (C₁-C₆-alkyl)amino, di(C₁-C₆-alkyl)amino, (C₁-C₆-alkyl)sulfinyl, (C₁-C₆-alkyl)sulfonyl, C₃-C₆-cycloalkyl, (C₃-C₆-cycloalkyl)oxy or phenyl;
wherein the cyclic groups of R³ are unsubstituted or substituted by substituents Rᵃ;

R⁴, R⁵, R⁶ and R⁷ independently of one another are H, halogen, CN, NO₂, C₁-C₆-alkyl, C₁-C₆-haloalkyl, C₁-C₆-alkylcarbonyl, C₂-C₆-alkenyl, C₂-C₆-haloalkenyl, C₂-C₆-alkynyl, C₂-C₆-haloalkynyl, C₁-C₆-alkoxy, C₁-C₆-haloalkoxy, C₃-C₆-alkenyloxy, C₃-C₆-haloalkenyloxy, C₃-C₆-alkynyloxy, C₃-C₆-haloalkynyloxy, C₁-C₆-alkoxy-C₁-C₆-alkoxy, hydroxycarbonyl, C₁-C₆-alkoxycarbonyl, C₁-C₆-alkylthio, C₁-C₆-haloalkylthio, NH₂, (C₁-C₆-alkyl)amino, di(C₁-C₆-alkyl)amino, (C₁-C₆-alkyl)sulfinyl, (C₁-C₆-alkyl)sulfonyl, C₃-C₆-cycloalkyl, (C₃-C₆-cycloalkyl)oxy or phenyl;
wherein the cyclic groups of R⁴, R⁵, R⁶ and R⁷ are unsubstituted or substituted by Rᵃ;

Rᵃ is halogen, CN, NO₂, C₁-C₆-alkyl, C₁-C₆-haloalkyl, C₁-C₆-alkoxy, or C₁-C₆-haloalkoxy.

The present invention also provides pyrimidine compounds of formula (I) as described herein including agriculturally acceptable salts or derivatives of the pyrimidine compounds of formula (I) having an acidic functionality, with the exception of
5-(2-bromophenyl)-2-cyclopropyl-4-methyl-pyrimidine;
5-(2-bromophenyl)-2-ethyl-4-methyl-pyrimidine; and
5-(2-bromophenyl)-2-methoxy-4-methyl-pyrimidine.

The present invention also provides pyrimidine compounds of formula (I) wherein the variables R², R³, R⁴, R⁵, R⁶ and R⁷ are as defined herein, and wherein R¹ is C₁-C₆-alkyl, C₁-C₆-haloalkyl, HO—C₁-C₆-alkyl, C₂-C₆-alkenyl, C₂-C₆-haloalkenyl, C₂-C₆-alkynyl, C₃-C₆-haloalkynyl, C₁-C₆-alkoxy-C₁-C₆-alkyl, C₁-C₆-alkoxy, C₃-C₆-alkenyloxy, C₃-C₆-haloalkenyloxy, C₃-C₆-alkynyloxy, C₃-C₆-haloalkynyloxy, C₁-C₆-haloalkoxy, C₃-C₆-cycloalkoxy, C₃-C₆-halocycloalkoxy, C₃-C₆-cycloalkenyloxy, C₃-C₆-halocycloalkenyloxy, C₁-C₆-alkylthio, C₁-C₆-haloalkylthio, (C₁-C₆-alkyl)amino, di(C₁-C₆-alkyl)amino, C₁-C₆-alkylsulfinyl, C₁-C₆-alkylsulfonyl, C₃-C₆-cycloalkyl, C₃-C₆-cycloalkenyl, C₃-C₆-halocycloalkyl, C₃-C₆-halocycloalkenyl, [1-(C₁-C₆-alkyl)]-C₃-C₆-cycloalkyl, [1-(C₂-C₆-alkenyl)]-C₃-C₆-cycloalkyl, [1-(C₂-C₆-alkynyl)]-C₃-C₆-cycloalkyl, [1-(C₁-C₆-haloalkyl)]-C₃-C₆-cycloalkyl, [1-(C₂-C₆-haloalkenyl)]-C₃-C₆-cycloalkyl, [1-(C₃-C₆-haloalkynyl)]-C₃-C₆-cycloalkyl, C₃-C₆-cycloalkyl-C₁-C₆-alkyl, C₃-C₆-cycloalkyl-C₁-C₆-haloalkyl, C₃-C₆-cycloalkyl-C₁-C₆-alkoxy, C₃-C₆-cycloalkyl-C₁-C₆-haloalkoxy, 5-membered heteroaryl, or 3- to 6-membered heterocyclyl;
wherein the cyclic groups of R¹ are unsubstituted or substituted by Rᵃ;

Rᵃ is halogen, CN, NO₂, C₁-C₆-alkyl, C₁-C₆-haloalkyl, C₁-C₆-alkoxy, or C₁-C₆-haloalkoxy;

including agriculturally acceptable salts or derivatives of the pyrimidine compounds of formula (I) having an acidic functionality, with the exception of
5-(2-bromophenyl)-2-cyclopropyl-4-methyl-pyrimidine;
5-(2-bromophenyl)-2-ethyl-4-methyl-pyrimidine; and
5-(2-bromophenyl)-2-methoxy-4-methyl-pyrimidine.

The pyrimidine compounds of formula (I) according to the invention can be prepared by standard processes of organic chemistry, e.g. by the following processes:

Process A:

The pyrimidines of formula (I) can be obtained by reacting respective pyrimidines of formula (I) (prepared analogous to known procedures like e.g. in WO 2013186229) with base and an electrophile, e.g. a carbonyl compound (III):

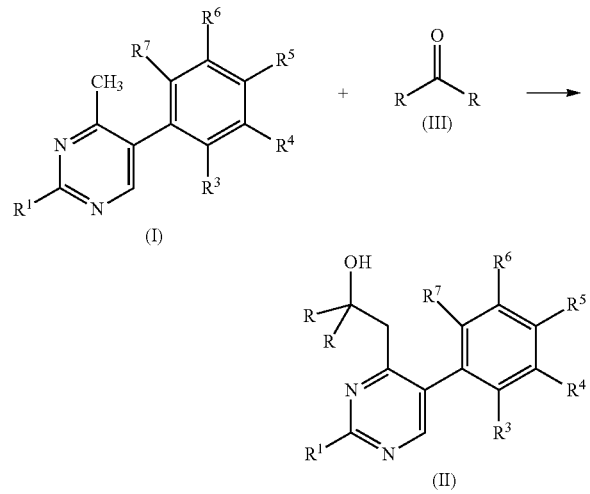

wherein R independent of each other are hydrogen, alkyl, cycloalkyl, halocycloalkyl, haloalkyl, cycloalkenyl, halocycloalkenyl, alkenyl, haloalkenyl, alkynyl, phenyl, heterocyclyl, heteroaryl or both R together form a carbocycle or a heterocycle, The reaction of the pyrimidine (I) with the electrophile (III), is usually carried out at temperatures of from −100° C. to the boiling point of the reaction mixture, preferably from −80° C. to 20° C., particularly from −80° C. to −20° C., in an inert organic solvent in the presence of a base.

Suitable solvents are aliphatic hydrocarbons, such as pentane, hexane, cyclohexane and mixtures of C₅-C₈-alkanes, aromatic hydrocarbons, such as toluene, o-, m- and p-xylene, ethers, such as diethyl ether, diisopropyl ether, tert-butyl methyl ether (TBME), dioxane, anisole and tetrahydrofuran (THF), and also dimethyl sulfoxide (DMSO), dimethylformamide (DMF) and N,N-dimethylacetamide (DMAC), particularly diethyl ether, dioxane and THF. It is also possible to use mixtures of the solvents mentioned.

Suitable bases are, in general, inorganic compounds, such as alkali metal and alkaline earth metal anhydrides, such as lithium hydride (LiH), sodium hydride (NaH), potassium hydride (KH) and calcium hydride (CaH), alkali metal amides, such as lithium hexamethyidisilazide (LHMDS) and lithium diisopropylamide (LDA), organometallic compounds, in particular alkali metal alkyls, such as methyllithium (MeLi), butyllithium (BuLi) and phenyllithium (PhLi), and also alkali metal and alkaline earth metal alkoxides, such as sodium methoxide (NaOCH$_3$), sodium ethoxide (NaOC$_2$H$_5$), potassium ethoxide (KOC$_2$H$_5$), potassium tert-butoxide (tBuOK), potassium tert-pentoxide and dimethoxymagnesium, moreover organic bases, e.g. tertiary amines, such as trimethylamine (TMA), triethylamine (TEA), diisopropylethylamine (DIPEA) and N-methylpiperidine, pyridine, substituted pyridines, such as collidine, lutidine and 4-dimethylaminpyridine, and also bicyclic amines. Particular preference is given to NaH, LHMDS and lithium diisopropylamide (LDA).

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the electrophile, based on the pyrimidine compounds (I).

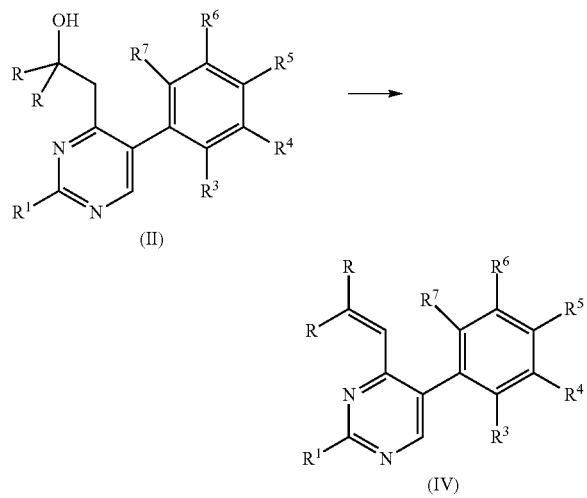

The elimination of the alcohol of the pyrimidine (II) is usually carried out at temperatures from −100° C. to the boiling point of the reaction mixture, preferably from 0° C. to 120° C., particularly from 20° C. to 100° C., in an inert solvent optionally in the presence of an acid.

Suitable solvents are aliphatic hydrocarbons, such as pentane, hexane, cyclohexane and mixtures of C$_5$-C$_8$-alkanes, aromatic hydrocarbons, such as toluene, o-, m- and p-xylene, ethers, such as diethyl ether, diisopropyl ether, TBME, dioxane, anisole, and THF, and also DMSO, DMF and DMAC, particularly toluene and o-xylene. It is also possible to use mixtures of the solvents mentioned.

Suitable acids are inorganic acids, such as HCl, HBr, sulfuric acid; organic acids, p-toluenesulfonic acid, benzene sulfonic acid, pyridinium p-toluol sulfonic acid, methansulfonic acid, acetic acid; preferably p-toluenesulfonic acid and HCl.

The acids are generally employed in equimolar amounts; however, they can also be employed in catalytic amounts, in excess or, if appropriate, as solvents.

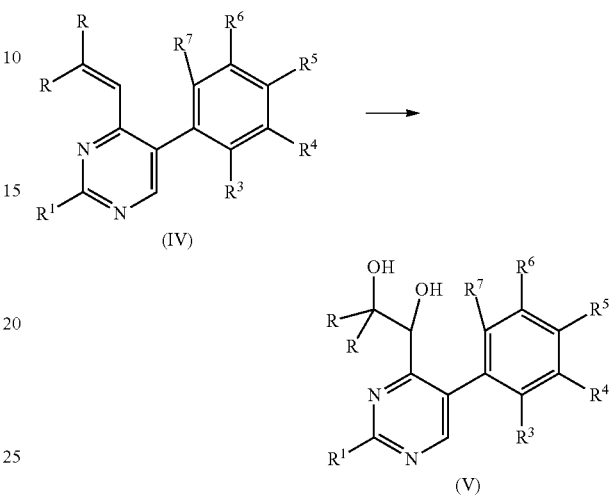

The oxidation of the olefin (IV) to the diol (V) is usually carried out at temperatures of from −100° C. to the boiling point of the reaction mixture, preferably from 0° C. to 120° C., particularly from 20° C. to 100° C., in an inert solvent.

The reaction may in principle be carried out in substance. However, preference is given to reacting the pyrimidines (IV) with the oxidant in an organic solvent with or without water as co-solvent.

Suitable solvents are those are capable of dissolving the pyrimidines (IV) and the oxidant at least partly and preferably fully under reaction conditions.

Suitable solvents are aliphatic hydrocarbons, such as pentane, hexane, cyclohexane and mixtures of C$_5$-C$_8$-alkanes, aromatic hydrocarbons, such as toluene, o-, m- and p-xylene, ethers, such as diethyl ether, diisopropyl ether, TBME, dioxane, anisole and THF, and also DMSO, DMF and DMAC, particularly tert-butyl methyl ether, THF. It is also possible to use mixtures of the solvents mentioned.

Suitable oxidants are e.g. potassium permanganate, potassium perruthenate, osmium tetroxide and other osmium salts, like potassium osmate. The oxidant can be used in equimolar amounts or in catalytic amounts together with a reoxidant like N-methylmorpholine-N-oxide or potassium hexacyanoferrate in stoichiometric amounts or in excess.

Process B:

The halopyrimidines VI are known or can be prepared by known procedures (X=Cl, Br, I).

The boronic acids or esters required for the preparation of pyrimidine compounds of formula (VII) are commercially available, known from literature or can easily be prepared analogously to published procedures (e.g. Kamei et al. Tetrahedron Lett. 2014, 55, 4245-4247).

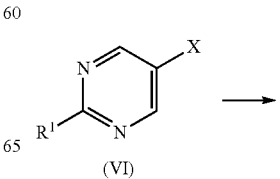

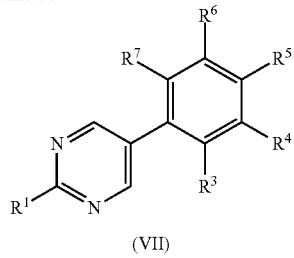

(VII)

The pyrimidine compounds of formula (VII) can be obtained by reacting phenyl boronic acids or esters with halides of formula (VI) in which X is Cl, Br, or I in presence of a base and a catalyst in analogy to WO 2014202493.

The reaction may in principle be carried out in substance. However, preference is given to reacting the pyrimidines (VI) with the boronic acid or ester in an organic solvent with or without water as co-solvent.

Suitable solvents are those capable of dissolving the pyrimidines (VI) and the boronic acid or ester at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, as well as dipolar aprotic solvents such as sulfolane, DMF, DMAC, 1,3-dimethyl-2-imidazolidinone (DMI), N,N'-dimethylpropylene urea (DMPU), DMSO and 1-methyl-2 pyrrolidinone (NMP).

Preferred solvents are ethers such as diethyl ether, diisopropyl ether, TBME, dioxane, anisole and THF and dipolar aprotic solvents such as sulfolane, DMF, DMAC, DMI, DMPU, DMSO, and NMP.

More preferred solvents are ethers such as diethyl ether, diisopropyl ether, TBME, dioxane, anisole and THF. It is also possible to use mixtures of the solvents mentioned.

Examples of suitable metal-containing bases are inorganic compounds including metal-containing bases such as alkali metal and alkaline earth metal hydroxides, and other metal hydroxides, such as LiOH, NaOH, KOH, $Mg(OH)_2$, $Ca(OH)_2$ and $Al(OH)_3$; alkali metal and alkaline earth metal oxide, and other metal oxides, such as $Li_2O$, $Na_2O$, $K_2O$, MgO, and CaO, $Fe_2O_3$, $Ag_2O$; alkali metal and alkaline earth metal carbonates such as $Li_2CO_3$, $Na_2CO_3$, $K_2CO_3$, $Cs_2CO_3$, $MgCO_3$, and $CaCO_3$, as well as alkali metal hydrogen carbonates (bicarbonates) such as $LiHCO_3$, $NaHCO_3$, $KHCO_3$; alkali metal and alkaline earth metal phosphates such as potassium phosphate ($K_3PO_4$), calcium phosphate ($Ca_3(PO_4)_2$); alkali metal and alkaline earth metal acetates such as sodium acetate or potassium acetate.

Preferred bases are inorganic compounds such as alkali metal and alkaline earth metal hydroxides, and other metal hydroxides, such as LiOH, NaOH, KOH, MgOH, CaOH and AlOH and alkali metal or alkaline earth metal carbonates such as $Li_2CO_3$, $Na_2CO_3$, $K_2CO_3$, $Cs_2CO_3$, $MgCO_3$, and $CaCO_3$ and alkaline earth metal phosphates such as $K_3PO_4$; alkali metal and alkaline earth metal acetates such as sodium acetate. Especially preferred bases are inorganic compounds such as alkali metal and alkaline earth metal hydroxides, and other metal hydroxides, such as LiOH, NaOH, KOH, $Mg(OH)_2$, $Ca(OH)_2$ and $Al(OH)_3$ and alkaline earth metal phosphates such as $K_3PO_4$.

The term base as used herein also includes mixtures of two or more, preferably two of the above compounds. Particular preference is given to the use of one base.

The bases are used preferably at from 1 to 10 equivalents based on the pyrimidine (VI), more preferably at from 1.0 to 5.0 equivalents based on the pyrimidine (VI), most preferably from 1.2 to 2.5 equivalents based on the pyrimidine (VI).

It may be advantageous to add the base offset over a period of time.

The reaction of the pyrimidines (VI) with the phenyl boronic acid or ester is carried out in the presence of a catalyst. Examples of suitable catalysts include e.g., palladium based catalysts like, e.g., Palladium(II)acetate, tetrakis(triphenylphosphine)palladium(O), bis(triphenylphosphine)palladium(II)chloride, or (1,1,-bis(diphenylphosphino)ferrocene)-dichloropalladium(II), and optionally suitable additives such as, e.g., phosphines like, e.g., P(o-tolyl)$_3$, triphenylphosphine, or BINAP (2,2'-Bis(diphenylphospino)-1,1'-binaphthyl).

The amount of catalyst is usually 0.01 to 10 mol % (0.0001 to 0.1 equivalents) based on the pyrimidine (VI).

The pyrimidine compounds of formula (VIII) can be obtained by reacting respective pyrimidines of formula (VII) with base and an electrophile, e.g. a carbonyl compound (III):

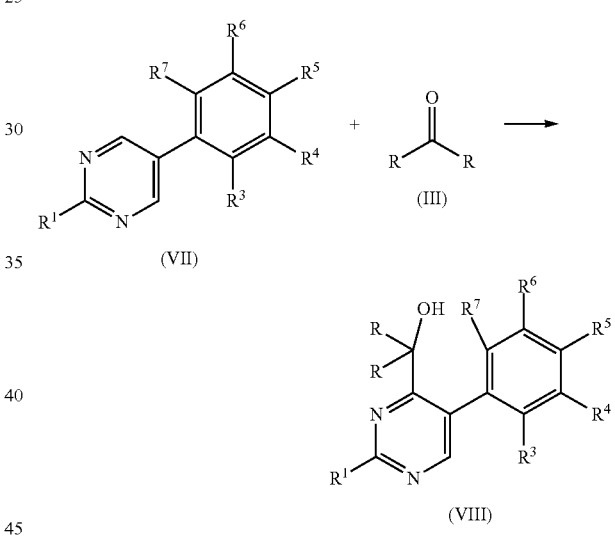

The reaction of the pyrimidine (VII) with the electrophile (III), with R independent of each other equals hydrogen, alkyl, cycloalkyl, halocycloalkyl, haloalkyl, cycloalkenyl, halocycloalkenyl, alkenyl, haloalkenyl, alkynyl, phenyl, heterocyclyl, heteroaryl or both R form together a carbocycle or a heterocycle, is usually carried out at temperatures from −100° C. to the boiling point of the reaction mixture, preferably from −80° C. to 20° C., particularly from −80° C. to −20° C., in an inert organic solvent in the presence of a base.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, ethers, such as diethyl ether, diisopropyl ether, tert-butyl methyl ether, dioxane, anisole and THF, and also DMSO, DMF and DMAC, particularly diethyl ether, dioxane and THF.

It is also possible to use mixtures of the solvents mentioned.

Suitable bases are, in general, inorganic compounds, such as alkali metal and alkaline earth metal anhydrides, such as LiH, NaH, KH and CaH, alkali metal amides, such as LDA, LHMDS, lithium 2,2,6,6-tetramethylpiperidide (LTMP), organometallic compounds, in particular alkali metal alkyls, such as MeLi, BuLi and PhLi, and also alkali metal and alkaline earth metal alkoxides, such as $NaOCH_3$, $NaOC_2H_5$, $KOC_2H_5$, tBuOK, potassium tert-pentoxide and dimethoxymagnesium, moreover organic bases, e.g. tertiary amines, such as TMA, TEA, DIPEA and N-methylpiperidine, pyridine, substituted pyridines, such as collidine, lutidine and 4-dimethylaminpyridine, and also bicyclic amines. Particular preference is given to NaH, LTMP and LDA.

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the electrophile, based on the pyrimidine (VII).

Process C:

The pyrimidine compounds of formula (IX,) can be obtained by reacting respective aminoketones of formula (X) with base and amidine (XI):

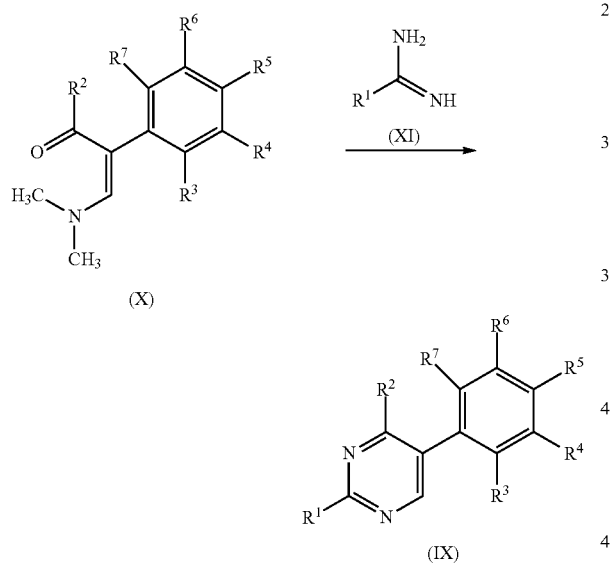

The reaction of the aminoketones (X) with amidines (XI) is usually carried out at temperatures of from −100° C. to the boiling point of the reaction mixture, preferably from 20° C. to the boiling point, particularly from 40° C. to 120° C., in an inert organic solvent in the presence of a base.

The reaction may in principle be carried out in substance. However, preference is given to reacting the aminoketones (X) with the amidine (XI) in an organic solvent.

Suitable solvents are those capable of dissolving the aminoketones (X) with the amidine (XI) at least partly and preferably fully under reaction conditions.

Examples of suitable solvents are aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride ($CCl_4$) and chlorobenzene, ethers such as diethyl ether, diisopropyl ether, TBME, dioxane, anisole and THF, esters such as ethyl acetate and butyl acetate; nitriles such as acetonitrile and propionitrile, alcohols such as methanol, ethanol, n-propanol, isopropanol, n-butanol and tert.-butanol, as well as dipolar aprotic solvents such as sulfolane, DMF, DMAC, DMI, DMPU, DMSO and NMP. Preferred solvents are alcohols such as methanol and ethanol. It is also possible to use mixtures of the solvents mentioned.

Suitable bases are, in general, inorganic compounds, such as alkali metal and alkaline earth metal anhydrides, such as LiH, NaH, KH and CaH, alkali metal amides, such as LHMDS or LDA, organometallic compounds, in particular alkali metal alkyls, such as MeLi, BuLi and PhLi, and also alkali metal and alkaline earth metal alkoxides, such as $NaOCH_3$, $NaOC_2H_5$, $KOC_2H_5$, tBuOK, potassium tert-pentoxide and dimethoxymagnesium, moreover organic bases, e.g. tertiary amines, such as TMA, TEA, DIPEA and N-methylpiperidine, pyridine, substituted pyridines, such as collidine, lutidine and 4-dimethylaminpyridine, and also bicyclic amines. Particular preference is given to $NaOCH_3$, $NaOC_2H_5$, $KOC_2H_5$, tBuOK and potassium tert-pentoxide.

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the amidine (XI), based on the aminoketone (X).

Amidines (XI) are known from literature or commercially available. In cases in which $R^2$ resembles a carbo-oder a heterocycle further, literature known, manipulations are possible: For example oxazoles can selectively be halogenated following published procedures (e.g. Bioorganic & Medicinal Chemistry, 2010, 18, 4821).

Preparation of Compound (X):

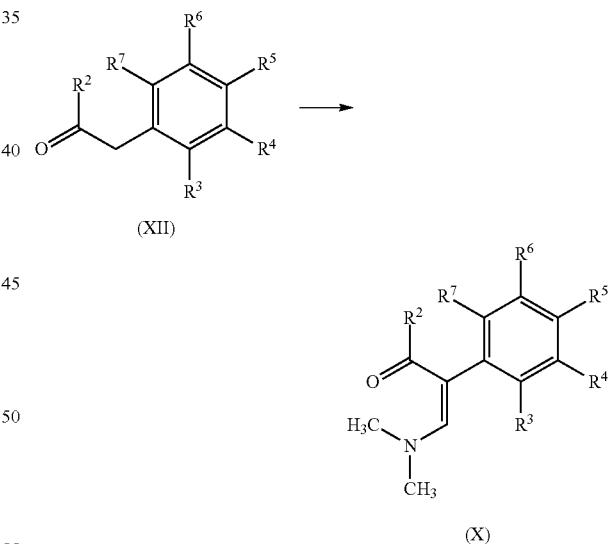

The aminoketones (X) are prepared from the corresponding ketones (XII) with N,N-Dimethylformamide dimethyl acetal (CAS 4637-24-5; DMFDMA). The reaction is usually carried out at temperatures from −100° C. to the boiling point of the reaction mixture, preferably from 20° C. to 160° C., particularly from 50° C. to 130° C. The reaction can optionally be catalyzed by an acid.

The reaction may be carried out in substance or in an organic solvent. Suitable solvents are those capable of dissolving the ketones (XII) and DMFDMA (CAS 4637-24-5) at least partly, preferably fully under reaction conditions.

Examples of suitable solvents are aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, TBME, dioxane, anisole and THF, esters such as ethyl acetate and butyl acetate; nitriles such as acetonitrile and propionitrile, as well as dipolar aprotic solvents such as sulfolane, DMF, DMAC, DMI, DMPU, DMSO and NMP; preferably DMFDMA is used as solvent. It is also possible to use mixtures of the solvents mentioned.

Suitable acids are inorganic acids, such as HCl, HBr, sulfuric acid ($H_2SO_4$); organic acids p-toluenesulfonic acid, benzene sulfonic acid, pyridinium p-toluol sulfonic acid, methanesulfonic acid, acetic acid; preferably p-toluenesulfonic acid and HCl. Most preferred is no use of acid.

The acids are generally employed in equimolar amounts; however, they can also be employed in catalytic amounts, in excess or, if appropriate, as solvents.

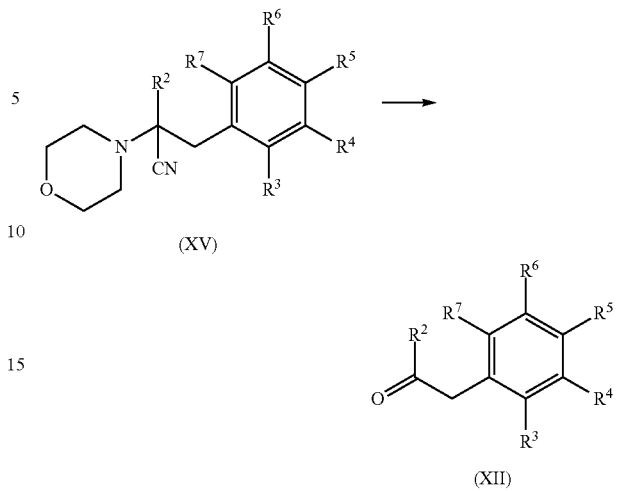

Ketones (XII) can as well be prepared from morpholinonitriles (XV) as described in the literature (European Journal of Organic Chemistry 2013, 36, 8083)

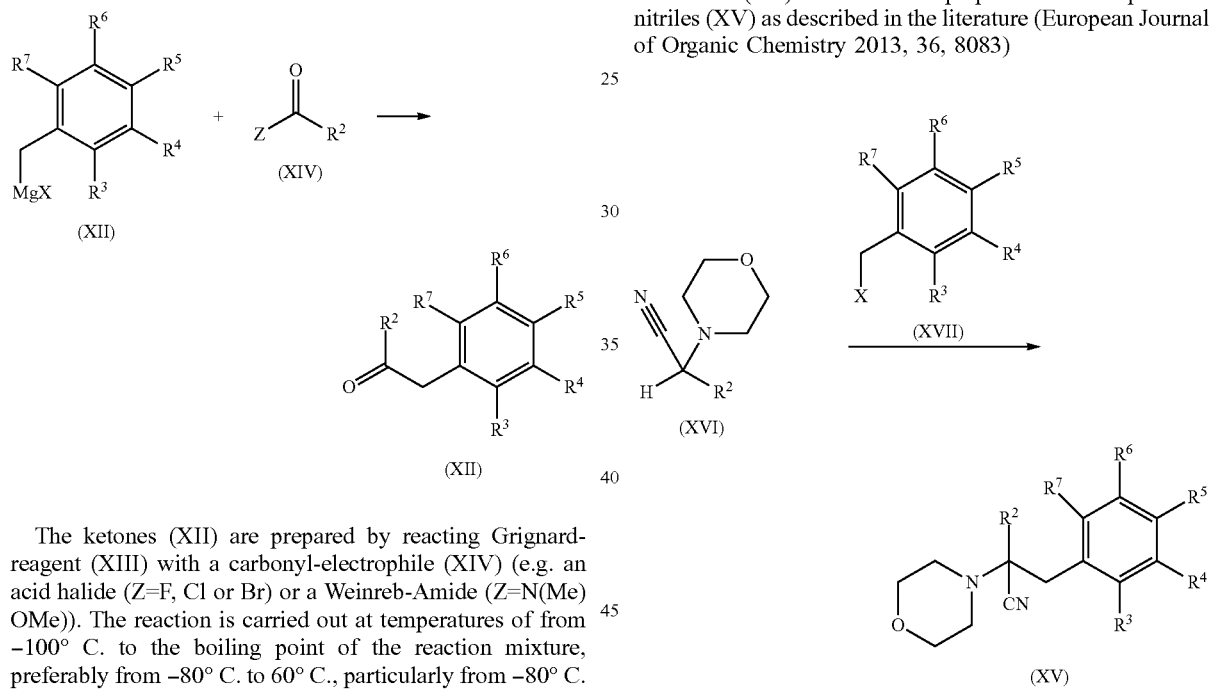

The ketones (XII) are prepared by reacting Grignard-reagent (XIII) with a carbonyl-electrophile (XIV) (e.g. an acid halide (Z=F, Cl or Br) or a Weinreb-Amide (Z=N(Me)OMe)). The reaction is carried out at temperatures of from −100° C. to the boiling point of the reaction mixture, preferably from −80° C. to 60° C., particularly from −80° C. to 20° C., in an inert solvent. Suitable solvents are those capable of dissolving the Grignard-reagent (XIII) and the carbonyl-electrophile (XIV) at least partly and preferably fully under reaction conditions. Examples of suitable solvents are aliphatic aromatic hydrocarbons such as benzene, chlorobenzene, toluene, cresols, o-, m- and p-xylene, ethers such as diethyl ether, diisopropyl ether, TBME, dioxane, anisole and THF, esters such as ethyl acetate and butyl acetate; nitriles such as acetonitrile and propionitrile, as well as dipolar aprotic solvents such as sulfolane, DMF, DMAC, DMI, DMPU, DMSO and NMP. Preferred solvents are ethers such as tert-butyl methyl ether or THF. It is also possible to use mixtures of the solvents mentioned.

The Grignard-reagents (XIII) are either commercially available or can be prepared from the corresponding halides by known methods.

The carbonyl electrophiles (XIV) are either commercially available or can be prepared from the corresponding carboxylic acid or carboxylic ester by known methods.

The morpholinonitriles (XV) are prepared from morpholinonitriles (XVI) and benzylhalides (XVII) in the presence of a base. The reaction is usually carried out at temperatures of from −100° C. to the boiling point of the reaction mixture, preferably from −80° C. to 60° C., particularly from −50° C. to 20° C., in an inert organic solvent in the presence of a base.

Suitable solvents are those capable of dissolving the morpholinonitriles (XVI) and the benzylhalides (XVII) at least partly and preferably fully under reaction conditions.

Examples of suitable solvents are aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, TBME, dioxane, anisole and THF, esters such as ethyl acetate and butyl acetate; nitriles such as acetonitrile and propionitrile, as well as dipolar aprotic solvents such as sulfolane, DMF, DMAC, DMI, DMPU, DMSO and NMP. Preferred solvents are dipolar aprotic solvents such as sulfolane, DMF, DMAC, DMI, DMPU, DMSO, and NMP. It is also possible to use mixtures of the solvents mentioned.

Suitable bases are, in general, inorganic compounds, such as alkali metal and alkaline earth metal anhydrides, such as LiH, NaH, KH and CaH, alkali metal amides, such as LHMDS and LDA, organometallic compounds, in particular alkali metal alkyls, such as MeLi, BuLi and PhLi, and also alkali metal and alkaline earth metal alkoxides, such as NaOCH$_3$, NaOC$_2$H$_5$, KOC$_2$H$_5$, tBuOK, potassium tert-pentoxide and dimethoxymagnesium, moreover organic bases, e.g. tertiary amines, such as TMA, TEA, DIPEA and N-methylpiperidine, pyridine, substituted pyridines, such as collidine, lutidine and 4-dimethylaminpyridine, and also bicyclic amines. Particular preference is given to NaH, LHMDS and LDA.

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the halide (XVII), based on the morpholinonitrile (XVI). Benzylhalides (XVII) are commercially available.

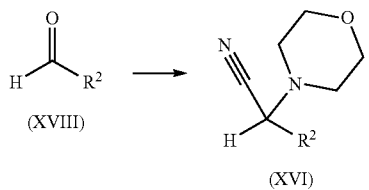

Morpholinonitriles (XVI) are prepared from the corresponding aldehydes (XVIII) as described in the literature (WO 2009/013462). Aldehydes (XVIII) are commercially available.

Process D:

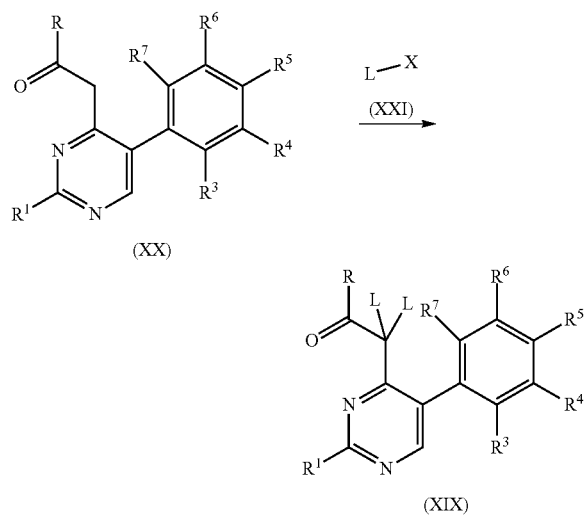

Pyrimidine compounds (XIX), with R equals alkyl, haloalkyl, alkoxy, haloalkoxy, X is a leaving group and L is halogen, alkyl, haloalkyl, alkenyl and alkynyl, can be obtained by reacting respective pyrimidine compounds of formula (XX) with base and an electrophile (XXI).

Electrophile (XXI) can be an alkyl-, alkenyl- or alkynylhalide, e.g. methyl iodide, allyl bromide or propargyl bromide, or a halogenating agent, e.g. Cl$_2$, Br$_2$, I$_2$, NCS (N-Chlorosuccinimide), NBS (N-Bromosuccinimide), NIS (N-Iodosuccinimide), NFSI (N-Fluorobenzenesulfonimide), Selectfluor (1-Chloromethyl-4-fluoro-1,4-diazoniabicyclo[2.2.2]octane bis(tetrafluoroborate)).

The reaction of the pyrimidine (XX) with the electrophile is usually carried out at temperatures of from −100° C. to the boiling point of the reaction mixture, preferably from −80° C. to 80° C., particularly from −80° C. to 30° C., in an inert organic solvent in the presence of a base.

Suitable solvents are those capable of dissolving the pyrimidine (XX) and the electrophile (XXI) at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, nitriles such as acetonitrile and propionitrile, as well as dipolar aprotic solvents such as sulfolane, DMF, DMAC, DMI, DMPU, DMSO and NMP. Preferred solvents are ethers such as diethyl ether, diisopropyl ether, TBME, dioxane, anisole and THF and dipolar aprotic solvents such as sulfolane, DMF, DMAC, DMI, DMPU, DMSO and NMP. More preferred solvents are ethers such as diethyl ether, diisopropyl ether, TBME, dioxane, anisole and THF. It is also possible to use mixtures of the solvents mentioned.

Suitable bases are, in general, inorganic compounds, such as alkali metal and alkaline earth metal anhydrides, such as LiH, NaH, KH and CaH, alkali metal amides, such as LHMDS and LDA, organometallic compounds, in particular alkali metal alkyls, such as MeLi, BuLi and PhLi, and also alkali metal and alkaline earth metal alkoxides, such as NaOCH$_3$, NaOC$_2$H$_5$, KOC$_2$H$_5$, tBuOK, potassium tert-pentoxide and dimethoxymagnesium, moreover organic bases, e.g. tertiary amines, such as TMA, TEA, DIPEA and N-methylpiperidine, pyridine, substituted pyridines, such as collidine, lutidine and 4-dimethylaminpyridine, and also bicyclic amines. Particular preference is given to NaH, lithium hexamethyldisilazide and LDA.

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the electrophile (XXI), based on the pyrimidine (XX).

The pyrimidine compounds of formula (XX) can be obtained by reacting respective pyrimidines of formula (I) (prepared analogous to known procedures e.g. in WO 2013186229) with base and an electrophile (XXII), e.g. a dialkylcarbonate (X=R=alkoxy), an alkyl chloroformiate (X=halogene, R=alkoxy) or an acid halide (X=halogene, R=alkyl or haloalkyl):

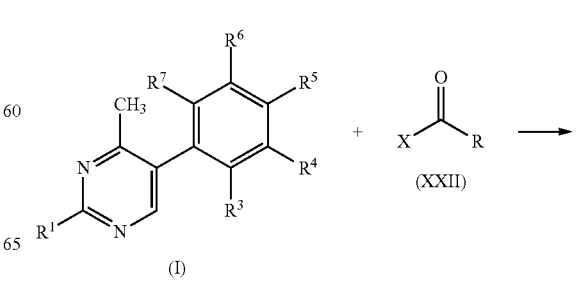

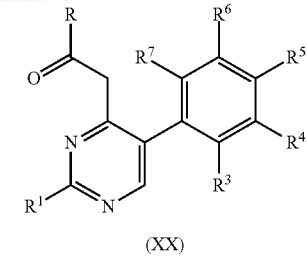

(XX)

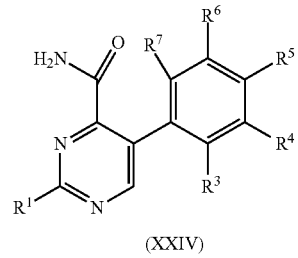

(XXIV)

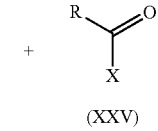

(XXV)

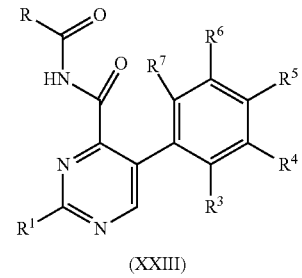

(XXIII)

The reaction of the pyrimidine (I) with the electrophile (XXII) is usually carried out at temperatures of from −100° C. to the boiling point of the reaction mixture, preferably from −80° C. to 80° C., particularly from −80° C. to 30° C., in an inert organic solvent in the presence of a base.

Suitable solvents are those capable of dissolving the pyrimidine (I) and the electrophile (XXII) at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, as well as dipolar aprotic solvents such as sulfolane, DMF, DMAC, DMI, DMPU, DMSO and NMP.

Preferred solvents are ethers such as diethyl ether, diisopropyl ether, TBME, dioxane, anisole and THF and dipolar aprotic solvents such as sulfolane, DMF, DMAC, DMI, DMPU, DMSO and NMP. More preferred solvents are ethers such as diethyl ether, diisopropyl ether, TBME, dioxane, anisole and THF. It is also possible to use mixtures of the solvents mentioned.

Suitable bases are, in general, inorganic compounds, such as alkali metal and alkaline earth metal anhydrides, such as LiH, NaH, KH and CaH, alkali metal amides, such as LHMDS and LDA, organometallic compounds, in particular alkali metal alkyls, such as MeLi, BuLi and PhLi, and also alkali metal and alkaline earth metal alkoxides, such as $NaOCH_3$, $NaOC_2H_5$, $KOC_2H_5$, tBuOK, potassium tert-pentoxide and dimethoxymagnesium, moreover organic bases, e.g. tertiary amines, such as TMA, TEA, DIPEA and N-methylpiperidine, pyridine, substituted pyridines, such as collidine, lutidine and 4-dimethylaminpyridine, and also bicyclic amines. Particular preference is given to NaH, lithium hexamethyldisilazide and LDA.

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the electrophile (XXII), based on the pyrimidine (I).

Process E:

The pyrimidine compounds of formula (XXIII), wherein R is alkyl, haloalkyl, alkenyl, alkynyl, cycloalkyl, phenyl, heterocyclyl, heteroaryl or dialkylamino, can be obtained by reacting respective pyrimidines of formula (XXIV) with base and an electrophile, e.g. an acid halide or an acid anhydride (XXV), wherein X stands for F, Cl, Br or OC(O)R:

The reaction of the pyrimidine (XXIV) with the electrophile (XXV) is usually carried out at temperatures of from −100° C. to the boiling point of the reaction mixture, preferably from −80° C. to 80° C., particularly from −30° C. to 60° C., in an inert organic solvent in the presence of a base.

Suitable solvents are those capable of dissolving the pyrimidine (XX) and the electrophile (XXI) at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, as well as dipolar aprotic solvents such as sulfolane, DMF, DMAC, DMI, DMPU, DMSO and NMP.

Preferred solvents are ethers such as diethyl ether, diisopropyl ether, TBME, dioxane, anisole and THF and dipolar aprotic solvents such as sulfolane, DMF, DMAC, DMI, DMPU, DMSO and NMP. More preferred solvents are ethers such as diethyl ether, diisopropyl ether, TBME, dioxane, anisole and THF. It is also possible to use mixtures of the solvents mentioned.

Suitable bases are, in general, inorganic compounds, such as alkali metal and alkaline earth metal anhydrides, such as LiH, NaH, KH and CaH, alkali metal amides, such as LHMDS and LDA, organometallic compounds, in particular alkali metal alkyls, such as MeLi, BuLi and PhLi, and also alkali metal and alkaline earth metal alkoxides, such as $NaOCH_3$, $NaOC_2H_5$, $KOC_2H_5$, tBuOK, potassium tert-pentoxide and dimethoxymagnesium, moreover organic bases, e.g. tertiary amines, such as TMA, TEA, DIPEA and N-methylpiperidine, pyridine, substituted pyridines, such as collidine, lutidine and 4-dimethylaminpyridine, and also bicyclic amines. Particular preference is given to NaH, lithium hexamethyldisilazide and LDA.

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the electrophile (XXV), based on the pyrimidine (XXIV).

The pyrimidines of formula (XXIV) can be obtained from the acid of formula (XXVI) by known methods (analogous to Kuhn, B. et. al. J. Med. Chem. 2010, 53, 2601-2611).

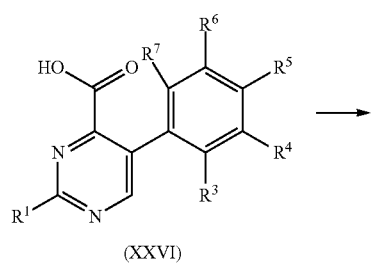

(XXVI)

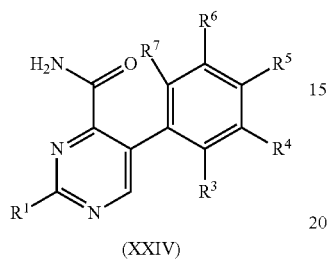

(XXIV)

Pyrimidine compounds (XXVI) can be easily obtained from a corresponding methyl ester (XXVII) by methods known to a person skilled in the art.

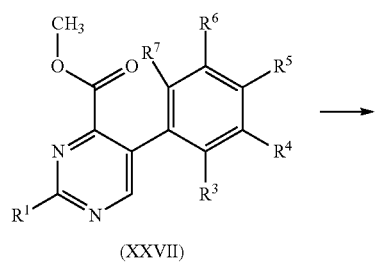

(XXVII)

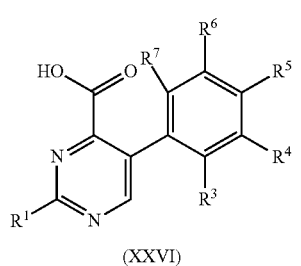

(XXVI)

The pyrimidines of formula (XXVII) can be obtained by reacting respective pyrimidines of formula (XXVIII) with boronic acids/esters of formula (XXIX):

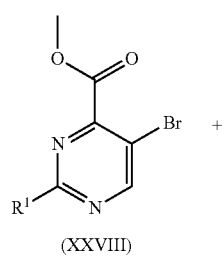

(XXVIII)

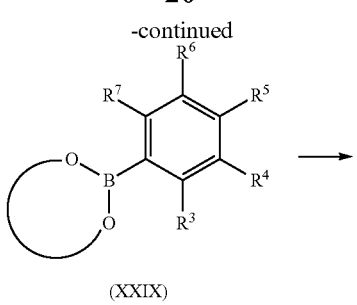

(XXIX)

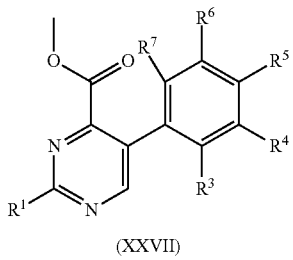

(XXVII)

The reaction of pyrimidines (XXVIII) with boronic acids/esters (XXIX) is usually carried out at from 0° C. to the boiling point of the reaction mixture, preferably at from 15° C. to 110° C., particularly at from 40° C. to 100° C., in an inert organic solvent in the presence of a base and a catalyst.

The reaction may in principle be carried out in substance. However, preference is given to reacting the pyrimidines (XXVIII) with the boronic acids/esters (XXIX) in an organic solvent with or without water as co-solvent.

Suitable solvents are those capable of dissolving the pyrimidines (XXVIII) and the boronic acids (XXIX) at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, as well as dipolar aprotic solvents such as sulfolane, DMF, DMAC, DMI, DMPU, DMSO and NMP.

Preferred solvents are ethers such as diethyl ether, diisopropyl ether, TBME, dioxane, anisole and THF and dipolar aprotic solvents such as sulfolane, DMF, DMAC, DMI, DMPU, DMSO and MP). More preferred solvents are ethers such as diethyl ether, diisopropyl ether, TBME, dioxane, anisole and THF. It is also possible to use mixtures of the solvents mentioned.

Examples of suitable metal-containing bases are inorganic compounds including metal-containing bases such as alkali metal and alkaline earth metal hydroxides, and other metal hydroxides, such as LiOH, NaOH, KOH, $Mg(OH)_2$, $Ca(OH)_2$ and $Al(OH)_3$; alkali metal and alkaline earth metal oxide, and other metal oxides, such as $Li_2O$, $Na_2O$, $K_2O$, MgO, and CaO, $Fe_2O_3$, $Ag_2O$; alkali metal and alkaline earth metal carbonates such as $Li_2CO_3$, $Na_2CO_3$, $K_2CO_3$, $Cs_2CO_3$, $MgCO_3$, and $CaCO_3$, as well as alkali metal bicarbonates such as $LiHCO_3$, $NaHCO_3$, $KHCO_3$; alkali metal and alkaline earth metal phosphates such as $K_3PO_4$, $Ca_3(PO_4)_2$; alkali metal and alkaline earth metal acetates such as sodium acetate or potassium acetate.

Preferred bases are inorganic compounds such as alkali metal and alkaline earth metal hydroxides, and other metal hydroxides, such as LiOH, NaOH, KOH, $Mg(OH)_2$, $Ca(OH)_2$ and $Al(OH)_3$ and alkali metal or alkaline earth metal carbonates such as $Li_2CO_3$, $Na_2CO_3$, $K_2CO_3$, $Cs_2CO_3$, $MgCO_3$, and $CaCO_3$ and alkaline earth metal phosphates such as $K_3PO_4$; alkali metal and alkaline earth metal acetates such as sodium acetate. Especially preferred bases are inorganic compounds such as alkali metal and alkaline earth metal hydroxides, and other metal hydroxides, such as LiOH, NaOH, KOH, $Mg(OH)_2$, $Ca(OH)_2$ and $Al(OH)_3$ and alkaline earth metal phosphates such as $K_3PO_4$.

The term base as used herein also includes mixtures of two or more, preferably two of the above compounds. Particular preference is given to the use of one base.

The bases are used preferably at from 1 to 10 equivalents based on the pyrimidine (XXVIII), more preferably at from 1.0 to 5.0 equivalents based on the pyrimidine (XXVIII), most preferably from 1.2 to 2.5 equivalents based on the pyrimidine (XXVIII).

It may be advantageous to add the base offset over a period of time.

The reaction of the pyridines (XXVIII) with the boronic acids/esters (XXIX) is carried out in the presence of a catalyst. Examples of suitable catalysts include e.g., palladium based catalysts like, e.g., palladium(II)acetate, tetrakis(triphenylphosphine)-palladium(O), bis(triphenylphosphine)palladium(II)chloride or (1,1,-bis(diphenylphosphino)-ferrocene)-dichloropalladium(II), and optionally suitable additives such as, e.g., phosphines like, e.g., $P(o-tolyl)_3$, triphenylphosphine or BINAP (2,2'-Bis(diphenylphospino)-1,1'-binaphthyl).

The amount of catalyst is usually 0.01 to 20 mol % (0.0001 to 0.2 equivalents) based on the pyrimidine (II).

The halopyrimidines XXVIII are known from the literature (e.g. WO 2011154327), are commercially available or can be prepared by known procedures.

The boronic acids/esters XXIX required for the preparation of pyrimidines of formula (XVII) are commercially available, known from literature or can easily be prepared analogously to published procedures (e.g. Kamei et al. Tetrahedron Lett. 2014, 55, 4245-4247).

Process F:
The pyrimidines of formula (XXX) can be obtained by reacting respective pyrimidines of formula (XXVII) with a reducing agent such as LAH or DIBAlH.

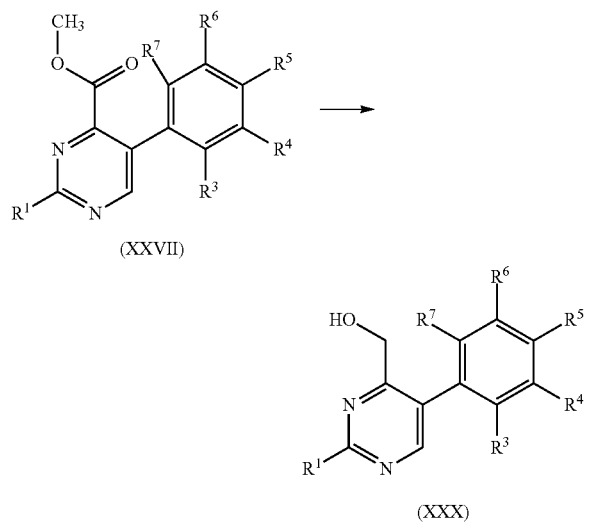

The reduction of pyrimidines (XXVII) is usually carried out from −80° C. to the boiling point of the reaction mixture, preferably at from −20° C. to 60° C., particularly at from 0° C. to 25° C., in an inert organic solvent.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, ethers, such as diethyl ether, diisopropyl ether, tert-butyl methyl ether, dioxane, anisole and THF, and also DMSO, DMF and DMAC, particularly diethyl ether, dioxane and THF. It is also possible to use mixtures of the solvents mentioned.

Examples of reducing agents for pyridines (XXVII) include LAH, DIBALH, $LiBH_4$ or lithium triethylborohydride. Preferred agents include LAH and DIBALH.

The hydride-source is used preferably from 1 to 10 equivalents based on the pyrimidine (XXVII), more preferably at from 1.0 to 5.0 equivalents based on the pyrimidine (XXVII), most preferably from 1.2 to 2.5 equivalents based on the pyrimidine (XXVII).

Process G:
The pyrimidines of formula (XXXI) can be obtained by reacting respective pyrimidines of formula (XXVII) with a metal organic species like a Grignard reagent (R'MgX, X=Cl, Br, I; R'=alkyl, haloalkyl, alkenyl, alkynyl, cycloalkyl, phenyl, heterocyclyl, or heteroaryl).

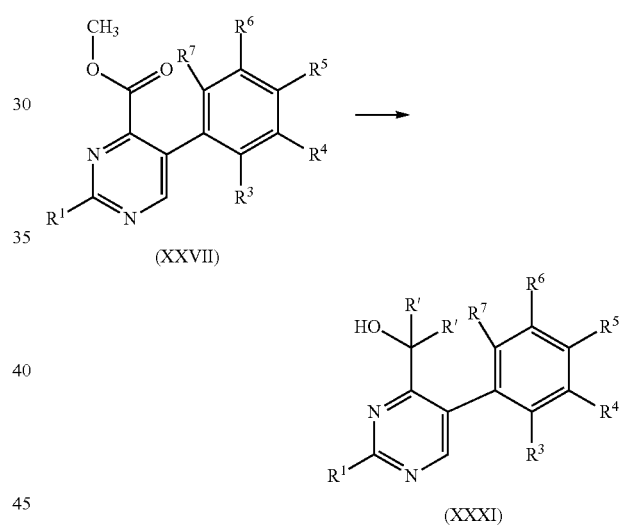

The reaction of pyrimidines (XXVII) with a metal organic species is usually carried out from −80° C. to the boiling point of the reaction mixture, preferably at from −20° C. to 60° C., particularly at from −20° C. to 25° C., in an inert organic solvent.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, ethers, such as diethyl ether, diisopropyl ether, tert-butyl methyl ether, dioxane, anisole and THF, and also DMSO, DMF and DMAC, particularly diethyl ether, dioxane and THF. It is also possible to use mixtures of the solvents mentioned.

Examples of metal organic species for the synthesis of pyridines (XXXI) Grignard reagents like R'MgCl, R'MgBr or R'MgI, lithium organic species, aluminum organic species like $R'_3Al$, $R'_2AlX$ and $R'AlX_2$, titanium organic species like $R'_4Ti$, $R'_3TiX$, $R'_2TiX_2$ and $R'TiX_3$, Preferred agents include Grignard reagents and lithium organic species.

The metal organic species is used preferably from 2 to 10 equivalents based on the pyrimidine (XXVII), more preferably at from 2.0 to 5.0 equivalents based on the pyrimidine (XXVII), most preferably from 2.0 to 3.0 equivalents based on the pyrimidine (XXVII).

Process H:

The pyrimidines of formula (XXXII) can be obtained by reacting respective pyrimidines of formula (XXIII) with a metal organic species like a Grignard reagent (R'MgX, X=Cl, Br, I; R'=alkyl, haloalkyl, alkenyl, alkynyl, cycloalkyl, phenyl, heterocyclyl or heteroaryl).

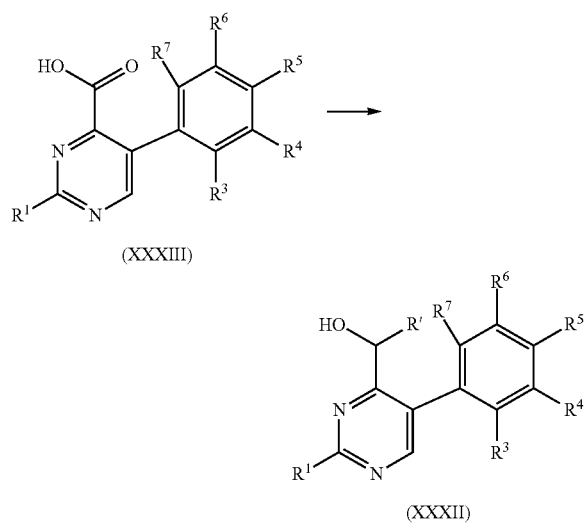

(XXXIII)

(XXXII)

The reaction of pyrimidines (XXXIII) with a metal organic species is usually carried out from −80° C. to the boiling point of the reaction mixture, preferably at from −20° C. to 60° C., particularly at from −20° C. to 25° C., in an inert organic solvent.

Suitable solvents are aliphatic hydrocarbons, such as pentane, hexane, cyclohexane and mixtures of $C_5$-$C_8$-alkanes, aromatic hydrocarbons, such as toluene, o-, m- and p-xylene, ethers, such as diethyl ether, diisopropyl ether, tert-butyl methyl ether, dioxane, anisole and THF, and also DMSO, DMF and DMAC, particularly diethyl ether, dioxane and THF.

It is also possible to use mixtures of the solvents mentioned.

Examples of metal organic species for the synthesis of pyridines (XXXII) Grignard reagents like R'MgCl, R'MgBr or R'MgI, lithium organic species, aluminum organic species like R'$_3$Al, R'$_2$AlX and R'AlX$_2$, titanium organic species like R'$_4$Ti, R'$_3$TiX, R'$_2$TiX$_2$ and R'TiX$_3$.

Preferred agents include Grignard reagents and lithium organic species.

The metal organic species is used preferably from 2 to 10 equivalents based on the pyrimidine (XXXIII), more preferably at from 2.0 to 5.0 equivalents based on the pyrimidine (XXXIII), most preferably from 2.0 to 3.0 equivalents based on the pyrimidine (XXXIII).

Process I:

The pyrimidines of formula (XXXIII) can be obtained by oxidizing respective pyrimidines of formula (XXX).

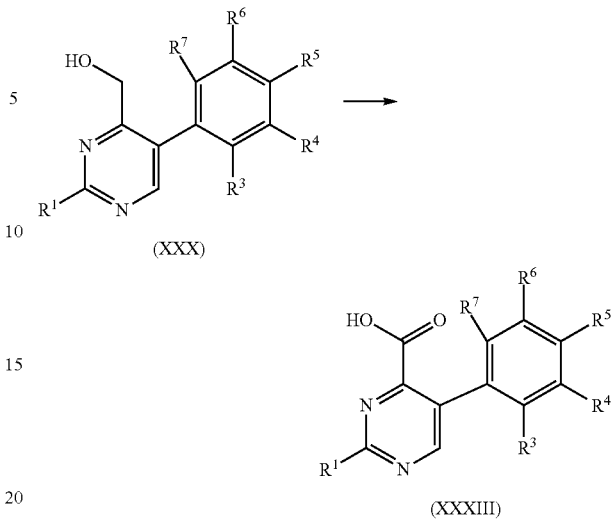

(XXX)

(XXXIII)

The oxidation of pyrimidines (XXX) is usually carried out from −80° C. to the boiling point of the reaction mixture, preferably at from −20° C. to 100° C., particularly at from 0° C. to 75° C., in an inert organic solvent.

The reaction may in principle be carried out in substance. However, preference is given to reacting the pyrimidines (XXX) in an organic solvent.

Suitable solvents are those capable of dissolving the pyrimidines (XXX) at least partly and preferably fully under reaction conditions.

Examples of suitable solvents are aromatic hydrocarbons such as benzene, chlorobenzene, toluene, cresols, o-, m- and p-xylene, halogenated hydrocarbons such as $CH_2Cl_2$, $CHCl_3$, $CCH_2ClCH_2Cl$ or $CCl_4$, ethers such as diethyl ether, diisopropyl ether, TBME, dioxane, anisole and THF, as well as dipolar aprotic solvents such as sulfolane, DMF, DMAC, DMI, DMPU, DMSO and NMP.

Preferred solvents are halogenated hydrocarbons such as $CH_2Cl_2$, $CHCl_3$, $CCH_2ClCH_2Cl$ or $CCl_4$, and dipolar aprotic solvents such as sulfolane, DMF, DMAC, DMI, N,N'-dimethyl-propylene urea (DMPU), DMSO and NMP. More preferred solvents halogenated hydrocarbons such as $CH_2Cl_2$, $CHCl_3$, $CCH_2ClCH_2Cl$ or $CCl_4$. It is also possible to use mixtures of the solvents mentioned.

Examples of oxidizing agents for the synthesis of pyridines (XXXIII) are metal oxides such as $MnO_2$, $KMnO_4$, $CrO_3$ or PCC, and non-metal oxides such as NaClO, $NaIO_4$ or pyridine/$SO_3$-complex. In addition methods like the Swern oxidation or the TEMPO oxidation known to a person skilled in the art can be used to obtain pyridines of formula (XXXIII).

Preferred agents include $MnO_2$, $KMnO_4$ and PCC, more preferred $MnO_2$.

The oxidizing agent is used preferably from 1 to 50 equivalents based on the pyrimidine (XXX), more preferably at from 1.0 to 20.0 equivalents based on the pyrimidine (XXX), most preferably from 1.0 to 10.0 equivalents based on the pyrimidine (XXX).

Process J:

The pyrimidines of formula (XXXIV; Z=cycloalkyl, halocycloalkyl, alkyl, haloalkyl, alkenyl, alkynyl, phenyl, heteroaryl, heterocyclyl, alkylidenyl or halo alkylidenyl and R'=alkyl, haloalkyl, alkenyl, alkynyl, cycloalkyl, heterocyclyl, alkoxycarbonylalkyl) can be obtained reacting respective pyrimidines of formula (XXXV) with base and an electrophile.

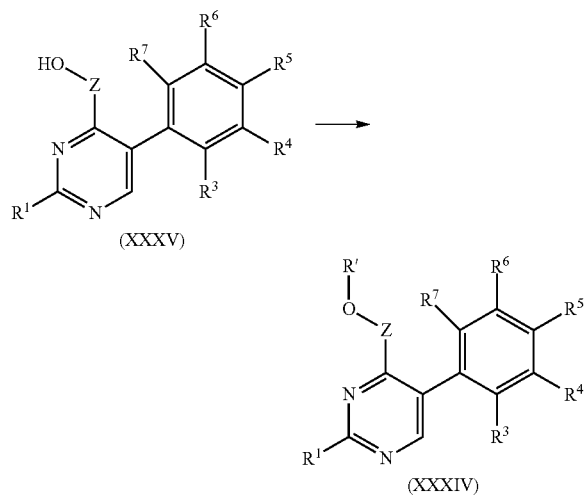

(XXXV)

(XXXIV)

Electrophiles can be an alkyl-, alkenyl- or alkynyl-halide, e.g. methyl iodide, allyl bromide propargyl bromide, ethyl iodide, propyl bromide, or ethyl 2-bromoacetate.

The reaction of the pyrimidine (XXXV) with the electrophile is usually carried out at temperatures of from −100° C. to the boiling point of the reaction mixture, preferably from −20° C. to 100° C., particularly from −0° C. to 30° C., in an inert organic solvent in the presence of a base.

Suitable solvents are those capable of dissolving the pyrimidine (XXXV) and the electrophile at least partly and preferably fully under reaction conditions.

Examples of suitable solvents are aromatic hydrocarbons such as benzene, chlorobenzene, toluene, cresols, o-, m- and p-xylene, ethers such as diethyl ether, diisopropyl ether, TBME, dioxane, anisole and THF, nitriles such as acetonitrile and propionitrile, as well as dipolar aprotic solvents such as sulfolane, DMF, DMAC, DMI, DMPU, DMSO and NMP.

Preferred solvents are ethers such as diethyl ether, diisopropyl ether, TBME, dioxane, anisole and THF and dipolar aprotic solvents such as sulfolane, DMF, DMAC, DMI, DMPU, DMSO and NMP. More preferred solvents are dipolar aprotic solvents such as DMF, and NMP. It is also possible to use mixtures of the solvents mentioned.

Suitable bases are, in general, inorganic compounds, such as alkali metal and alkaline earth metal anhydrides, such as LiH, NaH, KH and CaH, alkali metal amides, such as LHMDS and LDA, organometallic compounds, in particular alkali metal alkyls, such as MeLi, BuLi and PhLi, and also alkali metal and alkaline earth metal alkoxides, such as $NaOCH_3$, $NaOC_2H_5$, $KOC_2H_5$, tBuOK, potassium tert-pentoxide and dimethoxymagnesium, moreover organic bases, e.g. tertiary amines, such as TMA, TEA, DIPEA and N-methylpiperidine, pyridine, substituted pyridines, such as collidine, lutidine and 4-dimethylaminpyridine, and also bicyclic amines. Particular preference is given to NaH, lithium hexamethyldisilazide and LDA.

The bases are generally employed in equimolar amounts; however, they can also be employed in catalytic amounts, in excess or, if appropriate, as solvents.

The starting materials are reacted with one another in equimolar amounts. It may be advantageous to employ an excess of base and/or the electrophile, based on the pyrimidine (XXXV).

The end of the reaction can easily be determined by the skilled worker by means of routine methods.

The reaction mixtures are worked up in a customary manner, e.g. by mixing with water, separation of the phases and, if appropriate, chromatographic purification of the crude product.

Some of the intermediates and end products are obtained in the form of viscous oils, which can be purified or freed from volatile components under reduced pressure and at moderately elevated temperature.

If the intermediates and the end products are obtained as solid, purification can also be carried out by recrystallization or digestion.

The present invention also provides agrochemical compositions comprising at least one pyrimidine compounds of formula (I) and auxiliaries customary for formulating crop protection agents.

The present invention furthermore provides a method for controlling unwanted vegetation where a herbicidal effective amount of at least one pyrimidine compounds of formula (I) is allowed to act on plants, their seeds and/or their habitat. Application can be done before, during and/or after, preferably during and/or after, the emergence of the undesirable plants.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the pyrimidine compounds of formula (I) as described herein are capable of forming geometrical isomers, e.g. E/Z isomers, it is possible to use both, the pure isomers and mixtures thereof, in the compositions according to the invention.

If the pyrimidine compounds of formula (I) as described herein have one or more centres of chirality and, as a consequence, are present as enantiomers or diastereomers, it is possible to use both, the pure enantiomers and diastereomers and their mixtures, in the compositions according to the invention.

If the pyrimidine compounds of formula (I) as described herein have ionisable functional groups, they can also be employed in the form of their agriculturally acceptable salts. Suitable are, in general, the salts of those cations and the acid addition salts of those acids whose cations and anions, respectively, have no adverse effect on the activity of the active compounds.

Preferred cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four H atoms are replaced by $C_1$-$C_4$-alkyl, HO—$C_1$-$C_4$-alkyl, $C_1$-$C_4$-alkoxy-$C_1$-$C_4$-alkyl, HO—$C_1$-$C_4$-alkoxy-$C_1$-$C_4$-alkyl, phenyl or benzyl, preferably ammonium, methyl-ammonium, isopropylammonium, dimethylammonium, diethylammonium, diisopropylammonium, trimethylammonium, triethylammonium, tris(isopropyl)ammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-HO-ethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

Anions of useful acid addition salts are primarily chloride, bromide, fluoride, iodide, hydrogensulfate, methylsulfate, sulfate, dihydrogenphosphate, hydrogenphosphate, nitrate, bicarbonate, carbonate, hexafluorosilicate, hexafluorophosphate, benzoate and also the anions of $C_1$-$C_4$-alkanoic acids, preferably formate, acetate, propionate and butyrate.

Pyrimidine compounds of formula (I) as described herein having an acidic functionality can be employed, if applicable, in the form of the acid, in the form of an agriculturally suitable salt as mentioned above or else in the form of an agriculturally acceptable derivative, e.g. as amides, such as mono- and di-$C_1$-$C_6$-alkylamides or arylamides, as esters, e.g. as allyl esters, propargyl esters, $C_1$-$C_{10}$-alkyl esters, alkoxyalkyl esters, tefuryl ((tetrahydrofuran-2-yl)methyl) esters and also as thioesters, e.g. as $C_1$-$C_{10}$-alkylthio esters. Preferred mono- and di-$C_1$-$C_6$-alkylamides are the CH$_3$ and the dimethylamides. Preferred arylamides are, e.g., the anilides and the 2-chloroanilides. Preferred alkyl esters are, e.g., the methyl, ethyl, propyl, isopropyl, butyl, isobutyl, pentyl, mexyl (1-methylhexyl), meptyl (1-methylheptyl), heptyl, octyl or isooctyl (2-ethylhexyl) esters. Preferred $C_1$-$C_4$-alkoxy-$C_1$-$C_4$-alkyl esters are the straight-chain or branched $C_1$-$C_4$-alkoxy ethyl esters, e.g. the 2-methoxyethyl, 2-ethoxyethyl, 2-butoxyethyl (butotyl), 2-butoxypropyl or 3-butoxypropyl ester. An example of a straight-chain or branched $C_1$-$C_{10}$-alkylthio ester is the ethylthio ester.

The organic moieties mentioned in the definition of the variables $R^1$, $R^2$, A, Z, $R^3$, $R^{3,4}$, and $R^4$, are—like the term halogen—collective terms for individual enumerations of the individual group members. The term halogen denotes in each case F, Cl, Br, or I. All hydrocarbon chains, e.g. all alkyl, alkenyl, alkynyl, alkoxy chains can be straight-chain or branched, the prefix $C_n$-$C_m$ denoting in each case the possible number of carbon atoms in the group.

Examples of such meanings are:
$C_1$-$C_4$-alkyl: e.g. CH$_3$, C$_2$H$_5$, n-propyl, CH(CH$_3$)$_2$, n-butyl, CH(CH$_3$)—C$_2$H$_5$, CH$_2$—CH(CH$_3$)$_2$, and C(CH$_3$)$_3$;

$C_1$-$C_6$-alkyl: $C_1$-$C_4$-alkyl as mentioned above, and also, e.g., n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl, or n-hexyl;

$C_1$-$C_4$-haloalkyl: $C_1$-$C_4$-alkyl as mentioned above which is partially or fully substituted by fluorine, chlorine, bromine and/or iodine, e.g., chloromethyl, dichloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoro-propyl, 1-(fluoromethyl)-2-fluoroethyl, 1-(chloromethyl)-2-chloroethyl, 1-(bromomethyl)-2-bromo-ethyl, 4-fluorobutyl, 4-chlorobutyl, 4-bromobutyl, nonafluorobutyl, 1,1,2,2,-tetrafluoroethyl, and 1-trifluoromethyl-1,1,2,2-tetrafluoroethyl;

$C_1$-$C_6$-haloalkyl: $C_1$-$C_4$-haloalkyl as mentioned above, and also, e.g., 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl, and dodecafluorohexyl;

$C_3$-$C_6$-cycloalkyl: monocyclic saturated hydrocarbons having 3 to 6 ring members, such as cyclopropyl, cyclobutyl, cyclopentyl, and cyclohexyl;

$C_3$-$C_6$-alkenyl: e.g. 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl;

$C_3$-$C_6$-haloalkenyl: a $C_3$-$C_6$-alkenyl substituent as mentioned above which is partially or fully substituted by fluorine, chlorine, bromine and/or iodine, e.g. 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl, or 2,3-dibromobut-2-en-1-yl;

$C_3$-$C_6$-alkynyl: e.g. 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2- butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: a $C_3$-$C_6$-alkynyl radical as mentioned above which is partially or fully substituted by F, Cl, Br and/or I, e.g. 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl, or 6-iodohex-5-yn-1-yl;

$C_1$-$C_4$-alkoxy: e.g. methoxy, ethoxy, propoxy, 1-methylethoxy butoxy, 1-methylpropoxy, 2-methylpropoxy, and 1,1-dimethylethoxy;

$C_1$-$C_6$-alkoxy: $C_1$-$C_4$-alkoxy as mentioned above, and also, e.g., pentoxy, 1-methylbutoxy, 2-methylbutoxy, 3-methoxylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, and 1-ethyl-2-methyl propoxy.

$C_1$-$C_4$-haloalkoxy: a $C_1$-$C_4$-alkoxy radical as mentioned above which is partially or fully substituted by fluorine, chlorine, bromine and/or iodine, i.e., e.g., fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy, and nonafluorobutoxy;

$C_1$-$C_6$-haloalkoxy: a $C_1$-$C_4$-haloalkoxy as mentioned above, and also, e.g., 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$-$C_4$-alkylthio: e.g. methylthio, ethylthio, propylthio, 1-methylethylthio, butylthio, 1-methylpropylthio, 2-methylpropylthio, and 1,1-dimethylethylthio;

$C_1$-$C_6$-alkylthio: $C_1$-$C_4$-alkylthio as mentioned above, and also, e.g., pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, and 1-ethyl-2-methylpropylthio;

($C_1$-$C_4$-alkyl)amino: e.g. methylamino, ethylamino, propylamino, 1-methylethylamino, butylamino, 1-methylpropylamino, 2-methylpropylamino, or 1,1-dimethylethylamino;

($C_1$-$C_6$-alkyl)amino: ($C_1$-$C_4$-alkylamino) as mentioned above, and also, e.g., pentyl-amino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutyl-amino 3,3-dimethylbutylamino, 1-ethylbutylamino, 2-ethylbutylamino, 1,1,2-trimethylpropylamino, 1,2,2-trimethyl-propylamino, 1-ethyl-1-methylpropylamino, or 1-ethyl-2-methylpropylamino;

di($C_1$-$C_4$-alkyl)amino: e.g. N,N-dimethylamino, N,N-diethylamino, N,N-di(1-methyl-ethyl)amino, N,N-dipropylamino, N,N-dibutylamino, N,N-di(1-methylpropyl) amino, N,N-di(2-methyl-propyl)amino, N,N-di(1,1-dimethylethyl)amino, N-ethyl-N-methylamino, N-methyl-N-propyl-amino, N-methyl-N-(1-methylethyl)amino, N-butyl-N-methylamino, N-methyl-N-(1-methylpropyl)amino, N-methyl-N-(2-methylpropyl) amino, N-(1,1-dimethylethyl)-N-methylamino, N-ethyl-N-propylamino, N-ethyl-N-(1-methylethyl) amino, N-butyl-N-ethylamino, N-ethyl-N-(1-methylpropyl)-amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methyl-propyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethyl-ethyl)-N-(1-methylpropyl)amino, or N-(1,1-dimethylethyl)-N-(2-methylpropyl)amino;

di($C_1$-$C_6$-alkyl)amino: di($C_1$-$C_4$-alkyl)amino as mentioned above, and also, e.g., N-methyl-N-pentylamino, N-methyl-N-(1-methylbutyl)amino, N-methyl-N-(2-methylbutyl)amino, N-methyl-N-(3-methylbutyl) amino, N-methyl-N-(2,2-dimethylpropyl)amino, N-methyl-N-(1-ethylpropyl)amino, N-methyl-N-hexylamino, N-methyl-N-(1,1-dimethylpropyl)amino, N-methyl-N-(1,2-dimethylpropyl)amino, N-methyl-N-(1-methylpentyl)amino, N-methyl-N-(2-methylpentyl) amino, N-methyl-N-(3-methylpentyl)amino, N-methyl-N-(4-methylpentyl)amino, N-methyl-N-(1,1-dimethylbutyl)amino, N-methyl-N-(1,2-dimethylbutyl)amino, N-methyl-N-(1,3-dimethylbutyl)amino, N-methyl-N-(2,2-dimethylbutyl)amino, N-methyl-N-(2,3-dimethylbutyl)amino, N-methyl-N-(3,3-dimethylbutyl)amino, N-methyl-N-(1-ethylbutyl)amino, N-methyl-N-(2-ethylbutyl)amino, N-methyl-N-(1,1,2-trimethylpropyl)amino, N-methyl-N-(1,2,2-trimethylpropyl)amino, N-methyl-N-(1-ethyl-1-methylpropyl)amino, N-methyl-N-(1-ethyl-2-methylpropyl)amino, N-ethyl-N-pentylamino, N-ethyl-N-(1-methylbutyl)amino, N-ethyl-N-(2-methylbutyl)amino, N-ethyl-N-(3-methylbutyl)amino, N-ethyl-N-(2,2-dimethylpropyl)amino, N-ethyl-N-(1-ethylpropyl)amino, N-ethyl-N-hexylamino, N-ethyl-N-(1,1-dimethylpropyl)amino, N-ethyl-N-(1,2-dimethylpropyl)amino, N-ethyl-N-(1-methylpentyl)amino, N-ethyl-N-(2-methylpentyl)amino, N-ethyl-N-(3-methylpentyl)amino, N-ethyl-N-(4-methylpentyl)amino, N-ethyl-N-(1,1-dimethylbutyl)amino, N-ethyl-N-(1,2-dimethylbutyl)amino, N-ethyl-N-(1,3-dimethylbutyl)amino, N-ethyl-N-(2,2-dimethylbutyl)amino, N-ethyl-N-(2,3-dimethylbutyl)amino, N-ethyl-N-(3,3-dimethylbutyl)amino, N-ethyl-N-(1-ethylbutyl)amino, N-ethyl-N-(2-ethylbutyl)amino, N-ethyl-N-(1,1,2-trimethylpropyl)amino, N-ethyl-N-(1,2,2-trimethylpropyl)amino, N-ethyl-N-(1-ethyl-1-methylpropyl)amino, N-ethyl-N-(1-ethyl-2-methylpropyl)amino, N-propyl-N-pentylamino, N-butyl-N-pentylamino, N,N-dipentylamino, N-propyl-N-hexylamino, N-butyl-N-hexylamino, N-pentyl-N-hexylamino, or N,N-dihexylamino;

$C_1$-$C_6$-alkylsulfinyl ($C_1$-$C_6$-Alkyl-S(=O)—): e.g. methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropyl-sulfinyl, hexylsulfinyl, 1-methylpentylsulfinyl, 2-methylpentylsulfinyl, 3-methylpentylsulfinyl, 4-methylpentyl-sulfinyl, 1,1-dimethylbutylsulfinyl, 1,2-dimethylbutylsulfinyl, 1,3-dimethylbutyl-sulfinyl, 2,2-dimethylbutylsulfinyl, 2,3-dimethylbutylsulfinyl, 3,3-dimethylbutyl-sulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropyl-sulfinyl, and 1-ethyl-2-methylpropylsulfinyl;

$C_1$-$C_6$-alkylsulfonyl ($C_1$-$C_6$-alkyl-S(O)$_2$—): e.g. methylsulfonyl, ethylsulfonyl, propylsulfonyl, 1-methylethylsulfonyl, butylsulfonyl, 1-methylpropylsulfonyl, 2-methyl-propylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropyl-sulfonyl, 1-ethylpropylsulfonyl, hexylsulfonyl, 1-methylpentylsulfonyl, 2-methylpentylsulfonyl, 3-methyl pentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutyl-sulfonyl, 1-ethylbutylsulfonyl, 2-ethylbutylsulfonyl, 1,1,2-trimethyl-propylsulfonyl, 1,2,2-trimethyl-propylsulfonyl, 1-ethyl-1-methyl propylsulfonyl, and 1-ethyl-2-methylpropylsulfonyl;

$C_3$-$C_6$-cycloalkyl: a monocyclic saturated hydrocarbon having 3 to 6 ring members, such as cyclopropyl, cyclobutyl, cyclopentyl, and cyclohexyl;

$C_3$-$C_6$-cycloalkenyl: 1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, or 2,5-cyclohexadienyl;

heterocyclyl: a 3- to 6-membered heterocyclyl: a saturated or partial unsaturated cycle having three to six ring members which comprises apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, e.g. 3- or 4-membered heterocycles like 2-oxiranyl, 2-aziridinyl, 2-thiiranyl, 2-oxetanyl, 3-oxetanyl, 2-thietanyl, 3-thietanyl, 1-azetidinyl, 2-azetidinyl, 1-azetinyl, or 2-azetinyl;

5-membered saturated heterocycles like 2-tetrahydrofuranyl, 3-tetrahydrofuranyl, 2-tetrahydrothienyl, 3-tetrahydrothienyl, 1-pyrrolidinyl, 2-pyrrolidinyl, 3-pyrrolidinyl, 3-isoxazolidinyl, 4-isoxazolidinyl, 5-isoxazolidinyl, 2-isothiazolidinyl, 3-isothiazolidinyl, 4-isothiazolidinyl, 5-isothiazolidinyl, 1-pyrazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 1-imidazolidinyl, 2-imidazolidinyl, 4-imidazolidinyl, 3-oxazolidinyl, 1,2,4-oxadiazolidin-3-yl, 1,2,4-oxadiazolidin-5-yl, 3-thiazolidinyl, 1,2,4-thiadiazolidin-3-yl, 1,2,4-thiadiazolidin-5-yl, 1,2,4-triazolidin-3-yl, 1,2,4-oxadiazolidin-2-yl, 1,2,4-oxadiazolidin-4-yl, 1,3,4-oxadiazolidin-2-yl, 1,2,4-thiadiazolidin-2-yl, 1,2,4-thiadiazolidin-4-yl, 1,3,4-thiadiazolidin-2-yl, 1,2,4-triazolidin-1-yl, or 1,3,4-triazolidin-2-yl; 5-membered partial unsaturated heterocycles like 2,3-dihydrofur-2-yl, 2,3-dihydrofur-3-yl, 2,4-dihydrofur-2-yl, 2,4-dihydrofur-3-yl, dioxolan-2-yl, 1,3-dioxol-2-yl, 2,3-dihydrothien-2-yl, 2,3-dihydrothien-3-yl, 2,4-dihydrothien-2-yl, 2,4-dihydrothien-3-yl, 4,5-dihydropyrrol-1-yl, 4,5-dihydropyrrol-2-yl, 4,5-dihydropyrrol-3-yl, 2,5-dihydropyrrol-1-yl, 2,5-dihydropyrrol-2-yl, 2,5-dihydropyrrol-3-yl, 2,3-dihydroisoxazol-1-yl, 2,3-dihydroisoxazol-3-yl, 2,3-dihydroisoxazol-4-yl, 2,3-dihydroisoxazol-5-yl, 2,5-dihydroisoxazol-3-yl, 2,5-dihydroisoxazol-4-yl, 2,5-dihydroisoxazol-5-yl, 4,5-dihydroisoxazol-2-yl, 4,5-dihydroisoxazol-3-yl, 4,5-dihydroisoxazol-4-yl, 4,5-dihydroisoxazol-5-yl, 2,3-dihydroisothiazol-1-yl, 2,3-dihydroisothiazol-3-yl, 2,3-dihydroisothiazol-4-yl, 2,3-dihydroisothiazol-5-yl, 2,5-dihydroisothiazol-3-yl, 2,5-dihydroisothiazol-4-yl, 2,5-dihydroisothiazol-5-yl, 4,5-dihydroisothiazol-1-yl, 4,5-dihydroisothiazol-3-yl, 4,5-dihydroisothiazol-4-yl, 4,5-dihydroisothiazol-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydroimidazol-1-yl, 2,3-dihydroimidazol-2-yl, 2,3-dihydroimidazol-3-yl, 2,3-dihydroimidazol-4-yl, 2,3-dihydroimidazol-5-yl, 4,5-dihydroimidazol-1-yl, 4,5-dihydroimidazol-2-yl, 4,5-dihydroimidazol-4-yl, 4,5-dihydroimidazol-5-yl, 2,5-dihydroimidazol-1-yl, 2,5-dihydroimidazol-2-yl, 2,5-dihydroimidazol-4-yl, 2,5-dihydroimidazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2,3-dihydrothiazol-2-yl, 2,3-dihydrothiazol-3-yl, 2,3-dihydrothiazol-4-yl, 2,3-dihydrothiazol-5-yl, 3,4-dihydrothiazol-3-yl, 3,4-dihydrothiazol-4-yl, 3,4- dihydrothiazol-5-yl, 3,4-dihydrothiazol-2-yl, 3,4-dihydrothiazol-3-yl, or 3,4-dihydrothiazol-4-yl;

6-membered saturated heterocycles like 1-piperidinyl, 2-piperidinyl, 3-piperidinyl, 4-piperidinyl, 1,3-dioxan-5-yl, 1,4-dioxanyl, 1,3-dithian-5-yl, 1,3-dithianyl, 1,3-oxathian-5-yl, 1,4-oxathianyl, 2-tetrahydropyranyl, 3-tetrahydopyranyl, 4-tetrahydropyranyl, 2-tetrahydrothiopyranyl, 3-tetrahydrothiopyranyl, 4-tetrahydrothiopyranyl, 1-hexahydropyridazinyl, 3-hexahydropyridazinyl, 4-hexahydropyridazinyl, 1-hexahydropyrimidinyl, 2-hexahydropyrimidinyl, 4-hexahydropyrimidinyl, 5-hexahydropyrimidinyl, 1-piperazinyl, 2-piperazinyl, 1,3,5-hexahydrotriazin-1-yl, 1,3,5-hexahydrotriazin-2-yl, 1,2,4-hexahydrotriazin-1-yl, 1,2,4-hexahydrotriazin-3-yl, tetrahydro-1,3-oxazin-1-yl, tetrahydro-1,3-oxazin-2-yl, tetrahydro-1,3-oxazin-6-yl, 1-morpholinyl, or 2-morpholinyl, 3-morpholinyl;

6-membered partial unsaturated heterocycles like 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, or 5,6-dihydro-4H-1,3-oxazin-2-yl.

heteroaryl: a 5-, 6- or 9-membered heteroaryl: monocyclic or bicyclic aromatic heteroaryl having 5, 6 or 9 ring members which, in addition to carbon atoms and independent of their position in the ring, contains 1 to 4 nitrogen atoms, or 1 to 3 nitrogen atoms and an oxygen or sulfur atom, or an oxygen or a sulfur atom, e.g. 5-membered aromatic rings like furyl (e.g. 2-furyl, 3-furyl), thienyl (e.g. 2-thienyl, 3-thienyl), pyrrolyl (e.g. pyrrol-2-yl, pyrrol-3-yl), pyrazolyl (e.g. pyrazol-3-yl, pyrazol-4-yl), isoxazolyl (e.g. isoxazol-3-yl, isoxazol-4-yl, isoxazol-5-yl), isothiazolyl (e.g. isothiazol-3-yl, isothiazol-4-yl, isothiazol-5-yl), imidazolyl (e.g. imidazole-2-yl, imidazole-4-yl), oxazolyl (e.g. oxazol-2-yl, oxazol-4-yl, oxazol-5-yl), thiazolyl (e.g. thiazol-2-yl, thiazol-4-yl, thiazol-5-yl), oxadiazolyl (e.g. 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (e.g. 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (e.g. 1,2,3-triazol-4-yl, 1,2,4-triazol-3-yl); 1-tetrazolyl; 6-membered aromatic rings like pyridyl (e.g. pyridine-2-yl, pyridine-3-yl, pyridine-4-yl), pyrazinyl (e.g. pyridazin-3-yl, pyridazin-4-yl), pyrimidinyl (e.g. pyrimidin-2-yl, pyrimidin-4-yl, pyrimidin-5-yl), pyrazin-2-yl, triazinyl (e.g. 1,3,5-triazin-2-yl, or 1,2,4-triazin-3-yl, 1,2,4-triazin-5-yl, 1,2,4-triazin-6-yl); 9-membered bicyclic aromatic rings like benzothiophene, indole, benzofuran;

The term "substituted" if not specified otherwise refers to substituted by 1, 2 or maximum possible number of substituents. If substituents as defined in compounds of formula I are more than one then they are independently from each other are same or different if not mentioned otherwise.

The term "acidic functionality" if not specified otherwise refers to a functionality capable of donating a hydrogen (proton or hydrogen ion H+), such as a caboxylic group or a sulphonic group, or, alternatively, capable of forming a covalent bond with an electron pair.

The terms "compounds of formula (I)", "Pyrimidine compounds of formula (I)", "Compounds I" and "compounds of invention" are synonyms.

The preferred embodiments of the invention mentioned herein below have to be understood as being preferred either independently from each other or in combination with one another.

In general, pyrimidine compounds of formula (I) are suitable as herbicides.

According to a preferred embodiment of the invention preference is given pyrimidine compounds of formula (I), and their use as herbicides, wherein the variables, either independently of one another or in combination with one another, have the following meanings:

Preferred $R^1$ is $C_1$-$C_6$-alkyl, $C_1$-$C_6$-haloalkyl, HO—$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, 5-membered heteroaryl, or 3- to 6-membered heterocyclyl;

wherein the cyclic groups of $R^1$ are unsubstituted or substituted by $R^a$;

also preferred $R^1$ is $C_1$-$C_6$-alkyl, $C_1$-$C_6$-haloalkyl, HO—$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, or $C_3$-$C_6$-cycloalkyl-$C_1$-$C_6$-haloalkoxy, wherein the cyclic groups of $R^1$ are unsubstituted or substituted by $R^a$;

also preferred $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_4$-$C_6$-haloalkynyloxy, $C_1$-$C_6$-alkylthio, $C_3$-$C_6$-cycloalkyl, wherein the cycloalkyl substituent is unsubstituted;

particularly preferred $R^1$ is $C_1$-$C_6$-alkyl, $C_1$-$C_6$-alkoxy, or $C_3$-$C_6$-cycloalkyl, wherein the cycloalkyl substituent is unsubstituted;

especially preferred $R^1$ is $C_3$-$C_6$-cycloalkyl, wherein the cycloalkyl substituent is unsubstituted;

also especially preferred $R^1$ is $C_2H_5$, i-$C_3H_7$, i-$C_4H_9$, $OCH_3$, c-$C_3H_5$, or c-$C_4H_7$;

more preferred $R^1$ is $C_2H_5$, $OCH_3$, or c-$C_3H_5$; most preferred $R^1$ is c-$C_3H_5$.

Preferred $R^2$ is $C_2$-$C_6$-alkenyl, $C_2$-$C_6$-haloalkenyl, $C_1$-$C_6$-alkoxy-$C_2$-$C_6$-alkenyl, $C_2$-$C_6$-alkynyl, $C_3$-$C_6$-cycloalkenyl, $C_3$-$C_6$-cycloalkenyl-$C_1$-$C_6$-alkyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-cycloalkenyl-$C_1$-$C_6$-alkylidenyl, $C_3$-$C_6$-hydroxycycloalkyl-$C_1$-$C_6$-alkyl, $C_3$-$C_6$-hydroxycycloalkenyl-$C_1$-$C_6$-alkyl, $C_1$-$C_6$-hydroxyalkyl, $C_3$-$C_6$-cycloalkyl-$C_2$-$C_6$-hydroxyalkylidenyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-alkyl, $C_3$-$C_6$-hydroxycycloalkyl-$C_1$-$C_6$-hydroxyalkyl, $C_2$-$C_6$-dihydroxyalkyl, $C_3$-$C_6$-cycloalkyl-$C_3$-$C_6$-dihydroxyalkylidenyl, hydroxycarbonyl-$C_2$-$C_6$-dihydroxyalkyl, $C_1$-$C_6$-alkoxycarbonyl-$C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl; wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$.

Particularly preferred $R^2$ is $C_2$-$C_6$-alkenyl, $C_2$-$C_6$-alkynyl, $C_3$-$C_6$-cycloalkenyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-hydroxycycloalkyl-$C_1$-$C_6$-alkyl, $C_3$-$C_6$-hydroxycycloalkyl-$C_1$-$C_6$-hydroxyalkyl, $C_2$-$C_6$-dihydroxyalkyl, phenyl or 5- or 6-membered heteroaryl; wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$.

Also particularly preferred $R^2$ is $C_2$-$C_6$-alkenyl, $C_2$-$C_6$-alkynyl, $C_3$-$C_6$-cycloalkenyl-$C_1$-$C_6$-alkyl, $C_3$-$C_6$-cycloalkyl-$C_1$-$C_6$-alkylidenyl, $C_1$-$C_6$-hydroxyalkyl, $C_1$-$C_6$-alkoxycarbonyl-$C_1$-$C_6$-alkyl, $C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl; wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$.

Especially preferred $R^2$ is $C_2$-$C_6$-alkenyl, $C_2$-$C_6$-alkynyl, $C_3$-$C_6$-cycloalkyl-$C_1$-$C_6$-alkylidenyl, $C_3$-$C_6$-hydroxycycloalkyl-$C_1$-$C_6$-alkyl, and 5- or 6-membered heteroaryl;

also especially preferred $R^2$ is $C_2$-$C_6$-alkenyl, $C_1$-$C_6$-hydroxyalkyl, $C_3$-$C_6$-cycloalkyl-$C_1$-$C_6$-alkylidenyl, $C_2$-$C_6$-dihydroxyalkyl, $C_1$-$C_6$-dicyanoalkyl and 5- or 6-membered heteroaryl;

also especially preferred $R^2$ is $C_2$-$C_6$-alkenyl, $C_3$-$C_6$-cycloalkyl-$C_1$-$C_6$-alkylidenyl, $C_1$-$C_6$-hydroxyalkyl, $C_2$-$C_6$-dihydroxyalkyl, or 5- or 6-membered heteroaryl;

wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$.

More preferred $R^2$ is $C_2$-$C_6$-alkenyl, $C_3$-$C_6$-cycloalkyl-$C_1$-$C_6$-alkylidenyl, or 5- or 6-membered heteroaryl;

also more preferred $R^2$ is $C_1$-$C_6$-hydroxyalkyl, $C_2$-$C_6$-dihydroxyalkyl, $C_3$-$C_6$-cycloalkyl-$C_1$-$C_6$-alkylidenyl, or 5- or 6-membered heteroaryl;

wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$;

most preferred $R^2$ is $C_2$-$C_6$-alkenyl;

also most preferred $R^2$ is $C_3$-$C_6$-cycloalkyl-$C_1$-$C_6$-alkylidenyl;

also most preferred $R^2$ is 5- or 6-membered heteroaryl;

also most preferred $R^2$ is 5-membered heteroaryl;

also most preferred $R^2$ is $C_1$-$C_6$-hydroxyalkyl also most preferred $R^2$ is $C_2$-$C_6$-dihydroxyalkyl;

wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$.

also more preferred $R^2$ is CH=CH—$CH_3$, CH=C($CH_2$)$_3$, or CH=C($CH_2$)$_4$;

also more preferred $R^2$ is 2-furyl, 3-furyl, 2-methyl-3-furyl, or 3-methyl-2-furyl;

also most preferred $R^2$ is CH=CH—$CH_3$, CH=C($CH_2$)$_3$, 2-furyl, or 3-furyl; also most preferred $R^2$ is CHOH—CHOH—$C_6H_5$, CHOH—CHOH-2-furyl, CHOH—CHOH-2-furyl, or 4-methyloxazol-5-yl;

also most preferred $R^2$ is CHOH—CHOH—$C_6H_5$, CHOH—CHOH-2-furyl, CHOH—CHOH—$CH_3$, or 4-methyloxazol-5-yl;

also most preferred $R^2$ is selected from $R^2$-1 to $R^2$-16 as shown below,

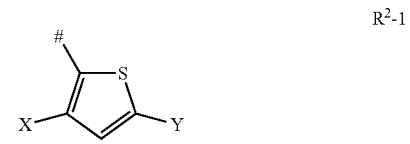

R²-1

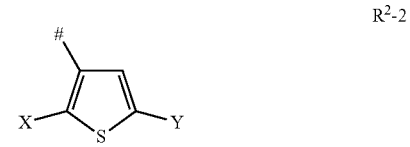

R²-2

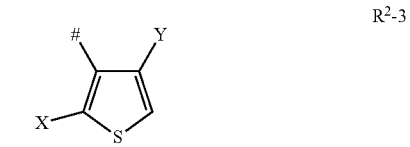

R²-3

R²-4

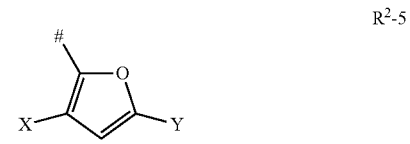

R²-5

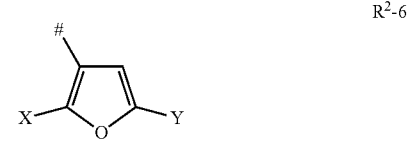

R²-6

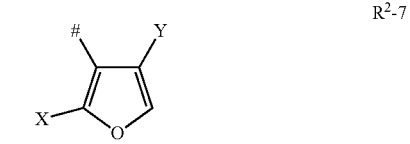

R²-7

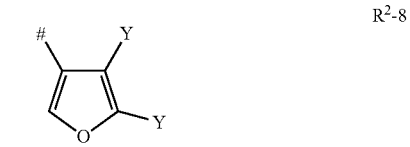

R²-8

-continued

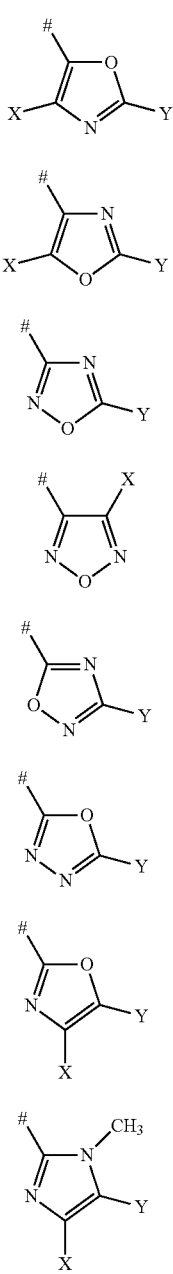

wherein # denotes attachment to the pyrimidine ring, X and Y denotes $R^c$ which independently of each other are identical or different;

preferred $R^2$ is $R^2$-1, $R^2$-2, $R^2$-3, $R^2$-4, $R^2$-5, $R^2$-6, $R^2$-7, or $R^2$-8;

also preferred $R^2$ is $R^2$-9, $R^2$-10, $R^2$-11, $R^2$-13, $R^2$-14, or $R^2$-15;

more preferred $R^2$ is $R^2$-9, $R^2$-10, or $R^2$-15;

most preferred $R^2$ is $R^2$-9;

preferred X is H, halogen, CN, $C_1$-$C_6$-alkyl, $C_1$-$C_6$-haloalkyl, OH, $C_1$-$C_6$-alkoxy, $C_1$-$C_6$-haloalkoxy, or $C_1$-$C_6$-alkylthio;

particularly preferred X is H, halogen, CN, $C_1$-$C_6$-alkyl, OH, $C_1$-$C_6$-alkoxy, or $C_1$-$C_6$-alkylthio;

also particularly preferred X is H, halogen, CN, $C_1$-$C_6$-alkyl, $C_1$-$C_6$-haloalkyl, $C_1$-$C_6$-alkoxy, or $C_1$-$C_6$-haloalkoxy;

especially preferred X is H, halogen, CN, $C_1$-$C_4$-alkyl, OH, $C_1$-$C_4$-alkoxy, or $C_1$-$C_4$-alkylthio;

more preferred X is H, $CH_3$, $C_2H_5$, n-propyl, iso-propyl, iso-butyl, n-butyl, OH, $OCH_3$, $SCH_3$, F, Cl, Br, or I;

most preferred X is H, $CH_3$, $C_2H_5$, OH, or $OCH_3$;

also most preferred X is H, $CH_3$, $C_2H_5$, or $SCH_3$;

also most preferred X is H, $CH_3$, $C_2H_5$, F, Cl, Br, or I.

Preferred Y is H, halogen, CN, $C_1$-$C_6$-alkyl, $C_1$-$C_6$-haloalkyl, OH, $C_1$-$C_6$-alkoxy, $C_1$-$C_6$-haloalkoxy, or $C_1$-$C_6$-alkylthio;

particularly preferred Y is H, halogen, CN, $C_1$-$C_6$-alkyl, OH, $C_1$-$C_6$-alkoxy, or $C_1$-$C_6$-alkylthio;

also particularly preferred Y is H, halogen, CN, $C_1$-$C_6$-alkyl, $C_1$-$C_6$-haloalkyl, $C_1$-$C_6$-alkoxy, or $C_1$-$C_6$-haloalkoxy;

especially preferred Y is H, halogen, CN, $C_1$-$C_4$-alkyl, $C_1$-$C_2$-fluoroalkyl, OH, $C_1$-$C_4$-alkoxy, or $C_1$-$C_4$-alkylthio;

more preferred Y is H, $CH_3$, $C_2H_5$, n-propyl, iso-propyl, iso-butyl, n-butyl, 2-butyl, t-butyl, OH, $OCH_3$, $SCH_3$, F, Cl, Br, or I;

most preferred Y is H, $CH_3$, $C_2H_5$, n-propyl, iso-propyl, iso-butyl, n-butyl, 2-butyl, OH, or $OCH_3$;

also most preferred Y is H, $CH_3$, $O_2H_5$, n-propyl, iso-propyl, OH, $OCH_3$, or $SCH_3$;

also most preferred Y is H, $CH_3$, $O_2H_5$, n-propyl, iso-propyl, F, Cl, Br, or I.

X and Y preferably are selected from H, halogen, $C_1$-$C_6$-alkyl, $C_1$-$C_6$-alkoxy, and $C_1$-$C_4$-alkylthio; more preferably from H, $CH_3$, $C_2H_5$, n-propyl, iso-propyl, t-butyl, $OCH_3$, $SCH_3$, and Cl;

Particularly preferred $R^2$ is 4-methyl-5-oxazolyl, 4-ethyl-5-oxazolyl, 2,4-dimethyl-5-oxazolyl, 2-ethyl-4-methyl-5-oxazolyl, 2-methyl-4-ethyl-5-oxazolyl, or 2,4-diethyl-5-oxazolyl.

Examples of particularly preferred $R^2$ are provided in Table $R^2$-9, Table $R^2$-10, and Table $R^2$-15.

Table $R^2$-9: examples of particularly preferred $R^2$ are $R^2$-9.1 to $R^2$-9.676 wherein $R^2$ is $R^2$-9 and combinations of variables X and Y are as defined in each row of table $R^2$, numbering of each compound e.g. $R^2$-9.1 means $R^2$ is $R^2$-9 wherein X and Y are as defined in row 1 of table $R^2$;

Table $R^2$-10: examples of particularly preferred $R^2$ are $R^2$-10.1 to $R^2$-10.676 wherein $R^2$ is $R^2$-10 and combinations of variables X and Y are as defined in each row of table $R^2$, numbering of each compound e.g. $R^2$-10.1 means $R^2$ is $R^2$-10 wherein X and Y are as defined in row 1 of table $R^2$;

Table $R^2$-15: examples of particularly preferred $R^2$ are $R^2$-15.1 to $R^2$-15.676 wherein $R^2$ is $R^2$-15 and combinations of variables X and Y are as defined in each row of table $R^2$, numbering of each compound e.g. $R^2$-15.1 means $R^2$ is $R^2$-15 wherein X and Y are as defined in row 1 of table $R^2$.

TABLE R2

| row | X | Y |
|---|---|---|
| 1 | H | H |
| 2 | H | $CH_3$ |
| 3 | H | $C_2H_5$ |
| 4 | H | n-propyl |
| 5 | H | $CH(CH_3)_2$ |
| 6 | H | iso-butyl |
| 7 | H | n-butyl |
| 8 | H | 2-butyl |
| 9 | H | $C(CH_3)_3$ |
| 10 | H | OH |
| 11 | H | $OCH_3$ |
| 12 | H | $SCH_3$ |
| 13 | H | $S(O)CH_3$ |
| 14 | H | $S(O)_2CH_3$ |

TABLE R2-continued

| row | X | Y |
|---|---|---|
| 15 | H | CN |
| 16 | H | F |
| 17 | H | Cl |
| 18 | H | Br |
| 19 | H | I |
| 20 | H | $CH_2CF_3$ |
| 21 | H | $CF_2CF_3$ |
| 22 | H | $CF_2CH_3$ |
| 23 | H | $CF_3$ |
| 24 | H | $CF_2H$ |
| 25 | H | $OCF_2H$ |
| 26 | H | $OCF_3$ |
| 27 | $CH_3$ | H |
| 28 | $CH_3$ | $CH_3$ |
| 29 | $CH_3$ | $C_2H_5$ |
| 30 | $CH_3$ | n-propyl |
| 31 | $CH_3$ | $CH(CH_3)_2$ |
| 32 | $CH_3$ | iso-butyl |
| 33 | $CH_3$ | n-butyl |
| 34 | $CH_3$ | 2-butyl |
| 35 | $CH_3$ | $C(CH_3)_3$ |
| 36 | $CH_3$ | OH |
| 37 | $CH_3$ | $OCH_3$ |
| 38 | $CH_3$ | $SCH_3$ |
| 39 | $CH_3$ | $S(O)CH_3$ |
| 40 | $CH_3$ | $S(O)_2CH_3$ |
| 41 | $CH_3$ | CN |
| 42 | $CH_3$ | F |
| 43 | $CH_3$ | Cl |
| 44 | $CH_3$ | Br |
| 45 | $CH_3$ | I |
| 46 | $CH_3$ | $CH_2CF_3$ |
| 47 | $CH_3$ | $CF_2CF_3$ |
| 48 | $CH_3$ | $CF_2CH_3$ |
| 49 | $CH_3$ | $CF_3$ |
| 50 | $CH_3$ | $CF_2H$ |
| 51 | $CH_3$ | $OCF_2H$ |
| 52 | $CH_3$ | $OCF_3$ |
| 53 | $C_2H_5$ | H |
| 54 | $C_2H_5$ | $CH_3$ |
| 55 | $C_2H_5$ | $C_2H_5$ |
| 56 | $C_2H_5$ | n-propyl |
| 57 | $C_2H_5$ | $CH(CH_3)_2$ |
| 58 | $C_2H_5$ | iso-butyl |
| 59 | $C_2H_5$ | n-butyl |
| 60 | $C_2H_5$ | 2-butyl |
| 61 | $C_2H_5$ | $C(CH_3)_3$ |
| 62 | $C_2H_5$ | OH |
| 63 | $C_2H_5$ | $OCH_3$ |
| 64 | $C_2H_5$ | $SCH_3$ |
| 65 | $C_2H_5$ | $S(O)CH_3$ |
| 66 | $C_2H_5$ | $S(O)_2CH_3$ |
| 67 | $C_2H_5$ | CN |
| 68 | $C_2H_5$ | F |
| 69 | $C_2H_5$ | Cl |
| 70 | $C_2H_5$ | Br |
| 71 | $C_2H_5$ | I |
| 72 | $C_2H_5$ | $CH_2CF_3$ |
| 73 | $C_2H_5$ | $CF_2CF_3$ |
| 74 | $C_2H_5$ | $CF_2CH_3$ |
| 75 | $C_2H_5$ | $CF_3$ |
| 76 | $C_2H_5$ | $CF_2H$ |
| 77 | $C_2H_5$ | $OCF_2H$ |
| 78 | $C_2H_5$ | $OCF_3$ |
| 79 | n-propyl | H |
| 80 | n-propyl | $CH_3$ |
| 81 | n-propyl | $C_2H_5$ |
| 82 | n-propyl | n-propyl |
| 83 | n-propyl | $CH(CH_3)_2$ |
| 84 | n-propyl | iso-butyl |
| 85 | n-propyl | n-butyl |
| 86 | n-propyl | 2-butyl |
| 87 | n-propyl | $C(CH_3)_3$ |
| 88 | n-propyl | OH |
| 89 | n-propyl | $OCH_3$ |
| 90 | n-propyl | $SCH_3$ |
| 91 | n-propyl | $S(O)CH_3$ |
| 92 | n-propyl | $S(O)_2CH_3$ |
| 93 | n-propyl | CN |
| 94 | n-propyl | F |
| 95 | n-propyl | Cl |
| 96 | n-propyl | Br |
| 97 | n-propyl | I |
| 98 | n-propyl | $CH_2CF_3$ |
| 99 | n-propyl | $CF_2CF_3$ |
| 100 | n-propyl | $CF_2CH_3$ |
| 101 | n-propyl | $CF_3$ |
| 102 | n-propyl | $CF_2H$ |
| 103 | n-propyl | $OCF_2H$ |
| 104 | n-propyl | $OCF_3$ |
| 105 | $CH(CH_3)_2$ | H |
| 106 | $CH(CH_3)_2$ | $CH_3$ |
| 107 | $CH(CH_3)_2$ | $C_2H_5$ |
| 108 | $CH(CH_3)_2$ | n-propyl |
| 109 | $CH(CH_3)_2$ | $CH(CH_3)_2$ |
| 110 | $CH(CH_3)_2$ | iso-butyl |
| 111 | $CH(CH_3)_2$ | n-butyl |
| 112 | $CH(CH_3)_2$ | 2-butyl |
| 113 | $CH(CH_3)_2$ | $C(CH_3)_3$ |
| 114 | $CH(CH_3)_2$ | OH |
| 115 | $CH(CH_3)_2$ | $OCH_3$ |
| 116 | $CH(CH_3)_2$ | $SCH_3$ |
| 117 | $CH(CH_3)_2$ | $S(O)CH_3$ |
| 118 | $CH(CH_3)_2$ | $S(O)_2CH_3$ |
| 119 | $CH(CH_3)_2$ | CN |
| 120 | $CH(CH_3)_2$ | F |
| 121 | $CH(CH_3)_2$ | Cl |
| 122 | $CH(CH_3)_2$ | Br |
| 123 | $CH(CH_3)_2$ | I |
| 124 | $CH(CH_3)_2$ | $CH_2CF_3$ |
| 125 | $CH(CH_3)_2$ | $CF_2CF_3$ |
| 126 | $CH(CH_3)_2$ | $CF_2CH_3$ |
| 127 | $CH(CH_3)_2$ | $CF_3$ |
| 128 | $CH(CH_3)_2$ | $CF_2H$ |
| 129 | $CH(CH_3)_2$ | $OCF_2H$ |
| 130 | $CH(CH_3)_2$ | $OCF_3$ |
| 131 | iso-butyl | H |
| 132 | iso-butyl | $CH_3$ |
| 133 | iso-butyl | $C_2H_5$ |
| 134 | iso-butyl | n-propyl |
| 135 | iso-butyl | $CH(CH_3)_2$ |
| 136 | iso-butyl | iso-butyl |
| 137 | iso-butyl | n-butyl |
| 138 | iso-butyl | 2-butyl |
| 139 | iso-butyl | $C(CH_3)_3$ |
| 140 | iso-butyl | OH |
| 141 | iso-butyl | $OCH_3$ |
| 142 | iso-butyl | $SCH_3$ |
| 143 | iso-butyl | $S(O)CH_3$ |
| 144 | iso-butyl | $S(O)_2CH_3$ |
| 145 | iso-butyl | CN |
| 146 | iso-butyl | F |
| 147 | iso-butyl | Cl |
| 148 | iso-butyl | Br |
| 149 | iso-butyl | I |
| 150 | iso-butyl | $CH_2CF_3$ |
| 151 | iso-butyl | $CF_2CF_3$ |
| 152 | iso-butyl | $CF_2CH_3$ |
| 153 | iso-butyl | $CF_3$ |
| 154 | iso-butyl | $CF_2H$ |
| 155 | iso-butyl | $OCF_2H$ |
| 156 | iso-butyl | $OCF_3$ |
| 157 | n-butyl | H |
| 158 | n-butyl | $CH_3$ |
| 159 | n-butyl | $C_2H_5$ |
| 160 | n-butyl | n-propyl |
| 161 | n-butyl | $CH(CH_3)_2$ |
| 162 | n-butyl | iso-butyl |
| 163 | n-butyl | n-butyl |
| 164 | n-butyl | 2-butyl |
| 165 | n-butyl | $C(CH_3)_3$ |
| 166 | n-butyl | OH |
| 167 | n-butyl | $OCH_3$ |
| 168 | n-butyl | $SCH_3$ |
| 169 | n-butyl | $S(O)CH_3$ |
| 170 | n-butyl | $S(O)_2CH_3$ |

TABLE R2-continued

| row | X | Y |
|---|---|---|
| 171 | n-butyl | CN |
| 172 | n-butyl | F |
| 173 | n-butyl | Cl |
| 174 | n-butyl | Br |
| 175 | n-butyl | I |
| 176 | n-butyl | $CH_2CF_3$ |
| 177 | n-butyl | $CF_2CF_3$ |
| 178 | n-butyl | $CF_2CH_3$ |
| 179 | n-butyl | $CF_3$ |
| 180 | n-butyl | $CF_2H$ |
| 181 | n-butyl | $OCF_2H$ |
| 182 | n-butyl | $OCF_3$ |
| 183 | 2-butyl | H |
| 184 | 2-butyl | $CH_3$ |
| 185 | 2-butyl | $C_2H_5$ |
| 186 | 2-butyl | n-propyl |
| 187 | 2-butyl | $CH(CH_3)_2$ |
| 188 | 2-butyl | iso-butyl |
| 189 | 2-butyl | n-butyl |
| 190 | 2-butyl | 2-butyl |
| 191 | 2-butyl | $C(CH_3)_3$ |
| 192 | 2-butyl | OH |
| 193 | 2-butyl | $OCH_3$ |
| 194 | 2-butyl | $SCH_3$ |
| 195 | 2-butyl | $S(O)CH_3$ |
| 196 | 2-butyl | $S(O)_2CH_3$ |
| 197 | 2-butyl | CN |
| 198 | 2-butyl | F |
| 199 | 2-butyl | Cl |
| 200 | 2-butyl | Br |
| 201 | 2-butyl | I |
| 202 | 2-butyl | $CH_2CF_3$ |
| 203 | 2-butyl | $CF_2CF_3$ |
| 204 | 2-butyl | $CF_2CH_3$ |
| 205 | 2-butyl | $CF_3$ |
| 206 | 2-butyl | $CF_2H$ |
| 207 | 2-butyl | $OCF_2H$ |
| 208 | 2-butyl | $OCF_3$ |
| 209 | $C(CH_3)_3$ | H |
| 210 | $C(CH_3)_3$ | $CH_3$ |
| 211 | $C(CH_3)_3$ | $C_2H_5$ |
| 212 | $C(CH_3)_3$ | n-propyl |
| 213 | $C(CH_3)_3$ | $CH(CH_3)_2$ |
| 214 | $C(CH_3)_3$ | iso-butyl |
| 215 | $C(CH_3)_3$ | n-butyl |
| 216 | $C(CH_3)_3$ | 2-butyl |
| 217 | $C(CH_3)_3$ | $C(CH_3)_3$ |
| 218 | $C(CH_3)_3$ | OH |
| 219 | $C(CH_3)_3$ | $OCH_3$ |
| 220 | $C(CH_3)_3$ | $SCH_3$ |
| 221 | $C(CH_3)_3$ | $S(O)CH_3$ |
| 222 | $C(CH_3)_3$ | $S(O)_2CH_3$ |
| 223 | $C(CH_3)_3$ | CN |
| 224 | $C(CH_3)_3$ | F |
| 225 | $C(CH_3)_3$ | Cl |
| 226 | $C(CH_3)_3$ | Br |
| 227 | $C(CH_3)_3$ | I |
| 228 | $C(CH_3)_3$ | $CH_2CF_3$ |
| 229 | $C(CH_3)_3$ | $CF_2CF_3$ |
| 230 | $C(CH_3)_3$ | $CF_2CH_3$ |
| 231 | $C(CH_3)_3$ | $CF_3$ |
| 232 | $C(CH_3)_3$ | $CF_2H$ |
| 233 | $C(CH_3)_3$ | $OCF_2H$ |
| 234 | $C(CH_3)_3$ | $OCF_3$ |
| 235 | OH | H |
| 236 | OH | $CH_3$ |
| 237 | OH | $C_2H_5$ |
| 238 | OH | n-propyl |
| 239 | OH | $CH(CH_3)_2$ |
| 240 | OH | iso-butyl |
| 241 | OH | n-butyl |
| 242 | OH | 2-butyl |
| 243 | OH | $C(CH_3)_3$ |
| 244 | OH | OH |
| 245 | OH | $OCH_3$ |
| 246 | OH | $SCH_3$ |
| 247 | OH | $S(O)CH_3$ |
| 248 | OH | $S(O)_2CH_3$ |
| 249 | OH | CN |
| 250 | OH | F |
| 251 | OH | Cl |
| 252 | OH | Br |
| 253 | OH | I |
| 254 | OH | $CH_2CF_3$ |
| 255 | OH | $CF_2CF_3$ |
| 256 | OH | $CF_2CH_3$ |
| 257 | OH | $CF_3$ |
| 258 | OH | $CF_2H$ |
| 259 | OH | $OCF_2H$ |
| 260 | OH | $OCF_3$ |
| 261 | $OCH_3$ | H |
| 262 | $OCH_3$ | $CH_3$ |
| 263 | $OCH_3$ | $C_2H_5$ |
| 264 | $OCH_3$ | n-propyl |
| 265 | $OCH_3$ | $CH(CH_3)_2$ |
| 266 | $OCH_3$ | iso-butyl |
| 267 | $OCH_3$ | n-butyl |
| 268 | $OCH_3$ | 2-butyl |
| 269 | $OCH_3$ | $C(CH_3)_3$ |
| 270 | $OCH_3$ | OH |
| 271 | $OCH_3$ | $OCH_3$ |
| 272 | $OCH_3$ | $SCH_3$ |
| 273 | $OCH_3$ | $S(O)CH_3$ |
| 274 | $OCH_3$ | $S(O)_2CH_3$ |
| 275 | $OCH_3$ | CN |
| 276 | $OCH_3$ | F |
| 277 | $OCH_3$ | Cl |
| 278 | $OCH_3$ | Br |
| 279 | $OCH_3$ | I |
| 280 | $OCH_3$ | $CH_2CF_3$ |
| 281 | $OCH_3$ | $CF_2CF_3$ |
| 282 | $OCH_3$ | $CF_2CH_3$ |
| 283 | $OCH_3$ | $CF_3$ |
| 284 | $OCH_3$ | $CF_2H$ |
| 285 | $OCH_3$ | $OCF_2H$ |
| 286 | $OCH_3$ | $OCF_3$ |
| 287 | $SCH_3$ | H |
| 288 | $SCH_3$ | $CH_3$ |
| 289 | $SCH_3$ | $C_2H_5$ |
| 290 | $SCH_3$ | n-propyl |
| 291 | $SCH_3$ | $CH(CH_3)_2$ |
| 292 | $SCH_3$ | iso-butyl |
| 293 | $SCH_3$ | n-butyl |
| 294 | $SCH_3$ | 2-butyl |
| 295 | $SCH_3$ | $C(CH_3)_3$ |
| 296 | $SCH_3$ | OH |
| 297 | $SCH_3$ | $OCH_3$ |
| 298 | $SCH_3$ | $SCH_3$ |
| 299 | $SCH_3$ | $S(O)CH_3$ |
| 300 | $SCH_3$ | $S(O)_2CH_3$ |
| 301 | $SCH_3$ | CN |
| 302 | $SCH_3$ | F |
| 303 | $SCH_3$ | Cl |
| 304 | $SCH_3$ | Br |
| 305 | $SCH_3$ | I |
| 306 | $SCH_3$ | $CH_2CF_3$ |
| 307 | $SCH_3$ | $CF_2CF_3$ |
| 308 | $SCH_3$ | $CF_2CH_3$ |
| 309 | $SCH_3$ | $CF_3$ |
| 310 | $SCH_3$ | $CF_2H$ |
| 311 | $SCH_3$ | $OCF_2H$ |
| 312 | $SCH_3$ | $OCF_3$ |
| 313 | $S(O)CH_3$ | H |
| 314 | $S(O)CH_3$ | $CH_3$ |
| 315 | $S(O)CH_3$ | $C_2H_5$ |
| 316 | $S(O)CH_3$ | n-propyl |
| 317 | $S(O)CH_3$ | $CH(CH_3)_2$ |
| 318 | $S(O)CH_3$ | iso-butyl |
| 319 | $S(O)CH_3$ | n-butyl |
| 320 | $S(O)CH_3$ | 2-butyl |
| 321 | $S(O)CH_3$ | $C(CH_3)_3$ |
| 322 | $S(O)CH_3$ | OH |
| 323 | $S(O)CH_3$ | $OCH_3$ |
| 324 | $S(O)CH_3$ | $SCH_3$ |
| 325 | $S(O)CH_3$ | $S(O)CH_3$ |
| 326 | $S(O)CH_3$ | $S(O)_2CH_3$ |

TABLE R2-continued

| row | X | Y |
|---|---|---|
| 327 | S(O)CH$_3$ | CN |
| 328 | S(O)CH$_3$ | F |
| 329 | S(O)CH$_3$ | Cl |
| 330 | S(O)CH$_3$ | Br |
| 331 | S(O)CH$_3$ | I |
| 332 | S(O)CH$_3$ | CH$_2$CF$_3$ |
| 333 | S(O)CH$_3$ | CF$_2$CF$_3$ |
| 334 | S(O)CH$_3$ | CF$_2$CH$_3$ |
| 335 | S(O)CH$_3$ | CF$_3$ |
| 336 | S(O)CH$_3$ | CF$_2$H |
| 337 | S(O)CH$_3$ | OCF$_2$H |
| 338 | S(O)CH$_3$ | OCF$_3$ |
| 339 | S(O)$_2$CH$_3$ | H |
| 340 | S(O)$_2$CH$_3$ | CH$_3$ |
| 341 | S(O)$_2$CH$_3$ | C$_2$H$_5$ |
| 342 | S(O)$_2$CH$_3$ | n-propyl |
| 343 | S(O)$_2$CH$_3$ | CH(CH$_3$)$_2$ |
| 344 | S(O)$_2$CH$_3$ | iso-butyl |
| 345 | S(O)$_2$CH$_3$ | n-butyl |
| 346 | S(O)$_2$CH$_3$ | 2-butyl |
| 347 | S(O)$_2$CH$_3$ | C(CH$_3$)$_3$ |
| 348 | S(O)$_2$CH$_3$ | OH |
| 349 | S(O)$_2$CH$_3$ | OCH$_3$ |
| 350 | S(O)$_2$CH$_3$ | SCH$_3$ |
| 351 | S(O)$_2$CH$_3$ | S(O)CH$_3$ |
| 352 | S(O)$_2$CH$_3$ | S(O)$_2$CH$_3$ |
| 353 | S(O)$_2$CH$_3$ | CN |
| 354 | S(O)$_2$CH$_3$ | F |
| 355 | S(O)$_2$CH$_3$ | Cl |
| 356 | S(O)$_2$CH$_3$ | Br |
| 357 | S(O)$_2$CH$_3$ | I |
| 358 | S(O)$_2$CH$_3$ | CH$_2$CF$_3$ |
| 359 | S(O)$_2$CH$_3$ | CF$_2$CF$_3$ |
| 360 | S(O)$_2$CH$_3$ | CF$_2$CH$_3$ |
| 361 | S(O)$_2$CH$_3$ | CF$_3$ |
| 362 | S(O)$_2$CH$_3$ | CF$_2$H |
| 363 | S(O)$_2$CH$_3$ | OCF$_2$H |
| 364 | S(O)$_2$CH$_3$ | OCF$_3$ |
| 365 | CN | H |
| 366 | CN | CH$_3$ |
| 367 | CN | C$_2$H$_5$ |
| 368 | CN | n-propyl |
| 369 | CN | CH(CH$_3$)$_2$ |
| 370 | CN | iso-butyl |
| 371 | CN | n-butyl |
| 372 | CN | 2-butyl |
| 373 | CN | C(CH$_3$)$_3$ |
| 374 | CN | OH |
| 375 | CN | OCH$_3$ |
| 376 | CN | SCH$_3$ |
| 377 | CN | S(O)CH$_3$ |
| 378 | CN | S(O)$_2$CH$_3$ |
| 379 | CN | CN |
| 380 | CN | F |
| 381 | CN | Cl |
| 382 | CN | Br |
| 383 | CN | I |
| 384 | CN | CH$_2$CF$_3$ |
| 385 | CN | CF$_2$CF$_3$ |
| 386 | CN | CF$_2$CH$_3$ |
| 387 | CN | CF$_3$ |
| 388 | CN | CF$_2$H |
| 389 | CN | OCF$_2$H |
| 390 | CN | OCF$_3$ |
| 391 | F | H |
| 392 | F | CH$_3$ |
| 393 | F | C$_2$H$_5$ |
| 394 | F | n-propyl |
| 395 | F | CH(CH$_3$)$_2$ |
| 396 | F | iso-butyl |
| 397 | F | n-butyl |
| 398 | F | 2-butyl |
| 399 | F | C(CH$_3$)$_3$ |
| 400 | F | OH |
| 401 | F | OCH$_3$ |
| 402 | F | SCH$_3$ |
| 403 | F | S(O)CH$_3$ |
| 404 | F | S(O)$_2$CH$_3$ |
| 405 | F | CN |
| 406 | F | F |
| 407 | F | Cl |
| 408 | F | Br |
| 409 | F | I |
| 410 | F | CH$_2$CF$_3$ |
| 411 | F | CF$_2$CF$_3$ |
| 412 | F | CF$_2$CH$_3$ |
| 413 | F | CF$_3$ |
| 414 | F | CF$_2$H |
| 415 | F | OCF$_2$H |
| 416 | F | OCF$_3$ |
| 417 | Cl | H |
| 418 | Cl | CH$_3$ |
| 419 | Cl | C$_2$H$_5$ |
| 420 | Cl | n-propyl |
| 421 | Cl | CH(CH$_3$)$_2$ |
| 422 | Cl | iso-butyl |
| 423 | Cl | n-butyl |
| 424 | Cl | 2-butyl |
| 425 | Cl | C(CH$_3$)$_3$ |
| 426 | Cl | OH |
| 427 | Cl | OCH$_3$ |
| 428 | Cl | SCH$_3$ |
| 429 | Cl | S(O)CH$_3$ |
| 430 | Cl | S(O)$_2$CH$_3$ |
| 431 | Cl | CN |
| 432 | Cl | F |
| 433 | Cl | Cl |
| 434 | Cl | Br |
| 435 | Cl | I |
| 436 | Cl | CH$_2$CF$_3$ |
| 437 | Cl | CF$_2$CF$_3$ |
| 438 | Cl | CF$_2$CH$_3$ |
| 439 | Cl | CF$_3$ |
| 440 | Cl | CF$_2$H |
| 441 | Cl | OCF$_2$H |
| 442 | Cl | OCF$_3$ |
| 443 | Br | H |
| 444 | Br | CH$_3$ |
| 445 | Br | C$_2$H$_5$ |
| 446 | Br | n-propyl |
| 447 | Br | CH(CH$_3$)$_2$ |
| 448 | Br | iso-butyl |
| 449 | Br | n-butyl |
| 450 | Br | 2-butyl |
| 451 | Br | C(CH$_3$)$_3$ |
| 452 | Br | OH |
| 453 | Br | OCH$_3$ |
| 454 | Br | SCH$_3$ |
| 455 | Br | S(O)CH$_3$ |
| 456 | Br | S(O)$_2$CH$_3$ |
| 457 | Br | CN |
| 458 | Br | F |
| 459 | Br | Cl |
| 460 | Br | Br |
| 461 | Br | I |
| 462 | Br | CH$_2$CF$_3$ |
| 463 | Br | CF$_2$CF$_3$ |
| 464 | Br | CF$_2$CH$_3$ |
| 465 | Br | CF$_3$ |
| 466 | Br | CF$_2$H |
| 467 | Br | OCF$_2$H |
| 468 | Br | OCF$_3$ |
| 469 | I | H |
| 470 | I | CH$_3$ |
| 471 | I | C$_2$H$_5$ |
| 472 | I | n-propyl |
| 473 | I | CH(CH$_3$)$_2$ |
| 474 | I | iso-butyl |
| 475 | I | n-butyl |
| 476 | I | 2-butyl |
| 477 | I | C(CH$_3$)$_3$ |
| 478 | I | OH |
| 479 | I | OCH$_3$ |
| 480 | I | SCH$_3$ |
| 481 | I | S(O)CH$_3$ |
| 482 | I | S(O)$_2$CH$_3$ |

TABLE R2-continued

| row | X | Y |
|---|---|---|
| 483 | I | CN |
| 484 | I | F |
| 485 | I | Cl |
| 486 | I | Br |
| 487 | I | I |
| 488 | I | $CH_2CF_3$ |
| 489 | I | $CF_2CF_3$ |
| 490 | I | $CF_2CH_3$ |
| 491 | I | $CF_3$ |
| 492 | I | $CF_2H$ |
| 493 | I | $OCF_2H$ |
| 494 | I | $OCF_3$ |
| 495 | $CH_2CF_3$ | H |
| 496 | $CH_2CF_3$ | $CH_3$ |
| 497 | $CH_2CF_3$ | $C_2H_5$ |
| 498 | $CH_2CF_3$ | n-propyl |
| 499 | $CH_2CF_3$ | $CH(CH_3)_2$ |
| 500 | $CH_2CF_3$ | iso-butyl |
| 501 | $CH_2CF_3$ | n-butyl |
| 502 | $CH_2CF_3$ | 2-butyl |
| 503 | $CH_2CF_3$ | $C(CH_3)_3$ |
| 504 | $CH_2CF_3$ | OH |
| 505 | $CH_2CF_3$ | $OCH_3$ |
| 506 | $CH_2CF_3$ | $SCH_3$ |
| 507 | $CH_2CF_3$ | $S(O)CH_3$ |
| 508 | $CH_2CF_3$ | $S(O)_2CH_3$ |
| 509 | $CH_2CF_3$ | CN |
| 510 | $CH_2CF_3$ | F |
| 511 | $CH_2CF_3$ | Cl |
| 512 | $CH_2CF_3$ | Br |
| 513 | $CH_2CF_3$ | I |
| 514 | $CH_2CF_3$ | $CH_2CF_3$ |
| 515 | $CH_2CF_3$ | $CF_2CF_3$ |
| 516 | $CH_2CF_3$ | $CF_2CH_3$ |
| 517 | $CH_2CF_3$ | $CF_3$ |
| 518 | $CH_2CF_3$ | $CF_2H$ |
| 519 | $CH_2CF_3$ | $OCF_2H$ |
| 520 | $CH_2CF_3$ | $OCF_3$ |
| 521 | $CF_2CF_3$ | H |
| 522 | $CF_2CF_3$ | $CH_3$ |
| 523 | $CF_2CF_3$ | $C_2H_5$ |
| 524 | $CF_2CF_3$ | n-propyl |
| 525 | $CF_2CF_3$ | $CH(CH_3)_2$ |
| 526 | $CF_2CF_3$ | iso-butyl |
| 527 | $CF_2CF_3$ | n-butyl |
| 528 | $CF_2CF_3$ | 2-butyl |
| 529 | $CF_2CF_3$ | $C(CH_3)_3$ |
| 530 | $CF_2CF_3$ | OH |
| 531 | $CF_2CF_3$ | $OCH_3$ |
| 532 | $CF_2CF_3$ | $SCH_3$ |
| 533 | $CF_2CF_3$ | $S(O)CH_3$ |
| 534 | $CF_2CF_3$ | $S(O)_2CH_3$ |
| 535 | $CF_2CF_3$ | CN |
| 536 | $CF_2CF_3$ | F |
| 537 | $CF_2CF_3$ | Cl |
| 538 | $CF_2CF_3$ | Br |
| 539 | $CF_2CF_3$ | I |
| 540 | $CF_2CF_3$ | $CH_2CF_3$ |
| 541 | $CF_2CF_3$ | $CF_2CF_3$ |
| 542 | $CF_2CF_3$ | $CF_2CH_3$ |
| 543 | $CF_2CF_3$ | $CF_3$ |
| 544 | $CF_2CF_3$ | $CF_2H$ |
| 545 | $CF_2CF_3$ | $OCF_2H$ |
| 546 | $CF_2CF_3$ | $OCF_3$ |
| 547 | $CF_2CH_3$ | H |
| 548 | $CF_2CH_3$ | $CH_3$ |
| 549 | $CF_2CH_3$ | $C_2H_5$ |
| 550 | $CF_2CH_3$ | n-propyl |
| 551 | $CF_2CH_3$ | $CH(CH_3)_2$ |
| 552 | $CF_2CH_3$ | iso-butyl |
| 553 | $CF_2CH_3$ | n-butyl |
| 554 | $CF_2CH_3$ | 2-butyl |
| 555 | $CF_2CH_3$ | $C(CH_3)_3$ |
| 556 | $CF_2CH_3$ | OH |
| 557 | $CF_2CH_3$ | $OCH_3$ |
| 558 | $CF_2CH_3$ | $SCH_3$ |
| 559 | $CF_2CH_3$ | $S(O)CH_3$ |
| 560 | $CF_2CH_3$ | $S(O)_2CH_3$ |
| 561 | $CF_2CH_3$ | CN |
| 562 | $CF_2CH_3$ | F |
| 563 | $CF_2CH_3$ | Cl |
| 564 | $CF_2CH_3$ | Br |
| 565 | $CF_2CH_3$ | I |
| 566 | $CF_2CH_3$ | $CH_2CF_3$ |
| 567 | $CF_2CH_3$ | $CF_2CF_3$ |
| 568 | $CF_2CH_3$ | $CF_2CH_3$ |
| 569 | $CF_2CH_3$ | $CF_3$ |
| 570 | $CF_2CH_3$ | $CF_2H$ |
| 571 | $CF_2CH_3$ | $OCF_2H$ |
| 572 | $CF_2CH_3$ | $OCF_3$ |
| 573 | $CF_3$ | H |
| 574 | $CF_3$ | $CH_3$ |
| 575 | $CF_3$ | $C_2H_5$ |
| 576 | $CF_3$ | n-propyl |
| 577 | $CF_3$ | $CH(CH_3)_2$ |
| 578 | $CF_3$ | iso-butyl |
| 579 | $CF_3$ | n-butyl |
| 580 | $CF_3$ | 2-butyl |
| 581 | $CF_3$ | $C(CH_3)_3$ |
| 582 | $CF_3$ | OH |
| 583 | $CF_3$ | $OCH_3$ |
| 584 | $CF_3$ | $SCH_3$ |
| 585 | $CF_3$ | $S(O)CH_3$ |
| 586 | $CF_3$ | $S(O)_2CH_3$ |
| 587 | $CF_3$ | CN |
| 588 | $CF_3$ | F |
| 589 | $CF_3$ | Cl |
| 590 | $CF_3$ | Br |
| 591 | $CF_3$ | I |
| 592 | $CF_3$ | $CH_2CF_3$ |
| 593 | $CF_3$ | $CF_2CF_3$ |
| 594 | $CF_3$ | $CF_2CH_3$ |
| 595 | $CF_3$ | $CF_3$ |
| 596 | $CF_3$ | $CF_2H$ |
| 597 | $CF_3$ | $OCF_2H$ |
| 598 | $CF_3$ | $OCF_3$ |
| 599 | $CF_2H$ | H |
| 600 | $CF_2H$ | $CH_3$ |
| 601 | $CF_2H$ | $C_2H_5$ |
| 602 | $CF_2H$ | n-propyl |
| 603 | $CF_2H$ | $CH(CH_3)_2$ |
| 604 | $CF_2H$ | iso-butyl |
| 605 | $CF_2H$ | n-butyl |
| 606 | $CF_2H$ | 2-butyl |
| 607 | $CF_2H$ | $C(CH_3)_3$ |
| 608 | $CF_2H$ | OH |
| 609 | $CF_2H$ | $OCH_3$ |
| 610 | $CF_2H$ | $SCH_3$ |
| 611 | $CF_2H$ | $S(O)CH_3$ |
| 612 | $CF_2H$ | $S(O)_2CH_3$ |
| 613 | $CF_2H$ | CN |
| 614 | $CF_2H$ | F |
| 615 | $CF_2H$ | Cl |
| 616 | $CF_2H$ | Br |
| 617 | $CF_2H$ | I |
| 618 | $CF_2H$ | $CH_2CF_3$ |
| 619 | $CF_2H$ | $CF_2CF_3$ |
| 620 | $CF_2H$ | $CF_2CH_3$ |
| 621 | $CF_2H$ | $CF_3$ |
| 622 | $CF_2H$ | $CF_2H$ |
| 623 | $CF_2H$ | $OCF_2H$ |
| 624 | $CF_2H$ | $OCF_3$ |
| 625 | $OCF_2H$ | H |
| 626 | $OCF_2H$ | $CH_3$ |
| 627 | $OCF_2H$ | $C_2H_5$ |
| 628 | $OCF_2H$ | n-propyl |
| 629 | $OCF_2H$ | $CH(CH_3)_2$ |
| 630 | $OCF_2H$ | iso-butyl |
| 631 | $OCF_2H$ | n-butyl |
| 632 | $OCF_2H$ | 2-butyl |
| 633 | $OCF_2H$ | $C(CH_3)_3$ |
| 634 | $OCF_2H$ | OH |
| 635 | $OCF_2H$ | $OCH_3$ |
| 636 | $OCF_2H$ | $SCH_3$ |
| 637 | $OCF_2H$ | $S(O)CH_3$ |
| 638 | $OCF_2H$ | $S(O)_2CH_3$ |

TABLE R2-continued

| row | X | Y |
|---|---|---|
| 639 | OCF$_2$H | CN |
| 640 | OCF$_2$H | F |
| 641 | OCF$_2$H | Cl |
| 642 | OCF$_2$H | Br |
| 643 | OCF$_2$H | I |
| 644 | OCF$_2$H | CH$_2$CF$_3$ |
| 645 | OCF$_2$H | CF$_2$CF$_3$ |
| 646 | OCF$_2$H | CF$_2$CH$_3$ |
| 647 | OCF$_2$H | CF$_3$ |
| 648 | OCF$_2$H | CF$_2$H |
| 649 | OCF$_2$H | OCF$_2$H |
| 650 | OCF$_2$H | OCF$_3$ |
| 651 | OCF$_3$ | H |
| 652 | OCF$_3$ | CH$_3$ |
| 653 | OCF$_3$ | C$_2$H$_5$ |
| 654 | OCF$_3$ | n-propyl |
| 655 | OCF$_3$ | CH(CH$_3$)$_2$ |
| 656 | OCF$_3$ | iso-butyl |
| 657 | OCF$_3$ | n-butyl |
| 658 | OCF$_3$ | 2-butyl |
| 659 | OCF$_3$ | C(CH$_3$)$_3$ |
| 660 | OCF$_3$ | OH |
| 661 | OCF$_3$ | OCH$_3$ |
| 662 | OCF$_3$ | SCH$_3$ |
| 663 | OCF$_3$ | S(O)CH$_3$ |
| 664 | OCF$_3$ | S(O)$_2$CH$_3$ |
| 665 | OCF$_3$ | CN |
| 666 | OCF$_3$ | F |
| 667 | OCF$_3$ | Cl |
| 668 | OCF$_3$ | Br |
| 669 | OCF$_3$ | I |
| 670 | OCF$_3$ | CH$_2$CF$_3$ |
| 671 | OCF$_3$ | CF$_2$CF$_3$ |
| 672 | OCF$_3$ | CF$_2$CH$_3$ |
| 673 | OCF$_3$ | CF$_3$ |
| 674 | OCF$_3$ | CF$_2$H |
| 675 | OCF$_3$ | OCF$_2$H |
| 676 | OCF$_3$ | OCF$_3$ |

Preferred $R^3$ is halogen, CN, NO$_2$, C$_1$-C$_6$-alkyl, C$_1$-C$_6$-haloalkyl, C$_1$-C$_6$-alkoxy, or C$_3$-C$_6$-cycloalkyl;
also preferred $R^3$ is halogen, CN, C$_1$-C$_6$-alkyl, C$_1$-C$_6$-haloalkyl, or C$_1$-C$_6$-alkoxy;
particularly preferred halogen, CN, C$_1$-C$_6$-alkyl, or C$_1$-C$_6$-alkoxy;
especially preferred $R^3$ is halogen or CH$_3$;
also especially preferred $R^3$ is halogen;
more preferred $R^3$ is Cl, Br, or I;
most preferred $R^3$ is Br or I.
also most preferred $R^3$ is Br or Cl.

Also preferred are compounds of formula (I), and their use as herbicide, wherein $R^4$, $R^5$, $R^6$ and $R^7$ independently of one another are H, halogen, CN, NO$_2$, C$_1$-C$_6$-alkyl, C$_1$-C$_6$-haloalkyl, C$_1$-C$_6$-alkylcarbonyl, C$_2$-C$_6$-alkenyl, C$_1$-C$_6$-alkoxy, C$_1$-C$_6$-haloalkoxy, C$_1$-C$_6$-alkoxy-C$_1$-C$_6$-alkoxy, hydroxycarbonyl, C$_1$-C$_6$-alkoxycarbonyl, C$_1$-C$_6$-alkylthio, C$_1$-C$_6$-haloalkylthio, NH$_2$, (C$_1$-C$_6$-alkyl)amino, di(C$_1$-C$_6$-alkyl)amino, (C$_1$-C$_6$-alkyl)sulfinyl, (C$_1$-C$_6$-alkyl)sulfonyl, C$_3$-C$_6$-cycloalkyl, (C$_3$-C$_6$-cycloalkyl)oxy, or phenyl;
wherein the cyclic groups are unsubstituted or substituted by $R^a$.

Preferred $R^4$ is H, halogen, CN, C$_1$-C$_6$-alkyl, C$_1$-C$_6$-haloalkyl, or C$_1$-C$_6$-alkoxy;
particularly preferred $R^4$ is H, halogen, or C$_1$-C$_6$-alkyl,
especially preferred $R^4$ is H or halogen;
more preferred $R^4$ is H or F;
most preferred $R^4$ is H;
also most preferred $R^4$ is F.

Preferred $R^5$ is H, halogen, CN, C$_1$-C$_6$-alkyl, C$_1$-C$_6$-haloalkyl, or C$_1$-C$_6$-alkoxy;
particularly preferred $R^5$ is H, halogen, C$_1$-C$_6$-alkyl C$_1$-C$_6$-haloalkyl, or C$_1$-C$_6$-alkoxy;
especially preferred $R^5$ is H, halogen, C$_1$-C$_6$-alkyl, or C$_1$-C$_6$-haloalkyl;
more preferred $R^5$ is H, F, Cl, CH$_3$, or CF$_3$;
also more preferred $R^5$ is H or halogen;
most preferred $R^5$ is H or F;
also most preferred $R^5$ is H;
also most preferred $R^5$ is F.

Preferred $R^6$ is H, halogen, C$_1$-C$_6$-alkyl, or C$_1$-C$_6$-haloalkyl;
particularly preferred $R^6$ is H, halogen, or C$_1$-C$_6$-haloalkyl;
especially preferred $R^6$ is H, halogen, or CF$_3$;
more preferred $R^6$ is H or CF$_3$;
also more preferred $R^6$ is halogen or CF$_3$;
also more preferred $R^6$ is H or halogen;
most preferred $R^6$ is H, F or CF$_3$;
also most preferred $R^6$ is H or CF$_3$;
also most preferred $R^6$ is F or CF$_3$;
also most preferred $R^6$ is H or F;
also most preferred $R^6$ is H;
also most preferred $R^6$ is F;
also most preferred $R^6$ is CF$_3$.

Preferred $R^7$ is H, halogen, CN, C$_1$-C$_6$-alkyl, or C$_1$-C$_6$-alkoxy;
particularly preferred $R^7$ is H, halogen, C$_1$-C$_6$-alkyl, or C$_1$-C$_6$-alkoxy;
especially preferred $R^7$ is H, halogen, or C$_1$-C$_6$-haloalkyl;
more preferred $R^7$ is H, F, Cl, or CF$_3$
most preferred $R^7$ is H, F, or Cl;
also most preferred $R^7$ is CF$_3$;
also most preferred $R^7$ is H.

Also preferred are compounds of formula (I), and their use as herbicide, wherein
$R^1$ is C$_1$-C$_6$-alkyl, C$_1$-C$_6$-alkoxy, C$_1$-C$_6$-alkylthio, or C$_3$-C$_6$-cycloalkyl wherein cycloalkyl is unsubstituted;
$R^2$ C$_1$-C$_6$-alkyl, C$_1$-C$_6$-hydroxyalkyl, C$_1$-C$_6$-alkoxy-C$_1$-C$_6$-alkyl, C$_1$-C$_6$-alkoxycarbonyl-C$_1$-C$_6$-alkyl, C$_1$-C$_6$-alkoxycarbonyl-C$_2$-C$_6$-alkenyl, C$_1$-C$_6$-alkoxy-C$_2$-C$_6$-alkenyl, C$_1$-C$_6$-dicyanoalkyl, C$_2$-C$_6$-alkynyl, C$_1$-C$_6$-alkoxy-C$_2$-C$_6$-alkynyl, C$_1$-C$_6$-haloalkyl, C$_2$-C$_6$-alkenyl, hydroxycarbonyl-C$_1$-C$_6$-hydroxyalkyl, hydroxycarbonyl-C$_2$-C$_6$-alkenyl, hydroxycarbonyl-C$_1$-C$_6$-alkyl, C$_1$-C$_6$-alkylcarbonyl-C$_1$-C$_6$-alkyl, C$_2$-C$_6$-dihydroxyalkyl, C$_1$-C$_6$-alkoxycarbonyl-C$_1$-C$_6$-haloalkyl, C$_2$-C$_6$-hydroxyhaloalkyl, C$_3$-C$_6$-hydroxyalkenyl, hydroxycarbonyl-C$_2$-C$_6$-dihydroxyalkyl, C$_1$-C$_6$-alkoxycarbonyl-C$_1$-C$_6$-hydroxyalkyl, C$_4$-C$_6$-dihydroxyalkenyl, C$_3$-C$_6$-cycloalkenyl, C$_3$-C$_6$-cycloalkenyl-C$_2$-C$_6$-alkenyl, C$_3$-C$_6$-cycloalkenyl-C$_1$-C$_6$-alkylidenyl, C$_3$-C$_6$-cycloalkyl-C$_1$-C$_6$-alkyl, C$_3$-C$_6$-hydroxycycloalkyl-C$_1$-C$_6$-alkyl, C$_3$-C$_6$-hydroxycycloalkyl-C$_1$-C$_6$-hydroxyalkyl, C$_3$-C$_6$-cycloalkyl-C$_1$-C$_6$-hydroxyalkyl, di(C$_1$-C$_6$-alkoxyl)phosphoryl-C$_1$-C$_6$-alkyl, diphosphoryl-C$_1$-C$_6$-alkyl, phosphoryl-C$_1$-C$_6$-alkyl, di[di(C$_1$-C$_6$-alkoxyl)phosphoryl-)]C$_1$-C$_6$-alkyl, heterocyclyl-C$_1$-C$_6$-alkylidenyl, phenyl, 5-, 6- or 9 membered heteroaryl, 3- to 6-membered heterocyclyl,
wherein OH groups of $R^2$ are unsubstituted or substituted by $R^b$;
$R^b$ is C$_1$-C$_6$-alkyl, C$_1$-C$_6$-haloalkyl, C$_3$-C$_6$-alkenyl, C$_3$-C$_6$-haloalkenyl, C$_3$-C$_6$-alkynyl, C$_3$-C$_6$-haloalkynyl, C$_3$-C$_6$-cycloalkyl, C$_3$-C$_6$-halocycloalkyl, C$_4$-C$_6$-cycloalkenyl, C$_3$-C$_6$-halocycloalkenyl, C$_1$-C$_6$-alkoxycarbonyl-C$_1$-C$_6$-alkyl, C$_1$-C$_6$-haloalkoxycarbonyl-C$_1$-C$_6$-alkyl, C$_1$-C$_6$-alkoxycarbonyl-C$_1$-C$_6$-haloalkyl, C$_1$-C$_6$- haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

cyclic groups of $R^2$ are unsubstituted or substituted by $R^c$; and $R^c$ is halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $C_1$-$C_6$-alkylthio, $C_1$-$C_6$-alkylsulfinyl, or $C_1$-$C_6$-alkylsulfonyl;

acyclic aliphatic groups of $R^2$ are unsubstituted or substituted by $R^d$;

$R^d$ is phenyl, 5- or 6-membered heteroaryl, or 3- to 6-membered heterocyclyl; wherein $R^d$ is unsubstituted or substituted by $R^e$;

$R^e$ is halogen, CN, $NO_2$, $C_1$-$C_6$-alkyl, $C_1$-$C_6$-haloalkyl, OH, $C_1$-$C_6$-alkoxy or $C_1$-$C_6$-haloalkoxy, $C_1$-$C_6$-alkylsulfonyl;

$R^3$ is halogen, CN, $NO_2$, $C_1$-$C_6$-alkyl, $C_1$-$C_6$-haloalkyl, $C_1$-$C_6$-alkoxy, or $C_3$-$C_6$-cycloalkyl;

$R^4$ is H, halogen, CN, $C_1$-$C_6$-alkyl, $C_1$-$C_6$-haloalkyl, or $C_1$-$C_6$-alkoxy;

$R^5$ is H, halogen, CN, $C_1$-$C_6$-alkyl, $C_1$-$C_6$-haloalkyl, or $C_1$-$C_6$-alkoxy;

$R^6$ is H, halogen, $C_1$-$C_6$-alkyl, or $C_1$-$C_6$-haloalkyl; and $R^7$ is H, halogen, CN, $C_1$-$C_6$-alkyl, or $C_1$-$C_6$-alkoxy.

Also preferred are compounds of formula (I), and their use as herbicide, wherein $R^1$ is $C_1$-$C_6$-alkyl, $C_1$-$C_6$-alkoxy, $C_1$-$C_6$-alkylthio, or $C_3$-$C_6$-cycloalkyl wherein cycloalkyl is unsubstituted;

$R^2$ $C_1$-$C_6$-alkyl, $C_1$-$C_6$-hydroxyalkyl, $C_1$-$C_6$-alkoxy-$C_1$-$C_6$-alkyl, $C_1$-$C_6$-alkoxycarbonyl-$C_1$-$C_6$-alkyl, $C_1$-$C_6$-alkoxycarbonyl-$C_2$-$C_6$-alkenyl, $C_1$-$C_6$-alkoxy-$C_2$-$C_6$-alkenyl, $C_1$-$C_6$-dicyanoalkyl, $C_2$-$C_6$-alkynyl, $C_1$-$C_6$-alkoxy-$C_2$-$C_6$-alkynyl, $C_1$-$C_6$-haloalkyl, $C_2$-$C_6$-alkenyl, hydroxycarbonyl-$C_1$-$C_6$-hydroxyalkyl, hydroxycarbonyl-$C_2$-$C_6$-alkenyl, hydroxycarbonyl-$C_1$-$C_6$-alkyl, $C_1$-$C_6$-alkylcarbonyl-$C_1$-$C_6$-alkyl, $C_2$-$C_6$-dihydroxyalkyl, $C_1$-$C_6$-alkoxycarbonyl-$C_1$-$C_6$-haloalkyl, $C_2$-$C_6$-hydroxyhaloalkyl, $C_3$-$C_6$-hydroxyalkenyl, hydroxycarbonyl-$C_2$-$C_6$-dihydroxyalkyl, $C_1$-$C_6$-alkoxycarbonyl-$C_1$-$C_6$-hydroxyalkyl, $C_4$-$C_6$-dihydroxyalkenyl, $C_3$-$C_6$-cycloalkenyl, $C_3$-$C_6$-cycloalkenyl-$C_2$-$C_6$-alkenyl, $C_3$-$C_6$-cycloalkenyl-$C_1$-$C_6$-alkylidenyl, $C_3$-$C_6$-cycloalkyl-$C_1$-$C_6$-alkyl, $C_3$-$C_6$-hydroxycycloalkyl-$C_1$-$C_6$-alkyl, $C_3$-$C_6$-hydroxycycloalkyl-$C_1$-$C_6$-hydroxyalkyl, $C_3$-$C_6$-cycloalkyl-$C_1$-$C_6$-hydroxyalkyl, di($C_1$-$C_6$-alkoxyl)phosphoryl-$C_1$-$C_6$-alkyl, diphosphoryl-$C_1$-$C_6$-alkyl, phosphoryl-$C_1$-$C_6$-alkyl, di[di($C_1$-$C_6$-alkoxyl)phosphoryl-)]$C_1$-$C_6$-alkyl, heterocyclyl-$C_1$-$C_6$-alkylidenyl, phenyl, 5-, 6- or 9 membered heteroaryl, 3- to 6-membered heterocyclyl, wherein OH groups of $R^2$ are unsubstituted or substituted by $R^b$;

$R^b$ is $C_1$-$C_6$-alkyl, $C_3$-$C_6$-alkynyl, $C_1$-$C_6$-alkoxycarbonyl-$C_1$-$C_6$-alkyl, $C_1$-$C_6$-alkylcarbonyl, hydroxycarbonyl-$C_1$-$C_6$-alkyl, or phenyl-$C_1$-$C_6$-alkyl;

cyclic groups of $R^2$ are unsubstituted or substituted by $R^c$;

$R^c$ is halogen, CN, $C_1$-$C_6$-alkyl, $C_1$-$C_6$-haloalkyl, OH, $C_1$-$C_6$-alkoxy, $C_1$-$C_6$-alkylthio, or $C_1$-$C_6$-alkylsulfonyl; and acyclic aliphatic groups of $R^2$ are unsubstituted or substituted by $R^d$;

$R^d$ is phenyl, 5- or 6-membered heteroaryl, or 3- to 6-membered heterocyclyl; wherein $R^d$ is unsubstituted or substituted by $R^e$; and $R^e$ is halogen or hydroxy;

$R^3$ is halogen, CN, $NO_2$, $C_1$-$C_6$-alkyl, or $C_1$-$C_6$-haloalkyl;

$R^4$ is H;

$R^5$ is H, halogen, or $C_1$-$C_6$-haloalkyl;

$R^6$ is H, halogen, or $C_1$-$C_6$-haloalkyl; and $R^7$ is H, halogen, or $C_1$-$C_6$-alkoxy.

Also preferred are compounds of formula (I), and their use as herbicide, wherein $R^1$ is $C_1$-$C_3H_5$;

$R^2$ is $C_2$-$C_6$-alkenyl, $C_2$-$C_6$-haloalkenyl, $C_1$-$C_6$-alkoxy-$C_2$-$C_6$-alkenyl, $C_2$-$C_6$-alkynyl, $C_3$-$C_6$-cycloalkenyl, $C_3$-$C_6$-cycloalkenyl-$C_1$-$C_6$-alkyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-cycloalkenyl-$C_1$-$C_6$-alkylidenyl, $C_3$-$C_6$-hydroxycycloalkyl-$C_1$-$C_6$-alkyl, $C_3$-$C_6$-hydroxycycloalkenyl-$C_1$-$C_6$-alkyl, $C_1$-$C_6$-hydroxyalkyl, $C_3$-$C_6$-cycloalkyl-$C_2$-$C_6$-hydroxyalkylidenyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-alkyl, $C_3$-$C_6$-hydroxycycloalkyl-$C_1$-$C_6$-hydroxyalkyl, $C_2$-$C_6$-dihydroxyalkyl, $C_3$-$C_6$-cycloalkyl-$C_3$-$C_6$-dihydroxyalkylidenyl, hydroxycarbonyl-$C_2$-$C_6$-dihydroxyalkyl, $C_1$-$C_6$-alkoxycarbonyl-$C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl;

wherein OH groups of $R^2$ are unsubstituted or substituted by $R^b$, $R^b$ is $C_1$-$C_6$-alkyl, $C_1$-$C_6$-haloalkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

cyclic groups of $R^2$ are unsubstituted or substituted by $R^c$, $R^c$ is halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $C_1$-$C_6$-alkylthio, $C_1$-$C_6$-alkylsulfinyl, or $C_1$-$C_6$-alkylsulfonyl;

acyclic aliphatic groups of $R^2$ are unsubstituted or substituted by $R^d$;

$R^d$ is phenyl, 5- or 6-membered heteroaryl, or 3- to 6-membered heterocyclyl; wherein $R^d$ is unsubstituted or substituted by $R^e$;

$R^e$ is halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $C_1$-$C_6$-alkylsulfonyl;

$R^3$ is Cl, Br, I, $CH_3$, $CF_3$, or $CF_2H$;
$R^4$ is H;
$R^5$ is H or F;
$R^6$ is H, F, $CF_3$, Cl, or Br; and
$R^7$ is H or F.

Also preferred are compounds of formula (I), and their use as herbicide, wherein $R^1$ is $C_1$-$C_6$-alkyl, $C_1$-$C_6$-alkoxy, or $C_3$-$C_6$-cycloalkyl wherein cycloalkyl is unsubstituted;

$R^2$ is preferably $C_2$-$C_6$-alkenyl, $C_3$-$C_6$-cycloalkyl-$C_1$-$C_6$-alkylidenyl, 5- or 6-membered heteroaryl, $C_1$-$C_6$-hydroxyalkyl, or $C_2$-$C_6$-dihydroxyalkyl;

particularly preferred $R^2$ is $C_2$-$C_6$-alkenyl, 5- or 6-membered heteroaryl, or $C_1$-$C_6$-hydroxyalkyl;

also particularly preferred $R^2$ is $C_3$-$C_6$-cycloalkyl-$C_1$-$C_6$-alkylidenyl, $C_2$-$C_6$-dihydroxyalkyl or 5- or 6-membered heteroaryl;

more preferred $R^2$ is CH=CH—$CH_3$, CH=C($CH_2$)$_3$, or CH=C($CH_2$)$_4$;

also more preferred $R^2$ is 2-furyl, 3-furyl, 2-methyl-3-furyl, or 3-methyl-2-furyl;

most preferred $R^2$ is CH=CH—$CH_3$, CH=C($CH_2$)$_3$, 2-furyl, 3-furyl, CHOH—CHOH—$C_6H_5$, CHOH—CHOH-2-furyl, or 4-methyloxazol-5-yl, wherein acyclic aliphatic groups of $R^2$ are unsubstituted or substituted by $R^d$;

$R^3$ is preferably halogen, CN, $C_1$-$C_6$-alkyl, $C_1$-$C_6$-haloalkyl, or $C_1$-$C_6$-alkoxy; particularly preferred halogen or $CH_3$;

$R^4$ is preferably H;

$R^5$ is preferably H or halogen;

$R^6$ is preferably H or halogen;

$R^7$ is H, halogen, $C_1$-$C_6$-alkyl, or $C_1$-$C_6$-alkoxy.

Also preferred are compounds of formula (I) wherein $R^4$ is H, which correspond to formula (I.1), and their use as herbicide,

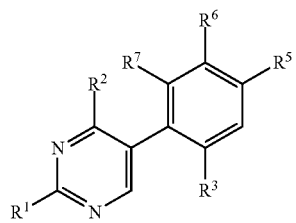
(I.1)

wherein $R^1$ is $C_3$-$C_6$-cycloalkyl, $C_1$-$C_6$-alkyl, or $C_1$-$C_6$-alkoxy;

$R^2$ is CH=CH—$CH_3$, CH=C($CH_2$)$_3$, 2-furyl, 3-furyl, CHOH—CHOH—$C_6H_5$, CHOH—CHOH-2-furyl, or 4-methyloxazol-5-yl;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy.

Also preferred are compounds of formula (I) wherein $R^2$ is CH=CH—$CH_3$, $R^4$ is H, which correspond to formula (I.A), and their use as herbicide,

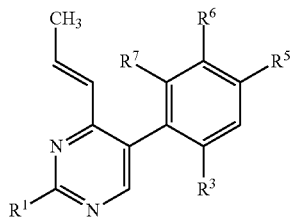
(I.A)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy.

Also preferred are compounds of formula (I) wherein $R^2$ is CH=C($CH_2$)$_3$, $R^4$ is H, which corresponds to formula (I.B), and their use as herbicide,

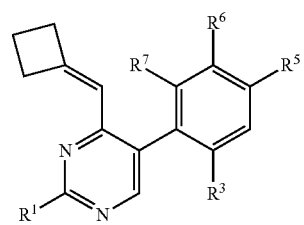
(I.B)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy.

Also preferred are compounds of formula (I) wherein $R^2$ is CH=C($CH_2$)$_4$, $R^4$ is H which correspond to formula (I.C), and their use as herbicide,

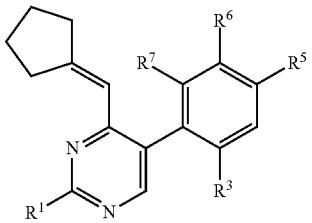
(I.C)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy;

Also preferred are compounds of formula (I) wherein $R^2$ is 2-furyl, $R^4$ is H, which correspond to formula (I.D), and their use as herbicide,

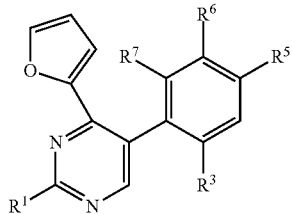

(I.D)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy;

Also preferred are compounds of formula (I) wherein $R^2$ is 3-methyl-2-furyl, $R^4$ is H, which correspond to formula (I.F), and their use as herbicide,

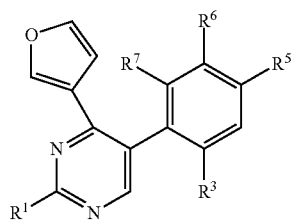

(I.E)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy;

Also preferred are compounds of formula (I) wherein $R^2$ is 3-methyl-2-furyl, $R^4$ is H, which correspond to formula (I.F). and their use as herbicide,

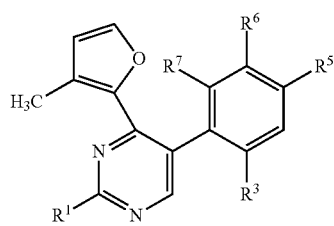

(I.F)

wherein $R^1$ is $C_3$-$C_6$-cycloalkyl, $C_1$-$C_6$-alkyl, or $C_1$-$C_6$-alkoxy; $R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy;

Also preferred are compounds of formula (I) wherein $R^2$ is 2-methyl-3-furyl, $R^4$ is H, which correspond to formula (I.G), and their use as herbicide,

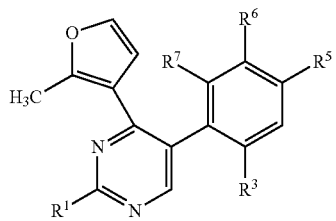

(I.G)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy;

Also preferred are compounds of formula (I) wherein $R^2$ is CHOH—CHOH—$C_6H_5$, $R^4$ is H, which correspond to formula (I.H), and their use as herbicide,

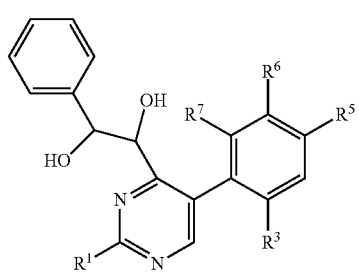

(I.H)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy;

Also preferred are compounds of formula (I) wherein $R^2$ is CHOH—CHOH-2-furyl, $R^4$ is H, which correspond to formula (I.I), and their use as herbicide,

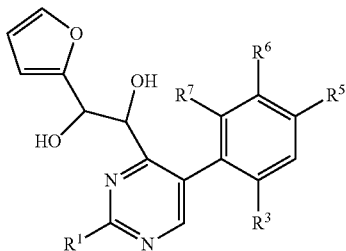

(I.I)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and $R^7$ is H, halogen, $C_1$-$C_6$-alkyl, or $C_1$-$C_6$-alkoxy;

Also preferred are compounds of formula (I) wherein $R^2$ is 4-methyloxazol-5-yl, $R^4$ is H, which correspond to formula (I.J), and their use as herbicide,

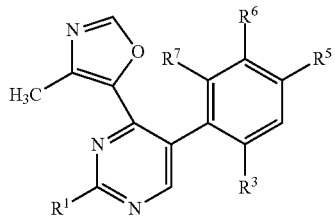

(I.J)

wherein $R^1$ is $C_3$-$C_6$-cycloalkyl, $C_1$-$C_6$-alkyl, or $C_1$-$C_6$-alkoxy;

$R^3$ is halogen, $C_1$-$C_6$-alkyl, $C_1$-$C_6$-haloalkyl, or $C_1$-$C_6$-alkoxy;

$R^5$ is H or halogen;

$R^6$ is H, halogen, or haloalkyl; preferably H or halogen; and

Also preferred are compounds of formula (I) wherein $R^4$ is H, which correspond to formula (I.K), and their use as herbicide,

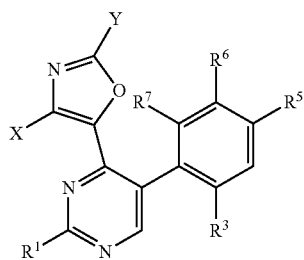

(I.K)

wherein

X and Y independently are selected from H, $CH_3$, $O_2H_5$, n-propyl, iso-propyl, iso-butyl, n-butyl, 2-butyl, t-butyl, OH, $OCH_3$, $SCH_3$, $S(O)CH_3$, $S(O)_2CH_3$, CN, F, Cl, Br, I, $CH_2CF_3$, $CF_2CF_3$, $CF_2CH_3$, $CF_3$, $CF_2H$, $OCF_2H$, and $OCF_3$;

$R^1$ is c-$C_3H_5$;

$R^3$ is Cl, Br, I, $OH_3$, $CF_3$, or $CF_2H$;

$R^5$ is H or F;

$R^6$ is H, F, $CF_3$, Cl, or Br;

$R^7$ is H or F.

Particularly preferred are compounds of formula I.1, wherein $R^1$ is $C_2H_5$, c-$C_3H_5$, c-$C_4H_7$, or $OCH_3$;

$R^2$ is selected from CH=CH—$CH_3$, CH=$C(CH_2)_3$, CH=$C(CH_2)_4$, 2-furyl, 3-furyl, 2-$CH_3$-3-furyl, CHOH—CHOH—$C_6H_5$, CHOH—CHOH-2-furyl, CHOH—CHOH-2-furyl, 4-$CH_3$-oxazol-5-yl, $R^2$-9.1 to $R^2$-9.676 from Table $R^2$-9, $R^2$-10.1 to $R^2$-10.676 from Table $R^2$-10, and $R^2$-15.1 to $R^2$-15.676 from Table $R^2$-15; preferably $R^2$-9.1 to $R^2$-9.676 from Table $R^2$-9, $R^2$-10.1 to $R^2$-10.676 from Table $R^2$-10, and $R^2$-15.1 to $R^2$-15.676 from Table $R^2$-15; more preferably $R^2$-9.1 to $R^2$-9.676 from Table $R^2$-9, $R^2$-10.1 to $R^2$-10.676 from Table $R^2$-10; most preferably $R^2$-9.1 to $R^2$-9.676 from Table $R^2$-9;

$R^3$ is F, Cl, Br, I, $CH_3$, $OCH_3$, $CF_3$, or $CF_2H$;

$R^5$ is H or F;

$R^6$ is H r F;

$R^7$ is H, Cl, Br, $CH_3$, $OCH_3$ or F.

According to a particularly preferred embodiment of the compounds of formula I and their use as herbicide, compounds of the invention are the compounds of the formulae I that are compiled in the Tables 1 to 10, wherein the meaning for the combination of variables $R^1$, $R^2$, $R^5$, $R^6$ and $R^7$ for each individual compound of tables 1 to 10 corresponds to each line of Table A. Each of the groups mentioned for a substituent in the tables is furthermore per se, independently of the combination in which it is mentioned, a particularly preferred aspect of the substituent in question. The term "formula" used in below tables 1 to 10 denotes "compounds of formula".

Table 1. Compounds of formula I.1, wherein $R^2$ is CH=CH—$CH_3$ (=formula I.1).

Table 2. Compounds of formula I.1, wherein $R^2$ is CH=$C(CH_2)_3$ (=formula I.2).

Table 3. Compounds of formula I.1, wherein $R^2$ is CH=$C(CH_2)_4$ (=formula I.3).

Table 4. Compounds of formula I.1, wherein $R^2$ is 2-furyl (=formula I.4).

Table 5. Compounds of formula I.1, wherein $R^2$ is 3-furyl (=formula I.5).

Table 6. Compounds of formula I.1, wherein $R^2$ is 3-$CH_3$-2-furyl (=formula I.6).

Table 7. Compounds of formula I.1, wherein $R^2$ is 2-$CH_3$-3-furyl (=formula I.7).

Table 8. Compounds of formula I.1, wherein $R^2$ is CHOH—CHOH—$C_6H_5$ (=formula I.8).

Table 9. Compounds of formula I.1, wherein $R^2$ is CHOH—CHOH-2-furyl (=formula I.9).

Table 10. Compounds of formula I.1, wherein $R^2$ is 4-$CH_3$-oxazol-5-yl (=formula I.10).

According to a particularly preferred embodiment of the compounds of formula I and their use as herbicide, compounds of the invention are the compounds of formulae I that are compiled in tables 11 to 2038, wherein the meaning for the combination of variables $R^1$, $R^3$, $R^5$, $R^6$ and $R^7$ for each individual compound tables 11 to 2038 corresponds to each line of Table A. Each of the groups mentioned for a substituent in the tables is furthermore per se, independently of the combination in which it is mentioned, a particularly preferred aspect of the substituent in question. The term "formula" used in below tables 11 to 2038 denotes "compounds of formula".

Table 11. Compounds of formula I.1, wherein $R^2$ is $R^2$-9.1 (=formula I.11).
Table 12. Compounds of formula I.1, wherein $R^2$ is $R^2$-9.2 (=formula I.12).
Table 13. Compounds of formula I.1, wherein $R^2$ is $R^2$-9.3 (=formula I.13).
Table 14. Compounds of formula I.1, wherein $R^2$ is $R^2$-9.4 (=formula I.14).
Table 15. Compounds of formula I.1, wherein $R^2$ is $R^2$-9.5 (=formula I.15).
Table 16. Compounds of formula I.1, wherein $R^2$ is $R^2$-9.6 (=formula I.16).
Table 17. Compounds of formula I.1, wherein $R^2$ is $R^2$-9.7 (=formula I.17).
Table 18. Compounds of formula I.1, wherein $R^2$ is $R^2$-9.8 (=formula I.18).
Table 19. Compounds of formula I.1, wherein $R^2$ is $R^2$-9.9 (=formula I.19).
Table 20. Compounds of formula I.1, wherein $R^2$ is $R^2$-9.10 (=formula I.20).
Table 21. Compounds of formula I.1, wherein $R^2$ is $R^2$-9.11 (=formula I.21).
Table 22. Compounds of formula I.1, wherein $R^2$ is $R^2$-9.12 (=formula I.22).
Table 23. Compounds of formula I.1, wherein $R^2$ is $R^2$-9.13 (=formula I.23).
Table 24. Compounds of formula I.1, wherein $R^2$ is $R^2$-9.14 (=formula I.24).
Table 25. Compounds of formula I.1, wherein $R^2$ is $R^2$-9.15 (=formula I.25).
Table 26. Compounds of formula I.1, wherein $R^2$ is $R^2$-9.16 (=formula I.26).
Table 27. Compounds of formula I.1, wherein $R^2$ is $R^2$-9.17 (=formula I.27).
Table 28. Compounds of formula I.1, wherein $R^2$ is $R^2$-9.18 (=formula I.28).
Table 29. Compounds of formula I.1, wherein $R^2$ is $R^2$-9.19 (=formula I.29).
Table 30. Compounds of formula I.1, wherein $R^2$ is $R^2$-9.20 (=formula I.30).
Table 31. Compounds of formula I.1, wherein $R^2$ is $R^2$-9.21 (=formula I.31).
Table 32. Compounds of formula I.1, wherein $R^2$ is $R^2$-9.22 (=formula I.32).
Table 33. Compounds of formula I.1, wherein $R^2$ is $R^2$-9.23 (=formula I.33).
Table 34. Compounds of formula I.1, wherein $R^2$ is $R^2$-9.24 (=formula I.34).
Table 35. Compounds of formula I.1, wherein $R^2$ is $R^2$-9.25 (=formula I.35).
Table 36. Compounds of formula I.1, wherein $R^2$ is $R^2$-9.26 (=formula I.36).
Table 37. Compounds of formula I.1, wherein $R^2$ is $R^2$-9.27 (=formula I.37).
Table 38. Compounds of formula I.1, wherein $R^2$ is $R^2$-9.28 (=formula I.38).
Table 39. Compounds of formula I.1, wherein $R^2$ is $R^2$-9.29 (=formula I.39).
Table 40. Compounds of formula I.1, wherein $R^2$ is $R^2$-9.30 (=formula I.40).
Table 41. Compounds of formula I.1, wherein $R^2$ is $R^2$-9.31 (=formula I.41).
Table 42. Compounds of formula I.1, wherein $R^2$ is $R^2$-9.32 (=formula I.42).
Table 43. Compounds of formula I.1, wherein $R^2$ is $R^2$-9.33 (=formula I.43).
Table 44. Compounds of formula I.1, wherein $R^2$ is $R^2$-9.34 (=formula I.44).
Table 45. Compounds of formula I.1, wherein $R^2$ is $R^2$-9.35 (=formula I.45).
Table 46. Compounds of formula I.1, wherein $R^2$ is $R^2$-9.36 (=formula I.46).
Table 47. Compounds of formula I.1, wherein $R^2$ is $R^2$-9.37 (=formula I.47).
Table 48. Compounds of formula I.1, wherein $R^2$ is $R^2$-9.38 (=formula I.48).
Table 49. Compounds of formula I.1, wherein $R^2$ is $R^2$-9.39 (=formula I.49).
Table 50. Compounds of formula I.1, wherein $R^2$ is $R^2$-9.40 (=formula I.50).
Table 51. Compounds of formula I.1, wherein $R^2$ is $R^2$-9.41 (=formula I.51).
Table 52. Compounds of formula I.1, wherein $R^2$ is $R^2$-9.42 (=formula I.52).
Table 53. Compounds of formula I.1, wherein $R^2$ is $R^2$-9.43 (=formula I.53).
Table 54. Compounds of formula I.1, wherein $R^2$ is $R^2$-9.44 (=formula I.54).
Table 55. Compounds of formula I.1, wherein $R^2$ is $R^2$-9.45 (=formula I.55).
Table 56. Compounds of formula I.1, wherein $R^2$ is $R^2$-9.46 (=formula I.56).
Table 57. Compounds of formula I.1, wherein $R^2$ is $R^2$-9.47 (=formula I.57).
Table 58. Compounds of formula I.1, wherein $R^2$ is $R^2$-9.48 (=formula I.58).
Table 59. Compounds of formula I.1, wherein $R^2$ is $R^2$-9.49 (=formula I.59).
Table 60. Compounds of formula I.1, wherein $R^2$ is $R^2$-9.50 (=formula I.60).
Table 61. Compounds of formula I.1, wherein $R^2$ is $R^2$-9.51 (=formula I.61).
Table 62. Compounds of formula I.1, wherein $R^2$ is $R^2$-9.52 (=formula I.62).
Table 63. Compounds of formula I.1, wherein $R^2$ is $R^2$-9.53 (=formula I.63).
Table 64. Compounds of formula I.1, wherein $R^2$ is $R^2$-9.54 (=formula I.64).
Table 65. Compounds of formula I.1, wherein $R^2$ is $R^2$-9.55 (=formula I.65).
Table 66. Compounds of formula I.1, wherein $R^2$ is $R^2$-9.56 (=formula I.66).
Table 67. Compounds of formula I.1, wherein $R^2$ is $R^2$-9.57 (=formula I.67).
Table 68. Compounds of formula I.1, wherein $R^2$ is $R^2$-9.58 (=formula I.68).
Table 69. Compounds of formula I.1, wherein $R^2$ is $R^2$-9.59 (=formula I.69).
Table 70. Compounds of formula I.1, wherein $R^2$ is $R^2$-9.60 (=formula I.70).
Table 71. Compounds of formula I.1, wherein $R^2$ is $R^2$-9.61 (=formula I.71).
Table 72. Compounds of formula I.1, wherein $R^2$ is $R^2$-9.62 (=formula I.72).
Table 73. Compounds of formula I.1, wherein $R^2$ is $R^2$-9.63 (=formula I.73).
Table 74. Compounds of formula I.1, wherein $R^2$ is $R^2$-9.64 (=formula I.74).
Table 75. Compounds of formula I.1, wherein $R^2$ is $R^2$-9.65 (=formula I.75).
Table 76. Compounds of formula I.1, wherein $R^2$ is $R^2$-9.66 (=formula I.76).

Table 77. Compounds of formula I.1, wherein $R^2$ is $R^2$-9.67 (=formula I.77).
Table 78. Compounds of formula I.1, wherein $R^2$ is $R^2$-9.68 (=formula I.78).
Table 79. Compounds of formula I.1, wherein $R^2$ is $R^2$-9.69 (=formula I.79).
Table 80. Compounds of formula I.1, wherein $R^2$ is $R^2$-9.70 (=formula I.80).
Table 81. Compounds of formula I.1, wherein $R^2$ is $R^2$-9.71 (=formula I.81).
Table 82. Compounds of formula I.1, wherein $R^2$ is $R^2$-9.72 (=formula I.82).
Table 83. Compounds of formula I.1, wherein $R^2$ is $R^2$-9.73 (=formula I.83).
Table 84. Compounds of formula I.1, wherein $R^2$ is $R^2$-9.74 (=formula I.84).
Table 85. Compounds of formula I.1, wherein $R^2$ is $R^2$-9.75 (=formula I.85).
Table 86. Compounds of formula I.1, wherein $R^2$ is $R^2$-9.76 (=formula I.86).
Table 87. Compounds of formula I.1, wherein $R^2$ is $R^2$-9.77 (=formula I.87).
Table 88. Compounds of formula I.1, wherein $R^2$ is $R^2$-9.78 (=formula I.88).
Table 89. Compounds of formula I.1, wherein $R^2$ is $R^2$-9.79 (=formula I.89).
Table 90. Compounds of formula I.1, wherein $R^2$ is $R^2$-9.80 (=formula I.90).
Table 91. Compounds of formula I.1, wherein $R^2$ is $R^2$-9.81 (=formula I.91).
Table 92. Compounds of formula I.1, wherein $R^2$ is $R^2$-9.82 (=formula I.92).
Table 93. Compounds of formula I.1, wherein $R^2$ is $R^2$-9.83 (=formula I.93).
Table 94. Compounds of formula I.1, wherein $R^2$ is $R^2$-9.84 (=formula I.94).
Table 95. Compounds of formula I.1, wherein $R^2$ is $R^2$-9.85 (=formula I.95).
Table 96. Compounds of formula I.1, wherein $R^2$ is $R^2$-9.86 (=formula I.96).
Table 97. Compounds of formula I.1, wherein $R^2$ is $R^2$-9.87 (=formula I.97).
Table 98. Compounds of formula I.1, wherein $R^2$ is $R^2$-9.88 (=formula I.98).
Table 99. Compounds of formula I.1, wherein $R^2$ is $R^2$-9.89 (=formula I.99).
Table 100. Compounds of formula I.1, wherein $R^2$ is $R^2$-9.90 (=formula I.100).
Table 101. Compounds of formula I.1, wherein $R^2$ is $R^2$-9.91 (=formula I.101).
Table 102. Compounds of formula I.1, wherein $R^2$ is $R^2$-9.92 (=formula I.102).
Table 103. Compounds of formula I.1, wherein $R^2$ is $R^2$-9.93 (=formula I.103).
Table 104. Compounds of formula I.1, wherein $R^2$ is $R^2$-9.94 (=formula I.104).
Table 105. Compounds of formula I.1, wherein $R^2$ is $R^2$-9.95 (=formula I.105).
Table 106. Compounds of formula I.1, wherein $R^2$ is $R^2$-9.96 (=formula I.106).
Table 107. Compounds of formula I.1, wherein $R^2$ is $R^2$-9.97 (=formula I.107).
Table 108. Compounds of formula I.1, wherein $R^2$ is $R^2$-9.98 (=formula I.108).
Table 109. Compounds of formula I.1, wherein $R^2$ is $R^2$-9.99 (=formula I.109).
Table 110. Compounds of formula I.1, wherein $R^2$ is $R^2$-9.100 (=formula I.110).
Table 111. Compounds of formula I.1, wherein $R^2$ is $R^2$-9.101 (=formula I.111).
Table 112. Compounds of formula I.1, wherein $R^2$ is $R^2$-9.102 (=formula I.112).
Table 113. Compounds of formula I.1, wherein $R^2$ is $R^2$-9.103 (=formula I.113).
Table 114. Compounds of formula I.1, wherein $R^2$ is $R^2$-9.104 (=formula I.114).
Table 115. Compounds of formula I.1, wherein $R^2$ is $R^2$-9.105 (=formula I.115).
Table 116. Compounds of formula I.1, wherein $R^2$ is $R^2$-9.106 (=formula I.116).
Table 117. Compounds of formula I.1, wherein $R^2$ is $R^2$-9.107 (=formula I.117).
Table 118. Compounds of formula I.1, wherein $R^2$ is $R^2$-9.108 (=formula I.118).
Table 119. Compounds of formula I.1, wherein $R^2$ is $R^2$-9.109 (=formula I.119).
Table 120. Compounds of formula I.1, wherein $R^2$ is $R^2$-9.110 (=formula I.120).
Table 121. Compounds of formula I.1, wherein $R^2$ is $R^2$-9.111 (=formula I.121).
Table 122. Compounds of formula I.1, wherein $R^2$ is $R^2$-9.112 (=formula I.122).
Table 123. Compounds of formula I.1, wherein $R^2$ is $R^2$-9.113 (=formula I.123).
Table 124. Compounds of formula I.1, wherein $R^2$ is $R^2$-9.114 (=formula I.124).
Table 125. Compounds of formula I.1, wherein $R^2$ is $R^2$-9.115 (=formula I.125).
Table 126. Compounds of formula I.1, wherein $R^2$ is $R^2$-9.116 (=formula I.126).
Table 127. Compounds of formula I.1, wherein $R^2$ is $R^2$-9.117 (=formula I.127).
Table 128. Compounds of formula I.1, wherein $R^2$ is $R^2$-9.118 (=formula I.128).
Table 129. Compounds of formula I.1, wherein $R^2$ is $R^2$-9.119 (=formula I.129).
Table 130. Compounds of formula I.1, wherein $R^2$ is $R^2$-9.120 (=formula I.130).
Table 131. Compounds of formula I.1, wherein $R^2$ is $R^2$-9.121 (=formula I.131).
Table 132. Compounds of formula I.1, wherein $R^2$ is $R^2$-9.122 (=formula I.132).
Table 133. Compounds of formula I.1, wherein $R^2$ is $R^2$-9.123 (=formula I.133).
Table 134. Compounds of formula I.1, wherein $R^2$ is $R^2$-9.124 (=formula I.134).
Table 135. Compounds of formula I.1, wherein $R^2$ is $R^2$-9.125 (=formula I.135).
Table 136. Compounds of formula I.1, wherein $R^2$ is $R^2$-9.126 (=formula I.136).
Table 137. Compounds of formula I.1, wherein $R^2$ is $R^2$-9.127 (=formula I.137).
Table 138. Compounds of formula I.1, wherein $R^2$ is $R^2$-9.128 (=formula I.138).
Table 139. Compounds of formula I.1, wherein $R^2$ is $R^2$-9.129 (=formula I.139).
Table 140. Compounds of formula I.1, wherein $R^2$ is $R^2$-9.130 (=formula I.140).
Table 141. Compounds of formula I.1, wherein $R^2$ is $R^2$-9.131 (=formula I.141).
Table 142. Compounds of formula I.1, wherein $R^2$ is $R^2$-9.132 (=formula I.142).

Table 143. Compounds of formula I.1, wherein $R^2$ is $R^2$-9.133 (=formula I.143).
Table 144. Compounds of formula I.1, wherein $R^2$ is $R^2$-9.134 (=formula I.144).
Table 145. Compounds of formula I.1, wherein $R^2$ is $R^2$-9.135 (=formula I.145).
Table 146. Compounds of formula I.1, wherein $R^2$ is $R^2$-9.136 (=formula I.146).
Table 147. Compounds of formula I.1, wherein $R^2$ is $R^2$-9.137 (=formula I.147).
Table 148. Compounds of formula I.1, wherein $R^2$ is $R^2$-9.138 (=formula I.148).
Table 149. Compounds of formula I.1, wherein $R^2$ is $R^2$-9.139 (=formula I.149).
Table 150. Compounds of formula I.1, wherein $R^2$ is $R^2$-9.140 (=formula I.150).
Table 151. Compounds of formula I.1, wherein $R^2$ is $R^2$-9.141 (=formula I.151).
Table 152. Compounds of formula I.1, wherein $R^2$ is $R^2$-9.142 (=formula I.152).
Table 153. Compounds of formula I.1, wherein $R^2$ is $R^2$-9.143 (=formula I.153).
Table 154. Compounds of formula I.1, wherein $R^2$ is $R^2$-9.144 (=formula I.154).
Table 155. Compounds of formula I.1, wherein $R^2$ is $R^2$-9.145 (=formula I.155).
Table 156. Compounds of formula I.1, wherein $R^2$ is $R^2$-9.146 (=formula I.156).
Table 157. Compounds of formula I.1, wherein $R^2$ is $R^2$-9.147 (=formula I.157).
Table 158. Compounds of formula I.1, wherein $R^2$ is $R^2$-9.148 (=formula I.158).
Table 159. Compounds of formula I.1, wherein $R^2$ is $R^2$-9.149 (=formula I.159).
Table 160. Compounds of formula I.1, wherein $R^2$ is $R^2$-9.150 (=formula I.160).
Table 161. Compounds of formula I.1, wherein $R^2$ is $R^2$-9.151 (=formula I.161).
Table 162. Compounds of formula I.1, wherein $R^2$ is $R^2$-9.152 (=formula I.162).
Table 163. Compounds of formula I.1, wherein $R^2$ is $R^2$-9.153 (=formula I.163).
Table 164. Compounds of formula I.1, wherein $R^2$ is $R^2$-9.154 (=formula I.164).
Table 165. Compounds of formula I.1, wherein $R^2$ is $R^2$-9.155 (=formula I.165).
Table 166. Compounds of formula I.1, wherein $R^2$ is $R^2$-9.156 (=formula I.166).
Table 167. Compounds of formula I.1, wherein $R^2$ is $R^2$-9.157 (=formula I.167).
Table 168. Compounds of formula I.1, wherein $R^2$ is $R^2$-9.158 (=formula I.168).
Table 169. Compounds of formula I.1, wherein $R^2$ is $R^2$-9.159 (=formula I.169).
Table 170. Compounds of formula I.1, wherein $R^2$ is $R^2$-9.160 (=formula I.170).
Table 171. Compounds of formula I.1, wherein $R^2$ is $R^2$-9.161 (=formula I.171).
Table 172. Compounds of formula I.1, wherein $R^2$ is $R^2$-9.162 (=formula I.172).
Table 173. Compounds of formula I.1, wherein $R^2$ is $R^2$-9.163 (=formula I.173).
Table 174. Compounds of formula I.1, wherein $R^2$ is $R^2$-9.164 (=formula I.174).
Table 175. Compounds of formula I.1, wherein $R^2$ is $R^2$-9.165 (=formula I.175).
Table 176. Compounds of formula I.1, wherein $R^2$ is $R^2$-9.166 (=formula I.176).
Table 177. Compounds of formula I.1, wherein $R^2$ is $R^2$-9.167 (=formula I.177).
Table 178. Compounds of formula I.1, wherein $R^2$ is $R^2$-9.168 (=formula I.178).
Table 179. Compounds of formula I.1, wherein $R^2$ is $R^2$-9.169 (=formula I.179).
Table 180. Compounds of formula I.1, wherein $R^2$ is $R^2$-9.170 (=formula I.180).
Table 181. Compounds of formula I.1, wherein $R^2$ is $R^2$-9.171 (=formula I.181).
Table 182. Compounds of formula I.1, wherein $R^2$ is $R^2$-9.172 (=formula I.182).
Table 183. Compounds of formula I.1, wherein $R^2$ is $R^2$-9.173 (=formula I.183).
Table 184. Compounds of formula I.1, wherein $R^2$ is $R^2$-9.174 (=formula I.184).
Table 185. Compounds of formula I.1, wherein $R^2$ is $R^2$-9.175 (=formula I.185).
Table 186. Compounds of formula I.1, wherein $R^2$ is $R^2$-9.176 (=formula I.186).
Table 187. Compounds of formula I.1, wherein $R^2$ is $R^2$-9.177 (=formula I.187).
Table 188. Compounds of formula I.1, wherein $R^2$ is $R^2$-9.178 (=formula I.188).
Table 189. Compounds of formula I.1, wherein $R^2$ is $R^2$-9.179 (=formula I.189).
Table 190. Compounds of formula I.1, wherein $R^2$ is $R^2$-9.180 (=formula I.190).
Table 191. Compounds of formula I.1, wherein $R^2$ is $R^2$-9.181 (=formula I.191).
Table 192. Compounds of formula I.1, wherein $R^2$ is $R^2$-9.182 (=formula I.192).
Table 193. Compounds of formula I.1, wherein $R^2$ is $R^2$-9.183 (=formula I.193).
Table 194. Compounds of formula I.1, wherein $R^2$ is $R^2$-9.184 (=formula I.194).
Table 195. Compounds of formula I.1, wherein $R^2$ is $R^2$-9.185 (=formula I.195).
Table 196. Compounds of formula I.1, wherein $R^2$ is $R^2$-9.186 (=formula I.196).
Table 197. Compounds of formula I.1, wherein $R^2$ is $R^2$-9.187 (=formula I.197).
Table 198. Compounds of formula I.1, wherein $R^2$ is $R^2$-9.188 (=formula I.198).
Table 199. Compounds of formula I.1, wherein $R^2$ is $R^2$-9.189 (=formula I.199).
Table 200. Compounds of formula I.1, wherein $R^2$ is $R^2$-9.190 (=formula I.200).
Table 201. Compounds of formula I.1, wherein $R^2$ is $R^2$-9.191 (=formula I.201).
Table 202. Compounds of formula I.1, wherein $R^2$ is $R^2$-9.192 (=formula I.202).
Table 203. Compounds of formula I.1, wherein $R^2$ is $R^2$-9.193 (=formula I.203).
Table 204. Compounds of formula I.1, wherein $R^2$ is $R^2$-9.194 (=formula I.204).
Table 205. Compounds of formula I.1, wherein $R^2$ is $R^2$-9.195 (=formula I.205).
Table 206. Compounds of formula I.1, wherein $R^2$ is $R^2$-9.196 (=formula I.206).
Table 207. Compounds of formula I.1, wherein $R^2$ is $R^2$-9.197 (=formula I.207).
Table 208. Compounds of formula I.1, wherein $R^2$ is $R^2$-9.198 (=formula I.208).

Table 209. Compounds of formula I.1, wherein $R^2$ is $R^2$-9.199 (=formula I.209).
Table 210. Compounds of formula I.1, wherein $R^2$ is $R^2$-9.200 (=formula I.210).
Table 211. Compounds of formula I.1, wherein $R^2$ is $R^2$-9.201 (=formula I.211).
Table 212. Compounds of formula I.1, wherein $R^2$ is $R^2$-9.202 (=formula I.212).
Table 213. Compounds of formula I.1, wherein $R^2$ is $R^2$-9.203 (=formula I.213).
Table 214. Compounds of formula I.1, wherein $R^2$ is $R^2$-9.204 (=formula I.214).
Table 215. Compounds of formula I.1, wherein $R^2$ is $R^2$-9.205 (=formula I.215).
Table 216. Compounds of formula I.1, wherein $R^2$ is $R^2$-9.206 (=formula I.216).
Table 217. Compounds of formula I.1, wherein $R^2$ is $R^2$-9.207 (=formula I.217).
Table 218. Compounds of formula I.1, wherein $R^2$ is $R^2$-9.208 (=formula I.218).
Table 219. Compounds of formula I.1, wherein $R^2$ is $R^2$-9.209 (=formula I.219).
Table 220. Compounds of formula I.1, wherein $R^2$ is $R^2$-9.210 (=formula I.220).
Table 221. Compounds of formula I.1, wherein $R^2$ is $R^2$-9.211 (=formula I.221).
Table 222. Compounds of formula I.1, wherein $R^2$ is $R^2$-9.212 (=formula I.222).
Table 223. Compounds of formula I.1, wherein $R^2$ is $R^2$-9.213 (=formula I.223).
Table 224. Compounds of formula I.1, wherein $R^2$ is $R^2$-9.214 (=formula I.224).
Table 225. Compounds of formula I.1, wherein $R^2$ is $R^2$-9.215 (=formula I.225).
Table 226. Compounds of formula I.1, wherein $R^2$ is $R^2$-9.216 (=formula I.226).
Table 227. Compounds of formula I.1, wherein $R^2$ is $R^2$-9.217 (=formula I.227).
Table 228. Compounds of formula I.1, wherein $R^2$ is $R^2$-9.218 (=formula I.228).
Table 229. Compounds of formula I.1, wherein $R^2$ is $R^2$-9.219 (=formula I.229).
Table 230. Compounds of formula I.1, wherein $R^2$ is $R^2$-9.220 (=formula I.230).
Table 231. Compounds of formula I.1, wherein $R^2$ is $R^2$-9.221 (=formula I.231).
Table 232. Compounds of formula I.1, wherein $R^2$ is $R^2$-9.222 (=formula I.232).
Table 233. Compounds of formula I.1, wherein $R^2$ is $R^2$-9.223 (=formula I.233).
Table 234. Compounds of formula I.1, wherein $R^2$ is $R^2$-9.224 (=formula I.234).
Table 235. Compounds of formula I.1, wherein $R^2$ is $R^2$-9.225 (=formula I.235).
Table 236. Compounds of formula I.1, wherein $R^2$ is $R^2$-9.226 (=formula I.236).
Table 237. Compounds of formula I.1, wherein $R^2$ is $R^2$-9.227 (=formula I.237).
Table 238. Compounds of formula I.1, wherein $R^2$ is $R^2$-9.228 (=formula I.238).
Table 239. Compounds of formula I.1, wherein $R^2$ is $R^2$-9.229 (=formula I.239).
Table 240. Compounds of formula I.1, wherein $R^2$ is $R^2$-9.230 (=formula I.240).
Table 241. Compounds of formula I.1, wherein $R^2$ is $R^2$-9.231 (=formula I.241).
Table 242. Compounds of formula I.1, wherein $R^2$ is $R^2$-9.232 (=formula I.242).
Table 243. Compounds of formula I.1, wherein $R^2$ is $R^2$-9.233 (=formula I.243).
Table 244. Compounds of formula I.1, wherein $R^2$ is $R^2$-9.234 (=formula I.244).
Table 245. Compounds of formula I.1, wherein $R^2$ is $R^2$-9.235 (=formula I.245).
Table 246. Compounds of formula I.1, wherein $R^2$ is $R^2$-9.236 (=formula I.246).
Table 247. Compounds of formula I.1, wherein $R^2$ is $R^2$-9.237 (=formula I.247).
Table 248. Compounds of formula I.1, wherein $R^2$ is $R^2$-9.238 (=formula I.248).
Table 249. Compounds of formula I.1, wherein $R^2$ is $R^2$-9.239 (=formula I.249).
Table 250. Compounds of formula I.1, wherein $R^2$ is $R^2$-9.240 (=formula I.250).
Table 251. Compounds of formula I.1, wherein $R^2$ is $R^2$-9.241 (=formula I.251).
Table 252. Compounds of formula I.1, wherein $R^2$ is $R^2$-9.242 (=formula I.252).
Table 253. Compounds of formula I.1, wherein $R^2$ is $R^2$-9.243 (=formula I.253).
Table 254. Compounds of formula I.1, wherein $R^2$ is $R^2$-9.244 (=formula I.254).
Table 255. Compounds of formula I.1, wherein $R^2$ is $R^2$-9.245 (=formula I.255).
Table 256. Compounds of formula I.1, wherein $R^2$ is $R^2$-9.246 (=formula I.256).
Table 257. Compounds of formula I.1, wherein $R^2$ is $R^2$-9.247 (=formula I.257).
Table 258. Compounds of formula I.1, wherein $R^2$ is $R^2$-9.248 (=formula I.258).
Table 259. Compounds of formula I.1, wherein $R^2$ is $R^2$-9.249 (=formula I.259).
Table 260. Compounds of formula I.1, wherein $R^2$ is $R^2$-9.250 (=formula I.260).
Table 261. Compounds of formula I.1, wherein $R^2$ is $R^2$-9.251 (=formula I.261).
Table 262. Compounds of formula I.1, wherein $R^2$ is $R^2$-9.252 (=formula I.262).
Table 263. Compounds of formula I.1, wherein $R^2$ is $R^2$-9.253 (=formula I.263).
Table 264. Compounds of formula I.1, wherein $R^2$ is $R^2$-9.254 (=formula I.264).
Table 265. Compounds of formula I.1, wherein $R^2$ is $R^2$-9.255 (=formula I.265).
Table 266. Compounds of formula I.1, wherein $R^2$ is $R^2$-9.256 (=formula I.266).
Table 267. Compounds of formula I.1, wherein $R^2$ is $R^2$-9.257 (=formula I.267).
Table 268. Compounds of formula I.1, wherein $R^2$ is $R^2$-9.258 (=formula I.268).
Table 269. Compounds of formula I.1, wherein $R^2$ is $R^2$-9.259 (=formula I.269).
Table 270. Compounds of formula I.1, wherein $R^2$ is $R^2$-9.260 (=formula I.270).
Table 271. Compounds of formula I.1, wherein $R^2$ is $R^2$-9.261 (=formula I.271).
Table 272. Compounds of formula I.1, wherein $R^2$ is $R^2$-9.262 (=formula I.272).
Table 273. Compounds of formula I.1, wherein $R^2$ is $R^2$-9.263 (=formula I.273).
Table 274. Compounds of formula I.1, wherein $R^2$ is $R^2$-9.264 (=formula I.274).

Table 275. Compounds of formula I.1, wherein $R^2$ is $R^2$-9.265 (=formula I.275).
Table 276. Compounds of formula I.1, wherein $R^2$ is $R^2$-9.266 (=formula I.276).
Table 277. Compounds of formula I.1, wherein $R^2$ is $R^2$-9.267 (=formula I.277).
Table 278. Compounds of formula I.1, wherein $R^2$ is $R^2$-9.268 (=formula I.278).
Table 279. Compounds of formula I.1, wherein $R^2$ is $R^2$-9.269 (=formula I.279).
Table 280. Compounds of formula I.1, wherein $R^2$ is $R^2$-9.270 (=formula I.280).
Table 281. Compounds of formula I.1, wherein $R^2$ is $R^2$-9.271 (=formula I.281).
Table 282. Compounds of formula I.1, wherein $R^2$ is $R^2$-9.272 (=formula I.282).
Table 283. Compounds of formula I.1, wherein $R^2$ is $R^2$-9.273 (=formula I.283).
Table 284. Compounds of formula I.1, wherein $R^2$ is $R^2$-9.274 (=formula I.284).
Table 285. Compounds of formula I.1, wherein $R^2$ is $R^2$-9.275 (=formula I.285).
Table 286. Compounds of formula I.1, wherein $R^2$ is $R^2$-9.276 (=formula I.286).
Table 287. Compounds of formula I.1, wherein $R^2$ is $R^2$-9.277 (=formula I.287).
Table 288. Compounds of formula I.1, wherein $R^2$ is $R^2$-9.278 (=formula I.288).
Table 289. Compounds of formula I.1, wherein $R^2$ is $R^2$-9.279 (=formula I.289).
Table 290. Compounds of formula I.1, wherein $R^2$ is $R^2$-9.280 (=formula I.290).
Table 291. Compounds of formula I.1, wherein $R^2$ is $R^2$-9.281 (=formula I.291).
Table 292. Compounds of formula I.1, wherein $R^2$ is $R^2$-9.282 (=formula I.292).
Table 293. Compounds of formula I.1, wherein $R^2$ is $R^2$-9.283 (=formula I.293).
Table 294. Compounds of formula I.1, wherein $R^2$ is $R^2$-9.284 (=formula I.294).
Table 295. Compounds of formula I.1, wherein $R^2$ is $R^2$-9.285 (=formula I.295).
Table 296. Compounds of formula I.1, wherein $R^2$ is $R^2$-9.286 (=formula I.296).
Table 297. Compounds of formula I.1, wherein $R^2$ is $R^2$-9.287 (=formula I.297).
Table 298. Compounds of formula I.1, wherein $R^2$ is $R^2$-9.288 (=formula I.298).
Table 299. Compounds of formula I.1, wherein $R^2$ is $R^2$-9.289 (=formula I.299).
Table 300. Compounds of formula I.1, wherein $R^2$ is $R^2$-9.290 (=formula I.300).
Table 301. Compounds of formula I.1, wherein $R^2$ is $R^2$-9.291 (=formula I.301).
Table 302. Compounds of formula I.1, wherein $R^2$ is $R^2$-9.292 (=formula I.302).
Table 303. Compounds of formula I.1, wherein $R^2$ is $R^2$-9.293 (=formula I.303).
Table 304. Compounds of formula I.1, wherein $R^2$ is $R^2$-9.294 (=formula I.304).
Table 305. Compounds of formula I.1, wherein $R^2$ is $R^2$-9.295 (=formula I.305).
Table 306. Compounds of formula I.1, wherein $R^2$ is $R^2$-9.296 (=formula I.306).
Table 307. Compounds of formula I.1, wherein $R^2$ is $R^2$-9.297 (=formula I.307).
Table 308. Compounds of formula I.1, wherein $R^2$ is $R^2$-9.298 (=formula I.308).
Table 309. Compounds of formula I.1, wherein $R^2$ is $R^2$-9.299 (=formula I.309).
Table 310. Compounds of formula I.1, wherein $R^2$ is $R^2$-9.300 (=formula I.310).
Table 311. Compounds of formula I.1, wherein $R^2$ is $R^2$-9.301 (=formula I.311).
Table 312. Compounds of formula I.1, wherein $R^2$ is $R^2$-9.302 (=formula I.312).
Table 313. Compounds of formula I.1, wherein $R^2$ is $R^2$-9.303 (=formula I.313).
Table 314. Compounds of formula I.1, wherein $R^2$ is $R^2$-9.304 (=formula I.314).
Table 315. Compounds of formula I.1, wherein $R^2$ is $R^2$-9.305 (=formula I.315).
Table 316. Compounds of formula I.1, wherein $R^2$ is $R^2$-9.306 (=formula I.316).
Table 317. Compounds of formula I.1, wherein $R^2$ is $R^2$-9.307 (=formula I.317).
Table 318. Compounds of formula I.1, wherein $R^2$ is $R^2$-9.308 (=formula I.318).
Table 319. Compounds of formula I.1, wherein $R^2$ is $R^2$-9.309 (=formula I.319).
Table 320. Compounds of formula I.1, wherein $R^2$ is $R^2$-9.310 (=formula I.320).
Table 321. Compounds of formula I.1, wherein $R^2$ is $R^2$-9.311 (=formula I.321).
Table 322. Compounds of formula I.1, wherein $R^2$ is $R^2$-9.312 (=formula I.322).
Table 323. Compounds of formula I.1, wherein $R^2$ is $R^2$-9.313 (=formula I.323).
Table 324. Compounds of formula I.1, wherein $R^2$ is $R^2$-9.314 (=formula I.324).
Table 325. Compounds of formula I.1, wherein $R^2$ is $R^2$-9.315 (=formula I.325).
Table 326. Compounds of formula I.1, wherein $R^2$ is $R^2$-9.316 (=formula I.326).
Table 327. Compounds of formula I.1, wherein $R^2$ is $R^2$-9.317 (=formula I.327).
Table 328. Compounds of formula I.1, wherein $R^2$ is $R^2$-9.318 (=formula I.328).
Table 329. Compounds of formula I.1, wherein $R^2$ is $R^2$-9.319 (=formula I.329).
Table 330. Compounds of formula I.1, wherein $R^2$ is $R^2$-9.320 (=formula I.330).
Table 331. Compounds of formula I.1, wherein $R^2$ is $R^2$-9.321 (=formula I.331).
Table 332. Compounds of formula I.1, wherein $R^2$ is $R^2$-9.322 (=formula I.332).
Table 333. Compounds of formula I.1, wherein $R^2$ is $R^2$-9.323 (=formula I.333).
Table 334. Compounds of formula I.1, wherein $R^2$ is $R^2$-9.324 (=formula I.334).
Table 335. Compounds of formula I.1, wherein $R^2$ is $R^2$-9.325 (=formula I.335).
Table 336. Compounds of formula I.1, wherein $R^2$ is $R^2$-9.326 (=formula I.336).
Table 337. Compounds of formula I.1, wherein $R^2$ is $R^2$-9.327 (=formula I.337).
Table 338. Compounds of formula I.1, wherein $R^2$ is $R^2$-9.328 (=formula I.338).
Table 339. Compounds of formula I.1, wherein $R^2$ is $R^2$-9.329 (=formula I.339).
Table 340. Compounds of formula I.1, wherein $R^2$ is $R^2$-9.330 (=formula I.340).

Table 341. Compounds of formula I.1, wherein $R^2$ is $R^2$-9.331 (=formula I.341).
Table 342. Compounds of formula I.1, wherein $R^2$ is $R^2$-9.332 (=formula I.342).
Table 343. Compounds of formula I.1, wherein $R^2$ is $R^2$-9.333 (=formula I.343).
Table 344. Compounds of formula I.1, wherein $R^2$ is $R^2$-9.334 (=formula I.344).
Table 345. Compounds of formula I.1, wherein $R^2$ is $R^2$-9.335 (=formula I.345).
Table 346. Compounds of formula I.1, wherein $R^2$ is $R^2$-9.336 (=formula I.346).
Table 347. Compounds of formula I.1, wherein $R^2$ is $R^2$-9.334 (=formula I.347).
Table 348. Compounds of formula I.1, wherein $R^2$ is $R^2$-9.338 (=formula I.348).
Table 349. Compounds of formula I.1, wherein $R^2$ is $R^2$-9.339 (=formula I.349).
Table 350. Compounds of formula I.1, wherein $R^2$ is $R^2$-9.340 (=formula I.350).
Table 351. Compounds of formula I.1, wherein $R^2$ is $R^2$-9.341 (=formula I.351).
Table 352. Compounds of formula I.1, wherein $R^2$ is $R^2$-9.342 (=formula I.352).
Table 353. Compounds of formula I.1, wherein $R^2$ is $R^2$-9.343 (=formula I.353).
Table 354. Compounds of formula I.1, wherein $R^2$ is $R^2$-9.344 (=formula I.354).
Table 355. Compounds of formula I.1, wherein $R^2$ is $R^2$-9.345 (=formula I.355).
Table 356. Compounds of formula I.1, wherein $R^2$ is $R^2$-9.346 (=formula I.356).
Table 357. Compounds of formula I.1, wherein $R^2$ is $R^2$-9.347 (=formula I.357).
Table 358. Compounds of formula I.1, wherein $R^2$ is $R^2$-9.348 (=formula I.358).
Table 359. Compounds of formula I.1, wherein $R^2$ is $R^2$-9.349 (=formula I.359).
Table 360. Compounds of formula I.1, wherein $R^2$ is $R^2$-9.350 (=formula I.360).
Table 361. Compounds of formula I.1, wherein $R^2$ is $R^2$-9.351 (=formula I.361).
Table 362. Compounds of formula I.1, wherein $R^2$ is $R^2$-9.352 (=formula I.362).
Table 363. Compounds of formula I.1, wherein $R^2$ is $R^2$-9.353 (=formula I.363).
Table 364. Compounds of formula I.1, wherein $R^2$ is $R^2$-9.354 (=formula I.364).
Table 365. Compounds of formula I.1, wherein $R^2$ is $R^2$-9.355 (=formula I.365).
Table 366. Compounds of formula I.1, wherein $R^2$ is $R^2$-9.356 (=formula I.366).
Table 367. Compounds of formula I.1, wherein $R^2$ is $R^2$-9.357 (=formula I.367).
Table 368. Compounds of formula I.1, wherein $R^2$ is $R^2$-9.358 (=formula I.368).
Table 369. Compounds of formula I.1, wherein $R^2$ is $R^2$-9.359 (=formula I.369).
Table 370. Compounds of formula I.1, wherein $R^2$ is $R^2$-9.360 (=formula I.370).
Table 371. Compounds of formula I.1, wherein $R^2$ is $R^2$-9.361 (=formula I.371).
Table 372. Compounds of formula I.1, wherein $R^2$ is $R^2$-9.362 (=formula I.372).
Table 373. Compounds of formula I.1, wherein $R^2$ is $R^2$-9.363 (=formula I.373).
Table 374. Compounds of formula I.1, wherein $R^2$ is $R^2$-9.364 (=formula I.374).
Table 375. Compounds of formula I.1, wherein $R^2$ is $R^2$-9.365 (=formula I.375).
Table 376. Compounds of formula I.1, wherein $R^2$ is $R^2$-9.366 (=formula I.376).
Table 377. Compounds of formula I.1, wherein $R^2$ is $R^2$-9.367 (=formula I.377).
Table 378. Compounds of formula I.1, wherein $R^2$ is $R^2$-9.368 (=formula I.378).
Table 379. Compounds of formula I.1, wherein $R^2$ is $R^2$-9.369 (=formula I.379).
Table 380. Compounds of formula I.1, wherein $R^2$ is $R^2$-9.370 (=formula I.380).
Table 381. Compounds of formula I.1, wherein $R^2$ is $R^2$-9.371 (=formula I.381).
Table 382. Compounds of formula I.1, wherein $R^2$ is $R^2$-9.372 (=formula I.382).
Table 383. Compounds of formula I.1, wherein $R^2$ is $R^2$-9.373 (=formula I.383).
Table 384. Compounds of formula I.1, wherein $R^2$ is $R^2$-9.374 (=formula I.384).
Table 385. Compounds of formula I.1, wherein $R^2$ is $R^2$-9.375 (=formula I.385).
Table 386. Compounds of formula I.1, wherein $R^2$ is $R^2$-9.376 (=formula I.386).
Table 387. Compounds of formula I.1, wherein $R^2$ is $R^2$-9.377 (=formula I.387).
Table 388. Compounds of formula I.1, wherein $R^2$ is $R^2$-9.378 (=formula I.388).
Table 389. Compounds of formula I.1, wherein $R^2$ is $R^2$-9.379 (=formula I.389).
Table 390. Compounds of formula I.1, wherein $R^2$ is $R^2$-9.380 (=formula I.390).
Table 391. Compounds of formula I.1, wherein $R^2$ is $R^2$-9.381 (=formula I.391).
Table 392. Compounds of formula I.1, wherein $R^2$ is $R^2$-9.382 (=formula I.392).
Table 393. Compounds of formula I.1, wherein $R^2$ is $R^2$-9.383 (=formula I.393).
Table 394. Compounds of formula I.1, wherein $R^2$ is $R^2$-9.384 (=formula I.394).
Table 395. Compounds of formula I.1, wherein $R^2$ is $R^2$-9.385 (=formula I.395).
Table 396. Compounds of formula I.1, wherein $R^2$ is $R^2$-9.386 (=formula I.396).
Table 397. Compounds of formula I.1, wherein $R^2$ is $R^2$-9.387 (=formula I.397).
Table 398. Compounds of formula I.1, wherein $R^2$ is $R^2$-9.388 (=formula I.398).
Table 399. Compounds of formula I.1, wherein $R^2$ is $R^2$-9.389 (=formula I.399).
Table 400. Compounds of formula I.1, wherein $R^2$ is $R^2$-9.390 (=formula I.400).
Table 401. Compounds of formula I.1, wherein $R^2$ is $R^2$-9.391 (=formula I.401).
Table 402. Compounds of formula I.1, wherein $R^2$ is $R^2$-9.392 (=formula I.402).
Table 403. Compounds of formula I.1, wherein $R^2$ is $R^2$-9.393 (=formula I.403).
Table 404. Compounds of formula I.1, wherein $R^2$ is $R^2$-9.394 (=formula I.404).
Table 405. Compounds of formula I.1, wherein $R^2$ is $R^2$-9.395 (=formula I.405).
Table 406. Compounds of formula I.1, wherein $R^2$ is $R^2$-9.396 (=formula I.406).

Table 407. Compounds of formula I.1, wherein $R^2$ is $R^2$-9.397 (=formula I.407).
Table 408. Compounds of formula I.1, wherein $R^2$ is $R^2$-9.398 (=formula I.408).
Table 409. Compounds of formula I.1, wherein $R^2$ is $R^2$-9.399 (=formula I.409).
Table 410. Compounds of formula I.1, wherein $R^2$ is $R^2$-9.400 (=formula I.410).
Table 411. Compounds of formula I.1, wherein $R^2$ is $R^2$-9.401 (=formula I.411).
Table 412. Compounds of formula I.1, wherein $R^2$ is $R^2$-9.402 (=formula I.412).
Table 413. Compounds of formula I.1, wherein $R^2$ is $R^2$-9.403 (=formula I.413).
Table 414. Compounds of formula I.1, wherein $R^2$ is $R^2$-9.404 (=formula I.414).
Table 415. Compounds of formula I.1, wherein $R^2$ is $R^2$-9.405 (=formula I.415).
Table 416. Compounds of formula I.1, wherein $R^2$ is $R^2$-9.406 (=formula I.416).
Table 417. Compounds of formula I.1, wherein $R^2$ is $R^2$-9.407 (=formula I.417).
Table 418. Compounds of formula I.1, wherein $R^2$ is $R^2$-9.408 (=formula I.418).
Table 419. Compounds of formula I.1, wherein $R^2$ is $R^2$-9.409 (=formula I.419).
Table 420. Compounds of formula I.1, wherein $R^2$ is $R^2$-9.410 (=formula I.420).
Table 421. Compounds of formula I.1, wherein $R^2$ is $R^2$-9.411 (=formula I.421).
Table 422. Compounds of formula I.1, wherein $R^2$ is $R^2$-9.412 (=formula I.422).
Table 423. Compounds of formula I.1, wherein $R^2$ is $R^2$-9.413 (=formula I.423).
Table 424. Compounds of formula I.1, wherein $R^2$ is $R^2$-9.414 (=formula I.424).
Table 425. Compounds of formula I.1, wherein $R^2$ is $R^2$-9.415 (=formula I.425).
Table 426. Compounds of formula I.1, wherein $R^2$ is $R^2$-9.416 (=formula I.426).
Table 427. Compounds of formula I.1, wherein $R^2$ is $R^2$-9.417 (=formula I.427).
Table 428. Compounds of formula I.1, wherein $R^2$ is $R^2$-9.418 (=formula I.428).
Table 429. Compounds of formula I.1, wherein $R^2$ is $R^2$-9.419 (=formula I.429).
Table 430. Compounds of formula I.1, wherein $R^2$ is $R^2$-9.420 (=formula I.430).
Table 431. Compounds of formula I.1, wherein $R^2$ is $R^2$-9.421 (=formula I.431).
Table 432. Compounds of formula I.1, wherein $R^2$ is $R^2$-9.422 (=formula I.432).
Table 433. Compounds of formula I.1, wherein $R^2$ is $R^2$-9.423 (=formula I.433).
Table 434. Compounds of formula I.1, wherein $R^2$ is $R^2$-9.424 (=formula I.434).
Table 435. Compounds of formula I.1, wherein $R^2$ is $R^2$-9.425 (=formula I.435).
Table 436. Compounds of formula I.1, wherein $R^2$ is $R^2$-9.426 (=formula I.436).
Table 437. Compounds of formula I.1, wherein $R^2$ is $R^2$-9.427 (=formula I.437).
Table 438. Compounds of formula I.1, wherein $R^2$ is $R^2$-9.428 (=formula I.438).
Table 439. Compounds of formula I.1, wherein $R^2$ is $R^2$-9.429 (=formula I.439).
Table 440. Compounds of formula I.1, wherein $R^2$ is $R^2$-9.430 (=formula I.440).
Table 441. Compounds of formula I.1, wherein $R^2$ is $R^2$-9.431 (=formula I.441).
Table 442. Compounds of formula I.1, wherein $R^2$ is $R^2$-9.432 (=formula I.442).
Table 443. Compounds of formula I.1, wherein $R^2$ is $R^2$-9.433 (=formula I.443).
Table 444. Compounds of formula I.1, wherein $R^2$ is $R^2$-9.434 (=formula I.444).
Table 445. Compounds of formula I.1, wherein $R^2$ is $R^2$-9.435 (=formula I.445).
Table 446. Compounds of formula I.1, wherein $R^2$ is $R^2$-9.436 (=formula I.446).
Table 447. Compounds of formula I.1, wherein $R^2$ is $R^2$-9.437 (=formula I.447).
Table 448. Compounds of formula I.1, wherein $R^2$ is $R^2$-9.438 (=formula I.448).
Table 449. Compounds of formula I.1, wherein $R^2$ is $R^2$-9.439 (=formula I.449).
Table 450. Compounds of formula I.1, wherein $R^2$ is $R^2$-9.440 (=formula I.450).
Table 451. Compounds of formula I.1, wherein $R^2$ is $R^2$-9.441 (=formula I.451).
Table 452. Compounds of formula I.1, wherein $R^2$ is $R^2$-9.442 (=formula I.452).
Table 453. Compounds of formula I.1, wherein $R^2$ is $R^2$-9.443 (=formula I.453).
Table 454. Compounds of formula I.1, wherein $R^2$ is $R^2$-9.444 (=formula I.454).
Table 455. Compounds of formula I.1, wherein $R^2$ is $R^2$-9.445 (=formula I.455).
Table 456. Compounds of formula I.1, wherein $R^2$ is $R^2$-9.446 (=formula I.456).
Table 457. Compounds of formula I.1, wherein $R^2$ is $R^2$-9.447 (=formula I.457).
Table 458. Compounds of formula I.1, wherein $R^2$ is $R^2$-9.448 (=formula I.458).
Table 459. Compounds of formula I.1, wherein $R^2$ is $R^2$-9.449 (=formula I.459).
Table 460. Compounds of formula I.1, wherein $R^2$ is $R^2$-9.450 (=formula I.460).
Table 461. Compounds of formula I.1, wherein $R^2$ is $R^2$-9.451 (=formula I.461).
Table 462. Compounds of formula I.1, wherein $R^2$ is $R^2$-9.452 (=formula I.462).
Table 463. Compounds of formula I.1, wherein $R^2$ is $R^2$-9.453 (=formula I.463).
Table 464. Compounds of formula I.1, wherein $R^2$ is $R^2$-9.454 (=formula I.464).
Table 465. Compounds of formula I.1, wherein $R^2$ is $R^2$-9.455 (=formula I.465).
Table 466. Compounds of formula I.1, wherein $R^2$ is $R^2$-9.456 (=formula I.466).
Table 467. Compounds of formula I.1, wherein $R^2$ is $R^2$-9.457 (=formula I.467).
Table 468. Compounds of formula I.1, wherein $R^2$ is $R^2$-9.458 (=formula I.468).
Table 469. Compounds of formula I.1, wherein $R^2$ is $R^2$-9.459 (=formula I.469).
Table 470. Compounds of formula I.1, wherein $R^2$ is $R^2$-9.460 (=formula I.470).
Table 471. Compounds of formula I.1, wherein $R^2$ is $R^2$-9.461 (=formula I.471).
Table 472. Compounds of formula I.1, wherein $R^2$ is $R^2$-9.462 (=formula I.472).

Table 473. Compounds of formula I.1, wherein $R^2$ is $R^2$-9.463 (=formula I.473).
Table 474. Compounds of formula I.1, wherein $R^2$ is $R^2$-9.464 (=formula I.474).
Table 475. Compounds of formula I.1, wherein $R^2$ is $R^2$-9.465 (=formula I.475).
Table 476. Compounds of formula I.1, wherein $R^2$ is $R^2$-9.466 (=formula I.476).
Table 477. Compounds of formula I.1, wherein $R^2$ is $R^2$-9.467 (=formula I.477).
Table 478. Compounds of formula I.1, wherein $R^2$ is $R^2$-9.468 (=formula I.478).
Table 479. Compounds of formula I.1, wherein $R^2$ is $R^2$-9.469 (=formula I.479).
Table 480. Compounds of formula I.1, wherein $R^2$ is $R^2$-9.470 (=formula I.480).
Table 481. Compounds of formula I.1, wherein $R^2$ is $R^2$-9.471 (=formula I.481).
Table 482. Compounds of formula I.1, wherein $R^2$ is $R^2$-9.472 (=formula I.482).
Table 483. Compounds of formula I.1, wherein $R^2$ is $R^2$-9.473 (=formula I.483).
Table 484. Compounds of formula I.1, wherein $R^2$ is $R^2$-9.474 (=formula I.484).
Table 485. Compounds of formula I.1, wherein $R^2$ is $R^2$-9.475 (=formula I.485).
Table 486. Compounds of formula I.1, wherein $R^2$ is $R^2$-9.476 (=formula I.486).
Table 487. Compounds of formula I.1, wherein $R^2$ is $R^2$-9.477 (=formula I.487).
Table 488. Compounds of formula I.1, wherein $R^2$ is $R^2$-9.478 (=formula I.488).
Table 489. Compounds of formula I.1, wherein $R^2$ is $R^2$-9.479 (=formula I.489).
Table 490. Compounds of formula I.1, wherein $R^2$ is $R^2$-9.480 (=formula I.490).
Table 491. Compounds of formula I.1, wherein $R^2$ is $R^2$-9.481 (=formula I.491).
Table 492. Compounds of formula I.1, wherein $R^2$ is $R^2$-9.482 (=formula I.492).
Table 493. Compounds of formula I.1, wherein $R^2$ is $R^2$-9.483 (=formula I.493).
Table 494. Compounds of formula I.1, wherein $R^2$ is $R^2$-9.484 (=formula I.494).
Table 495. Compounds of formula I.1, wherein $R^2$ is $R^2$-9.485 (=formula I.495).
Table 496. Compounds of formula I.1, wherein $R^2$ is $R^2$-9.486 (=formula I.496).
Table 497. Compounds of formula I.1, wherein $R^2$ is $R^2$-9.487 (=formula I.497).
Table 498. Compounds of formula I.1, wherein $R^2$ is $R^2$-9.488 (=formula I.498).
Table 499. Compounds of formula I.1, wherein $R^2$ is $R^2$-9.489 (=formula I.499).
Table 500. Compounds of formula I.1, wherein $R^2$ is $R^2$-9.490 (=formula I.500).
Table 501. Compounds of formula I.1, wherein $R^2$ is $R^2$-9.491 (=formula I.501).
Table 502. Compounds of formula I.1, wherein $R^2$ is $R^2$-9.492 (=formula I.502).
Table 503. Compounds of formula I.1, wherein $R^2$ is $R^2$-9.493 (=formula I.503).
Table 504. Compounds of formula I.1, wherein $R^2$ is $R^2$-9.494 (=formula I.504).
Table 505. Compounds of formula I.1, wherein $R^2$ is $R^2$-9.495 (=formula I.505).
Table 506. Compounds of formula I.1, wherein $R^2$ is $R^2$-9.496 (=formula I.506).
Table 507. Compounds of formula I.1, wherein $R^2$ is $R^2$-9.497 (=formula I.507).
Table 508. Compounds of formula I.1, wherein $R^2$ is $R^2$-9.498 (=formula I.508).
Table 509. Compounds of formula I.1, wherein $R^2$ is $R^2$-9.499 (=formula I.509).
Table 510. Compounds of formula I.1, wherein $R^2$ is $R^2$-9.500 (=formula I.510).
Table 511. Compounds of formula I.1, wherein $R^2$ is $R^2$-9.501 (=formula I.511).
Table 512. Compounds of formula I.1, wherein $R^2$ is $R^2$-9.502 (=formula I.512).
Table 513. Compounds of formula I.1, wherein $R^2$ is $R^2$-9.503 (=formula I.513).
Table 514. Compounds of formula I.1, wherein $R^2$ is $R^2$-9.504 (=formula I.514).
Table 515. Compounds of formula I.1, wherein $R^2$ is $R^2$-9.505 (=formula I.515).
Table 516. Compounds of formula I.1, wherein $R^2$ is $R^2$-9.506 (=formula I.516).
Table 517. Compounds of formula I.1, wherein $R^2$ is $R^2$-9.507 (=formula I.517).
Table 518. Compounds of formula I.1, wherein $R^2$ is $R^2$-9.508 (=formula I.518).
Table 519. Compounds of formula I.1, wherein $R^2$ is $R^2$-9.509 (=formula I.519).
Table 520. Compounds of formula I.1, wherein $R^2$ is $R^2$-9.510 (=formula I.520).
Table 521. Compounds of formula I.1, wherein $R^2$ is $R^2$-9.511 (=formula I.521).
Table 522. Compounds of formula I.1, wherein $R^2$ is $R^2$-9.512 (=formula I.522).
Table 523. Compounds of formula I.1, wherein $R^2$ is $R^2$-9.513 (=formula I.523).
Table 524. Compounds of formula I.1, wherein $R^2$ is $R^2$-9.514 (=formula I.524).
Table 525. Compounds of formula I.1, wherein $R^2$ is $R^2$-9.515 (=formula I.525).
Table 526. Compounds of formula I.1, wherein $R^2$ is $R^2$-9.516 (=formula I.526).
Table 527. Compounds of formula I.1, wherein $R^2$ is $R^2$-9.517 (=formula I.527).
Table 528. Compounds of formula I.1, wherein $R^2$ is $R^2$-9.518 (=formula I.528).
Table 529. Compounds of formula I.1, wherein $R^2$ is $R^2$-9.519 (=formula I.529).
Table 530. Compounds of formula I.1, wherein $R^2$ is $R^2$-9.520 (=formula I.530).
Table 531. Compounds of formula I.1, wherein $R^2$ is $R^2$-9.521 (=formula I.531).
Table 532. Compounds of formula I.1, wherein $R^2$ is $R^2$-9.522 (=formula I.532).
Table 533. Compounds of formula I.1, wherein $R^2$ is $R^2$-9.523 (=formula I.533).
Table 534. Compounds of formula I.1, wherein $R^2$ is $R^2$-9.524 (=formula I.534).
Table 535. Compounds of formula I.1, wherein $R^2$ is $R^2$-9.525 (=formula I.535).
Table 536. Compounds of formula I.1, wherein $R^2$ is $R^2$-9.526 (=formula I.536).
Table 537. Compounds of formula I.1, wherein $R^2$ is $R^2$-9.527 (=formula I.537).
Table 538. Compounds of formula I.1, wherein $R^2$ is $R^2$-9.528 (=formula I.538).

Table 539. Compounds of formula I.1, wherein $R^2$ is $R^2$-9.529 (=formula I.539).
Table 540. Compounds of formula I.1, wherein $R^2$ is $R^2$-9.530 (=formula I.540).
Table 541. Compounds of formula I.1, wherein $R^2$ is $R^2$-9.531 (=formula I.541).
Table 542. Compounds of formula I.1, wherein $R^2$ is $R^2$-9.532 (=formula I.542).
Table 543. Compounds of formula I.1, wherein $R^2$ is $R^2$-9.533 (=formula I.543).
Table 544. Compounds of formula I.1, wherein $R^2$ is $R^2$-9.534 (=formula I.544).
Table 545. Compounds of formula I.1, wherein $R^2$ is $R^2$-9.535 (=formula I.545).
Table 546. Compounds of formula I.1, wherein $R^2$ is $R^2$-9.536 (=formula I.546).
Table 547. Compounds of formula I.1, wherein $R^2$ is $R^2$-9.537 (=formula I.547).
Table 548. Compounds of formula I.1, wherein $R^2$ is $R^2$-9.538 (=formula I.548).
Table 549. Compounds of formula I.1, wherein $R^2$ is $R^2$-9.539 (=formula I.549).
Table 550. Compounds of formula I.1, wherein $R^2$ is $R^2$-9.540 (=formula I.550).
Table 551. Compounds of formula I.1, wherein $R^2$ is $R^2$-9.541 (=formula I.551).
Table 552. Compounds of formula I.1, wherein $R^2$ is $R^2$-9.542 (=formula I.552).
Table 553. Compounds of formula I.1, wherein $R^2$ is $R^2$-9.543 (=formula I.553).
Table 554. Compounds of formula I.1, wherein $R^2$ is $R^2$-9.544 (=formula I.554).
Table 555. Compounds of formula I.1, wherein $R^2$ is $R^2$-9.545 (=formula I.555).
Table 556. Compounds of formula I.1, wherein $R^2$ is $R^2$-9.546 (=formula I.556).
Table 557. Compounds of formula I.1, wherein $R^2$ is $R^2$-9.547 (=formula I.557).
Table 558. Compounds of formula I.1, wherein $R^2$ is $R^2$-9.548 (=formula I.558).
Table 559. Compounds of formula I.1, wherein $R^2$ is $R^2$-9.549 (=formula I.559).
Table 560. Compounds of formula I.1, wherein $R^2$ is $R^2$-9.550 (=formula I.560).
Table 561. Compounds of formula I.1, wherein $R^2$ is $R^2$-9.551 (=formula I.561).
Table 562. Compounds of formula I.1, wherein $R^2$ is $R^2$-9.552 (=formula I.562).
Table 563. Compounds of formula I.1, wherein $R^2$ is $R^2$-9.553 (=formula I.563).
Table 564. Compounds of formula I.1, wherein $R^2$ is $R^2$-9.554 (=formula I.564).
Table 565. Compounds of formula I.1, wherein $R^2$ is $R^2$-9.555 (=formula I.565).
Table 566. Compounds of formula I.1, wherein $R^2$ is $R^2$-9.556 (=formula I.566).
Table 567. Compounds of formula I.1, wherein $R^2$ is $R^2$-9.557 (=formula I.567).
Table 568. Compounds of formula I.1, wherein $R^2$ is $R^2$-9.558 (=formula I.568).
Table 569. Compounds of formula I.1, wherein $R^2$ is $R^2$-9.559 (=formula I.569).
Table 570. Compounds of formula I.1, wherein $R^2$ is $R^2$-9.560 (=formula I.570).
Table 571. Compounds of formula I.1, wherein $R^2$ is $R^2$-9.561 (=formula I.571).
Table 572. Compounds of formula I.1, wherein $R^2$ is $R^2$-9.562 (=formula I.572).
Table 573. Compounds of formula I.1, wherein $R^2$ is $R^2$-9.563 (=formula I.573).
Table 574. Compounds of formula I.1, wherein $R^2$ is $R^2$-9.564 (=formula I.574).
Table 575. Compounds of formula I.1, wherein $R^2$ is $R^2$-9.565 (=formula I.575).
Table 576. Compounds of formula I.1, wherein $R^2$ is $R^2$-9.566 (=formula I.576).
Table 577. Compounds of formula I.1, wherein $R^2$ is $R^2$-9.567 (=formula I.577).
Table 578. Compounds of formula I.1, wherein $R^2$ is $R^2$-9.568 (=formula I.578).
Table 579. Compounds of formula I.1, wherein $R^2$ is $R^2$-9.569 (=formula I.579).
Table 580. Compounds of formula I.1, wherein $R^2$ is $R^2$-9.570 (=formula I.580).
Table 581. Compounds of formula I.1, wherein $R^2$ is $R^2$-9.571 (=formula I.581).
Table 582. Compounds of formula I.1, wherein $R^2$ is $R^2$-9.572 (=formula I.582).
Table 583. Compounds of formula I.1, wherein $R^2$ is $R^2$-9.573 (=formula I.583).
Table 584. Compounds of formula I.1, wherein $R^2$ is $R^2$-9.574 (=formula I.584).
Table 585. Compounds of formula I.1, wherein $R^2$ is $R^2$-9.575 (=formula I.585).
Table 586. Compounds of formula I.1, wherein $R^2$ is $R^2$-9.576 (=formula I.586).
Table 587. Compounds of formula I.1, wherein $R^2$ is $R^2$-9.577 (=formula I.587).
Table 588. Compounds of formula I.1, wherein $R^2$ is $R^2$-9.578 (=formula I.588).
Table 589. Compounds of formula I.1, wherein $R^2$ is $R^2$-9.579 (=formula I.589).
Table 590. Compounds of formula I.1, wherein $R^2$ is $R^2$-9.580 (=formula I.590).
Table 591. Compounds of formula I.1, wherein $R^2$ is $R^2$-9.581 (=formula I.591).
Table 592. Compounds of formula I.1, wherein $R^2$ is $R^2$-9.582 (=formula I.592).
Table 593. Compounds of formula I.1, wherein $R^2$ is $R^2$-9.583 (=formula I.593).
Table 594. Compounds of formula I.1, wherein $R^2$ is $R^2$-9.584 (=formula I.594).
Table 595. Compounds of formula I.1, wherein $R^2$ is $R^2$-9.585 (=formula I.595).
Table 596. Compounds of formula I.1, wherein $R^2$ is $R^2$-9.586 (=formula I.596).
Table 597. Compounds of formula I.1, wherein $R^2$ is $R^2$-9.587 (=formula I.597).
Table 598. Compounds of formula I.1, wherein $R^2$ is $R^2$-9.588 (=formula I.598).
Table 599. Compounds of formula I.1, wherein $R^2$ is $R^2$-9.589 (=formula I.599).
Table 600. Compounds of formula I.1, wherein $R^2$ is $R^2$-9.590 (=formula I.600).
Table 601. Compounds of formula I.1, wherein $R^2$ is $R^2$-9.591 (=formula I.601).
Table 602. Compounds of formula I.1, wherein $R^2$ is $R^2$-9.592 (=formula I.602).
Table 603. Compounds of formula I.1, wherein $R^2$ is $R^2$-9.593 (=formula I.603).
Table 604. Compounds of formula I.1, wherein $R^2$ is $R^2$-9.594 (=formula I.604).

Table 605. Compounds of formula I.1, wherein $R^2$ is $R^2$-9.595 (=formula I.605).
Table 606. Compounds of formula I.1, wherein $R^2$ is $R^2$-9.596 (=formula I.606).
Table 607. Compounds of formula I.1, wherein $R^2$ is $R^2$-9.597 (=formula I.607).
Table 608. Compounds of formula I.1, wherein $R^2$ is $R^2$-9.598 (=formula I.608).
Table 609. Compounds of formula I.1, wherein $R^2$ is $R^2$-9.599 (=formula I.609).
Table 610. Compounds of formula I.1, wherein $R^2$ is $R^2$-9.600 (=formula I.610).
Table 611. Compounds of formula I.1, wherein $R^2$ is $R^2$-9.601 (=formula I.611).
Table 612. Compounds of formula I.1, wherein $R^2$ is $R^2$-9.602 (=formula I.612).
Table 613. Compounds of formula I.1, wherein $R^2$ is $R^2$-9.603 (=formula I.613).
Table 614. Compounds of formula I.1, wherein $R^2$ is $R^2$-9.604 (=formula I.614).
Table 615. Compounds of formula I.1, wherein $R^2$ is $R^2$-9.605 (=formula I.615).
Table 616. Compounds of formula I.1, wherein $R^2$ is $R^2$-9.606 (=formula I.616).
Table 617. Compounds of formula I.1, wherein $R^2$ is $R^2$-9.607 (=formula I.617).
Table 618. Compounds of formula I.1, wherein $R^2$ is $R^2$-9.608 (=formula I.618).
Table 619. Compounds of formula I.1, wherein $R^2$ is $R^2$-9.609 (=formula I.619).
Table 620. Compounds of formula I.1, wherein $R^2$ is $R^2$-9.610 (=formula I.620).
Table 621. Compounds of formula I.1, wherein $R^2$ is $R^2$-9.611 (=formula I.621).
Table 622. Compounds of formula I.1, wherein $R^2$ is $R^2$-9.612 (=formula I.622).
Table 623. Compounds of formula I.1, wherein $R^2$ is $R^2$-9.613 (=formula I.623).
Table 624. Compounds of formula I.1, wherein $R^2$ is $R^2$-9.614 (=formula I.624).
Table 625. Compounds of formula I.1, wherein $R^2$ is $R^2$-9.615 (=formula I.625).
Table 626. Compounds of formula I.1, wherein $R^2$ is $R^2$-9.616 (=formula I.626).
Table 627. Compounds of formula I.1, wherein $R^2$ is $R^2$-9.617 (=formula I.627).
Table 628. Compounds of formula I.1, wherein $R^2$ is $R^2$-9.618 (=formula I.628).
Table 629. Compounds of formula I.1, wherein $R^2$ is $R^2$-9.619 (=formula I.629).
Table 630. Compounds of formula I.1, wherein $R^2$ is $R^2$-9.620 (=formula I.630).
Table 631. Compounds of formula I.1, wherein $R^2$ is $R^2$-9.621 (=formula I.631).
Table 632. Compounds of formula I.1, wherein $R^2$ is $R^2$-9.622 (=formula I.632).
Table 633. Compounds of formula I.1, wherein $R^2$ is $R^2$-9.623 (=formula I.633).
Table 634. Compounds of formula I.1, wherein $R^2$ is $R^2$-9.624 (=formula I.634).
Table 635. Compounds of formula I.1, wherein $R^2$ is $R^2$-9.625 (=formula I.635).
Table 636. Compounds of formula I.1, wherein $R^2$ is $R^2$-9.626 (=formula I.636).
Table 637. Compounds of formula I.1, wherein $R^2$ is $R^2$-9.627 (=formula I.637).
Table 638. Compounds of formula I.1, wherein $R^2$ is $R^2$-9.628 (=formula I.638).
Table 639. Compounds of formula I.1, wherein $R^2$ is $R^2$-9.629 (=formula I.639).
Table 640. Compounds of formula I.1, wherein $R^2$ is $R^2$-9.630 (=formula I.640).
Table 641. Compounds of formula I.1, wherein $R^2$ is $R^2$-9.631 (=formula I.641).
Table 642. Compounds of formula I.1, wherein $R^2$ is $R^2$-9.632 (=formula I.642).
Table 643. Compounds of formula I.1, wherein $R^2$ is $R^2$-9.633 (=formula I.643).
Table 644. Compounds of formula I.1, wherein $R^2$ is $R^2$-9.634 (=formula I.644).
Table 645. Compounds of formula I.1, wherein $R^2$ is $R^2$-9.635 (=formula I.645).
Table 646. Compounds of formula I.1, wherein $R^2$ is $R^2$-9.636 (=formula I.646).
Table 647. Compounds of formula I.1, wherein $R^2$ is $R^2$-9.637 (=formula I.647).
Table 648. Compounds of formula I.1, wherein $R^2$ is $R^2$-9.638 (=formula I.648).
Table 649. Compounds of formula I.1, wherein $R^2$ is $R^2$-9.639 (=formula I.649).
Table 650. Compounds of formula I.1, wherein $R^2$ is $R^2$-9.640 (=formula I.650).
Table 651. Compounds of formula I.1, wherein $R^2$ is $R^2$-9.641 (=formula I.651).
Table 652. Compounds of formula I.1, wherein $R^2$ is $R^2$-9.642 (=formula I.652).
Table 653. Compounds of formula I.1, wherein $R^2$ is $R^2$-9.643 (=formula I.653).
Table 654. Compounds of formula I.1, wherein $R^2$ is $R^2$-9.644 (=formula I.654).
Table 655. Compounds of formula I.1, wherein $R^2$ is $R^2$-9.645 (=formula I.655).
Table 656. Compounds of formula I.1, wherein $R^2$ is $R^2$-9.646 (=formula I.656).
Table 657. Compounds of formula I.1, wherein $R^2$ is $R^2$-9.647 (=formula I.657).
Table 658. Compounds of formula I.1, wherein $R^2$ is $R^2$-9.648 (=formula I.658).
Table 659. Compounds of formula I.1, wherein $R^2$ is $R^2$-9.649 (=formula I.659).
Table 660. Compounds of formula I.1, wherein $R^2$ is $R^2$-9.650 (=formula I.660).
Table 661. Compounds of formula I.1, wherein $R^2$ is $R^2$-9.651 (=formula I.661).
Table 662. Compounds of formula I.1, wherein $R^2$ is $R^2$-9.652 (=formula I.662).
Table 663. Compounds of formula I.1, wherein $R^2$ is $R^2$-9.653 (=formula I.663).
Table 664. Compounds of formula I.1, wherein $R^2$ is $R^2$-9.654 (=formula I.664).
Table 665. Compounds of formula I.1, wherein $R^2$ is $R^2$-9.655 (=formula I.665).
Table 666. Compounds of formula I.1, wherein $R^2$ is $R^2$-9.656 (=formula I.666).
Table 667. Compounds of formula I.1, wherein $R^2$ is $R^2$-9.657 (=formula I.667).
Table 668. Compounds of formula I.1, wherein $R^2$ is $R^2$-9.658 (=formula I.668).
Table 669. Compounds of formula I.1, wherein $R^2$ is $R^2$-9.659 (=formula I.669).
Table 670. Compounds of formula I.1, wherein $R^2$ is $R^2$-9.660 (=formula I.670).

Table 671. Compounds of formula I.1, wherein $R^2$ is $R^2$-9.661 (=formula I.671).
Table 672. Compounds of formula I.1, wherein $R^2$ is $R^2$-9.662 (=formula I.672).
Table 673. Compounds of formula I.1, wherein $R^2$ is $R^2$-9.663 (=formula I.673).
Table 674. Compounds of formula I.1, wherein $R^2$ is $R^2$-9.664 (=formula I.674).
Table 675. Compounds of formula I.1, wherein $R^2$ is $R^2$-9.665 (=formula I.675).
Table 676. Compounds of formula I.1, wherein $R^2$ is $R^2$-9.666 (=formula I.676).
Table 677. Compounds of formula I.1, wherein $R^2$ is $R^2$-9.667 (=formula I.677).
Table 678. Compounds of formula I.1, wherein $R^2$ is $R^2$-9.668 (=formula I.678).
Table 679. Compounds of formula I.1, wherein $R^2$ is $R^2$-9.669 (=formula I.679).
Table 680. Compounds of formula I.1, wherein $R^2$ is $R^2$-9.670 (=formula I.680).
Table 681. Compounds of formula I.1, wherein $R^2$ is $R^2$-9.671 (=formula I.681).
Table 682. Compounds of formula I.1, wherein $R^2$ is $R^2$-9.672 (=formula I.682).
Table 683. Compounds of formula I.1, wherein $R^2$ is $R^2$-9.673 (=formula I.683).
Table 684. Compounds of formula I.1, wherein $R^2$ is $R^2$-9.674 (=formula I.684).
Table 685. Compounds of formula I.1, wherein $R^2$ is $R^2$-9.675 (=formula I.685).
Table 686. Compounds of formula I.1, wherein $R^2$ is $R^2$-9.676 (=formula I.686).
Table 687. Compounds of formula I.1, wherein $R^2$ is $R^2$-10.1 (=formula I.687).
Table 688. Compounds of formula I.1, wherein $R^2$ is $R^2$-10.2 (=formula I.688).
Table 689. Compounds of formula I.1, wherein $R^2$ is $R^2$-10.3 (=formula I.689).
Table 690. Compounds of formula I.1, wherein $R^2$ is $R^2$-10.4 (=formula I.690).
Table 691. Compounds of formula I.1, wherein $R^2$ is $R^2$-10.5 (=formula I.691).
Table 692. Compounds of formula I.1, wherein $R^2$ is $R^2$-10.6 (=formula I.692).
Table 693. Compounds of formula I.1, wherein $R^2$ is $R^2$-10.7 (=formula I.693).
Table 694. Compounds of formula I.1, wherein $R^2$ is $R^2$-10.8 (=formula I.694).
Table 695. Compounds of formula I.1, wherein $R^2$ is $R^2$-10.9 (=formula I.695).
Table 696. Compounds of formula I.1, wherein $R^2$ is $R^2$-10.10 (=formula I.696).
Table 697. Compounds of formula I.1, wherein $R^2$ is $R^2$-10.11 (=formula I.697).
Table 698. Compounds of formula I.1, wherein $R^2$ is $R^2$-10.12 (=formula I.698).
Table 699. Compounds of formula I.1, wherein $R^2$ is $R^2$-10.13 (=formula I.699).
Table 700. Compounds of formula I.1, wherein $R^2$ is $R^2$-10.14 (=formula I.700).
Table 701. Compounds of formula I.1, wherein $R^2$ is $R^2$-10.15 (=formula I.701).
Table 702. Compounds of formula I.1, wherein $R^2$ is $R^2$-10.16 (=formula I.702).
Table 703. Compounds of formula I.1, wherein $R^2$ is $R^2$-10.17 (=formula I.703).
Table 704. Compounds of formula I.1, wherein $R^2$ is $R^2$-10.18 (=formula I.704).
Table 705. Compounds of formula I.1, wherein $R^2$ is $R^2$-10.19 (=formula I.705).
Table 706. Compounds of formula I.1, wherein $R^2$ is $R^2$-10.20 (=formula I.706).
Table 707. Compounds of formula I.1, wherein $R^2$ is $R^2$-10.21 (=formula I.707).
Table 708. Compounds of formula I.1, wherein $R^2$ is $R^2$-10.22 (=formula I.708).
Table 709. Compounds of formula I.1, wherein $R^2$ is $R^2$-10.23 (=formula I.709).
Table 710. Compounds of formula I.1, wherein $R^2$ is $R^2$-10.24 (=formula I.710).
Table 711. Compounds of formula I.1, wherein $R^2$ is $R^2$-10.25 (=formula I.711).
Table 712. Compounds of formula I.1, wherein $R^2$ is $R^2$-10.26 (=formula I.712).
Table 713. Compounds of formula I.1, wherein $R^2$ is $R^2$-10.27 (=formula I.713).
Table 714. Compounds of formula I.1, wherein $R^2$ is $R^2$-10.28 (=formula I.714).
Table 715. Compounds of formula I.1, wherein $R^2$ is $R^2$-10.29 (=formula I.715).
Table 716. Compounds of formula I.1, wherein $R^2$ is $R^2$-10.30 (=formula I.716).
Table 717. Compounds of formula I.1, wherein $R^2$ is $R^2$-10.31 (=formula I.717).
Table 718. Compounds of formula I.1, wherein $R^2$ is $R^2$-10.32 (=formula I.718).
Table 719. Compounds of formula I.1, wherein $R^2$ is $R^2$-10.33 (=formula I.719).
Table 720. Compounds of formula I.1, wherein $R^2$ is $R^2$-10.34 (=formula I.720).
Table 721. Compounds of formula I.1, wherein $R^2$ is $R^2$-10.35 (=formula I.721).
Table 722. Compounds of formula I.1, wherein $R^2$ is $R^2$-10.36 (=formula I.722).
Table 723. Compounds of formula I.1, wherein $R^2$ is $R^2$-10.37 (=formula I.723).
Table 724. Compounds of formula I.1, wherein $R^2$ is $R^2$-10.38 (=formula I.724).
Table 725. Compounds of formula I.1, wherein $R^2$ is $R^2$-10.39 (=formula I.725).
Table 726. Compounds of formula I.1, wherein $R^2$ is $R^2$-10.40 (=formula I.726).
Table 727. Compounds of formula I.1, wherein $R^2$ is $R^2$-10.41 (=formula I.727).
Table 728. Compounds of formula I.1, wherein $R^2$ is $R^2$-10.42 (=formula I.728).
Table 729. Compounds of formula I.1, wherein $R^2$ is $R^2$-10.43 (=formula I.729).
Table 730. Compounds of formula I.1, wherein $R^2$ is $R^2$-10.44 (=formula I.730).
Table 731. Compounds of formula I.1, wherein $R^2$ is $R^2$-10.45 (=formula I.731).
Table 732. Compounds of formula I.1, wherein $R^2$ is $R^2$-10.46 (=formula I.732).
Table 733. Compounds of formula I.1, wherein $R^2$ is $R^2$-10.47 (=formula I.733).
Table 734. Compounds of formula I.1, wherein $R^2$ is $R^2$-10.48 (=formula I.734).
Table 735. Compounds of formula I.1, wherein $R^2$ is $R^2$-10.49 (=formula I.735).
Table 736. Compounds of formula I.1, wherein $R^2$ is $R^2$-10.50 (=formula I.736).

Table 737. Compounds of formula I.1, wherein $R^2$ is $R^2$-10.51 (=formula I.737).
Table 738. Compounds of formula I.1, wherein $R^2$ is $R^2$-10.52 (=formula I.738).
Table 739. Compounds of formula I.1, wherein $R^2$ is $R^2$-10.53 (=formula I.739).
Table 740. Compounds of formula I.1, wherein $R^2$ is $R^2$-10.54 (=formula I.740).
Table 741. Compounds of formula I.1, wherein $R^2$ is $R^2$-10.55 (=formula I.741).
Table 742. Compounds of formula I.1, wherein $R^2$ is $R^2$-10.56 (=formula I.742).
Table 743. Compounds of formula I.1, wherein $R^2$ is $R^2$-10.57 (=formula I.743).
Table 744. Compounds of formula I.1, wherein $R^2$ is $R^2$-10.58 (=formula I.744).
Table 745. Compounds of formula I.1, wherein $R^2$ is $R^2$-10.59 (=formula I.745).
Table 746. Compounds of formula I.1, wherein $R^2$ is $R^2$-10.60 (=formula I.746).
Table 747. Compounds of formula I.1, wherein $R^2$ is $R^2$-10.61 (=formula I.747).
Table 748. Compounds of formula I.1, wherein $R^2$ is $R^2$-10.62 (=formula I.748).
Table 749. Compounds of formula I.1, wherein $R^2$ is $R^2$-10.63 (=formula I.749).
Table 750. Compounds of formula I.1, wherein $R^2$ is $R^2$-10.64 (=formula I.750).
Table 751. Compounds of formula I.1, wherein $R^2$ is $R^2$-10.65 (=formula I.751).
Table 752. Compounds of formula I.1, wherein $R^2$ is $R^2$-10.66 (=formula I.752).
Table 753. Compounds of formula I.1, wherein $R^2$ is $R^2$-10.67 (=formula I.753).
Table 754. Compounds of formula I.1, wherein $R^2$ is $R^2$-10.68 (=formula I.754).
Table 755. Compounds of formula I.1, wherein $R^2$ is $R^2$-10.69 (=formula I.755).
Table 756. Compounds of formula I.1, wherein $R^2$ is $R^2$-10.70 (=formula I.756).
Table 757. Compounds of formula I.1, wherein $R^2$ is $R^2$-10.71 (=formula I.757).
Table 758. Compounds of formula I.1, wherein $R^2$ is $R^2$-10.72 (=formula I.758).
Table 759. Compounds of formula I.1, wherein $R^2$ is $R^2$-10.73 (=formula I.759).
Table 760. Compounds of formula I.1, wherein $R^2$ is $R^2$-10.74 (=formula I.760).
Table 761. Compounds of formula I.1, wherein $R^2$ is $R^2$-10.75 (=formula I.761).
Table 762. Compounds of formula I.1, wherein $R^2$ is $R^2$-10.76 (=formula I.762).
Table 763. Compounds of formula I.1, wherein $R^2$ is $R^2$-10.77 (=formula I.763).
Table 764. Compounds of formula I.1, wherein $R^2$ is $R^2$-10.78 (=formula I.764).
Table 765. Compounds of formula I.1, wherein $R^2$ is $R^2$-10.79 (=formula I.765).
Table 766. Compounds of formula I.1, wherein $R^2$ is $R^2$-10.80 (=formula I.766).
Table 767. Compounds of formula I.1, wherein $R^2$ is $R^2$-10.81 (=formula I.767).
Table 768. Compounds of formula I.1, wherein $R^2$ is $R^2$-10.82 (=formula I.768).
Table 769. Compounds of formula I.1, wherein $R^2$ is $R^2$-10.83 (=formula I.769).
Table 770. Compounds of formula I.1, wherein $R^2$ is $R^2$-10.84 (=formula I.770).
Table 771. Compounds of formula I.1, wherein $R^2$ is $R^2$-10.85 (=formula I.771).
Table 772. Compounds of formula I.1, wherein $R^2$ is $R^2$-10.86 (=formula I.772).
Table 773. Compounds of formula I.1, wherein $R^2$ is $R^2$-10.87 (=formula I.773).
Table 774. Compounds of formula I.1, wherein $R^2$ is $R^2$-10.88 (=formula I.774).
Table 775. Compounds of formula I.1, wherein $R^2$ is $R^2$-10.89 (=formula I.775).
Table 776. Compounds of formula I.1, wherein $R^2$ is $R^2$-10.90 (=formula I.776).
Table 777. Compounds of formula I.1, wherein $R^2$ is $R^2$-10.91 (=formula I.777).
Table 778. Compounds of formula I.1, wherein $R^2$ is $R^2$-10.92 (=formula I.778).
Table 779. Compounds of formula I.1, wherein $R^2$ is $R^2$-10.93 (=formula I.779).
Table 780. Compounds of formula I.1, wherein $R^2$ is $R^2$-10.94 (=formula I.780).
Table 781. Compounds of formula I.1, wherein $R^2$ is $R^2$-10.95 (=formula I.781).
Table 782. Compounds of formula I.1, wherein $R^2$ is $R^2$-10.96 (=formula I.782).
Table 783. Compounds of formula I.1, wherein $R^2$ is $R^2$-10.97 (=formula I.783).
Table 784. Compounds of formula I.1, wherein $R^2$ is $R^2$-10.98 (=formula I.784).
Table 785. Compounds of formula I.1, wherein $R^2$ is $R^2$-10.99 (=formula I.785).
Table 786. Compounds of formula I.1, wherein $R^2$ is $R^2$-10.100 (=formula I.786).
Table 787. Compounds of formula I.1, wherein $R^2$ is $R^2$-10.101 (=formula I.787).
Table 788. Compounds of formula I.1, wherein $R^2$ is $R^2$-10.102 (=formula I.788).
Table 789. Compounds of formula I.1, wherein $R^2$ is $R^2$-10.103 (=formula I.789).
Table 790. Compounds of formula I.1, wherein $R^2$ is $R^2$-10.104 (=formula I.790).
Table 791. Compounds of formula I.1, wherein $R^2$ is $R^2$-10.105 (=formula I.791).
Table 792. Compounds of formula I.1, wherein $R^2$ is $R^2$-10.106 (=formula I.792).
Table 793. Compounds of formula I.1, wherein $R^2$ is $R^2$-10.107 (=formula I.793).
Table 794. Compounds of formula I.1, wherein $R^2$ is $R^2$-10.108 (=formula I.794).
Table 795. Compounds of formula I.1, wherein $R^2$ is $R^2$-10.109 (=formula I.795).
Table 796. Compounds of formula I.1, wherein $R^2$ is $R^2$-10.110 (=formula I.796).
Table 797. Compounds of formula I.1, wherein $R^2$ is $R^2$-10.111 (=formula I.797).
Table 798. Compounds of formula I.1, wherein $R^2$ is $R^2$-10.112 (=formula I.798).
Table 799. Compounds of formula I.1, wherein $R^2$ is $R^2$-10.113 (=formula I.799).
Table 800. Compounds of formula I.1, wherein $R^2$ is $R^2$-10.114 (=formula I.800).
Table 801. Compounds of formula I.1, wherein $R^2$ is $R^2$-10.115 (=formula I.801).
Table 802. Compounds of formula I.1, wherein $R^2$ is $R^2$-10.116 (=formula I.802).

Table 803. Compounds of formula I.1, wherein $R^2$ is $R^2$-10.117 (=formula I.803).
Table 804. Compounds of formula I.1, wherein $R^2$ is $R^2$-10.118 (=formula I.804).
Table 805. Compounds of formula I.1, wherein $R^2$ is $R^2$-10.119 (=formula I.805).
Table 806. Compounds of formula I.1, wherein $R^2$ is $R^2$-10.120 (=formula I.806).
Table 807. Compounds of formula I.1, wherein $R^2$ is $R^2$-10.121 (=formula I.807).
Table 808. Compounds of formula I.1, wherein $R^2$ is $R^2$-10.122 (=formula I.808).
Table 809. Compounds of formula I.1, wherein $R^2$ is $R^2$-10.123 (=formula I.809).
Table 810. Compounds of formula I.1, wherein $R^2$ is $R^2$-10.124 (=formula I.810).
Table 811. Compounds of formula I.1, wherein $R^2$ is $R^2$-10.125 (=formula I.811).
Table 812. Compounds of formula I.1, wherein $R^2$ is $R^2$-10.126 (=formula I.812).
Table 813. Compounds of formula I.1, wherein $R^2$ is $R^2$-10.127 (=formula I.813).
Table 814. Compounds of formula I.1, wherein $R^2$ is $R^2$-10.128 (=formula I.814).
Table 815. Compounds of formula I.1, wherein $R^2$ is $R^2$-10.129 (=formula I.815).
Table 816. Compounds of formula I.1, wherein $R^2$ is $R^2$-10.130 (=formula I.816).
Table 817. Compounds of formula I.1, wherein $R^2$ is $R^2$-10.131 (=formula I.817).
Table 818. Compounds of formula I.1, wherein $R^2$ is $R^2$-10.132 (=formula I.818).
Table 819. Compounds of formula I.1, wherein $R^2$ is $R^2$-10.133 (=formula I.819).
Table 820. Compounds of formula I.1, wherein $R^2$ is $R^2$-10.134 (=formula I.820).
Table 821. Compounds of formula I.1, wherein $R^2$ is $R^2$-10.135 (=formula I.821).
Table 822. Compounds of formula I.1, wherein $R^2$ is $R^2$-10.136 (=formula I.822).
Table 823. Compounds of formula I.1, wherein $R^2$ is $R^2$-10.137 (=formula I.823).
Table 824. Compounds of formula I.1, wherein $R^2$ is $R^2$-10.138 (=formula I.824).
Table 825. Compounds of formula I.1, wherein $R^2$ is $R^2$-10.139 (=formula I.825).
Table 826. Compounds of formula I.1, wherein $R^2$ is $R^2$-10.140 (=formula I.826).
Table 827. Compounds of formula I.1, wherein $R^2$ is $R^2$-10.141 (=formula I.827).
Table 828. Compounds of formula I.1, wherein $R^2$ is $R^2$-10.142 (=formula I.828).
Table 829. Compounds of formula I.1, wherein $R^2$ is $R^2$-10.143 (=formula I.829).
Table 830. Compounds of formula I.1, wherein $R^2$ is $R^2$-10.144 (=formula I.830).
Table 831. Compounds of formula I.1, wherein $R^2$ is $R^2$-10.145 (=formula I.831).
Table 832. Compounds of formula I.1, wherein $R^2$ is $R^2$-10.146 (=formula I.832).
Table 833. Compounds of formula I.1, wherein $R^2$ is $R^2$-10.147 (=formula I.833).
Table 834. Compounds of formula I.1, wherein $R^2$ is $R^2$-10.148 (=formula I.834).
Table 835. Compounds of formula I.1, wherein $R^2$ is $R^2$-10.149 (=formula I.835).
Table 836. Compounds of formula I.1, wherein $R^2$ is $R^2$-10.150 (=formula I.836).
Table 837. Compounds of formula I.1, wherein $R^2$ is $R^2$-10.151 (=formula I.837).
Table 838. Compounds of formula I.1, wherein $R^2$ is $R^2$-10.152 (=formula I.838).
Table 839. Compounds of formula I.1, wherein $R^2$ is $R^2$-10.153 (=formula I.839).
Table 840. Compounds of formula I.1, wherein $R^2$ is $R^2$-10.154 (=formula I.840).
Table 841. Compounds of formula I.1, wherein $R^2$ is $R^2$-10.155 (=formula I.841).
Table 842. Compounds of formula I.1, wherein $R^2$ is $R^2$-10.156 (=formula I.842).
Table 843. Compounds of formula I.1, wherein $R^2$ is $R^2$-10.157 (=formula I.843).
Table 844. Compounds of formula I.1, wherein $R^2$ is $R^2$-10.158 (=formula I.844).
Table 845. Compounds of formula I.1, wherein $R^2$ is $R^2$-10.159 (=formula I.845).
Table 846. Compounds of formula I.1, wherein $R^2$ is $R^2$-10.160 (=formula I.846).
Table 847. Compounds of formula I.1, wherein $R^2$ is $R^2$-10.161 (=formula I.847).
Table 848. Compounds of formula I.1, wherein $R^2$ is $R^2$-10.162 (=formula I.848).
Table 849. Compounds of formula I.1, wherein $R^2$ is $R^2$-10.163 (=formula I.849).
Table 850. Compounds of formula I.1, wherein $R^2$ is $R^2$-10.164 (=formula I.850).
Table 851. Compounds of formula I.1, wherein $R^2$ is $R^2$-10.165 (=formula I.851).
Table 852. Compounds of formula I.1, wherein $R^2$ is $R^2$-10.166 (=formula I.852).
Table 853. Compounds of formula I.1, wherein $R^2$ is $R^2$-10.167 (=formula I.853).
Table 854. Compounds of formula I.1, wherein $R^2$ is $R^2$-10.168 (=formula I.854).
Table 855. Compounds of formula I.1, wherein $R^2$ is $R^2$-10.169 (=formula I.855).
Table 856. Compounds of formula I.1, wherein $R^2$ is $R^2$-10.170 (=formula I.856).
Table 857. Compounds of formula I.1, wherein $R^2$ is $R^2$-10.171 (=formula I.857).
Table 858. Compounds of formula I.1, wherein $R^2$ is $R^2$-10.172 (=formula I.858).
Table 859. Compounds of formula I.1, wherein $R^2$ is $R^2$-10.173 (=formula I.859).
Table 860. Compounds of formula I.1, wherein $R^2$ is $R^2$-10.174 (=formula I.860).
Table 861. Compounds of formula I.1, wherein $R^2$ is $R^2$-10.175 (=formula I.861).
Table 862. Compounds of formula I.1, wherein $R^2$ is $R^2$-10.176 (=formula I.862).
Table 863. Compounds of formula I.1, wherein $R^2$ is $R^2$-10.177 (=formula I.863).
Table 864. Compounds of formula I.1, wherein $R^2$ is $R^2$-10.178 (=formula I.864).
Table 865. Compounds of formula I.1, wherein $R^2$ is $R^2$-10.179 (=formula I.865).
Table 866. Compounds of formula I.1, wherein $R^2$ is $R^2$-10.180 (=formula I.866).
Table 867. Compounds of formula I.1, wherein $R^2$ is $R^2$-10.181 (=formula I.867).
Table 868. Compounds of formula I.1, wherein $R^2$ is $R^2$-10.182 (=formula I.868).

Table 869. Compounds of formula I.1, wherein $R^2$ is $R^2$-10.183 (=formula I.869).
Table 870. Compounds of formula I.1, wherein $R^2$ is $R^2$-10.184 (=formula I.870).
Table 871. Compounds of formula I.1, wherein $R^2$ is $R^2$-10.185 (=formula I.871).
Table 872. Compounds of formula I.1, wherein $R^2$ is $R^2$-10.186 (=formula I.872).
Table 873. Compounds of formula I.1, wherein $R^2$ is $R^2$-10.187 (=formula I.873).
Table 874. Compounds of formula I.1, wherein $R^2$ is $R^2$-10.188 (=formula I.874).
Table 875. Compounds of formula I.1, wherein $R^2$ is $R^2$-10.189 (=formula I.875).
Table 876. Compounds of formula I.1, wherein $R^2$ is $R^2$-10.190 (=formula I.876).
Table 877. Compounds of formula I.1, wherein $R^2$ is $R^2$-10.191 (=formula I.877).
Table 878. Compounds of formula I.1, wherein $R^2$ is $R^2$-10.192 (=formula I.878).
Table 879. Compounds of formula I.1, wherein $R^2$ is $R^2$-10.193 (=formula I.879).
Table 880. Compounds of formula I.1, wherein $R^2$ is $R^2$-10.194 (=formula I.880).
Table 881. Compounds of formula I.1, wherein $R^2$ is $R^2$-10.195 (=formula I.881).
Table 882. Compounds of formula I.1, wherein $R^2$ is $R^2$-10.196 (=formula I.882).
Table 883. Compounds of formula I.1, wherein $R^2$ is $R^2$-10.197 (=formula I.883).
Table 884. Compounds of formula I.1, wherein $R^2$ is $R^2$-10.198 (=formula I.884).
Table 885. Compounds of formula I.1, wherein $R^2$ is $R^2$-10.199 (=formula I.885).
Table 886. Compounds of formula I.1, wherein $R^2$ is $R^2$-10.200 (=formula I.886).
Table 887. Compounds of formula I.1, wherein $R^2$ is $R^2$-10.201 (=formula I.887).
Table 888. Compounds of formula I.1, wherein $R^2$ is $R^2$-10.202 (=formula I.888).
Table 889. Compounds of formula I.1, wherein $R^2$ is $R^2$-10.203 (=formula I.889).
Table 890. Compounds of formula I.1, wherein $R^2$ is $R^2$-10.204 (=formula I.890).
Table 891. Compounds of formula I.1, wherein $R^2$ is $R^2$-10.205 (=formula I.891).
Table 892. Compounds of formula I.1, wherein $R^2$ is $R^2$-10.206 (=formula I.892).
Table 893. Compounds of formula I.1, wherein $R^2$ is $R^2$-10.207 (=formula I.893).
Table 894. Compounds of formula I.1, wherein $R^2$ is $R^2$-10.208 (=formula I.894).
Table 895. Compounds of formula I.1, wherein $R^2$ is $R^2$-10.209 (=formula I.895).
Table 896. Compounds of formula I.1, wherein $R^2$ is $R^2$-10.210 (=formula I.896).
Table 897. Compounds of formula I.1, wherein $R^2$ is $R^2$-10.211 (=formula I.897).
Table 898. Compounds of formula I.1, wherein $R^2$ is $R^2$-10.212 (=formula I.898).
Table 899. Compounds of formula I.1, wherein $R^2$ is $R^2$-10.213 (=formula I.899).
Table 900. Compounds of formula I.1, wherein $R^2$ is $R^2$-10.214 (=formula I.900).
Table 901. Compounds of formula I.1, wherein $R^2$ is $R^2$-10.215 (=formula I.901).
Table 902. Compounds of formula I.1, wherein $R^2$ is $R^2$-10.216 (=formula I.902).
Table 903. Compounds of formula I.1, wherein $R^2$ is $R^2$-10.217 (=formula I.903).
Table 904. Compounds of formula I.1, wherein $R^2$ is $R^2$-10.218 (=formula I.904).
Table 905. Compounds of formula I.1, wherein $R^2$ is $R^2$-10.219 (=formula I.905).
Table 906. Compounds of formula I.1, wherein $R^2$ is $R^2$-10.220 (=formula I.906).
Table 907. Compounds of formula I.1, wherein $R^2$ is $R^2$-10.221 (=formula I.907).
Table 908. Compounds of formula I.1, wherein $R^2$ is $R^2$-10.222 (=formula I.908).
Table 909. Compounds of formula I.1, wherein $R^2$ is $R^2$-10.223 (=formula I.909).
Table 910. Compounds of formula I.1, wherein $R^2$ is $R^2$-10.224 (=formula I.910).
Table 911. Compounds of formula I.1, wherein $R^2$ is $R^2$-10.225 (=formula I.911).
Table 912. Compounds of formula I.1, wherein $R^2$ is $R^2$-10.226 (=formula I.912).
Table 913. Compounds of formula I.1, wherein $R^2$ is $R^2$-10.227 (=formula I.913).
Table 914. Compounds of formula I.1, wherein $R^2$ is $R^2$-10.228 (=formula I.914).
Table 915. Compounds of formula I.1, wherein $R^2$ is $R^2$-10.229 (=formula I.915).
Table 916. Compounds of formula I.1, wherein $R^2$ is $R^2$-10.230 (=formula I.916).
Table 917. Compounds of formula I.1, wherein $R^2$ is $R^2$-10.231 (=formula I.917).
Table 918. Compounds of formula I.1, wherein $R^2$ is $R^2$-10.232 (=formula I.918).
Table 919. Compounds of formula I.1, wherein $R^2$ is $R^2$-10.233 (=formula I.919).
Table 920. Compounds of formula I.1, wherein $R^2$ is $R^2$-10.234 (=formula I.920).
Table 921. Compounds of formula I.1, wherein $R^2$ is $R^2$-10.235 (=formula I.921).
Table 922. Compounds of formula I.1, wherein $R^2$ is $R^2$-10.236 (=formula I.922).
Table 923. Compounds of formula I.1, wherein $R^2$ is $R^2$-10.237 (=formula I.923).
Table 924. Compounds of formula I.1, wherein $R^2$ is $R^2$-10.238 (=formula I.924).
Table 925. Compounds of formula I.1, wherein $R^2$ is $R^2$-10.239 (=formula I.925).
Table 926. Compounds of formula I.1, wherein $R^2$ is $R^2$-10.240 (=formula I.926).
Table 927. Compounds of formula I.1, wherein $R^2$ is $R^2$-10.241 (=formula I.927).
Table 928. Compounds of formula I.1, wherein $R^2$ is $R^2$-10.242 (=formula I.928).
Table 929. Compounds of formula I.1, wherein $R^2$ is $R^2$-10.243 (=formula I.929).
Table 930. Compounds of formula I.1, wherein $R^2$ is $R^2$-10.244 (=formula I.930).
Table 931. Compounds of formula I.1, wherein $R^2$ is $R^2$-10.245 (=formula I.931).
Table 932. Compounds of formula I.1, wherein $R^2$ is $R^2$-10.246 (=formula I.932).
Table 933. Compounds of formula I.1, wherein $R^2$ is $R^2$-10.247 (=formula I.933).
Table 934. Compounds of formula I.1, wherein $R^2$ is $R^2$-10.248 (=formula I.934).

Table 935. Compounds of formula I.1, wherein $R^2$ is $R^2$-10.249 (=formula I.935).
Table 936. Compounds of formula I.1, wherein $R^2$ is $R^2$-10.250 (=formula I.936).
Table 937. Compounds of formula I.1, wherein $R^2$ is $R^2$-10.251 (=formula I.937).
Table 938. Compounds of formula I.1, wherein $R^2$ is $R^2$-10.252 (=formula I.938).
Table 939. Compounds of formula I.1, wherein $R^2$ is $R^2$-10.253 (=formula I.939).
Table 940. Compounds of formula I.1, wherein $R^2$ is $R^2$-10.254 (=formula I.940).
Table 941. Compounds of formula I.1, wherein $R^2$ is $R^2$-10.255 (=formula I.941).
Table 942. Compounds of formula I.1, wherein $R^2$ is $R^2$-10.256 (=formula I.942).
Table 943. Compounds of formula I.1, wherein $R^2$ is $R^2$-10.257 (=formula I.943).
Table 944. Compounds of formula I.1, wherein $R^2$ is $R^2$-10.258 (=formula I.944).
Table 945. Compounds of formula I.1, wherein $R^2$ is $R^2$-10.259 (=formula I.945).
Table 946. Compounds of formula I.1, wherein $R^2$ is $R^2$-10.260 (=formula I.946).
Table 947. Compounds of formula I.1, wherein $R^2$ is $R^2$-10.261 (=formula I.947).
Table 948. Compounds of formula I.1, wherein $R^2$ is $R^2$-10.262 (=formula I.948).
Table 949. Compounds of formula I.1, wherein $R^2$ is $R^2$-10.263 (=formula I.949).
Table 950. Compounds of formula I.1, wherein $R^2$ is $R^2$-10.264 (=formula I.950).
Table 951. Compounds of formula I.1, wherein $R^2$ is $R^2$-10.265 (=formula I.951).
Table 952. Compounds of formula I.1, wherein $R^2$ is $R^2$-10.266 (=formula I.952).
Table 953. Compounds of formula I.1, wherein $R^2$ is $R^2$-10.267 (=formula I.953).
Table 954. Compounds of formula I.1, wherein $R^2$ is $R^2$-10.268 (=formula I.954).
Table 955. Compounds of formula I.1, wherein $R^2$ is $R^2$-10.269 (=formula I.955).
Table 956. Compounds of formula I.1, wherein $R^2$ is $R^2$-10.270 (=formula I.956).
Table 957. Compounds of formula I.1, wherein $R^2$ is $R^2$-10.271 (=formula I.957).
Table 958. Compounds of formula I.1, wherein $R^2$ is $R^2$-10.272 (=formula I.958).
Table 959. Compounds of formula I.1, wherein $R^2$ is $R^2$-10.273 (=formula I.959).
Table 960. Compounds of formula I.1, wherein $R^2$ is $R^2$-10.274 (=formula I.960).
Table 961. Compounds of formula I.1, wherein $R^2$ is $R^2$-10.275 (=formula I.961).
Table 962. Compounds of formula I.1, wherein $R^2$ is $R^2$-10.276 (=formula I.962).
Table 963. Compounds of formula I.1, wherein $R^2$ is $R^2$-10.277 (=formula I.963).
Table 964. Compounds of formula I.1, wherein $R^2$ is $R^2$-10.278 (=formula I.964).
Table 965. Compounds of formula I.1, wherein $R^2$ is $R^2$-10.279 (=formula I.965).
Table 966. Compounds of formula I.1, wherein $R^2$ is $R^2$-10.280 (=formula I.966).
Table 967. Compounds of formula I.1, wherein $R^2$ is $R^2$-10.281 (=formula I.967).
Table 968. Compounds of formula I.1, wherein $R^2$ is $R^2$-10.282 (=formula I.968).
Table 969. Compounds of formula I.1, wherein $R^2$ is $R^2$-10.283 (=formula I.969).
Table 970. Compounds of formula I.1, wherein $R^2$ is $R^2$-10.284 (=formula I.970).
Table 971. Compounds of formula I.1, wherein $R^2$ is $R^2$-10.285 (=formula I.971).
Table 972. Compounds of formula I.1, wherein $R^2$ is $R^2$-10.286 (=formula I.972).
Table 973. Compounds of formula I.1, wherein $R^2$ is $R^2$-10.287 (=formula I.973).
Table 974. Compounds of formula I.1, wherein $R^2$ is $R^2$-10.288 (=formula I.974).
Table 975. Compounds of formula I.1, wherein $R^2$ is $R^2$-10.289 (=formula I.975).
Table 976. Compounds of formula I.1, wherein $R^2$ is $R^2$-10.290 (=formula I.976).
Table 977. Compounds of formula I.1, wherein $R^2$ is $R^2$-10.291 (=formula I.977).
Table 978. Compounds of formula I.1, wherein $R^2$ is $R^2$-10.292 (=formula I.978).
Table 979. Compounds of formula I.1, wherein $R^2$ is $R^2$-10.293 (=formula I.979).
Table 980. Compounds of formula I.1, wherein $R^2$ is $R^2$-10.294 (=formula I.980).
Table 981. Compounds of formula I.1, wherein $R^2$ is $R^2$-10.295 (=formula I.981).
Table 982. Compounds of formula I.1, wherein $R^2$ is $R^2$-10.296 (=formula I.982).
Table 983. Compounds of formula I.1, wherein $R^2$ is $R^2$-10.297 (=formula I.983).
Table 984. Compounds of formula I.1, wherein $R^2$ is $R^2$-10.298 (=formula I.984).
Table 985. Compounds of formula I.1, wherein $R^2$ is $R^2$-10.299 (=formula I.985).
Table 986. Compounds of formula I.1, wherein $R^2$ is $R^2$-10.300 (=formula I.986).
Table 987. Compounds of formula I.1, wherein $R^2$ is $R^2$-10.301 (=formula I.987).
Table 988. Compounds of formula I.1, wherein $R^2$ is $R^2$-10.302 (=formula I.988).
Table 989. Compounds of formula I.1, wherein $R^2$ is $R^2$-10.303 (=formula I.989).
Table 990. Compounds of formula I.1, wherein $R^2$ is $R^2$-10.304 (=formula I.990).
Table 991. Compounds of formula I.1, wherein $R^2$ is $R^2$-10.305 (=formula I.991).
Table 992. Compounds of formula I.1, wherein $R^2$ is $R^2$-10.306 (=formula I.992).
Table 993. Compounds of formula I.1, wherein $R^2$ is $R^2$-10.307 (=formula I.993).
Table 994. Compounds of formula I.1, wherein $R^2$ is $R^2$-10.308 (=formula I.994).
Table 995. Compounds of formula I.1, wherein $R^2$ is $R^2$-10.309 (=formula I.995).
Table 996. Compounds of formula I.1, wherein $R^2$ is $R^2$-10.310 (=formula I.996).
Table 997. Compounds of formula I.1, wherein $R^2$ is $R^2$-10.311 (=formula I.997).
Table 998. Compounds of formula I.1, wherein $R^2$ is $R^2$-10.312 (=formula I.998).
Table 999. Compounds of formula I.1, wherein $R^2$ is $R^2$-10.313 (=formula I.999).
Table 1000. Compounds of formula I.1, wherein $R^2$ is $R^2$-10.314 (=formula I.1000).

Table 1001. Compounds of formula I.1, wherein $R^2$ is $R^2$-10.315 (=formula I.1001).
Table 1002. Compounds of formula I.1, wherein $R^2$ is $R^2$-10.316 (=formula I.1002).
Table 1003. Compounds of formula I.1, wherein $R^2$ is $R^2$-10.317 (=formula I.1003).
Table 1004. Compounds of formula I.1, wherein $R^2$ is $R^2$-10.318 (=formula I.1004).
Table 1005. Compounds of formula I.1, wherein $R^2$ is $R^2$-10.319 (=formula I.1005).
Table 1006. Compounds of formula I.1, wherein $R^2$ is $R^2$-10.320 (=formula I.1006).
Table 1007. Compounds of formula I.1, wherein $R^2$ is $R^2$-10.321 (=formula I.1007).
Table 1008. Compounds of formula I.1, wherein $R^2$ is $R^2$-10.322 (=formula I.1008).
Table 1009. Compounds of formula I.1, wherein $R^2$ is $R^2$-10.323 (=formula I.1009).
Table 1010. Compounds of formula I.1, wherein $R^2$ is $R^2$-10.324 (=formula I.1010).
Table 1011. Compounds of formula I.1, wherein $R^2$ is $R^2$-10.325 (=formula I.1011).
Table 1012. Compounds of formula I.1, wherein $R^2$ is $R^2$-10.326 (=formula I.1012).
Table 1013. Compounds of formula I.1, wherein $R^2$ is $R^2$-10.327 (=formula I.1013).
Table 1014. Compounds of formula I.1, wherein $R^2$ is $R^2$-10.328 (=formula I.1014).
Table 1015. Compounds of formula I.1, wherein $R^2$ is $R^2$-10.329 (=formula I.1015).
Table 1016. Compounds of formula I.1, wherein $R^2$ is $R^2$-10.330 (=formula I.1016).
Table 1017. Compounds of formula I.1, wherein $R^2$ is $R^2$-10.331 (=formula I.1017).
Table 1018. Compounds of formula I.1, wherein $R^2$ is $R^2$-10.332 (=formula I.1018).
Table 1019. Compounds of formula I.1, wherein $R^2$ is $R^2$-10.333 (=formula I.1019).
Table 1020. Compounds of formula I.1, wherein $R^2$ is $R^2$-10.334 (=formula I.1020).
Table 1021. Compounds of formula I.1, wherein $R^2$ is $R^2$-10.335 (=formula I.1021).
Table 1022. Compounds of formula I.1, wherein $R^2$ is $R^2$-10.336 (=formula I.1022).
Table 1023. Compounds of formula I.1, wherein $R^2$ is $R^2$-10.334 (=formula I.1023).
Table 1024. Compounds of formula I.1, wherein $R^2$ is $R^2$-10.338 (=formula I.1024).
Table 1025. Compounds of formula I.1, wherein $R^2$ is $R^2$-10.339 (=formula I.1025).
Table 1026. Compounds of formula I.1, wherein $R^2$ is $R^2$-10.340 (=formula I.1026).
Table 1027. Compounds of formula I.1, wherein $R^2$ is $R^2$-10.341 (=formula I.1027).
Table 1028. Compounds of formula I.1, wherein $R^2$ is $R^2$-10.342 (=formula I.1028).
Table 1029. Compounds of formula I.1, wherein $R^2$ is $R^2$-10.343 (=formula I.1029).
Table 1030. Compounds of formula I.1, wherein $R^2$ is $R^2$-10.344 (=formula I.1030).
Table 1031. Compounds of formula I.1, wherein $R^2$ is $R^2$-10.345 (=formula I.1031).
Table 1032. Compounds of formula I.1, wherein $R^2$ is $R^2$-10.346 (=formula I.1032).
Table 1033. Compounds of formula I.1, wherein $R^2$ is $R^2$-10.347 (=formula I.1033).
Table 1034. Compounds of formula I.1, wherein $R^2$ is $R^2$-10.348 (=formula I.1034).
Table 1035. Compounds of formula I.1, wherein $R^2$ is $R^2$-10.349 (=formula I.1035).
Table 1036. Compounds of formula I.1, wherein $R^2$ is $R^2$-10.350 (=formula I.1036).
Table 1037. Compounds of formula I.1, wherein $R^2$ is $R^2$-10.351 (=formula I.1037).
Table 1038. Compounds of formula I.1, wherein $R^2$ is $R^2$-10.352 (=formula I.1038).
Table 1039. Compounds of formula I.1, wherein $R^2$ is $R^2$-10.353 (=formula I.1039).
Table 1040. Compounds of formula I.1, wherein $R^2$ is $R^2$-10.354 (=formula I.1040).
Table 1041. Compounds of formula I.1, wherein $R^2$ is $R^2$-10.355 (=formula I.1041).
Table 1042. Compounds of formula I.1, wherein $R^2$ is $R^2$-10.356 (=formula I.1042).
Table 1043. Compounds of formula I.1, wherein $R^2$ is $R^2$-10.357 (=formula I.1043).
Table 1044. Compounds of formula I.1, wherein $R^2$ is $R^2$-10.358 (=formula I.1044).
Table 1045. Compounds of formula I.1, wherein $R^2$ is $R^2$-10.359 (=formula I.1045).
Table 1046. Compounds of formula I.1, wherein $R^2$ is $R^2$-10.360 (=formula I.1046).
Table 1047. Compounds of formula I.1, wherein $R^2$ is $R^2$-10.361 (=formula I.1047).
Table 1048. Compounds of formula I.1, wherein $R^2$ is $R^2$-10.362 (=formula I.1048).
Table 1049. Compounds of formula I.1, wherein $R^2$ is $R^2$-10.363 (=formula I.1049).
Table 1050. Compounds of formula I.1, wherein $R^2$ is $R^2$-10.364 (=formula I.1050).
Table 1051. Compounds of formula I.1, wherein $R^2$ is $R^2$-10.365 (=formula I.1051).
Table 1052. Compounds of formula I.1, wherein $R^2$ is $R^2$-10.366 (=formula I.1052).
Table 1053. Compounds of formula I.1, wherein $R^2$ is $R^2$-10.367 (=formula I.1053).
Table 1054. Compounds of formula I.1, wherein $R^2$ is $R^2$-10.368 (=formula I.1054).
Table 1055. Compounds of formula I.1, wherein $R^2$ is $R^2$-10.369 (=formula I.1055).
Table 1056. Compounds of formula I.1, wherein $R^2$ is $R^2$-10.370 (=formula I.1056).
Table 1057. Compounds of formula I.1, wherein $R^2$ is $R^2$-10.371 (=formula I.1057).
Table 1058. Compounds of formula I.1, wherein $R^2$ is $R^2$-10.372 (=formula I.1058).
Table 1059. Compounds of formula I.1, wherein $R^2$ is $R^2$-10.373 (=formula I.1059).
Table 1060. Compounds of formula I.1, wherein $R^2$ is $R^2$-10.374 (=formula I.1060).
Table 1061. Compounds of formula I.1, wherein $R^2$ is $R^2$-10.375 (=formula I.1061).
Table 1062. Compounds of formula I.1, wherein $R^2$ is $R^2$-10.376 (=formula I.1062).
Table 1063. Compounds of formula I.1, wherein $R^2$ is $R^2$-10.377 (=formula I.1063).
Table 1064. Compounds of formula I.1, wherein $R^2$ is $R^2$-10.378 (=formula I.1064).
Table 1065. Compounds of formula I.1, wherein $R^2$ is $R^2$-10.379 (=formula I.1065).
Table 1066. Compounds of formula I.1, wherein $R^2$ is $R^2$-10.380 (=formula I.1066).

Table 1067. Compounds of formula I.1, wherein $R^2$ is $R^2$-10.381 (=formula I.1067).
Table 1068. Compounds of formula I.1, wherein $R^2$ is $R^2$-10.382 (=formula I.1068).
Table 1069. Compounds of formula I.1, wherein $R^2$ is $R^2$-10.383 (=formula I.1069).
Table 1070. Compounds of formula I.1, wherein $R^2$ is $R^2$-10.384 (=formula I.1070).
Table 1071. Compounds of formula I.1, wherein $R^2$ is $R^2$-10.385 (=formula I.1071).
Table 1072. Compounds of formula I.1, wherein $R^2$ is $R^2$-10.386 (=formula I.1072).
Table 1073. Compounds of formula I.1, wherein $R^2$ is $R^2$-10.387 (=formula I.1073).
Table 1074. Compounds of formula I.1, wherein $R^2$ is $R^2$-10.388 (=formula I.1074).
Table 1075. Compounds of formula I.1, wherein $R^2$ is $R^2$-10.389 (=formula I.1075).
Table 1076. Compounds of formula I.1, wherein $R^2$ is $R^2$-10.390 (=formula I.7076).
Table 1077. Compounds of formula I.1, wherein $R^2$ is $R^2$-10.391 (=formula I.1077).
Table 1078. Compounds of formula I.1, wherein $R^2$ is $R^2$-10.392 (=formula I.1078).
Table 1079. Compounds of formula I.1, wherein $R^2$ is $R^2$-10.393 (=formula I.1079).
Table 1080. Compounds of formula I.1, wherein $R^2$ is $R^2$-10.394 (=formula I.1080).
Table 1081. Compounds of formula I.1, wherein $R^2$ is $R^2$-10.395 (=formula I.1081).
Table 1082. Compounds of formula I.1, wherein $R^2$ is $R^2$-10.396 (=formula I.1082).
Table 1083. Compounds of formula I.1, wherein $R^2$ is $R^2$-10.397 (=formula I.1083).
Table 1084. Compounds of formula I.1, wherein $R^2$ is $R^2$-10.398 (=formula I.1084).
Table 1085. Compounds of formula I.1, wherein $R^2$ is $R^2$-10.399 (=formula I.1085).
Table 1086. Compounds of formula I.1, wherein $R^2$ is $R^2$-10.400 (=formula I.1086).
Table 1087. Compounds of formula I.1, wherein $R^2$ is $R^2$-10.401 (=formula I.1087).
Table 1088. Compounds of formula I.1, wherein $R^2$ is $R^2$-10.402 (=formula I.1088).
Table 1089. Compounds of formula I.1, wherein $R^2$ is $R^2$-10.403 (=formula I.1089).
Table 1090. Compounds of formula I.1, wherein $R^2$ is $R^2$-10.404 (=formula I.1090).
Table 1091. Compounds of formula I.1, wherein $R^2$ is $R^2$-10.405 (=formula I.1091).
Table 1092. Compounds of formula I.1, wherein $R^2$ is $R^2$-10.406 (=formula I.1092).
Table 1093. Compounds of formula I.1, wherein $R^2$ is $R^2$-10.407 (=formula I.1093).
Table 1094. Compounds of formula I.1, wherein $R^2$ is $R^2$-10.408 (=formula I.1094).
Table 1095. Compounds of formula I.1, wherein $R^2$ is $R^2$-10.409 (=formula I.1095).
Table 1096. Compounds of formula I.1, wherein $R^2$ is $R^2$-10.410 (=formula I.1096).
Table 1097. Compounds of formula I.1, wherein $R^2$ is $R^2$-10.411 (=formula I.1097).
Table 1098. Compounds of formula I.1, wherein $R^2$ is $R^2$-10.412 (=formula I.1098).
Table 1099. Compounds of formula I.1, wherein $R^2$ is $R^2$-10.413 (=formula I.1099).
Table 1100. Compounds of formula I.1, wherein $R^2$ is $R^2$-10.414 (=formula I.1100).
Table 1101. Compounds of formula I.1, wherein $R^2$ is $R^2$-10.415 (=formula I.1101).
Table 1102. Compounds of formula I.1, wherein $R^2$ is $R^2$-10.416 (=formula I.1102).
Table 1103. Compounds of formula I.1, wherein $R^2$ is $R^2$-10.417 (=formula I.1103).
Table 1104. Compounds of formula I.1, wherein $R^2$ is $R^2$-10.418 (=formula I.1104).
Table 1105. Compounds of formula I.1, wherein $R^2$ is $R^2$-10.419 (=formula I.1105).
Table 1106. Compounds of formula I.1, wherein $R^2$ is $R^2$-10.420 (=formula I.1106).
Table 1107. Compounds of formula I.1, wherein $R^2$ is $R^2$-10.421 (=formula I.1107).
Table 1108. Compounds of formula I.1, wherein $R^2$ is $R^2$-10.422 (=formula I.1108).
Table 1109. Compounds of formula I.1, wherein $R^2$ is $R^2$-10.423 (=formula I.1109).
Table 1110. Compounds of formula I.1, wherein $R^2$ is $R^2$-10.424 (=formula I.1110).
Table 1111. Compounds of formula I.1, wherein $R^2$ is $R^2$-10.425 (=formula I.1111).
Table 1112. Compounds of formula I.1, wherein $R^2$ is $R^2$-10.426 (=formula I.1112).
Table 1113. Compounds of formula I.1, wherein $R^2$ is $R^2$-10.427 (=formula I.1113).
Table 1114. Compounds of formula I.1, wherein $R^2$ is $R^2$-10.428 (=formula I.1114).
Table 1115. Compounds of formula I.1, wherein $R^2$ is $R^2$-10.429 (=formula I.1115).
Table 1116. Compounds of formula I.1, wherein $R^2$ is $R^2$-10.430 (=formula I.1116).
Table 1117. Compounds of formula I.1, wherein $R^2$ is $R^2$-10.431 (=formula I.1117).
Table 1118. Compounds of formula I.1, wherein $R^2$ is $R^2$-10.432 (=formula I.1118).
Table 1119. Compounds of formula I.1, wherein $R^2$ is $R^2$-10.433 (=formula I.1119).
Table 1120. Compounds of formula I.1, wherein $R^2$ is $R^2$-10.434 (=formula I.1120).
Table 1121. Compounds of formula I.1, wherein $R^2$ is $R^2$-10.435 (=formula I.1121).
Table 1122. Compounds of formula I.1, wherein $R^2$ is $R^2$-10.436 (=formula I.1122).
Table 1123. Compounds of formula I.1, wherein $R^2$ is $R^2$-10.437 (=formula I.1123).
Table 1124. Compounds of formula I.1, wherein $R^2$ is $R^2$-10.438 (=formula I.1124).
Table 1125. Compounds of formula I.1, wherein $R^2$ is $R^2$-10.439 (=formula I.1125).
Table 1126. Compounds of formula I.1, wherein $R^2$ is $R^2$-10.440 (=formula I.1126).
Table 1127. Compounds of formula I.1, wherein $R^2$ is $R^2$-10.441 (=formula I.1127).
Table 1128. Compounds of formula I.1, wherein $R^2$ is $R^2$-10.442 (=formula I.1128).
Table 1129. Compounds of formula I.1, wherein $R^2$ is $R^2$-10.443 (=formula I.1129).
Table 1130. Compounds of formula I.1, wherein $R^2$ is $R^2$-10.444 (=formula I.1130).
Table 1131. Compounds of formula I.1, wherein $R^2$ is $R^2$-10.445 (=formula I.1131).
Table 1132. Compounds of formula I.1, wherein $R^2$ is $R^2$-10.446 (=formula I.1132).

Table 1133. Compounds of formula I.1, wherein $R^2$ is $R^2$-10.447 (=formula I.1133).
Table 1134. Compounds of formula I.1, wherein $R^2$ is $R^2$-10.448 (=formula I.1134).
Table 1135. Compounds of formula I.1, wherein $R^2$ is $R^2$-10.449 (=formula I.1135).
Table 1136. Compounds of formula I.1, wherein $R^2$ is $R^2$-10.450 (=formula I.1136).
Table 1137. Compounds of formula I.1, wherein $R^2$ is $R^2$-10.451 (=formula I.1137).
Table 1138. Compounds of formula I.1, wherein $R^2$ is $R^2$-10.452 (=formula I.1138).
Table 1139. Compounds of formula I.1, wherein $R^2$ is $R^2$-10.453 (=formula I.1139).
Table 1140. Compounds of formula I.1, wherein $R^2$ is $R^2$-10.454 (=formula I.1140).
Table 1141. Compounds of formula I.1, wherein $R^2$ is $R^2$-10.455 (=formula I.1141).
Table 1142. Compounds of formula I.1, wherein $R^2$ is $R^2$-10.456 (=formula I.1142).
Table 1143. Compounds of formula I.1, wherein $R^2$ is $R^2$-10.457 (=formula I.1143).
Table 1144. Compounds of formula I.1, wherein $R^2$ is $R^2$-10.458 (=formula I.1144).
Table 1145. Compounds of formula I.1, wherein $R^2$ is $R^2$-10.459 (=formula I.1145).
Table 1146. Compounds of formula I.1, wherein $R^2$ is $R^2$-10.460 (=formula I.1146).
Table 1147. Compounds of formula I.1, wherein $R^2$ is $R^2$-10.461 (=formula I.1147).
Table 1148. Compounds of formula I.1, wherein $R^2$ is $R^2$-10.462 (=formula I.1148).
Table 1149. Compounds of formula I.1, wherein $R^2$ is $R^2$-10.463 (=formula I.1149).
Table 1150. Compounds of formula I.1, wherein $R^2$ is $R^2$-10.464 (=formula I.1150).
Table 1151. Compounds of formula I.1, wherein $R^2$ is $R^2$-10.465 (=formula I.1151).
Table 1152. Compounds of formula I.1, wherein $R^2$ is $R^2$-10.466 (=formula I.1152).
Table 1153. Compounds of formula I.1, wherein $R^2$ is $R^2$-10.467 (=formula I.1153).
Table 1154. Compounds of formula I.1, wherein $R^2$ is $R^2$-10.468 (=formula I.1154).
Table 1155. Compounds of formula I.1, wherein $R^2$ is $R^2$-10.469 (=formula I.1154).
Table 1156. Compounds of formula I.1, wherein $R^2$ is $R^2$-10.470 (=formula I.1156).
Table 1157. Compounds of formula I.1, wherein $R^2$ is $R^2$-10.471 (=formula I.1157).
Table 1158. Compounds of formula I.1, wherein $R^2$ is $R^2$-10.472 (=formula I.1158).
Table 1159. Compounds of formula I.1, wherein $R^2$ is $R^2$-10.473 (=formula I.1159).
Table 1160. Compounds of formula I.1, wherein $R^2$ is $R^2$-10.474 (=formula I.1160).
Table 1161. Compounds of formula I.1, wherein $R^2$ is $R^2$-10.475 (=formula I.1161).
Table 1162. Compounds of formula I.1, wherein $R^2$ is $R^2$-10.476 (=formula I.1162).
Table 1163. Compounds of formula I.1, wherein $R^2$ is $R^2$-10.477 (=formula I.1163).
Table 1164. Compounds of formula I.1, wherein $R^2$ is $R^2$-10.478 (=formula I.1164).
Table 1165. Compounds of formula I.1, wherein $R^2$ is $R^2$-10.479 (=formula I.1165).
Table 1166. Compounds of formula I.1, wherein $R^2$ is $R^2$-10.480 (=formula I.1166).
Table 1167. Compounds of formula I.1, wherein $R^2$ is $R^2$-10.481 (=formula I.1167).
Table 1168. Compounds of formula I.1, wherein $R^2$ is $R^2$-10.482 (=formula I.1168).
Table 1169. Compounds of formula I.1, wherein $R^2$ is $R^2$-10.483 (=formula I.1169).
Table 1170. Compounds of formula I.1, wherein $R^2$ is $R^2$-10.484 (=formula I.1170).
Table 1171. Compounds of formula I.1, wherein $R^2$ is $R^2$-10.485 (=formula I.1171).
Table 1172. Compounds of formula I.1, wherein $R^2$ is $R^2$-10.486 (=formula I.1172).
Table 1173. Compounds of formula I.1, wherein $R^2$ is $R^2$-10.487 (=formula I.1173).
Table 1174. Compounds of formula I.1, wherein $R^2$ is $R^2$-10.488 (=formula I.1174).
Table 1175. Compounds of formula I.1, wherein $R^2$ is $R^2$-10.489 (=formula I.1175).
Table 1176. Compounds of formula I.1, wherein $R^2$ is $R^2$-10.490 (=formula I.1176).
Table 1177. Compounds of formula I.1, wherein $R^2$ is $R^2$-10.491 (=formula I.1177).
Table 1178. Compounds of formula I.1, wherein $R^2$ is $R^2$-10.492 (=formula I.1178).
Table 1179. Compounds of formula I.1, wherein $R^2$ is $R^2$-10.493 (=formula I.1179).
Table 1180. Compounds of formula I.1, wherein $R^2$ is $R^2$-10.494 (=formula I.1180).
Table 1181. Compounds of formula I.1, wherein $R^2$ is $R^2$-10.495 (=formula I.1181).
Table 1182. Compounds of formula I.1, wherein $R^2$ is $R^2$-10.496 (=formula I.1182).
Table 1183. Compounds of formula I.1, wherein $R^2$ is $R^2$-10.497 (=formula I.1183).
Table 1184. Compounds of formula I.1, wherein $R^2$ is $R^2$-10.498 (=formula I.1184).
Table 1185. Compounds of formula I.1, wherein $R^2$ is $R^2$-10.499 (=formula I.1185).
Table 1186. Compounds of formula I.1, wherein $R^2$ is $R^2$-10.500 (=formula I.1186).
Table 1187. Compounds of formula I.1, wherein $R^2$ is $R^2$-10.501 (=formula I.1187).
Table 1188. Compounds of formula I.1, wherein $R^2$ is $R^2$-10.502 (=formula I.1188).
Table 1189. Compounds of formula I.1, wherein $R^2$ is $R^2$-10.503 (=formula I.1189).
Table 1190. Compounds of formula I.1, wherein $R^2$ is $R^2$-10.504 (=formula I.1190).
Table 1191. Compounds of formula I.1, wherein $R^2$ is $R^2$-10.505 (=formula I.1191).
Table 1192. Compounds of formula I.1, wherein $R^2$ is $R^2$-10.506 (=formula I.1192).
Table 1193. Compounds of formula I.1, wherein $R^2$ is $R^2$-10.507 (=formula I.1193).
Table 1194. Compounds of formula I.1, wherein $R^2$ is $R^2$-10.508 (=formula I.1194).
Table 1195. Compounds of formula I.1, wherein $R^2$ is $R^2$-10.509 (=formula I.1195).
Table 1196. Compounds of formula I.1, wherein $R^2$ is $R^2$-10.510 (=formula I.1196).
Table 1197. Compounds of formula I.1, wherein $R^2$ is $R^2$-10.511 (=formula I.1197).
Table 1198. Compounds of formula I.1, wherein $R^2$ is $R^2$-10.512 (=formula I.1198).

Table 1199. Compounds of formula I.1, wherein $R^2$ is $R^2$-10.513 (=formula I.1199).
Table 1200. Compounds of formula I.1, wherein $R^2$ is $R^2$-10.514 (=formula I.1200).
Table 1201. Compounds of formula I.1, wherein $R^2$ is $R^2$-10.515 (=formula I.1201).
Table 1202. Compounds of formula I.1, wherein $R^2$ is $R^2$-10.516 (=formula I.1202).
Table 1203. Compounds of formula I.1, wherein $R^2$ is $R^2$-10.517 (=formula I.1203).
Table 1204. Compounds of formula I.1, wherein $R^2$ is $R^2$-10.518 (=formula I.1204).
Table 1205. Compounds of formula I.1, wherein $R^2$ is $R^2$-10.519 (=formula I.1205).
Table 1206. Compounds of formula I.1, wherein $R^2$ is $R^2$-10.520 (=formula I.1206).
Table 1207. Compounds of formula I.1, wherein $R^2$ is $R^2$-10.521 (=formula I.1207).
Table 1208. Compounds of formula I.1, wherein $R^2$ is $R^2$-10.522 (=formula I.1208).
Table 1209. Compounds of formula I.1, wherein $R^2$ is $R^2$-10.523 (=formula I.1209).
Table 1210. Compounds of formula I.1, wherein $R^2$ is $R^2$-10.524 (=formula I.1210).
Table 1211. Compounds of formula I.1, wherein $R^2$ is $R^2$-10.525 (=formula I.1211).
Table 1212. Compounds of formula I.1, wherein $R^2$ is $R^2$-10.526 (=formula I.1212).
Table 1213. Compounds of formula I.1, wherein $R^2$ is $R^2$-10.527 (=formula I.1213).
Table 1214. Compounds of formula I.1, wherein $R^2$ is $R^2$-10.528 (=formula I.1212).
Table 1215. Compounds of formula I.1, wherein $R^2$ is $R^2$-10.529 (=formula I.1215).
Table 1216. Compounds of formula I.1, wherein $R^2$ is $R^2$-10.530 (=formula I.1216).
Table 1217. Compounds of formula I.1, wherein $R^2$ is $R^2$-10.531 (=formula I.1217).
Table 1218. Compounds of formula I.1, wherein $R^2$ is $R^2$-10.532 (=formula I.1218).
Table 1219. Compounds of formula I.1, wherein $R^2$ is $R^2$-10.533 (=formula I.1219).
Table 1220. Compounds of formula I.1, wherein $R^2$ is $R^2$-10.534 (=formula I.1220).
Table 1221. Compounds of formula I.1, wherein $R^2$ is $R^2$-10.535 (=formula I.1221).
Table 1222. Compounds of formula I.1, wherein $R^2$ is $R^2$-10.536 (=formula I.1222).
Table 1223. Compounds of formula I.1, wherein $R^2$ is $R^2$-10.537 (=formula I.1223).
Table 1224. Compounds of formula I.1, wherein $R^2$ is $R^2$-10.538 (=formula I.1224).
Table 1225. Compounds of formula I.1, wherein $R^2$ is $R^2$-10.539 (=formula I.1225).
Table 1226. Compounds of formula I.1, wherein $R^2$ is $R^2$-10.540 (=formula I.1226).
Table 1227. Compounds of formula I.1, wherein $R^2$ is $R^2$-10.541 (=formula I.1227).
Table 1228. Compounds of formula I.1, wherein $R^2$ is $R^2$-10.542 (=formula I.1228).
Table 1229. Compounds of formula I.1, wherein $R^2$ is $R^2$-10.543 (=formula I.1229).
Table 1230. Compounds of formula I.1, wherein $R^2$ is $R^2$-10.544 (=formula I.1230).
Table 1231. Compounds of formula I.1, wherein $R^2$ is $R^2$-10.545 (=formula I.1231).
Table 1232. Compounds of formula I.1, wherein $R^2$ is $R^2$-10.546 (=formula I.1232).
Table 1233. Compounds of formula I.1, wherein $R^2$ is $R^2$-10.547 (=formula I.1233).
Table 1234. Compounds of formula I.1, wherein $R^2$ is $R^2$-10.548 (=formula I.1234).
Table 1235. Compounds of formula I.1, wherein $R^2$ is $R^2$-10.549 (=formula I.1235).
Table 1236. Compounds of formula I.1, wherein $R^2$ is $R^2$-10.550 (=formula I.1236).
Table 1237. Compounds of formula I.1, wherein $R^2$ is $R^2$-10.551 (=formula I.1237).
Table 1238. Compounds of formula I.1, wherein $R^2$ is $R^2$-10.552 (=formula I.1238).
Table 1239. Compounds of formula I.1, wherein $R^2$ is $R^2$-10.553 (=formula I.1239).
Table 1240. Compounds of formula I.1, wherein $R^2$ is $R^2$-10.554 (=formula I.1240).
Table 1241. Compounds of formula I.1, wherein $R^2$ is $R^2$-10.555 (=formula I.1241).
Table 1242. Compounds of formula I.1, wherein $R^2$ is $R^2$-10.556 (=formula I.1242).
Table 1243. Compounds of formula I.1, wherein $R^2$ is $R^2$-10.557 (=formula I.1243).
Table 1244. Compounds of formula I.1, wherein $R^2$ is $R^2$-10.558 (=formula I.1244).
Table 1245. Compounds of formula I.1, wherein $R^2$ is $R^2$-10.559 (=formula I.1245).
Table 1246. Compounds of formula I.1, wherein $R^2$ is $R^2$-10.560 (=formula I.1246).
Table 1247. Compounds of formula I.1, wherein $R^2$ is $R^2$-10.561 (=formula I.1247).
Table 1248. Compounds of formula I.1, wherein $R^2$ is $R^2$-10.562 (=formula I.1248).
Table 1249. Compounds of formula I.1, wherein $R^2$ is $R^2$-10.563 (=formula I.1249).
Table 1250. Compounds of formula I.1, wherein $R^2$ is $R^2$-10.564 (=formula I.1350).
Table 1251. Compounds of formula I.1, wherein $R^2$ is $R^2$-10.565 (=formula I.1251).
Table 1252. Compounds of formula I.1, wherein $R^2$ is $R^2$-10.566 (=formula I.1252).
Table 1253. Compounds of formula I.1, wherein $R^2$ is $R^2$-10.567 (=formula I.1253).
Table 1254. Compounds of formula I.1, wherein $R^2$ is $R^2$-10.568 (=formula I.1254).
Table 1255. Compounds of formula I.1, wherein $R^2$ is $R^2$-10.569 (=formula I.1255).
Table 1256. Compounds of formula I.1, wherein $R^2$ is $R^2$-10.570 (=formula I.1256).
Table 1257. Compounds of formula I.1, wherein $R^2$ is $R^2$-10.571 (=formula I.1257).
Table 1258. Compounds of formula I.1, wherein $R^2$ is $R^2$-10.572 (=formula I.1258).
Table 1259. Compounds of formula I.1, wherein $R^2$ is $R^2$-10.573 (=formula I.1259).
Table 1260. Compounds of formula I.1, wherein $R^2$ is $R^2$-10.574 (=formula I.1260).
Table 1261. Compounds of formula I.1, wherein $R^2$ is $R^2$-10.575 (=formula I.1261).
Table 1262. Compounds of formula I.1, wherein $R^2$ is $R^2$-10.576 (=formula I.1262).
Table 1263. Compounds of formula I.1, wherein $R^2$ is $R^2$-10.577 (=formula I.1263).
Table 1264. Compounds of formula I.1, wherein $R^2$ is $R^2$-10.578 (=formula I.1264).

Table 1265. Compounds of formula I.1, wherein $R^2$ is $R^2$-10.579 (=formula I.1265).
Table 1266. Compounds of formula I.1, wherein $R^2$ is $R^2$-10.580 (=formula I.1266).
Table 1267. Compounds of formula I.1, wherein $R^2$ is $R^2$-10.581 (=formula I.1267).
Table 1268. Compounds of formula I.1, wherein $R^2$ is $R^2$-10.582 (=formula I.1268).
Table 1269. Compounds of formula I.1, wherein $R^2$ is $R^2$-10.583 (=formula I.1269).
Table 1270. Compounds of formula I.1, wherein $R^2$ is $R^2$-10.584 (=formula I.1270).
Table 1271. Compounds of formula I.1, wherein $R^2$ is $R^2$-10.585 (=formula I.1271).
Table 1272. Compounds of formula I.1, wherein $R^2$ is $R^2$-10.586 (=formula I.1272).
Table 1273. Compounds of formula I.1, wherein $R^2$ is $R^2$-10.587 (=formula I.1273).
Table 1274. Compounds of formula I.1, wherein $R^2$ is $R^2$-10.588 (=formula I.1274).
Table 1275. Compounds of formula I.1, wherein $R^2$ is $R^2$-10.589 (=formula I.1275).
Table 1276. Compounds of formula I.1, wherein $R^2$ is $R^2$-10.590 (=formula I.1276).
Table 1277. Compounds of formula I.1, wherein $R^2$ is $R^2$-10.591 (=formula I.1277).
Table 1278. Compounds of formula I.1, wherein $R^2$ is $R^2$-10.592 (=formula I.1278).
Table 1279. Compounds of formula I.1, wherein $R^2$ is $R^2$-10.593 (=formula I.1279).
Table 1280. Compounds of formula I.1, wherein $R^2$ is $R^2$-10.594 (=formula I.1280).
Table 1281. Compounds of formula I.1, wherein $R^2$ is $R^2$-10.595 (=formula I.1281).
Table 1282. Compounds of formula I.1, wherein $R^2$ is $R^2$-10.596 (=formula I.1282).
Table 1283. Compounds of formula I.1, wherein $R^2$ is $R^2$-10.597 (=formula I.1283).
Table 1284. Compounds of formula I.1, wherein $R^2$ is $R^2$-10.598 (=formula I.1284).
Table 1285. Compounds of formula I.1, wherein $R^2$ is $R^2$-10.599 (=formula I.1285).
Table 1286. Compounds of formula I.1, wherein $R^2$ is $R^2$-10.600 (=formula I.1286).
Table 1287. Compounds of formula I.1, wherein $R^2$ is $R^2$-10.601 (=formula I.1287).
Table 1288. Compounds of formula I.1, wherein $R^2$ is $R^2$-10.602 (=formula I.1288).
Table 1289. Compounds of formula I.1, wherein $R^2$ is $R^2$-10.603 (=formula I.1289).
Table 1290. Compounds of formula I.1, wherein $R^2$ is $R^2$-10.604 (=formula I.1290).
Table 1291. Compounds of formula I.1, wherein $R^2$ is $R^2$-10.605 (=formula I.1291).
Table 1292. Compounds of formula I.1, wherein $R^2$ is $R^2$-10.606 (=formula I.1292).
Table 1293. Compounds of formula I.1, wherein $R^2$ is $R^2$-10.607 (=formula I.1293).
Table 1294. Compounds of formula I.1, wherein $R^2$ is $R^2$-10.608 (=formula I.1294).
Table 1295. Compounds of formula I.1, wherein $R^2$ is $R^2$-10.609 (=formula I.1295).
Table 1296. Compounds of formula I.1, wherein $R^2$ is $R^2$-10.610 (=formula I.1296).
Table 1297. Compounds of formula I.1, wherein $R^2$ is $R^2$-10.611 (=formula I.1297).
Table 1298. Compounds of formula I.1, wherein $R^2$ is $R^2$-10.612 (=formula I.1298).
Table 1299. Compounds of formula I.1, wherein $R^2$ is $R^2$-10.613 (=formula I.1299).
Table 1300. Compounds of formula I.1, wherein $R^2$ is $R^2$-10.614 (=formula I.1300).
Table 1301. Compounds of formula I.1, wherein $R^2$ is $R^2$-10.615 (=formula I.1301).
Table 1302. Compounds of formula I.1, wherein $R^2$ is $R^2$-10.616 (=formula I.1302).
Table 1303. Compounds of formula I.1, wherein $R^2$ is $R^2$-10.617 (=formula I.1303).
Table 1304. Compounds of formula I.1, wherein $R^2$ is $R^2$-10.618 (=formula I.1304).
Table 1305. Compounds of formula I.1, wherein $R^2$ is $R^2$-10.619 (=formula I.1305).
Table 1306. Compounds of formula I.1, wherein $R^2$ is $R^2$-10.620 (=formula I.1306).
Table 1307. Compounds of formula I.1, wherein $R^2$ is $R^2$-10.621 (=formula I.1307).
Table 1308. Compounds of formula I.1, wherein $R^2$ is $R^2$-10.622 (=formula I.1308).
Table 1309. Compounds of formula I.1, wherein $R^2$ is $R^2$-10.623 (=formula I.1309).
Table 1310. Compounds of formula I.1, wherein $R^2$ is $R^2$-10.624 (=formula I.1310).
Table 1311. Compounds of formula I.1, wherein $R^2$ is $R^2$-10.625 (=formula I.1311).
Table 1312. Compounds of formula I.1, wherein $R^2$ is $R^2$-10.626 (=formula I.1312).
Table 1313. Compounds of formula I.1, wherein $R^2$ is $R^2$-10.627 (=formula I.1313).
Table 1314. Compounds of formula I.1, wherein $R^2$ is $R^2$-10.628 (=formula I.1314).
Table 1315. Compounds of formula I.1, wherein $R^2$ is $R^2$-10.629 (=formula I.1315).
Table 1316. Compounds of formula I.1, wherein $R^2$ is $R^2$-10.630 (=formula I.1316).
Table 1317. Compounds of formula I.1, wherein $R^2$ is $R^2$-10.631 (=formula I.1317).
Table 1318. Compounds of formula I.1, wherein $R^2$ is $R^2$-10.632 (=formula I.1318).
Table 1319. Compounds of formula I.1, wherein $R^2$ is $R^2$-10.633 (=formula I.1319).
Table 1320. Compounds of formula I.1, wherein $R^2$ is $R^2$-10.634 (=formula I.1320).
Table 1321. Compounds of formula I.1, wherein $R^2$ is $R^2$-10.635 (=formula I.1321).
Table 1322. Compounds of formula I.1, wherein $R^2$ is $R^2$-10.636 (=formula I.1322).
Table 1323. Compounds of formula I.1, wherein $R^2$ is $R^2$-10.637 (=formula I.1323).
Table 1324. Compounds of formula I.1, wherein $R^2$ is $R^2$-10.638 (=formula I.1324).
Table 1325. Compounds of formula I.1, wherein $R^2$ is $R^2$-10.639 (=formula I.1325).
Table 1326. Compounds of formula I.1, wherein $R^2$ is $R^2$-10.640 (=formula I.1326).
Table 1327. Compounds of formula I.1, wherein $R^2$ is $R^2$-10.641 (=formula I.1327).
Table 1328. Compounds of formula I.1, wherein $R^2$ is $R^2$-10.642 (=formula I.1328).
Table 1329. Compounds of formula I.1, wherein $R^2$ is $R^2$-10.643 (=formula I.1329).
Table 1330. Compounds of formula I.1, wherein $R^2$ is $R^2$-10.644 (=formula I.1330).

Table 1331. Compounds of formula I.1, wherein $R^2$ is $R^2$-10.645 (=formula I.1331).
Table 1332. Compounds of formula I.1, wherein $R^2$ is $R^2$-10.646 (=formula I.1332).
Table 1333. Compounds of formula I.1, wherein $R^2$ is $R^2$-10.647 (=formula I.1333).
Table 1334. Compounds of formula I.1, wherein $R^2$ is $R^2$-10.648 (=formula I.1334).
Table 1335. Compounds of formula I.1, wherein $R^2$ is $R^2$-10.649 (=formula I.1335).
Table 1336. Compounds of formula I.1, wherein $R^2$ is $R^2$-10.650 (=formula I.1336).
Table 1337. Compounds of formula I.1, wherein $R^2$ is $R^2$-10.651 (=formula I.1337).
Table 1338. Compounds of formula I.1, wherein $R^2$ is $R^2$-10.652 (=formula I.1338).
Table 1339. Compounds of formula I.1, wherein $R^2$ is $R^2$-10.653 (=formula I.1339).
Table 1340. Compounds of formula I.1, wherein $R^2$ is $R^2$-10.654 (=formula I.1340).
Table 1341. Compounds of formula I.1, wherein $R^2$ is $R^2$-10.655 (=formula I.1341).
Table 1342. Compounds of formula I.1, wherein $R^2$ is $R^2$-10.656 (=formula I.1342).
Table 1343. Compounds of formula I.1, wherein $R^2$ is $R^2$-10.657 (=formula I.1343).
Table 1344. Compounds of formula I.1, wherein $R^2$ is $R^2$-10.658 (=formula I.1344).
Table 1345. Compounds of formula I.1, wherein $R^2$ is $R^2$-10.659 (=formula I.1345).
Table 1346. Compounds of formula I.1, wherein $R^2$ is $R^2$-10.660 (=formula I.1346).
Table 1347. Compounds of formula I.1, wherein $R^2$ is $R^2$-10.661 (=formula I.1347).
Table 1348. Compounds of formula I.1, wherein $R^2$ is $R^2$-10.662 (=formula I.1348).
Table 1349. Compounds of formula I.1, wherein $R^2$ is $R^2$-10.663 (=formula I.1349).
Table 1350. Compounds of formula I.1, wherein $R^2$ is $R^2$-10.664 (=formula I.1350).
Table 1351. Compounds of formula I.1, wherein $R^2$ is $R^2$-10.665 (=formula I.1351).
Table 1352. Compounds of formula I.1, wherein $R^2$ is $R^2$-10.666 (=formula I.1352).
Table 1353. Compounds of formula I.1, wherein $R^2$ is $R^2$-10.667 (=formula I.1353).
Table 1354. Compounds of formula I.1, wherein $R^2$ is $R^2$-10.668 (=formula I.1354).
Table 1355. Compounds of formula I.1, wherein $R^2$ is $R^2$-10.669 (=formula I.1355).
Table 1356. Compounds of formula I.1, wherein $R^2$ is $R^2$-10.670 (=formula I.1356).
Table 1357. Compounds of formula I.1, wherein $R^2$ is $R^2$-10.671 (=formula I.1357).
Table 1358. Compounds of formula I.1, wherein $R^2$ is $R^2$-10.672 (=formula I.1358).
Table 1359. Compounds of formula I.1, wherein $R^2$ is $R^2$-10.673 (=formula I.1359).
Table 1360. Compounds of formula I.1, wherein $R^2$ is $R^2$-10.674 (=formula I.1360).
Table 1361. Compounds of formula I.1, wherein $R^2$ is $R^2$-10.675 (=formula I.1361).
Table 1362. Compounds of formula I.1, wherein $R^2$ is $R^2$-10.676 (=formula I.1362).
Table 1363. Compounds of formula I.1, wherein $R^2$ is $R^2$-15.1 (=formula I.1363).
Table 1364. Compounds of formula I.1, wherein $R^2$ is $R^2$-15.2 (=formula I.1364).
Table 1365. Compounds of formula I.1, wherein $R^2$ is $R^2$-15.3 (=formula I.1365).
Table 1366. Compounds of formula I.1, wherein $R^2$ is $R^2$-15.4 (=formula I.1366).
Table 1367. Compounds of formula I.1, wherein $R^2$ is $R^2$-15.5 (=formula I.1367).
Table 1368. Compounds of formula I.1, wherein $R^2$ is $R^2$-15.6 (=formula I.1368).
Table 1369. Compounds of formula I.1, wherein $R^2$ is $R^2$-15.7 (=formula I.1369).
Table 1370. Compounds of formula I.1, wherein $R^2$ is $R^2$-15.8 (=formula I.1370).
Table 1371. Compounds of formula I.1, wherein $R^2$ is $R^2$-15.9 (=formula I.1371).
Table 1372. Compounds of formula I.1, wherein $R^2$ is $R^2$-15.10 (=formula I.1372).
Table 1373. Compounds of formula I.1, wherein $R^2$ is $R^2$-15.11 (=formula I.1373).
Table 1374. Compounds of formula I.1, wherein $R^2$ is $R^2$-15.12 (=formula I.1374).
Table 1375. Compounds of formula I.1, wherein $R^2$ is $R^2$-15.13 (=formula I.1375).
Table 1376. Compounds of formula I.1, wherein $R^2$ is $R^2$-15.14 (=formula I.1376).
Table 1377. Compounds of formula I.1, wherein $R^2$ is $R^2$-15.15 (=formula I.1377).
Table 1378. Compounds of formula I.1, wherein $R^2$ is $R^2$-15.16 (=formula I.1378).
Table 1379. Compounds of formula I.1, wherein $R^2$ is $R^2$-15.17 (=formula I.1379).
Table 1380. Compounds of formula I.1, wherein $R^2$ is $R^2$-15.18 (=formula I.1380).
Table 1381. Compounds of formula I.1, wherein $R^2$ is $R^2$-15.19 (=formula I.1381).
Table 1382. Compounds of formula I.1, wherein $R^2$ is $R^2$-15.20 (=formula I.1382).
Table 1383. Compounds of formula I.1, wherein $R^2$ is $R^2$-15.21 (=formula I.1383).
Table 1384. Compounds of formula I.1, wherein $R^2$ is $R^2$-15.22 (=formula I.1384).
Table 1385. Compounds of formula I.1, wherein $R^2$ is $R^2$-15.23 (=formula I.1385).
Table 1386. Compounds of formula I.1, wherein $R^2$ is $R^2$-15.24 (=formula I.1386).
Table 1387. Compounds of formula I.1, wherein $R^2$ is $R^2$-15.25 (=formula I.1387).
Table 1388. Compounds of formula I.1, wherein $R^2$ is $R^2$-15.26 (=formula I.1388).
Table 1389. Compounds of formula I.1, wherein $R^2$ is $R^2$-15.27 (=formula I.1389).
Table 1390. Compounds of formula I.1, wherein $R^2$ is $R^2$-15.28 (=formula I.1390).
Table 1391. Compounds of formula I.1, wherein $R^2$ is $R^2$-15.29 (=formula I.1391).
Table 1392. Compounds of formula I.1, wherein $R^2$ is $R^2$-15.30 (=formula I.1392).
Table 1393. Compounds of formula I.1, wherein $R^2$ is $R^2$-15.31 (=formula I.1393).
Table 1394. Compounds of formula I.1, wherein $R^2$ is $R^2$-15.32 (=formula I.1394).
Table 1395. Compounds of formula I.1, wherein $R^2$ is $R^2$-15.33 (=formula I.1395).
Table 1396. Compounds of formula I.1, wherein $R^2$ is $R^2$-15.34 (=formula I.1396).

Table 1397. Compounds of formula I.1, wherein $R^2$ is $R^2$-15.35 (=formula I.1397).
Table 1398. Compounds of formula I.1, wherein $R^2$ is $R^2$-15.36 (=formula I.1398).
Table 1399. Compounds of formula I.1, wherein $R^2$ is $R^2$-15.37 (=formula I.1399).
Table 1400. Compounds of formula I.1, wherein $R^2$ is $R^2$-15.38 (=formula I.1400).
Table 1401. Compounds of formula I.1, wherein $R^2$ is $R^2$-15.39 (=formula I.1401).
Table 1402. Compounds of formula I.1, wherein $R^2$ is $R^2$-15.40 (=formula I.1402).
Table 1403. Compounds of formula I.1, wherein $R^2$ is $R^2$-15.41 (=formula I.1403).
Table 1404. Compounds of formula I.1, wherein $R^2$ is $R^2$-15.42 (=formula I.1404).
Table 1405. Compounds of formula I.1, wherein $R^2$ is $R^2$-15.43 (=formula I.1405).
Table 1406. Compounds of formula I.1, wherein $R^2$ is $R^2$-15.44 (=formula I.1406).
Table 1407. Compounds of formula I.1, wherein $R^2$ is $R^2$-15.45 (=formula I.1407).
Table 1408. Compounds of formula I.1, wherein $R^2$ is $R^2$-15.46 (=formula I.1408).
Table 1409. Compounds of formula I.1, wherein $R^2$ is $R^2$-15.47 (=formula I.1409).
Table 1410. Compounds of formula I.1, wherein $R^2$ is $R^2$-15.48 (=formula I.1410).
Table 1411. Compounds of formula I.1, wherein $R^2$ is $R^2$-15.49 (=formula I.1411).
Table 1412. Compounds of formula I.1, wherein $R^2$ is $R^2$-15.50 (=formula I.1412).
Table 1413. Compounds of formula I.1, wherein $R^2$ is $R^2$-15.51 (=formula I.1413).
Table 1414. Compounds of formula I.1, wherein $R^2$ is $R^2$-15.52 (=formula I.1414).
Table 1415. Compounds of formula I.1, wherein $R^2$ is $R^2$-15.53 (=formula I.1415).
Table 1416. Compounds of formula I.1, wherein $R^2$ is $R^2$-15.54 (=formula I.1416).
Table 1417. Compounds of formula I.1, wherein $R^2$ is $R^2$-15.55 (=formula I.1417).
Table 1418. Compounds of formula I.1, wherein $R^2$ is $R^2$-15.56 (=formula I.1418).
Table 1419. Compounds of formula I.1, wherein $R^2$ is $R^2$-15.57 (=formula I.1419).
Table 1420. Compounds of formula I.1, wherein $R^2$ is $R^2$-15.58 (=formula I.1420).
Table 1421. Compounds of formula I.1, wherein $R^2$ is $R^2$-15.59 (=formula I.1421).
Table 1422. Compounds of formula I.1, wherein $R^2$ is $R^2$-15.60 (=formula I.1422).
Table 1423. Compounds of formula I.1, wherein $R^2$ is $R^2$-15.61 (=formula I.1423).
Table 1424. Compounds of formula I.1, wherein $R^2$ is $R^2$-15.62 (=formula I.1424).
Table 1425. Compounds of formula I.1, wherein $R^2$ is $R^2$-15.63 (=formula I.1425).
Table 1426. Compounds of formula I.1, wherein $R^2$ is $R^2$-15.64 (=formula I.1426).
Table 1427. Compounds of formula I.1, wherein $R^2$ is $R^2$-15.65 (=formula I.1427).
Table 1428. Compounds of formula I.1, wherein $R^2$ is $R^2$-15.66 (=formula I.1428).
Table 1429. Compounds of formula I.1, wherein $R^2$ is $R^2$-15.67 (=formula I.1429).
Table 1430. Compounds of formula I.1, wherein $R^2$ is $R^2$-15.68 (=formula I.1430).
Table 1431. Compounds of formula I.1, wherein $R^2$ is $R^2$-15.69 (=formula I.1431).
Table 1432. Compounds of formula I.1, wherein $R^2$ is $R^2$-15.70 (=formula I.1432).
Table 1433. Compounds of formula I.1, wherein $R^2$ is $R^2$-15.71 (=formula I.1433).
Table 1434. Compounds of formula I.1, wherein $R^2$ is $R^2$-15.72 (=formula I.1434).
Table 1435. Compounds of formula I.1, wherein $R^2$ is $R^2$-15.73 (=formula I.1435).
Table 1436. Compounds of formula I.1, wherein $R^2$ is $R^2$-15.74 (=formula I.1436).
Table 1437. Compounds of formula I.1, wherein $R^2$ is $R^2$-15.75 (=formula I.1437).
Table 1438. Compounds of formula I.1, wherein $R^2$ is $R^2$-15.76 (=formula I.1438).
Table 1439. Compounds of formula I.1, wherein $R^2$ is $R^2$-15.77 (=formula I.1439).
Table 1440. Compounds of formula I.1, wherein $R^2$ is $R^2$-15.78 (=formula I.1440).
Table 1441. Compounds of formula I.1, wherein $R^2$ is $R^2$-15.79 (=formula I.1441).
Table 1442. Compounds of formula I.1, wherein $R^2$ is $R^2$-15.80 (=formula I.1442).
Table 1443. Compounds of formula I.1, wherein $R^2$ is $R^2$-15.81 (=formula I.1443).
Table 1444. Compounds of formula I.1, wherein $R^2$ is $R^2$-15.82 (=formula I.1444).
Table 1445. Compounds of formula I.1, wherein $R^2$ is $R^2$-15.83 (=formula I.1445).
Table 1446. Compounds of formula I.1, wherein $R^2$ is $R^2$-15.84 (=formula I.1446).
Table 1447. Compounds of formula I.1, wherein $R^2$ is $R^2$-15.85 (=formula I.1447).
Table 1448. Compounds of formula I.1, wherein $R^2$ is $R^2$-15.86 (=formula I.1448).
Table 1449. Compounds of formula I.1, wherein $R^2$ is $R^2$-15.87 (=formula I.1449).
Table 1450. Compounds of formula I.1, wherein $R^2$ is $R^2$-15.88 (=formula I.1450).
Table 1451. Compounds of formula I.1, wherein $R^2$ is $R^2$-15.89 (=formula I.1451).
Table 1452. Compounds of formula I.1, wherein $R^2$ is $R^2$-15.90 (=formula I.1452).
Table 1453. Compounds of formula I.1, wherein $R^2$ is $R^2$-15.91 (=formula I.1453).
Table 1454. Compounds of formula I.1, wherein $R^2$ is $R^2$-15.92 (=formula I.1454).
Table 1455. Compounds of formula I.1, wherein $R^2$ is $R^2$-15.93 (=formula I.1455).
Table 1456. Compounds of formula I.1, wherein $R^2$ is $R^2$-15.94 (=formula I.1456).
Table 1457. Compounds of formula I.1, wherein $R^2$ is $R^2$-15.95 (=formula I.1457).
Table 1458. Compounds of formula I.1, wherein $R^2$ is $R^2$-15.96 (=formula I.1458).
Table 1459. Compounds of formula I.1, wherein $R^2$ is $R^2$-15.97 (=formula I.1459).
Table 1460. Compounds of formula I.1, wherein $R^2$ is $R^2$-15.98 (=formula I.1460).
Table 1461. Compounds of formula I.1, wherein $R^2$ is $R^2$-15.99 (=formula I.1461).
Table 1462. Compounds of formula I.1, wherein $R^2$ is $R^2$-15.100 (=formula I.1462).

Table 1463. Compounds of formula I.1, wherein $R^2$ is $R^2$-15.101 (=formula I.1463).
Table 1464. Compounds of formula I.1, wherein $R^2$ is $R^2$-15.102 (=formula I.1464).
Table 1465. Compounds of formula I.1, wherein $R^2$ is $R^2$-15.103 (=formula I.1465).
Table 1466. Compounds of formula I.1, wherein $R^2$ is $R^2$-15.104 (=formula I.1466).
Table 1467. Compounds of formula I.1, wherein $R^2$ is $R^2$-15.105 (=formula I.1467).
Table 1468. Compounds of formula I.1, wherein $R^2$ is $R^2$-15.106 (=formula I.1468).
Table 1469. Compounds of formula I.1, wherein $R^2$ is $R^2$-15.107 (=formula I.1469).
Table 1470. Compounds of formula I.1, wherein $R^2$ is $R^2$-15.108 (=formula I.1470).
Table 1471. Compounds of formula I.1, wherein $R^2$ is $R^2$-15.109 (=formula I.1471).
Table 1472. Compounds of formula I.1, wherein $R^2$ is $R^2$-15.110 (=formula I.1472).
Table 1473. Compounds of formula I.1, wherein $R^2$ is $R^2$-15.111 (=formula I.1473).
Table 1474. Compounds of formula I.1, wherein $R^2$ is $R^2$-15.112 (=formula I.1475).
Table 1475. Compounds of formula I.1, wherein $R^2$ is $R^2$-15.113 (=formula I.1475).
Table 1476. Compounds of formula I.1, wherein $R^2$ is $R^2$-15.114 (=formula I.1476).
Table 1477. Compounds of formula I.1, wherein $R^2$ is $R^2$-15.115 (=formula I.1477).
Table 1478. Compounds of formula I.1, wherein $R^2$ is $R^2$-15.116 (=formula I.1478).
Table 1479. Compounds of formula I.1, wherein $R^2$ is $R^2$-15.117 (=formula I.1479).
Table 1480. Compounds of formula I.1, wherein $R^2$ is $R^2$-15.118 (=formula I.1480).
Table 1481. Compounds of formula I.1, wherein $R^2$ is $R^2$-15.119 (=formula I.1481).
Table 1482. Compounds of formula I.1, wherein $R^2$ is $R^2$-15.120 (=formula I.1482).
Table 1483. Compounds of formula I.1, wherein $R^2$ is $R^2$-15.121 (=formula I.1483).
Table 1484. Compounds of formula I.1, wherein $R^2$ is $R^2$-15.122 (=formula I.1484).
Table 1485. Compounds of formula I.1, wherein $R^2$ is $R^2$-15.123 (=formula I.1485).
Table 1486. Compounds of formula I.1, wherein $R^2$ is $R^2$-15.124 (=formula I.1486).
Table 1487. Compounds of formula I.1, wherein $R^2$ is $R^2$-15.125 (=formula I.1487).
Table 1488. Compounds of formula I.1, wherein $R^2$ is $R^2$-15.126 (=formula I.1488).
Table 1489. Compounds of formula I.1, wherein $R^2$ is $R^2$-15.127 (=formula I.1489).
Table 1490. Compounds of formula I.1, wherein $R^2$ is $R^2$-15.128 (=formula I.1490).
Table 1491. Compounds of formula I.1, wherein $R^2$ is $R^2$-15.129 (=formula I.1491).
Table 1492. Compounds of formula I.1, wherein $R^2$ is $R^2$-15.130 (=formula I.1492).
Table 1493. Compounds of formula I.1, wherein $R^2$ is $R^2$-15.131 (=formula I.1493).
Table 1494. Compounds of formula I.1, wherein $R^2$ is $R^2$-15.132 (=formula I.1494).
Table 1495. Compounds of formula I.1, wherein $R^2$ is $R^2$-15.133 (=formula I.1495).
Table 1496. Compounds of formula I.1, wherein $R^2$ is $R^2$-15.134 (=formula I.1496).
Table 1497. Compounds of formula I.1, wherein $R^2$ is $R^2$-15.135 (=formula I.1497).
Table 1498. Compounds of formula I.1, wherein $R^2$ is $R^2$-15.136 (=formula I.1498).
Table 1499. Compounds of formula I.1, wherein $R^2$ is $R^2$-15.137 (=formula I.1499).
Table 1500. Compounds of formula I.1, wherein $R^2$ is $R^2$-15.138 (=formula I.1500).
Table 1501. Compounds of formula I.1, wherein $R^2$ is $R^2$-15.139 (=formula I.1501).
Table 1502. Compounds of formula I.1, wherein $R^2$ is $R^2$-15.140 (=formula I.1502).
Table 1503. Compounds of formula I.1, wherein $R^2$ is $R^2$-15.141 (=formula I.1503).
Table 1504. Compounds of formula I.1, wherein $R^2$ is $R^2$-15.142 (=formula I.1504).
Table 1505. Compounds of formula I.1, wherein $R^2$ is $R^2$-15.143 (=formula I.1505).
Table 1506. Compounds of formula I.1, wherein $R^2$ is $R^2$-15.144 (=formula I.1506).
Table 1507. Compounds of formula I.1, wherein $R^2$ is $R^2$-15.145 (=formula I.1507).
Table 1508. Compounds of formula I.1, wherein $R^2$ is $R^2$-15.146 (=formula I.1508).
Table 1509. Compounds of formula I.1, wherein $R^2$ is $R^2$-15.147 (=formula I.1509).
Table 1510. Compounds of formula I.1, wherein $R^2$ is $R^2$-15.148 (=formula I.1510).
Table 1511. Compounds of formula I.1, wherein $R^2$ is $R^2$-15.149 (=formula I.1511).
Table 1512. Compounds of formula I.1, wherein $R^2$ is $R^2$-15.150 (=formula I.1512).
Table 1513. Compounds of formula I.1, wherein $R^2$ is $R^2$-15.151 (=formula I.1513).
Table 1514. Compounds of formula I.1, wherein $R^2$ is $R^2$-15.152 (=formula I.1514).
Table 1515. Compounds of formula I.1, wherein $R^2$ is $R^2$-15.153 (=formula I.1515).
Table 1516. Compounds of formula I.1, wherein $R^2$ is $R^2$-15.154 (=formula I.1516).
Table 1517. Compounds of formula I.1, wherein $R^2$ is $R^2$-15.155 (=formula I.1517).
Table 1518. Compounds of formula I.1, wherein $R^2$ is $R^2$-15.156 (=formula I.1518).
Table 1519. Compounds of formula I.1, wherein $R^2$ is $R^2$-15.157 (=formula I.1519).
Table 1520. Compounds of formula I.1, wherein $R^2$ is $R^2$-15.158 (=formula I.1520).
Table 1521. Compounds of formula I.1, wherein $R^2$ is $R^2$-15.159 (=formula I.1521).
Table 1522. Compounds of formula I.1, wherein $R^2$ is $R^2$-15.160 (=formula I.1522).
Table 1523. Compounds of formula I.1, wherein $R^2$ is $R^2$-15.161 (=formula I.1523).
Table 1524. Compounds of formula I.1, wherein $R^2$ is $R^2$-15.162 (=formula I.1524).
Table 1525. Compounds of formula I.1, wherein $R^2$ is $R^2$-15.163 (=formula I.1525).
Table 1526. Compounds of formula I.1, wherein $R^2$ is $R^2$-15.164 (=formula I.1526).
Table 1527. Compounds of formula I.1, wherein $R^2$ is $R^2$-15.165 (=formula I.1527).
Table 1528. Compounds of formula I.1, wherein $R^2$ is $R^2$-15.166 (=formula I.1528).

Table 1529. Compounds of formula I.1, wherein $R^2$ is $R^2$-15.167 (=formula I.1529).
Table 1530. Compounds of formula I.1, wherein $R^2$ is $R^2$-15.168 (=formula I.1530).
Table 1531. Compounds of formula I.1, wherein $R^2$ is $R^2$-15.169 (=formula I.1531).
Table 1532. Compounds of formula I.1, wherein $R^2$ is $R^2$-15.170 (=formula I.1532).
Table 1533. Compounds of formula I.1, wherein $R^2$ is $R^2$-15.171 (=formula I.1533).
Table 1534. Compounds of formula I.1, wherein $R^2$ is $R^2$-15.172 (=formula I.1534).
Table 1535. Compounds of formula I.1, wherein $R^2$ is $R^2$-15.173 (=formula I.1535).
Table 1536. Compounds of formula I.1, wherein $R^2$ is $R^2$-15.174 (=formula I.1536).
Table 1537. Compounds of formula I.1, wherein $R^2$ is $R^2$-15.175 (=formula I.1537).
Table 1538. Compounds of formula I.1, wherein $R^2$ is $R^2$-15.176 (=formula I.1538).
Table 1539. Compounds of formula I.1, wherein $R^2$ is $R^2$-15.177 (=formula I.1539).
Table 1540. Compounds of formula I.1, wherein $R^2$ is $R^2$-15.178 (=formula I.1540).
Table 1541. Compounds of formula I.1, wherein $R^2$ is $R^2$-15.179 (=formula I.1541).
Table 1542. Compounds of formula I.1, wherein $R^2$ is $R^2$-15.180 (=formula I.1542).
Table 1543. Compounds of formula I.1, wherein $R^2$ is $R^2$-15.181 (=formula I.1543).
Table 1544. Compounds of formula I.1, wherein $R^2$ is $R^2$-15.182 (=formula I.1544).
Table 1545. Compounds of formula I.1, wherein $R^2$ is $R^2$-15.183 (=formula I.1545).
Table 1546. Compounds of formula I.1, wherein $R^2$ is $R^2$-15.184 (=formula I.1546).
Table 1547. Compounds of formula I.1, wherein $R^2$ is $R^2$-15.185 (=formula I.1547).
Table 1548. Compounds of formula I.1, wherein $R^2$ is $R^2$-15.186 (=formula I.1548).
Table 1549. Compounds of formula I.1, wherein $R^2$ is $R^2$-15.187 (=formula I.1549).
Table 1550. Compounds of formula I.1, wherein $R^2$ is $R^2$-15.188 (=formula I.1550).
Table 1551. Compounds of formula I.1, wherein $R^2$ is $R^2$-15.189 (=formula I.1551).
Table 1552. Compounds of formula I.1, wherein $R^2$ is $R^2$-15.190 (=formula I.1552).
Table 1553. Compounds of formula I.1, wherein $R^2$ is $R^2$-15.191 (=formula I.1553).
Table 1554. Compounds of formula I.1, wherein $R^2$ is $R^2$-15.192 (=formula I.1554).
Table 1555. Compounds of formula I.1, wherein $R^2$ is $R^2$-15.193 (=formula I.1555).
Table 1556. Compounds of formula I.1, wherein $R^2$ is $R^2$-15.194 (=formula I.1556).
Table 1557. Compounds of formula I.1, wherein $R^2$ is $R^2$-15.195 (=formula I.1557).
Table 1558. Compounds of formula I.1, wherein $R^2$ is $R^2$-15.196 (=formula I.1558).
Table 1559. Compounds of formula I.1, wherein $R^2$ is $R^2$-15.197 (=formula I.1559).
Table 1560. Compounds of formula I.1, wherein $R^2$ is $R^2$-15.198 (=formula I.1560).
Table 1561. Compounds of formula I.1, wherein $R^2$ is $R^2$-15.199 (=formula I.1561).
Table 1562. Compounds of formula I.1, wherein $R^2$ is $R^2$-15.200 (=formula I.1562).
Table 1563. Compounds of formula I.1, wherein $R^2$ is $R^2$-15.201 (=formula I.1563).
Table 1564. Compounds of formula I.1, wherein $R^2$ is $R^2$-15.202 (=formula I.1564).
Table 1565. Compounds of formula I.1, wherein $R^2$ is $R^2$-15.203 (=formula I.1565).
Table 1566. Compounds of formula I.1, wherein $R^2$ is $R^2$-15.204 (=formula I.1566).
Table 1567. Compounds of formula I.1, wherein $R^2$ is $R^2$-15.205 (=formula I.1567).
Table 1568. Compounds of formula I.1, wherein $R^2$ is $R^2$-15.206 (=formula I.1568).
Table 1569. Compounds of formula I.1, wherein $R^2$ is $R^2$-15.207 (=formula I.1569).
Table 1570. Compounds of formula I.1, wherein $R^2$ is $R^2$-15.208 (=formula I.1570).
Table 1571. Compounds of formula I.1, wherein $R^2$ is $R^2$-15.209 (=formula I.1571).
Table 1572. Compounds of formula I.1, wherein $R^2$ is $R^2$-15.210 (=formula I.1572).
Table 1573. Compounds of formula I.1, wherein $R^2$ is $R^2$-15.211 (=formula I.1573).
Table 1574. Compounds of formula I.1, wherein $R^2$ is $R^2$-15.212 (=formula I.1574).
Table 1575. Compounds of formula I.1, wherein $R^2$ is $R^2$-15.213 (=formula I.1575).
Table 1576. Compounds of formula I.1, wherein $R^2$ is $R^2$-15.214 (=formula I.1576).
Table 1577. Compounds of formula I.1, wherein $R^2$ is $R^2$-15.215 (=formula I.1577).
Table 1578. Compounds of formula I.1, wherein $R^2$ is $R^2$-15.216 (=formula I.1578).
Table 1579. Compounds of formula I.1, wherein $R^2$ is $R^2$-15.217 (=formula I.1579).
Table 1580. Compounds of formula I.1, wherein $R^2$ is $R^2$-15.218 (=formula I.1580).
Table 1581. Compounds of formula I.1, wherein $R^2$ is $R^2$-15.219 (=formula I.1581).
Table 1582. Compounds of formula I.1, wherein $R^2$ is $R^2$-15.220 (=formula I.1582).
Table 1583. Compounds of formula I.1, wherein $R^2$ is $R^2$-15.221 (=formula I.1583).
Table 1584. Compounds of formula I.1, wherein $R^2$ is $R^2$-15.222 (=formula I.1584).
Table 1585. Compounds of formula I.1, wherein $R^2$ is $R^2$-15.223 (=formula I.1585).
Table 1586. Compounds of formula I.1, wherein $R^2$ is $R^2$-15.224 (=formula I.1586).
Table 1587. Compounds of formula I.1, wherein $R^2$ is $R^2$-15.225 (=formula I.1587).
Table 1588. Compounds of formula I.1, wherein $R^2$ is $R^2$-15.226 (=formula I.1588).
Table 1589. Compounds of formula I.1, wherein $R^2$ is $R^2$-15.227 (=formula I.1589).
Table 1590. Compounds of formula I.1, wherein $R^2$ is $R^2$-15.228 (=formula I.1590).
Table 1591. Compounds of formula I.1, wherein $R^2$ is $R^2$-15.229 (=formula I.1591).
Table 1592. Compounds of formula I.1, wherein $R^2$ is $R^2$-15.230 (=formula I.1592).
Table 1593. Compounds of formula I.1, wherein $R^2$ is $R^2$-15.231 (=formula I.1593).
Table 1594. Compounds of formula I.1, wherein $R^2$ is $R^2$-15.232 (=formula I.1594).

Table 1595. Compounds of formula I.1, wherein $R^2$ is $R^2$-15.233 (=formula I.1595).
Table 1596. Compounds of formula I.1, wherein $R^2$ is $R^2$-15.234 (=formula I.1596).
Table 1597. Compounds of formula I.1, wherein $R^2$ is $R^2$-15.235 (=formula I.1597).
Table 1598. Compounds of formula I.1, wherein $R^2$ is $R^2$-15.236 (=formula I.1598).
Table 1599. Compounds of formula I.1, wherein $R^2$ is $R^2$-15.237 (=formula I.1599).
Table 1600. Compounds of formula I.1, wherein $R^2$ is $R^2$-15.238 (=formula I.1600).
Table 1601. Compounds of formula I.1, wherein $R^2$ is $R^2$-15.239 (=formula I.1601).
Table 1602. Compounds of formula I.1, wherein $R^2$ is $R^2$-15.240 (=formula I.1602).
Table 1603. Compounds of formula I.1, wherein $R^2$ is $R^2$-15.241 (=formula I.1603).
Table 1604. Compounds of formula I.1, wherein $R^2$ is $R^2$-15.242 (=formula I.1604).
Table 1605. Compounds of formula I.1, wherein $R^2$ is $R^2$-15.243 (=formula I.1605).
Table 1606. Compounds of formula I.1, wherein $R^2$ is $R^2$-15.244 (=formula I.1606).
Table 1607. Compounds of formula I.1, wherein $R^2$ is $R^2$-15.245 (=formula I.1607).
Table 1608. Compounds of formula I.1, wherein $R^2$ is $R^2$-15.246 (=formula I.1608).
Table 1609. Compounds of formula I.1, wherein $R^2$ is $R^2$-15.247 (=formula I.1609).
Table 1610. Compounds of formula I.1, wherein $R^2$ is $R^2$-15.248 (=formula I.1610).
Table 1611. Compounds of formula I.1, wherein $R^2$ is $R^2$-15.249 (=formula I.1611).
Table 1612. Compounds of formula I.1, wherein $R^2$ is $R^2$-15.250 (=formula I.1612).
Table 1613. Compounds of formula I.1, wherein $R^2$ is $R^2$-15.251 (=formula I.1613).
Table 1614. Compounds of formula I.1, wherein $R^2$ is $R^2$-15.252 (=formula I.1614).
Table 1615. Compounds of formula I.1, wherein $R^2$ is $R^2$-15.253 (=formula I.1615).
Table 1616. Compounds of formula I.1, wherein $R^2$ is $R^2$-15.254 (=formula I.1616).
Table 1617. Compounds of formula I.1, wherein $R^2$ is $R^2$-15.255 (=formula I.1617).
Table 1618. Compounds of formula I.1, wherein $R^2$ is $R^2$-15.256 (=formula I.1618).
Table 1619. Compounds of formula I.1, wherein $R^2$ is $R^2$-15.257 (=formula I.1619).
Table 1620. Compounds of formula I.1, wherein $R^2$ is $R^2$-15.258 (=formula I.1620).
Table 1621. Compounds of formula I.1, wherein $R^2$ is $R^2$-15.259 (=formula I.1621).
Table 1622. Compounds of formula I.1, wherein $R^2$ is $R^2$-15.260 (=formula I.1622).
Table 1623. Compounds of formula I.1, wherein $R^2$ is $R^2$-15.261 (=formula I.1623).
Table 1624. Compounds of formula I.1, wherein $R^2$ is $R^2$-15.262 (=formula I.1624).
Table 1625. Compounds of formula I.1, wherein $R^2$ is $R^2$-15.263 (=formula I.1625).
Table 1626. Compounds of formula I.1, wherein $R^2$ is $R^2$-15.264 (=formula I.1626).
Table 1627. Compounds of formula I.1, wherein $R^2$ is $R^2$-15.265 (=formula I.1627).
Table 1628. Compounds of formula I.1, wherein $R^2$ is $R^2$-15.266 (=formula I.1628).
Table 1629. Compounds of formula I.1, wherein $R^2$ is $R^2$-15.267 (=formula I.1629).
Table 1630. Compounds of formula I.1, wherein $R^2$ is $R^2$-15.268 (=formula I.1630).
Table 1631. Compounds of formula I.1, wherein $R^2$ is $R^2$-15.269 (=formula I.1631).
Table 1632. Compounds of formula I.1, wherein $R^2$ is $R^2$-15.270 (=formula I.1632).
Table 1633. Compounds of formula I.1, wherein $R^2$ is $R^2$-15.271 (=formula I.1633).
Table 1634. Compounds of formula I.1, wherein $R^2$ is $R^2$-15.272 (=formula I.1634).
Table 1635. Compounds of formula I.1, wherein $R^2$ is $R^2$-15.273 (=formula I.1635).
Table 1636. Compounds of formula I.1, wherein $R^2$ is $R^2$-15.274 (=formula I.1636).
Table 1637. Compounds of formula I.1, wherein $R^2$ is $R^2$-15.275 (=formula I.1637).
Table 1638. Compounds of formula I.1, wherein $R^2$ is $R^2$-15.276 (=formula I.1638).
Table 1639. Compounds of formula I.1, wherein $R^2$ is $R^2$-15.277 (=formula I.1639).
Table 1640. Compounds of formula I.1, wherein $R^2$ is $R^2$-15.278 (=formula I.1640).
Table 1641. Compounds of formula I.1, wherein $R^2$ is $R^2$-15.279 (=formula I.1641).
Table 1642. Compounds of formula I.1, wherein $R^2$ is $R^2$-15.280 (=formula I.1642).
Table 1643. Compounds of formula I.1, wherein $R^2$ is $R^2$-15.281 (=formula I.1643).
Table 1644. Compounds of formula I.1, wherein $R^2$ is $R^2$-15.282 (=formula I.1644).
Table 1645. Compounds of formula I.1, wherein $R^2$ is $R^2$-15.283 (=formula I.1645).
Table 1646. Compounds of formula I.1, wherein $R^2$ is $R^2$-15.284 (=formula I.1646).
Table 1647. Compounds of formula I.1, wherein $R^2$ is $R^2$-15.285 (=formula I.1647).
Table 1648. Compounds of formula I.1, wherein $R^2$ is $R^2$-15.286 (=formula I.1648).
Table 1649. Compounds of formula I.1, wherein $R^2$ is $R^2$-15.287 (=formula I.1649).
Table 1650. Compounds of formula I.1, wherein $R^2$ is $R^2$-15.288 (=formula I.1650).
Table 1651. Compounds of formula I.1, wherein $R^2$ is $R^2$-15.289 (=formula I.1651).
Table 1652. Compounds of formula I.1, wherein $R^2$ is $R^2$-15.290 (=formula I.1652).
Table 1653. Compounds of formula I.1, wherein $R^2$ is $R^2$-15.291 (=formula I.1653).
Table 1654. Compounds of formula I.1, wherein $R^2$ is $R^2$-15.292 (=formula I.1654).
Table 1655. Compounds of formula I.1, wherein $R^2$ is $R^2$-15.293 (=formula I.1655).
Table 1656. Compounds of formula I.1, wherein $R^2$ is $R^2$-15.294 (=formula I.1656).
Table 1657. Compounds of formula I.1, wherein $R^2$ is $R^2$-15.295 (=formula I.1657).
Table 1658. Compounds of formula I.1, wherein $R^2$ is $R^2$-15.296 (=formula I.1658).
Table 1659. Compounds of formula I.1, wherein $R^2$ is $R^2$-15.297 (=formula I.1659).
Table 1660. Compounds of formula I.1, wherein $R^2$ is $R^2$-15.298 (=formula I.1660).

Table 1661. Compounds of formula I.1, wherein $R^2$ is $R^2$-15.299 (=formula I.1661).
Table 1662. Compounds of formula I.1, wherein $R^2$ is $R^2$-15.300 (=formula I.1662).
Table 1663. Compounds of formula I.1, wherein $R^2$ is $R^2$-15.301 (=formula I.1663).
Table 1664. Compounds of formula I.1, wherein $R^2$ is $R^2$-15.302 (=formula I.1664).
Table 1665. Compounds of formula I.1, wherein $R^2$ is $R^2$-15.303 (=formula I.1665).
Table 1666. Compounds of formula I.1, wherein $R^2$ is $R^2$-15.304 (=formula I.1666).
Table 1667. Compounds of formula I.1, wherein $R^2$ is $R^2$-15.305 (=formula I.1667).
Table 1668. Compounds of formula I.1, wherein $R^2$ is $R^2$-15.306 (=formula I.1668).
Table 1669. Compounds of formula I.1, wherein $R^2$ is $R^2$-15.307 (=formula I.1669).
Table 1670. Compounds of formula I.1, wherein $R^2$ is $R^2$-15.308 (=formula I.1670).
Table 1671. Compounds of formula I.1, wherein $R^2$ is $R^2$-15.309 (=formula I.1671).
Table 1672. Compounds of formula I.1, wherein $R^2$ is $R^2$-15.310 (=formula I.1672).
Table 1673. Compounds of formula I.1, wherein $R^2$ is $R^2$-15.311 (=formula I.1673).
Table 1674. Compounds of formula I.1, wherein $R^2$ is $R^2$-15.312 (=formula I.1674).
Table 1675. Compounds of formula I.1, wherein $R^2$ is $R^2$-15.313 (=formula I.1675).
Table 1676. Compounds of formula I.1, wherein $R^2$ is $R^2$-15.314 (=formula I.1676).
Table 1677. Compounds of formula I.1, wherein $R^2$ is $R^2$-15.315 (=formula I.1676).
Table 1678. Compounds of formula I.1, wherein $R^2$ is $R^2$-15.316 (=formula I.1678).
Table 1679. Compounds of formula I.1, wherein $R^2$ is $R^2$-15.317 (=formula I.1679).
Table 1680. Compounds of formula I.1, wherein $R^2$ is $R^2$-15.318 (=formula I.1680).
Table 1681. Compounds of formula I.1, wherein $R^2$ is $R^2$-15.319 (=formula I.1681).
Table 1682. Compounds of formula I.1, wherein $R^2$ is $R^2$-15.320 (=formula I.1682).
Table 1683. Compounds of formula I.1, wherein $R^2$ is $R^2$-15.321 (=formula I.1683).
Table 1684. Compounds of formula I.1, wherein $R^2$ is $R^2$-15.322 (=formula I.1684).
Table 1685. Compounds of formula I.1, wherein $R^2$ is $R^2$-15.323 (=formula I.1685).
Table 1686. Compounds of formula I.1, wherein $R^2$ is $R^2$-15.324 (=formula I.1686).
Table 1687. Compounds of formula I.1, wherein $R^2$ is $R^2$-15.325 (=formula I.1687).
Table 1688. Compounds of formula I.1, wherein $R^2$ is $R^2$-15.326 (=formula I.1688).
Table 1689. Compounds of formula I.1, wherein $R^2$ is $R^2$-15.327 (=formula I.1689).
Table 1690. Compounds of formula I.1, wherein $R^2$ is $R^2$-15.328 (=formula I.1690).
Table 1691. Compounds of formula I.1, wherein $R^2$ is $R^2$-15.329 (=formula I.1691).
Table 1692. Compounds of formula I.1, wherein $R^2$ is $R^2$-15.330 (=formula I.1692).
Table 1693. Compounds of formula I.1, wherein $R^2$ is $R^2$-15.331 (=formula I.1693).
Table 1694. Compounds of formula I.1, wherein $R^2$ is $R^2$-15.332 (=formula I.1694).
Table 1695. Compounds of formula I.1, wherein $R^2$ is $R^2$-15.333 (=formula I.1695).
Table 1696. Compounds of formula I.1, wherein $R^2$ is $R^2$-15.334 (=formula I.1696).
Table 1697. Compounds of formula I.1, wherein $R^2$ is $R^2$-15.335 (=formula I.1697).
Table 1698. Compounds of formula I.1, wherein $R^2$ is $R^2$-15.336 (=formula I.1698).
Table 1699. Compounds of formula I.1, wherein $R^2$ is $R^2$-15.334 (=formula I.1699).
Table 1700. Compounds of formula I.1, wherein $R^2$ is $R^2$-15.338 (=formula I.1700).
Table 1701. Compounds of formula I.1, wherein $R^2$ is $R^2$-15.339 (=formula I.1701).
Table 1702. Compounds of formula I.1, wherein $R^2$ is $R^2$-15.340 (=formula I.1702).
Table 1703. Compounds of formula I.1, wherein $R^2$ is $R^2$-15.341 (=formula I.1703).
Table 1704. Compounds of formula I.1, wherein $R^2$ is $R^2$-15.342 (=formula I.1704).
Table 1705. Compounds of formula I.1, wherein $R^2$ is $R^2$-15.343 (=formula I.1705).
Table 1706. Compounds of formula I.1, wherein $R^2$ is $R^2$-15.344 (=formula I.1706).
Table 1707. Compounds of formula I.1, wherein $R^2$ is $R^2$-15.345 (=formula I.1707).
Table 1708. Compounds of formula I.1, wherein $R^2$ is $R^2$-15.346 (=formula I.1708).
Table 1709. Compounds of formula I.1, wherein $R^2$ is $R^2$-15.347 (=formula I.1709).
Table 1710. Compounds of formula I.1, wherein $R^2$ is $R^2$-15.348 (=formula I.1710).
Table 1711. Compounds of formula I.1, wherein $R^2$ is $R^2$-15.349 (=formula I.1711).
Table 1712. Compounds of formula I.1, wherein $R^2$ is $R^2$-15.350 (=formula I.1712).
Table 1713. Compounds of formula I.1, wherein $R^2$ is $R^2$-15.351 (=formula I.1713).
Table 1714. Compounds of formula I.1, wherein $R^2$ is $R^2$-15.352 (=formula I.1714).
Table 1715. Compounds of formula I.1, wherein $R^2$ is $R^2$-15.353 (=formula I.1715).
Table 1716. Compounds of formula I.1, wherein $R^2$ is $R^2$-15.354 (=formula I.1716).
Table 1717. Compounds of formula I.1, wherein $R^2$ is $R^2$-15.355 (=formula I.1717).
Table 1718. Compounds of formula I.1, wherein $R^2$ is $R^2$-15.356 (=formula I.1718).
Table 1719. Compounds of formula I.1, wherein $R^2$ is $R^2$-15.357 (=formula I.1719).
Table 1720. Compounds of formula I.1, wherein $R^2$ is $R^2$-15.358 (=formula I.1720).
Table 1721. Compounds of formula I.1, wherein $R^2$ is $R^2$-15.359 (=formula I.1721).
Table 1722. Compounds of formula I.1, wherein $R^2$ is $R^2$-15.360 (=formula I.1722).
Table 1723. Compounds of formula I.1, wherein $R^2$ is $R^2$-15.361 (=formula I.1723).
Table 1724. Compounds of formula I.1, wherein $R^2$ is $R^2$-15.362 (=formula I.1724).
Table 1725. Compounds of formula I.1, wherein $R^2$ is $R^2$-15.363 (=formula I.1725).
Table 1726. Compounds of formula I.1, wherein $R^2$ is $R^2$-15.364 (=formula I.1726).

Table 1727. Compounds of formula I.1, wherein $R^2$ is $R^2$-15.365 (=formula I.1727).
Table 1728. Compounds of formula I.1, wherein $R^2$ is $R^2$-15.366 (=formula I.1728).
Table 1729. Compounds of formula I.1, wherein $R^2$ is $R^2$-15.367 (=formula I.1729).
Table 1730. Compounds of formula I.1, wherein $R^2$ is $R^2$-15.368 (=formula I.1730).
Table 1731. Compounds of formula I.1, wherein $R^2$ is $R^2$-15.369 (=formula I.1731).
Table 1732. Compounds of formula I.1, wherein $R^2$ is $R^2$-15.370 (=formula I.1732).
Table 1733. Compounds of formula I.1, wherein $R^2$ is $R^2$-15.371 (=formula I.1733).
Table 1734. Compounds of formula I.1, wherein $R^2$ is $R^2$-15.372 (=formula I.1734).
Table 1735. Compounds of formula I.1, wherein $R^2$ is $R^2$-15.373 (=formula I.1735).
Table 1736. Compounds of formula I.1, wherein $R^2$ is $R^2$-15.374 (=formula I.1736).
Table 1737. Compounds of formula I.1, wherein $R^2$ is $R^2$-15.375 (=formula I.1737).
Table 1738. Compounds of formula I.1, wherein $R^2$ is $R^2$-15.376 (=formula I.1738).
Table 1739. Compounds of formula I.1, wherein $R^2$ is $R^2$-15.377 (=formula I.1739).
Table 1740. Compounds of formula I.1, wherein $R^2$ is $R^2$-15.378 (=formula I.1740).
Table 1741. Compounds of formula I.1, wherein $R^2$ is $R^2$-15.379 (=formula I.1741).
Table 1742. Compounds of formula I.1, wherein $R^2$ is $R^2$-15.380 (=formula I.1742).
Table 1743. Compounds of formula I.1, wherein $R^2$ is $R^2$-15.381 (=formula I.1743).
Table 1744. Compounds of formula I.1, wherein $R^2$ is $R^2$-15.382 (=formula I.1744).
Table 1745. Compounds of formula I.1, wherein $R^2$ is $R^2$-15.383 (=formula I.1745).
Table 1746. Compounds of formula I.1, wherein $R^2$ is $R^2$-15.384 (=formula I.1746).
Table 1747. Compounds of formula I.1, wherein $R^2$ is $R^2$-15.385 (=formula I.1747).
Table 1748. Compounds of formula I.1, wherein $R^2$ is $R^2$-15.386 (=formula I.1748).
Table 1749. Compounds of formula I.1, wherein $R^2$ is $R^2$-15.387 (=formula I.1749).
Table 1750. Compounds of formula I.1, wherein $R^2$ is $R^2$-15.388 (=formula I.1750).
Table 1751. Compounds of formula I.1, wherein $R^2$ is $R^2$-15.389 (=formula I.1751).
Table 1752. Compounds of formula I.1, wherein $R^2$ is $R^2$-15.390 (=formula I.1752).
Table 1753. Compounds of formula I.1, wherein $R^2$ is $R^2$-15.391 (=formula I.1753).
Table 1754. Compounds of formula I.1, wherein $R^2$ is $R^2$-15.392 (=formula I.1754).
Table 1755. Compounds of formula I.1, wherein $R^2$ is $R^2$-15.393 (=formula I.1755).
Table 1756. Compounds of formula I.1, wherein $R^2$ is $R^2$-15.394 (=formula I.1756).
Table 1757. Compounds of formula I.1, wherein $R^2$ is $R^2$-15.395 (=formula I.1757).
Table 1758. Compounds of formula I.1, wherein $R^2$ is $R^2$-15.396 (=formula I.1758).
Table 1759. Compounds of formula I.1, wherein $R^2$ is $R^2$-15.397 (=formula I.1759).
Table 1760. Compounds of formula I.1, wherein $R^2$ is $R^2$-15.398 (=formula I.1760).
Table 1761. Compounds of formula I.1, wherein $R^2$ is $R^2$-15.399 (=formula I.1761).
Table 1762. Compounds of formula I.1, wherein $R^2$ is $R^2$-15.400 (=formula I.1762).
Table 1763. Compounds of formula I.1, wherein $R^2$ is $R^2$-15.401 (=formula I.1763).
Table 1764. Compounds of formula I.1, wherein $R^2$ is $R^2$-15.402 (=formula I.1764).
Table 1765. Compounds of formula I.1, wherein $R^2$ is $R^2$-15.403 (=formula I.1765).
Table 1766. Compounds of formula I.1, wherein $R^2$ is $R^2$-15.404 (=formula I.1766).
Table 1767. Compounds of formula I.1, wherein $R^2$ is $R^2$-15.405 (=formula I.1767).
Table 1768. Compounds of formula I.1, wherein $R^2$ is $R^2$-15.406 (=formula I.1768).
Table 1769. Compounds of formula I.1, wherein $R^2$ is $R^2$-15.407 (=formula I.1769).
Table 1770. Compounds of formula I.1, wherein $R^2$ is $R^2$-15.408 (=formula I.1770).
Table 1771. Compounds of formula I.1, wherein $R^2$ is $R^2$-15.409 (=formula I.1771).
Table 1772. Compounds of formula I.1, wherein $R^2$ is $R^2$-15.410 (=formula I.1772).
Table 1773. Compounds of formula I.1, wherein $R^2$ is $R^2$-15.411 (=formula I.1773).
Table 1774. Compounds of formula I.1, wherein $R^2$ is $R^2$-15.412 (=formula I.1774).
Table 1775. Compounds of formula I.1, wherein $R^2$ is $R^2$-15.413 (=formula I.1775).
Table 1776. Compounds of formula I.1, wherein $R^2$ is $R^2$-15.414 (=formula I.1776).
Table 1777. Compounds of formula I.1, wherein $R^2$ is $R^2$-15.415 (=formula I.1777).
Table 1778. Compounds of formula I.1, wherein $R^2$ is $R^2$-15.416 (=formula I.1778).
Table 1779. Compounds of formula I.1, wherein $R^2$ is $R^2$-15.417 (=formula I.1779).
Table 1780. Compounds of formula I.1, wherein $R^2$ is $R^2$-15.418 (=formula I.1780).
Table 1781. Compounds of formula I.1, wherein $R^2$ is $R^2$-15.419 (=formula I.1781).
Table 1782. Compounds of formula I.1, wherein $R^2$ is $R^2$-15.420 (=formula I.1782).
Table 1783. Compounds of formula I.1, wherein $R^2$ is $R^2$-15.421 (=formula I.1783).
Table 1784. Compounds of formula I.1, wherein $R^2$ is $R^2$-15.422 (=formula I.1784).
Table 1785. Compounds of formula I.1, wherein $R^2$ is $R^2$-15.423 (=formula I.1785).
Table 1786. Compounds of formula I.1, wherein $R^2$ is $R^2$-15.424 (=formula I.1786).
Table 1787. Compounds of formula I.1, wherein $R^2$ is $R^2$-15.425 (=formula I.1787).
Table 1788. Compounds of formula I.1, wherein $R^2$ is $R^2$-15.426 (=formula I.1788).
Table 1789. Compounds of formula I.1, wherein $R^2$ is $R^2$-15.427 (=formula I.1789).
Table 1790. Compounds of formula I.1, wherein $R^2$ is $R^2$-15.428 (=formula I.1790).
Table 1791. Compounds of formula I.1, wherein $R^2$ is $R^2$-15.429 (=formula I.1791).
Table 1792. Compounds of formula I.1, wherein $R^2$ is $R^2$-15.430 (=formula I.1792).

Table 1793. Compounds of formula I.1, wherein $R^2$ is $R^2$-15.431 (=formula I.1793).
Table 1794. Compounds of formula I.1, wherein $R^2$ is $R^2$-15.432 (=formula I.1794).
Table 1795. Compounds of formula I.1, wherein $R^2$ is $R^2$-15.433 (=formula I.1795).
Table 1796. Compounds of formula I.1, wherein $R^2$ is $R^2$-15.434 (=formula I.1796).
Table 1797. Compounds of formula I.1, wherein $R^2$ is $R^2$-15.435 (=formula I.1797).
Table 1798. Compounds of formula I.1, wherein $R^2$ is $R^2$-15.436 (=formula I.1798).
Table 1799. Compounds of formula I.1, wherein $R^2$ is $R^2$-15.437 (=formula I.1799).
Table 1800. Compounds of formula I.1, wherein $R^2$ is $R^2$-15.438 (=formula I.1800).
Table 1801. Compounds of formula I.1, wherein $R^2$ is $R^2$-15.439 (=formula I.1801).
Table 1802. Compounds of formula I.1, wherein $R^2$ is $R^2$-15.440 (=formula I.1802).
Table 1803. Compounds of formula I.1, wherein $R^2$ is $R^2$-15.441 (=formula I.1803).
Table 1804. Compounds of formula I.1, wherein $R^2$ is $R^2$-15.442 (=formula I.1804).
Table 1805. Compounds of formula I.1, wherein $R^2$ is $R^2$-15.443 (=formula I.1805).
Table 1806. Compounds of formula I.1, wherein $R^2$ is $R^2$-15.444 (=formula I.1806).
Table 1807. Compounds of formula I.1, wherein $R^2$ is $R^2$-15.445 (=formula I.1807).
Table 1808. Compounds of formula I.1, wherein $R^2$ is $R^2$-15.446 (=formula I.1808).
Table 1809. Compounds of formula I.1, wherein $R^2$ is $R^2$-15.447 (=formula I.1809).
Table 1810. Compounds of formula I.1, wherein $R^2$ is $R^2$-15.448 (=formula I.1810).
Table 1811. Compounds of formula I.1, wherein $R^2$ is $R^2$-15.449 (=formula I.1811).
Table 1812. Compounds of formula I.1, wherein $R^2$ is $R^2$-15.450 (=formula I.1812).
Table 1813. Compounds of formula I.1, wherein $R^2$ is $R^2$-15.451 (=formula I.1813).
Table 1814. Compounds of formula I.1, wherein $R^2$ is $R^2$-15.452 (=formula I.1814).
Table 1815. Compounds of formula I.1, wherein $R^2$ is $R^2$-15.453 (=formula I.1815).
Table 1816. Compounds of formula I.1, wherein $R^2$ is $R^2$-15.454 (=formula I.1816).
Table 1817. Compounds of formula I.1, wherein $R^2$ is $R^2$-15.455 (=formula I.1817).
Table 1818. Compounds of formula I.1, wherein $R^2$ is $R^2$-15.456 (=formula I.1818).
Table 1819. Compounds of formula I.1, wherein $R^2$ is $R^2$-15.457 (=formula I.1819).
Table 1820. Compounds of formula I.1, wherein $R^2$ is $R^2$-15.458 (=formula I.1820).
Table 1821. Compounds of formula I.1, wherein $R^2$ is $R^2$-15.459 (=formula I.1821).
Table 1822. Compounds of formula I.1, wherein $R^2$ is $R^2$-15.460 (=formula I.1822).
Table 1823. Compounds of formula I.1, wherein $R^2$ is $R^2$-15.461 (=formula I.1823).
Table 1824. Compounds of formula I.1, wherein $R^2$ is $R^2$-15.462 (=formula I.1824).
Table 1825. Compounds of formula I.1, wherein $R^2$ is $R^2$-15.463 (=formula I.1825).
Table 1826. Compounds of formula I.1, wherein $R^2$ is $R^2$-15.464 (=formula I.1826).
Table 1827. Compounds of formula I.1, wherein $R^2$ is $R^2$-15.465 (=formula I.1827).
Table 1828. Compounds of formula I.1, wherein $R^2$ is $R^2$-15.466 (=formula I.1828).
Table 1829. Compounds of formula I.1, wherein $R^2$ is $R^2$-15.467 (=formula I.1829).
Table 1830. Compounds of formula I.1, wherein $R^2$ is $R^2$-15.468 (=formula I.1830).
Table 1831. Compounds of formula I.1, wherein $R^2$ is $R^2$-15.469 (=formula I.1831).
Table 1832. Compounds of formula I.1, wherein $R^2$ is $R^2$-15.470 (=formula I.1832).
Table 1833. Compounds of formula I.1, wherein $R^2$ is $R^2$-15.471 (=formula I.1833).
Table 1834. Compounds of formula I.1, wherein $R^2$ is $R^2$-15.472 (=formula I.1834).
Table 1835. Compounds of formula I.1, wherein $R^2$ is $R^2$-15.473 (=formula I.1835).
Table 1836. Compounds of formula I.1, wherein $R^2$ is $R^2$-15.474 (=formula I.1836).
Table 1837. Compounds of formula I.1, wherein $R^2$ is $R^2$-15.475 (=formula I.1837).
Table 1838. Compounds of formula I.1, wherein $R^2$ is $R^2$-15.476 (=formula I.1838).
Table 1839. Compounds of formula I.1, wherein $R^2$ is $R^2$-15.477 (=formula I.1839).
Table 1840. Compounds of formula I.1, wherein $R^2$ is $R^2$-15.478 (=formula I.1840).
Table 1841. Compounds of formula I.1, wherein $R^2$ is $R^2$-15.479 (=formula I.1841).
Table 1842. Compounds of formula I.1, wherein $R^2$ is $R^2$-15.480 (=formula I.1842).
Table 1843. Compounds of formula I.1, wherein $R^2$ is $R^2$-15.481 (=formula I.1843).
Table 1844. Compounds of formula I.1, wherein $R^2$ is $R^2$-15.482 (=formula I.1844).
Table 1845. Compounds of formula I.1, wherein $R^2$ is $R^2$-15.483 (=formula I.1845).
Table 1846. Compounds of formula I.1, wherein $R^2$ is $R^2$-15.484 (=formula I.1846).
Table 1847. Compounds of formula I.1, wherein $R^2$ is $R^2$-15.485 (=formula I.1847).
Table 1848. Compounds of formula I.1, wherein $R^2$ is $R^2$-15.486 (=formula I.1848).
Table 1849. Compounds of formula I.1, wherein $R^2$ is $R^2$-15.487 (=formula I.1849).
Table 1850. Compounds of formula I.1, wherein $R^2$ is $R^2$-15.488 (=formula I.1850).
Table 1851. Compounds of formula I.1, wherein $R^2$ is $R^2$-15.489 (=formula I.1851).
Table 1852. Compounds of formula I.1, wherein $R^2$ is $R^2$-15.490 (=formula I.1852).
Table 1853. Compounds of formula I.1, wherein $R^2$ is $R^2$-15.491 (=formula I.1853).
Table 1854. Compounds of formula I.1, wherein $R^2$ is $R^2$-15.492 (=formula I.1854).
Table 1855. Compounds of formula I.1, wherein $R^2$ is $R^2$-15.493 (=formula I.1855).
Table 1856. Compounds of formula I.1, wherein $R^2$ is $R^2$-15.494 (=formula I.1856).
Table 1857. Compounds of formula I.1, wherein $R^2$ is $R^2$-15.495 (=formula I.1857).
Table 1858. Compounds of formula I.1, wherein $R^2$ is $R^2$-15.496 (=formula I.1858).

Table 1859. Compounds of formula I.1, wherein $R^2$ is $R^2$-15.497 (=formula I.1859).
Table 1860. Compounds of formula I.1, wherein $R^2$ is $R^2$-15.498 (=formula I.1860).
Table 1861. Compounds of formula I.1, wherein $R^2$ is $R^2$-15.499 (=formula I.1861).
Table 1862. Compounds of formula I.1, wherein $R^2$ is $R^2$-15.500 (=formula I.1862).
Table 1863. Compounds of formula I.1, wherein $R^2$ is $R^2$-15.501 (=formula I.1863).
Table 1864. Compounds of formula I.1, wherein $R^2$ is $R^2$-15.502 (=formula I.1864).
Table 1865. Compounds of formula I.1, wherein $R^2$ is $R^2$-15.503 (=formula I.1865).
Table 1866. Compounds of formula I.1, wherein $R^2$ is $R^2$-15.504 (=formula I.1866).
Table 1867. Compounds of formula I.1, wherein $R^2$ is $R^2$-15.505 (=formula I.1867).
Table 1868. Compounds of formula I.1, wherein $R^2$ is $R^2$-15.506 (=formula I.1868).
Table 1869. Compounds of formula I.1, wherein $R^2$ is $R^2$-15.507 (=formula I.1869).
Table 1870. Compounds of formula I.1, wherein $R^2$ is $R^2$-15.508 (=formula I.1870).
Table 1871. Compounds of formula I.1, wherein $R^2$ is $R^2$-15.509 (=formula I.1871).
Table 1872. Compounds of formula I.1, wherein $R^2$ is $R^2$-15.510 (=formula I.1872).
Table 1873. Compounds of formula I.1, wherein $R^2$ is $R^2$-15.511 (=formula I.1873).
Table 1874. Compounds of formula I.1, wherein $R^2$ is $R^2$-15.512 (=formula I.1874).
Table 1875. Compounds of formula I.1, wherein $R^2$ is $R^2$-15.513 (=formula I.1875).
Table 1876. Compounds of formula I.1, wherein $R^2$ is $R^2$-15.514 (=formula I.1876).
Table 1877. Compounds of formula I.1, wherein $R^2$ is $R^2$-15.515 (=formula I.1877).
Table 1878. Compounds of formula I.1, wherein $R^2$ is $R^2$-15.516 (=formula I.1878).
Table 1879. Compounds of formula I.1, wherein $R^2$ is $R^2$-15.517 (=formula I.1879).
Table 1880. Compounds of formula I.1, wherein $R^2$ is $R^2$-15.518 (=formula I.1880).
Table 1881. Compounds of formula I.1, wherein $R^2$ is $R^2$-15.519 (=formula I.1881).
Table 1882. Compounds of formula I.1, wherein $R^2$ is $R^2$-15.520 (=formula I.1882).
Table 1883. Compounds of formula I.1, wherein $R^2$ is $R^2$-15.521 (=formula I.1883).
Table 1884. Compounds of formula I.1, wherein $R^2$ is $R^2$-15.522 (=formula I.1884).
Table 1885. Compounds of formula I.1, wherein $R^2$ is $R^2$-15.523 (=formula I.1885).
Table 1886. Compounds of formula I.1, wherein $R^2$ is $R^2$-15.524 (=formula I.1886).
Table 1887. Compounds of formula I.1, wherein $R^2$ is $R^2$-15.525 (=formula I.1887).
Table 1888. Compounds of formula I.1, wherein $R^2$ is $R^2$-15.526 (=formula I.1888).
Table 1889. Compounds of formula I.1, wherein $R^2$ is $R^2$-15.527 (=formula I.1889).
Table 1890. Compounds of formula I.1, wherein $R^2$ is $R^2$-15.528 (=formula I.1890).
Table 1891. Compounds of formula I.1, wherein $R^2$ is $R^2$-15.529 (=formula I.1891).
Table 1892. Compounds of formula I.1, wherein $R^2$ is $R^2$-15.530 (=formula I.1892).
Table 1893. Compounds of formula I.1, wherein $R^2$ is $R^2$-15.531 (=formula I.1893).
Table 1894. Compounds of formula I.1, wherein $R^2$ is $R^2$-15.532 (=formula I.1894).
Table 1895. Compounds of formula I.1, wherein $R^2$ is $R^2$-15.533 (=formula I.1895).
Table 1896. Compounds of formula I.1, wherein $R^2$ is $R^2$-15.534 (=formula I.1896).
Table 1897. Compounds of formula I.1, wherein $R^2$ is $R^2$-15.535 (=formula I.1897).
Table 1898. Compounds of formula I.1, wherein $R^2$ is $R^2$-15.536 (=formula I.1898).
Table 1899. Compounds of formula I.1, wherein $R^2$ is $R^2$-15.537 (=formula I.1899).
Table 1900. Compounds of formula I.1, wherein $R^2$ is $R^2$-15.538 (=formula I.1900).
Table 1901. Compounds of formula I.1, wherein $R^2$ is $R^2$-15.539 (=formula I.1901).
Table 1902. Compounds of formula I.1, wherein $R^2$ is $R^2$-15.540 (=formula I.1902).
Table 1903. Compounds of formula I.1, wherein $R^2$ is $R^2$-15.541 (=formula I.1903).
Table 1904. Compounds of formula I.1, wherein $R^2$ is $R^2$-15.542 (=formula I.1904).
Table 1905. Compounds of formula I.1, wherein $R^2$ is $R^2$-15.543 (=formula I.1905).
Table 1906. Compounds of formula I.1, wherein $R^2$ is $R^2$-15.544 (=formula I.1906).
Table 1907. Compounds of formula I.1, wherein $R^2$ is $R^2$-15.545 (=formula I.1907).
Table 1908. Compounds of formula I.1, wherein $R^2$ is $R^2$-15.546 (=formula I.1908).
Table 1909. Compounds of formula I.1, wherein $R^2$ is $R^2$-15.547 (=formula I.1909).
Table 1910. Compounds of formula I.1, wherein $R^2$ is $R^2$-15.548 (=formula I.1910).
Table 1911. Compounds of formula I.1, wherein $R^2$ is $R^2$-15.549 (=formula I.1911).
Table 1912. Compounds of formula I.1, wherein $R^2$ is $R^2$-15.550 (=formula I.1912).
Table 1913. Compounds of formula I.1, wherein $R^2$ is $R^2$-15.551 (=formula I.1913).
Table 1914. Compounds of formula I.1, wherein $R^2$ is $R^2$-15.552 (=formula I.1914).
Table 1915. Compounds of formula I.1, wherein $R^2$ is $R^2$-15.553 (=formula I.1915).
Table 1916. Compounds of formula I.1, wherein $R^2$ is $R^2$-15.554 (=formula I.1916).
Table 1917. Compounds of formula I.1, wherein $R^2$ is $R^2$-15.555 (=formula I.1917).
Table 1918. Compounds of formula I.1, wherein $R^2$ is $R^2$-15.556 (=formula I.1918).
Table 1919. Compounds of formula I.1, wherein $R^2$ is $R^2$-15.557 (=formula I.1919).
Table 1920. Compounds of formula I.1, wherein $R^2$ is $R^2$-15.558 (=formula I.1920).
Table 1921. Compounds of formula I.1, wherein $R^2$ is $R^2$-15.559 (=formula I.1921).
Table 1922. Compounds of formula I.1, wherein $R^2$ is $R^2$-15.560 (=formula I.1922).
Table 1923. Compounds of formula I.1, wherein $R^2$ is $R^2$-15.561 (=formula I.1923).
Table 1924. Compounds of formula I.1, wherein $R^2$ is $R^2$-15.562 (=formula I.1924).

Table 1925. Compounds of formula I.1, wherein $R^2$ is $R^2$-15.563 (=formula I.1925).
Table 1926. Compounds of formula I.1, wherein $R^2$ is $R^2$-15.564 (=formula I.1926).
Table 1927. Compounds of formula I.1, wherein $R^2$ is $R^2$-15.565 (=formula I.1927).
Table 1928. Compounds of formula I.1, wherein $R^2$ is $R^2$-15.566 (=formula I.1928).
Table 1929. Compounds of formula I.1, wherein $R^2$ is $R^2$-15.567 (=formula I.1929).
Table 1930. Compounds of formula I.1, wherein $R^2$ is $R^2$-15.568 (=formula I.1930).
Table 1931. Compounds of formula I.1, wherein $R^2$ is $R^2$-15.569 (=formula I.1931).
Table 1932. Compounds of formula I.1, wherein $R^2$ is $R^2$-15.570 (=formula I.1932).
Table 1933. Compounds of formula I.1, wherein $R^2$ is $R^2$-15.571 (=formula I.1933).
Table 1934. Compounds of formula I.1, wherein $R^2$ is $R^2$-15.572 (=formula I.1934).
Table 1935. Compounds of formula I.1, wherein $R^2$ is $R^2$-15.573 (=formula I.1935).
Table 1936. Compounds of formula I.1, wherein $R^2$ is $R^2$-15.574 (=formula I.1936).
Table 1937. Compounds of formula I.1, wherein $R^2$ is $R^2$-15.575 (=formula I.1937).
Table 1938. Compounds of formula I.1, wherein $R^2$ is $R^2$-15.576 (=formula I.1938).
Table 1939. Compounds of formula I.1, wherein $R^2$ is $R^2$-15.577 (=formula I.1939).
Table 1940. Compounds of formula I.1, wherein $R^2$ is $R^2$-15.578 (=formula I.1940).
Table 1941. Compounds of formula I.1, wherein $R^2$ is $R^2$-15.579 (=formula I.1941).
Table 1942. Compounds of formula I.1, wherein $R^2$ is $R^2$-15.580 (=formula I.1942).
Table 1943. Compounds of formula I.1, wherein $R^2$ is $R^2$-15.581 (=formula I.1943).
Table 1944. Compounds of formula I.1, wherein $R^2$ is $R^2$-15.582 (=formula I.1944).
Table 1945. Compounds of formula I.1, wherein $R^2$ is $R^2$-15.583 (=formula I.1945).
Table 1946. Compounds of formula I.1, wherein $R^2$ is $R^2$-15.584 (=formula I.1946).
Table 1947. Compounds of formula I.1, wherein $R^2$ is $R^2$-15.585 (=formula I.1947).
Table 1948. Compounds of formula I.1, wherein $R^2$ is $R^2$-15.586 (=formula I.1948).
Table 1949. Compounds of formula I.1, wherein $R^2$ is $R^2$-15.587 (=formula I.1949).
Table 1950. Compounds of formula I.1, wherein $R^2$ is $R^2$-15.588 (=formula I.1950).
Table 1951. Compounds of formula I.1, wherein $R^2$ is $R^2$-15.589 (=formula I.1951).
Table 1952. Compounds of formula I.1, wherein $R^2$ is $R^2$-15.590 (=formula I.1952).
Table 1953. Compounds of formula I.1, wherein $R^2$ is $R^2$-15.591 (=formula I.1953).
Table 1954. Compounds of formula I.1, wherein $R^2$ is $R^2$-15.592 (=formula I.1954).
Table 1955. Compounds of formula I.1, wherein $R^2$ is $R^2$-15.593 (=formula I.1955).
Table 1956. Compounds of formula I.1, wherein $R^2$ is $R^2$-15.594 (=formula I.1956).
Table 1957. Compounds of formula I.1, wherein $R^2$ is $R^2$-15.595 (=formula I.1957).
Table 1958. Compounds of formula I.1, wherein $R^2$ is $R^2$-15.596 (=formula I.1958).
Table 1959. Compounds of formula I.1, wherein $R^2$ is $R^2$-15.597 (=formula I.1959).
Table 1960. Compounds of formula I.1, wherein $R^2$ is $R^2$-15.598 (=formula I.1960).
Table 1961. Compounds of formula I.1, wherein $R^2$ is $R^2$-15.599 (=formula I.1961).
Table 1962. Compounds of formula I.1, wherein $R^2$ is $R^2$-15.600 (=formula I.1962).
Table 1963. Compounds of formula I.1, wherein $R^2$ is $R^2$-15.601 (=formula I.1963).
Table 1964. Compounds of formula I.1, wherein $R^2$ is $R^2$-15.602 (=formula I.1964).
Table 1965. Compounds of formula I.1, wherein $R^2$ is $R^2$-15.603 (=formula I.1965).
Table 1966. Compounds of formula I.1, wherein $R^2$ is $R^2$-15.604 (=formula I.1966).
Table 1967. Compounds of formula I.1, wherein $R^2$ is $R^2$-15.605 (=formula I.1967).
Table 1968. Compounds of formula I.1, wherein $R^2$ is $R^2$-15.606 (=formula I.1968).
Table 1969. Compounds of formula I.1, wherein $R^2$ is $R^2$-15.607 (=formula I.1969).
Table 1970. Compounds of formula I.1, wherein $R^2$ is $R^2$-15.608 (=formula I.1970).
Table 1971. Compounds of formula I.1, wherein $R^2$ is $R^2$-15.609 (=formula I.1971).
Table 1972. Compounds of formula I.1, wherein $R^2$ is $R^2$-15.610 (=formula I.1972).
Table 1973. Compounds of formula I.1, wherein $R^2$ is $R^2$-15.611 (=formula I.1973).
Table 1974. Compounds of formula I.1, wherein $R^2$ is $R^2$-15.612 (=formula I.1974).
Table 1975. Compounds of formula I.1, wherein $R^2$ is $R^2$-15.613 (=formula I.1975).
Table 1976. Compounds of formula I.1, wherein $R^2$ is $R^2$-15.614 (=formula I.1976).
Table 1977. Compounds of formula I.1, wherein $R^2$ is $R^2$-15.615 (=formula I.1977).
Table 1978. Compounds of formula I.1, wherein $R^2$ is $R^2$-15.616 (=formula I.1978).
Table 1979. Compounds of formula I.1, wherein $R^2$ is $R^2$-15.617 (=formula I.1979).
Table 1980. Compounds of formula I.1, wherein $R^2$ is $R^2$-15.618 (=formula I.1980).
Table 1981. Compounds of formula I.1, wherein $R^2$ is $R^2$-15.619 (=formula I.1981).
Table 1982. Compounds of formula I.1, wherein $R^2$ is $R^2$-15.620 (=formula I.1982).
Table 1983. Compounds of formula I.1, wherein $R^2$ is $R^2$-15.621 (=formula I.1983).
Table 1984. Compounds of formula I.1, wherein $R^2$ is $R^2$-15.622 (=formula I.1984).
Table 1985. Compounds of formula I.1, wherein $R^2$ is $R^2$-15.623 (=formula I.1985).
Table 1986. Compounds of formula I.1, wherein $R^2$ is $R^2$-15.624 (=formula I.1986).
Table 1987. Compounds of formula I.1, wherein $R^2$ is $R^2$-15.625 (=formula I.1987).
Table 1988. Compounds of formula I.1, wherein $R^2$ is $R^2$-15.626 (=formula I.1988).
Table 1989. Compounds of formula I.1, wherein $R^2$ is $R^2$-15.627 (=formula I.1989).
Table 1990. Compounds of formula I.1, wherein $R^2$ is $R^2$-15.628 (=formula I.1990).

Table 1991. Compounds of formula I.1, wherein $R^2$ is $R^2$-15.629 (=formula I.1991).
Table 1992. Compounds of formula I.1, wherein $R^2$ is $R^2$-15.630 (=formula I.1992).
Table 1993. Compounds of formula I.1, wherein $R^2$ is $R^2$-15.631 (=formula I.1993).
Table 1994. Compounds of formula I.1, wherein $R^2$ is $R^2$-15.632 (=formula I.1994).
Table 1995. Compounds of formula I.1, wherein $R^2$ is $R^2$-15.633 (=formula I.1995).
Table 1996. Compounds of formula I.1, wherein $R^2$ is $R^2$-15.634 (=formula I.1996).
Table 1997. Compounds of formula I.1, wherein $R^2$ is $R^2$-15.635 (=formula I.1997).
Table 1998. Compounds of formula I.1, wherein $R^2$ is $R^2$-15.636 (=formula I.1998).
Table 1999. Compounds of formula I.1, wherein $R^2$ is $R^2$-15.637 (=formula I.1999).
Table 2000. Compounds of formula I.1, wherein $R^2$ is $R^2$-15.638 (=formula I.2000).
Table 2001. Compounds of formula I.1, wherein $R^2$ is $R^2$-15.639 (=formula I.2001).
Table 2002. Compounds of formula I.1, wherein $R^2$ is $R^2$-15.640 (=formula I.2002).
Table 2003. Compounds of formula I.1, wherein $R^2$ is $R^2$-15.641 (=formula I.2003).
Table 2004. Compounds of formula I.1, wherein $R^2$ is $R^2$-15.642 (=formula I.2004).
Table 2005. Compounds of formula I.1, wherein $R^2$ is $R^2$-15.643 (=formula I.2005).
Table 2006. Compounds of formula I.1, wherein $R^2$ is $R^2$-15.644 (=formula I.2006).
Table 2007. Compounds of formula I.1, wherein $R^2$ is $R^2$-15.645 (=formula I.2007).
Table 2008. Compounds of formula I.1, wherein $R^2$ is $R^2$-15.646 (=formula I.2008).
Table 2009. Compounds of formula I.1, wherein $R^2$ is $R^2$-15.647 (=formula I.2009).
Table 2010. Compounds of formula I.1, wherein $R^2$ is $R^2$-15.648 (=formula I.2010).
Table 2011. Compounds of formula I.1, wherein $R^2$ is $R^2$-15.649 (=formula I.2011).
Table 2012. Compounds of formula I.1, wherein $R^2$ is $R^2$-15.650 (=formula I.2012).
Table 2013. Compounds of formula I.1, wherein $R^2$ is $R^2$-15.651 (=formula I.2013).
Table 2014. Compounds of formula I.1, wherein $R^2$ is $R^2$-15.652 (=formula I.2014).
Table 2015. Compounds of formula I.1, wherein $R^2$ is $R^2$-15.653 (=formula I.2015).
Table 2016. Compounds of formula I.1, wherein $R^2$ is $R^2$-15.654 (=formula I.2016).
Table 2017. Compounds of formula I.1, wherein $R^2$ is $R^2$-15.655 (=formula I.2017).
Table 2018. Compounds of formula I.1, wherein $R^2$ is $R^2$-15.656 (=formula I.2018).
Table 2019. Compounds of formula I.1, wherein $R^2$ is $R^2$-15.657 (=formula I.2019).
Table 2020. Compounds of formula I.1, wherein $R^2$ is $R^2$-15.658 (=formula I.2020).
Table 2021. Compounds of formula I.1, wherein $R^2$ is $R^2$-15.659 (=formula I.2021).
Table 2022. Compounds of formula I.1, wherein $R^2$ is $R^2$-15.660 (=formula I.2022).
Table 2023. Compounds of formula I.1, wherein $R^2$ is $R^2$-15.661 (=formula I.2023).
Table 2024. Compounds of formula I.1, wherein $R^2$ is $R^2$-15.662 (=formula I.2024).
Table 2025. Compounds of formula I.1, wherein $R^2$ is $R^2$-15.663 (=formula I.2025).
Table 2026. Compounds of formula I.1, wherein $R^2$ is $R^2$-15.664 (=formula I.2026).
Table 2027. Compounds of formula I.1, wherein $R^2$ is $R^2$-15.665 (=formula I.2027).
Table 2028. Compounds of formula I.1, wherein $R^2$ is $R^2$-15.666 (=formula I.2028).
Table 2029. Compounds of formula I.1, wherein $R^2$ is $R^2$-15.667 (=formula I.2029).
Table 2030. Compounds of formula I.1, wherein $R^2$ is $R^2$-15.668 (=formula I.2030).
Table 2031. Compounds of formula I.1, wherein $R^2$ is $R^2$-15.669 (=formula I.2031).
Table 2032. Compounds of formula I.1, wherein $R^2$ is $R^2$-15.670 (=formula I.2032).
Table 2033. Compounds of formula I.1, wherein $R^2$ is $R^2$-15.671 (=formula I.2033).
Table 2034. Compounds of formula I.1, wherein $R^2$ is $R^2$-15.672 (=formula I.2034).
Table 2035. Compounds of formula I.1, wherein $R^2$ is $R^2$-15.673 (=formula I.2035).
Table 2036. Compounds of formula I.1, wherein $R^2$ is $R^2$-15.674 (=formula I.2036).
Table 2037. Compounds of formula I.1, wherein $R^2$ is $R^2$-15.675 (=formula I.2037).
Table 2038. Compounds of formula I.1, wherein $R^2$ is $R^2$-15.676 (=formula I.2038).

TABLE A

| No. | $R^1$ | $R^3$ | $R^5$ | $R^6$ | $R^7$ |
|---|---|---|---|---|---|
| I-1 | c-$C_3H_5$ | F | H | H | H |
| I-2 | c-$C_3H_5$ | F | H | H | F |
| I-3 | c-$C_3H_5$ | F | H | H | Cl |
| I-4 | c-$C_3H_5$ | F | H | H | Br |
| I-5 | c-$C_3H_5$ | F | H | H | $CH_3$ |
| I-6 | c-$C_3H_5$ | F | H | H | $OCH_3$ |
| I-7 | c-$C_3H_5$ | F | H | F | H |
| I-8 | c-$C_3H_5$ | F | H | F | F |
| I-9 | c-$C_3H_5$ | F | H | F | Cl |
| I-10 | c-$C_3H_5$ | F | H | F | Br |
| I-11 | c-$C_3H_5$ | F | H | F | $CH_3$ |
| I-12 | c-$C_3H_5$ | F | H | F | $OCH_3$ |
| I-13 | c-$C_3H_5$ | F | F | H | H |
| I-14 | c-$C_3H_5$ | F | F | H | F |
| I-15 | c-$C_3H_5$ | F | F | H | Cl |
| I-16 | c-$C_3H_5$ | F | F | H | Br |
| I-17 | c-$C_3H_5$ | F | F | H | $CH_3$ |
| I-18 | c-$C_3H_5$ | F | F | H | $OCH_3$ |
| I-19 | c-$C_3H_5$ | F | F | F | H |
| I-20 | c-$C_3H_5$ | F | F | F | F |
| I-21 | c-$C_3H_5$ | F | F | F | Cl |
| I-22 | c-$C_3H_5$ | F | F | F | Br |
| I-23 | c-$C_3H_5$ | F | F | F | $CH_3$ |
| I-24 | c-$C_3H_5$ | F | F | F | $OCH_3$ |
| I-25 | c-$C_3H_5$ | Cl | H | H | H |
| I-26 | c-$C_3H_5$ | Cl | H | H | F |
| I-27 | c-$C_3H_5$ | Cl | H | H | Cl |
| I-28 | c-$C_3H_5$ | Cl | H | H | Br |
| I-29 | c-$C_3H_5$ | Cl | H | H | $CH_3$ |
| I-30 | c-$C_3H_5$ | Cl | H | H | $OCH_3$ |
| I-31 | c-$C_3H_5$ | Cl | H | F | H |
| I-32 | c-$C_3H_5$ | Cl | H | F | F |
| I-33 | c-$C_3H_5$ | Cl | H | F | Cl |
| I-34 | c-$C_3H_5$ | Cl | H | F | Br |
| I-35 | c-$C_3H_5$ | Cl | H | F | $CH_3$ |
| I-36 | c-$C_3H_5$ | Cl | H | F | $OCH_3$ |
| I-37 | c-$C_3H_5$ | Cl | F | H | H |
| I-38 | c-$C_3H_5$ | Cl | F | H | F |
| I-39 | c-$C_3H_5$ | Cl | F | H | Cl |

TABLE A-continued

| No. | R¹ | R³ | R⁵ | R⁶ | R⁷ |
|---|---|---|---|---|---|
| I-40 | c-C₃H₅ | Cl | F | H | Br |
| I-41 | c-C₃H₅ | Cl | F | H | CH₃ |
| I-42 | c-C₃H₅ | Cl | F | H | OCH₃ |
| I-43 | c-C₃H₅ | Cl | F | F | H |
| I-44 | c-C₃H₅ | Cl | F | F | F |
| I-45 | c-C₃H₅ | Cl | F | F | Cl |
| I-46 | c-C₃H₅ | Cl | F | F | Br |
| I-47 | c-C₃H₅ | Cl | F | F | CH₃ |
| I-48 | c-C₃H₅ | Cl | F | F | OCH₃ |
| I-49 | c-C₃H₅ | Br | H | H | H |
| I-50 | c-C₃H₅ | Br | H | H | F |
| I-51 | c-C₃H₅ | Br | H | H | Cl |
| I-52 | c-C₃H₅ | Br | H | H | Br |
| I-53 | c-C₃H₅ | Br | H | H | CH₃ |
| I-54 | c-C₃H₅ | Br | H | H | OCH₃ |
| I-55 | c-C₃H₅ | Br | H | F | H |
| I-56 | c-C₃H₅ | Br | H | F | F |
| I-57 | c-C₃H₅ | Br | H | F | Cl |
| I-58 | c-C₃H₅ | Br | H | F | Br |
| I-59 | c-C₃H₅ | Br | H | F | CH₃ |
| I-60 | c-C₃H₅ | Br | H | F | OCH₃ |
| I-61 | c-C₃H₅ | Br | F | H | H |
| I-62 | c-C₃H₅ | Br | F | H | F |
| I-63 | c-C₃H₅ | Br | F | H | Cl |
| I-64 | c-C₃H₅ | Br | F | H | Br |
| I-65 | c-C₃H₅ | Br | F | H | CH₃ |
| I-66 | c-C₃H₅ | Br | F | H | OCH₃ |
| I-67 | c-C₃H₅ | Br | F | F | H |
| I-68 | c-C₃H₅ | Br | F | F | F |
| I-69 | c-C₃H₅ | Br | F | F | Cl |
| I-70 | c-C₃H₅ | Br | F | F | Br |
| I-71 | c-C₃H₅ | Br | F | F | CH₃ |
| I-72 | c-C₃H₅ | Br | F | F | OCH₃ |
| I-73 | c-C₃H₅ | I | H | H | H |
| I-74 | c-C₃H₅ | I | H | H | F |
| I-75 | c-C₃H₅ | I | H | H | Cl |
| I-76 | c-C₃H₅ | I | H | H | Br |
| I-77 | c-C₃H₅ | I | H | H | CH₃ |
| I-78 | c-C₃H₅ | I | H | H | OCH₃ |
| I-79 | c-C₃H₅ | I | H | F | H |
| I-80 | c-C₃H₅ | I | H | F | F |
| I-81 | c-C₃H₅ | I | H | F | Cl |
| I-82 | c-C₃H₅ | I | H | F | Br |
| I-83 | c-C₃H₅ | I | H | F | CH₃ |
| I-84 | c-C₃H₅ | I | H | F | OCH₃ |
| I-85 | c-C₃H₅ | I | F | H | H |
| I-86 | c-C₃H₅ | I | F | H | F |
| I-87 | c-C₃H₅ | I | F | H | Cl |
| I-88 | c-C₃H₅ | I | F | H | Br |
| I-89 | c-C₃H₅ | I | F | H | CH₃ |
| I-90 | c-C₃H₅ | I | F | H | OCH₃ |
| I-91 | c-C₃H₅ | I | F | F | H |
| I-92 | c-C₃H₅ | I | F | F | F |
| I-93 | c-C₃H₅ | I | F | F | Cl |
| I-94 | c-C₃H₅ | I | F | F | Br |
| I-95 | c-C₃H₅ | I | F | F | CH₃ |
| I-96 | c-C₃H₅ | I | F | F | OCH₃ |
| I-97 | c-C₃H₅ | CH₃ | H | H | H |
| I-98 | c-C₃H₅ | CH₃ | H | H | F |
| I-99 | c-C₃H₅ | CH₃ | H | H | Cl |
| I-100 | c-C₃H₅ | CH₃ | H | H | Br |
| I-101 | c-C₃H₅ | CH₃ | H | H | CH₃ |
| I-102 | c-C₃H₅ | CH₃ | H | H | OCH₃ |
| I-103 | c-C₃H₅ | CH₃ | H | F | H |
| I-104 | c-C₃H₅ | CH₃ | H | F | F |
| I-105 | c-C₃H₅ | CH₃ | H | F | Cl |
| I-106 | c-C₃H₅ | CH₃ | H | F | Br |
| I-107 | c-C₃H₅ | CH₃ | H | F | CH₃ |
| I-108 | c-C₃H₅ | CH₃ | H | F | OCH₃ |
| I-109 | c-C₃H₅ | CH₃ | F | H | H |
| I-110 | c-C₃H₅ | CH₃ | F | H | F |
| I-111 | c-C₃H₅ | CH₃ | F | H | Cl |
| I-112 | c-C₃H₅ | CH₃ | F | H | Br |
| I-113 | c-C₃H₅ | CH₃ | F | H | CH₃ |
| I-114 | c-C₃H₅ | CH₃ | F | H | OCH₃ |
| I-115 | c-C₃H₅ | CH₃ | F | F | H |
| I-116 | c-C₃H₅ | CH₃ | F | F | F |
| I-117 | c-C₃H₅ | CH₃ | F | F | Cl |
| I-118 | c-C₃H₅ | CH₃ | F | F | Br |
| I-119 | c-C₃H₅ | CH₃ | F | F | CH₃ |
| I-120 | c-C₃H₅ | CH₃ | F | F | OCH₃ |
| I-121 | c-C₃H₅ | OCH₃ | H | H | H |
| I-122 | c-C₃H₅ | OCH₃ | H | H | F |
| I-123 | c-C₃H₅ | OCH₃ | H | H | Cl |
| I-124 | c-C₃H₅ | OCH₃ | H | H | Br |
| I-125 | c-C₃H₅ | OCH₃ | H | H | CH₃ |
| I-126 | c-C₃H₅ | OCH₃ | H | H | OCH₃ |
| I-127 | c-C₃H₅ | OCH₃ | H | F | H |
| I-128 | c-C₃H₅ | OCH₃ | H | F | F |
| I-129 | c-C₃H₅ | OCH₃ | H | F | Cl |
| I-130 | c-C₃H₅ | OCH₃ | H | F | Br |
| I-131 | c-C₃H₅ | OCH₃ | H | F | CH₃ |
| I-132 | c-C₃H₅ | OCH₃ | H | F | OCH₃ |
| I-133 | c-C₃H₅ | OCH₃ | F | H | H |
| I-134 | c-C₃H₅ | OCH₃ | F | H | F |
| I-135 | c-C₃H₅ | OCH₃ | F | H | Cl |
| I-136 | c-C₃H₅ | OCH₃ | F | H | Br |
| I-137 | c-C₃H₅ | OCH₃ | F | H | CH₃ |
| I-138 | c-C₃H₅ | OCH₃ | F | H | OCH₃ |
| I-139 | c-C₃H₅ | OCH₃ | F | F | H |
| I-140 | c-C₃H₅ | OCH₃ | F | F | F |
| I-141 | c-C₃H₅ | OCH₃ | F | F | Cl |
| I-142 | c-C₃H₅ | OCH₃ | F | F | Br |
| I-143 | c-C₃H₅ | OCH₃ | F | F | CH₃ |
| I-144 | c-C₃H₅ | OCH₃ | F | F | OCH₃ |
| I-145 | c-C₃H₅ | CF₃ | H | H | H |
| I-146 | c-C₃H₅ | CF₃ | H | H | F |
| I-147 | c-C₃H₅ | CF₃ | H | H | Cl |
| I-148 | c-C₃H₅ | CF₃ | H | H | Br |
| I-149 | c-C₃H₅ | CF₃ | H | H | CH₃ |
| I-150 | c-C₃H₅ | CF₃ | H | H | OCH₃ |
| I-151 | c-C₃H₅ | CF₃ | H | F | H |
| I-152 | c-C₃H₅ | CF₃ | H | F | F |
| I-153 | c-C₃H₅ | CF₃ | H | F | Cl |
| I-154 | c-C₃H₅ | CF₃ | H | F | Br |
| I-155 | c-C₃H₅ | CF₃ | H | F | CH₃ |
| I-156 | c-C₃H₅ | CF₃ | H | F | OCH₃ |
| I-157 | c-C₃H₅ | CF₃ | F | H | H |
| I-158 | c-C₃H₅ | CF₃ | F | H | F |
| I-159 | c-C₃H₅ | CF₃ | F | H | Cl |
| I-160 | c-C₃H₅ | CF₃ | F | H | Br |
| I-161 | c-C₃H₅ | CF₃ | F | H | CH₃ |
| I-162 | c-C₃H₅ | CF₃ | F | H | OCH₃ |
| I-163 | c-C₃H₅ | CF₃ | F | F | H |
| I-164 | c-C₃H₅ | CF₃ | F | F | F |
| I-165 | c-C₃H₅ | CF₃ | F | F | Cl |
| I-166 | c-C₃H₅ | CF₃ | F | F | Br |
| I-167 | c-C₃H₅ | CF₃ | F | F | CH₃ |
| I-168 | c-C₃H₅ | CF₃ | F | F | OCH₃ |
| I-169 | c-C₄H₇ | F | H | H | H |
| I-170 | c-C₄H₇ | F | H | H | F |
| I-171 | c-C₄H₇ | F | H | H | Cl |
| I-172 | c-C₄H₇ | F | H | H | Br |
| I-173 | c-C₄H₇ | F | H | H | CH₃ |
| I-174 | c-C₄H₇ | F | H | H | OCH₃ |
| I-175 | c-C₄H₇ | F | H | F | H |
| I-176 | c-C₄H₇ | F | H | F | F |
| I-177 | c-C₄H₇ | F | H | F | Cl |
| I-178 | c-C₄H₇ | F | H | F | Br |
| I-179 | c-C₄H₇ | F | H | F | CH₃ |
| I-180 | c-C₄H₇ | F | H | F | OCH₃ |
| I-181 | c-C₄H₇ | F | F | H | H |
| I-182 | c-C₄H₇ | F | F | H | F |
| I-183 | c-C₄H₇ | F | F | H | Cl |
| I-184 | c-C₄H₇ | F | F | H | Br |
| I-185 | c-C₄H₇ | F | F | H | CH₃ |
| I-186 | c-C₄H₇ | F | F | H | OCH₃ |
| I-187 | c-C₄H₇ | F | F | F | H |
| I-188 | c-C₄H₇ | F | F | F | F |
| I-189 | c-C₄H₇ | F | F | F | Cl |
| I-190 | c-C₄H₇ | F | F | F | Br |
| I-191 | c-C₄H₇ | F | F | F | CH₃ |
| I-192 | c-C₄H₇ | F | F | F | OCH₃ |
| I-193 | c-C₄H₇ | Cl | H | H | H |
| I-194 | c-C₄H₇ | Cl | H | H | F |
| I-195 | c-C₄H₇ | Cl | H | H | Cl |

TABLE A-continued

| No. | R¹ | R³ | R⁵ | R⁶ | R⁷ |
|---|---|---|---|---|---|
| I-196 | c-C₄H₇ | Cl | H | H | Br |
| I-197 | c-C₄H₇ | Cl | H | H | CH₃ |
| I-198 | c-C₄H₇ | Cl | H | H | OCH₃ |
| I-199 | c-C₄H₇ | Cl | H | F | H |
| I-200 | c-C₄H₇ | Cl | H | F | F |
| I-201 | c-C₄H₇ | Cl | H | F | Cl |
| I-202 | c-C₄H₇ | Cl | H | F | Br |
| I-203 | c-C₄H₇ | Cl | H | F | CH₃ |
| I-204 | c-C₄H₇ | Cl | H | F | OCH₃ |
| I-205 | c-C₄H₇ | Cl | F | H | H |
| I-206 | c-C₄H₇ | Cl | F | H | F |
| I-207 | c-C₄H₇ | Cl | F | H | Cl |
| I-208 | c-C₄H₇ | Cl | F | H | Br |
| I-209 | c-C₄H₇ | Cl | F | H | CH₃ |
| I-210 | c-C₄H₇ | Cl | F | H | OCH₃ |
| I-211 | c-C₄H₇ | Cl | F | F | H |
| I-212 | c-C₄H₇ | Cl | F | F | F |
| I-213 | c-C₄H₇ | Cl | F | F | Cl |
| I-214 | c-C₄H₇ | Cl | F | F | Br |
| I-215 | c-C₄H₇ | Cl | F | F | CH₃ |
| I-216 | c-C₄H₇ | Cl | F | F | OCH₃ |
| I-217 | c-C₄H₇ | Br | H | H | H |
| I-218 | c-C₄H₇ | Br | H | H | F |
| I-219 | c-C₄H₇ | Br | H | H | Cl |
| I-220 | c-C₄H₇ | Br | H | H | Br |
| I-221 | c-C₄H₇ | Br | H | H | CH₃ |
| I-222 | c-C₄H₇ | Br | H | H | OCH₃ |
| I-223 | c-C₄H₇ | Br | H | F | H |
| I-224 | c-C₄H₇ | Br | H | F | F |
| I-225 | c-C₄H₇ | Br | H | F | Cl |
| I-226 | c-C₄H₇ | Br | H | F | Br |
| I-227 | c-C₄H₇ | Br | H | F | CH₃ |
| I-228 | c-C₄H₇ | Br | H | F | OCH₃ |
| I-229 | c-C₄H₇ | Br | F | H | H |
| I-230 | c-C₄H₇ | Br | F | H | F |
| I-231 | c-C₄H₇ | Br | F | H | Cl |
| I-232 | c-C₄H₇ | Br | F | H | Br |
| I-233 | c-C₄H₇ | Br | F | H | CH₃ |
| I-234 | c-C₄H₇ | Br | F | H | OCH₃ |
| I-235 | c-C₄H₇ | Br | F | F | H |
| I-236 | c-C₄H₇ | Br | F | F | F |
| I-237 | c-C₄H₇ | Br | F | F | Cl |
| I-238 | c-C₄H₇ | Br | F | F | Br |
| I-239 | c-C₄H₇ | Br | F | F | CH₃ |
| I-240 | c-C₄H₇ | Br | F | F | OCH₃ |
| I-241 | c-C₄H₇ | I | H | H | H |
| I-242 | c-C₄H₇ | I | H | H | F |
| I-243 | c-C₄H₇ | I | H | H | Cl |
| I-244 | c-C₄H₇ | I | H | H | Br |
| I-245 | c-C₄H₇ | I | H | H | CH₃ |
| I-246 | c-C₄H₇ | I | H | H | OCH₃ |
| I-247 | c-C₄H₇ | I | H | F | H |
| I-248 | c-C₄H₇ | I | H | F | F |
| I-249 | c-C₄H₇ | I | H | F | Cl |
| I-250 | c-C₄H₇ | I | H | F | Br |
| I-251 | c-C₄H₇ | I | H | F | CH₃ |
| I-252 | c-C₄H₇ | I | H | F | OCH₃ |
| I-253 | c-C₄H₇ | I | F | H | H |
| I-254 | c-C₄H₇ | I | F | H | F |
| I-255 | c-C₄H₇ | I | F | H | Cl |
| I-256 | c-C₄H₇ | I | F | H | Br |
| I-257 | c-C₄H₇ | I | F | H | CH₃ |
| I-258 | c-C₄H₇ | I | F | H | OCH₃ |
| I-259 | c-C₄H₇ | I | F | F | H |
| I-260 | c-C₄H₇ | I | F | F | F |
| I-261 | c-C₄H₇ | I | F | F | Cl |
| I-262 | c-C₄H₇ | I | F | F | Br |
| I-263 | c-C₄H₇ | I | F | F | CH₃ |
| I-264 | c-C₄H₇ | I | F | F | OCH₃ |
| I-265 | c-C₄H₇ | CH₃ | H | H | H |
| I-266 | c-C₄H₇ | CH₃ | H | H | F |
| I-267 | c-C₄H₇ | CH₃ | H | H | Cl |
| I-268 | c-C₄H₇ | CH₃ | H | H | Br |
| I-269 | c-C₄H₇ | CH₃ | H | H | CH₃ |
| I-270 | c-C₄H₇ | CH₃ | H | H | OCH₃ |
| I-271 | c-C₄H₇ | CH₃ | H | F | H |
| I-272 | c-C₄H₇ | CH₃ | H | F | F |
| I-273 | c-C₄H₇ | CH₃ | H | F | Cl |
| I-274 | c-C₄H₇ | CH₃ | H | F | Br |
| I-275 | c-C₄H₇ | CH₃ | H | F | CH₃ |
| I-276 | c-C₄H₇ | CH₃ | H | F | OCH₃ |
| I-277 | c-C₄H₇ | CH₃ | F | H | H |
| I-278 | c-C₄H₇ | CH₃ | F | H | F |
| I-279 | c-C₄H₇ | CH₃ | F | H | Cl |
| I-280 | c-C₄H₇ | CH₃ | F | H | Br |
| I-281 | c-C₄H₇ | CH₃ | F | H | CH₃ |
| I-282 | c-C₄H₇ | CH₃ | F | H | OCH₃ |
| I-283 | c-C₄H₇ | CH₃ | F | F | H |
| I-284 | c-C₄H₇ | CH₃ | F | F | F |
| I-285 | c-C₄H₇ | CH₃ | F | F | Cl |
| I-286 | c-C₄H₇ | CH₃ | F | F | Br |
| I-287 | c-C₄H₇ | CH₃ | F | F | CH₃ |
| I-288 | c-C₄H₇ | CH₃ | F | F | OCH₃ |
| I-289 | c-C₄H₇ | OCH₃ | H | H | H |
| I-290 | c-C₄H₇ | OCH₃ | H | H | F |
| I-291 | c-C₄H₇ | OCH₃ | H | H | Cl |
| I-292 | c-C₄H₇ | OCH₃ | H | H | Br |
| I-293 | c-C₄H₇ | OCH₃ | H | H | CH₃ |
| I-294 | c-C₄H₇ | OCH₃ | H | H | OCH₃ |
| I-295 | c-C₄H₇ | OCH₃ | H | F | H |
| I-296 | c-C₄H₇ | OCH₃ | H | F | F |
| I-297 | c-C₄H₇ | OCH₃ | H | F | Cl |
| I-298 | c-C₄H₇ | OCH₃ | H | F | Br |
| I-299 | c-C₄H₇ | OCH₃ | H | F | CH₃ |
| I-300 | c-C₄H₇ | OCH₃ | H | F | OCH₃ |
| I-301 | c-C₄H₇ | OCH₃ | F | H | H |
| I-302 | c-C₄H₇ | OCH₃ | F | H | F |
| I-303 | c-C₄H₇ | OCH₃ | F | H | Cl |
| I-304 | c-C₄H₇ | OCH₃ | F | H | Br |
| I-305 | c-C₄H₇ | OCH₃ | F | H | CH₃ |
| I-306 | c-C₄H₇ | OCH₃ | F | H | OCH₃ |
| I-307 | c-C₄H₇ | OCH₃ | F | F | H |
| I-308 | c-C₄H₇ | OCH₃ | F | F | F |
| I-309 | c-C₄H₇ | OCH₃ | F | F | Cl |
| I-310 | c-C₄H₇ | OCH₃ | F | F | Br |
| I-311 | c-C₄H₇ | OCH₃ | F | F | CH₃ |
| I-312 | c-C₄H₇ | OCH₃ | F | F | OCH₃ |
| I-313 | c-C₄H₇ | CF₃ | H | H | H |
| I-314 | c-C₄H₇ | CF₃ | H | H | F |
| I-315 | c-C₄H₇ | CF₃ | H | H | Cl |
| I-316 | c-C₄H₇ | CF₃ | H | H | Br |
| I-317 | c-C₄H₇ | CF₃ | H | H | CH₃ |
| I-318 | c-C₄H₇ | CF₃ | H | H | OCH₃ |
| I-319 | c-C₄H₇ | CF₃ | H | F | H |
| I-320 | c-C₄H₇ | CF₃ | H | F | F |
| I-321 | c-C₄H₇ | CF₃ | H | F | Cl |
| I-322 | c-C₄H₇ | CF₃ | H | F | Br |
| I-323 | c-C₄H₇ | CF₃ | H | F | CH₃ |
| I-324 | c-C₄H₇ | CF₃ | H | F | OCH₃ |
| I-325 | c-C₄H₇ | CF₃ | F | H | H |
| I-326 | c-C₄H₇ | CF₃ | F | H | F |
| I-327 | c-C₄H₇ | CF₃ | F | H | Cl |
| I-328 | c-C₄H₇ | CF₃ | F | H | Br |
| I-329 | c-C₄H₇ | CF₃ | F | H | CH₃ |
| I-330 | c-C₄H₇ | CF₃ | F | H | OCH₃ |
| I-331 | c-C₄H₇ | CF₃ | F | F | H |
| I-332 | c-C₄H₇ | CF₃ | F | F | F |
| I-333 | c-C₄H₇ | CF₃ | F | F | Cl |
| I-334 | c-C₄H₇ | CF₃ | F | F | Br |
| I-335 | c-C₄H₇ | CF₃ | F | F | CH₃ |
| I-336 | c-C₄H₇ | CF₃ | F | F | OCH₃ |
| I-337 | C₂H₅ | F | H | H | H |
| I-338 | C₂H₅ | F | H | H | F |
| I-339 | C₂H₅ | F | H | H | Cl |
| I-340 | C₂H₅ | F | H | H | Br |
| I-341 | C₂H₅ | F | H | H | CH₃ |
| I-342 | C₂H₅ | F | H | H | OCH₃ |
| I-343 | C₂H₅ | F | H | F | H |
| I-344 | C₂H₅ | F | H | F | F |
| I-345 | C₂H₅ | F | H | F | Cl |
| I-346 | C₂H₅ | F | H | F | Br |
| I-347 | C₂H₅ | F | H | F | CH₃ |
| I-348 | C₂H₅ | F | H | F | OCH₃ |
| I-349 | C₂H₅ | F | F | H | H |
| I-350 | C₂H₅ | F | F | H | F |
| I-351 | C₂H₅ | F | F | H | Cl |

TABLE A-continued

| No. | R¹ | R³ | R⁵ | R⁶ | R⁷ |
|---|---|---|---|---|---|
| I-352 | C₂H₅ | F | F | H | Br |
| I-353 | C₂H₅ | F | F | H | CH₃ |
| I-354 | C₂H₅ | F | F | H | OCH₃ |
| I-355 | C₂H₅ | F | F | F | H |
| I-356 | C₂H₅ | F | F | F | F |
| I-357 | C₂H₅ | F | F | F | Cl |
| I-358 | C₂H₅ | F | F | F | Br |
| I-359 | C₂H₅ | F | F | F | CH₃ |
| I-360 | C₂H₅ | F | F | F | OCH₃ |
| I-361 | C₂H₅ | Cl | H | H | H |
| I-362 | C₂H₅ | Cl | H | H | F |
| I-363 | C₂H₅ | Cl | H | H | Cl |
| I-364 | C₂H₅ | Cl | H | H | Br |
| I-365 | C₂H₅ | Cl | H | H | CH₃ |
| I-366 | C₂H₅ | Cl | H | H | OCH₃ |
| I-367 | C₂H₅ | Cl | H | F | H |
| I-368 | C₂H₅ | Cl | H | F | F |
| I-369 | C₂H₅ | Cl | H | F | Cl |
| I-370 | C₂H₅ | Cl | H | F | Br |
| I-371 | C₂H₅ | Cl | H | F | CH₃ |
| I-372 | C₂H₅ | Cl | H | F | OCH₃ |
| I-373 | C₂H₅ | Cl | F | H | H |
| I-374 | C₂H₅ | Cl | F | H | F |
| I-375 | C₂H₅ | Cl | F | H | Cl |
| I-376 | C₂H₅ | Cl | F | H | Br |
| I-377 | C₂H₅ | Cl | F | H | CH₃ |
| I-378 | C₂H₅ | Cl | F | H | OCH₃ |
| I-379 | C₂H₅ | Cl | F | F | H |
| I-380 | C₂H₅ | Cl | F | F | F |
| I-381 | C₂H₅ | Cl | F | F | Cl |
| I-382 | C₂H₅ | Cl | F | F | Br |
| I-383 | C₂H₅ | Cl | F | F | CH₃ |
| I-384 | C₂H₅ | Cl | F | F | OCH₃ |
| I-385 | C₂H₅ | Br | H | H | H |
| I-386 | C₂H₅ | Br | H | H | F |
| I-387 | C₂H₅ | Br | H | H | Cl |
| I-388 | C₂H₅ | Br | H | H | Br |
| I-389 | C₂H₅ | Br | H | H | CH₃ |
| I-390 | C₂H₅ | Br | H | H | OCH₃ |
| I-391 | C₂H₅ | Br | H | F | H |
| I-392 | C₂H₅ | Br | H | F | F |
| I-393 | C₂H₅ | Br | H | F | Cl |
| I-394 | C₂H₅ | Br | H | F | Br |
| I-395 | C₂H₅ | Br | H | F | CH₃ |
| I-396 | C₂H₅ | Br | H | F | OCH₃ |
| I-397 | C₂H₅ | Br | F | H | H |
| I-398 | C₂H₅ | Br | F | H | F |
| I-399 | C₂H₅ | Br | F | H | Cl |
| I-400 | C₂H₅ | Br | F | H | Br |
| I-401 | C₂H₅ | Br | F | H | CH₃ |
| I-402 | C₂H₅ | Br | F | H | OCH₃ |
| I-403 | C₂H₅ | Br | F | F | H |
| I-404 | C₂H₅ | Br | F | F | F |
| I-405 | C₂H₅ | Br | F | F | Cl |
| I-406 | C₂H₅ | Br | F | F | Br |
| I-407 | C₂H₅ | Br | F | F | CH₃ |
| I-408 | C₂H₅ | Br | F | F | OCH₃ |
| I-409 | C₂H₅ | I | H | H | H |
| I-410 | C₂H₅ | I | H | H | F |
| I-411 | C₂H₅ | I | H | H | Cl |
| I-412 | C₂H₅ | I | H | H | Br |
| I-413 | C₂H₅ | I | H | H | CH₃ |
| I-414 | C₂H₅ | I | H | H | OCH₃ |
| I-415 | C₂H₅ | I | H | F | H |
| I-416 | C₂H₅ | I | H | F | F |
| I-417 | C₂H₅ | I | H | F | Cl |
| I-418 | C₂H₅ | I | H | F | Br |
| I-419 | C₂H₅ | I | H | F | CH₃ |
| I-420 | C₂H₅ | I | H | F | OCH₃ |
| I-421 | C₂H₅ | I | F | H | H |
| I-422 | C₂H₅ | I | F | H | F |
| I-423 | C₂H₅ | I | F | H | Cl |
| I-424 | C₂H₅ | I | F | H | Br |
| I-425 | C₂H₅ | I | F | H | CH₃ |
| I-426 | C₂H₅ | I | F | H | OCH₃ |
| I-427 | C₂H₅ | I | F | F | H |
| I-428 | C₂H₅ | I | F | F | F |
| I-429 | C₂H₅ | I | F | F | Cl |
| I-430 | C₂H₅ | I | F | F | Br |
| I-431 | C₂H₅ | I | F | F | CH₃ |
| I-432 | C₂H₅ | I | F | F | OCH₃ |
| I-433 | C₂H₅ | CH₃ | H | H | H |
| I-434 | C₂H₅ | CH₃ | H | H | F |
| I-435 | C₂H₅ | CH₃ | H | H | Cl |
| I-436 | C₂H₅ | CH₃ | H | H | Br |
| I-437 | C₂H₅ | CH₃ | H | H | CH₃ |
| I-438 | C₂H₅ | CH₃ | H | H | OCH₃ |
| I-439 | C₂H₅ | CH₃ | H | F | H |
| I-440 | C₂H₅ | CH₃ | H | F | F |
| I-441 | C₂H₅ | CH₃ | H | F | Cl |
| I-442 | C₂H₅ | CH₃ | H | F | Br |
| I-443 | C₂H₅ | CH₃ | H | F | CH₃ |
| I-444 | C₂H₅ | CH₃ | H | F | OCH₃ |
| I-445 | C₂H₅ | CH₃ | F | H | H |
| I-446 | C₂H₅ | CH₃ | F | H | F |
| I-447 | C₂H₅ | CH₃ | F | H | Cl |
| I-448 | C₂H₅ | CH₃ | F | H | Br |
| I-449 | C₂H₅ | CH₃ | F | H | CH₃ |
| I-450 | C₂H₅ | CH₃ | F | H | OCH₃ |
| I-451 | C₂H₅ | CH₃ | F | F | H |
| I-452 | C₂H₅ | CH₃ | F | F | F |
| I-453 | C₂H₅ | CH₃ | F | F | Cl |
| I-454 | C₂H₅ | CH₃ | F | F | Br |
| I-455 | C₂H₅ | CH₃ | F | F | CH₃ |
| I-456 | C₂H₅ | CH₃ | F | F | OCH₃ |
| I-457 | C₂H₅ | OCH₃ | H | H | H |
| I-458 | C₂H₅ | OCH₃ | H | H | F |
| I-459 | C₂H₅ | OCH₃ | H | H | Cl |
| I-460 | C₂H₅ | OCH₃ | H | H | Br |
| I-461 | C₂H₅ | OCH₃ | H | H | CH₃ |
| I-462 | C₂H₅ | OCH₃ | H | H | OCH₃ |
| I-463 | C₂H₅ | OCH₃ | H | F | H |
| I-464 | C₂H₅ | OCH₃ | H | F | F |
| I-465 | C₂H₅ | OCH₃ | H | F | Cl |
| I-466 | C₂H₅ | OCH₃ | H | F | Br |
| I-467 | C₂H₅ | OCH₃ | H | F | CH₃ |
| I-468 | C₂H₅ | OCH₃ | H | F | OCH₃ |
| I-469 | C₂H₅ | OCH₃ | F | H | H |
| I-470 | C₂H₅ | OCH₃ | F | H | F |
| I-471 | C₂H₅ | OCH₃ | F | H | Cl |
| I-472 | C₂H₅ | OCH₃ | F | H | Br |
| I-473 | C₂H₅ | OCH₃ | F | H | CH₃ |
| I-474 | C₂H₅ | OCH₃ | F | H | OCH₃ |
| I-475 | C₂H₅ | OCH₃ | F | F | H |
| I-476 | C₂H₅ | OCH₃ | F | F | F |
| I-477 | C₂H₅ | OCH₃ | F | F | Cl |
| I-478 | C₂H₅ | OCH₃ | F | F | Br |
| I-479 | C₂H₅ | OCH₃ | F | F | CH₃ |
| I-480 | C₂H₅ | OCH₃ | F | F | OCH₃ |
| I-481 | C₂H₅ | CF₃ | H | H | H |
| I-482 | C₂H₅ | CF₃ | H | H | F |
| I-483 | C₂H₅ | CF₃ | H | H | Cl |
| I-484 | C₂H₅ | CF₃ | H | H | Br |
| I-485 | C₂H₅ | CF₃ | H | H | CH₃ |
| I-486 | C₂H₅ | CF₃ | H | H | OCH₃ |
| I-487 | C₂H₅ | CF₃ | H | F | H |
| I-488 | C₂H₅ | CF₃ | H | F | F |
| I-489 | C₂H₅ | CF₃ | H | F | Cl |
| I-490 | C₂H₅ | CF₃ | H | F | Br |
| I-491 | C₂H₅ | CF₃ | H | F | CH₃ |
| I-492 | C₂H₅ | CF₃ | H | F | OCH₃ |
| I-493 | C₂H₅ | CF₃ | F | H | H |
| I-494 | C₂H₅ | CF₃ | F | H | F |
| I-495 | C₂H₅ | CF₃ | F | H | Cl |
| I-496 | C₂H₅ | CF₃ | F | H | Br |
| I-497 | C₂H₅ | CF₃ | F | H | CH₃ |
| I-498 | C₂H₅ | CF₃ | F | H | OCH₃ |
| I-499 | C₂H₅ | CF₃ | F | F | H |
| I-500 | C₂H₅ | CF₃ | F | F | F |
| I-501 | C₂H₅ | CF₃ | F | F | Cl |
| I-502 | C₂H₅ | CF₃ | F | F | Br |
| I-503 | C₂H₅ | CF₃ | F | F | CH₃ |
| I-504 | C₂H₅ | CF₃ | F | F | OCH₃ |
| I-505 | OCH₃ | F | H | H | H |
| I-506 | OCH₃ | F | H | H | F |
| I-507 | OCH₃ | F | H | H | Cl |

TABLE A-continued

| No. | R¹ | R³ | R⁵ | R⁶ | R⁷ |
|---|---|---|---|---|---|
| I-508 | OCH₃ | F | H | H | Br |
| I-509 | OCH₃ | F | H | H | CH₃ |
| I-510 | OCH₃ | F | H | H | OCH₃ |
| I-511 | OCH₃ | F | H | F | H |
| I-512 | OCH₃ | F | H | F | F |
| I-513 | OCH₃ | F | H | F | Cl |
| I-514 | OCH₃ | F | H | F | Br |
| I-515 | OCH₃ | F | H | F | CH₃ |
| I-516 | OCH₃ | F | H | F | OCH₃ |
| I-517 | OCH₃ | F | F | H | H |
| I-518 | OCH₃ | F | F | H | F |
| I-519 | OCH₃ | F | F | H | Cl |
| I-520 | OCH₃ | F | F | H | Br |
| I-521 | OCH₃ | F | F | H | CH₃ |
| I-522 | OCH₃ | F | F | H | OCH₃ |
| I-523 | OCH₃ | F | F | F | H |
| I-524 | OCH₃ | F | F | F | F |
| I-525 | OCH₃ | F | F | F | Cl |
| I-526 | OCH₃ | F | F | F | Br |
| I-527 | OCH₃ | F | F | F | CH₃ |
| I-528 | OCH₃ | F | F | F | OCH₃ |
| I-529 | OCH₃ | Cl | H | H | H |
| I-530 | OCH₃ | Cl | H | H | F |
| I-531 | OCH₃ | Cl | H | H | Cl |
| I-532 | OCH₃ | Cl | H | H | Br |
| I-533 | OCH₃ | Cl | H | H | CH₃ |
| I-534 | OCH₃ | Cl | H | H | OCH₃ |
| I-535 | OCH₃ | Cl | H | F | H |
| I-536 | OCH₃ | Cl | H | F | F |
| I-537 | OCH₃ | Cl | H | F | Cl |
| I-538 | OCH₃ | Cl | H | F | Br |
| I-539 | OCH₃ | Cl | H | F | CH₃ |
| I-540 | OCH₃ | Cl | H | F | OCH₃ |
| I-541 | OCH₃ | Cl | F | H | H |
| I-542 | OCH₃ | Cl | F | H | F |
| I-543 | OCH₃ | Cl | F | H | Cl |
| I-544 | OCH₃ | Cl | F | H | Br |
| I-545 | OCH₃ | Cl | F | H | CH₃ |
| I-546 | OCH₃ | Cl | F | H | OCH₃ |
| I-547 | OCH₃ | Cl | F | F | H |
| I-548 | OCH₃ | Cl | F | F | F |
| I-549 | OCH₃ | Cl | F | F | Cl |
| I-550 | OCH₃ | Cl | F | F | Br |
| I-551 | OCH₃ | Cl | F | F | CH₃ |
| I-552 | OCH₃ | Cl | F | F | OCH₃ |
| I-553 | OCH₃ | Br | H | H | H |
| I-554 | OCH₃ | Br | H | H | F |
| I-555 | OCH₃ | Br | H | H | Cl |
| I-556 | OCH₃ | Br | H | H | Br |
| I-557 | OCH₃ | Br | H | H | CH₃ |
| I-558 | OCH₃ | Br | H | H | OCH₃ |
| I-559 | OCH₃ | Br | H | F | H |
| I-560 | OCH₃ | Br | H | F | F |
| I-561 | OCH₃ | Br | H | F | Cl |
| I-562 | OCH₃ | Br | H | F | Br |
| I-563 | OCH₃ | Br | H | F | CH₃ |
| I-564 | OCH₃ | Br | H | F | OCH₃ |
| I-565 | OCH₃ | Br | F | H | H |
| I-566 | OCH₃ | Br | F | H | F |
| I-567 | OCH₃ | Br | F | H | Cl |
| I-568 | OCH₃ | Br | F | H | Br |
| I-569 | OCH₃ | Br | F | H | CH₃ |
| I-570 | OCH₃ | Br | F | H | OCH₃ |
| I-571 | OCH₃ | Br | F | F | H |
| I-572 | OCH₃ | Br | F | F | F |
| I-573 | OCH₃ | Br | F | F | Cl |
| I-574 | OCH₃ | Br | F | F | Br |
| I-575 | OCH₃ | Br | F | F | CH₃ |
| I-576 | OCH₃ | Br | F | F | OCH₃ |
| I-577 | OCH₃ | I | H | H | H |
| I-578 | OCH₃ | I | H | H | F |
| I-579 | OCH₃ | I | H | H | Cl |
| I-580 | OCH₃ | I | H | H | Br |
| I-581 | OCH₃ | I | H | H | CH₃ |
| I-582 | OCH₃ | I | H | H | OCH₃ |
| I-583 | OCH₃ | I | H | F | H |
| I-584 | OCH₃ | I | H | F | F |
| I-585 | OCH₃ | I | H | F | Cl |
| I-586 | OCH₃ | I | H | F | Br |
| I-587 | OCH₃ | I | H | F | CH₃ |
| I-588 | OCH₃ | I | H | F | OCH₃ |
| I-589 | OCH₃ | I | F | H | H |
| I-590 | OCH₃ | I | F | H | F |
| I-591 | OCH₃ | I | F | H | Cl |
| I-592 | OCH₃ | I | F | H | Br |
| I-593 | OCH₃ | I | F | H | CH₃ |
| I-594 | OCH₃ | I | F | H | OCH₃ |
| I-595 | OCH₃ | I | F | F | H |
| I-596 | OCH₃ | I | F | F | F |
| I-597 | OCH₃ | I | F | F | Cl |
| I-598 | OCH₃ | I | F | F | Br |
| I-599 | OCH₃ | I | F | F | CH₃ |
| I-600 | OCH₃ | I | F | F | OCH₃ |
| I-601 | OCH₃ | CH₃ | H | H | H |
| I-602 | OCH₃ | CH₃ | H | H | F |
| I-603 | OCH₃ | CH₃ | H | H | Cl |
| I-604 | OCH₃ | CH₃ | H | H | Br |
| I-605 | OCH₃ | CH₃ | H | H | CH₃ |
| I-606 | OCH₃ | CH₃ | H | H | OCH₃ |
| I-607 | OCH₃ | CH₃ | H | F | H |
| I-608 | OCH₃ | CH₃ | H | F | F |
| I-609 | OCH₃ | CH₃ | H | F | Cl |
| I-610 | OCH₃ | CH₃ | H | F | Br |
| I-611 | OCH₃ | CH₃ | H | F | CH₃ |
| I-612 | OCH₃ | CH₃ | H | F | OCH₃ |
| I-613 | OCH₃ | CH₃ | F | H | H |
| I-614 | OCH₃ | CH₃ | F | H | F |
| I-615 | OCH₃ | CH₃ | F | H | Cl |
| I-616 | OCH₃ | CH₃ | F | H | Br |
| I-617 | OCH₃ | CH₃ | F | H | CH₃ |
| I-618 | OCH₃ | CH₃ | F | H | OCH₃ |
| I-619 | OCH₃ | CH₃ | F | F | H |
| I-620 | OCH₃ | CH₃ | F | F | F |
| I-621 | OCH₃ | CH₃ | F | F | Cl |
| I-622 | OCH₃ | CH₃ | F | F | Br |
| I-623 | OCH₃ | CH₃ | F | F | CH₃ |
| I-624 | OCH₃ | CH₃ | F | F | OCH₃ |
| I-625 | OCH₃ | OCH₃ | H | H | H |
| I-626 | OCH₃ | OCH₃ | H | H | F |
| I-627 | OCH₃ | OCH₃ | H | H | Cl |
| I-628 | OCH₃ | OCH₃ | H | H | Br |
| I-629 | OCH₃ | OCH₃ | H | H | CH₃ |
| I-630 | OCH₃ | OCH₃ | H | H | OCH₃ |
| I-631 | OCH₃ | OCH₃ | H | F | H |
| I-632 | OCH₃ | OCH₃ | H | F | F |
| I-633 | OCH₃ | OCH₃ | H | F | Cl |
| I-634 | OCH₃ | OCH₃ | H | F | Br |
| I-635 | OCH₃ | OCH₃ | H | F | CH₃ |
| I-636 | OCH₃ | OCH₃ | H | F | OCH₃ |
| I-637 | OCH₃ | OCH₃ | F | H | H |
| I-638 | OCH₃ | OCH₃ | F | H | F |
| I-639 | OCH₃ | OCH₃ | F | H | Cl |
| I-640 | OCH₃ | OCH₃ | F | H | Br |
| I-641 | OCH₃ | OCH₃ | F | H | CH₃ |
| I-642 | OCH₃ | OCH₃ | F | H | OCH₃ |
| I-643 | OCH₃ | OCH₃ | F | F | H |
| I-644 | OCH₃ | OCH₃ | F | F | F |
| I-645 | OCH₃ | OCH₃ | F | F | Cl |
| I-646 | OCH₃ | OCH₃ | F | F | Br |
| I-647 | OCH₃ | OCH₃ | F | F | CH₃ |
| I-648 | OCH₃ | OCH₃ | F | F | OCH₃ |
| I-649 | OCH₃ | CF₃ | H | H | H |
| I-650 | OCH₃ | CF₃ | H | H | F |
| I-651 | OCH₃ | CF₃ | H | H | Cl |
| I-652 | OCH₃ | CF₃ | H | H | Br |
| I-653 | OCH₃ | CF₃ | H | H | CH₃ |
| I-654 | OCH₃ | CF₃ | H | H | OCH₃ |
| I-655 | OCH₃ | CF₃ | H | F | H |
| I-656 | OCH₃ | CF₃ | H | F | F |
| I-657 | OCH₃ | CF₃ | H | F | Cl |
| I-658 | OCH₃ | CF₃ | H | F | Br |
| I-659 | OCH₃ | CF₃ | H | F | CH₃ |
| I-660 | OCH₃ | CF₃ | H | F | OCH₃ |
| I-661 | OCH₃ | CF₃ | F | H | H |
| I-662 | OCH₃ | CF₃ | F | H | F |
| I-663 | OCH₃ | CF₃ | F | H | Cl |

TABLE A-continued

| No. | R$^1$ | R$^3$ | R$^5$ | R$^6$ | R$^7$ |
|---|---|---|---|---|---|
| I-664 | OCH$_3$ | CF$_3$ | F | H | Br |
| I-665 | OCH$_3$ | CF$_3$ | F | H | CH$_3$ |
| I-666 | OCH$_3$ | CF$_3$ | F | H | OCH$_3$ |
| I-667 | OCH$_3$ | CF$_3$ | F | F | H |
| I-668 | OCH$_3$ | CF$_3$ | F | F | F |
| I-669 | OCH$_3$ | CF$_3$ | F | F | Cl |
| I-670 | OCH$_3$ | CF$_3$ | F | F | Br |
| I-671 | OCH$_3$ | CF$_3$ | F | F | CH$_3$ |
| I-672 | OCH$_3$ | CF$_3$ | F | F | OCH$_3$ |

The specific number for each single compound is deductible as follows:

Compound 1.1.I-3 e.g. comprises the compound of formula I.1 from Table 1 and line 1-3 from Table A;

To widen the spectrum of action and to achieve synergistic effects, the pyrimidine compounds of formula (I) may be mixed with a large number of representatives of other herbicidal or growth-regulating active ingredient groups and then applied concomitantly. Suitable components for mixtures are, e.g., herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolocarboxamides, triazolopyrimidines, triketones, uracils, or ureas.

It may furthermore be beneficial to apply the pyrimidine compounds of formula (I) alone or in combination with other herbicides, or else in the form of a mixture with other crop protection agents, e.g. together with agents for controlling pests or phytopathogenic fungi or bacteria. Also of interest is the miscibility with mineral salt solutions, which are employed for treating nutritional and trace element deficiencies. Other additives such as non-phytotoxic oils and oil concentrates may also be added.

In one embodiment of the present invention the compositions according to the present invention comprise at least one pyrimidine compound of formula (I) (compound A) and at least one further active compound selected from herbicides B, preferably herbicides B of class b1) to b15), and safeners C (compound C).

In a preferred embodiment of the invention, the composition comprises as active compound A or component A at least one, preferably exactly one, pyrimidine compound of formula (I.A) (corresponds to pyrimidine compound of formula (I)), as defined herein;

In another preferred embodiment of the invention, the composition comprises as active compound A or component A at least one, preferably exactly one, pyrimidine compound of formula (I.B) (corresponds to pyrimidine compound of formula (I)), as defined herein;

In another preferred embodiment of the invention, the composition comprises as active compound A or component A at least one, preferably exactly one, pyrimidine compound of formula (I.C) (corresponds to pyrimidine compound of formula (I)), as defined herein;

In another preferred embodiment of the invention, the composition comprises as active compound A or component A at least one, preferably exactly one, pyrimidine compound of formula (I.D) (corresponds to pyrimidine compound of formula (I)), as defined herein;

In another preferred embodiment of the invention, the composition comprises as active compound A or component A at least one, preferably exactly one, pyrimidine compound of formula (I.E) (corresponds to pyrimidine compound of formula (I)), as defined herein;

In another preferred embodiment of the invention, the composition comprises as active compound A or component A at least one, preferably exactly one, pyrimidine compound of formula (I.F) (corresponds to pyrimidine compound of formula (I)), as defined herein;

In another preferred embodiment of the invention, the composition comprises as active compound A or component A at least one, preferably exactly one, pyrimidine compound of formula (I.G) (corresponds to pyrimidine compound of formula (I)), as defined herein;

In another preferred embodiment of the invention, the composition comprises as active compound A or component A at least one, preferably exactly one, pyrimidine compound of formula (I.H) (corresponds to pyrimidine compound of formula (I)), as defined herein;

In another preferred embodiment of the invention, the composition comprises as active compound A or component A at least one, preferably exactly one, pyrimidine compound of formula (I.I) (corresponds to pyrimidine compound of formula (I)), as defined herein;

In another preferred embodiment of the invention, the composition comprises as active compound A or component A at least one, preferably exactly one, pyrimidine compound of formula (I.J) (corresponds to pyrimidine compound of formula (I)), as defined herein; Preferred compounds of the formula (I) which, as component A, are constituent of the composition according to the invention are the compounds I.A to I.J, as defined above; In another embodiment of the present invention the compositions according to the present invention comprise at least one pyrimidine compound of formula (I) and at least one further active compound B (herbicide B).

The further herbicidal compound B (component B) is preferably selected from the herbicides of class b1) to b15):

Mixing partners for the composition can be selected from below herbicides B as defined below:

B) herbicides of class b1) to b15):
b1) lipid biosynthesis inhibitors;
b2) acetolactate synthase inhibitors (ALS inhibitors);
b3) photosynthesis inhibitors;
b4) protoporphyrinogen-IX oxidase inhibitors (PPO inhibitors);
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and b15) other herbicides selected from the group consisting of bromobutide, chlorflurenol, chlorflurenol-methyl, cinmethylin, cumyluron, dalapon, dazomet, difenzoquat, difenzoquatmetilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenolbutyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

including their agriculturally acceptable salts or derivatives;

In one embodiment of the invention, the compositions contain at least one inhibitor of the lipid biosynthesis (herbicide b1). These compounds inhibit lipid biosynthesis. Inhibition of the lipid biosynthesis can be affected either through inhibition of acetylCoA carboxylase (hereinafter-termed ACCase herbicides) or through a different mode of action (hereinafter termed non-ACCase herbicides). The ACCase herbicides belong to the group A of the HRAC classification system whereas the non-ACCase herbicides belong to the group N of the HRAC classification.

In another embodiment of the invention, the compositions contain at least one ALS inhibitor (herbicide b2). The herbicidal activity of these compounds is based on the inhibition of acetolactate synthase and thus on the inhibition of the branched chain amino acid biosynthesis. These inhibitors belong to the group B of the HRAC classification system.

In another embodiment of the invention, the compositions contain at least one inhibitor of photosynthesis (herbicide b3). The herbicidal activity of these compounds is based either on the inhibition of the photosystem II in plants (so-called PSII inhibitors, groups $C_1$, $C_2$ and $C_3$ of HRAC classification) or on diverting the electron transfer in photosystem I in plants (so-called PSI inhibitors, group D of HRAC classification) and thus on an inhibition of photosynthesis. Amongst these, PSII inhibitors are preferred.

In another embodiment of the invention, the compositions contain at least one inhibitor of protoporphyrinogen-IX-oxidase (herbicide b4). The herbicidal activity of these compounds is based on the inhibition of the protoporphyrinogen-IX-oxidase. These inhibitors belong to the group E of the HRAC classification system.

In another embodiment of the invention, the compositions contain at least one bleacher-herbicide (herbicide b5). The herbicidal activity of these compounds is based on the inhibition of the carotenoid biosynthesis. These include compounds which inhibit carotenoid biosynthesis by inhibition of phytoene desaturase (so-called PDS inhibitors, group F1 of HRAC classification), compounds that inhibit the 4-hydroxyphenylpyruvate-dioxygenase (HPPD inhibitors, group F2 of HRAC classification), compounds that inhibit DOXsynthase (group F4 of HRAC class) and compounds which inhibit carotenoid biosynthesis by an unknown mode of action (bleacher—unknown target, group F3 of HRAC classification).

In another embodiment of the invention, the compositions contain at least one EPSP synthase inhibitor (herbicide b6). The herbicidal activity of these compounds is based on the inhibition of enolpyruvyl shikimate 3-phosphate synthase, and thus on the inhibition of the amino acid biosynthesis in plants. These inhibitors belong to the group G of the HRAC classification system.

In another embodiment of the invention, the compositions contain at least one glutamine synthetase inhibitor (herbicide b7). The herbicidal activity of these compounds is based on the inhibition of glutamine synthetase, and thus on the inhibition of the aminoacid biosynthesis in plants. These inhibitors belong to the group H of the HRAC classification system.

In another embodiment of the invention, the compositions contain at least one DHP synthase inhibitor (herbicide b8). The herbicidal activity of these compounds is based on the inhibition of 7,8-dihydropteroate synthase. These inhibitors belong to the group I of the HRAC classification system.

In another embodiment of the invention, the compositions contain at least one mitosis inhibitor (herbicide b9). The herbicidal activity of these compounds is based on the disturbance or inhibition of microtubule formation or organization, and thus on the inhibition of mitosis. These inhibitors belong to the groups K1 and K2 of the HRAC classification system. Among these, compounds of the group K1, in particular dinitroanilines, are preferred.

In another embodiment of the invention, the compositions contain at least one VLCFA inhibitor (herbicide b10). The herbicidal activity of these compounds is based on the inhibition of the synthesis of very long chain fatty acids and thus on the disturbance or inhibition of cell division in plants. These inhibitors belong to the group K3 of the HRAC classification system.

In another embodiment of the invention, the compositions contain at least one cellulose biosynthesis inhibitor (herbicide b11). The herbicidal activity of these compounds is based on the inhibition of the biosynthesis of cellulose and thus on the inhibition of the synthesis of cell walls in plants. These inhibitors belong to the group L of the HRAC classification system.

In another embodiment of the invention, the compositions contain at least one decoupler herbicide (herbicide b12). The herbicidal activity of these compounds is based on the disruption of the cell membrane. These inhibitors belong to the group M of the HRAC classification system.

In another embodiment of the invention, the compositions contain at least one auxinic herbicide (herbicide b13). These include compounds that mimic auxins, i.e. plant hormones, and affect the growth of the plants. These compounds belong to the group O of the H RAC classification system.

In another embodiment of the invention, the compositions contain at least one auxin transport inhibitor (herbicide b14). The herbicidal activity of these compounds is based on the inhibition of the auxin transport in plants. These compounds belong to the group P of the HRAC classification system.

As to the given mechanisms of action and classification of the active substances, see e.g. "HRAC, Classification of Herbicides According to Mode of Action", http://www.plantprotection.org/hrac/MOA.html).

Preference is given to those compositions according to the present invention comprising at least one herbicide B selected from herbicides of class b1, b2, b3, b4, b5, b6, b9, b10, b13, and b14.

Specific preference is given to those compositions according to the present invention which comprise at least one herbicide B selected from the herbicides of class b1, b2, b4, b5, b9, b10, b13, and b14.

Particular preference is given to those compositions according to the present invention which comprise at least one herbicide B selected from the herbicides of class b1, b2, b4, b5, b9, b10, and b13

Examples of herbicides B which can be used in combination with the compound of formula (I) according to the present invention are:

b1) from the group of the lipid biosynthesis inhibitors:

ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofopP, quizalofop-P-ethyl, quizalofop-P-tefuryl, sethoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[, 1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuronethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8), 1-(5-tert-butylisoxazol-3-yl)-4-ethoxy-5-hydroxy-3-methyl-imidazolidin-2-one (CAS 1844836-64-1), triazine herbicides, including of chlorotriazine, triazinones, triazindiones, methylthiotriazines and pyridazinones such as ametryn, atrazine, chloridazone, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquatdimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, chlorphthalim, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethyl phenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-$C_3$-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), 1-methyl-6-trifluoromethyl-3-(2,2,7-trifluoro-3-oxo-4-prop-2-ynyl)-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate (CAS 948893-00-3), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:

PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquinotrione, isoxaflutole, mesotrione, oxotrione (CAS 1486617-21-3), pyrasulfotole, pyrazolynate, pyrazoxyfen, sulcotrione, tefuryltrione, tembotrione, tolpyralate, topramezone, bleacher, unknown target: aclonifen, amitrole flumeturon, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors: glyphosate, glyphosate-isopropylammonium, glyposate-potassium and glyphosate-trimesium (sulfosate);

b7) from the group of the glutamine synthase inhibitors: bilanaphos (bialaphos), bilanaphossodium, glufosinate, glufosinate-P and glufosinate-ammonium;

b8) from the group of the DHP synthase inhibitors: asulam;

b9) from the group of the mitosis inhibitors:

compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl, flamprop-M-methyl and propham; among these, compounds of group K1, in particular dinitroanilines are preferred;

b10) from the group of the VLCFA inhibitors:

chloroacetamides such as acetochlor, alachlor, amidochlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, napronilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

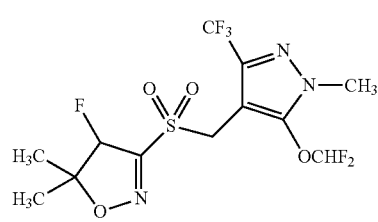

II.1

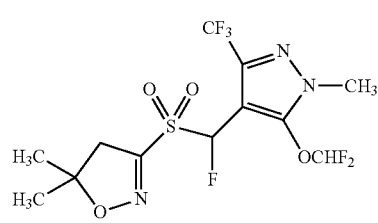

II.2

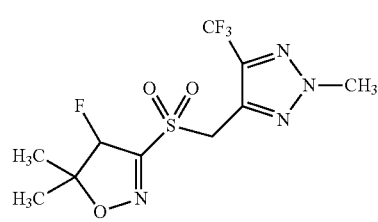

II.3

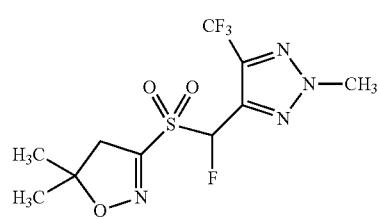

II.4

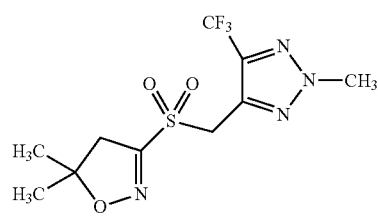

II.5

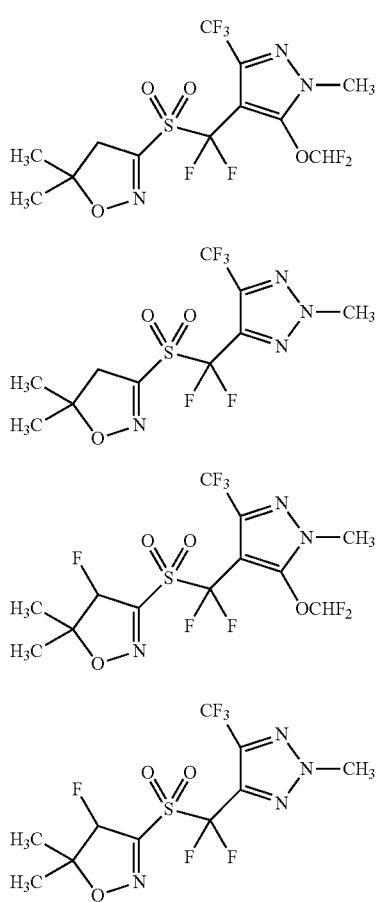

the isoxazoline compounds are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors: chlorthiamid, dichlobenil, flupoxam, indaziflam, isoxaben, triaziflam and 1-cyclohexyl-5-pentafluorphenyloxy-1⁴-[1,2,4,6]thiatriazin-3-ylamine (CAS 175899-01-1);

b12) from the group of the decoupler herbicides: dinoseb, dinoterb and DNOC and its salts;

b13) from the group of the auxinic herbicides:

2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, flopyrauxifen, fluroxypyr, fluroxypyr-butometyl, fluroxypyr-meptyl, halauxifen and its salts and esters (CAS 943832-60-8); MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6); b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, cyclopyrimorate (CAS 499223-49-3 and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preferred herbicides B that can be used in combination with the pyrimidine compounds of the formula (I) according to the present invention are:

b1) from the group of the lipid biosynthesis inhibitors:

clethodim, clodinafop-propargyl, cycloxydim, cyhalofop-butyl, diclofop-methyl, fenoxaprop-P-ethyl, fluazifop-P-butyl, haloxyfop-P-methyl, metamifop, pinoxaden, profoxydim, propaquizafop, quizalofop-P-ethyl, quizalofop-P-tefuryl, sethoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[, 1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[, 1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); benfuresate, dimepiperate, EPTC, esprocarb, ethofumesate, molinate, orbencarb, prosulfocarb, thiobencarb and triallate;

b2) from the group of the ALS inhibitors:

amidosulfuron, azimsulfuron, bensulfuron-methyl, bispyribac-sodium, chlorimuron-ethyl, chlorsulfuron, cloransulam-methyl, cyclosulfamuron, diclosulam, ethametsulfuron-methyl, ethoxysulfuron, flazasulfuron, florasulam, flucarbazone-sodium, flucetosulfuron, flumetsulam, flupyrsulfuron-methyl-sodium, foramsulfuron, halosulfuron-methyl, imazamethabenz-methyl, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, metosulam, metsulfuron-methyl, nicosulfuron, orthosulfamuron, oxasulfuron, penoxsulam, primisulfuron-methyl, propoxycarbazon-sodium, propyrisulfuron, prosulfuron, pyrazosulfuron-ethyl, pyribenzoxim, pyrimisulfan, pyriftalid, pyriminobac-methyl, pyrithiobac-sodium, pyroxsulam, rimsulfuron, sulfometuron-methyl, sulfosulfuron, thiencarbazone-methyl, thifensulfuron-methyl, triasulfuron, tribenuron-methyl, trifloxysulfuron, triflusulfuron-methyl, tritosulfuron and triafamone;

b3) from the group of the photosynthesis inhibitors:
ametryn, amicarbazone, atrazine, bentazone, bentazone-sodium, bromoxynil and its salts and esters, chloridazon, chlorotoluron, cyanazine, desmedipham, diquat-dibromide, diuron, fluometuron, hexazinone, ioxynil and its salts and esters, isoproturon, lenacil, linuron, metamitron, methaben-zthiazuron, metribuzin, paraquat, paraquat-dichloride, phenmedipham, propanil, pyridate, simazine, terbutryn, terbuthylazine, thidiazuron, 1-(6-tert-butylpyrimidin-4-yl)-2-hydroxy-4-methoxy-3-methyl-2H-pyrrol-5-one (CAS 1654744-66-7), 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butyl-1-methyl-pyrazol-3-yl)-4-chloro-2-hydroxy-3-methyl-2H-pyrrol-5-one (CAS 1654057-29-0), 1-(5-tert-butyl-1-methyl-pyrazol-3-yl)-3-chloro-2-hydroxy-4-methyl-2H-pyrrol-5-one (CAS 1654747-80-4), 4-hydroxy-1-methoxy-5-methyl-3-[4-(trifluoromethyl)-2-pyridyl]imidazolidin-2-one; (CAS 2023785-78-4), 4-hydroxy-1,5-dimethyl-3-[4-(trifluoromethyl)-2-pyridyl]imidazolidin-2-one (CAS 2023785-79-5), 5-ethoxy-4-hydroxy-1-methyl-3-[4-(trifluoromethyl)-2-pyridyl]imidazolidin-2-one (CAS 1701416-69-4), 4-hydroxy-1-methyl-3-[4-(trifluoromethyl)-2-pyridyl]imidazolidin-2-one (CAS 1708087-22-2), 4-hydroxy-1,5-dimethyl-3-[1-methyl-5-(trifluoromethyl)pyrazol-3-yl]imidazolidin-2-one (CAS 2023785-80-8) and 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors:
acifluorfen-sodium, bencarbazone, benzfendizone, butafenacil, carfentrazone-ethyl, cinidon-ethyl, flufenpyr-ethyl, flumiclorac-pentyl, flumioxazin, fluoroglycofen-ethyl, fomesafen, lactofen, oxadiargyl, oxadiazon, oxyfluorfen, pentoxazone, pyraflufen, pyraflufen-ethyl, saflufenacil, sulfentrazone, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethyl phenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-$C_3$-7), 3-[7-fluoro-3-oxo-4-(prop-2-ynyl)-3,4-dihydro-2H-benzo[1,4]oxazin-6-yl]-1,5-dimethyl-6-thioxo[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0); 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), and 3-[7-chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
aclonifen, amitrole, beflubutamid, benzobicyclon, bicyclopyrone, clomazone, diflufenican, fenquinotrione, flumeturon, flurochloridone, flurtamone, isoxaflutole, mesotrione, oxotrione (CAS 1486617-21-3), norflurazon, picolinafen, pyrasulfotole, pyrazolynate, sulcotrione, tefuryltrione, tembotrione, tolpyralate, topramezone, 4-(3-trifluoromethylphenoxy)-2-(4-trifluoromethylphenyl)pyrimidine (CAS 180608-33-7), 2-chloro-3-methylsulfanyl-N-(1-methyltetrazol-5-yl)-4-(trifluoromethyl)benzamide (CAS 1361139-71-0, 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7);

b6) from the group of the EPSP synthase inhibitors:
glyphosate, glyphosate-isopropylammonium, glyphosate-potassium and glyphosate-trimesium (sulfosate);

b7) from the group of the glutamine synthase inhibitors:
glufosinate, glufosinate-P, glufosinate-ammonium;

b8) from the group of the DHP synthase inhibitors:
asulam;

b9) from the group of the mitosis inhibitors:
benfluralin, dithiopyr, ethalfluralin, flamprop, flamprop-isopropyl, flamprop-methyl, flamprop-M-isopropyl, flamprop-M-methyl, oryzalin, pendimethalin, thiazopyr and trifluralin;

b10) from the group of the VLCFA inhibitors: acetochlor, alachlor, amidochlor, anilofos, butachlor, cafenstrole, dimethenamid, dimethenamid-P, fentrazamide, flufenacet, mefenacet, metazachlor, metolachlor, S-metolachlor, naproanilide, napropamide, napropamide-M, pretilachlor, fenoxasulfone, ipfencarbazone, pyroxasulfone thenylchlor and isoxazoline-compounds of the formulae II.1, II.2, II.3, II.4, II.5, II.6, II.7, II.8 and II.9 as mentioned above;

b11) from the group of the cellulose biosynthesis inhibitors: dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b13) from the group of the auxinic herbicides:
2,4-D and its salts and esters, aminocyclopyrachlor and its salts and esters, aminopyralid and its salts such as aminopyralid-dimethylammonium, aminopyralid-tris(2-hydroxypropyl)ammonium and its esters, clopyralid and its salts and esters, dicamba and its salts and esters, dichlorprop-P and its salts and esters, flopyrauxifen, fluroxypyr-meptyl, halauxifen and its salts and esters (CAS 943832-60-8), MCPA and its salts and esters, MCPB and its salts and esters, mecoprop-P and its salts and esters, picloram and its salts and esters, quinclorac, quinmerac, triclopyr and its salts and esters, florpyrauxifen, florpyrauxifen-benzyl (CAS 1390661-72-9) and 4-amino-3-chloro-5-fluoro-6-(7-fluoro-1H-indol-6-yl)picolinic acid (CAS 1629965-65-6); b14) from the group of the auxin transport inhibitors: diflufenzopyr and diflufenzopyr-sodium; b15) from the group of the other herbicides: bromobutide, cinmethylin, cumyluron, cyclopyrimorate (CAS 499223-49-3) and its salts and esters, dalapon, difenzoquat, difenzoquatmetilsulfate, DSMA, dymron (=daimuron), indanofan, metam, methylbromide, MSMA, oxaziclomefone, pyributicarb and tridiphane.

Particularly preferred herbicides B that can be used in combination with the pyrimidine compounds of the formula (I) according to the present invention are:
b1) from the group of the lipid biosynthesis inhibitors: clodinafop-propargyl, cycloxydim, cyhalofop-butyl, fenoxaprop-P-ethyl, pinoxaden, profoxydim, tepraloxydim, tralkoxydim, 4-(4'-Chloro-4-cyclopropyl-2'-fluoro[, 1'-biphenyl]-3-yl)-5-hydroxy-2,2,6,6-tetramethyl-2H-pyran-3 (6H)-one (CAS 1312337-72-6); 4-(2',4'-Dichloro-4-cyclopropyl[, 1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[, 1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[, 1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[, 1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[, 1'-biphenyl]-3-yl)-5,6-dihydro-2,2,6,6-tetramethyl-5-oxo-2H-pyran-3-yl carbonic acid methyl ester (CAS 1033760-58-5); esprocarb, prosulfocarb, thiobencarb and triallate;

b2) from the group of the ALS inhibitors: bensulfuron-methyl, bispyribac-sodium, cyclosulfamuron, diclosulam, flumetsulam, flupyrsulfuron-methyl-sodium, foramsulfuron, imazamox, imazapic, imazapyr, imazaquin, imazethapyr, imazosulfuron, iodosulfuron, iodosulfuron-methyl-sodium, iofensulfuron, iofensulfuron-sodium, mesosulfuron, metazosulfuron, nicosulfuron, penoxsulam, propoxycarbazon-sodium, propyrisulfuron, pyrazosulfuron-ethyl, pyroxsulam, rimsulfuron, sulfosulfuron, thiencarbazon-methyl, tritosulfuron and triafamone;

b3) from the group of the photosynthesis inhibitors: ametryn, atrazine, diuron, fluometuron, hexazinone, isoproturon, linuron, metribuzin, paraquat, paraquat-dichloride, propanil, terbutryn, terbuthylazine, 1-(5-tert-butylisoxazol-3-yl)-2-hydroxy-4-methoxy-3-methyl-2H-pyrrol-5-one (CAS 1637455-12-9), 1-(5-tert-butylisoxazol-3-yl)-4-chloro-2-hydroxy-3-methyl-2H-pyrrol-5-one (CAS 1637453-94-1), 1-(5-tert-butylisoxazol-3-yl)-4-ethoxy-5-hydroxy-3-methyl-imidazolidin-2-one (CAS 1844836-64-1);

b4) from the group of the protoporphyrinogen-IX oxidase inhibitors: flumioxazin, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione (CAS 451484-50-7), 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0), and 1-methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0);

b5) from the group of the bleacher herbicides: amitrole, bicyclopyrone, clomazone, diflufenican, fenquinotrione, flumeturon, flurochloridone, isoxaflutole, mesotrione, oxotrione (CAS 1486617-21-3), picolinafen, sulcotrione, tefuryltrione, tembotrione, tolpyralate, topramezone, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9); and 2-(2,5-dichlorophenyl)methyl-4,4-dimethyl-3-isoxazolidinone (CAS 81778-66-7);

b6) from the group of the EPSP synthase inhibitors: glyphosate, glyphosate-isopropylammonium and glyphosate-trimesium (sulfosate);

b7) from the group of the glutamine synthase inhibitors: glufosinate, glufosinate-P and glufosinate-ammonium;

b9) from the group of the mitosis inhibitors: pendimethalin and trifluralin;

b10) from the group of the VLCFA inhibitors: acetochlor, cafenstrole, dimethenamid-P, fentrazamide, flufenacet, mefenacet, metazachlor, metolachlor, S-metolachlor, fenoxasulfone, ipfencarbazone and pyroxasulfone; likewise, preference is given to isoxazoline compounds of the formulae II.1, II.2, II.3, II.4, II.5, II.6, II.7, II.8 and II.9 as mentioned above;

b11) from the group of the cellulose biosynthesis inhibitors: indaziflam, isoxaben and triaziflam;

b13) from the group of the auxinic herbicides: 2,4-D and its salts and esters such as clacyfos, and aminocyclopyrachlor and its salts and esters, aminopyralid and its salts and its esters, clopyralid and its salts and esters, dicamba and its salts and esters, flopyrauxifen, fluroxypyr-meptyl, halauxifen, halauxifen-methyl, quinclorac, quinmerac, florpyrauxifen, florpyrauxifen-benzyl (CAS 1390661-72-9) and 4-amino-3-chloro-5-fluoro-6-(7-fluoro-1H-indol-6-yl) picolinic acid (CAS 1629965-65-6);

b14) from the group of the auxin transport inhibitors: diflufenzopyr and diflufenzopyr-sodium, b15) from the group of the other herbicides: cinmethylin, dymon (=daimuron), indanofan, oxaziclomefone.

Particularly preferred herbicides B are the herbicides B as defined above; in particular, the herbicides B.1-B.202 listed below in table B:

TABLE B

| B | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-ethyl |
| B.6 | fenoxaprop-P-ethyl |
| B.7 | metamifop |
| B.8 | pinoxaden |
| B.9 | profoxydim |
| B.10 | sethoxydim |
| B.11 | tepraloxydim |
| B.12 | tralkoxydim |
| B.13 | esprocarb |
| B.14 | ethofumesate |
| B.15 | molinate |
| B.16 | prosulfocarb |
| B.17 | thiobencarb |
| B.18 | triallate |
| B.19 | bensulfuron-methyl |
| B.20 | bispyribac-sodium |
| B.21 | cloransulam-methyl |
| B.22 | chlorsulfuron |
| B.23 | clorimuron |
| B.24 | cyclosulfamuron |
| B.25 | diclosulam |
| B.26 | florasulam |
| B.27 | flumetsulam |
| B.28 | flupyrsulfuron-methyl-sodium |
| B.29 | foramsulfuron |
| B.30 | imazamox |
| B.31 | imazamox-ammonium |
| B.32 | imazapic |

TABLE B-continued

| B | Herbicide B |
|---|---|
| B.33 | imazapic-ammonium |
| B.34 | imazapic-isopropylammonium |
| B.35 | imazapyr |
| B.36 | imazapyr-ammonium |
| B.37 | imazapyr-isopropylammonium |
| B.38 | imazaquin |
| B.39 | imazaquin-ammonium |
| B.40 | imazethapyr |
| B.41 | imazethapyr-ammonium |
| B.42 | imazethapyr-isopropylammonium |
| B.43 | imazosulfuron |
| B.44 | iodosulfuron-methyl-sodium |
| B.45 | iofensulfuron |
| B.46 | iofensulfuron-sodium |
| B.47 | mesosulfuron-methyl |
| B.48 | metazosulfuron |
| B.49 | metsulfuron-methyl |
| B.50 | metosulam |
| B.51 | nicosulfuron |
| B.52 | penoxsulam |
| B.53 | propoxycarbazon-sodium |
| B.54 | pyrazosulfuron-ethyl |
| B.55 | pyribenzoxim |
| B.56 | pyriftalid |
| B.57 | pyroxsulam |
| B.58 | propyrisulfuron |
| B.59 | rimsulfuron |
| B.60 | sulfosulfuron |
| B.61 | thiencarbazone-methyl |
| B.62 | thifensulfuron-methyl |
| B.63 | tribenuron-methyl |
| B.64 | tritosulfuron |
| B.65 | triafamone |
| B.66 | ametryne |
| B.67 | atrazine |
| B.68 | bentazon |
| B.69 | bromoxynil |
| B.70 | bromoxynil-octanoate |
| B.71 | bromoxynil-heptanoate |
| B.72 | bromoxynil-potassium |
| B.73 | diuron |
| B.74 | fluometuron |
| B.75 | hexazinone |
| B.76 | isoproturon |
| B.77 | linuron |
| B.78 | metamitron |
| B.79 | metribuzin |
| B.80 | propanil |
| B.81 | simazin |
| B.82 | terbuthylazine |
| B.83 | terbutryn |
| B.84 | paraquat-dichloride |
| B.85 | acifluorfen |
| B.86 | butafenacil |
| B.87 | carfentrazone-ethyl |
| B.88 | flumioxazin |
| B.89 | fomesafen |
| B.90 | oxadiargyl |
| B.91 | oxyfluorfen |
| B.92 | pyraflufen |
| B.93 | pyraflufen-ethyl |
| B.94 | saflufenacil |
| B.95 | sulfentrazone |
| B.96 | trifludimoxazin |
| B.97 | ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6) |
| B.98 | benzobicyclon |
| B.99 | bicyclopyrone |
| B.100 | clomazone |
| B.101 | diflufenican |
| B.102 | flurochloridone |
| B.103 | isoxaflutole |
| B.104 | mesotrione |
| B.105 | norflurazone |
| B.106 | picolinafen |
| B.107 | sulcotrione |
| B.108 | tefuryltrione |
| B.109 | tembotrione |
| B.110 | tolpyralate |
| B.111 | topramezone |
| B.112 | topramezone-sodium |
| B.113 | amitrole |
| B.114 | fluometuron |
| B.115 | fenquinotrione |
| B.116 | glyphosate |
| B.117 | glyphosate-ammonium |
| B.118 | glyphosate-dimethylammonium |
| B.119 | glyphosate-isopropylammonium |
| B.120 | glyphosate-trimesium (sulfosate) |
| B.121 | glyphosate-potassium |
| B.122 | glufosinate |
| B.123 | glufosinate-ammonium |
| B.124 | glufosinate-P |
| B.125 | glufosinate-P-ammonium |
| B.126 | pendimethalin |
| B.127 | trifluralin |
| B.128 | acetochlor |
| B.129 | butachlor |
| B.130 | cafenstrole |
| B.131 | dimethenamid-P |
| B.132 | fentrazamide |
| B.133 | flufenacet |
| B.134 | mefenacet |
| B.135 | metazachlor |
| B.136 | metolachlor |
| B.137 | S-metolachlor |
| B.138 | pretilachlor |
| B.139 | fenoxasulfone |
| B.140 | indaziflam |
| B.141 | isoxaben |
| B.142 | triaziflam |
| B.143 | ipfencarbazone |
| B.144 | pyroxasulfone |
| B.145 | 2,4-D |
| B.146 | 2,4-D-isobutyl |
| B.147 | 2,4-D-dimethylammonium |
| B.148 | 2,4-D-N,N,N-trimethylethanolammonium |
| B.149 | aminopyralid |
| B.150 | aminopyralid-methyl |
| B.151 | aminopyralid-dimethylammonium |
| B.152 | aminopyralid-tris(2-hydroxypropyl)ammonium |
| B.153 | clopyralid |
| B.154 | clopyralid-methyl |
| B.155 | clopyralid-olamine |
| B.156 | dicamba |
| B.157 | dicamba-butotyl |
| B.158 | dicamba-diglycolamine |
| B.159 | dicamba-dimethylammonium |
| B.160 | dicamba-diolamine |
| B.161 | dicamba-isopropylammonium |
| B.162 | dicamba-potassium |
| B.163 | dicamba-sodium |
| B.164 | dicamba-trolamine |
| B.165 | dicamba-N,N-bis-(3-aminopropyl)methylamine |
| B.166 | dicamba-diethylenetriamine |
| B.167 | fluroxypyr |
| B.168 | fluroxypyr-meptyl |
| B.169 | halauxifen |
| B.170 | halauxifen-methyl |
| B.171 | MCPA |
| B.172 | MCPA-2-ethylhexyl |
| B.173 | MCPA-dimethylammonium |
| B.174 | quinclorac |
| B.175 | quinclorac-dimethylammonium |
| B.176 | quinmerac |
| B.177 | quinmerac-dimethylammonium |
| B.178 | florpyrauxifen |
| B.179 | florpyrauxifen-benzyl (CAS 1390661-72-9) |

TABLE B-continued

| B | Herbicide B |
| --- | --- |
| B.180 | aminocyclopyrachlor |
| B.181 | aminocyclopyrachlor-potassium |
| B.182 | aminocyclopyrachlor-methyl |
| B.183 | diflufenzopyr |
| B.184 | diflufenzopyr-sodium |
| B.185 | dymron |
| B.186 | indanofan |
| B.187 | oxaziclomefone |
| B.188 | II.1 |
| B.189 | II.2 |
| B.190 | II.3 |
| B.191 | II.4 |
| B.192 | II.5 |
| B.193 | II.6 |
| B.194 | II.7 |
| B.195 | II.8 |
| B.196 | II.9 |
| B.197 | 4-amino-3-chloro-5-fluoro-6-(7-fluoro-1H-indol-6-yl)picolinic acid (CAS 1629965-65-6) |
| B.198 | flopyrauxifen |
| B.199 | oxotrione (CAS 1486617-21-3) |
| B.200 | cinmethylin |
| B.201 | 2-chloro-3-methylsulfanyl-N-(1-methyltetrazol-5-yl)-4-(trifluoromethyl)benzamide (CAS 1361139-71-0) |
| B.202 | 2-(2,4-dichlorophenyl)methyl-4,4-dimethyl-3-isoxazolidone (CAS 81777-95-9) |

In another embodiment of the present invention the compositions according to the present invention comprise at least one pyrimidine compound of formula (I) and at least one safener C.

Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or in the pre-emergence application or post-emergence application of the useful plant. The safeners and the pyrimidine compounds of formula (I) and/or the herbicides B can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4), metcamifen and BPCMS (CAS 54091-$C_6$-4). Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and metcamifen.

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3), 2,2,5-trimethyl-3-(dichloroacetyl)-1,3-oxazolidine (R-29148, CAS 52836-31-4) and metcamifen.

Particularly preferred safeners C, which, as component C, are constituent of the composition according to the invention are the safeners C as defined above; in particular the safeners C.1-C.17 listed below in table C:

TABLE C

| C | Safener C |
| --- | --- |
| C.1 | benoxacor |
| C.2 | cloquintocet |
| C.3 | cloquintocet-mexyl |
| C.4 | cyprosulfamide |
| C.5 | dichlormid |
| C.6 | fenchlorazole |
| C.7 | fenchlorazole-ethyl |
| C.8 | fenclorim |
| C.9 | furilazole |
| C.10 | isoxadifen |
| C.11 | isoxadifen-ethyl |
| C.12 | mefenpyr |
| C.13 | mefenpyr-diethyl |
| C.14 | naphtalic acid anhydride |
| C.15 | 4-(dichloroacetyl)-1-oxa-4-azaspiro[4.5]decane (MON4660, CAS 71526-07-3) |
| C.16 | 2,2,5-trimethyl-3-(dichloroacetyl)-1,3-oxazolidine (R-29148, CAS 52836-31-4) |
| C.17 | metcamifen |

The active compounds B of groups b1) to b15) and the active compounds C are known herbicides and safeners, see, e.g., The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660.

The assignment of the active compounds to the respective mechanisms of action is based on current knowledge. If several mechanisms of action apply to one active compound, this substance was only assigned to one mechanism of action.

Active compounds B and C having a carboxyl group can be employed in the form of the acid, in the form of an agriculturally suitable salt as mentioned above or else in the form of an agriculturally acceptable derivative in the compositions according to the invention.

In the case of dicamba, suitable salts include those, where the counterion is an agriculturally acceptable cation. E.g., suitable salts of dicamba are dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine. Examples of a suitable ester are dicamba-methyl and dicamba-butotyl.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D-triethylammonium, 2,4-D-tris(2-hydroxypropyl)ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of 2,4-DB are e.g. 2,4-DB-sodium, 2,4-DB-potassium and 2,4-DB-dimethylammonium. Suitable esters of 2,4-DB are e.g. 2,4-DB-butyl and 2,4-DB-isoctyl.

Suitable salts of dichlorprop are e.g. dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethylammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl)ammonium. Example of suitable esters of clopyralid is clopyralid-methyl.

Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are e.g. triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are e.g. glyphosate-ammonium, glyphosate-diammonium, glyphosate-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is e.g. glufosinate-ammonium.

A suitable salt of glufosinate-P is e.g. glufosinate-P-ammonium.

Suitable salts and esters of bromoxynil are e.g. bromoxynil-butyrate, bromoxynil-heptanoate, bromoxynil-octanoate, bromoxynil-potassium and bromoxynil-sodium.

Suitable salts and esters of ioxonil are e.g. ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are e.g. mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is e.g. diflufenzopyr-sodium.

A suitable salt of naptalam is e.g. naptalam-sodium.

Suitable salts and esters of aminocyclopyrachlor are e.g. aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is e.g. quinclorac-dimethylammonium.

A suitable salt of quinmerac is e.g. quinmerac-dimethylammonium.

A suitable salt of imazamox is e.g. imazamox-ammonium.

Suitable salts of imazapic are e.g. imazapic-ammonium and imazapic-isopropylammonium.

Suitable salts of imazapyr are e.g. imazapyr-ammonium and imazapyr-isopropylammonium.

A suitable salt of imazaquin is e.g. imazaquin-ammonium.

Suitable salts of imazethapyr are e.g. imazethapyr-ammonium and imazethapyr-isopropylammonium.

A suitable salt of topramezone is e.g. topramezone-sodium.

According to a preferred embodiment of the invention, the composition comprises as herbicidal active compound B or component B at least one, preferably exactly one herbicide B.

According to another preferred embodiment of the invention, the composition comprises as herbicidal active compounds B or component B at least two, preferably exactly two herbicides B different from each other.

According to another preferred embodiment of the invention, the composition comprises as herbicidal active compounds B or component B at least three, preferably exactly three herbicides B different from each other.

According to another preferred embodiment of the invention, the composition comprises as safening component C or component C at least one, preferably exactly one safener C.

According to another preferred embodiment of the invention, the composition comprises as component B at least one, preferably exactly one herbicide B, and as component C at least one, preferably exactly one, safener C.

According to another preferred embodiment of the invention, the composition comprises at least two, preferably exactly two, herbicides B different from each other, and as component C at least one, preferably exactly one, safener C.

According to another preferred embodiment of the invention, the composition comprises at least three, preferably exactly three, herbicides B different from each other, and as component C at least one, preferably exactly one, safener C.

According to another preferred embodiment of the invention, the composition comprises as component A at least one, preferably exactly one pyrimidine compound of formula (I), preferably of formula (1.1), especially preferred the compound (1.1.I-25), (1.1.I-37), (1.1.I-31), (1.1.I-49), (1.1.I-61), (1.1.I-55), or (1.1.I-73), and as component B at least one, preferably exactly one, herbicide B.

According to another preferred embodiment of the invention, the composition comprises as component A at least one, preferably exactly one pyrimidine compound of formula (I), preferably of formula (1.1), especially preferred the compound (1.1.I-25), (1.1.I-37), (1.1.I-31), (1.1.I-49), (1.1.I-61), (1.1.I-55), or (1.1.I-73), and at least two, preferably exactly two, herbicides B different from each other.

According to another preferred embodiment of the invention, the composition comprises as component A at least one, preferably exactly one pyrimidine compound of formula (I), preferably of formula (1.2), especially preferred the compound (1.1.I-25), (1.1.I-37), (1.1.I-31), (1.1.I-49), (1.1.I-61), (1.1.I-55), or (1.1.I-73), and at least three, preferably exactly three, herbicides B different from each other.

According to another preferred embodiment of the invention, the composition comprises as component A at least one, preferably exactly one pyrimidine compound of formula (I), preferably of formula (1.1), especially preferred the compound (1.1.I-25), (1.1.I-37), (1.1.I-31), (1.1.I-49), (1.1.I-61), (1.1.I-55), or (1.1.I-73), and as component C at least one, preferably exactly one, safener C.

According to another preferred embodiment of the invention, the composition comprises as component A at least one, preferably exactly one pyrimidine compound of formula (I), preferably of formula (1.1), especially preferred the compound (1.1.I-25), (1.1.I-37), (1.1.I-31), (1.1.I-49), (1.1.I-61), (1.1.I-55), or (1.1.I-73), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.1), especially preferred the compound (1.1.I-25), (1.1.I-37), (1.1.I-31), (1.1.I-49), (1.1.I-61), (1.1.I-55), or (1.1.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.1), especially preferred the compound (1.1.I-25), (1.1.I-37), (1.1.I-31), (1.1.I-49), (1.1.I-61), (1.1.I-55), or (1.1.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.2), especially preferred the compound (1.2.I-25), (1.2.I-37), (1.2.I-31), (1.2.I-49), (1.2.I-61), (1.2.I-55), or (1.2.I-73), and as component B at least one, preferably exactly one, herbicide B.

According to another preferred embodiment of the invention, the composition comprises as component A at least one, preferably exactly one pyrimidine compound of formula (I), preferably of formula (1.2), especially preferred the compound (1.2.I-25), (1.2.I-37), (1.2.I-31), (1.2.I-49), (1.2.I-61), (1.2.I-55), or (1.2.I-73), and at least two, preferably exactly two, herbicides B different from each other.

According to another preferred embodiment of the invention, the composition comprises as component A at least one, preferably exactly one pyrimidine compound of formula (I), preferably of formula (1.2), especially preferred the compound (1.2.I-25), (1.2.I-37), (1.2.I-31), (1.2.I-49), (1.2.I-61), (1.2.I-55), or (1.2.I-73), and at least three, preferably exactly three, herbicides B different from each other.

According to another preferred embodiment of the invention, the composition comprises as component A at least one, preferably exactly one pyrimidine compound of formula (I), preferably of formula (1.2), especially preferred the compound (1.2.I-25), (1.2.I-37), (1.2.I-31), (1.2.I-49), (1.2.I-61), (1.2.I-55), or (1.2.I-73), and as component C at least one, preferably exactly one, safener C.

According to another preferred embodiment of the invention, the composition comprises as component A at least one, preferably exactly one pyrimidine compound of formula (I), preferably of formula (1.2), especially preferred the compound (1.2.I-25), (1.2.I-37), (1.2.I-31), (1.2.I-49), (1.2.I-61), (1.2.I-55), or (1.2.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.2), especially preferred the compound (1.2.I-25), (1.2.I-37), (1.2.I-31), (1.2.I-49), (1.2.I-61), (1.2.I-55), or (1.2.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.2), especially preferred the compound (1.2.I-25), (1.2.I-37), (1.2.I-31), (1.2.I-49), (1.2.I-61), (1.2.I-55), or (1.2.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.3), especially preferred the compound (1.3.I-25), (1.3.I-37), (1.3.I-31), (1.3.I-49), (1.3.I-61), (1.3.I-55), or (1.3.I-73), and as component B at least one, preferably exactly one, herbicide B.

According to another preferred embodiment of the invention, the composition comprises as component A at least one, preferably exactly one pyrimidine compound of formula (I), preferably of formula (1.3), especially preferred the compound (1.3.I-25), (1.3.I-37), (1.3.I-31), (1.3.I-49), (1.3.I-61), (1.3.I-55), or (1.3.I-73), and at least two, preferably exactly two, herbicides B different from each other.

According to another preferred embodiment of the invention, the composition comprises as component A at least one, preferably exactly one pyrimidine compound of formula (I), preferably of formula (1.3), especially preferred the compound (1.3.I-25), (1.3.I-37), (1.3.I-31), (1.3.I-49), (1.3.I-61), (1.3.I-55), or (1.3.I-73), and at least three, preferably exactly three, herbicides B different from each other.

According to another preferred embodiment of the invention, the composition comprises as component A at least one, preferably exactly one pyrimidine compound of formula (I), preferably of formula (1.3), especially preferred the compound (1.3.I-25), (1.3.I-37), (1.3.I-31), (1.3.I-49), (1.3.I-61), (1.3.I-55), or (1.3.I-73), and as component C at least one, preferably exactly one, safener C.

According to another preferred embodiment of the invention, the composition comprises as component A at least one, preferably exactly one pyrimidine compound of formula (I), preferably of formula (1.3), especially preferred the compound (1.3.I-25), (1.3.I-37), (1.3.I-31), (1.3.I-49), (1.3.I-61), (1.3.I-55), or (1.3.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.3), especially preferred the compound (1.3.I-25), (1.3.I-37), (1.3.I-31), (1.3.I-49), (1.3.I-61), (1.3.I-55), or (1.3.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.3), especially preferred the compound (1.3.I-25), (1.3.I-37), (1.3.I-31), (1.3.I-49), (1.3.I-61), (1.3.I-55), or (1.3.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.4), especially preferred the compound (1.4.I-25), (1.4.I-37), (1.4.I-31), (1.4.I-49), (1.4.I-61), (1.4.I-55), or (1.4.I-73), and as component B at least one, preferably exactly one, herbicide B.

According to another preferred embodiment of the invention, the composition comprises as component A at least one, preferably exactly one pyrimidine compound of formula (I), preferably of formula (1.4), especially preferred the compound (1.4.I-25), (1.4.I-37), (1.4.I-31), (1.4.I-49), (1.4.I-61), (1.4.I-55), or (1.4.I-73), and at least two, preferably exactly two, herbicides B different from each other.

According to another preferred embodiment of the invention, the composition comprises as component A at least one, preferably exactly one pyrimidine compound of formula (I), preferably of formula (1.4), especially preferred the compound (1.4.I-25), (1.4.I-37), (1.4.I-31), (1.4.I-49), (1.4.I-61), (1.4.I-55), or (1.4.I-73), and at least three, preferably exactly three, herbicides B different from each other.

According to another preferred embodiment of the invention, the composition comprises as component A at least one, preferably exactly one pyrimidine compound of formula (I), preferably of formula (1.4), especially preferred the compound (1.4.I-25), (1.4.I-37), (1.4.I-31), (1.4.I-49), (1.4.I-61), (1.4.I-55), or (1.4.I-73), and as component C at least one, preferably exactly one, safener C.

According to another preferred embodiment of the invention, the composition comprises as component A at least one, preferably exactly one pyrimidine compound of formula (I), preferably of formula (1.4), especially preferred the compound (1.4.I-25), (1.4.I-37), (1.4.I-31), (1.4.I-49), (1.4.I-61), (1.4.I-55), or (1.4.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.4), especially preferred the compound (1.4.I-25), (1.4.I-37), (1.4.I-31), (1.4.I-49), (1.4.I-61), (1.4.I-55), or (1.4.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.4), especially preferred the compound (1.4.I-25), (1.4.I-37), (1.4.I-31), (1.4.I-49), (1.4.I-61), (1.4.I-55), or (1.4.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.5), especially preferred the compound (1.5.I-25), (1.5.I-37), (1.5.I-31), (1.5.I-49), (1.5.I-61), (1.5.I-55), or (1.5.I-73), and as component B at least one, preferably exactly one, herbicide B.

According to another preferred embodiment of the invention, the composition comprises as component A at least one, preferably exactly one pyrimidine compound of formula (I), preferably of formula (1.5), especially preferred the compound (1.5.I-25), (1.5.I-37), (1.5.I-31), (1.5.I-49), (1.5.I-61), (1.5.I-55), or (1.5.I-73), and at least two, preferably exactly two, herbicides B different from each other.

According to another preferred embodiment of the invention, the composition comprises as component A at least one, preferably exactly one pyrimidine compound of formula (I), preferably of formula (1.5), especially preferred the compound (1.5.I-25), (1.5.I-37), (1.5.I-31), (1.5.I-49), (1.5.I-61), (1.5.I-55), or (1.5.I-73), and at least three, preferably exactly three, herbicides B different from each other.

According to another preferred embodiment of the invention, the composition comprises as component A at least one, preferably exactly one pyrimidine compound of formula (I), preferably of formula (1.5), especially preferred the compound (1.5.I-25), (1.5.I-37), (1.5.I-31), (1.5.I-49), (1.5.I-61), (1.5.I-55), or (1.5.I-73), and as component C at least one, preferably exactly one, safener C.

According to another preferred embodiment of the invention, the composition comprises as component A at least one, preferably exactly one pyrimidine compound of formula (I), preferably of formula (1.5), especially preferred the compound (1.5.I-25), (1.5.I-37), (1.5.I-31), (1.5.I-49), (1.5.I-61), (1.5.I-55), or (1.5.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.5), especially preferred the compound (1.5.I-25), (1.5.I-37), (1.5.I-31), (1.5.I-49), (1.5.I-61), (1.5.I-55), or (1.5.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.5), especially preferred the compound (1.5.I-25), (1.5.I-37), (1.5.I-31), (1.5.I-49), (1.5.I-61), (1.5.I-55), or (1.5.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.6), especially preferred the compound (1.6.I-25), (1.6.I-37), (1.6.I-31), (1.6.I-49), (1.6.I-61), (1.6.I-55), or (1.6.I-73), and as component B at least one, preferably exactly one, herbicide B.

According to another preferred embodiment of the invention, the composition comprises as component A at least one, preferably exactly one pyrimidine compound of formula (I), preferably of formula (1.6), especially preferred the compound (1.6.I-25), (1.6.I-37), (1.6.I-31), (1.6.I-49), (1.6.I-61), (1.6.I-55), or (1.6.I-73), and at least two, preferably exactly two, herbicides B different from each other.

According to another preferred embodiment of the invention, the composition comprises as component A at least one, preferably exactly one pyrimidine compound of formula (I), preferably of formula (1.6), especially preferred the compound (1.6.I-25), (1.6.I-37), (1.6.I-31), (1.6.I-49), (1.6.I-61), (1.6.I-55), or (1.6.I-73), and at least three, preferably exactly three, herbicides B different from each other.

According to another preferred embodiment of the invention, the composition comprises as component A at least one, preferably exactly one pyrimidine compound of formula (I), preferably of formula (1.6), especially preferred the compound (1.6.I-25), (1.6.I-37), (1.6.I-31), (1.6.I-49), (1.6.I-61), (1.6.I-55), or (1.6.I-73), and as component C at least one, preferably exactly one, safener C.

According to another preferred embodiment of the invention, the composition comprises as component A at least one, preferably exactly one pyrimidine compound of formula (I), preferably of formula (1.6), especially preferred the compound (1.6.I-25), (1.6.I-37), (1.6.I-31), (1.6.I-49), (1.6.I-61), (1.6.I-55), or (1.6.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.6), especially preferred the compound (1.6.I-25), (1.6.I-37), (1.6.I-31), (1.6.I-49), (1.6.I-61), (1.6.I-55), or (1.6.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.6), especially preferred the compound (1.6.I-25), (1.6.I-37), (1.6.I-31), (1.6.I-49), (1.6.I-61), (1.6.I-55), or (1.6.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.7), especially preferred the compound (1.7.I-25), (1.7.I-37), (1.7.I-31), (1.7.I-49), (1.7.I-61), (1.7.I-55), or (1.7.I-73), and as component B at least one, preferably exactly one, herbicide B.

According to another preferred embodiment of the invention, the composition comprises as component A at least one, preferably exactly one pyrimidine compound of formula (I), preferably of formula (1.7), especially preferred the compound (1.7.I-25), (1.7.I-37), (1.7.I-31), (1.7.I-49), (1.7.I-61), (1.7.I-55), or (1.7.I-73), and at least two, preferably exactly two, herbicides B different from each other.

According to another preferred embodiment of the invention, the composition comprises as component A at least one, preferably exactly one pyrimidine compound of formula (I), preferably of formula (1.7), especially preferred the compound (1.7.I-25), (1.7.I-37), (1.7.I-31), (1.7.I-49), (1.7.I-61), (1.7.I-55), or (1.7.I-73), and at least three, preferably exactly three, herbicides B different from each other.

According to another preferred embodiment of the invention, the composition comprises as component A at least one, preferably exactly one pyrimidine compound of formula (I), preferably of formula (1.7), especially preferred the compound (1.7.I-25), (1.7.I-37), (1.7.I-31), (1.7.I-49), (1.7.I-61), (1.7.I-55), or (1.7.I-73), and as component C at least one, preferably exactly one, safener C.

According to another preferred embodiment of the invention, the composition comprises as component A at least one, preferably exactly one pyrimidine compound of formula (I), preferably of formula (1.7), especially preferred the compound (1.7.I-25), (1.7.I-37), (1.7.I-31), (1.7.I-49), (1.7.I-61), (1.7.I-55), or (1.7.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.7), especially preferred the compound (1.7.I-25), (1.7.I-37), (1.7.I-31), (1.7.I-49), (1.7.I-61), (1.7.I-55), or (1.7.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.7), especially preferred the compound (1.7.I-25), (1.7.I-37), (1.7.I-31), (1.7.I-49), (1.7.I-61), (1.7.I-55), or (1.7.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.8), especially preferred the compound (1.8.I-25), (1.8.I-37), (1.8.I-31), (1.8.I-49), (1.8.I-61), (1.8.I-55), or (1.8.I-73), and as component B at least one, preferably exactly one, herbicide B.

According to another preferred embodiment of the invention, the composition comprises as component A at least one, preferably exactly one pyrimidine compound of formula (I), preferably of formula (1.8), especially preferred the compound (1.8.I-25), (1.8.I-37), (1.8.I-31), (1.8.I-49), (1.8.I-61), (1.8.I-55), or (1.8.I-73), and at least two, preferably exactly two, herbicides B different from each other.

According to another preferred embodiment of the invention, the composition comprises as component A at least one, preferably exactly one pyrimidine compound of formula (I), preferably of formula (1.8), especially preferred the compound (1.8.I-25), (1.8.I-37), (1.8.I-31), (1.8.I-49), (1.8.I-61), (1.8.I-55), or (1.8.I-73), and at least three, preferably exactly three, herbicides B different from each other.

According to another preferred embodiment of the invention, the composition comprises as component A at least one, preferably exactly one pyrimidine compound of formula (I), preferably of formula (1.8), especially preferred the compound (1.8.I-25), (1.8.I-37), (1.8.I-31), (1.8.I-49), (1.8.I-61), (1.8.I-55), or (1.8.I-73), and as component C at least one, preferably exactly one, safener C.

According to another preferred embodiment of the invention, the composition comprises as component A at least one, preferably exactly one pyrimidine compound of formula (I), preferably of formula (1.8), especially preferred the compound (1.8.I-25), (1.8.I-37), (1.8.I-31), (1.8.I-49), (1.8.I-61), (1.8.I-55), or (1.8.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.8), especially preferred the compound (1.8.I-25), (1.8.I-37), (1.8.I-31), (1.8.I-49), (1.8.I-61), (1.8.I-55), or (1.8.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.8), especially preferred the compound (1.8.I-25), (1.8.I-37), (1.8.I-31), (1.8.I-49), (1.8.I-61), (1.8.I-55), or (1.8.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.9), especially preferred the compound (1.9.I-25), (1.9.I-37), (1.9.I-31), (1.9.I-49), (1.9.I-61), (1.9.I-55), or (1.9.I-73), and as component B at least one, preferably exactly one, herbicide B.

According to another preferred embodiment of the invention, the composition comprises as component A at least one, preferably exactly one pyrimidine compound of formula (I), preferably of formula (1.9), especially preferred the compound (1.9.I-25), (1.9.I-37), (1.9.I-31), (1.9.I-49), (1.9.I-61), (1.9.I-55), or (1.9.I-73), and at least two, preferably exactly two, herbicides B different from each other.

According to another preferred embodiment of the invention, the composition comprises as component A at least one, preferably exactly one pyrimidine compound of formula (I), preferably of formula (1.9), especially preferred the compound (1.9.I-25), (1.9.I-37), (1.9.I-31), (1.9.I-49), (1.9.I-61), (1.9.I-55), or (1.9.I-73), and at least three, preferably exactly three, herbicides B different from each other.

According to another preferred embodiment of the invention, the composition comprises as component A at least one, preferably exactly one pyrimidine compound of formula (I), preferably of formula (1.9), especially preferred the compound (1.9.I-25), (1.9.I-37), (1.9.I-31), (1.9.I-49), (1.9.I-61), (1.9.I-55), or (1.9.I-73), and as component C at least one, preferably exactly one, safener C.

According to another preferred embodiment of the invention, the composition comprises as component A at least one, preferably exactly one pyrimidine compound of formula (I), preferably of formula (1.9), especially preferred the compound (1.9.I-25), (1.9.I-37), (1.9.I-31), (1.9.I-49), (1.9.I-61), (1.9.I-55), or (1.9.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.9), especially preferred the compound (1.9.I-25), (1.9.I-37), (1.9.I-31), (1.9.I-49), (1.9.I-61), (1.9.I-55), or (1.9.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.9), especially preferred the compound (1.9.I-25), (1.9.I-37), (1.9.I-31), (1.9.I-49), (1.9.I-61), (1.9.I-55), or (1.9.I-73), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.10), especially preferred the compound (1.10.I-25), (1.10.I-37), (1.10.I-31), (1.10.I-49), (1.10.I-61), (1.10.I-55), or (1.10.I-73), and as component B at least one, preferably exactly one, herbicide B.

According to another preferred embodiment of the invention, the composition comprises as component A at least one, preferably exactly one pyrimidine compound of formula (I), preferably of formula (1.10), especially preferred the compound (1.10.I-25), (1.10.I-37), (1.10.I-31), (1.10.I-49), (1.10.I-61), (1.10.I-55), or (1.10.I-73), and at least two, preferably exactly two, herbicides B different from each other.

According to another preferred embodiment of the invention, the composition comprises as component A at least one, preferably exactly one pyrimidine compound of formula (I), preferably of formula (1.10), especially preferred the compound (1.10.I-25), (1.10.I-37), (1.10.I-31), (1.10.I-49), (1.10.I-61), (1.10.I-55), or (1.10.I-73), and at least three, preferably exactly three, herbicides B different from each other.

According to another preferred embodiment of the invention, the composition comprises as component A at least one, preferably exactly one pyrimidine compound of formula (I), preferably of formula (1.10), especially preferred the compound (1.10.I-25), (1.10.I-37), (1.10.I-31), (1.10.I-49), (1.10.I-61), (1.10.I-55), or (1.10.I-73), and as component C at least one, preferably exactly one, safener C.

According to another preferred embodiment of the invention, the composition comprises as component A at least one, preferably exactly one pyrimidine compound of formula (I), preferably of formula (1.10), especially preferred the compound (1.10.I-25), (1.10.I-37), (1.10.I-31), (1.10.I-49), (1.10.I-61), (1.10.I-55), or (1.10.I-73), as component B at least one, preferably exactly one, herbicide B, and as component C at least one, preferably exactly one safener C.

According to another preferred embodiment of the invention, the composition comprises as component A at least one, preferably exactly pyrimidine compound of formula (I), preferably of formula (1.10), especially preferred the compound (1.10.I-25), (1.10.I-37), (1.10.I-31), (1.10.I-49), (1.10.I-61), (1.10.I-55), or (1.10.I-73), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.10), especially preferred the compound (1.10.I-25), (1.10.I-37), (1.10.I-31), (1.10.I-49), (1.10.I-61), (1.10.I-55), or (1.10.I-73), at least three, preferably exactly three herbicides B different from each other, and as component C at least one, preferably exactly one, safener C.

According to another preferred embodiment of the invention, the composition comprises as component A at least one, preferably exactly one compound of formula (I), preferably of formula (1.31), especially preferred the compound (1.31.I-25), (1.31.I-31), (1.31.I-37), (1.31.I-49), (1.31.I-55), or (1.31.I-61), and as component B at least one, preferably exactly one, herbicide B.

According to another preferred embodiment of the invention, the composition comprises as component A at least one, preferably exactly one compound of formula (I), preferably of formula (1.31), especially preferred the compound (1.31.I-25), (1.31.I-31), (1.31.I-37), (1.31.I-49), (1.31.I-55), or (1.31.I-61), and at least two, preferably exactly two, herbicides B different from each other.

According to another preferred embodiment of the invention, the composition comprises as component A at least one, preferably exactly one pyrimidine compound of formula (I), preferably of formula (1.31), especially preferred the compound (1.31.I-25), (1.31.I-31), (1.31.I-37), (1.31.I-49), (1.31.I-55), or (1.31.I-61), and at least three, preferably exactly three, herbicides B different from each other.

According to another preferred embodiment of the invention, the composition comprises as component A at least one, preferably exactly one pyrimidine compound of formula (I), preferably of formula (1.31), especially preferred the compound (1.31.I-25), (1.31.I-31), (1.31.I-37), (1.31.I-49), (1.31.I-55), or (1.31.I-61), and as component C at least one, preferably exactly one, safener C.

According to another preferred embodiment of the invention, the composition comprises as component A at least one, preferably exactly one pyrimidine compound of formula (I), preferably of formula (1.31), especially preferred the compound (1.31.I-25), (1.31.I-31), (1.31.I-37), (1.31.I-49), (1.31.I-55), or (1.31.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.31), especially preferred the compound (1.31.I-25), (1.31.I-31), (1.31.I-37), (1.31.I-49), (1.31.I-55), or (1.31.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.31), especially preferred the compound (1.31.I-25), (1.31.I-31), (1.31.I-37), (1.31.I-49), (1.31.I-55), or (1.31.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.37), especially preferred the compound (1.37.I-25), (1.37.I-31), (1.37.I-37), (1.37.I-49), (1.37.I-55), or (1.37.I-61), and as component B at least one, preferably exactly one, herbicide B.

According to another preferred embodiment of the invention, the composition comprises as component A at least one, preferably exactly one pyrimidine compound of formula (I), preferably of formula (1.37), especially preferred the compound (1.37.I-25), (1.37.I-31), (1.37.I-37), (1.37.I-49), (1.37.I-55), or (1.37.I-61), and at least two, preferably exactly two, herbicides B different from each other.

According to another preferred embodiment of the invention, the composition comprises as component A at least one, preferably exactly one pyrimidine compound of formula (I), preferably of formula (1.37), especially preferred the compound (1.37.I-25), (1.37.I-31), (1.37.I-37), (1.37.I-49), (1.37.I-55), or (1.37.I-61), and at least three, preferably exactly three, herbicides B different from each other.

According to another preferred embodiment of the invention, the composition comprises as component A at least one, preferably exactly one pyrimidine compound of formula (I), preferably of formula (1.37), especially preferred the compound (1.37.I-25), (1.37.I-31), (1.37.I-37), (1.37.I-49), (1.37.I-55), or (1.37.I-61), and as component C at least one, preferably exactly one, safener C.

According to another preferred embodiment of the invention, the composition comprises as component A at least one, preferably exactly one pyrimidine compound of formula (I), preferably of formula (1.37), especially preferred the compound (1.37.I-25), (1.37.I-31), (1.37.I-37), (1.37.I-49), (1.37.I-55), or (1.37.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.37), especially preferred the compound (1.37.I-25), (1.37.I-31), (1.37.I-37), (1.37.I-49), (1.37.I-55), or (1.37.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.37), especially preferred the compound (1.37.I-25), (1.37.I-31), (1.37.I-37), (1.37.I-49), (1.37.I-55), or (1.37.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.38), especially preferred the compound (1.38.I-25), (1.38.I-31), (1.38.I-37), (1.38.I-49), (1.38.I-55), or (1.38.I-61), and as component B at least one, preferably exactly one, herbicide B.

According to another preferred embodiment of the invention, the composition comprises as component A at least one, preferably exactly one pyrimidine compound of formula (I), preferably of formula (1.38), especially preferred the compound (1.38.I-25), (1.38.I-31), (1.38.I-37), (1.38.I-49), (1.38.I-55), or (1.38.I-61), and at least two, preferably exactly two, herbicides B different from each other.

According to another preferred embodiment of the invention, the composition comprises as component A at least one, preferably exactly one pyrimidine compound of formula (I), preferably of formula (1.38), especially preferred the compound (1.38.I-25), (1.38.I-31), (1.38.I-37), (1.38.I-49), (1.38.I-55), or (1.38.I-61), and at least three, preferably exactly three, herbicides B different from each other.

According to another preferred embodiment of the invention, the composition comprises as component A at least one, preferably exactly one pyrimidine compound of formula (I), preferably of formula (1.38), especially preferred the compound (1.38.I-25), (1.38.I-31), (1.38.I-37), (1.38.I-49), (1.38.I-55), or (1.38.I-61), and as component C at least one, preferably exactly one, safener C.

According to another preferred embodiment of the invention, the composition comprises as component A at least one, preferably exactly one pyrimidine compound of formula (I), preferably of formula (1.38), especially preferred the compound (1.38.I-25), (1.38.I-31), (1.38.I-37), (1.38.I-49), (1.38.I-55), or (1.38.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.38), especially preferred the compound (1.38.I-25), (1.38.I-31), (1.38.I-37), (1.38.I-49), (1.38.I-55), or (1.38.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.38), especially preferred the compound (1.38.I-25), (1.38.I-31), (1.38.I-37), (1.38.I-49), (1.38.I-55), or (1.38.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.39), especially preferred the compound (1.39.I-25), (1.39.I-31), (1.39.I-37), (1.39.I-49), (1.39.I-55), or (1.39.I-61), and as component B at least one, preferably exactly one, herbicide B.

According to another preferred embodiment of the invention, the composition comprises as component A at least one, preferably exactly one pyrimidine compound of formula (I), preferably of formula (1.39), especially preferred the compound (1.39.I-25), (1.39.I-31), (1.39.I-37), (1.39.I-49), (1.39.I-55), or (1.39.I-61), and at least two, preferably exactly two, herbicides B different from each other.

According to another preferred embodiment of the invention, the composition comprises as component A at least one, preferably exactly one pyrimidine compound of formula (I), preferably of formula (1.39), especially preferred the compound (1.39.I-25), (1.39.I-31), (1.39.I-37), (1.39.I-49), (1.39.I-55), or (1.39.I-61), and at least three, preferably exactly three, herbicides B different from each other.

According to another preferred embodiment of the invention, the composition comprises as component A at least one, preferably exactly one pyrimidine compound of formula (I), preferably of formula (1.39), especially preferred the compound (1.39.I-25), (1.39.I-31), (1.39.I-37), (1.39.I-49), (1.39.I-55), or (1.39.I-61), and as component C at least one, preferably exactly one, safener C.

According to another preferred embodiment of the invention, the composition comprises as component A at least one, preferably exactly one pyrimidine compound of formula (I), preferably of formula (1.39), especially preferred the compound (1.39.I-25), (1.39.I-31), (1.39.I-37), (1.39.I-49), (1.39.I-55), or (1.39.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.39), especially preferred the compound (1.39.I-25), (1.39.I-31), (1.39.I-37), (1.39.I-49), (1.39.I-55), or (1.39.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.39), especially preferred the compound (1.39.I-25), (1.39.I-31), (1.39.I-37), (1.39.I-49), (1.39.I-55), or (1.39.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.46), especially preferred the compound (1.46.I-25), (1.46.I-31), (1.46.I-37), (1.46.I-49), (1.46.I-55), or (1.46.I-61), and as component B at least one, preferably exactly one, herbicide B.

According to another preferred embodiment of the invention, the composition comprises as component A at least one, preferably exactly one pyrimidine compound of formula (I), preferably of formula (1.46), especially preferred the compound (1.46.I-25), (1.46.I-31), (1.46.I-37), (1.46.I-49), (1.46.I-55), or (1.46.I-61), and at least two, preferably exactly two, herbicides B different from each other.

According to another preferred embodiment of the invention, the composition comprises as component A at least one, preferably exactly one pyrimidine compound of formula (I), preferably of formula (1.46), especially preferred the compound (1.46.I-25), (1.46.I-31), (1.46.I-37), (1.46.I-49), (1.46.I-55), or (1.46.I-61), and at least three, preferably exactly three, herbicides B different from each other.

According to another preferred embodiment of the invention, the composition comprises as component A at least one, preferably exactly one pyrimidine compound of formula (I), preferably of formula (1.46), especially preferred the compound (1.46.I-25), (1.46.I-31), (1.46.I-37), (1.46.I-49), (1.46.I-55), or (1.46.I-61), and as component C at least one, preferably exactly one, safener C.

According to another preferred embodiment of the invention, the composition comprises as component A at least one, preferably exactly one pyrimidine compound of formula (I), preferably of formula (1.46), especially preferred the compound (1.46.I-25), (1.46.I-31), (1.46.I-37), (1.46.I-49), (1.46.I-55), or (1.46.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.46), especially preferred the compound (1.46.I-25), (1.46.I-31), (1.46.I-37), (1.46.I-49), (1.46.I-55), or (1.46.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.46), especially preferred the compound (1.46.I-25), (1.46.I-31), (1.46.I-37), (1.46.I-49), (1.46.I-55), or (1.46.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.47), especially preferred the compound (1.47.I-25), (1.47.I-31), (1.47.I-37), (1.47.I-49), (1.47.I-55), or (1.47.I-61), and as component B at least one, preferably exactly one, herbicide B.

According to another preferred embodiment of the invention, the composition comprises as component A at least one, preferably exactly one pyrimidine compound of formula (I), preferably of formula (1.47), especially preferred the compound (1.47.I-25), (1.47.I-31), (1.47.I-37), (1.47.I-49), (1.47.I-55), or (1.47.I-61), and at least two, preferably exactly two, herbicides B different from each other.

According to another preferred embodiment of the invention, the composition comprises as component A at least one, preferably exactly one pyrimidine compound of formula (I), preferably of formula (1.47), especially preferred the compound (1.47.I-25), (1.47.I-31), (1.47.I-37), (1.47.I-49), (1.47.I-55), or (1.47.I-61), and at least three, preferably exactly three, herbicides B different from each other.

According to another preferred embodiment of the invention, the composition comprises as component A at least one, preferably exactly one pyrimidine compound of formula (I), preferably of formula (1.47), especially preferred the compound (1.47.I-25), (1.47.I-31), (1.47.I-37), (1.47.I-49), (1.47.I-55), or (1.47.I-61), and as component C at least one, preferably exactly one, safener C.

According to another preferred embodiment of the invention, the composition comprises as component A at least one, preferably exactly one pyrimidine compound of formula (I), preferably of formula (1.47), especially preferred the compound (1.47.I-25), (1.47.I-31), (1.47.I-37), (1.47.I-49), (1.47.I-55), or (1.47.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.47), especially preferred the compound (1.47.I-25), (1.47.I-31), (1.47.I-37), (1.47.I-49), (1.47.I-55), or (1.47.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.47), especially preferred the compound (1.47.I-25), (1.47.I-31), (1.47.I-37), (1.47.I-49), (1.47.I-55), or (1.47.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.53), especially preferred the compound (1.53.I-25), (1.53.I-31), (1.53.I-37), (1.53.I-49), (1.53.I-55), or (1.53.I-61), and as component B at least one, preferably exactly one, herbicide B.

According to another preferred embodiment of the invention, the composition comprises as component A at least one, preferably exactly one pyrimidine compound of formula (I), preferably of formula (1.53), especially preferred the compound (1.53.I-25), (1.53.I-31), (1.53.I-37), (1.53.I-49), (1.53.I-55), or (1.53.I-61), and at least two, preferably exactly two, herbicides B different from each other.

According to another preferred embodiment of the invention, the composition comprises as component A at least one, preferably exactly one pyrimidine compound of formula (I), preferably of formula (1.53), especially preferred the compound (1.53.I-25), (1.53.I-31), (1.53.I-37), (1.53.I-49), (1.53.I-55), or (1.53.I-61), and at least three, preferably exactly three, herbicides B different from each other.

According to another preferred embodiment of the invention, the composition comprises as component A at least one, preferably exactly one pyrimidine compound of formula (I), preferably of formula (1.53), especially preferred the compound (1.53.I-25), (1.53.I-31), (1.53.I-37), (1.53.I-49), (1.53.I-55), or (1.53.I-61), and as component C at least one, preferably exactly one, safener C.

According to another preferred embodiment of the invention, the composition comprises as component A at least one, preferably exactly one pyrimidine compound of formula (I), preferably of formula (1.53), especially preferred the compound (1.53.I-25), (1.53.I-31), (1.53.I-37), (1.53.I-49), (1.53.I-55), or (1.53.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.53), especially preferred the compound (1.53.I-25), (1.53.I-31), (1.53.I-37), (1.53.I-49), (1.53.I-55), or (1.53.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.53), especially preferred the compound (1.53.I-25), (1.53.I-31), (1.53.I-37), (1.53.I-49), (1.53.I-55), or (1.53.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.59), especially preferred the compound (1.59.I-25), (1.59.I-31), (1.59.I-37), (1.59.I-49), (1.59.I-55), or (1.59.I-61), and as component B at least one, preferably exactly one, herbicide B.

According to another preferred embodiment of the invention, the composition comprises as component A at least one, preferably exactly one pyrimidine compound of formula (I), preferably of formula (1.59), especially preferred the compound (1.59.I-25), (1.59.I-31), (1.59.I-37), (1.59.I-49), (1.59.I-55), or (1.59.I-61), and at least two, preferably exactly two, herbicides B different from each other.

According to another preferred embodiment of the invention, the composition comprises as component A at least one, preferably exactly one pyrimidine compound of formula (I), preferably of formula (1.59), especially preferred the compound (1.59.I-25), (1.59.I-31), (1.59.I-37), (1.59.I-49), (1.59.I-55), or (1.59.I-61), and at least three, preferably exactly three, herbicides B different from each other.

According to another preferred embodiment of the invention, the composition comprises as component A at least one, preferably exactly one pyrimidine compound of formula (I), preferably of formula (1.59), especially preferred the compound (1.59.I-25), (1.59.I-31), (1.59.I-37), (1.59.I-49), (1.59.I-55), or (1.59.I-61), and as component C at least one, preferably exactly one, safener C.

According to another preferred embodiment of the invention, the composition comprises as component A at least one, preferably exactly one pyrimidine compound of formula (I), preferably of formula (1.59), especially preferred the compound (1.59.I-25), (1.59.I-31), (1.59.I-37), (1.59.I-49), (1.59.I-55), or (1.59.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.59), especially preferred the compound (1.59.I-25), (1.59.I-31), (1.59.I-37), (1.59.I-49), (1.59.I-55), or (1.59.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.59), especially preferred the compound (1.59.I-25), (1.59.I-31), (1.59.I-37), (1.59.I-49), (1.59.I-55), or (1.59.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.63), especially preferred the compound (1.63.I-25), (1.63.I-31), (1.63.I-37), (1.63.I-49), (1.63.I-55), or (1.63.I-61), and as component B at least one, preferably exactly one, herbicide B.

According to another preferred embodiment of the invention, the composition comprises as component A at least one, preferably exactly one pyrimidine compound of formula (I), preferably of formula (1.63), especially preferred the compound (1.63.I-25), (1.63.I-31), (1.63.I-37), (1.63.I-49), (1.63.I-55), or (1.63.I-61), and at least two, preferably exactly two, herbicides B different from each other.

According to another preferred embodiment of the invention, the composition comprises as component A at least one, preferably exactly one pyrimidine compound of formula (I), preferably of formula (1.63), especially preferred the compound (1.63.I-25), (1.63.I-31), (1.63.I-37), (1.63.I-49), (1.63.I-55), or (1.63.I-61), and at least three, preferably exactly three, herbicides B different from each other.

According to another preferred embodiment of the invention, the composition comprises as component A at least one, preferably exactly one pyrimidine compound of formula (I), preferably of formula (1.63), especially preferred the compound (1.63.I-25), (1.63.I-31), (1.63.I-37), (1.63.I-49), (1.63.I-55), or (1.63.I-61), and as component C at least one, preferably exactly one, safener C.

According to another preferred embodiment of the invention, the composition comprises as component A at least one, preferably exactly one pyrimidine compound of formula (I), preferably of formula (1.63), especially preferred the compound (1.63.I-25), (1.63.I-31), (1.63.I-37), (1.63.I-49), (1.63.I-55), or (1.63.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.63), especially preferred the compound (1.63.I-25), (1.63.I-31), (1.63.I-37), (1.63.I-49), (1.63.I-55), or (1.63.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.63), especially preferred the compound (1.63.I-25), (1.63.I-31), (1.63.I-37), (1.63.I-49), (1.63.I-55), or (1.63.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.64), especially preferred the compound (1.64.I-25), (1.64.I-31), (1.64.I-37), (1.64.I-49), (1.64.I-55), or (1.64.I-61), and as component B at least one, preferably exactly one, herbicide B.

According to another preferred embodiment of the invention, the composition comprises as component A at least one, preferably exactly one pyrimidine compound of formula (I), preferably of formula (1.64), especially preferred the compound (1.64.I-25), (1.64.I-31), (1.64.I-37), (1.64.I-49), (1.64.I-55), or (1.64.I-61), and at least two, preferably exactly two, herbicides B different from each other.

According to another preferred embodiment of the invention, the composition comprises as component A at least one, preferably exactly one pyrimidine compound of formula (I), preferably of formula (1.64), especially preferred the compound (1.64.I-25), (1.64.I-31), (1.64.I-37), (1.64.I-49), (1.64.I-55), or (1.64.I-61), and at least three, preferably exactly three, herbicides B different from each other.

According to another preferred embodiment of the invention, the composition comprises as component A at least one, preferably exactly one pyrimidine compound of formula (I), preferably of formula (1.64), especially preferred the compound (1.64.I-25), (1.64.I-31), (1.64.I-37), (1.64.I-49), (1.64.I-55), or (1.64.I-61), and as component C at least one, preferably exactly one, safener C.

According to another preferred embodiment of the invention, the composition comprises as component A at least one, preferably exactly one pyrimidine compound of formula (I), preferably of formula (1.64), especially preferred the compound (1.64.I-25), (1.64.I-31), (1.64.I-37), (1.64.I-49), (1.64.I-55), or (1.64.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.64), especially preferred the compound (1.64.I-25), (1.64.I-31), (1.64.I-37), (1.64.I-49), (1.64.I-55), or (1.64.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.64), especially preferred the compound (1.64.I-25), (1.64.I-31), (1.64.I-37), (1.64.I-49), (1.64.I-55), or (1.64.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.65), especially preferred the compound (1.65.I-25), (1.65.I-31), (1.65.I-37), (1.65.I-49), (1.65.I-55), or (1.65.I-61), and as component B at least one, preferably exactly one, herbicide B.

According to another preferred embodiment of the invention, the composition comprises as component A at least one, preferably exactly one pyrimidine compound of formula (I), preferably of formula (1.65), especially preferred the compound (1.65.I-25), (1.65.I-31), (1.65.I-37), (1.65.I-49), (1.65.I-55), or (1.65.I-61), and at least two, preferably exactly two, herbicides B different from each other.

According to another preferred embodiment of the invention, the composition comprises as component A at least one, preferably exactly one pyrimidine compound of formula (I), preferably of formula (1.65), especially preferred the compound (1.65.I-25), (1.65.I-31), (1.65.I-37), (1.65.I-49), (1.65.I-55), or (1.65.I-61), and at least three, preferably exactly three, herbicides B different from each other.

According to another preferred embodiment of the invention, the composition comprises as component A at least one, preferably exactly one pyrimidine compound of formula (I), preferably of formula (1.65), especially preferred the compound (1.65.I-25), (1.65.I-31), (1.65.I-37), (1.65.I-49), (1.65.I-55), or (1.65.I-61), and as component C at least one, preferably exactly one, safener C.

According to another preferred embodiment of the invention, the composition comprises as component A at least one, preferably exactly one pyrimidine compound of formula (I), preferably of formula (1.65), especially preferred the compound (1.65.I-25), (1.65.I-31), (1.65.I-37), (1.65.I-49), (1.65.I-55), or (1.65.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.65), especially preferred the compound (1.65.I-25), (1.65.I-31), (1.65.I-37), (1.65.I-49), (1.65.I-55), or (1.65.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.65), especially preferred the compound (1.65.I-25), (1.65.I-31), (1.65.I-37), (1.65.I-49), (1.65.I-55), or (1.65.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.72), especially preferred the compound (1.72.I-25), (1.72.I-31), (1.72.I-37), (1.72.I-49), (1.72.I-55), or (1.72.I-61), and as component B at least one, preferably exactly one, herbicide B.

According to another preferred embodiment of the invention, the composition comprises as component A at least one, preferably exactly one pyrimidine compound of formula (I), preferably of formula (1.72), especially preferred the compound (1.72.I-25), (1.72.I-31), (1.72.I-37), (1.72.I-49), (1.72.I-55), or (1.72.I-61), and at least two, preferably exactly two, herbicides B different from each other.

According to another preferred embodiment of the invention, the composition comprises as component A at least one, preferably exactly one pyrimidine compound of formula (I), preferably of formula (1.72), especially preferred the compound (1.72.I-25), (1.72.I-31), (1.72.I-37), (1.72.I-49), (1.72.I-55), or (1.72.I-61), and at least three, preferably exactly three, herbicides B different from each other.

According to another preferred embodiment of the invention, the composition comprises as component A at least one, preferably exactly one pyrimidine compound of formula (I), preferably of formula (1.72), especially preferred the compound (1.72.I-25), (1.72.I-31), (1.72.I-37), (1.72.I-49), (1.72.I-55), or (1.72.I-61), and as component C at least one, preferably exactly one, safener C.

According to another preferred embodiment of the invention, the composition comprises as component A at least one, preferably exactly one pyrimidine compound of formula (I), preferably of formula (1.72), especially preferred the compound (1.72.I-25), (1.72.I-31), (1.72.I-37), (1.72.I-49), (1.72.I-55), or (1.72.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.72), especially preferred the compound (1.72.I-25), (1.72.I-31), (1.72.I-37), (1.72.I-49), (1.72.I-55), or (1.72.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.72), especially preferred the compound (1.72.I-25), (1.72.I-31), (1.72.I-37), (1.72.I-49), (1.72.I-55), or (1.72.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.73), especially preferred the compound (1.73.I-25), (1.73.I-31), (1.73.I-37), (1.73.I-49), (1.73.I-55), or (1.73.I-61), and as component B at least one, preferably exactly one, herbicide B.

According to another preferred embodiment of the invention, the composition comprises as component A at least one, preferably exactly one pyrimidine compound of formula (I), preferably of formula (1.73), especially preferred the compound (1.73.I-25), (1.73.I-31), (1.73.I-37), (1.73.I-49), (1.73.I-55), or (1.73.I-61), and at least two, preferably exactly two, herbicides B different from each other.

According to another preferred embodiment of the invention, the composition comprises as component A at least one, preferably exactly one pyrimidine compound of formula (I), preferably of formula (1.73), especially preferred the compound (1.73.I-25), (1.73.I-31), (1.73.I-37), (1.73.I-49), (1.73.I-55), or (1.73.I-61), and at least three, preferably exactly three, herbicides B different from each other.

According to another preferred embodiment of the invention, the composition comprises as component A at least one, preferably exactly one pyrimidine compound of formula (I), preferably of formula (1.73), especially preferred the compound (1.73.I-25), (1.73.I-31), (1.73.I-37), (1.73.I-49), (1.73.I-55), or (1.73.I-61), and as component C at least one, preferably exactly one, safener C.

According to another preferred embodiment of the invention, the composition comprises as component A at least one, preferably exactly one pyrimidine compound of formula (I), preferably of formula (1.73), especially preferred the compound (1.73.I-25), (1.73.I-31), (1.73.I-37), (1.73.I-49), (1.73.I-55), or (1.73.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.73), especially preferred the compound (1.73.I-25), (1.73.I-31), (1.73.I-37), (1.73.I-49), (1.73.I-55), or (1.73.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.73), especially preferred the compound (1.73.I-25), (1.73.I-31), (1.73.I-37), (1.73.I-49), (1.73.I-55), or (1.73.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.79), especially preferred the compound (1.79.I-25), (1.79.I-37), (1.79.I-49), (1.79.I-31), (1.79.I-55), or (1.79.I-61), and as component B at least one, preferably exactly one, herbicide B.

According to another preferred embodiment of the invention, the composition comprises as component A at least one, preferably exactly one pyrimidine compound of formula (I), preferably of formula (1.79), especially preferred the compound (1.79.I-25), (1.79.I-37), (1.79.I-49), (1.79.I-31), (1.79.I-55), or (1.79.I-61), and at least two, preferably exactly two, herbicides B different from each other.

According to another preferred embodiment of the invention, the composition comprises as component A at least one, preferably exactly one pyrimidine compound of formula (I), preferably of formula (1.79), especially preferred the compound (1.79.I-25), (1.79.I-37), (1.79.I-49), (1.79.I-31), (1.79.I-55), or (1.79.I-61), and at least three, preferably exactly three, herbicides B different from each other.

According to another preferred embodiment of the invention, the composition comprises as component A at least one, preferably exactly one pyrimidine compound of formula (I), preferably of formula (1.79), especially preferred the compound (1.79.I-25), (1.79.I-37), (1.79.I-49), (1.79.I-31), (1.79.I-55), or (1.79.I-61), and as component C at least one, preferably exactly one, safener C.

According to another preferred embodiment of the invention, the composition comprises as component A at least one, preferably exactly one pyrimidine compound of formula (I), preferably of formula (1.79), especially preferred the compound (1.79.I-25), (1.79.I-37), (1.79.I-49), (1.79.I-31), (1.79.I-55), or (1.79.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.79), especially preferred the compound (1.79.I-25), (1.79.I-37), (1.79.I-49), (1.79.I-31), (1.79.I-55), or (1.79.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.79), especially preferred the compound (1.79.I-25), (1.79.I-37), (1.79.I-49), (1.79.I-31), (1.79.I-55), or (1.79.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.272), especially preferred the compound (1.272.I-25), (1.272.I-31), (1.272.I-37), (1.272.I-49), (1.272.I-55), or (1.272.I-61), and as component B at least one, preferably exactly one, herbicide B.

According to another preferred embodiment of the invention, the composition comprises as component A at least one, preferably exactly one pyrimidine compound of formula (I), preferably of formula (1.272), especially preferred the compound (1.272.I-25), (1.272.I-31), (1.272.I-37), (1.272.I-49), (1.272.I-55), or (1.272.I-61), and at least two, preferably exactly two, herbicides B different from each other.

According to another preferred embodiment of the invention, the composition comprises as component A at least one, preferably exactly one pyrimidine compound of formula (I), preferably of formula (1.272), especially preferred the compound (1.272.I-25), (1.272.I-31), (1.272.I-37), (1.272.I-49), (1.272.I-55), or (1.272.I-61), and at least three, preferably exactly three, herbicides B different from each other.

According to another preferred embodiment of the invention, the composition comprises as component A at least one, preferably exactly one pyrimidine compound of formula (I), preferably of formula (1.272), especially preferred the compound (1.272.I-25), (1.272.I-31), (1.272.I-37), (1.272.I-49), (1.272.I-55), or (1.272.I-61), and as component C at least one, preferably exactly one, safener C.

According to another preferred embodiment of the invention, the composition comprises as component A at least one, preferably exactly one pyrimidine compound of formula (I), preferably of formula (1.272), especially preferred the compound (1.272.I-25), (1.272.I-31), (1.272.I-37), (1.272.I-49), (1.272.I-55), or (1.272.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.272), especially preferred the compound (1.272.I-25), (1.272.I-31), (1.272.I-37), (1.272.I-49), (1.272.I-55), or (1.272.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.272), especially preferred the compound (1.272.I-25), (1.272.I-31), (1.272.I-37), (1.272.I-49), (1.272.I-55), or (1.272.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.273), especially preferred the compound (1.273.I-25), (1.273.I-31), (1.273.I-37), (1.273.I-49), (1.273.I-55), or (1.273.I-61), and as component B at least one, preferably exactly one, herbicide B.

According to another preferred embodiment of the invention, the composition comprises as component A at least one, preferably exactly one pyrimidine compound of formula (I), preferably of formula (1.273), especially preferred the compound (1.273.I-25), (1.273.I-31), (1.273.I-37), (1.273.I-49), (1.273.I-55), or (1.273.I-61), and at least two, preferably exactly two, herbicides B different from each other.

According to another preferred embodiment of the invention, the composition comprises as component A at least one, preferably exactly one pyrimidine compound of formula (I), preferably of formula (1.273), especially preferred the compound (1.273.I-25), (1.273.I-31), (1.273.I-37), (1.273.I-49), (1.273.I-55), or (1.273.I-61), and at least three, preferably exactly three, herbicides B different from each other.

According to another preferred embodiment of the invention, the composition comprises as component A at least one, preferably exactly one pyrimidine compound of formula (I), preferably of formula (1.273), especially preferred the compound (1.273.I-25), (1.273.I-31), (1.273.I-37), (1.273.I-49), (1.273.I-55), or (1.273.I-61), and as component C at least one, preferably exactly one, safener C.

According to another preferred embodiment of the invention, the composition comprises as component A at least one, preferably exactly one pyrimidine compound of formula (I), preferably of formula (1.273), especially preferred the compound (1.273.I-25), (1.273.I-31), (1.273.I-37), (1.273.I-49), (1.273.I-55), or (1.273.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.273), especially preferred the compound (1.273.I-25), (1.273.I-31), (1.273.I-37), (1.273.I-49), (1.273.I-55), or (1.273.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.273), especially preferred the compound (1.273.I-25), (1.273.I-31), (1.273.I-37), (1.273.I-49), (1.273.I-55), or (1.273.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.584), especially preferred the compound (1.584.I-25), (1.584.I-31), (1.584.I-37), (1.584.I-49), (1.584.I-55), or (1.584.I-61), and as component B at least one, preferably exactly one, herbicide B.

According to another preferred embodiment of the invention, the composition comprises as component A at least one, preferably exactly one pyrimidine compound of formula (I), preferably of formula (1.584), especially preferred the compound (1.584.I-25), (1.584.I-31), (1.584.I-37), (1.584.I-49), (1.584.I-55), or (1.584.I-61), and at least two, preferably exactly two, herbicides B different from each other.

According to another preferred embodiment of the invention, the composition comprises as component A at least one, preferably exactly one pyrimidine compound of formula (I), preferably of formula (1.584), especially preferred the compound (1.584.I-25), (1.584.I-31), (1.584.I-37), (1.584.I-49), (1.584.I-55), or (1.584.I-61), and at least three, preferably exactly three, herbicides B different from each other.

According to another preferred embodiment of the invention, the composition comprises as component A at least one, preferably exactly one pyrimidine compound of formula (I), preferably of formula (1.584), especially preferred the compound (1.584.I-25), (1.584.I-31), (1.584.I-37), (1.584.I-49), (1.584.I-55), or (1.584.I-61), and as component C at least one, preferably exactly one, safener C.

According to another preferred embodiment of the invention, the composition comprises as component A at least one, preferably exactly one pyrimidine compound of formula (I), preferably of formula (1.584), especially preferred the compound (1.584.I-25), (1.584.I-31), (1.584.I-37), (1.584.I-49), (1.584.I-55), or (1.584.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.584), especially preferred the compound (1.584.I-25), (1.584.I-31), (1.584.I-37), (1.584.I-49), (1.584.I-55), or (1.584.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.584), especially preferred the compound (1.584.I-25), (1.584.I-31), (1.584.I-37), (1.584.I-49), (1.584.I-55), or (1.584.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.585), especially preferred the compound (1.585.I-25), (1.585.I-31), (1.585.I-37), (1.585.I-49), (1.585.I-55), or (1.585.I-61), and as component B at least one, preferably exactly one, herbicide B.

According to another preferred embodiment of the invention, the composition comprises as component A at least one, preferably exactly one pyrimidine compound of formula (I), preferably of formula (1.585), especially preferred the compound (1.585.I-25), (1.585.I-31), (1.585.I-37), (1.585.I-49), (1.585.I-55), or (1.585.I-61), and at least two, preferably exactly two, herbicides B different from each other.

According to another preferred embodiment of the invention, the composition comprises as component A at least one, preferably exactly one pyrimidine compound of formula (I), preferably of formula (1.585), especially preferred the compound (1.585.I-25), (1.585.I-31), (1.585.I-37), (1.585.I-49), (1.585.I-55), or (1.585.I-61), and at least three, preferably exactly three, herbicides B different from each other.

According to another preferred embodiment of the invention, the composition comprises as component A at least one, preferably exactly one pyrimidine compound of formula (I), preferably of formula (1.585), especially preferred the compound (1.585.I-25), (1.585.I-31), (1.585.I-37), (1.585.I-49), (1.585.I-55), or (1.585.I-61), and as component C at least one, preferably exactly one, safener C.

According to another preferred embodiment of the invention, the composition comprises as component A at least one, preferably exactly one pyrimidine compound of formula (I), preferably of formula (1.585), especially preferred the compound (1.585.I-25), (1.585.I-31), (1.585.I-37), (1.585.I-49), (1.585.I-55), or (1.585.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.585), especially preferred the compound (1.585.I-25), (1.585.I-31), (1.585.I-37), (1.585.I-49), (1.585.I-55), or (1.585.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.585), especially preferred the compound (1.585.I-25), (1.585.I-31), (1.585.I-37), (1.585.I-49), (1.585.I-55), or (1.585.I-61), at least three, preferably exactly three herbicides B different from each other, and as component C at least one, preferably exactly one, safener C.

According to another preferred embodiment of the invention, the composition comprises as component A at least one, preferably exactly one pyrimidine compound of formula (I), preferably of formula (1.592), especially preferred the compound (1.592.I-25), (1.592.I-31), (1.592.I-37), (1.592.I-49), (1.592.I-55), or (1.592.I-61), and as component B at least one, preferably exactly one, herbicide B.

According to another preferred embodiment of the invention, the composition comprises as component A at least one, preferably exactly one pyrimidine compound of formula (I), preferably of formula (1.592), especially preferred the compound (1.592.I-25), (1.592.I-31), (1.592.I-37), (1.592.I-49), (1.592.I-55), or (1.592.I-61), and at least two, preferably exactly two, herbicides B different from each other.

According to another preferred embodiment of the invention, the composition comprises as component A at least one, preferably exactly one pyrimidine compound of formula (I), preferably of formula (1.592), especially preferred the compound (1.592.I-25), (1.592.I-31), (1.592.I-37), (1.592.I-49), (1.592.I-55), or (1.592.I-61), and at least three, preferably exactly three, herbicides B different from each other.

According to another preferred embodiment of the invention, the composition comprises as component A at least one, preferably exactly one pyrimidine compound of formula (I), preferably of formula (1.592), especially preferred the compound (1.592.I-25), (1.592.I-31), (1.592.I-37), (1.592.I-49), (1.592.I-55), or (1.592.I-61), and as component C at least one, preferably exactly one, safener C.

According to another preferred embodiment of the invention, the composition comprises as component A at least one, preferably exactly one pyrimidine compound of formula (I), preferably of formula (1.592), especially preferred the compound (1.592.I-25), (1.592.I-31), (1.592.I-37), (1.592.I-49), (1.592.I-55), or (1.592.I-61), and as component B at least one, preferably exactly one, herbicide B, and as component C at least one, preferably exactly one safener C.

According to another preferred embodiment of the invention, the composition comprises as component A at least one, preferably exactly one pyrimidine compound of formula (I), preferably of formula (1.592), especially preferred the compound (1.592.I-25), (1.592.I-31), (1.592.I-37), (1.592.I-49), (1.592.I-55), or (1.592.I-61), at least two, preferably exactly two herbicides B different from each other, and as component C at least one, preferably exactly one, safener C.

According to another preferred embodiment of the invention, the composition comprises as component A at least one, preferably exactly one pyrimidine compound of formula (I), preferably of formula (1.592), especially preferred the compound (1.592.I-25), (1.592.I-31), (1.592.I-37), (1.592.I-49), (1.592.I-55), or (1.592.I-61), at least three, preferably exactly three herbicides B different from each other, and as component C at least one, preferably exactly one, safener C.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b1), in particular selected from the group consisting of clethodim, clodinafop-propargyl, cycloxydim, cyhalofop-butyl, fenoxaprop-ethyl, fenoxaprop-P-ethyl, metamifop, pinoxaden, profoxydim, sethoxydim, tepraloxydim, tralkoxydim, esprocarb, ethofumesate, molinate, prosulfocarb, thiobencarb and triallate.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b2), in particular selected from the group consisting of bensulfuron-methyl, bispyribac-sodium, cloransulam-methyl, chlorsulfuron, clorimuron, cyclosulfamuron, diclosulam, florasulam, flumetsulam, flupyrsulfuron-methyl-sodium, foramsulfuron, imazamox, imazamox-ammonium, imazapic, imazapic-ammonium, imazapic-isopropylammonium, imazapyr, imazapyr-ammonium, imazethapyr-isopropylammonium, imazaquin, imazaquin-ammonium, imazethapyr, imazethapyrammonium, imazapyr-isopropylammonium, imazosulfuron, iodosulfuron-methyl-sodium, iofensulfuron, iofensulfuron-sodium, mesosulfuron-methyl, metazosulfuron, metsulfuron-methyl, metosulam, nicosulfuron, penoxsulam, propoxycarbazon-sodium, pyrazosulfuron-ethyl, pyribenzoxim, pyriftalid, pyroxsulam, propyrisulfuron, rimsulfuron, sulfosulfuron, thiencarbazon-methyl, thifensulfuron-methyl, tribenuron-methyl, tritosulfuron and triafamone.

According to another preferred embodiment of the invention, the composition comprises, in addition to a pyrimidine compounds of formula (I), especially an active compound from the group consisting (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b3), in particular selected from the group consisting of ametryn, atrazine, bentazon, bromoxynil, bromoxynil-octanoate, bromoxynil-heptanoate, bromoxynil-potassium, diuron, fluometuron, hexazinone, isoproturon, linuron, metamitron, metribuzin, paraquat-dichloride, propanil, simazin, terbutryn and terbuthylazine.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b4), in particular selected from the group consisting of acifluorfen, butafencil, carfenetrazone-ethyl, flumioxazin, fomesafen, oxadiargyl, oxyfluorfen, pyraflufen, pyraflufen-ethyl, saflufenacil, sulfentrazone, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100).

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.1.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b5), in particular selected from the group consisting of amitrole, benzobicyclon, bicyclopyrone, clomazone, diflufenican, fenquintrone, fluometuron, flurochloridone, isoxaflutole, mesotrione, norflurazon, oxotrione (CAS 1486617-21-3), picolinafen, sulcotrione, tefuryltrione, tembotrione, tolpyralate, topramezone, topramezone-sodium, 2-chloro-3-methylsulfanyl-N-(1-methyltetrazol-5-yl)-4-(trifluoromethyl)benzamide (CAS 1361139-71-0), 2-(2,4-dichlorophenyl)methyl-4,4-dimethyl-3-isoxazolidone (CAS 81777-95-9) and 2-(2,5-dichlorophenyl)methyl-4,4-dimethyl-3-isoxazolidinone (CAS 81778-66-7).

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.1-25), (1.7.I-25), (1.7.I- 37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b6), in particular selected from the group consisting of glyphosate, glyphosate-ammonium, glyphosate-dimethylammonium, glyphosate-isopropylammonium and glyphosate-trimesium (sulfosate) and glyphosate-potassium.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), at least one and especially exactly one herbicidally active compound from group b7), in particular selected from the group consisting of glufosinate, glufosinate-ammonium, glufosinate-P and glufosinate-P-ammonium.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b9), in particular selected from the group consisting of pendimethalin and trifluralin.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b10), in particular selected from the group consisting of acetochlor, butachlor, cafenstrole, dimethenamid-P, fentrazamide, flufenacet, mefenacet, metazachlor, metolachlor, S-metolachlor, fenoxasulfone, ipfencarbazone and pyroxasulfone. Likewise, preference is given to compositions comprising in addition to a of formula (I), especially an active compound from the group consisting of, at least one and especially exactly one herbicidally active compound from group b10), in particular selected from the group consisting of isoxazoline compounds of the formulae 11.1, 11.2, 11.3, 11.4, 11.5, 11.6, 11.7, 11.8 and 11.9, as defined above.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-737.1-25), (1.6.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b11), in particular indaziflam, isoxaben and triaziflam.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b13), in particular selected from the group consisting of 2,4-D, 2,4-D-isobutyl, 2,4-D-dimethylammonium, 2,4-D-N,N,N-trimethylethanolammonium, aminocyclopyrachlor, aminocyclopyrachlor-potassium, aminocyclopyrachlor-methyl, aminopyralid, aminopyralid-methyl, aminopyralid-dimethylammonium, aminopyralid-tris(2-hydroxypropyl)ammonium, clopyralid, clopyralid-methyl, clopyralid-olamine, dicamba, dicamba-butotyl, dicamba-diglycolamine, dicamba-dimethylammonium, dicamba-diolamine, dicamba-isopropylammonium, dicamba-potassium, dicamba-sodium, dicamba-trolamine, dicamba-N,N-bis-(3-aminopropyl)methylamine, dicamba-diethylenetriamine, flopyrauxifen, fluroxypyr, fluroxypyr-meptyl, halauxifen, halauxifen-methyl, MCPA, MCPA-2-ethylhexyl, MCPA-dimethylammonium, quinclorac, quinclorac-dimethylammonium, quinmerac, quinmerac-dimethylammonium, florpyrauxifen, florpyrauxifen-benzyl (CAS 1390661-72-9), and 4-amino-3-chloro-5-fluoro-6-(7-fluoro-1H-indol-6-yl)picolinic acid (CAS 1629965-65-6).

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-737.1-25), (1.6.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b14), in particular selected from the group consisting of diflufenzopyr, diflufenzopyr-sodium, dymron, indanofan and diflufenzopyr-sodium.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one herbicidally active compound from group b15), in particular selected from the group consisting of cinmethylin, dymron (=daimuron), indanofan and oxaziclomefone.

According to another preferred embodiment of the invention, the composition comprises, in addition to a pyrimidine compounds of formula (I), especially an active compound from the group consisting of (1.1.I-25), (1.1.I-37), (1.1.I-31), (1.1.I-49), (1.1.I-61), (1.1.I-55), (1.1.I-73), (1.2.I-25), (1.2.I-37), (1.2.I-31), (1.2.I-49), (1.2.I-61), (1.2.I-55), (1.2.I-73), (1.3.I-25), (1.3.I-37), (1.3.I-31), (1.3.I-49), (1.3.I-61), (1.3.I-55), (1.3.I-73), (1.4.I-25), (1.4.I-37), (1.4.I-31), (1.4.I-49), (1.4.I-61), (1.4.I-55), (1.4.I-73), (1.5.I-25), (1.5.I-37), (1.5.I-31), (1.5.I-49), (1.5.I-61), (1.5.I-55), (1.5.I-73), (1.6.I-25), (1.6.I-37), (1.6.I-31), (1.6.I-49), (1.6.I-61), (1.6.I-55), (1.6.I-73), (1.7.I-25), (1.7.I-37), (1.7.I-31), (1.7.I-49), (1.7.I-61), (1.7.I-55), (1.7.I-73), (1.8.I-25), (1.8.I-37), (1.8.I-31), (1.8.I-49), (1.8.I-61), (1.8.I-55), (1.8.I-73), (1.9.I-25), (1.9.I-37), (1.9.I-31), (1.9.I-49), (1.9.I-61), (1.9.I-55), (1.9.I-73), (1.10.I-25), (1.10.I-37), (1.10.I-31), (1.10.I-49), (1.10.I-61), (1.10.I-55), (1.10.I-73), (1.31.I-25), (1.37.I-25), (1.37.I-31), (1.37.I-37), (1.37.I-49), (1.37.I-55), (1.37.I-61), (1.38.I-25), (1.38.I-31), (1.38.I-37), (1.38.I-49), (1.38.I-55), (1.38.I-61), (1.39.I-25), (1.39.I-31), (1.39.I-37), (1.39.I-49), (1.39.I-55), (1.39.I-61), (1.46.I-25), (1.46.I-31), (1.46.I-37), (1.46.I-49), (1.46.I-55), (1.46.I-61), (1.47.I-25), (1.47.I-31), (1.47.I-37), (1.47.I-49), (1.47.I-55), (1.47.I-61), (1.53.I-25), (1.53.I-31), (1.53.I-37), (1.53.I-49), (1.53.I-55), (1.53.I-61), (1.59.I-25), (1.59.I-31), (1.59.I-37), (1.59.I-49), (1.59.I-55), (1.59.I-61), (1.63.I-25), (1.63.I-31), (1.63.I-37), (1.63.I-49), (1.63.I-55), (1.63.I-61), (1.64.I-25), (1.64.I-31), (1.64.I-37), (1.64.I-49), (1.64.I-55), (1.64.I-61), (1.65.I-25), (1.65.I-31), (1.65.I-37), (1.65.I-49), (1.65.I-55), (1.65.I-61), (1.72.I-25), (1.72.I-31), (1.72.I-37), (1.72.I-49), (1.72.I-55), (1.72.I-61), (1.73.I-25), (1.73.I-31), (1.73.I-37), (1.73.I-49), (1.73.I-55), (1.73.I-61), (1.79.I-25), (1.79.I-37), (1.79.I-49), (1.79.I-31), (1.79.I-55), (1.79.I-61), (1.272.I-25), (1.272.I-31), (1.272.I-37), (1.272.I-49), (1.272.I-55), (1.272.I-61), (1.273.I-25), (1.273.I-31), (1.273.I-37), (1.273.I-49), (1.273.I-55), (1.273.I-61), (1.584.I-25), (1.584.I-31), (1.584.I-37), (1.584.I-49), (1.584.I-55), (1.584.I-61), (1.585.I-25), (1.585.I-31), (1.585.I-37), (1.585.I-49), (1.585.I-55), (1.585.I-61), (1.592.I-25), (1.592.I-31), (1.592.I-37), (1.592.I-49), (1.592.I-55), and (1.592.I-61), at least one and especially exactly one safener C, in particular selected from the group consisting of benoxacor, cloquintocet, cyprosulfamide, dichlormid, fenchlorazole, fenclorim, furilazole, isoxadifen, mefenpyr, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Here and below, the term "binary compositions" includes compositions comprising one or more, e.g. 1, 2 or 3, active compounds of the formula (I) and either one or more, e.g. 1, 2 or 3, herbicides B or one or more safeners C.

Correspondingly, the term "ternary compositions" includes compositions comprising one or more, e.g. 1, 2 or 3, active compounds of the formula (I), one or more, e.g. 1, 2 or 3, herbicides B and one or more, e.g. 1, 2 or 3, safeners C.

In binary compositions comprising at least one phenylpyrimidine of formula (I) as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly in the range of from 1:75 to 75:1.

In binary compositions comprising at least one phenylpyrimidine of formula (I) as component A and at least one safener C, the weight ratio of the active compounds A:C is generally in the range of from 1:1000 to 1000:1, preferably in the range of from 1:500 to 500:1, in particular in the range of from 1:250 to 250:1 and particularly in the range of from 1:75 to 75:1.

In ternary compositions comprising at least one phenylpyrimidine of formula (I) as component A, at least one herbicide B and at least one safener C, the relative proportions by weight of the components A:B are generally in the range of from 1:1000 to 1000:1, preferably in the range of from 1:500 to 500:1, in particular in the range of from 1:250 to 250:1 and particularly in the range of from 1:75 to 75:1, the weight ratio of the components A:C is generally in the range of from 1:1000 to 1000:1, preferably in the range of from 1:500 to 500:1, in particular in the range of from 1:250 to 250:1 and particularly in the range of from 1:75 to 75:1, and the weight ratio of the components B:C is generally in the range of from 1:1000 to 1000:1, preferably in the range of from 1:500 to 500:1, in particular in the range of from 1:250 to 250:1 and particularly in the range of from 1:75 to 75:1. The weight ratio of components A+B to component C is preferably in the range of from 1:500 to 500:1, in particular in the range of from 1:250 to 250:1 and particularly in the range of from 1:75 to 75:1.

The weight ratios of the individual components in the preferred mixtures mentioned below are within the limits given above, in particular within the preferred limits.

Particularly preferred are the compositions mentioned below comprising the compounds of formula I as defined and the substance(s) as defined in the respective row of table T;

especially preferred comprising as only herbicidal active compounds the compounds of formula I as defined and the substance(s) as defined in the respective row of table T;

most preferably comprising as only active compounds the compounds of formula I as defined and the substance(s) as defined in the respective row of table T.

Particularly preferred are compositions 1.1 to 1.3653, comprising the compound 1.1.I-25 and the substance(s) as defined in the respective row of table T:

TABLE T (compositions 1.1 to 1.3653):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |

TABLE T-continued (compositions 1.1 to 1.3653):

| comp. no. | herbicide B | safener C |
|---|---|---|
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58 | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.145 | — |
| 1.146 | B.146 | — |
| 1.147 | B.147 | — |
| 1.148 | B.148 | — |
| 1.149 | B.149 | — |
| 1.150 | B.150 | — |
| 1.151 | B.151 | — |
| 1.152 | B.152 | — |
| 1.153 | B.153 | — |
| 1.154 | B.154 | — |
| 1.155 | B.155 | — |
| 1.156 | B.156 | — |
| 1.157 | B.157 | — |
| 1.158 | B.158 | — |
| 1.159 | B.159 | — |
| 1.160 | B.160 | — |
| 1.161 | B.161 | — |
| 1.162 | B.162 | — |
| 1.163 | B.163 | — |
| 1.164 | B.164 | — |
| 1.165 | B.165 | — |
| 1.166 | B.166 | — |
| 1.167 | B.167 | — |
| 1.168 | B.168 | — |
| 1.169 | B.169 | — |
| 1.170 | B.170 | — |
| 1.171 | B.171 | — |
| 1.172 | B.172 | — |
| 1.173 | B.173 | — |
| 1.174 | B.174 | — |
| 1.175 | B.175 | — |
| 1.176 | B.176 | — |
| 1.177 | B.177 | — |
| 1.178 | B.178 | — |
| 1.179 | B.179 | — |

TABLE T-continued (compositions 1.1 to 1.3653):

| comp. no. | herbicide B | safener C |
|---|---|---|
| 1.180 | B.180 | — |
| 1.181 | B.181 | — |
| 1.182 | B.182 | — |
| 1.183 | B.183 | — |
| 1.184 | B.184 | — |
| 1.185 | B.185 | — |
| 1.186 | B.186 | — |
| 1.187 | B.187 | — |
| 1.188 | B.188 | — |
| 1.189 | B.189 | — |
| 1.190 | B.190 | — |
| 1.191 | B.191 | — |
| 1.192 | B.192 | — |
| 1.193 | B.193 | — |
| 1.194 | B.194 | — |
| 1.195 | B.195 | — |
| 1.196 | B.196 | — |
| 1.197 | B.197 | — |
| 1.198 | B.198 | — |
| 1.199 | B.199 | — |
| 1.200 | B.200 | — |
| 1.201 | B.201 | — |
| 1.202 | B.202 | — |
| 1.203 | B.1 | C.1 |
| 1.204 | B.2 | C.1 |
| 1.205 | B.3 | C.1 |
| 1.206 | B.4 | C.1 |
| 1.207 | B.5 | C.1 |
| 1.208 | B.6 | C.1 |
| 1.209 | B.7 | C.1 |
| 1.210 | B.8 | C.1 |
| 1.211 | B.9 | C.1 |
| 1.212 | B.10 | C.1 |
| 1.213 | B.11 | C.1 |
| 1.214 | B.12 | C.1 |
| 1.215 | B.13 | C.1 |
| 1.216 | B.14 | C.1 |
| 1.217 | B.15 | C.1 |
| 1.218 | B.16 | C.1 |
| 1.219 | B.17 | C.1 |
| 1.220 | B.18 | C.1 |
| 1.221 | B.19 | C.1 |
| 1.222 | B.20 | C.1 |
| 1.223 | B.21 | C.1 |
| 1.224 | B.22 | C.1 |
| 1.225 | B.23 | C.1 |
| 1.226 | B.24 | C.1 |
| 1.227 | B.25 | C.1 |
| 1.228 | B.26 | C.1 |
| 1.229 | B.27 | C.1 |
| 1.230 | B.28 | C.1 |
| 1.231 | B.29 | C.1 |
| 1.232 | B.30 | C.1 |
| 1.233 | B.31 | C.1 |
| 1.234 | B.32 | C.1 |
| 1.235 | B.33 | C.1 |
| 1.236 | B.34 | C.1 |
| 1.237 | B.35 | C.1 |
| 1.238 | B.36 | C.1 |
| 1.239 | B.37 | C.1 |
| 1.240 | B.38 | C.1 |
| 1.241 | B.39 | C.1 |
| 1.242 | B.40 | C.1 |
| 1.243 | B.41 | C.1 |
| 1.244 | B.42 | C.1 |
| 1.245 | B.43 | C.1 |
| 1.246 | B.44 | C.1 |
| 1.247 | B.45 | C.1 |
| 1.248 | B.46 | C.1 |
| 1.249 | B.47 | C.1 |
| 1.250 | B.48 | C.1 |
| 1.251 | B.49 | C.1 |
| 1.252 | B.50 | C.1 |
| 1.253 | B.51 | C.1 |
| 1.254 | B.52 | C.1 |
| 1.255 | B.53 | C.1 |
| 1.256 | B.54 | C.1 |
| 1.257 | B.55 | C.1 |
| 1.258 | B.56 | C.1 |
| 1.259 | B.57 | C.1 |
| 1.260 | B.58 | C.1 |
| 1.261 | B.59 | C.1 |
| 1.262 | B.60 | C.1 |
| 1.263 | B.61 | C.1 |
| 1.264 | B.62 | C.1 |
| 1.265 | B.63 | C.1 |
| 1.266 | B.64 | C.1 |
| 1.267 | B.65 | C.1 |
| 1.268 | B.66 | C.1 |
| 1.269 | B.67 | C.1 |
| 1.270 | B.68 | C.1 |
| 1.271 | B.69 | C.1 |
| 1.272 | B.70 | C.1 |
| 1.273 | B.71 | C.1 |
| 1.274 | B.72 | C.1 |
| 1.275 | B.73 | C.1 |
| 1.276 | B.74 | C.1 |
| 1.277 | B.75 | C.1 |
| 1.278 | B.76 | C.1 |
| 1.279 | B.77 | C.1 |
| 1.280 | B.78 | C.1 |
| 1.281 | B.79 | C.1 |
| 1.282 | B.80 | C.1 |
| 1.283 | B.81 | C.1 |
| 1.284 | B.82 | C.1 |
| 1.285 | B.83 | C.1 |
| 1.286 | B.84 | C.1 |
| 1.287 | B.85 | C.1 |
| 1.288 | B.86 | C.1 |
| 1.289 | B.87 | C.1 |
| 1.290 | B.88 | C.1 |
| 1.291 | B.89 | C.1 |
| 1.292 | B.90 | C.1 |
| 1.293 | B.91 | C.1 |
| 1.294 | B.92 | C.1 |
| 1.295 | B.93 | C.1 |
| 1.296 | B.94 | C.1 |
| 1.297 | B.95 | C.1 |
| 1.298 | B.96 | C.1 |
| 1.299 | B.97 | C.1 |
| 1.300 | B.98 | C.1 |
| 1.301 | B.99 | C.1 |
| 1.302 | B.100 | C.1 |
| 1.303 | B.101 | C.1 |
| 1.304 | B.102 | C.1 |
| 1.305 | B.103 | C.1 |
| 1.306 | B.104 | C.1 |
| 1.307 | B.105 | C.1 |
| 1.308 | B.106 | C.1 |
| 1.309 | B.107 | C.1 |
| 1.310 | B.108 | C.1 |
| 1.311 | B.109 | C.1 |
| 1.312 | B.110 | C.1 |
| 1.313 | B.111 | C.1 |
| 1.314 | B.112 | C.1 |
| 1.315 | B.113 | C.1 |
| 1.316 | B.114 | C.1 |
| 1.317 | B.115 | C.1 |
| 1.318 | B.116 | C.1 |
| 1.319 | B.117 | C.1 |
| 1.320 | B.118 | C.1 |
| 1.321 | B.119 | C.1 |
| 1.322 | B.120 | C.1 |
| 1.323 | B.121 | C.1 |
| 1.324 | B.122 | C.1 |
| 1.325 | B.123 | C.1 |
| 1.326 | B.124 | C.1 |
| 1.327 | B.125 | C.1 |
| 1.328 | B.126 | C.1 |
| 1.329 | B.127 | C.1 |
| 1.330 | B.128 | C.1 |
| 1.331 | B.129 | C.1 |

TABLE T-continued (compositions 1.1 to 1.3653):

| comp. no. | herbicide B | safener C |
|---|---|---|
| 1.332 | B.130 | C.1 |
| 1.333 | B.131 | C.1 |
| 1.334 | B.132 | C.1 |
| 1.335 | B.133 | C.1 |
| 1.336 | B.134 | C.1 |
| 1.337 | B.135 | C.1 |
| 1.338 | B.136 | C.1 |
| 1.339 | B.137 | C.1 |
| 1.340 | B.138 | C.1 |
| 1.341 | B.139 | C.1 |
| 1.342 | B.140 | C.1 |
| 1.343 | B.141 | C.1 |
| 1.344 | B.142 | C.1 |
| 1.345 | B.143 | C.1 |
| 1.346 | B.144 | C.1 |
| 1.347 | B.145 | C.1 |
| 1.348 | B.146 | C.1 |
| 1.349 | B.147 | C.1 |
| 1.350 | B.148 | C.1 |
| 1.351 | B.149 | C.1 |
| 1.352 | B.150 | C.1 |
| 1.353 | B.151 | C.1 |
| 1.354 | B.152 | C.1 |
| 1.355 | B.153 | C.1 |
| 1.356 | B.154 | C.1 |
| 1.357 | B.155 | C.1 |
| 1.358 | B.156 | C.1 |
| 1.359 | B.157 | C.1 |
| 1.360 | B.158 | C.1 |
| 1.361 | B.159 | C.1 |
| 1.362 | B.160 | C.1 |
| 1.363 | B.161 | C.1 |
| 1.364 | B.162 | C.1 |
| 1.365 | B.163 | C.1 |
| 1.366 | B.164 | C.1 |
| 1.367 | B.165 | C.1 |
| 1.368 | B.166 | C.1 |
| 1.369 | B.167 | C.1 |
| 1.370 | B.168 | C.1 |
| 1.371 | B.169 | C.1 |
| 1.372 | B.170 | C.1 |
| 1.373 | B.171 | C.1 |
| 1.374 | B.172 | C.1 |
| 1.375 | B.173 | C.1 |
| 1.376 | B.174 | C.1 |
| 1.377 | B.175 | C.1 |
| 1.378 | B.176 | C.1 |
| 1.379 | B.177 | C.1 |
| 1.380 | B.178 | C.1 |
| 1.381 | B.179 | C.1 |
| 1.382 | B.180 | C.1 |
| 1.383 | B.181 | C.1 |
| 1.384 | B.182 | C.1 |
| 1.385 | B.183 | C.1 |
| 1.386 | B.184 | C.1 |
| 1.387 | B.185 | C.1 |
| 1.388 | B.186 | C.1 |
| 1.389 | B.187 | C.1 |
| 1.390 | B.188 | C.1 |
| 1.391 | B.189 | C.1 |
| 1.392 | B.190 | C.1 |
| 1.393 | B.191 | C.1 |
| 1.394 | B.192 | C.1 |
| 1.395 | B.193 | C.1 |
| 1.396 | B.194 | C.1 |
| 1.397 | B.195 | C.1 |
| 1.398 | B.196 | C.1 |
| 1.399 | B.197 | C.1 |
| 1.400 | B.198 | C.1 |
| 1.401 | B.199 | C.1 |
| 1.402 | B.200 | C.1 |
| 1.403 | B.201 | C.1 |
| 1.404 | B.202 | C.1 |
| 1.405 | B.1 | C.2 |
| 1.406 | B.2 | C.2 |
| 1.407 | B.3 | C.2 |
| 1.408 | B.4 | C.2 |
| 1.409 | B.5 | C.2 |
| 1.410 | B.6 | C.2 |
| 1.411 | B.7 | C.2 |
| 1.412 | B.8 | C.2 |
| 1.413 | B.9 | C.2 |
| 1.414 | B.10 | C.2 |
| 1.415 | B.11 | C.2 |
| 1.416 | B.12 | C.2 |
| 1.417 | B.13 | C.2 |
| 1.418 | B.14 | C.2 |
| 1.419 | B.15 | C.2 |
| 1.420 | B.16 | C.2 |
| 1.421 | B.17 | C.2 |
| 1.422 | B.18 | C.2 |
| 1.423 | B.19 | C.2 |
| 1.424 | B.20 | C.2 |
| 1.425 | B.21 | C.2 |
| 1.426 | B.22 | C.2 |
| 1.427 | B.23 | C.2 |
| 1.428 | B.24 | C.2 |
| 1.429 | B.25 | C.2 |
| 1.430 | B.26 | C.2 |
| 1.431 | B.27 | C.2 |
| 1.432 | B.28 | C.2 |
| 1.433 | B.29 | C.2 |
| 1.434 | B.30 | C.2 |
| 1.435 | B.31 | C.2 |
| 1.436 | B.32 | C.2 |
| 1.437 | B.33 | C.2 |
| 1.438 | B.34 | C.2 |
| 1.439 | B.35 | C.2 |
| 1.440 | B.36 | C.2 |
| 1.441 | B.37 | C.2 |
| 1.442 | B.38 | C.2 |
| 1.443 | B.39 | C.2 |
| 1.444 | B.40 | C.2 |
| 1.445 | B.41 | C.2 |
| 1.446 | B.42 | C.2 |
| 1.447 | B.43 | C.2 |
| 1.448 | B.44 | C.2 |
| 1.449 | B.45 | C.2 |
| 1.450 | B.46 | C.2 |
| 1.451 | B.47 | C.2 |
| 1.452 | B.48 | C.2 |
| 1.453 | B.49 | C.2 |
| 1.454 | B.50 | C.2 |
| 1.455 | B.51 | C.2 |
| 1.456 | B.52 | C.2 |
| 1.457 | B.53 | C.2 |
| 1.458 | B.54 | C.2 |
| 1.459 | B.55 | C.2 |
| 1.460 | B.56 | C.2 |
| 1.461 | B.57 | C.2 |
| 1.462 | B.58 | C.2 |
| 1.463 | B.59 | C.2 |
| 1.464 | B.60 | C.2 |
| 1.465 | B.61 | C.2 |
| 1.466 | B.62 | C.2 |
| 1.467 | B.63 | C.2 |
| 1.468 | B.64 | C.2 |
| 1.469 | B.65 | C.2 |
| 1.470 | B.66 | C.2 |
| 1.471 | B.67 | C.2 |
| 1.472 | B.68 | C.2 |
| 1.473 | B.69 | C.2 |
| 1.474 | B.70 | C.2 |
| 1.475 | B.71 | C.2 |
| 1.476 | B.72 | C.2 |
| 1.477 | B.73 | C.2 |
| 1.478 | B.74 | C.2 |
| 1.479 | B.75 | C.2 |
| 1.480 | B.76 | C.2 |
| 1.481 | B.77 | C.2 |
| 1.482 | B.78 | C.2 |
| 1.483 | B.79 | C.2 |

TABLE T-continued

(compositions 1.1 to 1.3653):

| comp. no. | herbicide B | safener C |
|---|---|---|
| 1.484 | B.80 | C.2 |
| 1.485 | B.81 | C.2 |
| 1.486 | B.82 | C.2 |
| 1.487 | B.83 | C.2 |
| 1.488 | B.84 | C.2 |
| 1.489 | B.85 | C.2 |
| 1.490 | B.86 | C.2 |
| 1.491 | B.87 | C.2 |
| 1.492 | B.88 | C.2 |
| 1.493 | B.89 | C.2 |
| 1.494 | B.90 | C.2 |
| 1.495 | B.91 | C.2 |
| 1.496 | B.92 | C.2 |
| 1.497 | B.93 | C.2 |
| 1.498 | B.94 | C.2 |
| 1.499 | B.95 | C.2 |
| 1.500 | B.96 | C.2 |
| 1.501 | B.97 | C.2 |
| 1.502 | B.98 | C.2 |
| 1.503 | B.99 | C.2 |
| 1.504 | B.100 | C.2 |
| 1.505 | B.101 | C.2 |
| 1.506 | B.102 | C.2 |
| 1.507 | B.103 | C.2 |
| 1.508 | B.104 | C.2 |
| 1.509 | B.105 | C.2 |
| 1.510 | B.106 | C.2 |
| 1.511 | B.107 | C.2 |
| 1.512 | B.108 | C.2 |
| 1.513 | B.109 | C.2 |
| 1.514 | B.110 | C.2 |
| 1.515 | B.111 | C.2 |
| 1.516 | B.112 | C.2 |
| 1.517 | B.113 | C.2 |
| 1.518 | B.114 | C.2 |
| 1.519 | B.115 | C.2 |
| 1.520 | B.116 | C.2 |
| 1.521 | B.117 | C.2 |
| 1.522 | B.118 | C.2 |
| 1.523 | B.119 | C.2 |
| 1.524 | B.120 | C.2 |
| 1.525 | B.121 | C.2 |
| 1.526 | B.122 | C.2 |
| 1.527 | B.123 | C.2 |
| 1.528 | B.124 | C.2 |
| 1.529 | B.125 | C.2 |
| 1.530 | B.126 | C.2 |
| 1.531 | B.127 | C.2 |
| 1.532 | B.128 | C.2 |
| 1.533 | B.129 | C.2 |
| 1.534 | B.130 | C.2 |
| 1.535 | B.131 | C.2 |
| 1.536 | B.132 | C.2 |
| 1.537 | B.133 | C.2 |
| 1.538 | B.134 | C.2 |
| 1.539 | B.135 | C.2 |
| 1.540 | B.136 | C.2 |
| 1.541 | B.137 | C.2 |
| 1.542 | B.138 | C.2 |
| 1.543 | B.139 | C.2 |
| 1.544 | B.140 | C.2 |
| 1.545 | B.141 | C.2 |
| 1.546 | B.142 | C.2 |
| 1.547 | B.143 | C.2 |
| 1.548 | B.144 | C.2 |
| 1.549 | B.145 | C.2 |
| 1.550 | B.146 | C.2 |
| 1.551 | B.147 | C.2 |
| 1.552 | B.148 | C.2 |
| 1.553 | B.149 | C.2 |
| 1.554 | B.150 | C.2 |
| 1.555 | B.151 | C.2 |
| 1.556 | B.152 | C.2 |
| 1.557 | B.153 | C.2 |
| 1.558 | B.154 | C.2 |
| 1.559 | B.155 | C.2 |
| 1.560 | B.156 | C.2 |
| 1.561 | B.157 | C.2 |
| 1.562 | B.158 | C.2 |
| 1.563 | B.159 | C.2 |
| 1.564 | B.160 | C.2 |
| 1.565 | B.161 | C.2 |
| 1.566 | B.162 | C.2 |
| 1.567 | B.163 | C.2 |
| 1.568 | B.164 | C.2 |
| 1.569 | B.165 | C.2 |
| 1.570 | B.166 | C.2 |
| 1.571 | B.167 | C.2 |
| 1.572 | B.168 | C.2 |
| 1.573 | B.169 | C.2 |
| 1.574 | B.170 | C.2 |
| 1.575 | B.171 | C.2 |
| 1.576 | B.172 | C.2 |
| 1.577 | B.173 | C.2 |
| 1.578 | B.174 | C.2 |
| 1.579 | B.175 | C.2 |
| 1.580 | B.176 | C.2 |
| 1.581 | B.177 | C.2 |
| 1.582 | B.178 | C.2 |
| 1.583 | B.179 | C.2 |
| 1.584 | B.180 | C.2 |
| 1.585 | B.181 | C.2 |
| 1.586 | B.182 | C.2 |
| 1.587 | B.183 | C.2 |
| 1.588 | B.184 | C.2 |
| 1.589 | B.185 | C.2 |
| 1.590 | B.186 | C.2 |
| 1.591 | B.187 | C.2 |
| 1.592 | B.188 | C.2 |
| 1.593 | B.189 | C.2 |
| 1.594 | B.190 | C.2 |
| 1.595 | B.191 | C.2 |
| 1.596 | B.192 | C.2 |
| 1.597 | B.193 | C.2 |
| 1.598 | B.194 | C.2 |
| 1.599 | B.195 | C.2 |
| 1.600 | B.196 | C.2 |
| 1.601 | B.197 | C.2 |
| 1.602 | B.198 | C.2 |
| 1.603 | B.199 | C.2 |
| 1.604 | B.200 | C.2 |
| 1.605 | B.201 | C.2 |
| 1.606 | B.202 | C.2 |
| 1.607 | B.1 | C.3 |
| 1.608 | B.2 | C.3 |
| 1.609 | B.3 | C.3 |
| 1.610 | B.4 | C.3 |
| 1.611 | B.5 | C.3 |
| 1.612 | B.6 | C.3 |
| 1.613 | B.7 | C.3 |
| 1.614 | B.8 | C.3 |
| 1.615 | B.9 | C.3 |
| 1.616 | B.10 | C.3 |
| 1.617 | B.11 | C.3 |
| 1.618 | B.12 | C.3 |
| 1.619 | B.13 | C.3 |
| 1.620 | B.14 | C.3 |
| 1.621 | B.15 | C.3 |
| 1.622 | B.16 | C.3 |
| 1.623 | B.17 | C.3 |
| 1.624 | B.18 | C.3 |
| 1.625 | B.19 | C.3 |
| 1.626 | B.20 | C.3 |
| 1.627 | B.21 | C.3 |
| 1.628 | B.22 | C.3 |
| 1.629 | B.23 | C.3 |
| 1.630 | B.24 | C.3 |
| 1.631 | B.25 | C.3 |
| 1.632 | B.26 | C.3 |
| 1.633 | B.27 | C.3 |
| 1.634 | B.28 | C.3 |
| 1.635 | B.29 | C.3 |

TABLE T-continued (compositions 1.1 to 1.3653):

| comp. no. | herbicide B | safener C |
|---|---|---|
| 1.636 | B.30 | C.3 |
| 1.637 | B.31 | C.3 |
| 1.638 | B.32 | C.3 |
| 1.639 | B.33 | C.3 |
| 1.640 | B.34 | C.3 |
| 1.641 | B.35 | C.3 |
| 1.642 | B.36 | C.3 |
| 1.643 | B.37 | C.3 |
| 1.644 | B.38 | C.3 |
| 1.645 | B.39 | C.3 |
| 1.646 | B.40 | C.3 |
| 1.647 | B.41 | C.3 |
| 1.648 | B.42 | C.3 |
| 1.649 | B.43 | C.3 |
| 1.650 | B.44 | C.3 |
| 1.651 | B.45 | C.3 |
| 1.652 | B.46 | C.3 |
| 1.653 | B.47 | C.3 |
| 1.654 | B.48 | C.3 |
| 1.655 | B.49 | C.3 |
| 1.656 | B.50 | C.3 |
| 1.657 | B.51 | C.3 |
| 1.658 | B.52 | C.3 |
| 1.659 | B.53 | C.3 |
| 1.660 | B.54 | C.3 |
| 1.661 | B.55 | C.3 |
| 1.662 | B.56 | C.3 |
| 1.663 | B.57 | C.3 |
| 1.664 | B.58 | C.3 |
| 1.665 | B.59 | C.3 |
| 1.666 | B.60 | C.3 |
| 1.667 | B.61 | C.3 |
| 1.668 | B.62 | C.3 |
| 1.669 | B.63 | C.3 |
| 1.670 | B.64 | C.3 |
| 1.671 | B.65 | C.3 |
| 1.672 | B.66 | C.3 |
| 1.673 | B.67 | C.3 |
| 1.674 | B.68 | C.3 |
| 1.675 | B.69 | C.3 |
| 1.676 | B.70 | C.3 |
| 1.677 | B.71 | C.3 |
| 1.678 | B.72 | C.3 |
| 1.679 | B.73 | C.3 |
| 1.680 | B.74 | C.3 |
| 1.681 | B.75 | C.3 |
| 1.682 | B.76 | C.3 |
| 1.683 | B.77 | C.3 |
| 1.684 | B.78 | C.3 |
| 1.685 | B.79 | C.3 |
| 1.686 | B.80 | C.3 |
| 1.687 | B.81 | C.3 |
| 1.688 | B.82 | C.3 |
| 1.689 | B.83 | C.3 |
| 1.690 | B.84 | C.3 |
| 1.691 | B.85 | C.3 |
| 1.692 | B.86 | C.3 |
| 1.693 | B.87 | C.3 |
| 1.694 | B.88 | C.3 |
| 1.695 | B.89 | C.3 |
| 1.696 | B.90 | C.3 |
| 1.697 | B.91 | C.3 |
| 1.698 | B.92 | C.3 |
| 1.699 | B.93 | C.3 |
| 1.700 | B.94 | C.3 |
| 1.701 | B.95 | C.3 |
| 1.702 | B.96 | C.3 |
| 1.703 | B.97 | C.3 |
| 1.704 | B.98 | C.3 |
| 1.705 | B.99 | C.3 |
| 1.706 | B.100 | C.3 |
| 1.707 | B.101 | C.3 |
| 1.708 | B.102 | C.3 |
| 1.709 | B.103 | C.3 |
| 1.710 | B.104 | C.3 |
| 1.711 | B.105 | C.3 |
| 1.712 | B.106 | C.3 |
| 1.713 | B.107 | C.3 |
| 1.714 | B.108 | C.3 |
| 1.715 | B.109 | C.3 |
| 1.716 | B.110 | C.3 |
| 1.717 | B.111 | C.3 |
| 1.718 | B.112 | C.3 |
| 1.719 | B.113 | C.3 |
| 1.720 | B.114 | C.3 |
| 1.721 | B.115 | C.3 |
| 1.722 | B.116 | C.3 |
| 1.723 | B.117 | C.3 |
| 1.724 | B.118 | C.3 |
| 1.725 | B.119 | C.3 |
| 1.726 | B.120 | C.3 |
| 1.727 | B.121 | C.3 |
| 1.728 | B.122 | C.3 |
| 1.729 | B.123 | C.3 |
| 1.730 | B.124 | C.3 |
| 1.731 | B.125 | C.3 |
| 1.732 | B.126 | C.3 |
| 1.733 | B.127 | C.3 |
| 1.734 | B.128 | C.3 |
| 1.735 | B.129 | C.3 |
| 1.736 | B.130 | C.3 |
| 1.737 | B.131 | C.3 |
| 1.738 | B.132 | C.3 |
| 1.739 | B.133 | C.3 |
| 1.740 | B.134 | C.3 |
| 1.741 | B.135 | C.3 |
| 1.742 | B.136 | C.3 |
| 1.743 | B.137 | C.3 |
| 1.744 | B.138 | C.3 |
| 1.745 | B.139 | C.3 |
| 1.746 | B.140 | C.3 |
| 1.747 | B.141 | C.3 |
| 1.748 | B.142 | C.3 |
| 1.749 | B.143 | C.3 |
| 1.750 | B.144 | C.3 |
| 1.751 | B.145 | C.3 |
| 1.752 | B.146 | C.3 |
| 1.753 | B.147 | C.3 |
| 1.754 | B.148 | C.3 |
| 1.755 | B.149 | C.3 |
| 1.756 | B.150 | C.3 |
| 1.757 | B.151 | C.3 |
| 1.758 | B.152 | C.3 |
| 1.759 | B.153 | C.3 |
| 1.760 | B.154 | C.3 |
| 1.761 | B.155 | C.3 |
| 1.762 | B.156 | C.3 |
| 1.763 | B.157 | C.3 |
| 1.764 | B.158 | C.3 |
| 1.765 | B.159 | C.3 |
| 1.766 | B.160 | C.3 |
| 1.767 | B.161 | C.3 |
| 1.768 | B.162 | C.3 |
| 1.769 | B.163 | C.3 |
| 1.770 | B.164 | C.3 |
| 1.771 | B.165 | C.3 |
| 1.772 | B.166 | C.3 |
| 1.773 | B.167 | C.3 |
| 1.774 | B.168 | C.3 |
| 1.775 | B.169 | C.3 |
| 1.776 | B.170 | C.3 |
| 1.777 | B.171 | C.3 |
| 1.778 | B.172 | C.3 |
| 1.779 | B.173 | C.3 |
| 1.780 | B.174 | C.3 |
| 1.781 | B.175 | C.3 |
| 1.782 | B.176 | C.3 |
| 1.783 | B.177 | C.3 |
| 1.784 | B.178 | C.3 |
| 1.785 | B.179 | C.3 |
| 1.786 | B.180 | C.3 |
| 1.787 | B.181 | C.3 |

TABLE T-continued (compositions 1.1 to 1.3653):

| comp. no. | herbicide B | safener C |
|---|---|---|
| 1.788 | B.182 | C.3 |
| 1.789 | B.183 | C.3 |
| 1.790 | B.184 | C.3 |
| 1.791 | B.185 | C.3 |
| 1.792 | B.186 | C.3 |
| 1.793 | B.187 | C.3 |
| 1.794 | B.188 | C.3 |
| 1.795 | B.189 | C.3 |
| 1.796 | B.190 | C.3 |
| 1.797 | B.191 | C.3 |
| 1.798 | B.192 | C.3 |
| 1.799 | B.193 | C.3 |
| 1.800 | B.194 | C.3 |
| 1.801 | B.195 | C.3 |
| 1.802 | B.196 | C.3 |
| 1.803 | B.197 | C.3 |
| 1.804 | B.198 | C.3 |
| 1.805 | B.199 | C.3 |
| 1.806 | B.200 | C.3 |
| 1.807 | B.201 | C.3 |
| 1.808 | B.202 | C.3 |
| 1.809 | B.1 | C.4 |
| 1.810 | B.2 | C.4 |
| 1.811 | B.3 | C.4 |
| 1.812 | B.4 | C.4 |
| 1.813 | B.5 | C.4 |
| 1.814 | B.6 | C.4 |
| 1.815 | B.7 | C.4 |
| 1.816 | B.8 | C.4 |
| 1.817 | B.9 | C.4 |
| 1.818 | B.10 | C.4 |
| 1.819 | B.11 | C.4 |
| 1.820 | B.12 | C.4 |
| 1.821 | B.13 | C.4 |
| 1.822 | B.14 | C.4 |
| 1.823 | B.15 | C.4 |
| 1.824 | B.16 | C.4 |
| 1.825 | B.17 | C.4 |
| 1.826 | B.18 | C.4 |
| 1.827 | B.19 | C.4 |
| 1.828 | B.20 | C.4 |
| 1.829 | B.21 | C.4 |
| 1.830 | B.22 | C.4 |
| 1.831 | B.23 | C.4 |
| 1.832 | B.24 | C.4 |
| 1.833 | B.25 | C.4 |
| 1.834 | B.26 | C.4 |
| 1.835 | B.27 | C.4 |
| 1.836 | B.28 | C.4 |
| 1.837 | B.29 | C.4 |
| 1.838 | B.30 | C.4 |
| 1.839 | B.31 | C.4 |
| 1.840 | B.32 | C.4 |
| 1.841 | B.33 | C.4 |
| 1.842 | B.34 | C.4 |
| 1.843 | B.35 | C.4 |
| 1.844 | B.36 | C.4 |
| 1.845 | B.37 | C.4 |
| 1.846 | B.38 | C.4 |
| 1.847 | B.39 | C.4 |
| 1.848 | B.40 | C.4 |
| 1.849 | B.41 | C.4 |
| 1.850 | B.42 | C.4 |
| 1.851 | B.43 | C.4 |
| 1.852 | B.44 | C.4 |
| 1.853 | B.45 | C.4 |
| 1.854 | B.46 | C.4 |
| 1.855 | B.47 | C.4 |
| 1.856 | B.48 | C.4 |
| 1.857 | B.49 | C.4 |
| 1.858 | B.50 | C.4 |
| 1.859 | B.51 | C.4 |
| 1.860 | B.52 | C.4 |
| 1.861 | B.53 | C.4 |
| 1.862 | B.54 | C.4 |
| 1.863 | B.55 | C.4 |
| 1.864 | B.56 | C.4 |
| 1.865 | B.57 | C.4 |
| 1.866 | B.58 | C.4 |
| 1.867 | B.59 | C.4 |
| 1.868 | B.60 | C.4 |
| 1.869 | B.61 | C.4 |
| 1.870 | B.62 | C.4 |
| 1.871 | B.63 | C.4 |
| 1.872 | B.64 | C.4 |
| 1.873 | B.65 | C.4 |
| 1.874 | B.66 | C.4 |
| 1.875 | B.67 | C.4 |
| 1.876 | B.68 | C.4 |
| 1.877 | B.69 | C.4 |
| 1.878 | B.70 | C.4 |
| 1.879 | B.71 | C.4 |
| 1.880 | B.72 | C.4 |
| 1.881 | B.73 | C.4 |
| 1.882 | B.74 | C.4 |
| 1.883 | B.75 | C.4 |
| 1.884 | B.76 | C.4 |
| 1.885 | B.77 | C.4 |
| 1.886 | B.78 | C.4 |
| 1.887 | B.79 | C.4 |
| 1.888 | B.80 | C.4 |
| 1.889 | B.81 | C.4 |
| 1.890 | B.82 | C.4 |
| 1.891 | B.83 | C.4 |
| 1.892 | B.84 | C.4 |
| 1.893 | B.85 | C.4 |
| 1.894 | B.86 | C.4 |
| 1.895 | B.87 | C.4 |
| 1.896 | B.88 | C.4 |
| 1.897 | B.89 | C.4 |
| 1.898 | B.90 | C.4 |
| 1.899 | B.91 | C.4 |
| 1.900 | B.92 | C.4 |
| 1.901 | B.93 | C.4 |
| 1.902 | B.94 | C.4 |
| 1.903 | B.95 | C.4 |
| 1.904 | B.96 | C.4 |
| 1.905 | B.97 | C.4 |
| 1.906 | B.98 | C.4 |
| 1.907 | B.99 | C.4 |
| 1.908 | B.100 | C.4 |
| 1.909 | B.101 | C.4 |
| 1.910 | B.102 | C.4 |
| 1.911 | B.103 | C.4 |
| 1.912 | B.104 | C.4 |
| 1.913 | B.105 | C.4 |
| 1.914 | B.106 | C.4 |
| 1.915 | B.107 | C.4 |
| 1.916 | B.108 | C.4 |
| 1.917 | B.109 | C.4 |
| 1.918 | B.110 | C.4 |
| 1.919 | B.111 | C.4 |
| 1.920 | B.112 | C.4 |
| 1.921 | B.113 | C.4 |
| 1.922 | B.114 | C.4 |
| 1.923 | B.115 | C.4 |
| 1.924 | B.116 | C.4 |
| 1.925 | B.117 | C.4 |
| 1.926 | B.118 | C.4 |
| 1.927 | B.119 | C.4 |
| 1.928 | B.120 | C.4 |
| 1.929 | B.121 | C.4 |
| 1.930 | B.122 | C.4 |
| 1.931 | B.123 | C.4 |
| 1.932 | B.124 | C.4 |
| 1.933 | B.125 | C.4 |
| 1.934 | B.126 | C.4 |
| 1.935 | B.127 | C.4 |
| 1.936 | B.128 | C.4 |
| 1.937 | B.129 | C.4 |
| 1.938 | B.130 | C.4 |
| 1.939 | B.131 | C.4 |

TABLE T-continued (compositions 1.1 to 1.3653):

| comp. no. | herbicide B | safener C |
|---|---|---|
| 1.940 | B.132 | C.4 |
| 1.941 | B.133 | C.4 |
| 1.942 | B.134 | C.4 |
| 1.943 | B.135 | C.4 |
| 1.944 | B.136 | C.4 |
| 1.945 | B.137 | C.4 |
| 1.946 | B.138 | C.4 |
| 1.947 | B.139 | C.4 |
| 1.948 | B.140 | C.4 |
| 1.949 | B.141 | C.4 |
| 1.950 | B.142 | C.4 |
| 1.951 | B.143 | C.4 |
| 1.952 | B.144 | C.4 |
| 1.953 | B.145 | C.4 |
| 1.954 | B.146 | C.4 |
| 1.955 | B.147 | C.4 |
| 1.956 | B.148 | C.4 |
| 1.957 | B.149 | C.4 |
| 1.958 | B.150 | C.4 |
| 1.959 | B.151 | C.4 |
| 1.960 | B.152 | C.4 |
| 1.961 | B.153 | C.4 |
| 1.962 | B.154 | C.4 |
| 1.963 | B.155 | C.4 |
| 1.964 | B.156 | C.4 |
| 1.965 | B.157 | C.4 |
| 1.966 | B.158 | C.4 |
| 1.967 | B.159 | C.4 |
| 1.968 | B.160 | C.4 |
| 1.969 | B.161 | C.4 |
| 1.970 | B.162 | C.4 |
| 1.971 | B.163 | C.4 |
| 1.972 | B.164 | C.4 |
| 1.973 | B.165 | C.4 |
| 1.974 | B.166 | C.4 |
| 1.975 | B.167 | C.4 |
| 1.976 | B.168 | C.4 |
| 1.977 | B.169 | C.4 |
| 1.978 | B.170 | C.4 |
| 1.979 | B.171 | C.4 |
| 1.980 | B.172 | C.4 |
| 1.981 | B.173 | C.4 |
| 1.982 | B.174 | C.4 |
| 1.983 | B.175 | C.4 |
| 1.984 | B.176 | C.4 |
| 1.985 | B.177 | C.4 |
| 1.986 | B.178 | C.4 |
| 1.987 | B.179 | C.4 |
| 1.988 | B.180 | C.4 |
| 1.989 | B.181 | C.4 |
| 1.990 | B.182 | C.4 |
| 1.991 | B.183 | C.4 |
| 1.992 | B.184 | C.4 |
| 1.993 | B.185 | C.4 |
| 1.994 | B.186 | C.4 |
| 1.995 | B.187 | C.4 |
| 1.996 | B.188 | C.4 |
| 1.997 | B.189 | C.4 |
| 1.998 | B.190 | C.4 |
| 1.999 | B.191 | C.4 |
| 1.1000 | B.192 | C.4 |
| 1.1001 | B.193 | C.4 |
| 1.1002 | B.194 | C.4 |
| 1.1003 | B.195 | C.4 |
| 1.1004 | B.196 | C.4 |
| 1.1005 | B.197 | C.4 |
| 1.1006 | B.198 | C.4 |
| 1.1007 | B.199 | C.4 |
| 1.1008 | B.200 | C.4 |
| 1.1009 | B.201 | C.4 |
| 1.1010 | B.202 | C.4 |
| 1.1011 | B.1 | C.5 |
| 1.1012 | B.2 | C.5 |
| 1.1013 | B.3 | C.5 |
| 1.1014 | B.4 | C.5 |
| 1.1015 | B.5 | C.5 |
| 1.1016 | B.6 | C.5 |
| 1.1017 | B.7 | C.5 |
| 1.1018 | B.8 | C.5 |
| 1.1019 | B.9 | C.5 |
| 1.1020 | B.10 | C.5 |
| 1.1021 | B.11 | C.5 |
| 1.1022 | B.12 | C.5 |
| 1.1023 | B.13 | C.5 |
| 1.1024 | B.14 | C.5 |
| 1.1025 | B.15 | C.5 |
| 1.1026 | B.16 | C.5 |
| 1.1027 | B.17 | C.5 |
| 1.1028 | B.18 | C.5 |
| 1.1029 | B.19 | C.5 |
| 1.1030 | B.20 | C.5 |
| 1.1031 | B.21 | C.5 |
| 1.1032 | B.22 | C.5 |
| 1.1033 | B.23 | C.5 |
| 1.1034 | B.24 | C.5 |
| 1.1035 | B.25 | C.5 |
| 1.1036 | B.26 | C.5 |
| 1.1037 | B.27 | C.5 |
| 1.1038 | B.28 | C.5 |
| 1.1039 | B.29 | C.5 |
| 1.1040 | B.30 | C.5 |
| 1.1041 | B.31 | C.5 |
| 1.1042 | B.32 | C.5 |
| 1.1043 | B.33 | C.5 |
| 1.1044 | B.34 | C.5 |
| 1.1045 | B.35 | C.5 |
| 1.1046 | B.36 | C.5 |
| 1.1047 | B.37 | C.5 |
| 1.1048 | B.38 | C.5 |
| 1.1049 | B.39 | C.5 |
| 1.1050 | B.40 | C.5 |
| 1.1051 | B.41 | C.5 |
| 1.1052 | B.42 | C.5 |
| 1.1053 | B.43 | C.5 |
| 1.1054 | B.44 | C.5 |
| 1.1055 | B.45 | C.5 |
| 1.1056 | B.46 | C.5 |
| 1.1057 | B.47 | C.5 |
| 1.1058 | B.48 | C.5 |
| 1.1059 | B.49 | C.5 |
| 1.1060 | B.50 | C.5 |
| 1.1061 | B.51 | C.5 |
| 1.1062 | B.52 | C.5 |
| 1.1063 | B.53 | C.5 |
| 1.1064 | B.54 | C.5 |
| 1.1065 | B.55 | C.5 |
| 1.1066 | B.56 | C.5 |
| 1.1067 | B.57 | C.5 |
| 1.1068 | B.58 | C.5 |
| 1.1069 | B.59 | C.5 |
| 1.1070 | B.60 | C.5 |
| 1.1071 | B.61 | C.5 |
| 1.1072 | B.62 | C.5 |
| 1.1073 | B.63 | C.5 |
| 1.1074 | B.64 | C.5 |
| 1.1075 | B.65 | C.5 |
| 1.1076 | B.66 | C.5 |
| 1.1077 | B.67 | C.5 |
| 1.1078 | B.68 | C.5 |
| 1.1079 | B.69 | C.5 |
| 1.1080 | B.70 | C.5 |
| 1.1081 | B.71 | C.5 |
| 1.1082 | B.72 | C.5 |
| 1.1083 | B.73 | C.5 |
| 1.1084 | B.74 | C.5 |
| 1.1085 | B.75 | C.5 |
| 1.1086 | B.76 | C.5 |
| 1.1087 | B.77 | C.5 |
| 1.1088 | B.78 | C.5 |
| 1.1089 | B.79 | C.5 |
| 1.1090 | B.80 | C.5 |
| 1.1091 | B.81 | C.5 |

TABLE T-continued (compositions 1.1 to 1.3653):

| comp. no. | herbicide B | safener C |
|---|---|---|
| 1.1092 | B.82 | C.5 |
| 1.1093 | B.83 | C.5 |
| 1.1094 | B.84 | C.5 |
| 1.1095 | B.85 | C.5 |
| 1.1096 | B.86 | C.5 |
| 1.1097 | B.87 | C.5 |
| 1.1098 | B.88 | C.5 |
| 1.1099 | B.89 | C.5 |
| 1.1100 | B.90 | C.5 |
| 1.1101 | B.91 | C.5 |
| 1.1102 | B.92 | C.5 |
| 1.1103 | B.93 | C.5 |
| 1.1104 | B.94 | C.5 |
| 1.1105 | B.95 | C.5 |
| 1.1106 | B.96 | C.5 |
| 1.1107 | B.97 | C.5 |
| 1.1108 | B.98 | C.5 |
| 1.1109 | B.99 | C.5 |
| 1.1110 | B.100 | C.5 |
| 1.1111 | B.101 | C.5 |
| 1.1112 | B.102 | C.5 |
| 1.1113 | B.103 | C.5 |
| 1.1114 | B.104 | C.5 |
| 1.1115 | B.105 | C.5 |
| 1.1116 | B.106 | C.5 |
| 1.1117 | B.107 | C.5 |
| 1.1118 | B.108 | C.5 |
| 1.1119 | B.109 | C.5 |
| 1.1120 | B.110 | C.5 |
| 1.1121 | B.111 | C.5 |
| 1.1122 | B.112 | C.5 |
| 1.1123 | B.113 | C.5 |
| 1.1124 | B.114 | C.5 |
| 1.1125 | B.115 | C.5 |
| 1.1126 | B.116 | C.5 |
| 1.1127 | B.117 | C.5 |
| 1.1128 | B.118 | C.5 |
| 1.1129 | B.119 | C.5 |
| 1.1130 | B.120 | C.5 |
| 1.1131 | B.121 | C.5 |
| 1.1132 | B.122 | C.5 |
| 1.1133 | B.123 | C.5 |
| 1.1134 | B.124 | C.5 |
| 1.1135 | B.125 | C.5 |
| 1.1136 | B.126 | C.5 |
| 1.1137 | B.127 | C.5 |
| 1.1138 | B.128 | C.5 |
| 1.1139 | B.129 | C.5 |
| 1.1140 | B.130 | C.5 |
| 1.1141 | B.131 | C.5 |
| 1.1142 | B.132 | C.5 |
| 1.1143 | B.133 | C.5 |
| 1.1144 | B.134 | C.5 |
| 1.1145 | B.135 | C.5 |
| 1.1146 | B.136 | C.5 |
| 1.1147 | B.137 | C.5 |
| 1.1148 | B.138 | C.5 |
| 1.1149 | B.139 | C.5 |
| 1.1150 | B.140 | C.5 |
| 1.1151 | B.141 | C.5 |
| 1.1152 | B.142 | C.5 |
| 1.1153 | B.143 | C.5 |
| 1.1154 | B.144 | C.5 |
| 1.1155 | B.145 | C.5 |
| 1.1156 | B.146 | C.5 |
| 1.1157 | B.147 | C.5 |
| 1.1158 | B.148 | C.5 |
| 1.1159 | B.149 | C.5 |
| 1.1160 | B.150 | C.5 |
| 1.1161 | B.151 | C.5 |
| 1.1162 | B.152 | C.5 |
| 1.1163 | B.153 | C.5 |
| 1.1164 | B.154 | C.5 |
| 1.1165 | B.155 | C.5 |
| 1.1166 | B.156 | C.5 |
| 1.1167 | B.157 | C.5 |
| 1.1168 | B.158 | C.5 |
| 1.1169 | B.159 | C.5 |
| 1.1170 | B.160 | C.5 |
| 1.1171 | B.161 | C.5 |
| 1.1172 | B.162 | C.5 |
| 1.1173 | B.163 | C.5 |
| 1.1174 | B.164 | C.5 |
| 1.1175 | B.165 | C.5 |
| 1.1176 | B.166 | C.5 |
| 1.1177 | B.167 | C.5 |
| 1.1178 | B.168 | C.5 |
| 1.1179 | B.169 | C.5 |
| 1.1180 | B.170 | C.5 |
| 1.1181 | B.171 | C.5 |
| 1.1182 | B.172 | C.5 |
| 1.1183 | B.173 | C.5 |
| 1.1184 | B.174 | C.5 |
| 1.1185 | B.175 | C.5 |
| 1.1186 | B.176 | C.5 |
| 1.1187 | B.177 | C.5 |
| 1.1188 | B.178 | C.5 |
| 1.1189 | B.179 | C.5 |
| 1.1190 | B.180 | C.5 |
| 1.1191 | B.181 | C.5 |
| 1.1192 | B.182 | C.5 |
| 1.1193 | B.183 | C.5 |
| 1.1194 | B.184 | C.5 |
| 1.1195 | B.185 | C.5 |
| 1.1196 | B.186 | C.5 |
| 1.1197 | B.187 | C.5 |
| 1.1198 | B.188 | C.5 |
| 1.1199 | B.189 | C.5 |
| 1.1200 | B.190 | C.5 |
| 1.1201 | B.191 | C.5 |
| 1.1202 | B.192 | C.5 |
| 1.1203 | B.193 | C.5 |
| 1.1204 | B.194 | C.5 |
| 1.1205 | B.195 | C.5 |
| 1.1206 | B.196 | C.5 |
| 1.1207 | B.197 | C.5 |
| 1.1208 | B.198 | C.5 |
| 1.1209 | B.199 | C.5 |
| 1.1210 | B.200 | C.5 |
| 1.1211 | B.201 | C.5 |
| 1.1212 | B.202 | C.5 |
| 1.1213 | B.1 | C.6 |
| 1.1214 | B.2 | C.6 |
| 1.1215 | B.3 | C.6 |
| 1.1216 | B.4 | C.6 |
| 1.1217 | B.5 | C.6 |
| 1.1218 | B.6 | C.6 |
| 1.1219 | B.7 | C.6 |
| 1.1220 | B.8 | C.6 |
| 1.1221 | B.9 | C.6 |
| 1.1222 | B.10 | C.6 |
| 1.1223 | B.11 | C.6 |
| 1.1224 | B.12 | C.6 |
| 1.1225 | B.13 | C.6 |
| 1.1226 | B.14 | C.6 |
| 1.1227 | B.15 | C.6 |
| 1.1228 | B.16 | C.6 |
| 1.1229 | B.17 | C.6 |
| 1.1230 | B.18 | C.6 |
| 1.1231 | B.19 | C.6 |
| 1.1232 | B.20 | C.6 |
| 1.1233 | B.21 | C.6 |
| 1.1234 | B.22 | C.6 |
| 1.1235 | B.23 | C.6 |
| 1.1236 | B.24 | C.6 |
| 1.1237 | B.25 | C.6 |
| 1.1238 | B.26 | C.6 |
| 1.1239 | B.27 | C.6 |
| 1.1240 | B.28 | C.6 |
| 1.1241 | B.29 | C.6 |
| 1.1242 | B.30 | C.6 |
| 1.1243 | B.31 | C.6 |

TABLE T-continued (compositions 1.1 to 1.3653):

| comp. no. | herbicide B | safener C |
|---|---|---|
| 1.1244 | B.32 | C.6 |
| 1.1245 | B.33 | C.6 |
| 1.1246 | B.34 | C.6 |
| 1.1247 | B.35 | C.6 |
| 1.1248 | B.36 | C.6 |
| 1.1249 | B.37 | C.6 |
| 1.1250 | B.38 | C.6 |
| 1.1251 | B.39 | C.6 |
| 1.1252 | B.40 | C.6 |
| 1.1253 | B.41 | C.6 |
| 1.1254 | B.42 | C.6 |
| 1.1255 | B.43 | C.6 |
| 1.1256 | B.44 | C.6 |
| 1.1257 | B.45 | C.6 |
| 1.1258 | B.46 | C.6 |
| 1.1259 | B.47 | C.6 |
| 1.1260 | B.48 | C.6 |
| 1.1261 | B.49 | C.6 |
| 1.1262 | B.50 | C.6 |
| 1.1263 | B.51 | C.6 |
| 1.1264 | B.52 | C.6 |
| 1.1265 | B.53 | C.6 |
| 1.1266 | B.54 | C.6 |
| 1.1267 | B.55 | C.6 |
| 1.1268 | B.56 | C.6 |
| 1.1269 | B.57 | C.6 |
| 1.1270 | B.58 | C.6 |
| 1.1271 | B.59 | C.6 |
| 1.1272 | B.60 | C.6 |
| 1.1273 | B.61 | C.6 |
| 1.1274 | B.62 | C.6 |
| 1.1275 | B.63 | C.6 |
| 1.1276 | B.64 | C.6 |
| 1.1277 | B.65 | C.6 |
| 1.1278 | B.66 | C.6 |
| 1.1279 | B.67 | C.6 |
| 1.1280 | B.68 | C.6 |
| 1.1281 | B.69 | C.6 |
| 1.1282 | B.70 | C.6 |
| 1.1283 | B.71 | C.6 |
| 1.1284 | B.72 | C.6 |
| 1.1285 | B.73 | C.6 |
| 1.1286 | B.74 | C.6 |
| 1.1287 | B.75 | C.6 |
| 1.1288 | B.76 | C.6 |
| 1.1289 | B.77 | C.6 |
| 1.1290 | B.78 | C.6 |
| 1.1291 | B.79 | C.6 |
| 1.1292 | B.80 | C.6 |
| 1.1293 | B.81 | C.6 |
| 1.1294 | B.82 | C.6 |
| 1.1295 | B.83 | C.6 |
| 1.1296 | B.84 | C.6 |
| 1.1297 | B.85 | C.6 |
| 1.1298 | B.86 | C.6 |
| 1.1299 | B.87 | C.6 |
| 1.1300 | B.88 | C.6 |
| 1.1301 | B.89 | C.6 |
| 1.1302 | B.90 | C.6 |
| 1.1303 | B.91 | C.6 |
| 1.1304 | B.92 | C.6 |
| 1.1305 | B.93 | C.6 |
| 1.1306 | B.94 | C.6 |
| 1.1307 | B.95 | C.6 |
| 1.1308 | B.96 | C.6 |
| 1.1309 | B.97 | C.6 |
| 1.1310 | B.98 | C.6 |
| 1.1311 | B.99 | C.6 |
| 1.1312 | B.100 | C.6 |
| 1.1313 | B.101 | C.6 |
| 1.1314 | B.102 | C.6 |
| 1.1315 | B.103 | C.6 |
| 1.1316 | B.104 | C.6 |
| 1.1317 | B.105 | C.6 |
| 1.1318 | B.106 | C.6 |
| 1.1319 | B.107 | C.6 |
| 1.1320 | B.108 | C.6 |
| 1.1321 | B.109 | C.6 |
| 1.1322 | B.110 | C.6 |
| 1.1323 | B.111 | C.6 |
| 1.1324 | B.112 | C.6 |
| 1.1325 | B.113 | C.6 |
| 1.1326 | B.114 | C.6 |
| 1.1327 | B.115 | C.6 |
| 1.1328 | B.116 | C.6 |
| 1.1329 | B.117 | C.6 |
| 1.1330 | B.118 | C.6 |
| 1.1331 | B.119 | C.6 |
| 1.1332 | B.120 | C.6 |
| 1.1333 | B.121 | C.6 |
| 1.1334 | B.122 | C.6 |
| 1.1335 | B.123 | C.6 |
| 1.1336 | B.124 | C.6 |
| 1.1337 | B.125 | C.6 |
| 1.1338 | B.126 | C.6 |
| 1.1339 | B.127 | C.6 |
| 1.1340 | B.128 | C.6 |
| 1.1341 | B.129 | C.6 |
| 1.1342 | B.130 | C.6 |
| 1.1343 | B.131 | C.6 |
| 1.1344 | B.132 | C.6 |
| 1.1345 | B.133 | C.6 |
| 1.1346 | B.134 | C.6 |
| 1.1347 | B.135 | C.6 |
| 1.1348 | B.136 | C.6 |
| 1.1349 | B.137 | C.6 |
| 1.1350 | B.138 | C.6 |
| 1.1351 | B.139 | C.6 |
| 1.1352 | B.140 | C.6 |
| 1.1353 | B.141 | C.6 |
| 1.1354 | B.142 | C.6 |
| 1.1355 | B.143 | C.6 |
| 1.1356 | B.144 | C.6 |
| 1.1357 | B.145 | C.6 |
| 1.1358 | B.146 | C.6 |
| 1.1359 | B.147 | C.6 |
| 1.1360 | B.148 | C.6 |
| 1.1361 | B.149 | C.6 |
| 1.1362 | B.150 | C.6 |
| 1.1363 | B.151 | C.6 |
| 1.1364 | B.152 | C.6 |
| 1.1365 | B.153 | C.6 |
| 1.1366 | B.154 | C.6 |
| 1.1367 | B.155 | C.6 |
| 1.1368 | B.156 | C.6 |
| 1.1369 | B.157 | C.6 |
| 1.1370 | B.158 | C.6 |
| 1.1371 | B.159 | C.6 |
| 1.1372 | B.160 | C.6 |
| 1.1373 | B.161 | C.6 |
| 1.1374 | B.162 | C.6 |
| 1.1375 | B.163 | C.6 |
| 1.1376 | B.164 | C.6 |
| 1.1377 | B.165 | C.6 |
| 1.1378 | B.166 | C.6 |
| 1.1379 | B.167 | C.6 |
| 1.1380 | B.168 | C.6 |
| 1.1381 | B.169 | C.6 |
| 1.1382 | B.170 | C.6 |
| 1.1383 | B.171 | C.6 |
| 1.1384 | B.172 | C.6 |
| 1.1385 | B.173 | C.6 |
| 1.1386 | B.174 | C.6 |
| 1.1387 | B.175 | C.6 |
| 1.1388 | B.176 | C.6 |
| 1.1389 | B.177 | C.6 |
| 1.1390 | B.178 | C.6 |
| 1.1391 | B.179 | C.6 |
| 1.1392 | B.180 | C.6 |
| 1.1393 | B.181 | C.6 |
| 1.1394 | B.182 | C.6 |
| 1.1395 | B.183 | C.6 |

TABLE T-continued (compositions 1.1 to 1.3653):

| comp. no. | herbicide B | safener C |
|---|---|---|
| 1.1396 | B.184 | C.6 |
| 1.1397 | B.185 | C.6 |
| 1.1398 | B.186 | C.6 |
| 1.1399 | B.187 | C.6 |
| 1.1400 | B.188 | C.6 |
| 1.1401 | B.189 | C.6 |
| 1.1402 | B.190 | C.6 |
| 1.1403 | B.191 | C.6 |
| 1.1404 | B.192 | C.6 |
| 1.1405 | B.193 | C.6 |
| 1.1406 | B.194 | C.6 |
| 1.1407 | B.195 | C.6 |
| 1.1408 | B.196 | C.6 |
| 1.1409 | B.197 | C.6 |
| 1.1410 | B.198 | C.6 |
| 1.1411 | B.199 | C.6 |
| 1.1412 | B.200 | C.6 |
| 1.1413 | B.201 | C.6 |
| 1.1414 | B.202 | C.6 |
| 1.1415 | B.1 | C.7 |
| 1.1416 | B.2 | C.7 |
| 1.1417 | B.3 | C.7 |
| 1.1418 | B.4 | C.7 |
| 1.1419 | B.5 | C.7 |
| 1.1420 | B.6 | C.7 |
| 1.1421 | B.7 | C.7 |
| 1.1422 | B.8 | C.7 |
| 1.1423 | B.9 | C.7 |
| 1.1424 | B.10 | C.7 |
| 1.1425 | B.11 | C.7 |
| 1.1426 | B.12 | C.7 |
| 1.1427 | B.13 | C.7 |
| 1.1428 | B.14 | C.7 |
| 1.1429 | B.15 | C.7 |
| 1.1430 | B.16 | C.7 |
| 1.1431 | B.17 | C.7 |
| 1.1432 | B.18 | C.7 |
| 1.1433 | B.19 | C.7 |
| 1.1434 | B.20 | C.7 |
| 1.1435 | B.21 | C.7 |
| 1.1436 | B.22 | C.7 |
| 1.1437 | B.23 | C.7 |
| 1.1438 | B.24 | C.7 |
| 1.1439 | B.25 | C.7 |
| 1.1440 | B.26 | C.7 |
| 1.1441 | B.27 | C.7 |
| 1.1442 | B.28 | C.7 |
| 1.1443 | B.29 | C.7 |
| 1.1444 | B.30 | C.7 |
| 1.1445 | B.31 | C.7 |
| 1.1446 | B.32 | C.7 |
| 1.1447 | B.33 | C.7 |
| 1.1448 | B.34 | C.7 |
| 1.1449 | B.35 | C.7 |
| 1.1450 | B.36 | C.7 |
| 1.1451 | B.37 | C.7 |
| 1.1452 | B.38 | C.7 |
| 1.1453 | B.39 | C.7 |
| 1.1454 | B.40 | C.7 |
| 1.1455 | B.41 | C.7 |
| 1.1456 | B.42 | C.7 |
| 1.1457 | B.43 | C.7 |
| 1.1458 | B.44 | C.7 |
| 1.1459 | B.45 | C.7 |
| 1.1460 | B.46 | C.7 |
| 1.1461 | B.47 | C.7 |
| 1.1462 | B.48 | C.7 |
| 1.1463 | B.49 | C.7 |
| 1.1464 | B.50 | C.7 |
| 1.1465 | B.51 | C.7 |
| 1.1466 | B.52 | C.7 |
| 1.1467 | B.53 | C.7 |
| 1.1468 | B.54 | C.7 |
| 1.1469 | B.55 | C.7 |
| 1.1470 | B.56 | C.7 |
| 1.1471 | B.57 | C.7 |
| 1.1472 | B.58 | C.7 |
| 1.1473 | B.59 | C.7 |
| 1.1474 | B.60 | C.7 |
| 1.1475 | B.61 | C.7 |
| 1.1476 | B.62 | C.7 |
| 1.1477 | B.63 | C.7 |
| 1.1478 | B.64 | C.7 |
| 1.1479 | B.65 | C.7 |
| 1.1480 | B.66 | C.7 |
| 1.1481 | B.67 | C.7 |
| 1.1482 | B.68 | C.7 |
| 1.1483 | B.69 | C.7 |
| 1.1484 | B.70 | C.7 |
| 1.1485 | B.71 | C.7 |
| 1.1486 | B.72 | C.7 |
| 1.1487 | B.73 | C.7 |
| 1.1488 | B.74 | C.7 |
| 1.1489 | B.75 | C.7 |
| 1.1490 | B.76 | C.7 |
| 1.1491 | B.77 | C.7 |
| 1.1492 | B.78 | C.7 |
| 1.1493 | B.79 | C.7 |
| 1.1494 | B.80 | C.7 |
| 1.1495 | B.81 | C.7 |
| 1.1496 | B.82 | C.7 |
| 1.1497 | B.83 | C.7 |
| 1.1498 | B.84 | C.7 |
| 1.1499 | B.85 | C.7 |
| 1.1500 | B.86 | C.7 |
| 1.1501 | B.87 | C.7 |
| 1.1502 | B.88 | C.7 |
| 1.1503 | B.89 | C.7 |
| 1.1504 | B.90 | C.7 |
| 1.1505 | B.91 | C.7 |
| 1.1506 | B.92 | C.7 |
| 1.1507 | B.93 | C.7 |
| 1.1508 | B.94 | C.7 |
| 1.1509 | B.95 | C.7 |
| 1.1510 | B.96 | C.7 |
| 1.1511 | B.97 | C.7 |
| 1.1512 | B.98 | C.7 |
| 1.1513 | B.99 | C.7 |
| 1.1514 | B.100 | C.7 |
| 1.1515 | B.101 | C.7 |
| 1.1516 | B.102 | C.7 |
| 1.1517 | B.103 | C.7 |
| 1.1518 | B.104 | C.7 |
| 1.1519 | B.105 | C.7 |
| 1.1520 | B.106 | C.7 |
| 1.1521 | B.107 | C.7 |
| 1.1522 | B.108 | C.7 |
| 1.1523 | B.109 | C.7 |
| 1.1524 | B.110 | C.7 |
| 1.1525 | B.111 | C.7 |
| 1.1526 | B.112 | C.7 |
| 1.1527 | B.113 | C.7 |
| 1.1528 | B.114 | C.7 |
| 1.1529 | B.115 | C.7 |
| 1.1530 | B.116 | C.7 |
| 1.1531 | B.117 | C.7 |
| 1.1532 | B.118 | C.7 |
| 1.1533 | B.119 | C.7 |
| 1.1534 | B.120 | C.7 |
| 1.1535 | B.121 | C.7 |
| 1.1536 | B.122 | C.7 |
| 1.1537 | B.123 | C.7 |
| 1.1538 | B.124 | C.7 |
| 1.1539 | B.125 | C.7 |
| 1.1540 | B.126 | C.7 |
| 1.1541 | B.127 | C.7 |
| 1.1542 | B.128 | C.7 |
| 1.1543 | B.129 | C.7 |
| 1.1544 | B.130 | C.7 |
| 1.1545 | B.131 | C.7 |
| 1.1546 | B.132 | C.7 |
| 1.1547 | B.133 | C.7 |

TABLE T-continued (compositions 1.1 to 1.3653):

| comp. no. | herbicide B | safener C |
|---|---|---|
| 1.1548 | B.134 | C.7 |
| 1.1549 | B.135 | C.7 |
| 1.1550 | B.136 | C.7 |
| 1.1551 | B.137 | C.7 |
| 1.1552 | B.138 | C.7 |
| 1.1553 | B.139 | C.7 |
| 1.1554 | B.140 | C.7 |
| 1.1555 | B.141 | C.7 |
| 1.1556 | B.142 | C.7 |
| 1.1557 | B.143 | C.7 |
| 1.1558 | B.144 | C.7 |
| 1.1559 | B.145 | C.7 |
| 1.1560 | B.146 | C.7 |
| 1.1561 | B.147 | C.7 |
| 1.1562 | B.148 | C.7 |
| 1.1563 | B.149 | C.7 |
| 1.1564 | B.150 | C.7 |
| 1.1565 | B.151 | C.7 |
| 1.1566 | B.152 | C.7 |
| 1.1567 | B.153 | C.7 |
| 1.1568 | B.154 | C.7 |
| 1.1569 | B.155 | C.7 |
| 1.1570 | B.156 | C.7 |
| 1.1571 | B.157 | C.7 |
| 1.1572 | B.158 | C.7 |
| 1.1573 | B.159 | C.7 |
| 1.1574 | B.160 | C.7 |
| 1.1575 | B.161 | C.7 |
| 1.1576 | B.162 | C.7 |
| 1.1577 | B.163 | C.7 |
| 1.1578 | B.164 | C.7 |
| 1.1579 | B.165 | C.7 |
| 1.1580 | B.166 | C.7 |
| 1.1581 | B.167 | C.7 |
| 1.1582 | B.168 | C.7 |
| 1.1583 | B.169 | C.7 |
| 1.1584 | B.170 | C.7 |
| 1.1585 | B.171 | C.7 |
| 1.1586 | B.172 | C.7 |
| 1.1587 | B.173 | C.7 |
| 1.1588 | B.174 | C.7 |
| 1.1589 | B.175 | C.7 |
| 1.1590 | B.176 | C.7 |
| 1.1591 | B.177 | C.7 |
| 1.1592 | B.178 | C.7 |
| 1.1593 | B.179 | C.7 |
| 1.1594 | B.180 | C.7 |
| 1.1595 | B.181 | C.7 |
| 1.1596 | B.182 | C.7 |
| 1.1597 | B.183 | C.7 |
| 1.1598 | B.184 | C.7 |
| 1.1599 | B.185 | C.7 |
| 1.1600 | B.186 | C.7 |
| 1.1601 | B.187 | C.7 |
| 1.1602 | B.188 | C.7 |
| 1.1603 | B.189 | C.7 |
| 1.1604 | B.190 | C.7 |
| 1.1605 | B.191 | C.7 |
| 1.1606 | B.192 | C.7 |
| 1.1607 | B.193 | C.7 |
| 1.1608 | B.194 | C.7 |
| 1.1609 | B.195 | C.7 |
| 1.1610 | B.196 | C.7 |
| 1.1611 | B.197 | C.7 |
| 1.1612 | B.198 | C.7 |
| 1.1613 | B.199 | C.7 |
| 1.1614 | B.200 | C.7 |
| 1.1615 | B.201 | C.7 |
| 1.1616 | B.202 | C.7 |
| 1.1617 | B.1 | C.8 |
| 1.1618 | B.2 | C.8 |
| 1.1619 | B.3 | C.8 |
| 1.1620 | B.4 | C.8 |
| 1.1621 | B.5 | C.8 |
| 1.1622 | B.6 | C.8 |
| 1.1623 | B.7 | C.8 |
| 1.1624 | B.8 | C.8 |
| 1.1625 | B.9 | C.8 |
| 1.1626 | B.10 | C.8 |
| 1.1627 | B.11 | C.8 |
| 1.1628 | B.12 | C.8 |
| 1.1629 | B.13 | C.8 |
| 1.1630 | B.14 | C.8 |
| 1.1631 | B.15 | C.8 |
| 1.1632 | B.16 | C.8 |
| 1.1633 | B.17 | C.8 |
| 1.1634 | B.18 | C.8 |
| 1.1635 | B.19 | C.8 |
| 1.1636 | B.20 | C.8 |
| 1.1637 | B.21 | C.8 |
| 1.1638 | B.22 | C.8 |
| 1.1639 | B.23 | C.8 |
| 1.1640 | B.24 | C.8 |
| 1.1641 | B.25 | C.8 |
| 1.1642 | B.26 | C.8 |
| 1.1643 | B.27 | C.8 |
| 1.1644 | B.28 | C.8 |
| 1.1645 | B.29 | C.8 |
| 1.1646 | B.30 | C.8 |
| 1.1647 | B.31 | C.8 |
| 1.1648 | B.32 | C.8 |
| 1.1649 | B.33 | C.8 |
| 1.1650 | B.34 | C.8 |
| 1.1651 | B.35 | C.8 |
| 1.1652 | B.36 | C.8 |
| 1.1653 | B.37 | C.8 |
| 1.1654 | B.38 | C.8 |
| 1.1655 | B.39 | C.8 |
| 1.1656 | B.40 | C.8 |
| 1.1657 | B.41 | C.8 |
| 1.1658 | B.42 | C.8 |
| 1.1659 | B.43 | C.8 |
| 1.1660 | B.44 | C.8 |
| 1.1661 | B.45 | C.8 |
| 1.1662 | B.46 | C.8 |
| 1.1663 | B.47 | C.8 |
| 1.1664 | B.48 | C.8 |
| 1.1665 | B.49 | C.8 |
| 1.1666 | B.50 | C.8 |
| 1.1667 | B.51 | C.8 |
| 1.1668 | B.52 | C.8 |
| 1.1669 | B.53 | C.8 |
| 1.1670 | B.54 | C.8 |
| 1.1671 | B.55 | C.8 |
| 1.1672 | B.56 | C.8 |
| 1.1673 | B.57 | C.8 |
| 1.1674 | B.58 | C.8 |
| 1.1675 | B.59 | C.8 |
| 1.1676 | B.60 | C.8 |
| 1.1677 | B.61 | C.8 |
| 1.1678 | B.62 | C.8 |
| 1.1679 | B.63 | C.8 |
| 1.1680 | B.64 | C.8 |
| 1.1681 | B.65 | C.8 |
| 1.1682 | B.66 | C.8 |
| 1.1683 | B.67 | C.8 |
| 1.1684 | B.68 | C.8 |
| 1.1685 | B.69 | C.8 |
| 1.1686 | B.70 | C.8 |
| 1.1687 | B.71 | C.8 |
| 1.1688 | B.72 | C.8 |
| 1.1689 | B.73 | C.8 |
| 1.1690 | B.74 | C.8 |
| 1.1691 | B.75 | C.8 |
| 1.1692 | B.76 | C.8 |
| 1.1693 | B.77 | C.8 |
| 1.1694 | B.78 | C.8 |
| 1.1695 | B.79 | C.8 |
| 1.1696 | B.80 | C.8 |
| 1.1697 | B.81 | C.8 |
| 1.1698 | B.82 | C.8 |
| 1.1699 | B.83 | C.8 |

TABLE T-continued (compositions 1.1 to 1.3653):

| comp. no. | herbicide B | safener C |
|---|---|---|
| 1.1700 | B.84 | C.8 |
| 1.1701 | B.85 | C.8 |
| 1.1702 | B.86 | C.8 |
| 1.1703 | B.87 | C.8 |
| 1.1704 | B.88 | C.8 |
| 1.1705 | B.89 | C.8 |
| 1.1706 | B.90 | C.8 |
| 1.1707 | B.91 | C.8 |
| 1.1708 | B.92 | C.8 |
| 1.1709 | B.93 | C.8 |
| 1.1710 | B.94 | C.8 |
| 1.1711 | B.95 | C.8 |
| 1.1712 | B.96 | C.8 |
| 1.1713 | B.97 | C.8 |
| 1.1714 | B.98 | C.8 |
| 1.1715 | B.99 | C.8 |
| 1.1716 | B.100 | C.8 |
| 1.1717 | B.101 | C.8 |
| 1.1718 | B.102 | C.8 |
| 1.1719 | B.103 | C.8 |
| 1.1720 | B.104 | C.8 |
| 1.1721 | B.105 | C.8 |
| 1.1722 | B.106 | C.8 |
| 1.1723 | B.107 | C.8 |
| 1.1724 | B.108 | C.8 |
| 1.1725 | B.109 | C.8 |
| 1.1726 | B.110 | C.8 |
| 1.1727 | B.111 | C.8 |
| 1.1728 | B.112 | C.8 |
| 1.1729 | B.113 | C.8 |
| 1.1730 | B.114 | C.8 |
| 1.1731 | B.115 | C.8 |
| 1.1732 | B.116 | C.8 |
| 1.1733 | B.117 | C.8 |
| 1.1734 | B.118 | C.8 |
| 1.1735 | B.119 | C.8 |
| 1.1736 | B.120 | C.8 |
| 1.1737 | B.121 | C.8 |
| 1.1738 | B.122 | C.8 |
| 1.1739 | B.123 | C.8 |
| 1.1740 | B.124 | C.8 |
| 1.1741 | B.125 | C.8 |
| 1.1742 | B.126 | C.8 |
| 1.1743 | B.127 | C.8 |
| 1.1744 | B.128 | C.8 |
| 1.1745 | B.129 | C.8 |
| 1.1746 | B.130 | C.8 |
| 1.1747 | B.131 | C.8 |
| 1.1748 | B.132 | C.8 |
| 1.1749 | B.133 | C.8 |
| 1.1750 | B.134 | C.8 |
| 1.1751 | B.135 | C.8 |
| 1.1752 | B.136 | C.8 |
| 1.1753 | B.137 | C.8 |
| 1.1754 | B.138 | C.8 |
| 1.1755 | B.139 | C.8 |
| 1.1756 | B.140 | C.8 |
| 1.1757 | B.141 | C.8 |
| 1.1758 | B.142 | C.8 |
| 1.1759 | B.143 | C.8 |
| 1.1760 | B.144 | C.8 |
| 1.1761 | B.145 | C.8 |
| 1.1762 | B.146 | C.8 |
| 1.1763 | B.147 | C.8 |
| 1.1764 | B.148 | C.8 |
| 1.1765 | B.149 | C.8 |
| 1.1766 | B.150 | C.8 |
| 1.1767 | B.151 | C.8 |
| 1.1768 | B.152 | C.8 |
| 1.1769 | B.153 | C.8 |
| 1.1770 | B.154 | C.8 |
| 1.1771 | B.155 | C.8 |
| 1.1772 | B.156 | C.8 |
| 1.1773 | B.157 | C.8 |
| 1.1774 | B.158 | C.8 |
| 1.1775 | B.159 | C.8 |
| 1.1776 | B.160 | C.8 |
| 1.1777 | B.161 | C.8 |
| 1.1778 | B.162 | C.8 |
| 1.1779 | B.163 | C.8 |
| 1.1780 | B.164 | C.8 |
| 1.1781 | B.165 | C.8 |
| 1.1782 | B.166 | C.8 |
| 1.1783 | B.167 | C.8 |
| 1.1784 | B.168 | C.8 |
| 1.1785 | B.169 | C.8 |
| 1.1786 | B.170 | C.8 |
| 1.1787 | B.171 | C.8 |
| 1.1788 | B.172 | C.8 |
| 1.1789 | B.173 | C.8 |
| 1.1790 | B.174 | C.8 |
| 1.1791 | B.175 | C.8 |
| 1.1792 | B.176 | C.8 |
| 1.1793 | B.177 | C.8 |
| 1.1794 | B.178 | C.8 |
| 1.1795 | B.179 | C.8 |
| 1.1796 | B.180 | C.8 |
| 1.1797 | B.181 | C.8 |
| 1.1798 | B.182 | C.8 |
| 1.1799 | B.183 | C.8 |
| 1.1800 | B.184 | C.8 |
| 1.1801 | B.185 | C.8 |
| 1.1802 | B.186 | C.8 |
| 1.1803 | B.187 | C.8 |
| 1.1804 | B.188 | C.8 |
| 1.1805 | B.189 | C.8 |
| 1.1806 | B.190 | C.8 |
| 1.1807 | B.191 | C.8 |
| 1.1808 | B.192 | C.8 |
| 1.1809 | B.193 | C.8 |
| 1.1810 | B.194 | C.8 |
| 1.1811 | B.195 | C.8 |
| 1.1812 | B.196 | C.8 |
| 1.1813 | B.197 | C.8 |
| 1.1814 | B.198 | C.8 |
| 1.1815 | B.199 | C.8 |
| 1.1816 | B.200 | C.8 |
| 1.1817 | B.201 | C.8 |
| 1.1818 | B.202 | C.8 |
| 1.1819 | B.1 | C.9 |
| 1.1820 | B.2 | C.9 |
| 1.1821 | B.3 | C.9 |
| 1.1822 | B.4 | C.9 |
| 1.1823 | B.5 | C.9 |
| 1.1824 | B.6 | C.9 |
| 1.1825 | B.7 | C.9 |
| 1.1826 | B.8 | C.9 |
| 1.1827 | B.9 | C.9 |
| 1.1828 | B.10 | C.9 |
| 1.1829 | B.11 | C.9 |
| 1.1830 | B.12 | C.9 |
| 1.1831 | B.13 | C.9 |
| 1.1832 | B.14 | C.9 |
| 1.1833 | B.15 | C.9 |
| 1.1834 | B.16 | C.9 |
| 1.1835 | B.17 | C.9 |
| 1.1836 | B.18 | C.9 |
| 1.1837 | B.19 | C.9 |
| 1.1838 | B.20 | C.9 |
| 1.1839 | B.21 | C.9 |
| 1.1840 | B.22 | C.9 |
| 1.1841 | B.23 | C.9 |
| 1.1842 | B.24 | C.9 |
| 1.1843 | B.25 | C.9 |
| 1.1844 | B.26 | C.9 |
| 1.1845 | B.27 | C.9 |
| 1.1846 | B.28 | C.9 |
| 1.1847 | B.29 | C.9 |
| 1.1848 | B.30 | C.9 |
| 1.1849 | B.31 | C.9 |
| 1.1850 | B.32 | C.9 |
| 1.1851 | B.33 | C.9 |

TABLE T-continued (compositions 1.1 to 1.3653):

| comp. no. | herbicide B | safener C |
|---|---|---|
| 1.1852 | B.34 | C.9 |
| 1.1853 | B.35 | C.9 |
| 1.1854 | B.36 | C.9 |
| 1.1855 | B.37 | C.9 |
| 1.1856 | B.38 | C.9 |
| 1.1857 | B.39 | C.9 |
| 1.1858 | B.40 | C.9 |
| 1.1859 | B.41 | C.9 |
| 1.1860 | B.42 | C.9 |
| 1.1861 | B.43 | C.9 |
| 1.1862 | B.44 | C.9 |
| 1.1863 | B.45 | C.9 |
| 1.1864 | B.46 | C.9 |
| 1.1865 | B.47 | C.9 |
| 1.1866 | B.48 | C.9 |
| 1.1867 | B.49 | C.9 |
| 1.1868 | B.50 | C.9 |
| 1.1869 | B.51 | C.9 |
| 1.1870 | B.52 | C.9 |
| 1.1871 | B.53 | C.9 |
| 1.1872 | B.54 | C.9 |
| 1.1873 | B.55 | C.9 |
| 1.1874 | B.56 | C.9 |
| 1.1875 | B.57 | C.9 |
| 1.1876 | B.58 | C.9 |
| 1.1877 | B.59 | C.9 |
| 1.1878 | B.60 | C.9 |
| 1.1879 | B.61 | C.9 |
| 1.1880 | B.62 | C.9 |
| 1.1881 | B.63 | C.9 |
| 1.1882 | B.64 | C.9 |
| 1.1883 | B.65 | C.9 |
| 1.1884 | B.66 | C.9 |
| 1.1885 | B.67 | C.9 |
| 1.1886 | B.68 | C.9 |
| 1.1887 | B.69 | C.9 |
| 1.1888 | B.70 | C.9 |
| 1.1889 | B.71 | C.9 |
| 1.1890 | B.72 | C.9 |
| 1.1891 | B.73 | C.9 |
| 1.1892 | B.74 | C.9 |
| 1.1893 | B.75 | C.9 |
| 1.1894 | B.76 | C.9 |
| 1.1895 | B.77 | C.9 |
| 1.1896 | B.78 | C.9 |
| 1.1897 | B.79 | C.9 |
| 1.1898 | B.80 | C.9 |
| 1.1899 | B.81 | C.9 |
| 1.1900 | B.82 | C.9 |
| 1.1901 | B.83 | C.9 |
| 1.1902 | B.84 | C.9 |
| 1.1903 | B.85 | C.9 |
| 1.1904 | B.86 | C.9 |
| 1.1905 | B.87 | C.9 |
| 1.1906 | B.88 | C.9 |
| 1.1907 | B.89 | C.9 |
| 1.1908 | B.90 | C.9 |
| 1.1909 | B.91 | C.9 |
| 1.1910 | B.92 | C.9 |
| 1.1911 | B.93 | C.9 |
| 1.1912 | B.94 | C.9 |
| 1.1913 | B.95 | C.9 |
| 1.1914 | B.96 | C.9 |
| 1.1915 | B.97 | C.9 |
| 1.1916 | B.98 | C.9 |
| 1.1917 | B.99 | C.9 |
| 1.1918 | B.100 | C.9 |
| 1.1919 | B.101 | C.9 |
| 1.1920 | B.102 | C.9 |
| 1.1921 | B.103 | C.9 |
| 1.1922 | B.104 | C.9 |
| 1.1923 | B.105 | C.9 |
| 1.1924 | B.106 | C.9 |
| 1.1925 | B.107 | C.9 |
| 1.1926 | B.108 | C.9 |
| 1.1927 | B.109 | C.9 |
| 1.1928 | B.110 | C.9 |
| 1.1929 | B.111 | C.9 |
| 1.1930 | B.112 | C.9 |
| 1.1931 | B.113 | C.9 |
| 1.1932 | B.114 | C.9 |
| 1.1933 | B.115 | C.9 |
| 1.1934 | B.116 | C.9 |
| 1.1935 | B.117 | C.9 |
| 1.1936 | B.118 | C.9 |
| 1.1937 | B.119 | C.9 |
| 1.1938 | B.120 | C.9 |
| 1.1939 | B.121 | C.9 |
| 1.1940 | B.122 | C.9 |
| 1.1941 | B.123 | C.9 |
| 1.1942 | B.124 | C.9 |
| 1.1943 | B.125 | C.9 |
| 1.1944 | B.126 | C.9 |
| 1.1945 | B.127 | C.9 |
| 1.1946 | B.128 | C.9 |
| 1.1947 | B.129 | C.9 |
| 1.1948 | B.130 | C.9 |
| 1.1949 | B.131 | C.9 |
| 1.1950 | B.132 | C.9 |
| 1.1951 | B.133 | C.9 |
| 1.1952 | B.134 | C.9 |
| 1.1953 | B.135 | C.9 |
| 1.1954 | B.136 | C.9 |
| 1.1955 | B.137 | C.9 |
| 1.1956 | B.138 | C.9 |
| 1.1957 | B.139 | C.9 |
| 1.1958 | B.140 | C.9 |
| 1.1959 | B.141 | C.9 |
| 1.1960 | B.142 | C.9 |
| 1.1961 | B.143 | C.9 |
| 1.1962 | B.144 | C.9 |
| 1.1963 | B.145 | C.9 |
| 1.1964 | B.146 | C.9 |
| 1.1965 | B.147 | C.9 |
| 1.1966 | B.148 | C.9 |
| 1.1967 | B.149 | C.9 |
| 1.1968 | B.150 | C.9 |
| 1.1969 | B.151 | C.9 |
| 1.1970 | B.152 | C.9 |
| 1.1971 | B.153 | C.9 |
| 1.1972 | B.154 | C.9 |
| 1.1973 | B.155 | C.9 |
| 1.1974 | B.156 | C.9 |
| 1.1975 | B.157 | C.9 |
| 1.1976 | B.158 | C.9 |
| 1.1977 | B.159 | C.9 |
| 1.1978 | B.160 | C.9 |
| 1.1979 | B.161 | C.9 |
| 1.1980 | B.162 | C.9 |
| 1.1981 | B.163 | C.9 |
| 1.1982 | B.164 | C.9 |
| 1.1983 | B.165 | C.9 |
| 1.1984 | B.166 | C.9 |
| 1.1985 | B.167 | C.9 |
| 1.1986 | B.168 | C.9 |
| 1.1987 | B.169 | C.9 |
| 1.1988 | B.170 | C.9 |
| 1.1989 | B.171 | C.9 |
| 1.1990 | B.172 | C.9 |
| 1.1991 | B.173 | C.9 |
| 1.1992 | B.174 | C.9 |
| 1.1993 | B.175 | C.9 |
| 1.1994 | B.176 | C.9 |
| 1.1995 | B.177 | C.9 |
| 1.1996 | B.178 | C.9 |
| 1.1997 | B.179 | C.9 |
| 1.1998 | B.180 | C.9 |
| 1.1999 | B.181 | C.9 |
| 1.2000 | B.182 | C.9 |
| 1.2001 | B.183 | C.9 |
| 1.2002 | B.184 | C.9 |
| 1.2003 | B.185 | C.9 |

TABLE T-continued (compositions 1.1 to 1.3653):

| comp. no. | herbicide B | safener C |
|---|---|---|
| 1.2004 | B.186 | C.9 |
| 1.2005 | B.187 | C.9 |
| 1.2006 | B.188 | C.9 |
| 1.2007 | B.189 | C.9 |
| 1.2008 | B.190 | C.9 |
| 1.2009 | B.191 | C.9 |
| 1.2010 | B.192 | C.9 |
| 1.2011 | B.193 | C.9 |
| 1.2012 | B.194 | C.9 |
| 1.2013 | B.195 | C.9 |
| 1.2014 | B.196 | C.9 |
| 1.2015 | B.197 | C.9 |
| 1.2016 | B.198 | C.9 |
| 1.2017 | B.199 | C.9 |
| 1.2018 | B.200 | C.9 |
| 1.2019 | B.201 | C.9 |
| 1.2020 | B.202 | C.9 |
| 1.2021 | B.1 | C.10 |
| 1.2022 | B.2 | C.10 |
| 1.2023 | B.3 | C.10 |
| 1.2024 | B.4 | C.10 |
| 1.2025 | B.5 | C.10 |
| 1.2026 | B.6 | C.10 |
| 1.2027 | B.7 | C.10 |
| 1.2028 | B.8 | C.10 |
| 1.2029 | B.9 | C.10 |
| 1.2030 | B.10 | C.10 |
| 1.2031 | B.11 | C.10 |
| 1.2032 | B.12 | C.10 |
| 1.2033 | B.13 | C.10 |
| 1.2034 | B.14 | C.10 |
| 1.2035 | B.15 | C.10 |
| 1.2036 | B.16 | C.10 |
| 1.2037 | B.17 | C.10 |
| 1.2038 | B.18 | C.10 |
| 1.2039 | B.19 | C.10 |
| 1.2040 | B.20 | C.10 |
| 1.2041 | B.21 | C.10 |
| 1.2042 | B.22 | C.10 |
| 1.2043 | B.23 | C.10 |
| 1.2044 | B.24 | C.10 |
| 1.2045 | B.25 | C.10 |
| 1.2046 | B.26 | C.10 |
| 1.2047 | B.27 | C.10 |
| 1.2048 | B.28 | C.10 |
| 1.2049 | B.29 | C.10 |
| 1.2050 | B.30 | C.10 |
| 1.2051 | B.31 | C.10 |
| 1.2052 | B.32 | C.10 |
| 1.2053 | B.33 | C.10 |
| 1.2054 | B.34 | C.10 |
| 1.2055 | B.35 | C.10 |
| 1.2056 | B.36 | C.10 |
| 1.2057 | B.37 | C.10 |
| 1.2058 | B.38 | C.10 |
| 1.2059 | B.39 | C.10 |
| 1.2060 | B.40 | C.10 |
| 1.2061 | B.41 | C.10 |
| 1.2062 | B.42 | C.10 |
| 1.2063 | B.43 | C.10 |
| 1.2064 | B.44 | C.10 |
| 1.2065 | B.45 | C.10 |
| 1.2066 | B.46 | C.10 |
| 1.2067 | B.47 | C.10 |
| 1.2068 | B.48 | C.10 |
| 1.2069 | B.49 | C.10 |
| 1.2070 | B.50 | C.10 |
| 1.2071 | B.51 | C.10 |
| 1.2072 | B.52 | C.10 |
| 1.2073 | B.53 | C.10 |
| 1.2074 | B.54 | C.10 |
| 1.2075 | B.55 | C.10 |
| 1.2076 | B.56 | C.10 |
| 1.2077 | B.57 | C.10 |
| 1.2078 | B.58 | C.10 |
| 1.2079 | B.59 | C.10 |
| 1.2080 | B.60 | C.10 |
| 1.2081 | B.61 | C.10 |
| 1.2082 | B.62 | C.10 |
| 1.2083 | B.63 | C.10 |
| 1.2084 | B.64 | C.10 |
| 1.2085 | B.65 | C.10 |
| 1.2086 | B.66 | C.10 |
| 1.2087 | B.67 | C.10 |
| 1.2088 | B.68 | C.10 |
| 1.2089 | B.69 | C.10 |
| 1.2090 | B.70 | C.10 |
| 1.2091 | B.71 | C.10 |
| 1.2092 | B.72 | C.10 |
| 1.2093 | B.73 | C.10 |
| 1.2094 | B.74 | C.10 |
| 1.2095 | B.75 | C.10 |
| 1.2096 | B.76 | C.10 |
| 1.2097 | B.77 | C.10 |
| 1.2098 | B.78 | C.10 |
| 1.2099 | B.79 | C.10 |
| 1.2100 | B.80 | C.10 |
| 1.2101 | B.81 | C.10 |
| 1.2102 | B.82 | C.10 |
| 1.2103 | B.83 | C.10 |
| 1.2104 | B.84 | C.10 |
| 1.2105 | B.85 | C.10 |
| 1.2106 | B.86 | C.10 |
| 1.2107 | B.87 | C.10 |
| 1.2108 | B.88 | C.10 |
| 1.2109 | B.89 | C.10 |
| 1.2110 | B.90 | C.10 |
| 1.2111 | B.91 | C.10 |
| 1.2112 | B.92 | C.10 |
| 1.2113 | B.93 | C.10 |
| 1.2114 | B.94 | C.10 |
| 1.2115 | B.95 | C.10 |
| 1.2116 | B.96 | C.10 |
| 1.2117 | B.97 | C.10 |
| 1.2118 | B.98 | C.10 |
| 1.2119 | B.99 | C.10 |
| 1.2120 | B.100 | C.10 |
| 1.2121 | B.101 | C.10 |
| 1.2122 | B.102 | C.10 |
| 1.2123 | B.103 | C.10 |
| 1.2124 | B.104 | C.10 |
| 1.2125 | B.105 | C.10 |
| 1.2126 | B.106 | C.10 |
| 1.2127 | B.107 | C.10 |
| 1.2128 | B.108 | C.10 |
| 1.2129 | B.109 | C.10 |
| 1.2130 | B.110 | C.10 |
| 1.2131 | B.111 | C.10 |
| 1.2132 | B.112 | C.10 |
| 1.2133 | B.113 | C.10 |
| 1.2134 | B.114 | C.10 |
| 1.2135 | B.115 | C.10 |
| 1.2136 | B.116 | C.10 |
| 1.2137 | B.117 | C.10 |
| 1.2138 | B.118 | C.10 |
| 1.2139 | B.119 | C.10 |
| 1.2140 | B.120 | C.10 |
| 1.2141 | B.121 | C.10 |
| 1.2142 | B.122 | C.10 |
| 1.2143 | B.123 | C.10 |
| 1.2144 | B.124 | C.10 |
| 1.2145 | B.125 | C.10 |
| 1.2146 | B.126 | C.10 |
| 1.2147 | B.127 | C.10 |
| 1.2148 | B.128 | C.10 |
| 1.2149 | B.129 | C.10 |
| 1.2150 | B.130 | C.10 |
| 1.2151 | B.131 | C.10 |
| 1.2152 | B.132 | C.10 |
| 1.2153 | B.133 | C.10 |
| 1.2154 | B.134 | C.10 |
| 1.2155 | B.135 | C.10 |

TABLE T-continued (compositions 1.1 to 1.3653):

| comp. no. | herbicide B | safener C |
|---|---|---|
| 1.2156 | B.136 | C.10 |
| 1.2157 | B.137 | C.10 |
| 1.2158 | B.138 | C.10 |
| 1.2159 | B.139 | C.10 |
| 1.2160 | B.140 | C.10 |
| 1.2161 | B.141 | C.10 |
| 1.2162 | B.142 | C.10 |
| 1.2163 | B.143 | C.10 |
| 1.2164 | B.144 | C.10 |
| 1.2165 | B.145 | C.10 |
| 1.2166 | B.146 | C.10 |
| 1.2167 | B.147 | C.10 |
| 1.2168 | B.148 | C.10 |
| 1.2169 | B.149 | C.10 |
| 1.2170 | B.150 | C.10 |
| 1.2171 | B.151 | C.10 |
| 1.2172 | B.152 | C.10 |
| 1.2173 | B.153 | C.10 |
| 1.2174 | B.154 | C.10 |
| 1.2175 | B.155 | C.10 |
| 1.2176 | B.156 | C.10 |
| 1.2177 | B.157 | C.10 |
| 1.2178 | B.158 | C.10 |
| 1.2179 | B.159 | C.10 |
| 1.2180 | B.160 | C.10 |
| 1.2181 | B.161 | C.10 |
| 1.2182 | B.162 | C.10 |
| 1.2183 | B.163 | C.10 |
| 1.2184 | B.164 | C.10 |
| 1.2185 | B.165 | C.10 |
| 1.2186 | B.166 | C.10 |
| 1.2187 | B.167 | C.10 |
| 1.2188 | B.168 | C.10 |
| 1.2189 | B.169 | C.10 |
| 1.2190 | B.170 | C.10 |
| 1.2191 | B.171 | C.10 |
| 1.2192 | B.172 | C.10 |
| 1.2193 | B.173 | C.10 |
| 1.2194 | B.174 | C.10 |
| 1.2195 | B.175 | C.10 |
| 1.2196 | B.176 | C.10 |
| 1.2197 | B.177 | C.10 |
| 1.2198 | B.178 | C.10 |
| 1.2199 | B.179 | C.10 |
| 1.2200 | B.180 | C.10 |
| 1.2201 | B.181 | C.10 |
| 1.2202 | B.182 | C.10 |
| 1.2203 | B.183 | C.10 |
| 1.2204 | B.184 | C.10 |
| 1.2205 | B.185 | C.10 |
| 1.2206 | B.186 | C.10 |
| 1.2207 | B.187 | C.10 |
| 1.2208 | B.188 | C.10 |
| 1.2209 | B.189 | C.10 |
| 1.2210 | B.190 | C.10 |
| 1.2211 | B.191 | C.10 |
| 1.2212 | B.192 | C.10 |
| 1.2213 | B.193 | C.10 |
| 1.2214 | B.194 | C.10 |
| 1.2215 | B.195 | C.10 |
| 1.2216 | B.196 | C.10 |
| 1.2217 | B.197 | C.10 |
| 1.2218 | B.198 | C.10 |
| 1.2219 | B.199 | C.10 |
| 1.2220 | B.200 | C.10 |
| 1.2221 | B.201 | C.10 |
| 1.2222 | B.202 | C.10 |
| 1.2223 | B.1 | C.11 |
| 1.2224 | B.2 | C.11 |
| 1.2225 | B.3 | C.11 |
| 1.2226 | B.4 | C.11 |
| 1.2227 | B.5 | C.11 |
| 1.2228 | B.6 | C.11 |
| 1.2229 | B.7 | C.11 |
| 1.2230 | B.8 | C.11 |
| 1.2231 | B.9 | C.11 |
| 1.2232 | B.10 | C.11 |
| 1.2233 | B.11 | C.11 |
| 1.2234 | B.12 | C.11 |
| 1.2235 | B.13 | C.11 |
| 1.2236 | B.14 | C.11 |
| 1.2237 | B.15 | C.11 |
| 1.2238 | B.16 | C.11 |
| 1.2239 | B.17 | C.11 |
| 1.2240 | B.18 | C.11 |
| 1.2241 | B.19 | C.11 |
| 1.2242 | B.20 | C.11 |
| 1.2243 | B.21 | C.11 |
| 1.2244 | B.22 | C.11 |
| 1.2245 | B.23 | C.11 |
| 1.2246 | B.24 | C.11 |
| 1.2247 | B.25 | C.11 |
| 1.2248 | B.26 | C.11 |
| 1.2249 | B.27 | C.11 |
| 1.2250 | B.28 | C.11 |
| 1.2251 | B.29 | C.11 |
| 1.2252 | B.30 | C.11 |
| 1.2253 | B.31 | C.11 |
| 1.2254 | B.32 | C.11 |
| 1.2255 | B.33 | C.11 |
| 1.2256 | B.34 | C.11 |
| 1.2257 | B.35 | C.11 |
| 1.2258 | B.36 | C.11 |
| 1.2259 | B.37 | C.11 |
| 1.2260 | B.38 | C.11 |
| 1.2261 | B.39 | C.11 |
| 1.2262 | B.40 | C.11 |
| 1.2263 | B.41 | C.11 |
| 1.2264 | B.42 | C.11 |
| 1.2265 | B.43 | C.11 |
| 1.2266 | B.44 | C.11 |
| 1.2267 | B.45 | C.11 |
| 1.2268 | B.46 | C.11 |
| 1.2269 | B.47 | C.11 |
| 1.2270 | B.48 | C.11 |
| 1.2271 | B.49 | C.11 |
| 1.2272 | B.50 | C.11 |
| 1.2273 | B.51 | C.11 |
| 1.2274 | B.52 | C.11 |
| 1.2275 | B.53 | C.11 |
| 1.2276 | B.54 | C.11 |
| 1.2277 | B.55 | C.11 |
| 1.2278 | B.56 | C.11 |
| 1.2279 | B.57 | C.11 |
| 1.2280 | B.58 | C.11 |
| 1.2281 | B.59 | C.11 |
| 1.2282 | B.60 | C.11 |
| 1.2283 | B.61 | C.11 |
| 1.2284 | B.62 | C.11 |
| 1.2285 | B.63 | C.11 |
| 1.2286 | B.64 | C.11 |
| 1.2287 | B.65 | C.11 |
| 1.2288 | B.66 | C.11 |
| 1.2289 | B.67 | C.11 |
| 1.2290 | B.68 | C.11 |
| 1.2291 | B.69 | C.11 |
| 1.2292 | B.70 | C.11 |
| 1.2293 | B.71 | C.11 |
| 1.2294 | B.72 | C.11 |
| 1.2295 | B.73 | C.11 |
| 1.2296 | B.74 | C.11 |
| 1.2297 | B.75 | C.11 |
| 1.2298 | B.76 | C.11 |
| 1.2299 | B.77 | C.11 |
| 1.2300 | B.78 | C.11 |
| 1.2301 | B.79 | C.11 |
| 1.2302 | B.80 | C.11 |
| 1.2303 | B.81 | C.11 |
| 1.2304 | B.82 | C.11 |
| 1.2305 | B.83 | C.11 |
| 1.2306 | B.84 | C.11 |
| 1.2307 | B.85 | C.11 |

TABLE T-continued (compositions 1.1 to 1.3653):

| comp. no. | herbicide B | safener C |
|---|---|---|
| 1.2308 | B.86 | C.11 |
| 1.2309 | B.87 | C.11 |
| 1.2310 | B.88 | C.11 |
| 1.2311 | B.89 | C.11 |
| 1.2312 | B.90 | C.11 |
| 1.2313 | B.91 | C.11 |
| 1.2314 | B.92 | C.11 |
| 1.2315 | B.93 | C.11 |
| 1.2316 | B.94 | C.11 |
| 1.2317 | B.95 | C.11 |
| 1.2318 | B.96 | C.11 |
| 1.2319 | B.97 | C.11 |
| 1.2320 | B.98 | C.11 |
| 1.2321 | B.99 | C.11 |
| 1.2322 | B.100 | C.11 |
| 1.2323 | B.101 | C.11 |
| 1.2324 | B.102 | C.11 |
| 1.2325 | B.103 | C.11 |
| 1.2326 | B.104 | C.11 |
| 1.2327 | B.105 | C.11 |
| 1.2328 | B.106 | C.11 |
| 1.2329 | B.107 | C.11 |
| 1.2330 | B.108 | C.11 |
| 1.2331 | B.109 | C.11 |
| 1.2332 | B.110 | C.11 |
| 1.2333 | B.111 | C.11 |
| 1.2334 | B.112 | C.11 |
| 1.2335 | B.113 | C.11 |
| 1.2336 | B.114 | C.11 |
| 1.2337 | B.115 | C.11 |
| 1.2338 | B.116 | C.11 |
| 1.2339 | B.117 | C.11 |
| 1.2340 | B.118 | C.11 |
| 1.2341 | B.119 | C.11 |
| 1.2342 | B.120 | C.11 |
| 1.2343 | B.121 | C.11 |
| 1.2344 | B.122 | C.11 |
| 1.2345 | B.123 | C.11 |
| 1.2346 | B.124 | C.11 |
| 1.2347 | B.125 | C.11 |
| 1.2348 | B.126 | C.11 |
| 1.2349 | B.127 | C.11 |
| 1.2350 | B.128 | C.11 |
| 1.2351 | B.129 | C.11 |
| 1.2352 | B.130 | C.11 |
| 1.2353 | B.131 | C.11 |
| 1.2354 | B.132 | C.11 |
| 1.2355 | B.133 | C.11 |
| 1.2356 | B.134 | C.11 |
| 1.2357 | B.135 | C.11 |
| 1.2358 | B.136 | C.11 |
| 1.2359 | B.137 | C.11 |
| 1.2360 | B.138 | C.11 |
| 1.2361 | B.139 | C.11 |
| 1.2362 | B.140 | C.11 |
| 1.2363 | B.141 | C.11 |
| 1.2364 | B.142 | C.11 |
| 1.2365 | B.143 | C.11 |
| 1.2366 | B.144 | C.11 |
| 1.2367 | B.145 | C.11 |
| 1.2368 | B.146 | C.11 |
| 1.2369 | B.147 | C.11 |
| 1.2370 | B.148 | C.11 |
| 1.2371 | B.149 | C.11 |
| 1.2372 | B.150 | C.11 |
| 1.2373 | B.151 | C.11 |
| 1.2374 | B.152 | C.11 |
| 1.2375 | B.153 | C.11 |
| 1.2376 | B.154 | C.11 |
| 1.2377 | B.155 | C.11 |
| 1.2378 | B.156 | C.11 |
| 1.2379 | B.157 | C.11 |
| 1.2380 | B.158 | C.11 |
| 1.2381 | B.159 | C.11 |
| 1.2382 | B.160 | C.11 |
| 1.2383 | B.161 | C.11 |
| 1.2384 | B.162 | C.11 |
| 1.2385 | B.163 | C.11 |
| 1.2386 | B.164 | C.11 |
| 1.2387 | B.165 | C.11 |
| 1.2388 | B.166 | C.11 |
| 1.2389 | B.167 | C.11 |
| 1.2390 | B.168 | C.11 |
| 1.2391 | B.169 | C.11 |
| 1.2392 | B.170 | C.11 |
| 1.2393 | B.171 | C.11 |
| 1.2394 | B.172 | C.11 |
| 1.2395 | B.173 | C.11 |
| 1.2396 | B.174 | C.11 |
| 1.2397 | B.175 | C.11 |
| 1.2398 | B.176 | C.11 |
| 1.2399 | B.177 | C.11 |
| 1.2400 | B.178 | C.11 |
| 1.2401 | B.179 | C.11 |
| 1.2402 | B.180 | C.11 |
| 1.2403 | B.181 | C.11 |
| 1.2404 | B.182 | C.11 |
| 1.2405 | B.183 | C.11 |
| 1.2406 | B.184 | C.11 |
| 1.2407 | B.185 | C.11 |
| 1.2408 | B.186 | C.11 |
| 1.2409 | B.187 | C.11 |
| 1.2410 | B.188 | C.11 |
| 1.2411 | B.189 | C.11 |
| 1.2412 | B.190 | C.11 |
| 1.2413 | B.191 | C.11 |
| 1.2414 | B.192 | C.11 |
| 1.2415 | B.193 | C.11 |
| 1.2416 | B.194 | C.11 |
| 1.2417 | B.195 | C.11 |
| 1.2418 | B.196 | C.11 |
| 1.2419 | B.197 | C.11 |
| 1.2420 | B.198 | C.11 |
| 1.2421 | B.199 | C.11 |
| 1.2422 | B.200 | C.11 |
| 1.2423 | B.201 | C.11 |
| 1.2424 | B.202 | C.11 |
| 1.2425 | B.1 | C.12 |
| 1.2426 | B.2 | C.12 |
| 1.2427 | B.3 | C.12 |
| 1.2428 | B.4 | C.12 |
| 1.2429 | B.5 | C.12 |
| 1.2430 | B.6 | C.12 |
| 1.2431 | B.7 | C.12 |
| 1.2432 | B.8 | C.12 |
| 1.2433 | B.9 | C.12 |
| 1.2434 | B.10 | C.12 |
| 1.2435 | B.11 | C.12 |
| 1.2436 | B.12 | C.12 |
| 1.2437 | B.13 | C.12 |
| 1.2438 | B.14 | C.12 |
| 1.2439 | B.15 | C.12 |
| 1.2440 | B.16 | C.12 |
| 1.2441 | B.17 | C.12 |
| 1.2442 | B.18 | C.12 |
| 1.2443 | B.19 | C.12 |
| 1.2444 | B.20 | C.12 |
| 1.2445 | B.21 | C.12 |
| 1.2446 | B.22 | C.12 |
| 1.2447 | B.23 | C.12 |
| 1.2448 | B.24 | C.12 |
| 1.2449 | B.25 | C.12 |
| 1.2450 | B.26 | C.12 |
| 1.2451 | B.27 | C.12 |
| 1.2452 | B.28 | C.12 |
| 1.2453 | B.29 | C.12 |
| 1.2454 | B.30 | C.12 |
| 1.2455 | B.31 | C.12 |
| 1.2456 | B.32 | C.12 |
| 1.2457 | B.33 | C.12 |
| 1.2458 | B.34 | C.12 |
| 1.2459 | B.35 | C.12 |

TABLE T-continued (compositions 1.1 to 1.3653):

| comp. no. | herbicide B | safener C |
|---|---|---|
| 1.2460 | B.36 | C.12 |
| 1.2461 | B.37 | C.12 |
| 1.2462 | B.38 | C.12 |
| 1.2463 | B.39 | C.12 |
| 1.2464 | B.40 | C.12 |
| 1.2465 | B.41 | C.12 |
| 1.2466 | B.42 | C.12 |
| 1.2467 | B.43 | C.12 |
| 1.2468 | B.44 | C.12 |
| 1.2469 | B.45 | C.12 |
| 1.2470 | B.46 | C.12 |
| 1.2471 | B.47 | C.12 |
| 1.2472 | B.48 | C.12 |
| 1.2473 | B.49 | C.12 |
| 1.2474 | B.50 | C.12 |
| 1.2475 | B.51 | C.12 |
| 1.2476 | B.52 | C.12 |
| 1.2477 | B.53 | C.12 |
| 1.2478 | B.54 | C.12 |
| 1.2479 | B.55 | C.12 |
| 1.2480 | B.56 | C.12 |
| 1.2481 | B.57 | C.12 |
| 1.2482 | B.58 | C.12 |
| 1.2483 | B.59 | C.12 |
| 1.2484 | B.60 | C.12 |
| 1.2485 | B.61 | C.12 |
| 1.2486 | B.62 | C.12 |
| 1.2487 | B.63 | C.12 |
| 1.2488 | B.64 | C.12 |
| 1.2489 | B.65 | C.12 |
| 1.2490 | B.66 | C.12 |
| 1.2491 | B.67 | C.12 |
| 1.2492 | B.68 | C.12 |
| 1.2493 | B.69 | C.12 |
| 1.2494 | B.70 | C.12 |
| 1.2495 | B.71 | C.12 |
| 1.2496 | B.72 | C.12 |
| 1.2497 | B.73 | C.12 |
| 1.2498 | B.74 | C.12 |
| 1.2499 | B.75 | C.12 |
| 1.2500 | B.76 | C.12 |
| 1.2501 | B.77 | C.12 |
| 1.2502 | B.78 | C.12 |
| 1.2503 | B.79 | C.12 |
| 1.2504 | B.80 | C.12 |
| 1.2505 | B.81 | C.12 |
| 1.2506 | B.82 | C.12 |
| 1.2507 | B.83 | C.12 |
| 1.2508 | B.84 | C.12 |
| 1.2509 | B.85 | C.12 |
| 1.2510 | B.86 | C.12 |
| 1.2511 | B.87 | C.12 |
| 1.2512 | B.88 | C.12 |
| 1.2513 | B.89 | C.12 |
| 1.2514 | B.90 | C.12 |
| 1.2515 | B.91 | C.12 |
| 1.2516 | B.92 | C.12 |
| 1.2517 | B.93 | C.12 |
| 1.2518 | B.94 | C.12 |
| 1.2519 | B.95 | C.12 |
| 1.2520 | B.96 | C.12 |
| 1.2521 | B.97 | C.12 |
| 1.2522 | B.98 | C.12 |
| 1.2523 | B.99 | C.12 |
| 1.2524 | B.100 | C.12 |
| 1.2525 | B.101 | C.12 |
| 1.2526 | B.102 | C.12 |
| 1.2527 | B.103 | C.12 |
| 1.2528 | B.104 | C.12 |
| 1.2529 | B.105 | C.12 |
| 1.2530 | B.106 | C.12 |
| 1.2531 | B.107 | C.12 |
| 1.2532 | B.108 | C.12 |
| 1.2533 | B.109 | C.12 |
| 1.2534 | B.110 | C.12 |
| 1.2535 | B.111 | C.12 |
| 1.2536 | B.112 | C.12 |
| 1.2537 | B.113 | C.12 |
| 1.2538 | B.114 | C.12 |
| 1.2539 | B.115 | C.12 |
| 1.2540 | B.116 | C.12 |
| 1.2541 | B.117 | C.12 |
| 1.2542 | B.118 | C.12 |
| 1.2543 | B.119 | C.12 |
| 1.2544 | B.120 | C.12 |
| 1.2545 | B.121 | C.12 |
| 1.2546 | B.122 | C.12 |
| 1.2547 | B.123 | C.12 |
| 1.2548 | B.124 | C.12 |
| 1.2549 | B.125 | C.12 |
| 1.2550 | B.126 | C.12 |
| 1.2551 | B.127 | C.12 |
| 1.2552 | B.128 | C.12 |
| 1.2553 | B.129 | C.12 |
| 1.2554 | B.130 | C.12 |
| 1.2555 | B.131 | C.12 |
| 1.2556 | B.132 | C.12 |
| 1.2557 | B.133 | C.12 |
| 1.2558 | B.134 | C.12 |
| 1.2559 | B.135 | C.12 |
| 1.2560 | B.136 | C.12 |
| 1.2561 | B.137 | C.12 |
| 1.2562 | B.138 | C.12 |
| 1.2563 | B.139 | C.12 |
| 1.2564 | B.140 | C.12 |
| 1.2565 | B.141 | C.12 |
| 1.2566 | B.142 | C.12 |
| 1.2567 | B.143 | C.12 |
| 1.2568 | B.144 | C.12 |
| 1.2569 | B.145 | C.12 |
| 1.2570 | B.146 | C.12 |
| 1.2571 | B.147 | C.12 |
| 1.2572 | B.148 | C.12 |
| 1.2573 | B.149 | C.12 |
| 1.2574 | B.150 | C.12 |
| 1.2575 | B.151 | C.12 |
| 1.2576 | B.152 | C.12 |
| 1.2577 | B.153 | C.12 |
| 1.2578 | B.154 | C.12 |
| 1.2579 | B.155 | C.12 |
| 1.2580 | B.156 | C.12 |
| 1.2581 | B.157 | C.12 |
| 1.2582 | B.158 | C.12 |
| 1.2583 | B.159 | C.12 |
| 1.2584 | B.160 | C.12 |
| 1.2585 | B.161 | C.12 |
| 1.2586 | B.162 | C.12 |
| 1.2587 | B.163 | C.12 |
| 1.2588 | B.164 | C.12 |
| 1.2589 | B.165 | C.12 |
| 1.2590 | B.166 | C.12 |
| 1.2591 | B.167 | C.12 |
| 1.2592 | B.168 | C.12 |
| 1.2593 | B.169 | C.12 |
| 1.2594 | B.170 | C.12 |
| 1.2595 | B.171 | C.12 |
| 1.2596 | B.172 | C.12 |
| 1.2597 | B.173 | C.12 |
| 1.2598 | B.174 | C.12 |
| 1.2599 | B.175 | C.12 |
| 1.2600 | B.176 | C.12 |
| 1.2601 | B.177 | C.12 |
| 1.2602 | B.178 | C.12 |
| 1.2603 | B.179 | C.12 |
| 1.2604 | B.180 | C.12 |
| 1.2605 | B.181 | C.12 |
| 1.2606 | B.182 | C.12 |
| 1.2607 | B.183 | C.12 |
| 1.2608 | B.184 | C.12 |
| 1.2609 | B.185 | C.12 |
| 1.2610 | B.186 | C.12 |
| 1.2611 | B.187 | C.12 |

TABLE T-continued (compositions 1.1 to 1.3653):

| comp. no. | herbicide B | safener C |
|---|---|---|
| 1.2612 | B.188 | C.12 |
| 1.2613 | B.189 | C.12 |
| 1.2614 | B.190 | C.12 |
| 1.2615 | B.191 | C.12 |
| 1.2616 | B.192 | C.12 |
| 1.2617 | B.193 | C.12 |
| 1.2618 | B.194 | C.12 |
| 1.2619 | B.195 | C.12 |
| 1.2620 | B.196 | C.12 |
| 1.2621 | B.197 | C.12 |
| 1.2622 | B.198 | C.12 |
| 1.2623 | B.199 | C.12 |
| 1.2624 | B.200 | C.12 |
| 1.2625 | B.201 | C.12 |
| 1.2626 | B.202 | C.12 |
| 1.2627 | B.1 | C.13 |
| 1.2628 | B.2 | C.13 |
| 1.2629 | B.3 | C.13 |
| 1.2630 | B.4 | C.13 |
| 1.2631 | B.5 | C.13 |
| 1.2632 | B.6 | C.13 |
| 1.2633 | B.7 | C.13 |
| 1.2634 | B.8 | C.13 |
| 1.2635 | B.9 | C.13 |
| 1.2636 | B.10 | C.13 |
| 1.2637 | B.11 | C.13 |
| 1.2638 | B.12 | C.13 |
| 1.2639 | B.13 | C.13 |
| 1.2640 | B.14 | C.13 |
| 1.2641 | B.15 | C.13 |
| 1.2642 | B.16 | C.13 |
| 1.2643 | B.17 | C.13 |
| 1.2644 | B.18 | C.13 |
| 1.2645 | B.19 | C.13 |
| 1.2646 | B.20 | C.13 |
| 1.2647 | B.21 | C.13 |
| 1.2648 | B.22 | C.13 |
| 1.2649 | B.23 | C.13 |
| 1.2650 | B.24 | C.13 |
| 1.2651 | B.25 | C.13 |
| 1.2652 | B.26 | C.13 |
| 1.2653 | B.27 | C.13 |
| 1.2654 | B.28 | C.13 |
| 1.2655 | B.29 | C.13 |
| 1.2656 | B.30 | C.13 |
| 1.2657 | B.31 | C.13 |
| 1.2658 | B.32 | C.13 |
| 1.2659 | B.33 | C.13 |
| 1.2660 | B.34 | C.13 |
| 1.2661 | B.35 | C.13 |
| 1.2662 | B.36 | C.13 |
| 1.2663 | B.37 | C.13 |
| 1.2664 | B.38 | C.13 |
| 1.2665 | B.39 | C.13 |
| 1.2666 | B.40 | C.13 |
| 1.2667 | B.41 | C.13 |
| 1.2668 | B.42 | C.13 |
| 1.2669 | B.43 | C.13 |
| 1.2670 | B.44 | C.13 |
| 1.2671 | B.45 | C.13 |
| 1.2672 | B.46 | C.13 |
| 1.2673 | B.47 | C.13 |
| 1.2674 | B.48 | C.13 |
| 1.2675 | B.49 | C.13 |
| 1.2676 | B.50 | C.13 |
| 1.2677 | B.51 | C.13 |
| 1.2678 | B.52 | C.13 |
| 1.2679 | B.53 | C.13 |
| 1.2680 | B.54 | C.13 |
| 1.2681 | B.55 | C.13 |
| 1.2682 | B.56 | C.13 |
| 1.2683 | B.57 | C.13 |
| 1.2684 | B.58 | C.13 |
| 1.2685 | B.59 | C.13 |
| 1.2686 | B.60 | C.13 |
| 1.2687 | B.61 | C.13 |
| 1.2688 | B.62 | C.13 |
| 1.2689 | B.63 | C.13 |
| 1.2690 | B.64 | C.13 |
| 1.2691 | B.65 | C.13 |
| 1.2692 | B.66 | C.13 |
| 1.2693 | B.67 | C.13 |
| 1.2694 | B.68 | C.13 |
| 1.2695 | B.69 | C.13 |
| 1.2696 | B.70 | C.13 |
| 1.2697 | B.71 | C.13 |
| 1.2698 | B.72 | C.13 |
| 1.2699 | B.73 | C.13 |
| 1.2700 | B.74 | C.13 |
| 1.2701 | B.75 | C.13 |
| 1.2702 | B.76 | C.13 |
| 1.2703 | B.77 | C.13 |
| 1.2704 | B.78 | C.13 |
| 1.2705 | B.79 | C.13 |
| 1.2706 | B.80 | C.13 |
| 1.2707 | B.81 | C.13 |
| 1.2708 | B.82 | C.13 |
| 1.2709 | B.83 | C.13 |
| 1.2710 | B.84 | C.13 |
| 1.2711 | B.85 | C.13 |
| 1.2712 | B.86 | C.13 |
| 1.2713 | B.87 | C.13 |
| 1.2714 | B.88 | C.13 |
| 1.2715 | B.89 | C.13 |
| 1.2716 | B.90 | C.13 |
| 1.2717 | B.91 | C.13 |
| 1.2718 | B.92 | C.13 |
| 1.2719 | B.93 | C.13 |
| 1.2720 | B.94 | C.13 |
| 1.2721 | B.95 | C.13 |
| 1.2722 | B.96 | C.13 |
| 1.2723 | B.97 | C.13 |
| 1.2724 | B.98 | C.13 |
| 1.2725 | B.99 | C.13 |
| 1.2726 | B.100 | C.13 |
| 1.2727 | B.101 | C.13 |
| 1.2728 | B.102 | C.13 |
| 1.2729 | B.103 | C.13 |
| 1.2730 | B.104 | C.13 |
| 1.2731 | B.105 | C.13 |
| 1.2732 | B.106 | C.13 |
| 1.2733 | B.107 | C.13 |
| 1.2734 | B.108 | C.13 |
| 1.2735 | B.109 | C.13 |
| 1.2736 | B.110 | C.13 |
| 1.2737 | B.111 | C.13 |
| 1.2738 | B.112 | C.13 |
| 1.2739 | B.113 | C.13 |
| 1.2740 | B.114 | C.13 |
| 1.2741 | B.115 | C.13 |
| 1.2742 | B.116 | C.13 |
| 1.2743 | B.117 | C.13 |
| 1.2744 | B.118 | C.13 |
| 1.2745 | B.119 | C.13 |
| 1.2746 | B.120 | C.13 |
| 1.2747 | B.121 | C.13 |
| 1.2748 | B.122 | C.13 |
| 1.2749 | B.123 | C.13 |
| 1.2750 | B.124 | C.13 |
| 1.2751 | B.125 | C.13 |
| 1.2752 | B.126 | C.13 |
| 1.2753 | B.127 | C.13 |
| 1.2754 | B.128 | C.13 |
| 1.2755 | B.129 | C.13 |
| 1.2756 | B.130 | C.13 |
| 1.2757 | B.131 | C.13 |
| 1.2758 | B.132 | C.13 |
| 1.2759 | B.133 | C.13 |
| 1.2760 | B.134 | C.13 |
| 1.2761 | B.135 | C.13 |
| 1.2762 | B.136 | C.13 |
| 1.2763 | B.137 | C.13 |

TABLE T-continued (compositions 1.1 to 1.3653):

| comp. no. | herbicide B | safener C |
|---|---|---|
| 1.2764 | B.138 | C.13 |
| 1.2765 | B.139 | C.13 |
| 1.2766 | B.140 | C.13 |
| 1.2767 | B.141 | C.13 |
| 1.2768 | B.142 | C.13 |
| 1.2769 | B.143 | C.13 |
| 1.2770 | B.144 | C.13 |
| 1.2771 | B.145 | C.13 |
| 1.2772 | B.146 | C.13 |
| 1.2773 | B.147 | C.13 |
| 1.2774 | B.148 | C.13 |
| 1.2775 | B.149 | C.13 |
| 1.2776 | B.150 | C.13 |
| 1.2777 | B.151 | C.13 |
| 1.2778 | B.152 | C.13 |
| 1.2779 | B.153 | C.13 |
| 1.2780 | B.154 | C.13 |
| 1.2781 | B.155 | C.13 |
| 1.2782 | B.156 | C.13 |
| 1.2783 | B.157 | C.13 |
| 1.2784 | B.158 | C.13 |
| 1.2785 | B.159 | C.13 |
| 1.2786 | B.160 | C.13 |
| 1.2787 | B.161 | C.13 |
| 1.2788 | B.162 | C.13 |
| 1.2789 | B.163 | C.13 |
| 1.2790 | B.164 | C.13 |
| 1.2791 | B.165 | C.13 |
| 1.2792 | B.166 | C.13 |
| 1.2793 | B.167 | C.13 |
| 1.2794 | B.168 | C.13 |
| 1.2795 | B.169 | C.13 |
| 1.2796 | B.170 | C.13 |
| 1.2797 | B.171 | C.13 |
| 1.2798 | B.172 | C.13 |
| 1.2799 | B.173 | C.13 |
| 1.2800 | B.174 | C.13 |
| 1.2801 | B.175 | C.13 |
| 1.2802 | B.176 | C.13 |
| 1.2803 | B.177 | C.13 |
| 1.2804 | B.178 | C.13 |
| 1.2805 | B.179 | C.13 |
| 1.2806 | B.180 | C.13 |
| 1.2807 | B.181 | C.13 |
| 1.2808 | B.182 | C.13 |
| 1.2809 | B.183 | C.13 |
| 1.2810 | B.184 | C.13 |
| 1.2811 | B.185 | C.13 |
| 1.2812 | B.186 | C.13 |
| 1.2813 | B.187 | C.13 |
| 1.2814 | B.188 | C.13 |
| 1.2815 | B.189 | C.13 |
| 1.2816 | B.190 | C.13 |
| 1.2817 | B.191 | C.13 |
| 1.2818 | B.192 | C.13 |
| 1.2819 | B.193 | C.13 |
| 1.2820 | B.194 | C.13 |
| 1.2821 | B.195 | C.13 |
| 1.2822 | B.196 | C.13 |
| 1.2823 | B.197 | C.13 |
| 1.2824 | B.198 | C.13 |
| 1.2825 | B.199 | C.13 |
| 1.2826 | B.200 | C.13 |
| 1.2827 | B.201 | C.13 |
| 1.2828 | B.202 | C.13 |
| 1.2829 | B.1 | C.14 |
| 1.2830 | B.2 | C.14 |
| 1.2831 | B.3 | C.14 |
| 1.2832 | B.4 | C.14 |
| 1.2833 | B.5 | C.14 |
| 1.2834 | B.6 | C.14 |
| 1.2835 | B.7 | C.14 |
| 1.2836 | B.8 | C.14 |
| 1.2837 | B.9 | C.14 |
| 1.2838 | B.10 | C.14 |
| 1.2839 | B.11 | C.14 |
| 1.2840 | B.12 | C.14 |
| 1.2841 | B.13 | C.14 |
| 1.2842 | B.14 | C.14 |
| 1.2843 | B.15 | C.14 |
| 1.2844 | B.16 | C.14 |
| 1.2845 | B.17 | C.14 |
| 1.2846 | B.18 | C.14 |
| 1.2847 | B.19 | C.14 |
| 1.2848 | B.20 | C.14 |
| 1.2849 | B.21 | C.14 |
| 1.2850 | B.22 | C.14 |
| 1.2851 | B.23 | C.14 |
| 1.2852 | B.24 | C.14 |
| 1.2853 | B.25 | C.14 |
| 1.2854 | B.26 | C.14 |
| 1.2855 | B.27 | C.14 |
| 1.2856 | B.28 | C.14 |
| 1.2857 | B.29 | C.14 |
| 1.2858 | B.30 | C.14 |
| 1.2859 | B.31 | C.14 |
| 1.2860 | B.32 | C.14 |
| 1.2861 | B.33 | C.14 |
| 1.2862 | B.34 | C.14 |
| 1.2863 | B.35 | C.14 |
| 1.2864 | B.36 | C.14 |
| 1.2865 | B.37 | C.14 |
| 1.2866 | B.38 | C.14 |
| 1.2867 | B.39 | C.14 |
| 1.2868 | B.40 | C.14 |
| 1.2869 | B.41 | C.14 |
| 1.2870 | B.42 | C.14 |
| 1.2871 | B.43 | C.14 |
| 1.2872 | B.44 | C.14 |
| 1.2873 | B.45 | C.14 |
| 1.2874 | B.46 | C.14 |
| 1.2875 | B.47 | C.14 |
| 1.2876 | B.48 | C.14 |
| 1.2877 | B.49 | C.14 |
| 1.2878 | B.50 | C.14 |
| 1.2879 | B.51 | C.14 |
| 1.2880 | B.52 | C.14 |
| 1.2881 | B.53 | C.14 |
| 1.2882 | B.54 | C.14 |
| 1.2883 | B.55 | C.14 |
| 1.2884 | B.56 | C.14 |
| 1.2885 | B.57 | C.14 |
| 1.2886 | B.58 | C.14 |
| 1.2887 | B.59 | C.14 |
| 1.2888 | B.60 | C.14 |
| 1.2889 | B.61 | C.14 |
| 1.2890 | B.62 | C.14 |
| 1.2891 | B.63 | C.14 |
| 1.2892 | B.64 | C.14 |
| 1.2893 | B.65 | C.14 |
| 1.2894 | B.66 | C.14 |
| 1.2895 | B.67 | C.14 |
| 1.2896 | B.68 | C.14 |
| 1.2897 | B.69 | C.14 |
| 1.2898 | B.70 | C.14 |
| 1.2899 | B.71 | C.14 |
| 1.2900 | B.72 | C.14 |
| 1.2901 | B.73 | C.14 |
| 1.2902 | B.74 | C.14 |
| 1.2903 | B.75 | C.14 |
| 1.2904 | B.76 | C.14 |
| 1.2905 | B.77 | C.14 |
| 1.2906 | B.78 | C.14 |
| 1.2907 | B.79 | C.14 |
| 1.2908 | B.80 | C.14 |
| 1.2909 | B.81 | C.14 |
| 1.2910 | B.82 | C.14 |
| 1.2911 | B.83 | C.14 |
| 1.2912 | B.84 | C.14 |
| 1.2913 | B.85 | C.14 |
| 1.2914 | B.86 | C.14 |
| 1.2915 | B.87 | C.14 |

TABLE T-continued (compositions 1.1 to 1.3653):

| comp. no. | herbicide B | safener C |
|---|---|---|
| 1.2916 | B.88 | C.14 |
| 1.2917 | B.89 | C.14 |
| 1.2918 | B.90 | C.14 |
| 1.2919 | B.91 | C.14 |
| 1.2920 | B.92 | C.14 |
| 1.2921 | B.93 | C.14 |
| 1.2922 | B.94 | C.14 |
| 1.2923 | B.95 | C.14 |
| 1.2924 | B.96 | C.14 |
| 1.2925 | B.97 | C.14 |
| 1.2926 | B.98 | C.14 |
| 1.2927 | B.99 | C.14 |
| 1.2928 | B.100 | C.14 |
| 1.2929 | B.101 | C.14 |
| 1.2930 | B.102 | C.14 |
| 1.2931 | B.103 | C.14 |
| 1.2932 | B.104 | C.14 |
| 1.2933 | B.105 | C.14 |
| 1.2934 | B.106 | C.14 |
| 1.2935 | B.107 | C.14 |
| 1.2936 | B.108 | C.14 |
| 1.2937 | B.109 | C.14 |
| 1.2938 | B.110 | C.14 |
| 1.2939 | B.111 | C.14 |
| 1.2940 | B.112 | C.14 |
| 1.2941 | B.113 | C.14 |
| 1.2942 | B.114 | C.14 |
| 1.2943 | B.115 | C.14 |
| 1.2944 | B.116 | C.14 |
| 1.2945 | B.117 | C.14 |
| 1.2946 | B.118 | C.14 |
| 1.2947 | B.119 | C.14 |
| 1.2948 | B.120 | C.14 |
| 1.2949 | B.121 | C.14 |
| 1.2950 | B.122 | C.14 |
| 1.2951 | B.123 | C.14 |
| 1.2952 | B.124 | C.14 |
| 1.2953 | B.125 | C.14 |
| 1.2954 | B.126 | C.14 |
| 1.2955 | B.127 | C.14 |
| 1.2956 | B.128 | C.14 |
| 1.2957 | B.129 | C.14 |
| 1.2958 | B.130 | C.14 |
| 1.2959 | B.131 | C.14 |
| 1.2960 | B.132 | C.14 |
| 1.2961 | B.133 | C.14 |
| 1.2962 | B.134 | C.14 |
| 1.2963 | B.135 | C.14 |
| 1.2964 | B.136 | C.14 |
| 1.2965 | B.137 | C.14 |
| 1.2966 | B.138 | C.14 |
| 1.2967 | B.139 | C.14 |
| 1.2968 | B.140 | C.14 |
| 1.2969 | B.141 | C.14 |
| 1.2970 | B.142 | C.14 |
| 1.2971 | B.143 | C.14 |
| 1.2972 | B.144 | C.14 |
| 1.2973 | B.145 | C.14 |
| 1.2974 | B.146 | C.14 |
| 1.2975 | B.147 | C.14 |
| 1.2976 | B.148 | C.14 |
| 1.2977 | B.149 | C.14 |
| 1.2978 | B.150 | C.14 |
| 1.2979 | B.151 | C.14 |
| 1.2980 | B.152 | C.14 |
| 1.2981 | B.153 | C.14 |
| 1.2982 | B.154 | C.14 |
| 1.2983 | B.155 | C.14 |
| 1.2984 | B.156 | C.14 |
| 1.2985 | B.157 | C.14 |
| 1.2986 | B.158 | C.14 |
| 1.2987 | B.159 | C.14 |
| 1.2988 | B.160 | C.14 |
| 1.2989 | B.161 | C.14 |
| 1.2990 | B.162 | C.14 |
| 1.2991 | B.163 | C.14 |
| 1.2992 | B.164 | C.14 |
| 1.2993 | B.165 | C.14 |
| 1.2994 | B.166 | C.14 |
| 1.2995 | B.167 | C.14 |
| 1.2996 | B.168 | C.14 |
| 1.2997 | B.169 | C.14 |
| 1.2998 | B.170 | C.14 |
| 1.2999 | B.171 | C.14 |
| 1.3000 | B.172 | C.14 |
| 1.3001 | B.173 | C.14 |
| 1.3002 | B.174 | C.14 |
| 1.3003 | B.175 | C.14 |
| 1.3004 | B.176 | C.14 |
| 1.3005 | B.177 | C.14 |
| 1.3006 | B.178 | C.14 |
| 1.3007 | B.179 | C.14 |
| 1.3008 | B.180 | C.14 |
| 1.3009 | B.181 | C.14 |
| 1.3010 | B.182 | C.14 |
| 1.3011 | B.183 | C.14 |
| 1.3012 | B.184 | C.14 |
| 1.3013 | B.185 | C.14 |
| 1.3014 | B.186 | C.14 |
| 1.3015 | B.187 | C.14 |
| 1.3016 | B.188 | C.14 |
| 1.3017 | B.189 | C.14 |
| 1.3018 | B.190 | C.14 |
| 1.3019 | B.191 | C.14 |
| 1.3020 | B.192 | C.14 |
| 1.3021 | B.193 | C.14 |
| 1.3022 | B.194 | C.14 |
| 1.3023 | B.195 | C.14 |
| 1.3024 | B.196 | C.14 |
| 1.3025 | B.197 | C.14 |
| 1.3026 | B.198 | C.14 |
| 1.3027 | B.199 | C.14 |
| 1.3028 | B.200 | C.14 |
| 1.3029 | B.201 | C.14 |
| 1.3030 | B.202 | C.14 |
| 1.3031 | B.1 | C.15 |
| 1.3032 | B.2 | C.15 |
| 1.3033 | B.3 | C.15 |
| 1.3034 | B.4 | C.15 |
| 1.3035 | B.5 | C.15 |
| 1.3036 | B.6 | C.15 |
| 1.3037 | B.7 | C.15 |
| 1.3038 | B.8 | C.15 |
| 1.3039 | B.9 | C.15 |
| 1.3040 | B.10 | C.15 |
| 1.3041 | B.11 | C.15 |
| 1.3042 | B.12 | C.15 |
| 1.3043 | B.13 | C.15 |
| 1.3044 | B.14 | C.15 |
| 1.3045 | B.15 | C.15 |
| 1.3046 | B.16 | C.15 |
| 1.3047 | B.17 | C.15 |
| 1.3048 | B.18 | C.15 |
| 1.3049 | B.19 | C.15 |
| 1.3050 | B.20 | C.15 |
| 1.3051 | B.21 | C.15 |
| 1.3052 | B.22 | C.15 |
| 1.3053 | B.23 | C.15 |
| 1.3054 | B.24 | C.15 |
| 1.3055 | B.25 | C.15 |
| 1.3056 | B.26 | C.15 |
| 1.3057 | B.27 | C.15 |
| 1.3058 | B.28 | C.15 |
| 1.3059 | B.29 | C.15 |
| 1.3060 | B.30 | C.15 |
| 1.3061 | B.31 | C.15 |
| 1.3062 | B.32 | C.15 |
| 1.3063 | B.33 | C.15 |
| 1.3064 | B.34 | C.15 |
| 1.3065 | B.35 | C.15 |
| 1.3066 | B.36 | C.15 |
| 1.3067 | B.37 | C.15 |

TABLE T-continued (compositions 1.1 to 1.3653):

| comp. no. | herbicide B | safener C |
|---|---|---|
| 1.3068 | B.38 | C.15 |
| 1.3069 | B.39 | C.15 |
| 1.3070 | B.40 | C.15 |
| 1.3071 | B.41 | C.15 |
| 1.3072 | B.42 | C.15 |
| 1.3073 | B.43 | C.15 |
| 1.3074 | B.44 | C.15 |
| 1.3075 | B.45 | C.15 |
| 1.3076 | B.46 | C.15 |
| 1.3077 | B.47 | C.15 |
| 1.3078 | B.48 | C.15 |
| 1.3079 | B.49 | C.15 |
| 1.3080 | B.50 | C.15 |
| 1.3081 | B.51 | C.15 |
| 1.3082 | B.52 | C.15 |
| 1.3083 | B.53 | C.15 |
| 1.3084 | B.54 | C.15 |
| 1.3085 | B.55 | C.15 |
| 1.3086 | B.56 | C.15 |
| 1.3087 | B.57 | C.15 |
| 1.3088 | B.58 | C.15 |
| 1.3089 | B.59 | C.15 |
| 1.3090 | B.60 | C.15 |
| 1.3091 | B.61 | C.15 |
| 1.3092 | B.62 | C.15 |
| 1.3093 | B.63 | C.15 |
| 1.3094 | B.64 | C.15 |
| 1.3095 | B.65 | C.15 |
| 1.3096 | B.66 | C.15 |
| 1.3097 | B.67 | C.15 |
| 1.3098 | B.68 | C.15 |
| 1.3099 | B.69 | C.15 |
| 1.3100 | B.70 | C.15 |
| 1.3101 | B.71 | C.15 |
| 1.3102 | B.72 | C.15 |
| 1.3103 | B.73 | C.15 |
| 1.3104 | B.74 | C.15 |
| 1.3105 | B.75 | C.15 |
| 1.3106 | B.76 | C.15 |
| 1.3107 | B.77 | C.15 |
| 1.3108 | B.78 | C.15 |
| 1.3109 | B.79 | C.15 |
| 1.3110 | B.80 | C.15 |
| 1.3111 | B.81 | C.15 |
| 1.3112 | B.82 | C.15 |
| 1.3113 | B.83 | C.15 |
| 1.3114 | B.84 | C.15 |
| 1.3115 | B.85 | C.15 |
| 1.3116 | B.86 | C.15 |
| 1.3117 | B.87 | C.15 |
| 1.3118 | B.88 | C.15 |
| 1.3119 | B.89 | C.15 |
| 1.3120 | B.90 | C.15 |
| 1.3121 | B.91 | C.15 |
| 1.3122 | B.92 | C.15 |
| 1.3123 | B.93 | C.15 |
| 1.3124 | B.94 | C.15 |
| 1.3125 | B.95 | C.15 |
| 1.3126 | B.96 | C.15 |
| 1.3127 | B.97 | C.15 |
| 1.3128 | B.98 | C.15 |
| 1.3129 | B.99 | C.15 |
| 1.3130 | B.100 | C.15 |
| 1.3131 | B.101 | C.15 |
| 1.3132 | B.102 | C.15 |
| 1.3133 | B.103 | C.15 |
| 1.3134 | B.104 | C.15 |
| 1.3135 | B.105 | C.15 |
| 1.3136 | B.106 | C.15 |
| 1.3137 | B.107 | C.15 |
| 1.3138 | B.108 | C.15 |
| 1.3139 | B.109 | C.15 |
| 1.3140 | B.110 | C.15 |
| 1.3141 | B.111 | C.15 |
| 1.3142 | B.112 | C.15 |
| 1.3143 | B.113 | C.15 |
| 1.3144 | B.114 | C.15 |
| 1.3145 | B.115 | C.15 |
| 1.3146 | B.116 | C.15 |
| 1.3147 | B.117 | C.15 |
| 1.3148 | B.118 | C.15 |
| 1.3149 | B.119 | C.15 |
| 1.3150 | B.120 | C.15 |
| 1.3151 | B.121 | C.15 |
| 1.3152 | B.122 | C.15 |
| 1.3153 | B.123 | C.15 |
| 1.3154 | B.124 | C.15 |
| 1.3155 | B.125 | C.15 |
| 1.3156 | B.126 | C.15 |
| 1.3157 | B.127 | C.15 |
| 1.3158 | B.128 | C.15 |
| 1.3159 | B.129 | C.15 |
| 1.3160 | B.130 | C.15 |
| 1.3161 | B.131 | C.15 |
| 1.3162 | B.132 | C.15 |
| 1.3163 | B.133 | C.15 |
| 1.3164 | B.134 | C.15 |
| 1.3165 | B.135 | C.15 |
| 1.3166 | B.136 | C.15 |
| 1.3167 | B.137 | C.15 |
| 1.3168 | B.138 | C.15 |
| 1.3169 | B.139 | C.15 |
| 1.3170 | B.140 | C.15 |
| 1.3171 | B.141 | C.15 |
| 1.3172 | B.142 | C.15 |
| 1.3173 | B.143 | C.15 |
| 1.3174 | B.144 | C.15 |
| 1.3175 | B.145 | C.15 |
| 1.3176 | B.146 | C.15 |
| 1.3177 | B.147 | C.15 |
| 1.3178 | B.148 | C.15 |
| 1.3179 | B.149 | C.15 |
| 1.3180 | B.150 | C.15 |
| 1.3181 | B.151 | C.15 |
| 1.3182 | B.152 | C.15 |
| 1.3183 | B.153 | C.15 |
| 1.3184 | B.154 | C.15 |
| 1.3185 | B.155 | C.15 |
| 1.3186 | B.156 | C.15 |
| 1.3187 | B.157 | C.15 |
| 1.3188 | B.158 | C.15 |
| 1.3189 | B.159 | C.15 |
| 1.3190 | B.160 | C.15 |
| 1.3191 | B.161 | C.15 |
| 1.3192 | B.162 | C.15 |
| 1.3193 | B.163 | C.15 |
| 1.3194 | B.164 | C.15 |
| 1.3195 | B.165 | C.15 |
| 1.3196 | B.166 | C.15 |
| 1.3197 | B.167 | C.15 |
| 1.3198 | B.168 | C.15 |
| 1.3199 | B.169 | C.15 |
| 1.3200 | B.170 | C.15 |
| 1.3201 | B.171 | C.15 |
| 1.3202 | B.172 | C.15 |
| 1.3203 | B.173 | C.15 |
| 1.3204 | B.174 | C.15 |
| 1.3205 | B.175 | C.15 |
| 1.3206 | B.176 | C.15 |
| 1.3207 | B.177 | C.15 |
| 1.3208 | B.178 | C.15 |
| 1.3209 | B.179 | C.15 |
| 1.3210 | B.180 | C.15 |
| 1.3211 | B.181 | C.15 |
| 1.3212 | B.182 | C.15 |
| 1.3213 | B.183 | C.15 |
| 1.3214 | B.184 | C.15 |
| 1.3215 | B.185 | C.15 |
| 1.3216 | B.186 | C.15 |
| 1.3217 | B.187 | C.15 |
| 1.3218 | B.188 | C.15 |
| 1.3219 | B.189 | C.15 |

TABLE T-continued (compositions 1.1 to 1.3653):

| comp. no. | herbicide B | safener C |
|---|---|---|
| 1.3220 | B.190 | C.15 |
| 1.3221 | B.191 | C.15 |
| 1.3222 | B.192 | C.15 |
| 1.3223 | B.193 | C.15 |
| 1.3224 | B.194 | C.15 |
| 1.3225 | B.195 | C.15 |
| 1.3226 | B.196 | C.15 |
| 1.3227 | B.197 | C.15 |
| 1.3228 | B.198 | C.15 |
| 1.3229 | B.199 | C.15 |
| 1.3230 | B.200 | C.15 |
| 1.3231 | B.201 | C.15 |
| 1.3232 | B.202 | C.15 |
| 1.3233 | B.1 | C.16 |
| 1.3234 | B.2 | C.16 |
| 1.3235 | B.3 | C.16 |
| 1.3236 | B.4 | C.16 |
| 1.3237 | B.5 | C.16 |
| 1.3238 | B.6 | C.16 |
| 1.3239 | B.7 | C.16 |
| 1.3240 | B.8 | C.16 |
| 1.3241 | B.9 | C.16 |
| 1.3242 | B.10 | C.16 |
| 1.3243 | B.11 | C.16 |
| 1.3244 | B.12 | C.16 |
| 1.3245 | B.13 | C.16 |
| 1.3246 | B.14 | C.16 |
| 1.3247 | B.15 | C.16 |
| 1.3248 | B.16 | C.16 |
| 1.3249 | B.17 | C.16 |
| 1.3250 | B.18 | C.16 |
| 1.3251 | B.19 | C.16 |
| 1.3252 | B.20 | C.16 |
| 1.3253 | B.21 | C.16 |
| 1.3254 | B.22 | C.16 |
| 1.3255 | B.23 | C.16 |
| 1.3256 | B.24 | C.16 |
| 1.3257 | B.25 | C.16 |
| 1.3258 | B.26 | C.16 |
| 1.3259 | B.27 | C.16 |
| 1.3260 | B.28 | C.16 |
| 1.3261 | B.29 | C.16 |
| 1.3262 | B.30 | C.16 |
| 1.3263 | B.31 | C.16 |
| 1.3264 | B.32 | C.16 |
| 1.3265 | B.33 | C.16 |
| 1.3266 | B.34 | C.16 |
| 1.3267 | B.35 | C.16 |
| 1.3268 | B.36 | C.16 |
| 1.3269 | B.37 | C.16 |
| 1.3270 | B.38 | C.16 |
| 1.3271 | B.39 | C.16 |
| 1.3272 | B.40 | C.16 |
| 1.3273 | B.41 | C.16 |
| 1.3274 | B.42 | C.16 |
| 1.3275 | B.43 | C.16 |
| 1.3276 | B.44 | C.16 |
| 1.3277 | B.45 | C.16 |
| 1.3278 | B.46 | C.16 |
| 1.3279 | B.47 | C.16 |
| 1.3280 | B.48 | C.16 |
| 1.3281 | B.49 | C.16 |
| 1.3282 | B.50 | C.16 |
| 1.3283 | B.51 | C.16 |
| 1.3284 | B.52 | C.16 |
| 1.3285 | B.53 | C.16 |
| 1.3286 | B.54 | C.16 |
| 1.3287 | B.55 | C.16 |
| 1.3288 | B.56 | C.16 |
| 1.3289 | B.57 | C.16 |
| 1.3290 | B.58 | C.16 |
| 1.3291 | B.59 | C.16 |
| 1.3292 | B.60 | C.16 |
| 1.3293 | B.61 | C.16 |
| 1.3294 | B.62 | C.16 |
| 1.3295 | B.63 | C.16 |
| 1.3296 | B.64 | C.16 |
| 1.3297 | B.65 | C.16 |
| 1.3298 | B.66 | C.16 |
| 1.3299 | B.67 | C.16 |
| 1.3300 | B.68 | C.16 |
| 1.3301 | B.69 | C.16 |
| 1.3302 | B.70 | C.16 |
| 1.3303 | B.71 | C.16 |
| 1.3304 | B.72 | C.16 |
| 1.3305 | B.73 | C.16 |
| 1.3306 | B.74 | C.16 |
| 1.3307 | B.75 | C.16 |
| 1.3308 | B.76 | C.16 |
| 1.3309 | B.77 | C.16 |
| 1.3310 | B.78 | C.16 |
| 1.3311 | B.79 | C.16 |
| 1.3312 | B.80 | C.16 |
| 1.3313 | B.81 | C.16 |
| 1.3314 | B.82 | C.16 |
| 1.3315 | B.83 | C.16 |
| 1.3316 | B.84 | C.16 |
| 1.3317 | B.85 | C.16 |
| 1.3318 | B.86 | C.16 |
| 1.3319 | B.87 | C.16 |
| 1.3320 | B.88 | C.16 |
| 1.3321 | B.89 | C.16 |
| 1.3322 | B.90 | C.16 |
| 1.3323 | B.91 | C.16 |
| 1.3324 | B.92 | C.16 |
| 1.3325 | B.93 | C.16 |
| 1.3326 | B.94 | C.16 |
| 1.3327 | B.95 | C.16 |
| 1.3328 | B.96 | C.16 |
| 1.3329 | B.97 | C.16 |
| 1.3330 | B.98 | C.16 |
| 1.3331 | B.99 | C.16 |
| 1.3332 | B.100 | C.16 |
| 1.3333 | B.101 | C.16 |
| 1.3334 | B.102 | C.16 |
| 1.3335 | B.103 | C.16 |
| 1.3336 | B.104 | C.16 |
| 1.3337 | B.105 | C.16 |
| 1.3338 | B.106 | C.16 |
| 1.3339 | B.107 | C.16 |
| 1.3340 | B.108 | C.16 |
| 1.3341 | B.109 | C.16 |
| 1.3342 | B.110 | C.16 |
| 1.3343 | B.111 | C.16 |
| 1.3344 | B.112 | C.16 |
| 1.3345 | B.113 | C.16 |
| 1.3346 | B.114 | C.16 |
| 1.3347 | B.115 | C.16 |
| 1.3348 | B.116 | C.16 |
| 1.3349 | B.117 | C.16 |
| 1.3350 | B.118 | C.16 |
| 1.3351 | B.119 | C.16 |
| 1.3352 | B.120 | C.16 |
| 1.3353 | B.121 | C.16 |
| 1.3354 | B.122 | C.16 |
| 1.3355 | B.123 | C.16 |
| 1.3356 | B.124 | C.16 |
| 1.3357 | B.125 | C.16 |
| 1.3358 | B.126 | C.16 |
| 1.3359 | B.127 | C.16 |
| 1.3360 | B.128 | C.16 |
| 1.3361 | B.129 | C.16 |
| 1.3362 | B.130 | C.16 |
| 1.3363 | B.131 | C.16 |
| 1.3364 | B.132 | C.16 |
| 1.3365 | B.133 | C.16 |
| 1.3366 | B.134 | C.16 |
| 1.3367 | B.135 | C.16 |
| 1.3368 | B.136 | C.16 |
| 1.3369 | B.137 | C.16 |
| 1.3370 | B.138 | C.16 |
| 1.3371 | B.139 | C.16 |

TABLE T-continued (compositions 1.1 to 1.3653):

| comp. no. | herbicide B | safener C |
|---|---|---|
| 1.3372 | B.140 | C.16 |
| 1.3373 | B.141 | C.16 |
| 1.3374 | B.142 | C.16 |
| 1.3375 | B.143 | C.16 |
| 1.3376 | B.144 | C.16 |
| 1.3377 | B.145 | C.16 |
| 1.3378 | B.146 | C.16 |
| 1.3379 | B.147 | C.16 |
| 1.3380 | B.148 | C.16 |
| 1.3381 | B.149 | C.16 |
| 1.3382 | B.150 | C.16 |
| 1.3383 | B.151 | C.16 |
| 1.3384 | B.152 | C.16 |
| 1.3385 | B.153 | C.16 |
| 1.3386 | B.154 | C.16 |
| 1.3387 | B.155 | C.16 |
| 1.3388 | B.156 | C.16 |
| 1.3389 | B.157 | C.16 |
| 1.3390 | B.158 | C.16 |
| 1.3391 | B.159 | C.16 |
| 1.3392 | B.160 | C.16 |
| 1.3393 | B.161 | C.16 |
| 1.3394 | B.162 | C.16 |
| 1.3395 | B.163 | C.16 |
| 1.3396 | B.164 | C.16 |
| 1.3397 | B.165 | C.16 |
| 1.3398 | B.166 | C.16 |
| 1.3399 | B.167 | C.16 |
| 1.3400 | B.168 | C.16 |
| 1.3401 | B.169 | C.16 |
| 1.3402 | B.170 | C.16 |
| 1.3403 | B.171 | C.16 |
| 1.3404 | B.172 | C.16 |
| 1.3405 | B.173 | C.16 |
| 1.3406 | B.174 | C.16 |
| 1.3407 | B.175 | C.16 |
| 1.3408 | B.176 | C.16 |
| 1.3409 | B.177 | C.16 |
| 1.3410 | B.178 | C.16 |
| 1.3411 | B.179 | C.16 |
| 1.3412 | B.180 | C.16 |
| 1.3413 | B.181 | C.16 |
| 1.3414 | B.182 | C.16 |
| 1.3415 | B.183 | C.16 |
| 1.3416 | B.184 | C.16 |
| 1.3417 | B.185 | C.16 |
| 1.3418 | B.186 | C.16 |
| 1.3419 | B.187 | C.16 |
| 1.3420 | B.188 | C.16 |
| 1.3421 | B.189 | C.16 |
| 1.3422 | B.190 | C.16 |
| 1.3423 | B.191 | C.16 |
| 1.3424 | B.192 | C.16 |
| 1.3425 | B.193 | C.16 |
| 1.3426 | B.194 | C.16 |
| 1.3427 | B.195 | C.16 |
| 1.3428 | B.196 | C.16 |
| 1.3429 | B.197 | C.16 |
| 1.3430 | B.198 | C.16 |
| 1.3431 | B.199 | C.16 |
| 1.3432 | B.200 | C.16 |
| 1.3433 | B.201 | C.16 |
| 1.3434 | B.202 | C.16 |
| 1.3435 | B.1 | C.17 |
| 1.3436 | B.2 | C.17 |
| 1.3437 | B.3 | C.17 |
| 1.3438 | B.4 | C.17 |
| 1.3439 | B.5 | C.17 |
| 1.3440 | B.6 | C.17 |
| 1.3441 | B.7 | C.17 |
| 1.3442 | B.8 | C.17 |
| 1.3443 | B.9 | C.17 |
| 1.3444 | B.10 | C.17 |
| 1.3445 | B.11 | C.17 |
| 1.3446 | B.12 | C.17 |
| 1.3447 | B.13 | C.17 |
| 1.3448 | B.14 | C.17 |
| 1.3449 | B.15 | C.17 |
| 1.3450 | B.16 | C.17 |
| 1.3451 | B.17 | C.17 |
| 1.3452 | B.18 | C.17 |
| 1.3453 | B.19 | C.17 |
| 1.3454 | B.20 | C.17 |
| 1.3455 | B.21 | C.17 |
| 1.3456 | B.22 | C.17 |
| 1.3457 | B.23 | C.17 |
| 1.3458 | B.24 | C.17 |
| 1.3459 | B.25 | C.17 |
| 1.3460 | B.26 | C.17 |
| 1.3461 | B.27 | C.17 |
| 1.3462 | B.28 | C.17 |
| 1.3463 | B.29 | C.17 |
| 1.3464 | B.30 | C.17 |
| 1.3465 | B.31 | C.17 |
| 1.3466 | B.32 | C.17 |
| 1.3467 | B.33 | C.17 |
| 1.3468 | B.34 | C.17 |
| 1.3469 | B.35 | C.17 |
| 1.3470 | B.36 | C.17 |
| 1.3471 | B.37 | C.17 |
| 1.3472 | B.38 | C.17 |
| 1.3473 | B.39 | C.17 |
| 1.3474 | B.40 | C.17 |
| 1.3475 | B.41 | C.17 |
| 1.3476 | B.42 | C.17 |
| 1.3477 | B.43 | C.17 |
| 1.3478 | B.44 | C.17 |
| 1.3479 | B.45 | C.17 |
| 1.3480 | B.46 | C.17 |
| 1.3481 | B.47 | C.17 |
| 1.3482 | B.48 | C.17 |
| 1.3483 | B.49 | C.17 |
| 1.3484 | B.50 | C.17 |
| 1.3485 | B.51 | C.17 |
| 1.3486 | B.52 | C.17 |
| 1.3487 | B.53 | C.17 |
| 1.3488 | B.54 | C.17 |
| 1.3489 | B.55 | C.17 |
| 1.3490 | B.56 | C.17 |
| 1.3491 | B.57 | C.17 |
| 1.3492 | B.58 | C.17 |
| 1.3493 | B.59 | C.17 |
| 1.3494 | B.60 | C.17 |
| 1.3495 | B.61 | C.17 |
| 1.3496 | B.62 | C.17 |
| 1.3497 | B.63 | C.17 |
| 1.3498 | B.64 | C.17 |
| 1.3499 | B.65 | C.17 |
| 1.3500 | B.66 | C.17 |
| 1.3501 | B.67 | C.17 |
| 1.3502 | B.68 | C.17 |
| 1.3503 | B.69 | C.17 |
| 1.3504 | B.70 | C.17 |
| 1.3505 | B.71 | C.17 |
| 1.3506 | B.72 | C.17 |
| 1.3507 | B.73 | C.17 |
| 1.3508 | B.74 | C.17 |
| 1.3509 | B.75 | C.17 |
| 1.3510 | B.76 | C.17 |
| 1.3511 | B.77 | C.17 |
| 1.3512 | B.78 | C.17 |
| 1.3513 | B.79 | C.17 |
| 1.3514 | B.80 | C.17 |
| 1.3515 | B.81 | C.17 |
| 1.3516 | B.82 | C.17 |
| 1.3517 | B.83 | C.17 |
| 1.3518 | B.84 | C.17 |
| 1.3519 | B.85 | C.17 |
| 1.3520 | B.86 | C.17 |
| 1.3521 | B.87 | C.17 |
| 1.3522 | B.88 | C.17 |
| 1.3523 | B.89 | C.17 |

TABLE T-continued (compositions 1.1 to 1.3653):

| comp. no. | herbicide B | safener C |
|---|---|---|
| 1.3524 | B.90 | C.17 |
| 1.3525 | B.91 | C.17 |
| 1.3526 | B.92 | C.17 |
| 1.3527 | B.93 | C.17 |
| 1.3528 | B.94 | C.17 |
| 1.3529 | B.95 | C.17 |
| 1.3530 | B.96 | C.17 |
| 1.3531 | B.97 | C.17 |
| 1.3532 | B.98 | C.17 |
| 1.3533 | B.99 | C.17 |
| 1.3534 | B.100 | C.17 |
| 1.3535 | B.101 | C.17 |
| 1.3536 | B.102 | C.17 |
| 1.3537 | B.103 | C.17 |
| 1.3538 | B.104 | C.17 |
| 1.3539 | B.105 | C.17 |
| 1.3540 | B.106 | C.17 |
| 1.3541 | B.107 | C.17 |
| 1.3542 | B.108 | C.17 |
| 1.3543 | B.109 | C.17 |
| 1.3544 | B.110 | C.17 |
| 1.3545 | B.111 | C.17 |
| 1.3546 | B.112 | C.17 |
| 1.3547 | B.113 | C.17 |
| 1.3548 | B.114 | C.17 |
| 1.3549 | B.115 | C.17 |
| 1.3550 | B.116 | C.17 |
| 1.3551 | B.117 | C.17 |
| 1.3552 | B.118 | C.17 |
| 1.3553 | B.119 | C.17 |
| 1.3554 | B.120 | C.17 |
| 1.3555 | B.121 | C.17 |
| 1.3556 | B.122 | C.17 |
| 1.3557 | B.123 | C.17 |
| 1.3558 | B.124 | C.17 |
| 1.3559 | B.125 | C.17 |
| 1.3560 | B.126 | C.17 |
| 1.3561 | B.127 | C.17 |
| 1.3562 | B.128 | C.17 |
| 1.3563 | B.129 | C.17 |
| 1.3564 | B.130 | C.17 |
| 1.3565 | B.131 | C.17 |
| 1.3566 | B.132 | C.17 |
| 1.3567 | B.133 | C.17 |
| 1.3568 | B.134 | C.17 |
| 1.3569 | B.135 | C.17 |
| 1.3570 | B.136 | C.17 |
| 1.3571 | B.137 | C.17 |
| 1.3572 | B.138 | C.17 |
| 1.3573 | B.139 | C.17 |
| 1.3574 | B.140 | C.17 |
| 1.3575 | B.141 | C.17 |
| 1.3576 | B.142 | C.17 |
| 1.3577 | B.143 | C.17 |
| 1.3578 | B.144 | C.17 |
| 1.3579 | B.145 | C.17 |
| 1.3580 | B.146 | C.17 |
| 1.3581 | B.147 | C.17 |
| 1.3582 | B.148 | C.17 |
| 1.3583 | B.149 | C.17 |
| 1.3584 | B.150 | C.17 |
| 1.3585 | B.151 | C.17 |
| 1.3586 | B.152 | C.17 |
| 1.3587 | B.153 | C.17 |
| 1.3588 | B.154 | C.17 |
| 1.3589 | B.155 | C.17 |
| 1.3590 | B.156 | C.17 |
| 1.3591 | B.157 | C.17 |
| 1.3592 | B.158 | C.17 |
| 1.3593 | B.159 | C.17 |
| 1.3594 | B.160 | C.17 |
| 1.3595 | B.161 | C.17 |
| 1.3596 | B.162 | C.17 |
| 1.3597 | B.163 | C.17 |
| 1.3598 | B.164 | C.17 |
| 1.3599 | B.165 | C.17 |
| 1.3600 | B.166 | C.17 |
| 1.3601 | B.167 | C.17 |
| 1.3602 | B.168 | C.17 |
| 1.3603 | B.169 | C.17 |
| 1.3604 | B.170 | C.17 |
| 1.3605 | B.171 | C.17 |
| 1.3606 | B.172 | C.17 |
| 1.3607 | B.173 | C.17 |
| 1.3608 | B.174 | C.17 |
| 1.3609 | B.175 | C.17 |
| 1.3610 | B.176 | C.17 |
| 1.3611 | B.177 | C.17 |
| 1.3612 | B.178 | C.17 |
| 1.3613 | B.179 | C.17 |
| 1.3614 | B.180 | C.17 |
| 1.3615 | B.181 | C.17 |
| 1.3616 | B.182 | C.17 |
| 1.3617 | B.183 | C.17 |
| 1.3618 | B.184 | C.17 |
| 1.3619 | B.185 | C.17 |
| 1.3620 | B.186 | C.17 |
| 1.3621 | B.187 | C.17 |
| 1.3622 | B.188 | C.17 |
| 1.3623 | B.189 | C.17 |
| 1.3624 | B.190 | C.17 |
| 1.3625 | B.191 | C.17 |
| 1.3626 | B.192 | C.17 |
| 1.3627 | B.193 | C.17 |
| 1.3628 | B.194 | C.17 |
| 1.3629 | B.195 | C.17 |
| 1.3630 | B.196 | C.17 |
| 1.3631 | B.197 | C.17 |
| 1.3632 | B.198 | C.17 |
| 1.3633 | B.199 | C.17 |
| 1.3634 | B.200 | C.17 |
| 1.3635 | B.201 | C.17 |
| 1.3636 | B.202 | C.17 |
| 1.3637 | — | C.1 |
| 1.3638 | — | C.2 |
| 1.3639 | — | C.3 |
| 1.3640 | — | C.4 |
| 1.3641 | — | C.5 |
| 1.3642 | — | C.6 |
| 1.3643 | — | C.7 |
| 1.3644 | — | C.8 |
| 1.3645 | — | C.9 |
| 1.3646 | — | C.10 |
| 1.3647 | — | C.11 |
| 1.3648 | — | C.12 |
| 1.3649 | — | C.13 |
| 1.3650 | — | C.14 |
| 1.3651 | — | C.15 |
| 1.3652 | — | C.16 |
| 1.3653 | — | C.17 |

The specific number for each single composition is deductible as follows:

Composition 1.203 e.g. comprises the compound (1.1.I-25), clethodim (B.1) and benoxacor (C.1) (see table B, entry B.1 and table C, entry C.1).

Also preferred are compositions 2.1 to 2.3653 which differ from compositions 1.1 to 1.3653 wherein they comprise compound (1.1.I-37) instead of compound (1.1.I-25).

Also preferred are compositions 3.1 to 3.3653 which differ from compositions 1.1 to 1.3653 wherein they additionally comprise B.2 as further herbicide B.

Also preferred are compositions 4.1 to 4.3653 which differ from compositions 1.1 to 1.3653 wherein they additionally comprise B.8 as further herbicide B.

Also preferred are compositions 5.1 to 5.3653 which differ from compositions 1.1 to 1.3653 wherein they additionally comprise B.30 as further herbicide B.

Also preferred are compositions 6.1 to 6.3653 which differ from compositions 1.1 to 1.3653 wherein they additionally comprise B.32 as further herbicide B.

Also preferred are compositions 7.1 to 7.3653 which differ from the corresponding compositions 1.1 to 1.3653 wherein they additionally comprise B.35 as further herbicide B.

Also preferred are compositions 8.1 to 8.3653 which differ from the corresponding compositions 1.1 to 1.3653 wherein they additionally comprise B.38 as further herbicide B.

Also preferred are compositions 9.1 to 9.3653 which differ from the corresponding compositions 1.1 to 1.3653 wherein they additionally comprise B.40 as further herbicide B.

Also preferred are compositions 10.1 to 10.3653 which differ from the corresponding compositions 1.1 to 1.3653 wherein they additionally comprise B.51 as further herbicide B.

Also preferred are compositions 11.1 to 11.3653 which differ from compositions 1.1 to 1.3653 wherein they additionally comprise B.55 as further herbicide B.

Also preferred are compositions 12.1 to 12.3653 which differ from compositions 1.1 to 1.3653 wherein they additionally comprise B.56 as further herbicide B.

Also preferred are compositions 13.1 to 13.3653 which differ from compositions 1.1 to 1.3653 wherein they additionally comprise B.64 as further herbicide B.

Also preferred are compositions 14.1 to 14.3653 which differ from compositions 1.1 to 1.3653 wherein they additionally comprise B.66 as further herbicide B.

Also preferred are compositions 15.1 to 15.3653 which differ from compositions 1.1 to 1.3653 wherein they additionally comprise B.67 as further herbicide B.

Also preferred are compositions 16.1 to 16.3653 which differ from compositions 1.1 to 1.3653 wherein they additionally comprise B.68 as further herbicide B.

Also preferred are compositions 17.1 to 17.3653 which differ from compositions 1.1 to 1.3653 wherein they additionally comprise B.69 as further herbicide B.

Also preferred are compositions 18.1 to 18.3653 which differ from compositions 1.1 to 1.3653 wherein they additionally comprise B.73 as further herbicide B.

Also preferred are compositions 19.1 to 19.3653 which differ from compositions 1.1 to 1.3653 wherein they additionally comprise B.76 as further herbicide B.

Also preferred are compositions 20.1 to 20.3653 which differ from compositions 1.1 to 1.3653 wherein they additionally comprise B.81 as further herbicide B.

Also preferred are compositions 21.1 to 21.3653 which differ from compositions 1.1 to 1.3653 wherein they additionally comprise B.82 as further herbicide B.

Also preferred are compositions 22.1 to 22.3653 which differ from compositions 1.1 to 1.3653 wherein they additionally comprise B.85 as further herbicide B.

Also preferred are compositions 23.1 to 23.3653 which differ from compositions 1.1 to 1.3653 wherein they additionally comprise B.88 as further herbicide B.

Also preferred are compositions 24.1 to 24.3653 which differ from compositions 1.1 to 1.3653 wherein they additionally comprise B.89 as further herbicide B.

Also preferred are compositions 25.1 to 25.3653 which differ from compositions 1.1 to 1.3653 wherein they additionally comprise B.94 as further herbicide B.

Also preferred are compositions 26.1 to 26.3653 which differ from compositions 1.1 to 1.3653 wherein they additionally comprise B.95 as further herbicide B.

Also preferred are compositions 27.1 to 27.3653 which differ from compositions 1.1 to 1.3653 wherein they additionally comprise B.98 as further herbicide B.

Also preferred are compositions 28.1 to 28.3653 which differ from compositions 1.1 to 1.3653 wherein they additionally comprise B.100 as further herbicide B.

Also preferred are compositions 29.1 to 29.3653 which differ from compositions 1.1 to 1.3653 wherein they additionally comprise B.103 as further herbicide B.

Also preferred are compositions 30.1 to 30.3653 which differ from compositions 1.1 to 1.3653 wherein they additionally comprise B.103 and B.67 as further herbicides B.

Also preferred are compositions 31.1 to 31.3653 which differ from compositions 1.1 to 1.3653 wherein they additionally comprise B.103 and B.76 as further herbicides B.

Also preferred are compositions 32.1 to 32.3653 which differ from compositions 1.1 to 1.3653 wherein they additionally comprise B.103 and B.82 as further herbicides B.

Also preferred are compositions 33.1 to 33.3653 which differ from compositions 1.1 to 1.3653 wherein they additionally comprise B.104 as further herbicide B.

Also preferred are compositions 34.1 to 34.3653 which differ from compositions 1.1 to 1.3653 wherein they additionally comprise B.104 and B.67 as further herbicides B.

Also preferred are compositions 35.1 to 35.3653 which differ from compositions 1.1 to 1.3653 wherein they additionally comprise B.104 and B.76 as further herbicides B.

Also preferred are compositions 36.1 to 36.3653 which differ from compositions 1.1 to 1.3653 wherein they additionally comprise B.104 and B.82 as further herbicides B.

Also preferred are compositions 37.1 to 37.3653 which differ from compositions 1.1 to 1.3653 wherein they additionally comprise B.106 as further herbicide B.

Also preferred are compositions 38.1 to 38.3653 which differ from compositions 1.1 to 1.3653 wherein they additionally comprise B.107 as further herbicide B.

Also preferred are compositions 39.1 to 39.3653 which differ from compositions 1.1 to 1.3653 wherein they additionally comprise B. 107 and B.67 as further herbicides B.

Also preferred are compositions 40.1 to 40.3653 which differ from compositions 1.1 to 1.3653 wherein they additionally comprise B. 107 and B.76 as further herbicides B.

Also preferred are compositions 41.1 to 41.3653 which differ from compositions 1.1 to 1.3653 wherein they additionally comprise B. 107 and B.82 as further herbicides B.

Also preferred are compositions 42.1 to 42.3653 which differ from compositions 1.1 to 1.3653 wherein they additionally comprise B.109 as further herbicide B.

Also preferred are compositions 43.1 to 43.3653 which differ from compositions 1.1 to 1.3653 wherein they additionally comprise B.111 as further herbicide B.

Also preferred are compositions 44.1 to 44.3653 which differ from compositions 1.1 to 1.3653 wherein they additionally comprise B.111 and B.67 as further herbicides B.

Also preferred are compositions 45.1 to 45.3653 which differ from compositions 1.1 to 1.3653 wherein they additionally comprise B.111 and B.76 as further herbicides B.

Also preferred are compositions 46.1 to 46.3653 which differ from compositions 1.1 to 1.3653 wherein they additionally comprise B.111 and B.82 as further herbicides B.

Also preferred are compositions 47.1 to 47.3653 which differ from compositions 1.1 to 1.3653 wherein they additionally comprise B. 116 as further herbicide B.

Also preferred are compositions 48.1 to 48.3653 which differ from compositions 1.1 to 1.3653 wherein they additionally comprise B.116 and B.67 as further herbicides B.

Also preferred are compositions 49.1 to 49.3653 which differ from compositions 1.1 to 1.3653 wherein they additionally comprise B.116 and B.94 as further herbicides B.

Also preferred are compositions 50.1 to 50.3653 which differ from compositions 1.1 to 1.3653 wherein they additionally comprise B.116 and B.103 as further herbicides B.

Also preferred are compositions 51.1 to 51.3653 which differ from compositions 1.1 to 1.3653 wherein they additionally comprise B.116 and B.128 as further herbicides B.

Also preferred are compositions 52.1 to 52.3653 which differ from compositions 1.1 to 1.3653 wherein they additionally comprise B.116 and B.104 as further herbicides B.

Also preferred are compositions 53.1 to 53.3653 which differ from compositions 1.1 to 1.3653 wherein they additionally comprise B.116 and B.107 as further herbicides B.

Also preferred are compositions 54.1 to 54.3653 which differ from compositions 1.1 to 1.3653 wherein they additionally comprise B.116 and B.111 as further herbicides B.

Also preferred are compositions 55.1 to 55.3653 which differ from compositions 1.1 to 1.3653 wherein they additionally comprise B.122 as further herbicide B.

Also preferred are compositions 56.1 to 56.3653 which differ from compositions 1.1 to 1.3653 wherein they additionally comprise B.126 as further herbicide B.

Also preferred are compositions 57.1 to 57.3653 which differ from compositions 1.1 to 1.3653 wherein they additionally comprise B.128 as further herbicide B.

Also preferred are compositions 58.1 to 58.3653 which differ from compositions 1.1 to 1.3653 wherein they additionally comprise B.131 as further herbicide B.

Also preferred are compositions 59.1 to 59.3653 which differ from compositions 1.1 to 1.3653 wherein they additionally comprise B.132 as further herbicide B.

Also preferred are compositions 60.1 to 60.3653 which differ from compositions 1.1 to 1.3653 wherein they additionally comprise B.133 as further herbicide B.

Also preferred are compositions 61.1 to 61.3653 which differ from compositions 1.1 to 1.3653 wherein they additionally comprise B.135 as further herbicide B.

Also preferred are compositions 62.1 to 62.3653 which differ from compositions 1.1 to 1.3653 wherein they additionally comprise B.137 as further herbicide B.

Also preferred are compositions 63.1 to 63.3653 which differ from compositions 11.1 to 1.3653 wherein they additionally comprise B.138 as further herbicide B.

Also preferred are compositions 64.1 to 64.3653 which differ from compositions 1.1 to 1.3653 wherein they additionally comprise B.140 as further herbicide B.

Also preferred are compositions 65.1 to 65.3653 which differ from compositions 1.1 to 1.3653 wherein they additionally comprise B.145 as further herbicide B.

Also preferred are compositions 66.1 to 66.3653 which differ from compositions 1.1 to 1.3653 wherein they additionally comprise B.153 as further herbicide B.

Also preferred are compositions 67.1 to 67.3653 which differ from compositions 1.1 to 1.3653 wherein they additionally comprise B.156 as further herbicide B.

Also preferred are compositions 68.1 to 68.3653 which differ from compositions 1.1 to 1.3653 wherein they additionally comprise B.171 as further herbicide B.

Also preferred are compositions 69.1 to 69.3653 which differ from compositions 1.1 to 1.3653 wherein they additionally comprise B.174 as further herbicide B.

Also preferred are compositions 70.1 to 70.3653 which differ from compositions 1.1 to 1.3653 wherein they comprise compound (1.1.I-31) instead of compound (1.1.I-25).

Also preferred are compositions 71.1 to 71.3653 which differ from compositions 1.1 to 1.3653 wherein they comprise compound (1.1.I-49) instead of compound (1.1.I-25).

Also preferred are compositions 72.1 to 72.3653 which differ from compositions 1.1 to 1.3653 wherein they comprise compound (1.1.I-61) instead of compound (1.1.I-25).

Also preferred are compositions 73.1 to 73.3653 which differ from compositions 1.1 to 1.3653 wherein they comprise compound (1.1.I-55) instead of compound (1.1.I-25).

Also preferred are compositions 74.1 to 74.3653 which differ from compositions 1.1 to 1.3653 wherein they comprise compound (1.1.I-73) instead of compound (1.1.I-25).

Also preferred are compositions 76.1 to 76.3653 which differ from compositions 1.1 to 1.3653 wherein they comprise compound (1.2.I-25) instead of compound (1.1.I-25).

Also preferred are compositions 77.1 to 77.3653 which differ from compositions 1.1 to 1.3653 wherein they comprise compound (1.2.I-37) instead of compound (1.1.I-25).

Also preferred are compositions 78.1 to 78.3653 which differ from compositions 1.1 to 1.3653 wherein they comprise compound (1.2.I-31) instead of compound (1.1.I-25).

Also preferred are compositions 79.1 to 79.3653 which differ from compositions 1.1 to 1.3653 wherein they comprise compound (1.2.I-49) instead of compound (1.1.I-25).

Also preferred are compositions 80.1 to 80.3653 which differ from compositions 1.1 to 1.3653 wherein they comprise compound (1.2.I-61) instead of compound (1.1.I-25).

Also preferred are compositions 81.1 to 81.3653 which differ from compositions 1.1 to 1.3653 wherein they comprise compound (1.2.I-55) instead of compound (1.1.I-25).

Also preferred are compositions 82.1 to 82.3653 which differ from compositions 1.1 to 1.3653 wherein they comprise compound (1.2.I-73) instead of compound (1.1.I-25).

Also preferred are compositions 83.1 to 83.3653 which differ from compositions 1.1 to 1.3653 wherein they comprise compound (1.3.I-25) instead of compound (1.1.I-25).

Also preferred are compositions 84.1 to 84.3653 which differ from compositions 1.1 to 1.3653 wherein they comprise compound (1.3.I-37) instead of compound (1.1.I-25).

Also preferred are compositions 85.1 to 85.3653 which differ from compositions 1.1 to 1.3653 wherein they comprise compound (1.3.I-31) instead of compound (1.1.I-25).

Also preferred are compositions 86.1 to 86.3653 which differ from compositions 1.1 to 1.3653 wherein they comprise compound (1.3.I-49) instead of compound (1.1.I-25).

Also preferred are compositions 87.1 to 87.3653 which differ from compositions 1.1 to 1.3653 wherein they comprise compound (1.3.I-61) instead of compound (1.1.I-25).

Also preferred are compositions 88.1 to 88.3653 which differ from compositions 1.1 to 1.3653 wherein they comprise compound (1.3.I-55) instead of compound (1.1.I-25).

Also preferred are compositions 89.1 to 89.3653 which differ from compositions 1.1 to 1.3653 wherein they comprise compound (1.3.I-73) instead of compound (1.1.I-25).

Also preferred are compositions 90.1 to 90.3653 which differ from compositions 1.1 to 1.3653 wherein they comprise compound (1.4.I-25) instead of compound (1.1.I-25).

Also preferred are compositions 91.1 to 91.3653 which differ from compositions 1.1 to 1.3653 wherein they comprise compound (1.4.I-37) instead of compound (1.1.I-25).

Also preferred are compositions 92.1 to 92.3653 which differ from compositions 1.1 to 1.3653 wherein they comprise compound (1.4.I-31) instead of compound (1.1.I-25).

Also preferred are compositions 93.1 to 93.3653 which differ from compositions 1.1 to 1.3653 wherein they comprise compound (1.4.I-49) instead of compound (1.1.I-25).

Also preferred are compositions 94.1 to 94.3653 which differ from compositions 1.1 to 1.3653 wherein they comprise compound (1.4.I-61) instead of compound (1.1.I-25).

Also preferred are compositions 95.1 to 95.3653 which differ from compositions 1.1 to 1.3653 wherein they comprise compound (1.4.I-55) instead of compound (1.1.I-25).

Also preferred are compositions 96.1 to 96.3653 which differ from compositions 1.1 to 1.3653 wherein they comprise compound (1.4.I-73) instead of compound (1.1.I-25).

Also preferred are compositions 97.1 to 97.3653 which differ from compositions 1.1 to 1.3653 wherein they comprise compound (1.5.I-25) instead of compound (1.1.I-25).

Also preferred are compositions 98.1 to 98.3653 which differ from compositions 1.1 to 1.3653 wherein they comprise compound (1.5.I-37) instead of compound (1.1.I-25).

Also preferred are compositions 99.1 to 99.3653 which differ from compositions 1.1 to 1.3653 wherein they comprise compound (1.5.I-31) instead of compound (1.1.I-25).

Also preferred are compositions 100.1 to 100.3653 which differ from compositions 1.1 to 1.3653 wherein they comprise compound (1.5.I-49) instead of compound (1.1.I-25).

Also preferred are compositions 101.1 to 101.3653 which differ from compositions 1.1 to 1.3653 wherein they comprise compound (1.5.I-61) instead of compound (1.1.I-25).

Also preferred are compositions 102.1 to 102.3653 which differ from compositions 1.1 to 1.3653 wherein they comprise compound (1.5.I-55) instead of compound (1.1.I-25).

Also preferred are compositions 103.1 to 103.3653 which differ from compositions 1.1 to 1.3653 wherein they comprise compound (1.5.I-73) instead of compound (1.1.I-25).

Also preferred are compositions 104.1 to 104.3653 which differ from compositions 1.1 to 1.3653 wherein they comprise compound (1.6.I-25) instead of compound (1.1.I-25).

Also preferred are compositions 105.1 to 105.3653 which differ from compositions 1.1 to 1.3653 wherein they comprise compound (1.6.I-37) instead of compound (1.1.I-25).

Also preferred are compositions 105.1 to 106.3653 which differ from compositions 1.1 to 1.3653 wherein they comprise compound (1.6.I-31) instead of compound (1.1.I-25).

Also preferred are compositions 107.1 to 107.3653 which differ from compositions 1.1 to 1.3653 wherein they comprise compound (1.6.I-49) instead of compound (1.1.I-25).

Also preferred are compositions 108.1 to 108.3653 which differ from compositions 1.1 to 1.3653 wherein they comprise compound (1.6.I-61) instead of compound (1.1.I-25).

Also preferred are compositions 109.1 to 109.3653 which differ from compositions 1.1 to 1.3653 wherein they comprise compound (1.6.I-55) instead of compound (1.1.I-25).

Also preferred are compositions 110.1 to 110.3653 which differ from compositions 1.1 to 1.3653 wherein they comprise compound (1.6.I-73) instead of compound (1.1.I-25).

Also preferred are compositions 111.1 to 111.3653 which differ from compositions 1.1 to 1.3653 wherein they comprise compound (1.7.I-25) instead of compound (1.1.I-25).

Also preferred are compositions 112.1 to 112.3653 which differ from compositions 1.1 to 1.3653 wherein they comprise compound (1.7.I-37) instead of compound (1.1.I-25).

Also preferred are compositions 113.1 to 113.3653 which differ from compositions 1.1 to 1.3653 wherein they comprise compound (1.7.I-31) instead of compound (1.1.I-25).

Also preferred are compositions 114.1 to 114.3653 which differ from compositions 1.1 to 1.3653 wherein they comprise compound (1.7.I-49) instead of compound (1.1.I-25).

Also preferred are compositions 115.1 to 115.3653 which differ from compositions 1.1 to 1.3653 wherein they comprise compound (1.7.I-61) instead of compound (1.1.I-25).

Also preferred are compositions 116.1 to 116.3653 which differ from compositions 1.1 to 1.3653 wherein they comprise compound (1.7.I-55) instead of compound (1.1.I-25).

Also preferred are compositions 117.1 to 118.3653 which differ from compositions 1.1 to 1.3653 wherein they comprise compound (1.7.I-73) instead of compound (1.1.I-25).

Also preferred are compositions 119.1 to 119.3653 which differ from compositions 1.1 to 1.3653 wherein they comprise compound (1.8.I-25) instead of compound (1.1.I-25).

Also preferred are compositions 120.1 to 120.3653 which differ from compositions 1.1 to 1.3653 wherein they comprise compound (1.8.I-37) instead of compound (1.1.I-25).

Also preferred are compositions 121.1 to 121.3653 which differ from compositions 1.1 to 1.3653 wherein they comprise compound (1.8.I-31) instead of compound (1.1.I-25).

Also preferred are compositions 122.1 to 122.3653 which differ from compositions 1.1 to 1.3653 wherein they comprise compound (1.8.I-49) instead of compound (1.1.I-25).

Also preferred are compositions 123.1 to 123.3653 which differ from compositions 1.1 to 1.3653 wherein they comprise compound (1.8.I-61) instead of compound (1.1.I-25).

Also preferred are compositions 124.1 to 124.3653 which differ from compositions 1.1 to 1.3653 wherein they comprise compound (1.8.I-55) instead of compound (1.1.I-25).

Also preferred are compositions 125.1 to 125.3653 which differ from compositions 1.1 to 1.3653 wherein they comprise compound (1.8.I-73) instead of compound (1.1.I-25).

Also preferred are compositions 126.1 to 126.3653 which differ from compositions 1.1 to 1.3653 wherein they comprise compound (1.9.I-25) instead of compound (1.1.I-25).

Also preferred are compositions 127.1 to 127.3653 which differ from compositions 1.1 to 1.3653 wherein they comprise compound (1.9.I-37) instead of compound (1.1.I-25).

Also preferred are compositions 128.1 to 128.3653 which differ from compositions 1.1 to 1.3653 wherein they comprise compound (1.9.I-31) instead of compound (1.1.I-25).

Also preferred are compositions 129.1 to 129.3653 which differ from compositions 1.1 to 1.3653 wherein they comprise compound (1.9.I-49) instead of compound (1.1.I-25).

Also preferred are compositions 130.1 to 130.3653 which differ from compositions 1.1 to 1.3653 wherein they comprise compound (1.9.I-61) instead of compound (1.1.I-25).

Also preferred are compositions 131.1 to 131.3653 which differ from compositions 1.1 to 1.3653 wherein they comprise compound (1.9.I-55) instead of compound (1.1.I-25).

Also preferred are compositions 132.1 to 132.3653 which differ from compositions 1.1 to 1.3653 wherein they comprise compound (1.9.I-73) instead of compound (1.1.I-25).

Also preferred are compositions 133.1 to 133.3653 which differ from compositions 1.1 to 1.3653 wherein they comprise compound (1.10.I-25) instead of compound (1.1.I-25).

Also preferred are compositions 134.1 to 134.3653 which differ from compositions 1.1 to 1.3653 wherein they comprise compound (1.10.I-37) instead of compound (1.1.I-25).

Also preferred are compositions 135.1 to 135.3653 which differ from compositions 1.1 to 1.3653 wherein they comprise compound (1.10.I-31) instead of compound (1.1.I-25).

Also preferred are compositions 136.1 to 136.3653 which differ from compositions 1.1 to 1.3653 wherein they comprise compound (1.10.I-49) instead of compound (1.1.I-25).

Also preferred are compositions 137.1 to 137.3653 which differ from compositions 1.1 to 1.3653 wherein they comprise compound (1.10.I-61) instead of compound (1.1.I-25).

Also preferred are compositions 138.1 to 138.3653 which differ from compositions 1.1 to 1.3653 wherein they comprise compound (1.10.I-55) instead of compound (1.1.I-25).

Also preferred are compositions 139.1 to 139.3653 which differ from compositions 1.1 to 1.3653 wherein they comprise compound (1.10.I-73) instead of compound (1.1.I-25).

Also preferred are compositions 140.1 to 140.3653 which differ from compositions 1.1 to 1.3653 wherein they comprise compound (1.31.I-25) instead of compound (1.1.I-25).

Also preferred are compositions 141.1 to 141.3653 which differ from compositions 1.1 to 1.3653 wherein they comprise compound (1.31.I-31) instead of compound (1.1.I-25).

Also preferred are compositions 142.1 to 142.3653 which differ from compositions 1.1 to 1.3653 wherein they comprise compound (1.31.I-37) instead of compound (1.1.I-25).

Also preferred are compositions 143.1 to 143.3653 which differ from compositions 1.1 to 1.3653 wherein they comprise compound (1.31.I-49) instead of compound (1.1.I-25).

Also preferred are compositions 144.1 to 144.3653 which differ from compositions 1.1 to 1.3653 wherein they comprise compound (1.31.I-55) instead of compound (1.1.I-25).

Also preferred are compositions 145.1 to 145.3653 which differ from compositions 1.1 to 1.3653 wherein they comprise compound (1.31.I-61) instead of compound (1.1.I-25).

Also preferred are compositions 146.1 to 146.3653 which differ from compositions 1.1 to 1.3653 wherein they comprise compound (1.37.I-25) instead of compound (1.1.I-25).

Also preferred are compositions 147.1 to 147.3653 which differ from compositions 1.1 to 1.3653 wherein they comprise compound (1.37.I-31) instead of compound (1.1.I-25).

Also preferred are compositions 148.1 to 148.3653 which differ from compositions 1.1 to 1.3653 wherein they comprise compound (1.37.I-37) instead of compound (1.1.I-25).

Also preferred are compositions 149.1 to 149.3653 which differ from compositions 1.1 to 1.3653 wherein they comprise compound (1.37.I-49) instead of compound (1.1.I-25).

Also preferred are compositions 150.1 to 150.3653 which differ from compositions 1.1 to 1.3653 wherein they comprise compound (1.37.I-55) instead of compound (1.1.I-25).

Also preferred are compositions 151.1 to 151.3653 which differ from compositions 1.1 to 1.3653 wherein they comprise compound (1.37.I-61) instead of compound (1.1.I-25).

Also preferred are compositions 152.1 to 152.3653 which differ from compositions 1.1 to 1.3653 wherein they comprise compound (1.38.I-25) instead of compound (1.1.I-25).

Also preferred are compositions 153.1 to 153.3653 which differ from compositions 1.1 to 1.3653 wherein they comprise compound (1.38.I-31) instead of compound (1.1.I-25).

Also preferred are compositions 154.1 to 154.3653 which differ from compositions 1.1 to 1.3653 wherein they comprise compound (1.38.I-37) instead of compound (1.1.I-25).

Also preferred are compositions 155.1 to 156.3653 which differ from compositions 1.1 to 1.3653 wherein they comprise compound (1.38.I-49) instead of compound (1.1.I-25).

Also preferred are compositions 157.1 to 157.3653 which differ from compositions 1.1 to 1.3653 wherein they comprise compound (1.38.I-55) instead of compound (1.1.I-25).

Also preferred are compositions 158.1 to 158.3653 which differ from compositions 1.1 to 1.3653 wherein they comprise compound (1.38.I-61) instead of compound (1.1.I-25).

Also preferred are compositions 159.1 to 159.3653 which differ from compositions 1.1 to 1.3653 wherein they comprise compound (1.39.I-25) instead of compound (1.1.I-25).

Also preferred are compositions 160.1 to 160.3653 which differ from compositions 1.1 to 1.3653 wherein they comprise compound (1.39.I-31) instead of compound (1.1.I-25).

Also preferred are compositions 161.1 to 161.3653 which differ from compositions 1.1 to 1.3653 wherein they comprise compound (1.39.I-37) instead of compound (1.1.I-25).

Also preferred are compositions 162.1 to 162.3653 which differ from compositions 1.1 to 1.3653 wherein they comprise compound (1.39.I-49) instead of compound (1.1.I-25).

Also preferred are compositions 163.1 to 163.3653 which differ from compositions 1.1 to 1.3653 wherein they comprise compound (1.39.I-55) instead of compound (1.1.I-25).

Also preferred are compositions 164.1 to 164.3653 which differ from compositions 1.1 to 1.3653 wherein they comprise compound (1.39.I-61) instead of compound (1.1.I-25).

Also preferred are compositions 165.1 to 165.3653 which differ from compositions 1.1 to 1.3653 wherein they comprise compound (1.46.I-25) instead of compound (1.1.I-25).

Also preferred are compositions 166.1 to 166.3653 which differ from compositions 1.1 to 1.3653 wherein they comprise compound (1.46.I-31) instead of compound (1.1.I-25).

Also preferred are compositions 167.1 to 167.3653 which differ from compositions 1.1 to 1.3653 wherein they comprise compound (1.46.I-37) instead of compound (1.1.I-25).

Also preferred are compositions 168.1 to 168.3653 which differ from compositions 1.1 to 1.3653 wherein they comprise compound (1.46.I-49) instead of compound (1.1.I-25).

Also preferred are compositions 169.1 to 169.3653 which differ from compositions 1.1 to 1.3653 wherein they comprise compound (1.46.I-55) instead of compound (1.1.I-25).

Also preferred are compositions 170.1 to 170.3653 which differ from compositions 1.1 to 1.3653 wherein they comprise compound (1.46.I-61) instead of compound (1.1.I-25).

Also preferred are compositions 171.1 to 171.3653 which differ from compositions 1.1 to 1.3653 wherein they comprise compound (1.47.I-25) instead of compound (1.1.I-25).

Also preferred are compositions 172.1 to 172.3653 which differ from compositions 1.1 to 1.3653 wherein they comprise compound (1.47.I-31) instead of compound (1.1.I-25).

Also preferred are compositions 173.1 to 173.3653 which differ from compositions 1.1 to 1.3653 wherein they comprise compound (1.47.I-37) instead of compound (1.1.I-25).

Also preferred are compositions 174.1 to 174.3653 which differ from compositions 1.1 to 1.3653 wherein they comprise compound (1.47.I-49) instead of compound (1.1.I-25).

Also preferred are compositions 175.1 to 175.3653 which differ from compositions 1.1 to 1.3653 wherein they comprise compound (1.47.I-55) instead of compound (1.1.I-25).

Also preferred are compositions 176.1 to 176.3653 which differ from compositions 1.1 to 1.3653 wherein they comprise compound (1.47.I-61) instead of compound (1.1.I-25).

Also preferred are compositions 177.1 to 177.3653 which differ from compositions 1.1 to 1.3653 wherein they comprise compound (1.53.I-25) instead of compound (1.1.I-25).

Also preferred are compositions 178.1 to 178.3653 which differ from compositions 1.1 to 1.3653 wherein they comprise compound (1.53.I-31) instead of compound (1.1.I-25).

Also preferred are compositions 179.1 to 179.3653 which differ from compositions 1.1 to 1.3653 wherein they comprise compound (1.53.I-37) instead of compound (1.1.I-25).

Also preferred are compositions 180.1 to 180.3653 which differ from compositions 1.1 to 1.3653 wherein they comprise compound (1.53.I-49) instead of compound (1.1.I-25).

Also preferred are compositions 181.1 to 181.3653 which differ from compositions 1.1 to 1.3653 wherein they comprise compound (1.53.I-55) instead of compound (1.1.I-25).

Also preferred are compositions 182.1 to 182.3653 which differ from compositions 1.1 to 1.3653 wherein they comprise compound (1.53.I-61) instead of compound (1.1.I-25).

Also preferred are compositions 183.1 to 183.3653 which differ from compositions 1.1 to 1.3653 wherein they comprise compound (1.59.I-25) instead of compound (1.1.I-25).

Also preferred are compositions 184.1 to 184.3653 which differ from compositions 1.1 to 1.3653 wherein they comprise compound (1.59.I-31) instead of compound (1.1.I-25).

Also preferred are compositions 185.1 to 185.3653 which differ from compositions 1.1 to 1.3653 wherein they comprise compound (1.59.I-37) instead of compound (1.1.I-25).

Also preferred are compositions 186.1 to 186.3653 which differ from compositions 1.1 to 1.3653 wherein they comprise compound (1.59.I-49) instead of compound (1.1.I-25).

Also preferred are compositions 187.1 to 187.3653 which differ from compositions 1.1 to 1.3653 wherein they comprise compound (1.59.I-55) instead of compound (1.1.I-25).

Also preferred are compositions 188.1 to 188.3653 which differ from compositions 1.1 to 1.3653 wherein they comprise compound (1.59.I-61) instead of compound (1.1.I-25).

Also preferred are compositions 189.1 to 189.3653 which differ from compositions 1.1 to 1.3653 wherein they comprise compound (1.63.I-25) instead of compound (1.1.I-25).

Also preferred are compositions 190.1 to 190.3653 which differ from compositions 1.1 to 1.3653 wherein they comprise compound (1.63.I-31) instead of compound (1.1.I-25).

Also preferred are compositions 191.1 to 191.3653 which differ from compositions 1.1 to 1.3653 wherein they comprise compound (1.63.I-37) instead of compound (1.1.I-25).

Also preferred are compositions 192.1 to 192.3653 which differ from compositions 1.1 to 1.3653 wherein they comprise compound (1.63.I-49) instead of compound (1.1.I-25).

Also preferred are compositions 193.1 to 193.3653 which differ from compositions 1.1 to 1.3653 wherein they comprise compound (1.63.I-55) instead of compound (1.1.I-25).

Also preferred are compositions 194.1 to 194.3653 which differ from compositions 1.1 to 1.3653 wherein they comprise compound (1.63.I-61) instead of compound (1.1.I-25).

Also preferred are compositions 195.1 to 195.3653 which differ from compositions 1.1 to 1.3653 wherein they comprise compound (1.64.I-25) instead of compound (1.1.I-25).

Also preferred are compositions 196.1 to 196.3653 which differ from compositions 1.1 to 1.3653 wherein they comprise compound (1.64.I-31) instead of compound (1.1.I-25).

Also preferred are compositions 197.1 to 197.3653 which differ from compositions 1.1 to 1.3653 wherein they comprise compound (1.64.I-37) instead of compound (1.1.I-25).

Also preferred are compositions 198.1 to 198.3653 which differ from compositions 1.1 to 1.3653 wherein they comprise compound (1.64.I-49) instead of compound (1.1.I-25).

Also preferred are compositions 199.1 to 199.3653 which differ from compositions 1.1 to 1.3653 wherein they comprise compound (1.64.I-55) instead of compound (1.1.I-25).

Also preferred are compositions 200.1 to 200.3653 which differ from compositions 1.1 to 1.3653 wherein they comprise compound (1.64.I-61) instead of compound (1.1.I-25).

Also preferred are compositions 201.1 to 201.3653 which differ from compositions 1.1 to 1.3653 wherein they comprise compound (1.65.I-25) instead of compound (1.1.I-25).

Also preferred are compositions 202.1 to 202.3653 which differ from compositions 1.1 to 1.3653 wherein they comprise compound (1.65.I-31) instead of compound (1.1.I-25).

Also preferred are compositions 203.1 to 203.3653 which differ from compositions 1.1 to 1.3653 wherein they comprise compound (1.65.I-37) instead of compound (1.1.I-25).

Also preferred are compositions 204.1 to 204.3653 which differ from compositions 1.1 to 1.3653 wherein they comprise compound (1.65.I-49) instead of compound (1.1.I-25).

Also preferred are compositions 205.1 to 205.3653 which differ from compositions 1.1 to 1.3653 wherein they comprise compound (1.65.I-55) instead of compound (1.1.I-25).

Also preferred are compositions 206.1 to 206.3653 which differ from compositions 1.1 to 1.3653 wherein they comprise compound (1.65.I-61) instead of compound (1.1.I-25).

Also preferred are compositions 207.1 to 207.3653 which differ from compositions 1.1 to 1.3653 wherein they comprise compound (1.72.I-25) instead of compound (1.1.I-25).

Also preferred are compositions 208.1 to 208.3653 which differ from compositions 1.1 to 1.3653 wherein they comprise compound (1.72.I-31) instead of compound (1.1.I-25).

Also preferred are compositions 209.1 to 209.3653 which differ from compositions 1.1 to 1.3653 wherein they comprise compound (1.72.I-37) instead of compound (1.1.I-25).

Also preferred are compositions 210.1 to 210.3653 which differ from compositions 1.1 to 1.3653 wherein they comprise compound (1.72.I-49) instead of compound (1.1.I-25).

Also preferred are compositions 211.1 to 211.3653 which differ from compositions 1.1 to 1.3653 wherein they comprise compound (1.72.I-55) instead of compound (1.1.I-25).

Also preferred are compositions 212.1 to 212.3653 which differ from compositions 1.1 to 1.3653 wherein they comprise compound (1.72.I-61) instead of compound (1.1.I-25).

Also preferred are compositions 213.1 to 213.3653 which differ from compositions 1.1 to 1.3653 wherein they comprise compound (1.73.I-25) instead of compound (1.1.I-25).

Also preferred are compositions 214.1 to 214.3653 which differ from compositions 1.1 to 1.3653 wherein they comprise compound (1.73.I-31) instead of compound (1.1.I-25).

Also preferred are compositions 215.1 to 215.3653 which differ from compositions 1.1 to 1.3653 wherein they comprise compound (1.73.I-37) instead of compound (1.1.I-25).

Also preferred are compositions 216.1 to 216.3653 which differ from compositions 1.1 to 1.3653 wherein they comprise compound (1.73.I-49) instead of compound (1.1.I-25).

Also preferred are compositions 217.1 to 217.3653 which differ from compositions 1.1 to 1.3653 wherein they comprise compound (1.73.I-55) instead of compound (1.1.I-25).

Also preferred are compositions 218.1 to 218.3653 which differ from compositions 1.1 to 1.3653 wherein they comprise compound (1.73.I-61) instead of compound (1.1.I-25).

Also preferred are compositions 219.1 to 219.3653 which differ from compositions 1.1 to 1.3653 wherein they comprise compound (1.79.I-25) instead of compound (1.1.I-25).

Also preferred are compositions 220.1 to 220.3653 which differ from compositions 1.1 to 1.3653 wherein they comprise compound (1.79.I-31) instead of compound (1.1.I-25).

Also preferred are compositions 221.1 to 221.3653 which differ from compositions 1.1 to 1.3653 wherein they comprise compound (1.79.I-37) instead of compound (1.1.I-25).

Also preferred are compositions 222.1 to 222.3653 which differ from compositions 1.1 to 1.3653 wherein they comprise compound (1.79.I-49) instead of compound (1.1.I-25).

Also preferred are compositions 223.1 to 223.3653 which differ from compositions 1.1 to 1.3653 wherein they comprise compound (1.79.I-55) instead of compound (1.1.I-25).

Also preferred are compositions 224.1 to 224.3653 which differ from compositions 1.1 to 1.3653 wherein they comprise compound (1.79.I-61) instead of compound (1.1.I-25).

Also preferred are compositions 225.1 to 225.3653 which differ from compositions 1.1 to 1.3653 wherein they comprise compound (1.272.I-25) instead of compound (1.1.I-25).

Also preferred are compositions 226.1 to 226.3653 which differ from compositions 1.1 to 1.3653 wherein they comprise compound (1.272.I-31) instead of compound (1.1.I-25).

Also preferred are compositions 227.1 to 227.3653 which differ from compositions 1.1 to 1.3653 wherein they comprise compound (1.272.I-37) instead of compound (1.1.I-25).

Also preferred are compositions 228.1 to 228.3653 which differ from compositions 1.1 to 1.3653 wherein they comprise compound (1.272.I-49) instead of compound (1.1.I-25).

Also preferred are compositions 229.1 to 229.3653 which differ from compositions 1.1 to 1.3653 wherein they comprise compound (1.272.I-55) instead of compound (1.1.I-25).

Also preferred are compositions 230.1 to 230.3653 which differ from compositions 1.1 to 1.3653 wherein they comprise compound (1.272.I-61) instead of compound (1.1.I-25).

Also preferred are compositions 231.1 to 231.3653 which differ from compositions 1.1 to 1.3653 wherein they comprise compound (1.273.I-25) instead of compound (1.1.I-25).

Also preferred are compositions 232.1 to 232.3653 which differ from compositions 1.1 to 1.3653 wherein they comprise compound (1.273.I-31) instead of compound (1.1.I-25).

Also preferred are compositions 233.1 to 234.3653 which differ from compositions 1.1 to 1.3653 wherein they comprise compound (1.273.I-37) instead of compound (1.1.I-25).

Also preferred are compositions 235.1 to 235.3653 which differ from compositions 1.1 to 1.3653 wherein they comprise compound (1.273.I-49) instead of compound (1.1.I-25).

Also preferred are compositions 236.1 to 236.3653 which differ from compositions 1.1 to 1.3653 wherein they comprise compound (1.273.I-55) instead of compound (1.1.I-25).

Also preferred are compositions 237.1 to 237.3653 which differ from compositions 1.1 to 1.3653 wherein they comprise compound (1.273.I-61) instead of compound (1.1.I-25).

Also preferred are compositions 238.1 to 238.3653 which differ from compositions 1.1 to 1.3653 wherein they comprise compound (1.584.I-25) instead of compound (1.1.I-25).

Also preferred are compositions 239.1 to 239.3653 which differ from compositions 1.1 to 1.3653 wherein they comprise compound (1.584.I-31) instead of compound (1.1.I-25).

Also preferred are compositions 240.1 to 240.3653 which differ from compositions 1.1 to 1.3653 wherein they comprise compound (1.584.I-37) instead of compound (1.1.I-25).

Also preferred are compositions 241.1 to 241.3653 which differ from compositions 1.1 to 1.3653 wherein they comprise compound (1.584.I-49) instead of compound (1.1.I-25).

Also preferred are compositions 242.1 to 242.3653 which differ from compositions 1.1 to 1.3653 wherein they comprise compound (1.584.I-55) instead of compound (1.1.I-25).

Also preferred are compositions 243.1 to 243.3653 which differ from compositions 1.1 to 1.3653 wherein they comprise compound (1.584.I-61) instead of compound (1.1.I-25).

Also preferred are compositions 244.1 to 244.3653 which differ from compositions 1.1 to 1.3653 wherein they comprise compound (1.585.I-25) instead of compound (1.1.I-25).

Also preferred are compositions 245.1 to 245.3653 which differ from compositions 1.1 to 1.3653 wherein they comprise compound (1.585.I-31) instead of compound (1.1.I-25).

Also preferred are compositions 246.1 to 246.3653 which differ from compositions 1.1 to 1.3653 wherein they comprise compound (1.585.I-37) instead of compound (1.1.I-25).

Also preferred are compositions 247.1 to 247.3653 which differ from compositions 1.1 to 1.3653 wherein they comprise compound (1.585.I-49) instead of compound (1.1.I-25).

Also preferred are compositions 248.1 to 248.3653 which differ from compositions 1.1 to 1.3653 wherein they comprise compound (1.585.I-55) instead of compound (1.1.I-25).

Also preferred are compositions 249.1 to 249.3653 which differ from compositions 1.1 to 1.3653 wherein they comprise compound (1.585.I-61) instead of compound (1.1.I-25).

Also preferred are compositions 250.1 to 250.3653 which differ from compositions 1.1 to 1.3653 wherein they comprise compound (1.592.I-25) instead of compound (1.1.I-25).

Also preferred are compositions 251.1 to 251.3653 which differ from compositions 1.1 to 1.3653 wherein they comprise compound (1.592.I-31) instead of compound (1.1.I-25).

Also preferred are compositions 252.1 to 252.3653 which differ from compositions 1.1 to 1.3653 wherein they comprise compound (1.592.I-37) instead of compound (1.1.I-25).

Also preferred are compositions 253.1 to 253.3653 which differ from compositions 1.1 to 1.3653 wherein they comprise compound (1.592.I-49) instead of compound (1.1.I-25).

Also preferred are compositions 254.1 to 254.3653 which differ from compositions 1.1 to 1.3653 wherein they comprise compound (1.592.I-55) instead of compound (1.1.I-25).

Also preferred are compositions 255.1 to 255.3653 which differ from compositions 1.1 to 1.3653 wherein they comprise compound (1.592.I-61) instead of compound (1.1.I-25).

The invention also relates to agrochemical compositions comprising at least an auxiliary and at least one pyrimidine compound of formula (I) according to the invention.

An agrochemical composition comprises a pesticidal effective amount of a pyrimidine compound of formula (I). The term "effective amount" denotes an amount of the composition or of the compounds I, which is sufficient for controlling unwanted plants, especially for controlling unwanted plants in cultivated plants and which does not result in a substantial damage to the treated plants. Such an amount can vary in a broad range and is dependent on various factors, such as the plants to be controlled, the treated cultivated plant or material, the climatic conditions and the specific pyrimidine compound of formula (I) used.

The pyrimidine compounds of formula (I), their N-oxides, salts or derivatives can be converted into customary types of agrochemical compositions, e. g. solutions, emulsions, suspensions, dusts, powders, pastes, granules, pressings, capsules, and mixtures thereof. Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic, and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, non-ionic, and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids, or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters, or monoglycerides. Examples of sugar-based surfactants are sorbitans, ethoxylated sorbitans, sucrose, and glucose esters, or alkylpolyglucosides. Examples of polymeric surfactants are home- or copolymers of vinylpyrrolidone, vinylalcohols, or vinylacetate.

Suitable cationic surfactants are quaternary surfactants, e.g. quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the pyrimidine compounds of formula (I) on the target. Examples are surfactants, mineral or vegetable oils, and other auxiliaries. Further examples are listed by Knowles, Adjuvants, and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea, and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo-, and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for agrochemical composition types and their preparation are:

i) Water-Soluble Concentrates (SL, LS)

10-60 wt % of a pyrimidine compound of formula (I) according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a pyrimidine compound of formula (I) according to the invention and 1-10 wt % dispersant (e. g.

polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a pyrimidine compound of formula (I) according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a pyrimidine compound of formula (I) according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a pyrimidine compound of formula (I) according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a pyrimidine compound of formula (I) according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a pyrimidine compound of formula (I) according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a pyrimidine compound of formula (I) according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

iv) Microemulsion (ME)

5-20 wt % of a pyrimidine compound of formula (I) according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

iv) Microcapsules (CS)

An oil phase comprising 5-50 wt % of a pyrimidine compound of formula (I) according to the invention, 0-40 wt % water insoluble organic solvent (e.g. aromatic hydrocarbon), 2-15 wt % acrylic monomers (e.g. methylmethacrylate, methacrylic acid, and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a pyrimidine compound of formula (I) according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

ix) Dustable Powders (DP, DS)

1-10 wt % of a pyrimidine compound of formula (I) according to the invention are ground finely and mixed intimately with solid carrier (e.g. finely divided kaolin) ad 100 wt %.

x) Granules (GR, FG)

0.5-30 wt % of a pyrimidine compound of formula (I) according to the invention is ground finely and associated with solid carrier (e.g. silicate) ad 100 wt %. Granulation is achieved by extrusion, spray-drying or the fluidized bed.

xi) Ultra-Low Volume Liquids (UL)

1-50 wt % of a pyrimidine compound of formula (I) according to the invention are dissolved in organic solvent (e.g. aromatic hydrocarbon) ad 100 wt %.

The agrochemical compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions comprising generally comprise between 0.01 and 95%, preferably between 0.1 and 90%, and in particular between 0.5 and 75%, by weight of the pyrimidine compound of formula (I). The pyrimidine compounds of formula (I) are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The agrochemical compositions in question give, after two-to-tenfold dilution, active substance concentrations of from 0.01 to 60% by weight, preferably from 0.1 to 40% by weight, in the ready-to-use preparations. Application can be carried out before or during sowing.

Methods for applying pyrimidine compounds of formula (I) and agrochemical compositions thereof, on to plant propagation material, especially seeds, include dressing, coating, pelleting, dusting, soaking and in-furrow application methods of the propagation material. Preferably, pyrimidine compounds of formula (I) and agrochemical compositions thereof, are applied on to the plant propagation material by a method such that germination is not induced, e. g. by seed dressing, pelleting, coating and dusting.

Various types of oils, wetters, adjuvants, fertilizer, or micronutrients, and further pesticides (e.g. herbicides, insecticides, fungicides, growth regulators, safeners) may be added to the pyrimidine compounds of formula (I) and the agrochemical compositions comprising them as premix or, if appropriate not until immediately prior to use (tank mix).

These agents can be admixed with the agrochemical compositions according to the invention in a weight ratio of 1:100 to 100:1, preferably 1:10 to 10:1.

The user applies the pyrimidine compound of formula (I) according to the invention and the agrochemical compositions comprising them usually from a pre-dosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, either individual components of the agrochemical composition according to the invention or partially premixed components, e. g. components comprising pyrimidine compounds of formula (I) may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g components comprising pyrimidine compounds of formula (I) can be applied jointly (e.g. after tank mix) or consecutively.

The pyrimidine compounds of formula (I), are suitable as herbicides. They are suitable as such or as an appropriately formulated composition (agrochemical composition).

The pyrimidine compounds of formula (I), or the agrochemical compositions comprising the pyrimidine compounds of formula (I), control vegetation on non-crop areas very efficiently, especially at high rates of application. They act against broad-leaved weeds and grass weeds in crops such as wheat, rice, maize, soya, and cotton without causing any significant damage to the crop plants. This effect is mainly observed at low rates of application.

The pyrimidine compounds of formula (I), or the agrochemical compositions comprising them, are applied to the plants mainly by spraying the leaves. Here, the application can be carried out using, e.g., water as carrier by customary spraying techniques using spray liquor amounts of from about 100 to 1000 l/ha (e.g. from 300 to 400 l/ha). The pyrimidine compounds of formula (I), or the agrochemical compositions comprising them, may also be applied by the low-volume or the ultra-low-volume method, or in the form of micro granules.

Application of the pyrimidine compounds of formula (I), or the agrochemical compositions comprising them, can be done before, during, and/or after, preferably during and/or after, the emergence of the undesirable plants.

The pyrimidine compounds of formula (I), or the agrochemical compositions comprising them, can be applied pre-, post-emergence or pre-plant, or together with the seed of a crop plant. It is also possible to apply the pyrimidine compounds of formula (I), or the agrochemical compositions comprising them, by applying seed, pretreated with the pyrimidine compounds of formula (I), or the agrochemical compositions comprising them, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the pyrimidine compounds of formula (I), or the agrochemical compositions comprising them, can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the pyrimidine compounds of formula (I), or the agrochemical compositions prepared therefrom. Here, the herbicidal compositions can be applied diluted or undiluted.

The term "seed" comprises seed of all types, such as, e.g., corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

When employed in plant protection, the amounts of active substances applied, i.e. the pyrimidine compounds of formula (I) without formulation auxiliaries, are, depending on the kind of effect desired, from 0.001 to 2 kg per ha, preferably from 0.005 to 2 kg per ha, more preferably from 0.05 to 0.9 kg per ha and in particular from 0.1 to 0.75 kg per ha.

In another embodiment of the invention, the application rate of the pyrimidine compounds of formula (I) is from 0.001 to 3 kg/ha, preferably from 0.005 to 2.5 kg/ha and in particular from 0.01 to 2 kg/ha of active substance (a.s.).

In another preferred embodiment of the invention, the rates of application of the pyrimidine compounds of formula (I) according to the present invention (total amount of pyrimidine compounds of formula (I)) are from 0.1 g/ha to 3000 g/ha, preferably 10 g/ha to 1000 g/ha, depending on the control target, the season, the target plants and the growth stage.

In another preferred embodiment of the invention, the application rates of the pyrimidine compounds of formula (I) are in the range from 0.1 g/ha to 5000 g/ha and preferably in the range from 1 g/ha to 2500 g/ha or from 5 g/ha to 2000 g/ha.

In another preferred embodiment of the invention, the application rate of the pyrimidine compounds of formula (I) is 0.1 to 1000 g/ha, preferably to 750 g/ha, more preferably 5 to 500 g/ha.

In treatment of plant propagation materials such as seeds, e. g. by dusting, coating or drenching seed, amounts of active substance of from 0.1 to 1000 g, preferably from 1 to 1000 g, more preferably from 1 to 100 g, and most preferably from 5 to 100 g, per 100 kilogram of plant propagation material (preferably seeds) are generally required.

In another embodiment of the invention, to treat the seed, the amounts of active substances applied, i.e. the pyrimidine compounds of formula (I) are generally employed in amounts of from 0.001 to 10 kg per 100 kg of seed.

When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Depending on the application method in question, the compounds of formula (I), or the agrochemical compositions comprising them, can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera,* and *Zea mays.*

Preferred crops are *Arachis hypogaea, Beta vulgaris* spec. *altissima, Brassica napus* var. *napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec., *Medicago sativa, Nicotiana tabacum (N. rustica), Olea europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera,* and *Zea mays.*

Especially preferred crops are crops of cereals, corn, soybeans, rice, oilseed rape, cotton, potatoes, peanuts, or permanent crops.

The pyrimidine compounds of formula (I) according to the invention, or the agrochemical compositions comprising them, can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides. e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxin herbicides such as dicamba or 2,4-D; bleacher herbicides such as hydroxyphenylpyruvate dioxygenase (HPPD) inhibitors or phytoene desaturase (PDS) inhibitors; acetolactate synthase (ALS) inhibitors such as sulfonyl ureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are, e.g., described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones, and glufosinate, some of which are under development or commercially available under the brands or trade names RoundupReady® (glyphosate tolerant, Monsanto, USA), Cultivance® (imidazolinone tolerant, BASF SE, Germany), and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3, or VIP3A; insecticidal proteins of bacteria colonizing nematodes, e. g., *Photorhabdus* spp. or *Xenorhabdus* spp.; toxins produced by animals, such as scorpion toxins, arachnid toxins, wasp toxins, or other insect-specific neurotoxins; toxins produced by fungi, such as *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810, and WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the CrylAb toxin), YieldGard® Plus (corn cultivars producing CrylAb and Cry3Bbl toxins), Starlink® (corn cultivars producing the Cry9c toxin), Herculex® RW (corn cultivars producing Cry34Abl, Cry35Abl and the enzyme Phosphinothricin-N-Acetyltransferase [PAT]); NuCOTN® 33B (cotton cultivars producing the CrylAc toxin), Bollgard® I (cotton cultivars producing the CrylAc toxin), Bollgard® II (cotton cultivars producing CrylAc and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bbl toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modi-fied plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow AgroSciences, Canada).

Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

The preparation of the pyrimidine compounds of formula (I) is illustrated by the following examples.

A PREPARATION EXAMPLES

Example 1: 3-[5-(2-chlorophenyl)-2-cyclopropyl-pyrimidin-4-yl]-2-OH-propanoic acid

1.1 5-(2-chlorophenyl)-2-cyclopropyl-4-$CH_3$-pyrimidine

A solution of 1-(2-Chlorophenyl)-2-propanone (31 g) in dimethylformamiddimethylacetal (60 mL) was stirred for 2 h at 125° C. TLC showed that the SM was consumed (PE:EtOAc=1:1). The mixture was concentrated to give (E)-3-(2-chlorophenyl)-4-(dimethylamino)but-3-en-2-one (41 g, 99.5%) as a yellow oil and used directly without purification. To a solution of the crude (E)-3-(2-chlorophenyl)-4-(dimethylamino)but-3-en-2-one (33.6 g) in EtOH (600 mL) was added cyclopropanecarboxamidine hydrochloride (45 g) and t-BuOK (42 g). The resulting mixture was stirred for 16 h at 90° C. TLC (PE:EtOAc=3:1) showed that the SM was consumed. The mixture was filtered, and the filtrate was concentrated, purified by column (gradient EtOAc: PE=from 0:1 to 1:10) to give 5-(2-chlorophenyl)-2-cyclopropyl-4-$CH_3$-pyrimidine (29 g, 79.23%) as a yellow oil.

$^1$H NMR CDCl3 400 MHz: δ: 1.04-1.11 (m, 2H); 1.16-1.23 (m, 2H); 2.19-2.36 (m, 1H); 2.3 (s, 3H); 7.17-7.23 (m, 1H) 7.30-7.41 (m, 2H) 7.43-7.56 (m, 1H) 8.28 (s, 1H).

1.2 ethyl 3-[5-(2-chlorophenyl)-2-cyclopropyl-pyrimidin-4-yl]-2-OH-propanoate To a solution of 5-(2-chlorophenyl)-2-cyclopropyl-4-$CH_3$-pyrimidine (3 g) in THF (60 mL) was added LDA (8 mL) dropwise at −78° C. 10 min later, glyoxalic acid ethylester (1.6 g) in THF was added dropwise. The mixture was stirred at −78° C. for 1 h. aq. $NH_4Cl$ (60 mL) was added. The mixture was extracted with EtOAc, dried over $Na_2SO_4$ and concentrated. The crude was purified by column (PE: EtOAc=50:1 to 2:1) to give ethyl 3-[5-(2-chlorophenyl)-2-cyclopropyl-pyrimidin-4-yl]-2-OH-propanoate (3 g, 47.2%) as a yellow oil.

$^1$H NMR: $CDCl_3$ 400 MHz δ ppm 1.11-1.19 (m, 4H); 1.23 (m, 3H); 2.19-2.34 (m, 1H); 2.89-3.06 (m, 1H); 3.08-3.17 (m, 1H); 4.10-4.27 (m, 3H); 4.32-4.41 (m, 1H); 4.46-4.55 (m, 1H); 4.58-4.70 (m, 1H); 7.20-7.26 (m, 1H); 7.33-7.42 (m, 2H); 7.51 (d, 1H); 8.35 (s, 1H).

1.3 3-[5-(2-chlorophenyl)-2-cyclopropyl-pyrimidin-4-yl]-2-OH-propanoic acid

A solution of ethyl 3-[5-(2-chlorophenyl)-2-cyclopropyl-pyrimidin-4-yl]-2-OH-propanoate (1 g) in MeOH (30 ml) and THF (30 mL) and $H_2O$ (10 mL) was cooled to 0° C. Then $LiOH.H_2O$ (0.36 g) in $H_2O$ was added. The mixture was stirred at 20° C. for 15 h. The mixture was concentrated.

The residue was adjusted to pH=2-3 with 1N HCl, and extracted with EtOAc. The organic layer was dried over $Na_2SO_4$ and concentrated. The crude product was purified by prep-HPLC to give 3-[5-(2-chlorophenyl)-2-cyclopropyl-pyrimidin-4-yl]-2-OH-propanoic acid (0.6 g, 66.7%) as a yellow oil.

$^1$H NMR: $CDCl_3$ 400 MHz δ ppm 1.36 (m, 4H); 2.44 (m, 1H); 3.06-3.38 (m, 2H); 4.55 (m, 1H); 7.29 (m, 1H); 7.39-7.51 (m, 2H); 7.53-7.60 (m, 1H); 8.60 (s, 1H); 9.06 (br. s., 1H).

Example 2 1-[5-(2-chlorophenyl)-2-cyclopropyl-pyrimidin-4-yl]-2-$CH_3$-propane-1,2-diol 2.1 1-[5-(2-chlorophenyl)-2-cyclopropyl-pyrimidin-4-yl]-2-$CH_3$-propan-2-ol To a solution of 5-(2-chlorophenyl)-2-cyclopropyl-4-$CH_3$-pyrimidine (1.3 g) in THF (30 mL) was added 2M LDA solution in THF (3.5 mL) dropwise at −78° C. 10 min later, $CH_3COCH_3$ (0.4 g) in THF was added dropwise. Then the mixture was stirred at −78° C. for 1 h. aq. $NH_4Cl$ (30 mL) was added. The mixture was extracted with EtOAc, dried over $Na_2SO_4$ and concentrated. The crude product was purified by column chromatography (PE:EtOAc=50:1 to 5:1) to give 1-[5-(2-chlorophenyl)-2-cyclopropyl-pyrimidin-4-yl]-2-$CH_3$-propan-2-ol (1.1 g, 68.8%) as a yellow oil.

$^1$H NMR: $CDCl_3$ 400 MHz δ ppm 1.09 (s, 3H); 1.14-1.22 (m, 5H); 2.24-2.38 (m, 1H); 2.54-2.66 (m, 1H); 2.69-2.79 (m, 1H); 6.08 (s, 1H); 7.18 (m, 1H); 7.32-7.45 (m, 2H); 7.52 (m, 1H); 8.37 (s, 1H).

2.2 5-(2-chlorophenyl)-2-cyclopropyl-4-(2-$CH_3$-prop-1-enyl)pyrimidine

To a solution of 1-[5-(2-chlorophenyl)-2-cyclopropyl-pyrimidin-4-yl]-2-$CH_3$-propan-2-ol (1.1 g) in toluene (30 mL) was added PPTS (0.18 g). The mixture was stirred at 100° C. for 10 h. Brine (30 mL) was added. Then the mixture was extracted with EtOAc, dried over $Na_2SO_4$ and concentrated. The crude was purified by column (PE:EtOAc=50:1 to 30:1) to give 5-(2-chlorophenyl)-2-cyclopropyl-4-(2-$CH_3$-prop-1-enyl)pyrimidine (0.8 g, 81.6%) as a yellow oil.

2.3 1-[5-(2-chlorophenyl)-2-cyclopropyl-pyrimidin-4-yl]-2-$CH_3$-propane-1,2-diol To a solution of 5-(2-chlorophenyl)-2-cyclopropyl-4-(2-$CH_3$-prop-1-enyl)pyrimidine (0.45 g) in THF (10 mL) was added NMO (0.35 g) and $K_2OsO_4.2H_2O$ (0.049 g). Then the mixture was stirred at 30° C. for 12 h. The mixture was concentrated in vacuum. The crude product was purified by column chromatography (PE:EtOAc=50:1 to 5:1) to give -[5-(2-chlorophenyl)-2-cyclopropyl-pyrimidin-4-yl]-2-$CH_3$-propane-1,2-diol (0.2 g, 41.9%) as a yellow oil.

$^1$H NMR: $CDCl_3$ 400 MHz δ ppm (2 rotamers) 0.95-1.33 (m, 2×10 H); 2.38-2.55 (m, 2×1 H); 4.33 (s, 1H); 4.35 (s, 1H); 5.86 (br, 2×2 H); 7.23 (m, 2×1 H); 7.39-7.47 (m, 2×2 H); 7.54 7.58 (m, 2×1 H); 8.52-8.66 (s, 1H); 8.68-8.69 (s, 1H).

Example 3 methyl 2-[5-(2-chlorophenyl)-2-cyclopropyl-pyrimidin-4-yl]-2-OH-propanoate 3.1 5-(2-chlorophenyl)-2-cyclopropyl-pyrimidine To a solution of 5-bromo-2-cyclopropyl-pyrimidine (5.3 g) in dry dioxane (40 ml) was added 2-chloro-phenylboronic acid (8.5 g), $K_2CO_3$ (7.4 g) and $Pd(dppf)Cl_2.xCH_2Cl_2$ (550 mg) under $N_2$. The resulting mixture was heated at 100° C. overnight. Then the mixture was diluted with water, extracted with EtOAc. The combined organic layers were washed with brine, dried over anhydrous $Na_2SO_4$, filtered and concentrated to give crude product (8 g), which was purified by column (PE:EtOAc=5:1) to afford 5-(2-chlorophenyl)-2-cyclopropyl-pyrimidine (4 g, 60%).

$^1$H NMR: $CDCl_3$ 400 MHz δ 8.69 (s, 2H), 7.2-7.6 (m, 4H), 2.35 (br s, 1H), 1.05-1.30 (m, 4H).

3.2 methyl 2-[5-(2-chlorophenyl)-2-cyclopropyl-pyrimidin-4-yl]-2-OH-propanoate

To a solution of 2,2,6,6-tetramethylpiperidine (1.6 g) in dry THF (50 mL) was added dropwise n-BuLi (10.8 mL) at −78° C. under $N_2$. The resulting mixture was stirred at −78° C. for 1 h. Then 5-(2-chlorophenyl)-2-cyclopropyl-pyrimidine (1 g) in 10 mL THF was added dropwised at −78° C. After stirred for 5 min, methlypyruvate (2.2 g) was added. The mixture was stirred while warming from −78° C. to room temperature. Then aq. $NH_4Cl$ was added at 0° C. The mixture was extracted with EtOAc. The combined organic layers were washed with saturated brine, dried over anhydrous $Na_2SO_4$, filtered, concentrated and purified by column chromatography (PE:EtOAc=10:1) to give methyl 2-[5-(2-chlorophenyl)-2-cyclopropyl-pyrimidin-4-yl]-2-OH-propanoate (200 mg, 14%) as a white solid.

$^1$H NMR: MeOD 400 MHz (2 rotamers) δ 8.35 (s, 1H), 8.29 (s, 1H), 7.2-7.5 (m, 2×4 H), 3.66 3.73 (2s, 2×3H), 2.18-2.38 (m, 2×1 H), 1.63 (s, 3H), 1.53 (s, 3H), 1.06-1.25 (m, 2×4 H).

Example 4: 5-(2-chlorophenyl)-2-cyclopropyl-4-(3-$CH_3$-2-furyl)pyrimidine 4.1 a 2-(2-chlorophenyl)-1-(3-$CH_3$-2-furyl)ethanone To a solution of N-methoxy-N,3-dimethyl-furan-2-carboxamide (1.5 g) in dry THF (60 mL) under Argon is added at −78° C. chloro-[(2-chlorophenyl)-$CH_3$]magnesium (CAS 29874-00-8) drop wise. The reaction mixture is stirred for 1 h at −78° C. warmed to room temperature and stirred for 16 h. The reaction was quenched with brine (60 mL), extracted with ethyl acetate, dried and concentrated. The product was purified by column chromatography (gradient cyclohexane/ethyl acetate=from 1:0 to 3:2) to give 2-(2-chlorophenyl)-1-(3-$CH_3$-2-furyl)ethanone (1.05 g, 50.5%).

$^1$H NMR CDCl3 400 MHz: δ 7.46-7.36 (m, 2H), 7.30-7.19 (m, 3H), 6.41 (d, J=1.7 Hz, 1H), 4.33 (s, 2H), 2.39 (s, 3H).

4.1 b 2-(2-chlorophenyl)-1-(3-$CH_3$-2-furyl)ethanone

To a suspension of NaH (60%, 1.61 g) in dry DMF (60 mL) under Argon is added at −10° C. 2-(3-$CH_3$-2-furyl)-2-morpholino-acetonitrile (7.6 g). The reaction is stirred for 30 min. followed by addition of a solution of 1-(bromomethyl)-2-chloro-benzene (6.88 g) in dry DMF. The reaction is warmed to room temperature and stirred for 16 h. The mixture is poured into a saturated aq. ammonium chloride solution, extracted with ethyl acetate, washed with water and aq. LiCl solution (10%), dried and concentrated. The residue is dissolved in a mixture of methanol and water (7:3) and $CuSO_4$ (16.7 g) is added. The reaction mixture is stirred for 1.5 h at 60° C. After concentration of the mixture, water is added, the mixture is extracted with ethyl acetate, washed with saturated aq. sodium sulfite solution and brine, dried and concentrated. The product is purified by column chromatography (gradient cyclohexane/ethyl acetate=from 1:0 to 3:2) to give 2-(2-chlorophenyl)-1-(3-CH$_3$-2-furyl)ethanone (5.0 g, 63.6%).

$^1$H NMR CDCl3 400 MHz: δ 7.46-7.36 (m, 2H), 7.30-7.19 (m, 3H), 6.41 (d, J=1.7 Hz, 1H), 4.33 (s, 2H), 2.39 (s, 3H).

4.2 2-(2-chlorophenyl)-3-(dimethylamino)-1-(3-CH$_3$-2-furyl)prop-2-en-1-one A solution of 2-(2-chlorophenyl)-1-(3-CH$_3$-2-furyl)ethanone (1.05 g) in dimethylformamidedimethylacetal (6 mL) was stirred for 16 h at 65° C. TLC showed that the SM was consumed. The mixture was concentrated and purified by column chromatography (gradient cyclohexane/ethyl acetate=from 1:0 to 1:9) to give 2-(2-chlorophenyl)-3-(dimethylamino)-1-(3-CH$_3$-2-furyl)prop-2-en-1-one (700 mg, 54.0%).

$^1$H NMR CDCl3 400 MHz: δ 7.68 (s, 1H), 7.42-7.34 (m, 1H), 7.29-7.16 (m, 3H), 7.13 (d, J=1.7 Hz, 1H), 6.25 (d, J=1.7 Hz, 1H), 2.78 (s, 6H), 2.32 (s, 3H).

4.3 5-(2-chlorophenyl)-2-cyclopropyl-4-(3-C H$_3$-2-furyl)pyrimidine

To a solution of 2-(2-chlorophenyl)-3-(dimethylamino)-1-(3-CH$_3$-2-furyl)prop-2-en-1-one (4.9 g) in EtOH (100 mL) was added cyclopropanecarboxamidine hydrochloride (2.24 g) and NaOEt (21%, 6.93 g). The resulting mixture was stirred for 16 h at reflux. TLC (PE:EtOAc=3:1) showed that the SM was consumed. The mixture was filtered, and the filtrate was concentrated, purified by column (gradient EtOAc: PE=from 0:1 to 1:0) to give 5-(2-chlorophenyl)-2-cyclopropyl-4-CH$_3$-pyrimidine (4.0 g, 73%) as a yellow solid.

$^1$H NMR CDCl3 400 MHz: δ 8.38 (s, 1H), 7.52-7.36 (m, 1H), 7.37-7.17 (m, 3H), 7.05 (d, J=1.7 Hz, 1H), 6.27 (d, J=1.7 Hz, 1H), 2.43 (s, 3H), 2.37-2.28 (m, 1H), 1.27-1.21 (m, 2H), 1.14-1.08 (m, 2H).

Example 5: N-acetyl-5-(2-chlorophenyl)-2-cyclopropyl-pyrimidine-4-carboxamide

5.1 5-Bromo-2-cyclopropyl-pyrimidine-4-carboxylic acid

NaH (60% purity, 41.9 g) is added in portions to EtOH (800 mL) at 0° C. The resulting mixture is warmed to ambient temperature and the cyclopropanecarboxamidine hydrochlorid (93.5 g) is added in portions. The reaction is warmed to 50° C. and maintained at this temperature for 0.5 h and then cooled to ambient temperature before mucobromic acid (100 g) is added in EtOH while keeping the internal temperature below 55° C. The mixture is allowed to cool to ambient temperature and stirred for additional 16 h. All solid components are removed by filtration and the resulting solution is concentrated under reduced pressure. Aq. HCl (1 mol/L) is added, the aqueous phase is washed with EtOAc (3×), the combined organic extracts are dried over MgSO4 and the solid parts removed by filtration. The residue is concentrated under reduced pressure and the resulting solid titrated with (iPr)$_2$O. The solids are collected by filtration and dried yielding the title compound (68.0 g, yield 72%) as a colorless solid.

1H NMR (400 MHz, CDCl$_3$): δ=8.91 (s, 1H), 2.38-2.26 (m, 1H), 1.34-1.14 (m, 4H) ppm; MS (ESI) m/z 244.9 [M+H+].

5.2 Methyl 5-bromo-2-cyclopropyl-pyrimidine-4-carboxylate

5-Bromo-2-cyclopropyl-pyrimidine-4-carboxylic acid (91.0 g) is dissolved in MeOH (1200 mL) and conc. sulfuric acid (20 mL) is added dropwise at ambient temperature. The reaction is heated to reflux and stirred for 16 h. The resulting mixture is cooled to ambient temperature and neutralized with aq. sat. NaHCO$_3$. The residue is parted between EtOAc and aq. sat. NaHCO$_3$, the phases are separated, the aq. phase is extracted with EtOAc and the combined organics are dried over MgSO$_4$. Solid parts are removed by filtration and the organic phase is concentrated under reduced pressure. Column chromatography of the resulting crude product (ISCO-CombiFlash Rf, cyclohexane/EtOAc) yields the title compound (1.48 g, yield 63%) as a colorless solid.

$^1$H NMR (400 MHz, CDCl$_3$): δ=8.74 (s, 1H), 4.01 (s, 3H), 2.33-2.22 (m, 1H), 1.21-1.06 (m, 4H) ppm; MS (ESI) m/z 246.9 [M+H+].

5.3 methyl 5-(2-chlorophenyl)-2-cyclopropyl-pyrimidine-4-carboxylate

A mixture of methyl 5-bromo-2-cyclopropyl-pyrimidine-4-carboxylate (8.00 g), 2-(chlorophenyl)boronic acid (5.11 g), K$_3$PO$_4$ (8.89 g) and PdCl$_2$dppf (4.19 g) in dioxane (120 mL) and water is heated under reflux under an atmosphere of argon for 5 h. Water and EtOAc are added, the phases are separated and organic phase is dried over MgSO$_4$. The solids are removed via filtration and resulting solution is concentrated under reduced pressure. Column chromatography of the crude product (ISCO-CombiFlash Rf) yields the title compound (3.00 g, yield 48%).

$^1$H NMR (400 MHz, CDCl$_3$): δ 8.60 (s, 1H), 7.52-7.44 (m, 1H), 7.49-7.47 (m, 1H), 7.39-7.34 (m, 2H), 7.26-7.24 (m, 1H), 3.79 (s, 3H), 2.45-2.39 (m, 1H), 1.28-1.24 (m, 2H), 1.19-1.14 (m, 2H) ppm; MS (ESI) m/z 289.1 [M+H+].

5.4 5-(2-chlorophenyl)-2-cyclopropyl-pyrimidine-4-carboxylic acid

Methyl 5-(2-chlorophenyl)-2-cyclopropyl-pyrimidine-4-carboxylate (3.00 g) is dissolved in THF and lithiumhydroxid (373 mg) followed by water until the base is completely dissolved. The resulting mixture is stirred for 2 hours at ambient temperature; the volatiles are removed under reduced pressure and the remains are then acidified to pH=1-2 with aqueous hydrochloric acid. The aq. phase is extracted with EtOAc and the combined organics are dried over MgSO$_4$. Solid parts are removed by filtration and the organic phase is concentrated under reduced pressure yielding the title compound (2.00 g, yield 70%) as a colorless solid.

$^1$H NMR (400 MHz, CDCl$_3$): δ 10.94 (brs, 1H), 8.67 (s, 1H), 7.51-7.49 (m, 1H), 7.42-7.35 (m, 1H), 7.24-7.22 (m, 1H), 2.45-2.39 (m, 1H), 1.29-1.22 (m, 4H) ppm; MS (ESI) m/z 275.0 [M+H+].

5.5: 5-(2-chlorophenyl)-2-cyclopropyl-pyrimidine-4-carboxamide

To a solution of 5-(2-chlorophenyl)-2-cyclopropyl-pyrimidine-4-carboxylic acid (1.0 g) in DCM (15 mL) are added DMF (2 drops) and oxalyl chloride (924 mg) and the mixture is stirred for 16 h at room temperature. This mixture is added to a mixture of a 2 M solution of ammonia in dioxane (3.64 mL) and triethylamine (1.11 mL) in DCM (10 mL). The combined mixtures are stirred for 16 h at room temperature. After addition of water the mixture was stirred for 5 minutes and separated. The organic phase was concentrated and purified by column chromatography yielding 5-(2-chlorophenyl)-2-cyclopropyl-pyrimidine-4-carboxamide (696 mg 70%).

$^1$H NMR (400 MHz, Chloroform-d) δ 8.67 (s, 1H), 7.52-7.47 (m, 1H), 7.43-7.31 (m, 2H), 7.25-7.20 (m, 1H), 2.48-2.35 (m, 1H), 1.34-1.21 (m, 4H).

5.6: N-acetyl-5-(2-chlorophenyl)-2-cyclopropyl-pyrimidine-4-carboxamide

To a solution of 5-(2-chlorophenyl)-2-cyclopropyl-pyrimidine-4-carboxamide (230 mg) in dry THF (10 mL) is added a 1M solution of LiHMDS in THF (0.84 mL) at −20° C. After stirring for 10 min. at −20° C. acetic anhydride (129 mg) is added and the reaction is warmed to room temperature and stirred for 16 h. Water is added, the aq. phase is extracted with ethyl acetate. The combined organic extracts are washed with water and brine, dried and concentrated. Purification by column chromatography (gradient EtOAc:CH=from 0:1 to 1:4) yielded N-acetyl-5-(2-chlorophenyl)-2-cyclopropyl-pyrimidine-4-carboxamide (30 mg, 11%).

$^1$H NMR (400 MHz, Chloroform-d) δ 10.25 (s, 1H), 8.60 (d, J=0.9 Hz, 1H), 7.56-7.45 (m, 1H), 7.45-7.34 (m, 2H), 7.33-7.18 (m, 1H), 2.48 (s, 3H), 2.44-2.36 (m, 1H), 1.32-1.19 (m, 6H).

Example 6: ethyl 2-[5-(2-chlorophenyl)-2-methoxy-pyrimidin-4-yl]acetate

To a solution of 5-(2-chlorophenyl)-2-methoxy-4-CH$_3$-pyrimidine (1.0 g) in dry THF (25 mL) is added a 1 M solution of LiHMDS (8.52 mL) at 0° C. and the mixture is stirred for 30 min. at 0° C. To this mixture is added diethylcarbonate (2.11 g) and the mixture is slowly warmed to room temperature and stirred for 22 h. Saturated aq. Ammonium chloride solution is added and the mixtures is extracted 3 times with ethyl acetate. The organic phase was concentrated and purified by column chromatography yielding ethyl 2-[5-(2-chlorophenyl)-2-methoxy-pyrimidin-4-yl]acetate (900 mg, 95% purity, 65% yield).

$^1$H NMR DMSO-d6 500 MHz: 8.48 (s, 1H), 7.65-7.60 (m, 1H), 7.53-7.43 (m, 2H), 7.42-7.37 (m, 1H), 4.01-3.90 (m, 5H), 3.71-3.50 (m, 2H), 1.07 (t, J=7.1 Hz, 3H).

Example 7: methyl 2-[5-(2-bromophenyl)-2-cyclopropyl-pyrimidin-4-yl]-2-CH$_3$-propanoate To a solution of methyl 2-[5-(2-bromophenyl)-2-cyclopropyl-pyrimidin-4-yl]acetate (800 mg) in dry THF (30 mL) is added iodomethane (1.31 g) at −78° C., followed by addition of potassium tert-butanolate (776 mg). The mixture is stirred for 1 h at −78° C. The mixture is slowly warmed to room temperature and stirred for 65 h at room temperature. Reaction control shows conversion to mono- and di-methyl product. Another portion of Iodomethane (1.31 g) and potassium tert-butanolate (776 mg) is added and the mixture is stirred 16 h at room temperature. After addition of water, the mixture is extracted with ethyl acetate, washed with saturated aq. sodium bicarbonate solution, dried and concentrated. The product is purified by column chromatography to give methyl 2-[5-(2-bromophenyl)-2-cyclopropyl-pyrimidin-4-yl]-2-CH$_3$-propanoate (210 mg, 24.3%).

$^1$H NMR (400 MHz, Chloroform-d) δ 8.22 (s, 1H), 7.68 (dd, J=7.9, 1.3 Hz, 1H), 7.34 (td, J=7.5, 1.3 Hz, 1H), 7.30-7.22 (m, 1H), 7.19 (dd, J=7.5, 1.8 Hz, 1H), 3.48 (s, 3H), 2.33-2.24 (m, 1H), 1.48 (s, 3H), 1.37 (s, 3H), 1.23-1.14 (m, 2H), 1.15-1.04 (m, 2H).

Example 7: [5-(2-Chlorophenyl)-2-cyclopropyl-pyrimidin-4-yl]methanol

DIBAlH (1 N in THF, 38.8 mL) is added dropwise to a solution of methyl 5-(2-chlorophenyl)-2-cyclopropyl-pyrimidine-4-carboxylate (5.60 g) in THF (50 mL) at 0° C. Upon completion of the addition the reaction mixture is warmed to ambient temperature and stirred for 2 h. EtOAc (50 mL) is slowly added and the mixture is stirred for 15 min before aq. NaOH (2 mol/L) is added at 0° C. until the phases are clear. The phases are separated and the aq. phase is extracted with EtOAc (2×). The combined organics are dried over MgSO$_4$, solid parts are removed by filtration and the organic phase is concentrated under reduced pressure yielding the title compound (4.00 g, yield 79%).

$^1$H NMR (400 MHz, CDCl$_3$): δ 8.36 (s, 1H), 7.53-7.51 (m, 1H), 7.42-7.34 (m, 2H), 7.21-7.17 (m, 1H), 4.46 (d, J=22.0 Hz, 2H), 2.42-2.35 (m, 1H), 1.27-1.23 (m, 2H), 1.20-1.15 (m, 2H) ppm; MS (ESI) m/z 261.0 [M+H+].

Example 8: 2-[5-(2-chloro-4-fluorophenyl)-2-cyclopropyl-pyrimidin-4-yl]propan-2-ol MeMgBr (3N in Et$_2$O, 2.18 mL) is added dropwise to a solution of methyl 5-(2-chlorophenyl)-2-cyclopropyl-pyrimidine-4-carboxylate (1.00 g) in Et$_2$O (20 mL) at −20° C. Upon completion of the addition the reaction mixture is warmed to 0° C. and stirred for 1 h. EtOAc and aq. sat. NH$_4$Cl is added and the phases are separated. The organic phase is dried over MgSO$_4$, solid parts are removed by filtration and the organic phase is concentrated under reduced pressure. Purification by column chromatography (ISCO-CombiFlash Rf, reversed phase, MeCN/water)) yields the title compound (810 mg, 95%) as a colorless oil.

$^1$H NMR (400 MHz, DMSO-d$_6$): δ 8.22 (s, 1H), 7.48 (dd, J=9.0, 2.6 Hz, 1H), 7.40 (dd, J=8.6, 6.3 Hz, 1H), 7.23 (td, J=8.6, 2.6 Hz, 1H), 4.84 (s, 1H), 2.33-2.17 (m, 1H), 1.37 (s, 3H), 1.35 (s, 3H), 1.13-0.98 (m, 4H) ppm; MS (ESI) m/z 307.0 [M+H+].

Example 9: 1-[5-(2-chlorophenyl)-2-cyclopropyl-pyrimidin-4-yl]ethanol

9.1: 5-(2-chlorophenyl)-2-cyclopropyl-pyrimidine-4-carbaldehyde

A mixture of [5-(2-Chlorophenyl)-2-cyclopropyl-pyrimidin-4-yl]methanol (2.00 g) and MnO$_2$ (8.00 g) in chloroform (20 mL) are heated under reflux for 16 h. Solid parts are removed by filtration and the organic phase is concentrated under reduced pressure. Purification by column chromatography (ISCO-CombiFlash Rf, cyclohexane/EtOAc) yields the title compound (1.50 g, 76%).

$^1$H NMR (400 MHz, CDCl$_3$): δ 9.95 (s, 1H), 8.64 (s, 1H), 7.51-7.48 (m, 1H), 7.44-7.36 (m, 2H), 7.26-7.24 (m, 1H), 2.48-2.41 (m, 1H), (tt, J=8.1, 4.8 Hz, 1H), 1.31-1.26 (m, 2H), 1.23-1.17 (m, 2H) ppm; MS (ESI) m/z 259.0 [M+H+].

9.2: 1-[5-(2-chlorophenyl)-2-cyclopropyl-pyrimidin-4-yl]ethanol

MeMgBr (3N in Et$_2$O, 33.4 mL) is added dropwise to a solution of 5-(2-chlorophenyl)-2-cyclopropyl-pyrimidine-4-carbaldehyde (23.6 g) in Et$_2$O (200 mL) at −10° C. Upon completion of the addition the reaction mixture is warmed to 25° C. and stirred for 1 h. EtOAc and aq. sat. NH$_4$Cl are added and the phases are separated. The organic phase is dried over MgSO$_4$, solid parts are removed by filtration and the organic phase is concentrated under reduced pressure. Purification by column chromatography (ISCO-CombiFlash Rf, reversed phase, MeCN/water)) yields the title compound (17.9 g, 68%) as a colorless oil.

$^1$H NMR (400 MHz, CDCl$_3$, 2 rotamers): δ 8.37 (s, 1H), 8.31 (s, 1H), 7.55-7.50 (m, 2H), 7.42-7.33 (m, 4H), 7.25-7.16 (m, 2H), 4.79-4.69 (m, 1H), 4.36-4.33 (m, 1H), 2.38-2.32 (m, 2H), 1.25-1.22 (m, 4H), 1.18-1.12 (m, 10H) ppm; MS (ESI) m/z 275.0 [M+H+].

Example 10: 5-(2-chlorophenyl)-2-cyclopropyl-4-(1-methoxyethyl)pyrimidine

NaH (21.2 mg) is added to a solution of 1-[5-(2-chlorophenyl)-2-cyclopropyl-pyrimidin-4-yl]ethanol (210 mg) in DMF (5 mL) at 0° C. The mixture is warmed to 25° C. and stirred for 30 min before MeI (52.6 μL) is added. The reaction is stirred for 2 h at 25° C. Water and EtOAc are and the phases are separated. The organic phase is dried over MgSO$_4$, solid parts are removed by filtration and the organic phase is concentrated under reduced pressure. Purification by column chromatography (ISCO-CombiFlash Rf, reversed phase, MeCN/water)) yields the title compound (80.0 mg, 36%) as a colorless oil.

$^1$H NMR (400 MHz, CDCl$_3$, 2 rotamers): δ 8.46 (s, 1H), 8.33 (s, 1H), 7.65-7.60 (m, 2H), 7.53-7.39 (m, 6H), 4.15-4.08 (m, 2H), 3.00 (s, 3H), 2.93 (s, 3H), 2.31-2.25 (m, 2H), 1.34 (d, J=XX Hz, 3H), 1.25 (d, J=6.4 Hz, 3H), 1.12-1.05 (m, 8H) ppm; MS (ESI) m/z 289.0 [M+H+].

Below listed are the meaning of abbreviations used in preparation process above.
CH cyclohexane
EtOH ethanol
DCM dichloromethane
DMF dimethylformamide
PE petrol ether
TLC thin layer chromatography
EtOAc ethylacetate
SM starting material
LDA lithium diisopropylamide
LiHMDS lithium bis(trimethylsilyl)amide
MeOH methanol
NaHMDS sodium bis(trimethylsilyl)amide
TH F tetrahydrofuran
Prep-HPLC preparative high pressure liquid chromatography
NMO N-methylmorpholine-N-oxide
PPTS pyridinium p-tolouolsulfonate
LAH Lithium aluminium hydride
DIBAlH Diisobutylaluminium hydride
PCC Pyridinium Chlorochromate.

With appropriate modification of the starting materials, the procedures given in the synthesis examples below were used to obtain further compounds of formula I. The compounds obtained in this manner are listed in the Table X that follows, together with physical data.

The products shown below were characterized by melting point determination, by the masses ([m/z]) or retention time (RT; [min.]) determined by HPLC-MS or HPLC spectrometry.

HPLC-MS=high performance liquid chromatography-coupled mass spectrometry; HPLC methods:

Method: Column: Phenomenex Kinetex 1.7 μm XB-C18 100A; 50×2.1 mm; mobile phase: A: water+0.1% trifluoroacetic acid (TFA); B: acetonitrile+0.1% TFA; gradient: 5-100% B in 1.50 minutes; 100% B 0.25 min; flow: 0.8-1.0 ml/min in 1.51 minutes at 60° C. MS: quadrupole electrospray ionization, 80 V (positive mode).

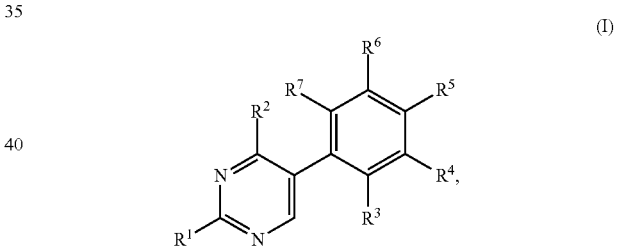

(I)

TABLE X

| Ex. | R$^1$ | R$^2$ | R$^3$ | R$^4$ | R$^5$ | R$^6$ | R$^7$ | HPLC/MS, R$_t$ [min] | HPLC/MS, m/z |
|---|---|---|---|---|---|---|---|---|---|
| Ex. 1 | c-C$_3$H$_5$ | -CH$_2$-O-C(O)-CH$_3$ | Cl | H | H | H | H | 1.170 | 303.0 |
| Ex. 2 | c-C$_3$H$_5$ | CH$_2$OH | Cl | H | H | H | H | 1.016 | 261.1 |
| Ex. 3 | c-C$_3$H$_5$ | CH$_3$ | Cl | H | H | H | H | 1.133 | 245.1 |
| Ex. 4 | c-C$_3$H$_5$ | C(=CH$_2$)-O-CH$_3$ | Cl | H | H | H | H | 1.362 | 301.1 |
| Ex. 5 | c-C$_3$H$_5$ | CH(CN)$_2$ | Cl | H | H | H | H | 0.894 | 295.0 |

TABLE X-continued

| Ex. | R¹ | R² | R³ | R⁴ | R⁵ | R⁶ | R⁷ | HPLC/MS, $R_t$ [min] | HPLC/MS, m/z |
|---|---|---|---|---|---|---|---|---|---|
| Ex. 6 | c-C₃H₅ | 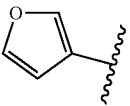 [SMILES: *c1ccoc1] | Cl | H | H | H | H | 1.273 | 297.0 |
| Ex. 7 | c-C₃H₅ | 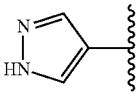 [SMILES: *c1cn[nH]c1] | Cl | H | H | H | H | 1.239 | 297.0 |
| Ex. 8 | c-C₃H₅ | 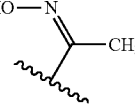 | Cl | H | H | H | H | 1.122 | 281.1 |
| Ex. 9 | c-C₃H₅ | 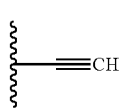 | Cl | H | H | H | H | 1.181 | 255.0 |
| Ex. 10 | c-C₃H₅ | CH₃ | Cl | H | Cl | H | H | 1.262 | 269.0 |
| Ex. 11 | c-C₃H₅ | 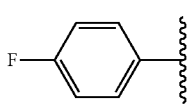 | Cl | H | H | H | H | 1.364 | 324.9 |
| Ex. 12 | c-C₃H₅ | CH₃ | Cl | H | H | H | F | 1.199 | 262.9 |
| Ex. 13 | c-C₃H₅ | CH₂OH | Br | H | H | H | H | 1.022 | 304.9 |
| Ex. 14 | c-C₃H₅ | CH₂OH | Cl | H | H | F | H | 1.041 | 279.0 |
| Ex. 15 | c-C₃H₅ | CH₂OH | Cl | H | F | H | H | 1.073 | 279.0 |
| Ex. 16 | c-C₃H₅ | CH₃ | Br | H | F | H | H | 1.200 | 309.7 |
| Ex. 17 | c-C₃H₅ | CH₃ | CF₃ | H | H | H | H | 1.151 | 279.0 |
| Ex. 18 | c-C₃H₅ | CH₃ | Br | H | H | H | H | 1.134 | 289.0 |
| Ex. 19 | c-C₃H₅ | CH₃ | CH₃ | H | H | H | H | 1.045 | 225.1 |
| Ex. 20 | c-C₃H₅ | CH₃ | I | H | H | H | H | 1.392 | 236.8 |
| Ex. 21 | c-C₃H₅ | 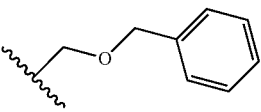 [SMILES: *COCc1ccccc1] | Cl | H | H | H | H | 1.363 | 351.0 |
| Ex. 22 | c-C₃H₅ | CH₂OCH₃ | Cl | H | H | H | H | 1.224 | 274.8 |
| Ex. 23 | c-C₃H₅ | 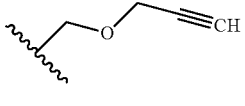 [SMILES: *COCC#C] | Cl | H | H | H | H | 1.187 | 299.0 |
| Ex. 24 | c-C₃H₅ | 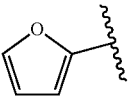 | Cl | H | H | H | H | 1.240 | 297.0 |
| Ex. 25 | c-C₃H₅ | CH(CN)₂ | Br | H | H | H | H | 0.91 | 341.0 |
| Ex. 26 | c-C₃H₅ | 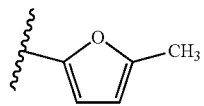 | Cl | H | H | H | H | 1.247 | 311.0 |
| Ex. 27 | c-C₃H₅ | 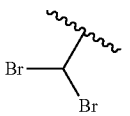 | Br | H | H | H | H | 1.386 | 448.4 |

TABLE X-continued
| Ex. | R¹ | R² | R³ | R⁴ | R⁵ | R⁶ | R⁷ | HPLC/MS, R_t [min] | HPLC/MS, m/z |
|---|---|---|---|---|---|---|---|---|---|
| Ex. 28 | c-C₃H₅ | 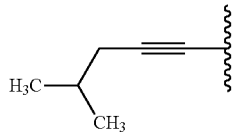 | Cl | H | H | H | H | 1.409 | 311.1 |
| Ex. 29 | c-C₃H₅ | 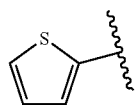 [SMILES: *c1cccs1] | Cl | H | H | H | H | 1.340 | 312.8 |
| Ex. 30 | c-C₃H₅ | 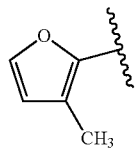 | Cl | H | H | H | H | 1.298 | 312.5 |
| Ex. 31 | c-C₃H₅ | 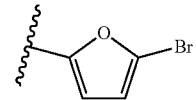 [SMILES: *c1ccc(Br)o1] | Cl | H | H | H | H | 1.381 | 374.6 |
| Ex. 32 | c-C₃H₅ | 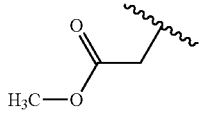 | Cl | H | H | H | H | 1.156 | 302.9 |
| Ex. 33 | c-C₃H₅ | 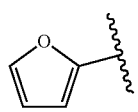 [SMILES: *c1ccco1] | Cl | F | H | H | H | 1.244 | 315.0 |
| Ex. 34 | c-C₃H₅ | 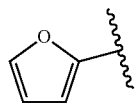 | Br | H | H | H | H | 1.229 | 341.0 |
| Ex. 35 | c-C₃H₅ | CHBr₂ | Cl | H | H | H | H | 1.369 | 403.0 |
| Ex. 36 | c-C₃H₅ | CH(CN)₂ | Br | H | F | H | H | 0.946 | 359.0 |
| Ex. 37 | c-C₃H₅ | 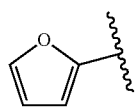 | NO₂ | H | H | H | H | 1.138 | 308.0 |
| Ex. 38 | c-C₃H₅ | 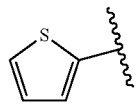 | NO₂ | H | H | H | H | 1.210 | 324.0 |
| Ex. 39 | c-C₃H₅ | c-C₃H₅ | Br | H | H | H | H | 1.244 | 315.0 |
| Ex. 40 | c-C₃H₅ | 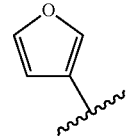 [SMILES: *c1ccoc1] | Br | H | H | H | H | 1.271 | 342.9 |
| Ex. 41 | c-C₃H₅ | 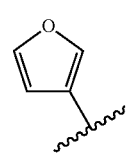 [SMILES: *c1ccoc1] | Cl | H | H | H | F | 1.300 | 315.2 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 42 | C₂H₅ | CH₃ | Cl | H | H | H | H | 1.046 | 223.0 |
| Ex. 43 | C₂H₅ | CH₃ | Br | H | H | H | H | 1.067 | 279.0 |
| Ex. 44 | c-C₃H₅ | 5-chlorobenzofuran-2-yl | Cl | H | F | H | H | 1.530 | 399.0 |
| Ex. 45 | OCH₃ | CH₃ | Cl | H | H | H | H | 1.083 | 235.0 |
| Ex. 46 | OCH₃ | CH₃ | Br | H | H | H | H | 1.098 | 281.0 |
| Ex. 47 | c-C₃H₅ | benzothiophen-3-yl | Br | H | H | H | H | 1.428 | 409.0 |
| Ex. 48 | c-C₃H₅ | benzofuran-3-yl | Cl | H | F | H | H | 1.433 | 365.0 |
| Ex. 49 | c-C₃H₅ | CH(OH)CH₃ | Cl | H | H | H | H | 1.076 | 275.1 |
| Ex. 50 | C(CH₃)(Br)₂ | CH₃ | Cl | H | H | H | H | 1.392 | 390.9 |
| Ex. 51 | CH(Br)CH₃ | CH₂Br | Cl | H | H | H | H | 1.320 | 390.9 |
| Ex. 52 | CH(Br)CH₃ | CH₃ | Cl | H | H | H | H | 1.257 | 313.0 |
| Ex. 53 | c-C₃H₅ | tetrahydrofuran-2-yl | Cl | H | H | H | H | 1.173 | 301.0 |
| Ex. 54 | c-C₃H₅ | furan-2-yl | Cl | H | F | H | H | 1.224 | 315.0 |
| Ex. 55 | c-C₃H₅ | 2,3-dihydrothiophen-2-yl | Cl | H | H | H | H | 1.292 | 317.0 |
| Ex. 56 | c-C₃H₅ | 2-methylthiophen-4-yl | Cl | H | H | H | H | 1.386 | 327.1 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 57 | c-C₃H₅ | (thiazol-4-yl) | Cl | H | H | H | H | 1.184 | 314.1 |
| Ex. 58 | c-C₃H₅ | (2-methylfuran-3-yl) | Cl | H | H | H | H | 1.302 | 311.1 |
| Ex. 59 | c-C₃H₅ | (tetrahydrofuran-3-yl) | Cl | H | H | H | H | 1.197 | 301.1 |
| Ex. 60 | c-C₃H₅ | (furan-2-yl) | Cl | H | H | H | F | 1.277 | 315.2 |
| Ex. 61 | C₂H₅ | (furan-3-yl) | Cl | H | H | H | H | 1.171 | 285.0 |
| Ex. 62 | C₂H₅ | (furan-2-yl) | Br | H | H | H | H | 1.129 | 329.0 |
| Ex. 63 | C₂H₅ | (furan-3-yl) | Br | H | H | H | H | 1.183 | 330.9 |
| Ex. 64 | c-C₃H₅ | (2-hydroxy-2-methylpropyl) | Cl | H | H | H | H | 1.189 | 303.0 |
| Ex. 65 | c-C₃H₅ | ((1-hydroxycyclobutyl)methyl) | Cl | H | H | H | H | 1.217 | 314.8 |
| Ex. 66 | c-C₃H₅ | (2-hydroxy-2-phenylethyl) | Cl | H | H | H | H | 1.256 | 351.1 |
| Ex. 67 | c-C₃H₅ | (methoxycarbonylmethyl) | Br | H | H | H | H | 1.188 | 348.9 |

TABLE X-continued
| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 68 | C₂H₅ | 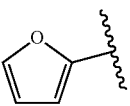 [SMILES: *c1ccco1] | Cl | H | H | H | H | 1.177 | 285.0 |
| Ex. 69 | c-C₄H₇ | CH₃ | Cl | H | H | H | H | 1.231 | 259.1 |
| Ex. 70 | c-C₃H₅ | 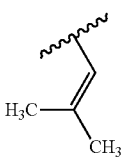 | Cl | H | H | H | H | 1.277 | 285.2 |
| Ex. 71 | c-C₃H₅ | 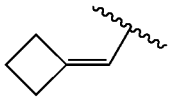 [SMILES: *C=C1CCC1] | Cl | H | H | H | H | 1.282 | 297.0 |
| Ex. 72 | c-C₃H₅ | 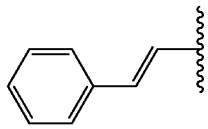 [SMILES: */C=C/c1ccccc1] | Cl | H | H | H | H | 1.420 | 333.2 |
| Ex. 73 | c-C₃H₅ | 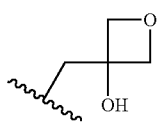 [SMILES: *CC1(O)COC1] | Cl | H | H | H | H | 1.051 | 316.9 |
| Ex. 74 | c-C₃H₅ | 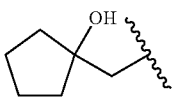 | Cl | H | H | H | H | 1.300 | 329.1 |
| Ex. 75 | c-C₃H₅ | 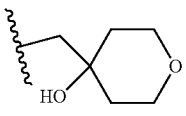 | Cl | H | H | H | H | 1.139 | 345.1 |
| Ex. 76 | c-C₃H₅ | 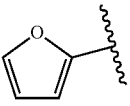 [SMILES: *c1ccco1] | I | H | H | H | H | 1.237 | 388.9 |
| Ex. 77 | c-C₃H₅ | 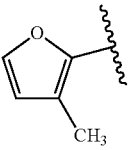 | I | H | H | H | H | 1.348 | 403.0 |
| Ex. 78 | c-C₄H₇ | 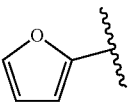 [SMILES: *c1ccco1] | I | H | H | H | H | 1.295 | 402.9 |
| Ex. 79 | c-C₃H₅ | 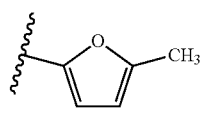 [SMILES: *c1ccc(C)o1] | Cl | H | F | F | H | 1.360 | 347.0 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 80 | c-C$_4$H$_7$ | 3-methylfuran-2-yl | I | H | H | H | H | 1.419 | 417.0 |
| Ex. 81 | c-C$_3$H$_5$ | 5-methylfuran-2-yl | I | H | F | H | H | 1.337 | 421.0 |
| Ex. 82 | c-C$_3$H$_5$ | 5-methylfuran-2-yl | Cl | H | H | Br | H | 1.417 | 390.9 |
| Ex. 83 | C$_2$H$_5$ | 3-methylfuran-2-yl | I | H | H | H | H | 1.318 | 391.0 |
| Ex. 84 | C$_2$H$_5$ | furan-2-yl | I | H | H | H | H | 1.173 | 376.9 |
| Ex. 85 | c-C$_3$H$_5$ | methyl 2-methylpropanoate | Br | H | H | H | H | 1.282 | 363.0 |
| Ex. 86 | c-C$_3$H$_5$ | 2-hydroxypropan-2-yl | Cl | H | H | H | H | 1.151 | 289.0 |
| Ex. 87 | c-C$_3$H$_5$ | methyl 2-methylpropanoate | Cl | H | H | H | H | 1.259 | 317.0 |
| Ex. 88 | c-C$_3$H$_5$ | bis(diethoxyphosphoryl) group | Cl | H | H | H | H | 1.144 | 531.1 |
| Ex. 89 | c-C$_3$H$_5$ | (diethoxyphosphoryl)(methanesulfonyloxy)methyl | Cl | H | H | H | H | 1.138 | 475.0 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 90 | c-C$_3$H$_5$ | (1-(phosphono)-2-phosphonoethyl) | Cl | H | H | H | H | 0.709 | 419.0 |
| Ex. 91 | c-C$_3$H$_5$ | (4-hydroxytetrahydropyran-4-yl) | Cl | H | H | H | H | 1.130 | 345.1 |
| Ex. 92 | c-C$_3$H$_5$ | (tetrahydropyran-4-ylidene)methyl | Cl | H | H | H | H | 1.208 | 327.1 |
| Ex. 93 | c-C$_3$H$_5$ | (E)-but-2-enyl | Cl | H | H | H | H | 1.271 | 271.1 |
| Ex. 94 | c-C$_3$H$_5$ | (E)-2-(furan-2-yl)vinyl | Cl | H | H | H | H | 1.315 | 323.1 |
| Ex. 95 | c-C$_3$H$_5$ | (E)-3,3-dimethylbut-1-enyl | Cl | H | H | H | H | 1.454 | 313.3 |
| Ex. 96 | c-C$_3$H$_5$ | (tetrahydropyran-4-yl)methyl | Cl | H | H | H | H | 1.243 | 329.1 |
| Ex. 97 | c-C$_3$H$_5$ | 2-hydroxy-2-carboxyethyl | Cl | H | H | H | H | 0.928 | 318.8 |
| Ex. 98 | c-C$_3$H$_5$ | cyclobutylmethyl | Cl | H | H | H | H | 1.424 | 299.0 |
| Ex. 99 | c-C$_3$H$_5$ | cyclopentylmethyl | Cl | H | H | H | H | 1.484 | 313.2 |
| Ex. 100 | c-C$_3$H$_5$ | 2-phenylethyl | Cl | H | H | H | H | 1.431 | 335.2 |
| Ex. 101 | c-C$_3$H$_5$ | n-C$_4$H$_7$ | Cl | H | H | H | H | 1.339 | 273.1 |
| Ex. 102 | c-C$_3$H$_5$ | 2-(furan-2-yl)ethyl | Cl | H | H | H | H | 1.361 | 325.1 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 103 | c-C₃H₅ | neopentyl (2,2-dimethylpropyl) | Cl | H | H | H | H | 1.476 | 315.1 |
| Ex. 104 | c-C₃H₅ | (tetrahydropyran-4-yl)methyl | Cl | H | H | H | H | 1.238 | 327.0 |
| Ex. 105 | c-C₃H₅ | 2-hydroxypropyl | Cl | H | H | H | H | 1.095 | 288.9 |
| Ex. 106 | c-C₃H₅ | 2-(furan-2-yl)-2-hydroxyethyl | Cl | H | H | H | H | 1.172 | 340.9 |
| Ex. 107 | c-C₃H₅ | 3-hydroxy-4,4-dimethylpentyl | Cl | H | H | H | H | 1.335 | 331.2 |
| Ex. 108 | c-C₃H₅ | 5-methylfuran-2-yl | I | H | H | H | H | 1.244 | 402.9 |
| Ex. 109 | c-C₃H₅ | 5-methylfuran-2-yl | Cl | H | H | H | F | 1.356 | 347.0 |
| Ex. 110 | c-C₃H₅ | 5-methylfuran-2-yl | CH₃ | H | H | F | H | 1.228 | 309.1 |
| Ex. 111 | c-C₃H₅ | 5-methylfuran-2-yl | CHF2 | H | H | H | H | 1.177 | 343.0 |
| Ex. 112 | c-C₃H₅ | 2-hydroxypropyl | Cl | H | F | H | H | 1.129 | 293.0 |
| Ex. 113 | c-C₃H₅ | 2-hydroxypropyl | Cl | H | H | F | H | 1.122 | 293.0 |
| Ex. 114 | c-C₃H₅ | 2-hydroxypropyl | Br | H | H | H | H | 1.117 | 320.9 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 115 | c-C₃H₅ | -CH(OH)CH₃ | Cl | H | H | H | OCH₃ | 1.121 | 305.0 |
| Ex. 116 | c-C₃H₅ | -CH(OH)CH₃ | I | H | H | H | H | 1.136 | 367.0 |
| Ex. 117 | c-C₃H₅ | -C(OH)(CH₃)₂ | Br | H | H | H | H | 1.219 | 333.0 |
| Ex. 118 | c-C₃H₅ | -C(CH₃)₂C(O)OCH₃ | Cl | H | H | H | H | 1.324 | 331.1 |
| Ex. 119 | c-C₃H₅ | 5-chlorothiophen-2-yl | Cl | H | H | H | H | 1.510 | 347.0 |
| Ex. 120 | c-C₃H₅ | 5-methylfuran-2-yl | CH₃ | H | H | H | H | 1.203 | 291.1 |
| Ex. 121 | c-C₃H₅ | 5-methylfuran-2-yl | Br | H | H | H | H | 1.259 | 356.9 |
| Ex. 122 | c-C₃H₅ | 2-methoxyphenyl | Cl | H | H | H | H | 1.274 | 337.0 |
| Ex. 123 | c-C₃H₅ | pyridin-3-yl | Cl | H | H | H | H | 0.969 | 308.0 |
| Ex. 124 | c-C₃H₅ | 4-bromothiophen-2-yl | Cl | H | H | H | H | 1.488 | 392.9 |
| Ex. 125 | c-C₃H₅ | 3-methoxyphenyl | Cl | H | H | H | H | 1.344 | 337.0 |
| Ex. 126 | c-C₃H₅ | 4-cyanothiophen-2-yl | Cl | H | H | H | H | 1.234 | 338.0 |

TABLE X-continued

| Ex. | R¹ | R² | R³ | R⁴ | R⁵ | R⁶ | R⁷ | HPLC/MS, R_t [min] | HPLC/MS, m/z |
|---|---|---|---|---|---|---|---|---|---|
| Ex. 127 | c-C₃H₅ | 1-hydroxycyclopentyl | Cl | H | H | H | H | 1.274 | 315.1 |
| Ex. 128 | c-C₃H₅ | cyclopentylidenemethyl | Cl | H | H | H | H | 1.300 | 311.1 |
| Ex. 129 | c-C₃H₅ | methyl 2-hydroxy-propanoate linker | Cl | H | H | H | H | 1.075 | 333.0 |
| Ex. 130 | c-C₃H₅ | (E)-methyl but-2-enoate | Cl | H | H | H | H | 1.307 | 315.0 |
| Ex. 131 | c-C₃H₅ | (E)-but-2-enoic acid | Cl | H | H | H | H | 1.109 | 300.9 |
| Ex. 132 | c-C₃H₅ | methyl butanoate | Cl | H | H | H | H | 1.208 | 317.0 |
| Ex. 133 | c-C₃H₅ | butanoic acid | Cl | H | H | H | H | 1.024 | 302.9 |
| Ex. 134 | c-C₃H₅ | i-C₄H₉ | Cl | H | H | H | H | 1.396 | 287.0 |
| Ex. 135 | c-C₃H₅ | 2-hydroxy-2-methylpropyl | Cl | H | F | H | H | 1.212 | 307.0 |
| Ex. 136 | c-C₃H₅ | 2-hydroxy-2-methylpropyl | Cl | H | H | H | H | 1.206 | 307.0 |
| Ex. 137 | c-C₃H₅ | C(CH₃)₂OCH₃ | Br | H | H | H | H | 1.384 | 349.0 |
| Ex. 138 | c-C₃H₅ | C(CH₃)₂OCH₃ | Cl | H | H | H | H | 1.365 | 303.1 |
| Ex. 139 | c-C₃H₅ | C(CH₃)₂OCH₃ | Cl | H | F | H | H | 1.388 | 321.0 |
| Ex. 140 | c-C₃H₅ | C(CH₃)₂OCH₃ | Cl | H | H | F | H | 1.392 | 321.1 |
| Ex. 141 | c-C₃H₅ | methyl 2-(isopropoxy)acetate linker | Cl | H | H | H | H | 1.202 | 347.0 |
| Ex. 142 | c-C₃H₅ | 2-(isopropoxy)acetic acid linker | Cl | H | H | H | H | 1.070 | 333.1 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 143 | c-C$_3$H$_5$ | 1-hydroxycyclobutyl | Cl | H | H | H | H | 1.206 | 301.0 |
| Ex. 144 | c-C$_3$H$_5$ | 3-hydroxyoxetan-3-yl | Cl | H | H | H | H | 1.040 | 302.9 |
| Ex. 145 | c-C$_3$H$_5$ | 3-hydroxytetrahydrofuran-3-yl | Cl | H | H | H | H | 1.078 | 317.0 |
| Ex. 146 | c-C$_3$H$_5$ | 2-oxopropyl | Cl | H | H | H | H | 0.878 | 285.8 |
| Ex. 147 | c-C$_3$H$_5$ | 1,2-dihydroxypropyl | Cl | H | H | H | H | 0.991 | 304.9 |
| Ex. 148 | c-C$_3$H$_5$ | 5-methyl-1,3,4-oxadiazol-2-yl | Cl | H | H | H | H | 1.163 | 313.0 |
| Ex. 149 | c-C$_3$H$_5$ | 1,3,4-oxadiazol-2-yl | Cl | H | H | H | H | 1.107 | 299.0 |
| Ex. 150 | c-C$_3$H$_5$ | methoxycarbonylmethyl | Cl | H | H | F | H | 1.296 | 321.0 |
| Ex. 151 | c-C$_3$H$_5$ | 2-hydroxy-1-methoxycarbonyl-2-methylpropyl | Cl | H | H | H | H | 1.167 | 333.0 |
| EX.152 | c-C$_3$H$_5$ | 2-(dimethoxyphosphoryl)ethyl | Cl | H | H | H | H | 1.042 | 352.9 |
| Ex. 153 | c-C$_3$H$_5$ | 1,2-dihydroxy-2-phenylethyl | Cl | H | H | H | H | 1.138 | 367.1 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 154 | c-C₃H₅ | 1-hydroxy-1-(hydroxymethyl)cyclobutyl | Cl | H | H | H | H | 1.098 | 331.0 |
| Ex. 155 | c-C₃H₅ | (3-hydroxyoxetan-3-yl)methyl | Br | H | H | H | H | 0.984 | 362.7 |
| Ex. 156 | c-C₃H₅ | (1-hydroxycyclobutyl)methyl | Br | H | H | H | H | 1.262 | 360.7 |
| Ex. 157 | c-C₃H₅ | cyclobutylidenemethyl | Br | H | H | H | H | 1.300 | 342.8 |
| Ex. 158 | c-C₃H₅ | (2-phosphonoethyl) | Cl | H | H | H | H | 0.801 | 324.8 |
| Ex. 159 | c-C₃H₅ | 1-(methoxycarbonyl)ethyl | Cl | H | H | F | H | 1.289 | 335.0 |
| Ex. 160 | c-C₃H₅ | 1-methyl-1H-pyrazol-5-yl | Cl | H | H | H | H | 1.172 | 311.1 |
| Ex. 161 | c-C₃H₅ | pyrimidin-5-yl | Cl | H | H | H | H | 1.171 | 309.0 |
| Ex. 162 | c-C₃H₅ | 1-methyl-1H-pyrazol-4-yl | Cl | H | H | H | H | 1.207 | 311.0 |
| Ex. 163 | c-C₃H₅ | 3-hydroxyphenyl | Cl | H | H | H | H | 1.168 | 323.1 |
| Ex. 164 | c-C₃H₅ | 4-methoxyphenyl | Cl | H | H | H | H | 1.413 | 337.0 |
| Ex. 165 | c-C₃H₅ | 4-hydroxyphenyl | Cl | H | H | H | H | 1.184 | 323.0 |

TABLE X-continued

| Ex. | R¹ | R² | R³ | R⁴ | R⁵ | R⁶ | R⁷ | HPLC/MS, R_t [min] | HPLC/MS, m/z |
|---|---|---|---|---|---|---|---|---|---|
| Ex. 166 | c-C₃H₅ | 1-methyl-pyrazol-3-yl | Cl | H | H | H | H | 1.176 | 311.0 |
| Ex. 167 | c-C₃H₅ | 4-methoxyphenyl | Cl | H | H | H | H | 1.413 | 337.0 |
| Ex. 168 | c-C₃H₅ | isoxazol-3-yl | Cl | H | H | H | H | 1.226 | 298.0 |
| Ex. 169 | c-C₃H₅ | -C(F)₂C(O)OCH₃ | Br | H | H | H | H | 1.405 | 383.0 |
| Ex. 170 | c-C₃H₅ | -C(CH₃)₂C(O)OCH₃ | Br | H | H | H | H | 1.463 | 376.9 |
| Ex. 171 | c-C₃H₅ | -C(F)₂C(O)OCH₃ | Cl | H | H | F | H | 1.305 | 357.0 |
| Ex. 172 | c-C₃H₅ | 5-methylfuran-2-yl | Br | H | H | CF₃ | H | 1.522 | 423.0 |
| Ex. 173 | c-C₃H₅ | 5-methylfuran-2-yl | Cl | H | H | CF₃ | H | 1.512 | 379.0 |
| Ex. 174 | c-C₃H₅ | -CH(OH)CF₃ | Cl | H | H | H | H | 1.199 | 328.9 |
| Ex. 175 | c-C₃H₅ | -CH(OH)C(CH₃)₂OH | Cl | H | H | H | H | 1.025 | 319.1 |
| Ex. 176 | c-C₃H₅ | -CH₂CH(OH)(furan-2-yl) | Br | H | H | H | H | 1.163 | 386.8 |
| Ex. 177 | c-C₃H₅ | -CH=CH-(furan-2-yl) | Br | H | H | H | H | 1.309 | 368.8 |
| Ex. 178 | c-C₃H₅ | -CH₂CH₂-(furan-2-yl) | Br | H | H | H | H | 1.349 | 370.8 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 179 | c-C₃H₅ | -CH₂-CH(OH)-CH₃ | Br | H | H | H | H | 1.085 | 334.7 |
| Ex. 180 | c-C₃H₅ | -CH=CH-CH₃ | Br | H | H | H | H | 1.277 | 316.8 |
| Ex. 181 | c-C₃H₅ | c-C₃H₇ | Br | H | H | H | H | 1.331 | 318.8 |
| Ex. 182 | c-C₃H₅ | -CH(OH)-CH(OH)-CH₃ | Br | H | H | H | H | 0.978 | 348.9 |
| Ex. 183 | c-C₃H₅ | furan-2-yl-CH(OH)-CH(OH)- | Br | H | H | H | H | 1.044 | 402.8 |
| Ex. 184 | c-C₃H₅ | -C(CH₃)₂-C(O)-OCH₃ | Cl | H | H | F | H | 1.341 | 349.2 |
| Ex. 185 | c-C₃H₅ | -C(CH₃)₂-OH | CH₃ | H | H | H | H | 1.198 | 269.2 |
| Ex. 186 | c-C₃H₅ | -C(CH₃)₂-OCH₃ | CH₃ | H | H | H | H | 1.429 | 283.1 |
| Ex. 187 | c-C₃H₅ | 5-methylisoxazol-3-yl | Cl | H | H | H | H | 1.255 | 312.0 |
| Ex. 188 | c-C₃H₅ | 3-methylisoxazol-4-yl | Cl | H | H | H | H | 1.241 | 312.0 |
| Ex. 189 | c-C₃H₅ | -CH₂-P(O)(OEt)₂ | Cl | H | H | H | H | 1.150 | 381.0 |

TABLE X-continued
| Ex. | R¹ | R² | R³ | R⁴ | R⁵ | R⁶ | R⁷ | HPLC/MS, R_t [min] | HPLC/MS, m/z |
|---|---|---|---|---|---|---|---|---|---|
| Ex. 190 | c-C₃H₅ | 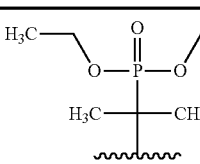 | Cl | H | H | H | H | 1.298 | 409.1 |
| Ex. 191 | c-C₃H₅ | 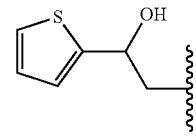 [SMILES: *CC(O)c1cccs1] | Cl | H | H | H | H | 1.348 | 339.0 |
| Ex. 192 | c-C₃H₅ | 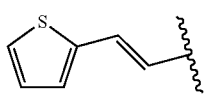 [SMILES: */C=C/c1cccs1] | Cl | H | H | H | H | 1.345 | 339.0 |
| Ex. 193 | c-C₃H₅ | 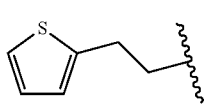 | Cl | H | H | H | H | 1.396 | 341.0 |
| Ex. 194 | c-C₃H₅ | 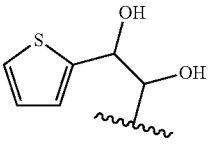 [SMILES: *C(O)C(O)c1cccs1] | Cl | H | H | H | H | 1.087 | 373.0 |
| Ex. 195 | c-C₃H₅ | 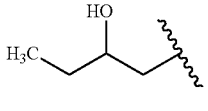 | Cl | H | H | H | H | 1.149 | 303.1 |
| Ex. 196 | c-C₃H₅ | 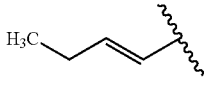 [SMILES: */C=C/CC] | Cl | H | H | H | H | 1.334 | 285.0 |
| Ex. 197 | c-C₃H₅ | 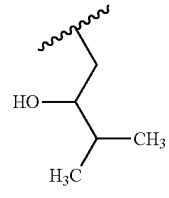 [SMILES: *CC(O)C(C)C] | Cl | H | H | H | H | 1.116 | 315.1 |
| Ex. 198 | c-C₃H₅ | 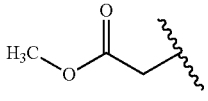 [SMILES: *CC(=O)OC] | Cl | H | F | H | H | 1.170 | 321.0 |
| Ex. 199 | c-C₃H₅ | 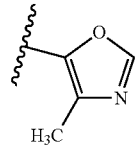 | Cl | H | H | H | H | 1.200 | 312.0 |
| Ex. 200 | c-C₃H₅ | 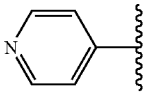 | Cl | H | H | H | H | 0.898 | 308.1 |
| Ex. 201 | c-C₃H₅ | 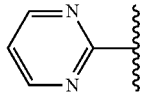 [SMILES: *c1ncccn1] | Cl | H | H | H | H | 1.036 | 309.0 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 202 | c-C₃H₅ | 2-pyridyl | Cl | H | H | H | H | 1.028 | 308.0 |
| Ex. 203 | c-C₃H₅ | 3-methylisoxazol-5-yl | Cl | H | H | H | H | 1.254 | 312.0 |
| Ex. 204 | c-C₃H₅ | pyrazin-2-yl | Cl | H | H | H | H | 1.166 | 309.0 |
| Ex. 205 | c-C₃H₅ | 2-hydroxyphenyl | Cl | H | H | H | H | 0.807 | 323.0 |
| Ex. 206 | c-C₃H₅ | (E)-4-methylpent-2-en-1-yl | Cl | H | H | H | H | 1.393 | 299.0 |
| Ex. 207 | c-C₃H₅ | 2-cyclopropyl-2-hydroxyethyl | Cl | H | H | H | H | 1.137 | 315.0 |
| Ex. 208 | c-C₃H₅ | (E)-2-cyclopropylvinyl | Cl | H | H | H | H | 1.258 | 297.0 |
| Ex. 209 | c-C₃H₅ | 2-hydroxybut-3-en-1-yl | Cl | H | H | H | H | 1.120 | 301.0 |
| Ex. 210 | c-C₃H₅ | cyclopent-1-en-1-yl | Cl | H | H | H | H | 1.388 | 296.9 |
| Ex. 211 | c-C₃H₅ | allyl | Cl | H | H | H | H | xxx | xxx |
| Ex. 212 | c-C₃H₅ | 2,3-dihydroxypropyl | Cl | H | H | H | H | 0.890 | 290.8 |
| Ex. 213 | c-C₃H₅ | 3-methyloxiran-2-yl | Br | H | H | H | H | xxx | xxx |

TABLE X-continued
| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 214 | c-C₃H₅ | 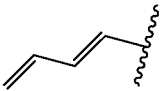 [SMILES: */C=C/C=C] | Cl | H | H | H | H | xxx | xxx |
| Ex. 215 | c-C₃H₅ | 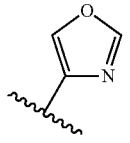 [SMILES: *c1cocn1] | Cl | H | H | H | H | 1.115 | 298.0 |
| Ex. 216 | c-C₃H₅ | 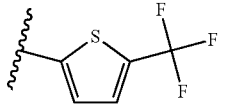 [SMILES: *c1ccc(C(F)(F)F)s1] | Cl | H | H | H | H | 1.544 | 380.8 |
| Ex. 217 | c-C₃H₅ | 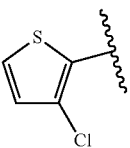 [SMILES: *c1sccc1Cl] | Cl | H | H | H | H | 1.399 | 346.8 |
| Ex. 218 | SCH₃ | 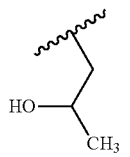 | Cl | H | H | H | H | 1.109 | 295.0 |
| Ex. 219 | SCH₃ | 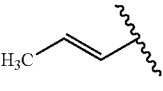 [SMILES: */C=C/C] | Cl | H | H | H | H | 1.387 | 2777.0 |
| Ex. 220 | c-C₃H₅ | 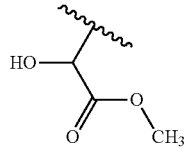 | Cl | H | H | H | H | 1.044 | 318.9 |
| Ex. 221 | c-C₃H₅ | 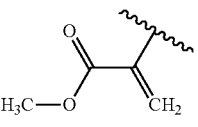 | Cl | H | H | H | H | 1.180 | 314.8 |
| Ex. 222 | c-C₃H₅ | 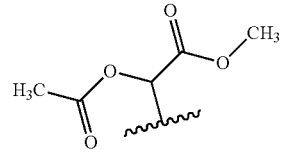 [SMILES: *C(OC(C)=O)C(=O)OC] | Cl | H | H | H | H | 1.174 | 360.9 |
| Ex. 223 | c-C₃H₅ | 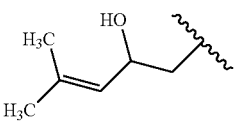 | Cl | H | H | H | H | xxx | xxx |
| Ex. 224 | c-C₃H₅ | 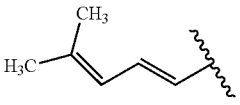 | Cl | H | H | H | H | 1.358 | 310.9 |

TABLE X-continued
| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 225 | c-C$_3$H$_5$ | 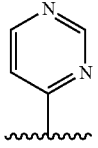 | Cl | H | H | H | H | 1.135 | 309.0 |
| Ex. 226 | OCH$_3$ | 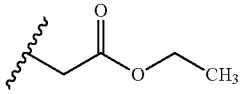 | Cl | H | H | H | H | 1.127 | 307.0 |
| Ex. 227 | OCH$_3$ | 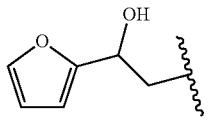 | Cl | H | H | H | H | 1.075 | 331.0 |
| Ex. 228 | OCH$_3$ | 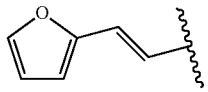 [SMILES: */C=C/c1ccco1] | Cl | H | H | H | H | 1.261 | 313.0 |
| Ex. 229 | c-C$_3$H$_5$ | 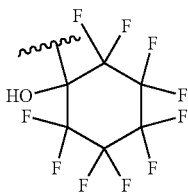 [SMILES: *C1(O)C(F)(F)C(F)(F)C(F)(F)C(F)(F)C1(F)F] | Cl | H | H | H | H | 1.481 | 508.8 |
| Ex. 230 | c-C$_3$H$_5$ | 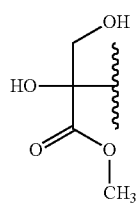 | Cl | H | H | H | H | 0.978 | 348.9 |
| Ex. 231 | c-C$_3$H$_5$ | 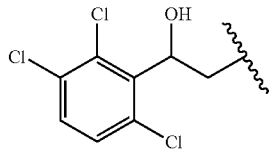 [SMILES: *CC(O)c1c(Cl)ccc(Cl)c1Cl] | Cl | H | H | H | H | 1.393 | 454.8 |
| Ex. 232 | c-C$_3$H$_5$ | 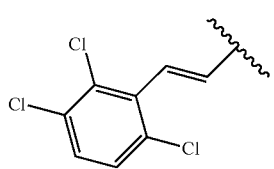 [SMILES: */C=C/c1c(Cl)ccc(Cl)c1Cl] | Cl | H | H | H | H | 1.636 | 436.8 |
| Ex. 233 | c-C$_3$H$_5$ | 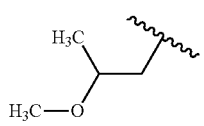 | Cl | H | H | H | H | 1.125 | 302.9 |
| Ex. 234 | c-C$_3$H$_5$ | 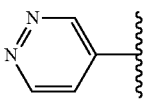 | Cl | H | H | H | H | 1.076 | 308.9 |

TABLE X-continued

| Ex. | R¹ | R² | R³ | R⁴ | R⁵ | R⁶ | R⁷ | HPLC/MS, R_t [min] | HPLC/MS, m/z |
|---|---|---|---|---|---|---|---|---|---|
| Ex. 235 | c-C₃H₅ | 4-methyl-oxazol-5-yl | Br | H | H | H | H | 1.235 | 355.8 |
| Ex. 236 | c-C₃H₅ | 4-methyl-oxazol-5-yl | Cl | H | H | F | H | 1.246 | 329.9 |
| Ex. 237 | c-C₃H₅ | 2,5-dimethyl-furan-3-yl | Br | H | H | H | H | 1.242 | 371.0 |
| Ex. 238 | c-C₃H₅ | 2-methyl-furan-3-yl | Br | H | H | H | H | 1.220 | 356.8 |
| Ex. 239 | c-C₃H₅ | C₂H₅ | Cl | H | H | H | H | 1.252 | 258.9 |
| Ex. 240 | c-C₃H₅ | 1,2-dihydroxy-1-(2,3,6-trichlorophenyl)ethyl (stereo) | Cl | H | H | H | H | 1.205 | 470.8 |
| Ex. 241 | c-C₃H₅ | 1,2-dihydroxy-1-(2,3,6-trichlorophenyl)ethyl | Cl | H | H | H | H | 1.205 | 470.8 |
| Ex. 242 | c-C₃H₅ | 4-methyl-oxazol-5-yl | Cl | H | F | H | H | 1.399 | 330.0 |
| Ex. 243 | c-C₃H₅ | 2,4-dimethyl-oxazol-5-yl | Cl | H | H | H | H | 1.210 | 326.1 |
| Ex. 244 | c-C₃H₅ | 2-methyl-oxazol-5-yl | Cl | H | H | H | H | 1.160 | 312.1 |

TABLE X-continued
| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 245 | c-C$_3$H$_5$ | 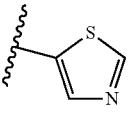 [SMILES: *c1cncs1] | Cl | H | H | H | H | 1.224 | 313.9 |
| Ex. 246 | c-C$_3$H$_5$ | 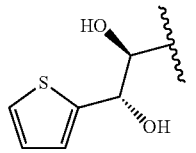 [SMILES: *[C@H](O)[C@H](O)c1cccs1] | Cl | H | H | H | H | 1.088 | 372.8 |
| Ex. 247 | c-C$_3$H$_5$ | 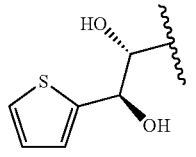 [SMILES: *[C@@H](O)[C@@H](O)c1cccs1] | Cl | H | H | H | H | 1.086 | 372.9 |
| Ex. 248 | c-C$_3$H$_5$ | 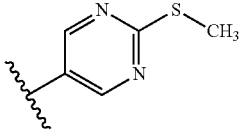 [SMILES: *c1cnc(SC)nc1] | Cl | H | H | H | H | 1.328 | 355.1 |
| Ex. 249 | c-C$_3$H$_5$ | 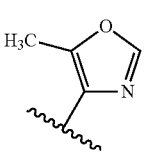 | Br | H | H | H | H | 1.220 | 356.8 |
| Ex. 250 | c-C$_3$H$_5$ | 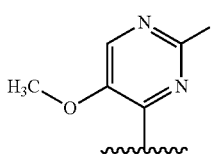 | Cl | H | H | H | H | 0.950 | 355.1 |
| Ex. 251 | c-C$_3$H$_5$ | 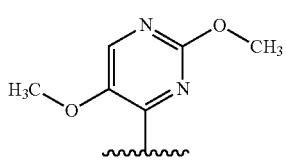 | Cl | H | H | H | H | 1.231 | 368.9 |
| Ex. 252 | c-C$_3$H$_5$ | 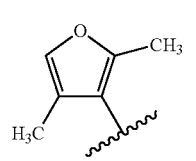 | Br | H | H | H | H | 1.351 | 371.0 |
| Ex. 253 | c-C$_3$H$_5$ | 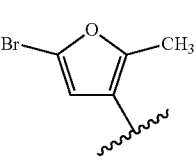 [SMILES: *c1cc(Br)oc1C] | Br | H | H | H | H | 1.456 | 434.9 |
| Ex. 254 | c-C$_3$H$_5$ | 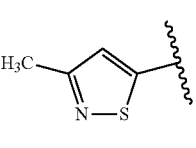 | Cl | H | H | H | H | 1.332 | 328.0 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 255 | c-C$_3$H$_5$ | HO-CH$_2$CH$_2$- | Cl | H | H | H | H | 0.994 | 274.9 |
| Ex. 256 | c-C$_3$H$_5$ | 3,6-dichloropyridin-2-yl-CH(OH)-CH$_2$- | Cl | H | H | H | H | 1.277 | 419.8 |
| Ex. 257 | c-C$_3$H$_5$ | (E)-3,6-dichloropyridin-2-yl-CH=CH- | Cl | H | H | H | H | 1.505 | 401.8 |
| Ex. 258 | c-C$_3$H$_5$ | 3,6-dichloropyridin-2-yl-CH(OH)-CH(OH)- | Cl | H | H | H | H | 1.162 | 435.8 |
| Ex. 259 | c-C$_3$H$_5$ | 3,6-dichloropyridin-2-yl-CH(OH)-CH(OH)- | Cl | H | H | H | H | 1.161 | 435.8 |
| Ex. 260 | c-C$_3$H$_5$ | oxazol-5-yl | Cl | H | H | H | H | 1.130 | 298.1 |
| Ex. 261 | c-C$_3$H$_5$ | oxazol-5-yl | Br | H | H | H | H | 1.140 | 344.0 |
| Ex. 262 | c-C$_3$H$_5$ | 4-methyloxazol-5-yl | Cl | H | H | CF$_3$ | H | 1.307 | 380.1 |
| Ex. 263 | c-C$_3$H$_5$ | 4-methyloxazol-5-yl | Br | H | H | CF$_3$ | H | 1.330 | 424.0 |
| Ex. 264 | c-C$_3$H$_5$ | 4-methyloxazol-5-yl | Cl | H | CF$_3$ | H | H | 1.321 | 380.1 |

TABLE X-continued
| Ex. | R¹ | R² | R³ | R⁴ | R⁵ | R⁶ | R⁷ | HPLC/MS, R_t [min] | HPLC/MS, m/z |
|---|---|---|---|---|---|---|---|---|---|
| Ex. 265 | c-C₃H₅ | 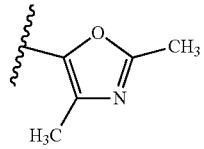 | Br | H | H | H | H | 1.251 | 370.0 |
| Ex. 266 | c-C₃H₅ | 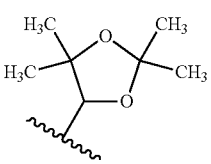 | Cl | H | H | H | H | 1.423 | 358.9 |
| Ex. 267 | c-C₃H₅ | 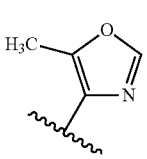 | Cl | H | H | H | H | 1.224 | 312.0 |
| Ex. 268 | c-C₃H₅ | 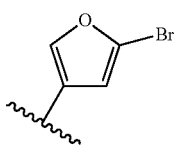 [SMILES: *c1coc(Br)c1] | Br | H | H | H | H | 1.458 | 420.7 |
| Ex. 269 | c-C₃H₅ | 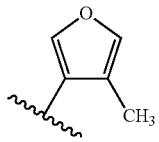 [SMILES: *c1cocc1C] | Br | H | H | H | H | 1.329 | 357.0 |
| Ex. 270 | c-C₃H₅ | 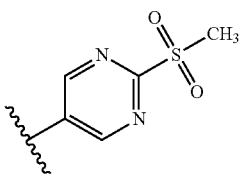 [SMILES: *c1cnc(S(C)(=O)=O)nc1] | Cl | H | H | H | H | 1.122 | 383.8 |
| Ex. 271 | c-C₃H₅ | 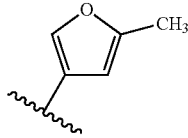 [SMILES: *c1coc(C)c1] | Br | H | H | H | H | 1.352 | 354.8 |
| Ex. 272 | c-C₃H₅ | 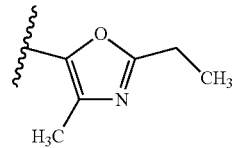 | Cl | H | H | H | H | 1.278 | 340.1 |
| Ex. 273 | c-C₃H₅ | 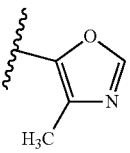 [SMILES: *c1ocnc1C] | Br | H | H | Br | H | 1.324 | 435.9 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 274 | c-C₃H₅ | (3-acetoxy-2-methyl-2-acetoxymethyl structure) | Cl | H | H | H | H | 1.296 | 402.9 |
| Ex. 275 | c-C₃H₅ | 2,4-dimethyloxazol-5-yl | Br | H | H | CF3 | H | 1.380 | 437.9 |
| Ex. 276 | c-C₃H₅ | 2,4-dimethyloxazol-5-yl | Cl | H | F | H | H | 1.253 | 343.9 |
| Ex. 277 | c-C₃H₅ | 2,5-dimethyloxazol-4-yl | Cl | H | H | H | H | 1.262 | 326.0 |
| Ex. 278 | c-C₃H₅ | 2,4-dimethyloxazol-5-yl | Cl | H | H | CF3 | H | 1.363 | 393.9 |
| Ex. 279 | c-C₃H₅ | 5-chloropyridin-3-yl | Cl | H | H | H | H | 1.333 | 341.9 |
| Ex. 280 | c-C₃H₅ | 1-methylimidazol-2-yl | Cl | H | H | H | H | 0.831 | 311.0 |
| Ex. 281 | c-C₃H₅ | 2-isopropyloxazol-4-yl | Cl | H | H | H | H | 1.406 | 323.1 |
| Ex. 282 | c-C₃H₅ | 5-ethyloxazol-4-yl | Cl | H | H | H | H | 1.341 | 326.0 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 283 | c-C₃H₅ | 5-methyl-2-isopropyl-oxazol-4-yl | Cl | H | H | H | H | 1.506 | 354.0 |
| Ex. 284 | c-C₃H₅ | 2,4-dimethyl-oxazol-5-yl | Cl | H | H | F | H | 1.239 | 344.0 |
| Ex. 285 | c-C₃H₅ | 2,4-dimethyl-oxazol-5-yl | Cl | H | H | H | H | 1.325 | 406.0 |
| Ex. 286 | c-C₃H₅ | 4-ethyl-oxazol-5-yl | Cl | H | H | H | H | 1.291 | 326.0 |
| Ex. 287 | c-C₃H₅ | oxazol-4-yl | Br | H | H | H | H | 1.107 | 342.0 |
| Ex. 288 | c-C₃H₅ | 2-methyl-oxazol-4-yl | Br | H | H | H | H | 1.131 | 358.0 |
| Ex. 289 | c-C₃H₅ | 3-methyl-2-oxo-oxazol-4-yl | Cl | H | H | H | H | 1.127 | 328.1 |
| Ex. 290 | c-C₃H₅ | 2-ethyl-4-methyl-oxazol-5-yl | Br | H | H | H | H | 1.312 | 383.9 |
| Ex. 291 | c-C₃H₅ | 2,4-dimethyl-oxazol-5-yl | Cl | H | H | CHF2 | H | 1.231 | 376.1 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 292 | c-C$_3$H$_5$ | 2,4-dimethyloxazol-5-yl | Br | H | H | Br | H | 1.330 | 450.0 |
| Ex. 293 | c-C$_3$H$_5$ | 3-methoxy-2-(methoxymethyl)prop-1-en-1-yl | Cl | H | H | H | H | 1.234 | 345.0 |
| Ex. 294 | c-C$_3$H$_5$ | 2-(tert-butyl)oxazol-5-yl (CH₂ shown) | Cl | H | H | H | H | 1.414 | 354.0 |
| Ex. 295 | c-C$_3$H$_5$ | 3-methyl-1,2,4-oxadiazol-5-yl | Cl | H | H | H | H | 1.203 | 313.1 |
| Ex. 296 | c-C$_3$H$_5$ | (2,2-dimethyl-1,3-dioxan-5-ylidene)methyl | Cl | H | H | H | H | 1.314 | 356.9 |
| Ex. 297 | c-C$_3$H$_5$ | 1H-benzimidazol-2-yl | Cl | H | H | H | H | 1.031 | 347.3 |
| Ex. 298 | c-C$_3$H$_5$ | 3-hydroxy-2-(hydroxymethyl)prop-1-en-1-yl | Cl | H | H | H | H | 0.937 | 316.9 |
| Ex. 299 | c-C$_3$H$_5$ | 2-chloro-4-methyloxazol-5-yl | Cl | H | H | H | H | 1.350 | 346.0 |
| Ex. 300 | c-C$_3$H$_5$ | 2-chloro-4-methyloxazol-5-yl | Br | H | H | H | H | 1.361 | 391.9 |
| Ex. 301 | c-C$_3$H$_5$ | 2-bromo-4-methyloxazol-5-yl | Cl | H | H | H | H | 1.375 | 391.9 |

TABLE X-continued

| Ex. | R¹ | R² | R³ | R⁴ | R⁵ | R⁶ | R⁷ | HPLC/MS, R$_t$ [min] | HPLC/MS, m/z |
|---|---|---|---|---|---|---|---|---|---|
| Ex. 302 | c-C₃H₅ | 4-methyl-2-methoxy-oxazol-5-yl | Cl | H | H | H | H | 1.206 | 342.1 |
| Ex. 303 | c-C₃H₅ | 4-methyl-2-tert-butyl-oxazol-5-yl | Cl | H | H | H | H | 1.422 | 368.0 |
| Ex. 304 | c-C₃H₅ | 4-methyl-isoxazol-5-yl | Cl | H | H | H | H | 1.270 | 312.0 |
| Ex. 305 | c-C₃H₅ | 4-methyl-2-methoxy-oxazol-5-yl | Br | H | H | H | H | 1.212 | 388.0 |
| Ex. 306 | c-C₃H₅ | 4-methyl-2-methylthio-oxazol-5-yl | Br | H | H | H | H | 1.346 | 401.9 |
| Ex. 307 | c-C₃H₅ | 4-methyl-2-methylthio-oxazol-5-yl | Cl | H | H | H | H | 1.336 | 357.9 |
| Ex. 308 | c-C₃H₅ | 5-methyl-2-methyl-oxazol-4-yl | I | H | H | H | H | 1.221 | 418 |
| Ex. 309 | c-C₃H₅ | 5-methyl-2-methyl-oxazol-4-yl | F | H | H | H | Cl | 1.236 | 344 |
| Ex. 310 | c-C₃H₅ | 5-ethyl-2-ethyl-oxazol-4-yl | Cl | H | H | H | H | 1.339 | 354.1 |

TABLE X-continued

| Ex. | R¹ | R² | R³ | R⁴ | R⁵ | R⁶ | R⁷ | HPLC/MS, R, [min] | HPLC/MS, m/z |
|---|---|---|---|---|---|---|---|---|---|
| Ex. 311 | c-C₃H₅ | 4-ethyl-2-ethyl-oxazol-5-yl | Br | H | H | H | H | 1.349 | 398.1 |
| Ex. 312 | c-C₃H₅ | 2-hydroxy-4-methyl-oxazol-5-yl | Br | H | H | H | H | 1.036 | 371.9 |
| Ex. 313 | c-C₃H₅ | 4-methyl-2-propyl-oxazol-5-yl | Cl | H | H | H | H | 1.37 | 354 |
| Ex. 314 | c-C₃H₅ | 5-methyl-oxazol-2-yl | Cl | H | H | H | H | 1.206 | 312 |
| Ex. 315 | c-C₃H₅ | oxazol-2-yl | Cl | H | H | H | H | 1.15 | 297.9 |
| Ex. 316 | c-C₃H₅ | 4,5-dimethyl-oxazol-2-yl | Cl | H | H | H | H | 1.265 | 326 |

B USE EXAMPLES

The herbicidal activity of the pyrimidine compounds of formula (I) was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this had been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C., respectively.

The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments were of the following species:

| Bayer code | Scientific name |
| --- | --- |
| ABUTH | *Abutilon theophrasti* |
| ALOMY | *Alopecurus myosuroides* |
| AMARE | *Amaranthus retroflexus* |
| APESV | *Apera spica-venti* |
| AVEFA | *Avena fatua* |
| ECHCG | *Echinocloa crus-galli* |
| SETVI | *Setaria viridis* |
| SETFA | *Setaria faberi* |
| POAAN | *Poa annua* |
| AGSST | *Agrostis stolonifera* |
| LOLMU | *Lolium multiflorum* |
| POLCO | *Polygonum convolvulus* |
| MATIN | *Matricaria inodora* |
| AGSST | *Agrostis stolonifera* |
| CHEAL | *Chenopodium album* |

At an application rate of 1000 g/ha, Ex.1 applied by the post-emergence method showed very good herbicidal activity against ALOMY, and good herbicidal activity against AVEFA and ECHCG, and applied by the pre-emergence method showed very good herbicidal activity against APESV and ECHCG.

At an application rate of 1000 g/ha, Ex.2 applied by the post-emergence method showed very good herbicidal activity against AVEFA and ALOMY, and good herbicidal activity against ECHCG, and applied by the pre-emergence method showed very good herbicidal activity against APESV and ECHCG.

At an application rate of 2000 g/ha, Ex.4 applied by the post-emergence method showed very good herbicidal activity against SETVI, AVEFA and ALOMY, and applied by the pre-emergence method showed very good herbicidal activity against AGSST, APESV and ECHCG.

At an application rate of 1819 g/ha, Ex.5 applied by the post-emergence method showed very good herbicidal activity against SETVI, AVEFA and ALOMY, and applied by the pre-emergence method showed very good herbicidal activity against APESV and ECHCG.

At an application rate of 2000 g/ha, Ex.6 applied by the post-emergence method showed very good herbicidal activity against ECHCG and APESV, and applied by the pre-emergence method showed very good herbicidal activity against ECHCG and APESV.

At an application rate of 2000 g/ha, Ex.7 applied by the post-emergence method showed good herbicidal activity against SETVI.

At an application rate of 2000 g/ha, Ex.8 applied by the post-emergence method showed very good herbicidal activity against MATIN, ABUTH and AMARE.

At an application rate of 1856 g/ha, Ex.9 applied by the post-emergence method showed very good herbicidal activity against ECHCG, AVEFA and ALOMY, and applied by the pre-emergence method showed very good herbicidal activity against APESV, and good herbicidal activity against ECHCG.

At an application rate of 2000 g/ha, Ex.10 applied by the post-emergence method showed very good herbicidal activity against SETVI, ABUTH and AMARE, and applied by the pre-emergence method showed very good herbicidal activity against AGSST, MATIN and SETFA.

At an application rate of 2000 g/ha, Ex.11 applied by the pre-emergence method showed very good herbicidal activity against SETFA and good herbicidal activity against ECHCG.

At an application rate of 250 g/ha, Ex.13 applied by the post-emergence method showed very good herbicidal activity against ALOMY, ECHCG and POLCO, and applied by the pre-emergence method showed very good herbicidal activity against APESV.

At an application rate of 250 g/ha, Ex.14 applied by the post-emergence method showed good herbicidal activity against LOLMU, and applied by the pre-emergence method showed very good herbicidal activity against APESV.

At an application rate of 1000 g/ha, Ex.15 applied by the post-emergence method showed very good herbicidal activity against AVEFA and ALOMY, and good herbicidal activity against AMARE, and applied by the pre-emergence method showed very good herbicidal activity against APESV and ECHCG.

At an application rate of 2000 g/ha, Ex.16 applied by the post-emergence method showed good herbicidal activity against AMARE, and applied by the pre-emergence method showed very good herbicidal activity against SETFA.

At an application rate of 2000 g/ha, Ex.17 applied by the pre-emergence method showed very good herbicidal activity against AGSST, ECHCG and SETFA. At an application rate of 2000 g/ha, example 19 applied by the post-emergence method showed very good herbicidal activity against AMARE and ABUTH.

At an application rate of 2000 g/ha, Ex.20 applied by the post-emergence method showed good herbicidal activity against AMARE and MATIN, and applied by the pre-emergence method showed good herbicidal activity against ECHCG.

At an application rate of 1000 g/ha, Ex.21 applied by the post-emergence method showed very good herbicidal activity against ALOMY, and applied by the pre-emergence method showed very good herbicidal activity against APESV.

At an application rate of 1000 g/ha, Ex.22 applied by the post-emergence method showed very good herbicidal activity against ALOMY, AVEFA and ECHCG, and applied by the pre-emergence method showed very good herbicidal activity against APESV.

At an application rate of 2000 g/ha, Ex.24 applied by the post-emergence method showed very good herbicidal activity against ECHCG and SETVI, and applied by the pre-emergence method showed very good herbicidal activity against ECHCG and APESV.

At an application rate of 2000 g/ha, Ex.25 applied by the post-emergence method showed very good herbicidal activity against MATIN, and applied by the pre-emergence method showed very good herbicidal activity against AGSST and POAAN.

At an application rate of 2000 g/ha, Ex.26 applied by the post-emergence method showed very good herbicidal activity against ECHCG and ALOMY, and applied by the pre-emergence method showed very good herbicidal activity against APESV and ECHCG.

At an application rate of 2000 g/ha, Ex.27 applied by the post-emergence method showed very good herbicidal activity against AMARE, ECHCG and ALOMY, and applied by the pre-emergence method showed very good herbicidal activity against AGSST, ECHCG and APESV.

At an application rate of 1163 g/ha, Ex.28 applied by the post-emergence method, showed very good herbicidal activity against AMARE, and good herbicidal activity against ABUTH.

At an application rate of 2000 g/ha, Ex.29 applied by the post-emergence method showed very good herbicidal activity against MATIN and AMARE.

At an application rate of 2000 g/ha, Ex.30 applied by the post-emergence method showed very good herbicidal activity against SETVI and ALOMY, and applied by the pre-emergence method showed very good herbicidal activity against ECHCG and APESV.

At an application rate of 2000 g/ha, Ex.31 applied by the post-emergence method showed very good herbicidal activity against SETVI and ALOMY, and applied by the pre-emergence method showed very good herbicidal activity against ECHCG and APESV.

At an application rate of 2000 g/ha, Ex.32 applied by the post-emergence method, showed very good herbicidal activity against ALOMY, AVEFA and ECHCG, and applied by the pre-emergence method showed very good herbicidal activity against ECHCG and APESV.

At an application rate of 2000 g/ha, Ex.33 applied by the post-emergence method showed good herbicidal activity against SETVI.

At an application rate of 2000 g/ha, Ex.34 applied by the post-emergence method showed very good herbicidal activity against ECHCG, and good herbicidal activity against ALOMY, and applied by the pre-emergence method showed very good herbicidal activity against APESV, and good herbicidal activity against ECHCG.

At an application rate of 2000 g/ha, Ex.35 applied by the post-emergence method showed very good herbicidal activity against AMARE, ECHCG and ALOMY, and applied by the pre-emergence method showed very good herbicidal activity against AGSST, ECHCG and APESV.

At an application rate of 2000 g/ha, Ex.36 applied by the post-emergence method showed very good herbicidal activity against MATIN, and applied by the pre-emergence method showed very good herbicidal activity against AGSST and POAAN.

At an application rate of 2000 g/ha, Ex.37 applied by the pre-emergence method showed good herbicidal activity against SETFA.

At an application rate of 1000 g/ha, Ex.38 applied by the post-emergence method showed good herbicidal activity against SETVI.

At an application rate of 2000 g/ha, Ex.39 applied by the post-emergence method showed very good herbicidal activity against AMARE and ABUTH, and applied by the pre-emergence method showed very good herbicidal activity against SETVI.

At an application rate of 2000 g/ha, Ex.40 applied by the post-emergence method showed very good herbicidal activity against AVEFA and ALOMY, and applied by the pre-emergence method showed very good herbicidal activity against ECHCG and APESV.

At an application rate of 2000 g/ha, Ex.41 applied by the post-emergence method showed very good herbicidal activity against MATIN and ALOMY.

At an application rate of 1000 g/ha, Ex.42 applied by the post-emergence method showed very good herbicidal activity against SETVI.

At an application rate of 1000 g/ha, Ex.44 applied by the post-emergence method showed very good herbicidal activity against AVEFA and ECHCG.

At an application rate of 1000 g/ha, Ex.47 applied by the post-emergence method showed very good herbicidal activity against AMARE.

At an application rate of 1000 g/ha, Ex.49 applied by the post-emergence method showed very good herbicidal activity against ALOMY and SETVI, and good herbicidal activity against ECHCG, and applied by the pre-emergence method showed good herbicidal activity against APESV and ECHCG.

At an application rate of 500 g/ha, Ex.50 applied by the post-emergence method showed very good herbicidal activity against AMARE and SETVI.

At an application rate of 1000 g/ha, Ex.51 applied by the post-emergence method showed very good herbicidal activity against SETVI.

At an application rate of 1000 g/ha, Ex.52 applied by the post-emergence method showed very good herbicidal activity against SETVI.

At an application rate of 1000 g/ha, Ex.54 applied by the post-emergence method showed very good herbicidal activity against AVEFA and ECHCG, and applied by the pre-emergence method showed very good herbicidal activity against APESV.

At an application rate of 1000 g/ha, Ex.55 applied by the post-emergence method showed very good herbicidal activity against SETVI and AMARE.

At an application rate of 1000 g/ha, Ex.58 applied by the post-emergence method showed very good herbicidal activity against SETVI, and good herbicidal activity against AVEFA.

At an application rate of 1000 g/ha, Ex.59 applied by the post-emergence method showed very good herbicidal activity against SETVI, and good herbicidal activity against ECHCG, and applied by the pre-emergence method showed very good herbicidal activity against ECHCG, and good herbicidal activity against SETFA.

At an application rate of 1000 g/ha, Ex.60 applied by the post-emergence method showed very good herbicidal activity against AVEFA and ALOMY.

At an application rate of 500 g/ha, Ex.62 applied by the post-emergence method showed very good herbicidal activity against SETVI.

At an application rate of 1000 g/ha, Ex.63 applied by the post-emergence method showed very good herbicidal activity against ECHCG.

At an application rate of 2000 g/ha, Ex.65 applied by the post-emergence method showed very good herbicidal activity against AMARE and ECHCG.

At an application rate of 2000 g/ha, Ex.66 applied by the post-emergence method showed very good herbicidal activity against ECHCG.

At an application rate of 2000 g/ha, Ex.67 applied by the post-emergence method showed very good herbicidal activity against ALOMY and AVEFA, and good herbicidal activity against ECHCG, and applied by the pre-emergence method showed very good herbicidal activity against APESV.

At an application rate of 2000 g/ha, Ex.70 applied by the post-emergence method showed very good herbicidal activity against ALOMY and SETVI.

At an application rate of 2000 g/ha, Ex.71 applied by the post-emergence method showed very good herbicidal activity against ALOMY and AVEFA, and good herbicidal activity against ECHCG, and applied by the pre-emergence method showed very good herbicidal activity against ECHCG and APESV.

At an application rate of 2000 g/ha, Ex.73 applied by the post-emergence method showed good herbicidal activity against ALOMY.

At an application rate of 2000 g/ha, Ex.74 applied by the post-emergence method showed very good herbicidal activity against SETVI.

At an application rate of 1000 g/ha, Ex.76 applied by the post-emergence method showed very good herbicidal activity against SETVI, and good herbicidal activity against ALOMY.

At an application rate of 1000 g/ha, Ex.77 applied by the post-emergence method showed very good herbicidal activity against AVEFA and ALOMY.

At an application rate of 1000 g/ha, Ex.78 applied by the post-emergence method showed very good herbicidal activity against SETVI.

At an application rate of 1000 g/ha, Ex.79 applied by the post-emergence method showed very good herbicidal activity against AVEFA and ALOMY.

At an application rate of 1000 g/ha, Ex.81 applied by the post-emergence method showed very good herbicidal activity against AVEFA and ALOMY.

At an application rate of 2000 g/ha, Ex.85 applied by the post-emergence method showed very good herbicidal activity against ABUTH, and good herbicidal activity against AMARE.

At an application rate of 1000 g/ha, Ex.86 applied by the post-emergence method showed very good herbicidal activity against SETVI, and good activity against ABUTH and AMARE, and applied by the pre-emergence method showed good herbicidal activity against APESV.

At an application rate of 2000 g/ha, Ex.87 applied by the post-emergence method showed very good herbicidal activity against ALOMY, and applied by the pre-emergence method showed good herbicidal activity against AMARE.

At an application rate of 2000 g/ha, Ex.88 applied by the post-emergence method showed very good herbicidal activity against SETVI.

At an application rate of 2000 g/ha, Ex.89 applied by the post-emergence method showed very good herbicidal activity against ALOMY, and good activity against AVEFA, and applied by the pre-emergence method showed good herbicidal activity against APESV.

At an application rate of 2000 g/ha, Ex.90 applied by the post-emergence method showed very good herbicidal activity against SETVI.

At an application rate of 2000 g/ha, Ex.92 applied by the post-emergence method showed good herbicidal activity against ALOMY, SETVI and ECHCG.

At an application rate of 2000 g/ha, Ex.93 applied by the post-emergence method showed very good herbicidal activity against ALOMY, AVEFA and ECHCG, and applied by the pre-emergence method showed very good herbicidal activity against APESV and ECHCG.

At an application rate of 2000 g/ha, Ex.94 applied by the post-emergence method showed very good herbicidal activity against ALOMY and AVEFA, and applied by the pre-emergence method showed very good herbicidal activity against APESV.

At an application rate of 2000 g/ha, Ex.95 applied by the post-emergence method showed very good herbicidal activity against ALOMY and ECHCG, and applied by the pre-emergence method showed very good herbicidal activity against APESV.

At an application rate of 1000 g/ha, Ex.96 applied by the post-emergence method showed very good herbicidal activity against SETVI.

At an application rate of 2000 g/ha, Ex.97 applied by the post-emergence method showed very good herbicidal activity against ECHCG, and applied by the pre-emergence method showed very good herbicidal activity against APESV.

At an application rate of 500 g/ha, Ex.98 applied by the post-emergence method showed good herbicidal activity against SETVI.

At an application rate of 2000 g/ha, Ex.99 applied by the post-emergence method showed very good herbicidal activity against SETVI.

At an application rate of 2000 g/ha, Ex.101 applied by the post-emergence method showed very good herbicidal activity against ABUTH, and AMARE.

At an application rate of 2000 g/ha, Ex.102 applied by the post-emergence method showed very good herbicidal activity against ECHCG.

At an application rate of 2000 g/ha, Ex.103 applied by the post-emergence method showed very good herbicidal activity against SETVI.

At an application rate of 2000 g/ha, Ex.104 applied by the post-emergence method showed very good herbicidal activity against ALOMY, and good herbicidal activity against ECHCG, and applied by the pre-emergence method showed very good herbicidal activity against APESV, and good herbicidal activity against ECHCG.

At an application rate of 2000 g/ha, Ex.105 applied by the post-emergence method showed very good herbicidal activity against APESV, and ECHCG, and applied by the pre-emergence method showed very good herbicidal activity against ALOMY, and ECHCG.

At an application rate of 2000 g/ha, Ex.106 applied by the post-emergence method showed very good herbicidal activity against ALOMY, AVEFA, and ECHCG, and applied by the pre-emergence method showed very good herbicidal activity against APESV, and ECHCG.

At an application rate of 500 g/ha, Ex.108 applied by the post-emergence method showed good herbicidal activity against ALOMY, and showed very good herbicidal activity against POLCO.

At an application rate of 1000 g/ha, Ex.110 applied by the post-emergence method showed good herbicidal activity against ECHCG.

At an application rate of 1000 g/ha, Ex. 112 applied by the post-emergence method showed good herbicidal activity against ECHCG.

At an application rate of 500 g/ha, Ex.1 14 applied by the post-emergence method showed very good herbicidal activity against SETVI.

At an application rate of 1000 g/ha, Ex.119 applied by the post-emergence method showed good herbicidal activity against SETVI, and showed very good herbicidal activity against ALOMY.

At an application rate of 1000 g/ha, Ex.120 applied by the post-emergence method showed good herbicidal activity against ALOMY.

At an application rate of 500 g/ha, Ex.121 applied by the post-emergence method showed very good herbicidal activity against LOLMU, ECHCG, POLCO and ALOMY.

At an application rate of 2000 g/ha, Ex.123 applied by the post-emergence method showed good herbicidal activity against SETVI, and very good herbicidal activity against AMARE.

At an application rate of 500 g/ha, Ex.125 applied by the post-emergence method showed very good herbicidal activity against ECHCG.

At an application rate of 2000 g/ha, Ex.126 applied by the post-emergence method showed very good herbicidal activity against ECHCG.

At an application rate of 2000 g/ha, Ex.127 applied by the post-emergence method showed very good herbicidal activity against AMARE.

At an application rate of 2000 g/ha, Ex.128 applied by the post-emergence method showed very good herbicidal activity against AVEFA, and ECHCG, and good herbicidal activity against ALOMY, and applied by the pre-emergence method showed very good herbicidal activity against APESV.

At an application rate of 2000 g/ha, Ex.129 applied by the post-emergence method showed very good herbicidal activity against AMARE, ALOMY, and ECHCG, and applied by the pre-emergence method showed very good herbicidal activity against APESV.

At an application rate of 2000 g/ha, Ex.131 applied by the post-emergence method showed very good herbicidal activity against AMARE, and ECHCG.

At an application rate of 2000 g/ha, Ex.132 applied by the post-emergence method showed very good herbicidal activity against ECHCG, and good herbicidal activity against AMARE.

At an application rate of 500 g/ha, Ex.135 applied by the post-emergence method showed good herbicidal activity against ALOMY.

At an application rate of 1000 g/ha, Ex.141 applied by the post-emergence method showed good herbicidal activity against SETVI.

At an application rate of 2000 g/ha, Ex.143 applied by the post-emergence method showed very good herbicidal activity against ECHCG.

At an application rate of 2000 g/ha, Ex.146 applied by the post-emergence method showed very good herbicidal activity against ABUTH, SETVI and ECHCG, and applied by the pre-emergence method showed very good herbicidal activity against APESV, and ECHCG.

At an application rate of 2000 g/ha, Ex.147 applied by the post-emergence method showed very good herbicidal activity against ALOMY, AVEFA, and ECHCG, and applied by the pre-emergence method showed very good herbicidal activity against APESV, and ECHCG.

At an application rate of 2000 g/ha, Ex.150 applied by the post-emergence method showed very good herbicidal activity against AMARE and ECHCG, and good herbicidal activity against ALOMY, and applied by the pre-emergence method showed very good herbicidal activity against APESV, and good herbicidal activity against ECHCG.

At an application rate of 2000 g/ha, Ex.153 applied by the post-emergence method showed very good herbicidal activity against ALOMY, AVEFA, and ECHCG, and applied by the pre-emergence method showed very good herbicidal activity against APESV, and ECHCG.

At an application rate of 2000 g/ha, Ex.154 applied by the post-emergence method showed very good herbicidal activity against ALOMY, AVEFA, and ECHCG, and applied by the pre-emergence method showed very good herbicidal activity against APESV, and ECHCG.

At an application rate of 2000 g/ha, Ex.155 applied by the post-emergence method showed very good herbicidal activity against ALOMY, and ECHCG.

At an application rate of 2000 g/ha, Ex.157 applied by the post-emergence method showed very good herbicidal activity against ALOMY, AVEFA and ECHCG, and applied by the pre-emergence method showed very good herbicidal activity against APESV, and ECHCG.

At an application rate of 2000 g/ha, Ex.159 applied by the post-emergence method showed very good herbicidal activity against ALOMY and AVEFA, and applied by the pre-emergence method showed good herbicidal activity against APESV, and ECHCG.

At an application rate of 2000 g/ha, Ex.164 applied by the post-emergence method showed very good herbicidal activity against AMARE.

At an application rate of 2000 g/ha, Ex.211 applied by the post-emergence method showed good herbicidal activity against ALOMY and very good herbicidal activity against ECHCG, and applied by the pre-emergence method showed good herbicidal activity against APESV, and POAAN.

At an application rate of 2000 g/ha, Ex.213 applied by the post-emergence method showed very good herbicidal activity against ALOMY, AFEFA and ECHCG, and applied by the pre-emergence method showed good herbicidal activity against APESV, ECHCG and POAAN.

At an application rate of 2000 g/ha, Ex.214 applied by the post-emergence method showed very good herbicidal activity against ALOMY, AMARE and ECHCG, and applied by the pre-emergence method showed good herbicidal activity against APESV and ECHCG, and good herbicidal activity against POAAN.

At an application rate of 2000 g/ha, Ex.215 applied by the post-emergence method showed very good herbicidal activity against ALOMY and applied by the pre-emergence method showed very good herbicidal activity against APESV.

At an application rate of 1000 g/ha, Ex.216 applied by the post-emergence method showed very good herbicidal activity against ALOMY and ECHCG, and applied by the pre-emergence method showed very good herbicidal activity against APESV.

At an application rate of 1000 g/ha, Ex.219 applied by the post-emergence method showed good herbicidal activity against SETVI.

At an application rate of 1000 g/ha, Ex.220 applied by the pre-emergence method showed good herbicidal activity against ECHCG.

At an application rate of 2000 g/ha, Ex.221 applied by the post-emergence method showed very good herbicidal activity against ABUTH, AGSST and ECHCG, and applied by the pre-emergence method showed very good herbicidal activity against APESV, ECHCG and POAAN.

At an application rate of 2000 g/ha, Ex.222 applied by the post-emergence method showed very good herbicidal activity against ABUTH, AMARE and MATIN.

At an application rate of 2000 g/ha, Ex.223 applied by the post-emergence method showed very good herbicidal activity against ABUTH, AMARE and ECHCG, and applied by the pre-emergence method showed very good herbicidal activity against APESV, ECHCG and POAAN.

At an application rate of 2000 g/ha, Ex.224 applied by the post-emergence method showed very good herbicidal activity against ALOMY and ECHCG, and applied by the pre-emergence method showed very good herbicidal activity against APESV and ECHCG.

At an application rate of 2000 g/ha, Ex.225 applied by the post-emergence method showed very good herbicidal activity against ALOMY, AVEFA and ECHCG, and applied by the pre-emergence method showed very good herbicidal activity against APESV, ECHCG and POAAN.

At an application rate of 500 g/ha, Ex.226 applied by the post-emergence method showed very good herbicidal activity against AMARE.

At an application rate of 1000 g/ha, Ex.228 applied by the post-emergence method showed good herbicidal activity against ABUTH and ECHCG, and applied by the pre-emergence method showed very good herbicidal activity against APESV.

At an application rate of 1000 g/ha, Ex.229 applied by the pre-emergence method showed very good herbicidal activity against APESV and good herbicidal activity against AMARE.

At an application rate of 2000 g/ha, Ex.230 applied by the post-emergence method showed good herbicidal activity against MATIN.

At an application rate of 2000 g/ha, Ex.231 applied by the post-emergence method showed very good herbicidal activity against ECHCG and good herbicidal activity against MATIN.

At an application rate of 2000 g/ha, Ex.232 applied by the post-emergence method showed very good herbicidal activity against AMARE.

At an application rate of 2000 g/ha, Ex.233 applied by the pre-emergence method showed very good herbicidal activity against AMARE.

At an application rate of 2000 g/ha, Ex.234 applied by the post-emergence method showed good herbicidal activity against POAAN, and applied by the pre-emergence method showed very good herbicidal activity against APESV.

At an application rate of 2000 g/ha, Ex.236 applied by the post-emergence method showed very good herbicidal activity against ALOMY, AVEFA and ECHCG, and applied by the pre-emergence method showed very good herbicidal activity against APESV and ECHCG.

At an application rate of 2000 g/ha, Ex.237 applied by the post-emergence method showed very good herbicidal activity against ALOMY, AVEFA and ECHCG, and applied by the pre-emergence method showed very good herbicidal activity against APESV and ECHCG.

At an application rate of 2000 g/ha, Ex.238 applied by the post-emergence method showed good herbicidal activity against ALOMY, and very good herbicidal activity against ALOMY, AMARE and ECHCG.

At an application rate of 2000 g/ha, Ex.240 applied by the pre-emergence method showed very good herbicidal activity against APESV and ECHCG.

At an application rate of 2000 g/ha, Ex.241 applied by the post-emergence method showed good herbicidal activity against ECHCG, and applied by the pre-emergence method showed very good herbicidal activity against APESV and POAAN.

At an application rate of 1000 g/ha, Ex.243 applied by the post-emergence method showed very good herbicidal activity against ALOMY, AVEFA and ECHCG, and applied by the pre-emergence method showed very good herbicidal activity against APESV and ECHCG.

At an application rate of 500 g/ha, Ex.244 applied by the post-emergence method showed good herbicidal activity against ALOMY, POAAN, and POLCO, and applied by the pre-emergence method showed very good herbicidal activity against APESV, ECHCG and POAAN.

At an application rate of 1000 g/ha, Ex.245 applied by the post-emergence method showed very good herbicidal activity against ALOMY, AVEFA and ECHCG, and applied by the pre-emergence method showed very good herbicidal activity against APESV and good herbicidal activity against ECHCG.

At an application rate of 500 g/ha, Ex.246 applied by the pre-emergence method showed very good herbicidal activity against AMARE.

At an application rate of 500 g/ha, Ex.247 applied by the post-emergence method showed very good herbicidal activity against ALOMY, AGSST, and AMARE, and applied by the pre-emergence method showed very good herbicidal activity against APESV, ECHCG and POAAN.

At an application rate of 2000 g/ha, Ex.248 applied by the post-emergence method showed very good herbicidal activity against ALOMY, ECHCG, and SETVI, and applied by the pre-emergence method showed very good herbicidal activity against APESV, ECHCG and POAAN.

At an application rate of 2000 g/ha, Ex.250 applied by the post-emergence method showed very good herbicidal activity against ALOMY, AVEFA and ECHCG, and applied by the pre-emergence method showed very good herbicidal activity against APESV and ECHCG.

At an application rate of 500 g/ha, Ex.251 applied by the pre-emergence method showed very good herbicidal activity against AMARE.

At an application rate of 1000 g/ha, Ex.252 applied by the post-emergence method showed very good herbicidal activity against ABUTH.

At an application rate of 1000 g/ha, Ex.253 applied by the post-emergence method showed very good herbicidal activity against ALOMY and AMARE, and good herbicidal activity against ABUTH.

At an application rate of 1000 g/ha, Ex.254 applied by the post-emergence method showed very good herbicidal activity against ECHCG and AMARE, and good herbicidal activity against ALOMY.

At an application rate of 500 g/ha, Ex.255 applied by the post-emergence method showed good herbicidal activity against AMARE.

At an application rate of 2000 g/ha, Ex.256 applied by the post-emergence method showed very good herbicidal activity against ECHCG, and applied by the pre-emergence method showed very good herbicidal activity against APESV and ECHCG.

At an application rate of 2000 g/ha, Ex.257 applied by the post-emergence method showed good herbicidal activity against MATIN.

At an application rate of 2000 g/ha, Ex.259 applied by the post-emergence method showed very good herbicidal activity against ALOMY, POAAN and ECHCG, and applied by the pre-emergence method showed good herbicidal activity against APESV and ECHCG.

At an application rate of 2000 g/ha, Ex.260 applied by the post-emergence method showed very good herbicidal activity against ALOMY, and good herbicidal activity against AVEFA and ECHCG, and applied by the pre-emergence method showed very good herbicidal activity against ECHCG and MATIN, and good herbicidal activity against APESV.

At an application rate of 1000 g/ha, Ex.261 applied by the post-emergence method showed very good herbicidal activity against ALOMY, AVEFA and ECHCG, and applied by the pre-emergence method showed very good herbicidal activity against APESV and ECHCG.

At an application rate of 1000 g/ha, Ex.262 applied by the post-emergence method showed very good herbicidal activity against AMARE, SETVI and ECHCG, and applied by the pre-emergence method showed very good herbicidal activity against APESV and ECHCG.

At an application rate of 1000 g/ha, Ex.263 applied by the post-emergence method showed very good herbicidal activity against ALOMY, AVEFA and ECHCG, and applied by the pre-emergence method showed very good herbicidal activity against APESV and ECHCG.

At an application rate of 500 g/ha, Ex.264 applied by the post-emergence method showed very good herbicidal activity against ALOMY and AVEFA.

At an application rate of 250 g/ha, Ex.265 applied by the post-emergence method showed good herbicidal activity against ALOMY and CHEAL, and very good herbicidal activity against AMARE.

At an application rate of 1000 g/ha, Ex.266 applied by the post-emergence method showed very good herbicidal activity against ALOMY, AMARE and ABUTH, and applied by the pre-emergence method showed very good herbicidal activity against APESV and ECHCG.

At an application rate of 2000 g/ha, Ex.267 applied by the post-emergence method showed very good herbicidal activity against ECHCG, POAAN and ABUTH, and applied by the pre-emergence method showed very good herbicidal activity against POAAN and ECHCG.

At an application rate of 1000 g/ha, Ex.268 applied by the post-emergence method showed very good herbicidal activity against ECHCG, and applied by the pre-emergence method showed very good herbicidal activity against POAAN and ECHCG.

At an application rate of 1000 g/ha, Ex.269 applied by the post-emergence method showed very good herbicidal activity against ECHCG, and applied by the pre-emergence method showed very good herbicidal activity against SETFA.

At an application rate of 1000 g/ha, Ex.270 applied by the post-emergence method showed very good herbicidal activity against ALOMY and ECHCG, and applied by the pre-emergence method showed very good herbicidal activity against APESV and ECHCG.

At an application rate of 1000 g/ha, Ex.271 applied by the post-emergence method showed good herbicidal activity against ECHCG, very good herbicidal activity against SETVI.

At an application rate of 2000 g/ha, Ex.272 applied by the post-emergence method showed very good herbicidal activity against ALOMY, AVEFA and SETVI, and applied by the pre-emergence method showed very good herbicidal activity against APESV and ECHCG.

At an application rate of 1000 g/ha, Ex.273 applied by the post-emergence method showed very good herbicidal activity against ALOMY, AMARE and SETVI, and applied by the pre-emergence method showed very good herbicidal activity against APESV and ECHCG.

At an application rate of 1000 g/ha, Ex.274 applied by the post-emergence method showed very good herbicidal activity against ALOMY and ECHCG, and applied by the pre-emergence method showed very good herbicidal activity against APESV and ECHCG.

At an application rate of 1000 g/ha, Ex.276 applied by the post-emergence method showed very good herbicidal activity against ALOMY, AMARE and ABUTH, and applied by the pre-emergence method showed very good herbicidal activity against APESV.

At an application rate of 1000 g/ha, Ex.277 applied by the post-emergence method showed very good herbicidal activity against ALOMY, SETVI and ECHCG, and applied by the pre-emergence method showed very good herbicidal activity against APESV and ECHCG.

At an application rate of 1000 g/ha, Ex.278 applied by the post-emergence method showed very good herbicidal activity against AMARE, ABUTH and ECHCG, and applied by the pre-emergence method showed very good herbicidal activity against APESV and ECHCG.

At an application rate of 1000 g/ha, Ex.279 applied by the post-emergence method showed very good herbicidal activity against AMARE, ABUTH and ALOMY, and applied by the pre-emergence method showed very good herbicidal activity against APESV and ECHCG.

At an application rate of 2000 g/ha, Ex.281 applied by the post-emergence method showed good herbicidal activity against AMARE, ABUTH and ALOMY, and very good herbicidal activity against ABUTH.

At an application rate of 2000 g/ha, Ex.282 applied by the post-emergence method showed very good herbicidal activity against ALOMY, AVEFA and SETVI, and applied by the pre-emergence method showed very good herbicidal activity against APESV and ECHCG.

At an application rate of 2000 g/ha, Ex.283 applied by the post-emergence method showed very good herbicidal activity against ALOMY, AVEFA and ECHCG, and applied by the pre-emergence method showed very good herbicidal activity against APESV and good herbicidal activity against ECHCG.

At an application rate of 2000 g/ha, Ex.284 applied by the post-emergence method showed very good herbicidal activity against ALOMY, AVEFA and ECHCG, and applied by the pre-emergence method showed very good herbicidal activity against APESV and ECHCG.

At an application rate of 1000 g/ha, Ex.285 applied by the post-emergence method showed very good herbicidal activity against ALOMY, AMARE and ABUTH, and applied by the pre-emergence method showed very good herbicidal activity against APESV and ECHCG.

At an application rate of 1000 g/ha, Ex.286 applied by the post-emergence method showed very good herbicidal activity against ECHCG, AMARE and ABUTH, and applied by the pre-emergence method showed very good herbicidal activity against AMARE, APESV and ECHCG.

At an application rate of 1000 g/ha, Ex.287 applied by the post-emergence method showed very good herbicidal activity against ALOMY, AVEFA and ECHCG, and applied by the pre-emergence method showed very good herbicidal activity against APESV and ECHCG.

At an application rate of 2000 g/ha, Ex.288 applied by the post-emergence method showed very good herbicidal activity against ALOMY.

At an application rate of 2000 g/ha, Ex.289 applied by the post-emergence method showed very good herbicidal activity against ALOMY, AMARE and SETVI, and applied by the pre-emergence method showed very good herbicidal activity against APESV and ECHCG.

At an application rate of 2000 g/ha, Ex.290 applied by the post-emergence method showed very good herbicidal activity against ALOMY, AVEFA and ECHCG, and applied by the pre-emergence method showed very good herbicidal activity against APESV and ECHCG.

At an application rate of 500 g/ha, Ex.291 applied by the post-emergence method showed good herbicidal activity against ALOMY, AVEFA and LOLMU, and applied by the pre-emergence method showed very good herbicidal activity against POAAN, APESV and ECHCG.

At an application rate of 1000 g/ha, Ex.292 applied by the post-emergence method showed very good herbicidal activity against ECHCG and SETVI, and good herbicidal activity against ALOMY, and applied by the pre-emergence method showed very good herbicidal activity against APESV and ECHCG.

At an application rate of 1000 g/ha, Ex.293 applied by the post-emergence method showed good herbicidal activity against ABUTH, and applied by the pre-emergence method showed very good herbicidal activity against SETFA, and good herbicidal activity against ECHCG.

At an application rate of 2000 g/ha, Ex.294 applied by the post-emergence method showed very good herbicidal activity against ALOMY, ABUTH and ECHCG, and applied by the pre-emergence method showed good herbicidal activity against APESV.

At an application rate of 2000 g/ha, Ex.295 applied by the post-emergence method showed very good herbicidal activity against ALOMY and AVEFA, and applied by the pre-emergence method showed very good herbicidal activity against APESV, AMARE and ECHCG.

At an application rate of 1000 g/ha, Ex.296 applied by the post-emergence method showed very good herbicidal activity against ABUTH.

At an application rate of 2000 g/ha, Ex.297 applied by the post-emergence method showed very good herbicidal activity against ALOMY, ECHCG and AVEFA, and applied by the pre-emergence method showed very good herbicidal activity against APESV, and good herbicidal activity against ECHCG and ABUTH.

At an application rate of 1000 g/ha, Ex.309 applied by the post-emergence method showed very good herbicidal activity against ALOMY, ECHCG and AMARE, and very good herbicidal activity against APESV.

At an application rate of 500 g/ha, Ex.310 applied by the post-emergence method showed very good herbicidal activity against ALOMY, AMARE and POLCO, and very good herbicidal activity against ALOMY, ECHCG and APESV.

At an application rate of 500 g/ha, Ex.311 applied by the post-emergence method showed very good herbicidal activity against ALOMY, AMARE and POLCO, and very good herbicidal activity against ALOMY, ECHCG and APESV.

At an application rate of 500 g/ha, Ex.312 applied by the post-emergence method showed very good herbicidal activity against ALOMY, ECHCG and POLCO, and very good herbicidal activity against ALOMY, ECHCG and APESV.

At an application rate of 1000 g/ha, Ex.313 applied by the post-emergence method showed very good herbicidal activity against ALOMY, ECHCG and SETVI, and very good herbicidal activity against ECHCG and APESV.

At an application rate of 1000 g/ha, Ex.314 applied by the post-emergence method showed very good herbicidal activity against AMARE, ECHCG and SETVI, and very good herbicidal activity against ECHCG and APESV.

At an application rate of 2000 g/ha, Ex.315 applied by the post-emergence method showed very good herbicidal activity against AMARE, ECHCG and ALOMY, and very good herbicidal activity against ECHCG and APESV.

The invention claimed is:
1. The pyrimidine compound of formula (I),

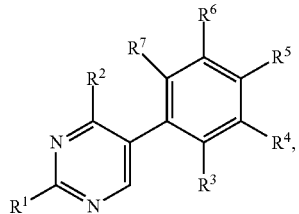

wherein
$R^1$ is $C_1$-$C_6$-alkyl, $C_1$-$C_6$-haloalkyl, HO—$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, or 3- to 6-membered heterocyclyl;
wherein the cyclic groups of $R^1$ are unsubstituted or substituted by $R^a$;
$R^a$ is halogen, CN, $NO_2$, $C_1$-$C_6$-alkyl, $C_1$-$C_6$-haloalkyl, $C_1$-$C_6$-alkoxy, or $C_1$-$C_6$-haloalkoxy;
$R^2$ is $C_1$-$C_6$-alkyl, $C_1$-$C_6$-haloalkyl, $C_2$-$C_6$-alkenyl, $C_2$-$C_6$-haloalkenyl, $C_1$-$C_6$-alkoxy-$C_2$-$C_6$-alkenyl, $C_1$-$C_6$-alkoxy-$C_2$-$C_6$-haloalkenyl, $C_1$-$C_6$-haloalkoxy-$C_2$-$C_6$-alkenyl, $C_1$-$C_6$-haloalkoxy-$C_2$-$C_6$-haloalkenyl, $C_2$-$C_6$-alkynyl, $C_2$-$C_6$-haloalkynyl, $C_1$-$C_6$-alkoxy-$C_2$-$C_6$-alkynyl, $C_1$-$C_6$-alkoxy-$C_3$-$C_6$-haloalkynyl, $C_1$-$C_6$-haloalkoxy-$C_2$-$C_6$-alkynyl, $C_1$-$C_6$-haloalkoxy-$C_3$-$C_6$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-halocycloalkyl-$C_1$-$C_6$-alkyl, $C_3$-$C_6$-halocycloalkyl-$C_1$-$C_6$-haloalkyl, $C_3$-$C_6$-cycloalkenyl-$C_1$-$C_6$-alkyl, $C_3$-$C_6$-cycloalkenyl-$C_1$-$C_6$-haloalkyl, $C_3$-$C_6$-halocycloalkenyl-$C_1$-$C_6$-alkyl, $C_3$-$C_6$-halocycloalkenyl-$C_1$-$C_6$-haloalkyl, $C_3$-$C_6$-cycloalkyl-$C_2$-$C_6$-alkenyl, $C_3$-$C_6$-cycloalkyl-$C_2$-$C_6$-haloalkenyl, $C_3$-$C_6$-halocycloalkyl-$C_2$-$C_6$-alkenyl, $C_3$-$C_6$-halocycloalkyl-$C_2$-$C_6$-haloalkenyl, $C_3$-$C_6$-cycloalkenyl-$C_2$-$C_6$-alkenyl, $C_3$-$C_6$-cycloalkenyl-$C_2$-$C_6$-haloalkenyl, $C_3$-$C_6$-halocycloalkenyl-$C_2$-$C_6$-alkenyl, $C_3$-$C_6$-halocycloalkenyl-$C_2$-$C_6$-haloalkenyl, $C_3$-$C_6$-cycloalkyl-$C_2$-$C_6$-alkynyl, $C_3$-$C_6$-cycloalkyl-$C_3$-$C_6$-haloalkynyl, $C_3$-$C_6$-halocycloalkyl-$C_2$-$C_6$-alkynyl, $C_3$-$C_6$-halocycloalkyl-$C_3$-$C_6$-haloalkynyl, $C_3$-$C_6$-cycloalkenyl-$C_2$-$C_6$-alkynyl, $C_3$-$C_6$-cycloalkenyl-$C_3$-$C_6$-haloalkynyl, $C_3$-$C_6$-halocycloalkenyl-$C_2$-$C_6$-alkynyl, $C_3$-$C_6$-halocycloalkenyl-$C_3$-$C_6$-haloalkynyl, $C_3$-$C_6$-cycloalkyl-$C_1$-$C_6$-alkylidenyl, $C_3$-$C_6$-cycloalkyl-$C_2$-$C_6$-haloalkylidenyl, $C_3$-$C_6$-halocycloalkyl-$C_1$-$C_6$-alkylidenyl, $C_3$-$C_6$-halocycloalkyl-$C_2$-$C_6$-haloalkylidenyl, $C_3$-$C_6$-cycloalkenyl-$C_1$-$C_6$-alkylidenyl, $C_3$-$C_6$-cycloalkenyl-$C_2$-$C_6$-haloalkylidenyl, $C_3$-$C_6$-halocycloalkenyl-$C_1$-$C_6$-alkylidenyl, $C_3$-$C_6$-halocycloalkenyl-$C_2$-$C_6$-haloalkylidenyl, heterocyclyl-$C_1$-$C_6$-alkylidenyl, heterocyclyl-$C_1$-$C_6$-haloalkylidenyl, $C_3$-$C_6$-hydroxycycloalkyl-$C_1$-$C_6$-alkyl, $C_3$-$C_6$-hydroxycycloalkyl-$C_1$-$C_6$-haloalkyl, $C_3$-$C_6$-hydroxycycloalkenyl-$C_1$-$C_6$-alkyl, $C_3$-$C_6$-hydroxycycloalkenyl-$C_1$-$C_6$-haloalkyl, $C_1$-$C_6$-hydroxyalkyl, $C_2$-$C_6$-hydroxyhaloalkyl, $C_3$-$C_6$-hydroxyalkenyl, $C_3$-$C_6$-hydroxyhaloalkenyl, $C_3$-$C_6$-hydroxyalkynyl, $C_4$-$C_6$-hydroxyhaloalkynyl, $C_3$-$C_6$-hydroxycycloalkyl, $C_3$-$C_6$-hydroxyhalocycloalkyl, $C_3$-$C_6$-hydroxycycloalkenyl, $C_3$-$C_6$-hydroxyhalocycloalkenyl, $C_3$-$C_6$-cycloalkyl-$C_1$-$C_6$-hydroxyalkyl, $C_3$-$C_6$-cycloalkyl-$C_2$-$C_6$-hydroxyhaloalkyl, $C_3$-$C_6$-halocycloalkyl-$C_1$-$C_6$-hydroxyalkyl, $C_3$-$C_6$-halocycloalkyl-$C_2$-$C_6$-hydroxyhaloalkyl, $C_3$-$C_6$-cycloalkenyl-$C_1$-$C_6$-hydroxyalkyl, $C_3$-$C_6$-cycloalkenyl-$C_2$-$C_6$-hydroxyhaloalkyl, $C_3$-$C_6$-halocycloalkenyl-$C_1$-$C_6$-hydroxyalkyl$C_3$-$C_6$-halocycloalkenyl-$C_2$-$C_6$-hydroxyhaloalkyl, $C_3$-$C_6$-cycloalkyl-$C_3$-$C_6$-hydroxyalkenyl, $C_3$-$C_6$-cycloalkyl-$C_3$-$C_6$-hydroxyhaloalkenyl, $C_3$-$C_6$-halocycloalkyl-$C_3$-$C_6$-hydroxyalkenyl, $C_3$-$C_6$-halocycloalkyl-$C_3$-$C_6$-hydroxyhaloalkenyl, $C_3$-$C_6$-cycloalkyl-$C_3$-$C_6$-hydroxyalkenyl, $C_3$-$C_6$-cycloalkyl-$C_3$-$C_6$-hydroxyhaloalkenyl, $C_3$-$C_6$-halocycloalkenyl-$C_3$-$C_6$-hydroxyalkenyl, $C_3$-$C_6$-halocycloalkenyl-$C_3$-$C_6$-hydroxyhaloalkenyl, $C_3$-$C_6$-cycloalkyl-$C_3$-$C_6$-hydroxyalkynyl, $C_3$-$C_6$-halocycloalkyl-$C_3$-$C_6$-hydroxyalkynyl, $C_3$-$C_6$-cycloalkenyl-$C_3$-$C_6$-hydroxyalkynyl, $C_3$-$C_6$-halocycloalkyl-$C_3$-$C_6$-hydroxyalkynyl, $C_3$-$C_6$-cycloalkyl-$C_2$-$C_6$-hydroxyalkylidenyl, $C_3$-$C_6$-halocycloalkyl-$C_2$-$C_6$-hydroxyalkylidenyl, $C_3$-$C_6$-cycloalkenyl-$C_2$-$C_6$-hydroxyalkylidenyl, $C_3$-$C_6$-halocycloalkenyl-$C_2$-$C_6$-hydroxyalkylidenyl, heterocyclyl-$C_2$-$C_6$-hydroxyalkylidenyl, hydroxy-carbonyl-$C_1$-$C_6$-hydroxyalkyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-hydroxyalkyl, $C_1$-$C_6$-haloalkoxycarbonyl-$C_1$-$C_6$-hydroxyalkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-hydroxycycloalkyl-$C_1$-$C_6$-hydroxyalkyl, $C_3$-$C_6$-hydroxycycloalkenyl-$C_1$-$C_6$-hydroxyalkyl, $C_3$-$C_6$-hydroxycycloalkyl-$C_3$-$C_6$-hydroxyalkenyl, $C_3$-$C_6$-hydroxycycloalkenyl-$C_3$-$C_6$-hydroxyalkenyl, $C_3$-$C_6$-hydroxycycloalkyl-$C_3$-$C_6$-hydroxyalkynyl, $C_3$-$C_6$-hydroxycycloalkenyl-$C_3$-$C_6$-hydroxyalkenyl, $C_2$-$C_6$-dihydroxyalkyl, $C_3$-$C_6$-dihydroxyhaloalkyl, $C_4$-$C_6$-dihydroxyalkenyl, $C_4$-$C_6$-dihydroxyhaloalkenyl, $C_4$-$C_6$-dihydroxyalkynyl, $C_5$-$C_6$-dihydroxyhaloalkynyl, $C_4$-$C_6$-dihydroxycycloalkyl, $C_4$-$C_6$-dihydroxyhalocycloalkyl, $C_4$-$C_6$-dihydroxycycloalkenyl, $C_4$-$C_6$-dihydroxyhalocycloalkenyl, $C_3$-$C_6$-cycloalkyl-$C_2$-$C_6$-dihydroxyalkyl, $C_3$-$C_6$-halocycloalkyl-$C_2$-$C_6$-dihydroxyalkyl, $C_3$-$C_6$-cycloalkenyl-$C_2$-$C_6$-dihydroxyalkyl, $C_3$-$C_6$-halocycloalkenyl-$C_2$-$C_6$-dihydroxyalkyl, $C_3$-$C_6$-cycloalkyl-$C_3$-$C_6$-dihydroxyalkenyl, $C_3$-$C_6$-halocycloalkyl-$C_3$-$C_6$-dihydroxyalkenyl, $C_3$-$C_6$-cycloalkenyl-$C_3$-$C_6$-dihydroxyalkenyl, $C_3$-$C_6$-halocycloalkenyl-$C_3$-$C_6$-dihydroxyalkenyl, $C_3$-$C_6$-cycloalkyl-$C_4$-$C_6$-dihydroxyalkynyl, $C_3$-$C_6$-halocycloalkyl-$C_4$-$C_6$-dihydroxyalkynyl, $C_3$-$C_6$-cycloalkyl-$C_4$-$C_6$-dihydroxyalkynyl, $C_3$-$C_6$-halocycloalkyl-$C_4$-$C_6$-dihydroxyalkynyl, $C_3$-$C_6$-cycloalkyl-$C_3$-$C_6$-dihydroxyalkylidenyl, $C_3$-$C_6$-halocycloalkyl-$C_3$-$C_6$-dihydroxyalkylidenyl, heterocyclyl-$C_3$-$C_6$-dihydroxyalkyl, hydroxycarbonyl-$C_2$-$C_6$-dihydroxyhaloalkyl, hydroxycarbonyl-$C_3$-$C_6$-dihydroxyalkyl, $C_1$-$C_6$-alkoxycarbonyl-$C_2$-$C_6$-dihydroxyalkyl, $C_1$-$C_6$-haloalkoxycarbonyl-$C_2$-$C_6$-dihydroxyalkyl, $C_1$-$C_6$-haloalkoxycarbonyl-$C_2$-$C_6$-dihydroxyhaloalkyl, $C_3$-$C_6$-dihydroxycycloalkyl-$C_1$-$C_6$-alkyl, $C_3$-$C_6$-dihydroxycycloalkyl-$C_1$-$C_6$-haloalkyl, $C_3$-$C_6$-dihydroxycycloalkyl-$C_2$-$C_6$-alkenyl, $C_3$-$C_6$-dihydroxycycloalkyl-$C_2$-$C_6$-haloalkenyl, $C_3$-$C_6$-dihydroxycycloalkyl-$C_2$-$C_6$-alkynyl, $C_3$-$C_6$-dihydroxycycloalkyl-$C_3$-$C_6$-haloalkynyl, $C_1$-$C_6$-alkylcarbonyl-$C_1$-$C_6$-alkyl, $C_1$-$C_6$-haloalkylcarbonyl-$C_1$-$C_6$-alkyl, $C_1$-$C_6$-alkylcarbonyl-$C_1$-$C_6$-haloalkyl, $C_1$-$C_6$-haloalkylcarbonyl-$C_1$-$C_6$-haloalkyl, hydroxycarbonyl-$C_2$-$C_6$-alkenyl, hydroxycarbonyl-$C_2$-$C_6$-haloalkenyl, $C_1$-$C_6$-alkoxycarbonyl-$C_2$-$C_6$-alkenyl, $C_1$-$C_6$-haloalkoxycarbonyl-$C_2$-$C_6$-alkenyl, $C_1$-$C_6$-alkoxycarbonyl-$C_2$-$C_6$-haloalkenyl, $C_1$-$C_6$-haloalkoxycarbonyl-$C_2$-$C_6$-haloalkenyl, hydroxycarbonyl-$C_2$-$C_6$-alkynyl, hydroxycarbonyl-$C_3$-$C_6$-haloalkynyl, $C_1$-$C_6$-alkoxycarbonyl-$C_2$-$C_6$-alkynyl, $C_1$-$C_6$-haloalkoxycarbonyl-$C_2$-$C_6$-alkynyl, $C_1$-$C_6$-alkoxycarbonyl-$C_3$-$C_6$-halo-alkynyl, $C_1$-$C_6$-haloalkoxycarbonyl-$C_3$-$C_6$-haloalkynyl, $C_1$-$C_6$-cyanoalkyl, $C_2$-$C_6$-cyanohaloalkyl, $C_1$-$C_6$-dicyanoalkyl, $C_2$-$C_6$-dicyanohaloalkyl, di(hydroxycarbonyl)-$C_1$-$C_6$-alkyl, di(hydroxycarbonyl)-$C_1$-$C_6$-haloalkyl, di($C_1$-$C_6$-alkoxycarbonyl)-$C_1$-$C_6$-alkyl, di($C_1$-$C_6$-haloalkoxycarbonyl)-$C_1$-$C_6$-alkyl, di($C_1$-$C_6$-alkoxycarbonyl)-$C_1$-$C_6$-haloalkyl, di($C_1$-$C_6$-haloalkoxycarbonyl)-$C_1$-$C_6$-haloalkyl, di($C_1$-$C_6$-alkoxyl)phosphoryl-$C_1$-$C_6$-alkyl, di($C_1$-$C_6$-haloalkoxyl)phosphoryl-$C_1$-$C_6$-alkyl, di($C_1$-$C_6$-alkoxyl)phosphoryl-$C_1$-$C_6$-haloalkyl, di($C_1$-$C_6$-haloalkoxyl)phosphoryl-$C_1$-$C_6$-haloalkyl, phosphoryl-$C_1$-$C_6$-alkyl, phosphoryl-$C_1$-$C_6$-haloalkyl, di[di($C_1$-$C_6$-alkoxyl)phosphoryl-)]$C_1$-$C_6$-alkyl, di[di($C_1$-$C_6$-haloalkoxyl)phosphoryl-)]$C_1$-$C_6$-alkyl, di[di($C_1$-$C_6$-alkoxyl)phosphoryl-)]$C_1$-$C_6$-haloalkyl, di[di($C_1$-$C_6$-haloalkoxyl)phosphoryl-)]$C_1$-$C_6$-haloalkyl, diphosphoryl-$C_1$-$C_6$-alkyl, diphosphoryl-$C_1$-$C_6$-haloalkyl, $C_1$-$C_6$-alkylthio-$C_1$-$C_6$-alkyl, $C_1$-$C_6$-haloalkylthio-$C_1$-$C_6$-alkyl, $C_1$-$C_6$-alkylthio-$C_1$-$C_6$-haloalkyl, $C_1$-$C_6$-haloalkylthio-$C_1$-$C_6$-haloalkyl, $C_1$-$C_6$-alkylsulfinly-$C_1$-$C_6$-alkyl, $C_1$-$C_6$-haloalkylsulfinly-$C_1$-$C_6$-alkyl, $C_1$-$C_6$-alkylsulfinly-$C_1$-$C_6$-haloalkyl, $C_1$-$C_6$-haloalkylsulfinly-$C_1$-$C_6$-haloalkyl, $C_1$-$C_6$-alkylsulfonyl-$C_1$-$C_6$-alkyl, $C_1$-$C_6$-haloalkylsulfonyl-$C_1$-$C_6$-haloalkyl, phenyl, 5-, 6- or 9 membered heteroaryl, 3- to 6-membered heterocyclyl, ($C_1$-$C_6$-alkyl)carbonylaminocarbonyl, ($C_2$-$C_6$-alkenyl)carbonylamino-carbonyl, ($C_3$-$C_6$-alkynyl)carbonylaminocarbonyl, ($C_1$-$C_6$-haloalkyl)carbonylaminocarbonyl, ($C_2$-$C_6$-haloalkenyl)carbonylaminocarbonyl, ($C_3$-$C_6$-haloalkynyl)carbonylaminocarbonyl, phenylcarbonylaminocarbonyl, ($C_3$-$C_6$-cycloalkyl)carbonylaminocarbonyl, [($C_1$-$C_6$-alkyl)amino]carbonylaminocarbonyl, or [di($C_1$-$C_6$-alkyl)amino]carbonylaminocarbonyl, heterocyclylcarbonylaminocarbonyl, heteroarylcarbonylaminocarbonyl, phenylcarbonylaminocarbonyl;

wherein OH groups of $R^2$ are unsubstituted or substituted by $R^b$;

cyclic groups of $R^2$ are unsubstituted or substituted by $R^c$; and acyclic aliphatic groups of $R^2$ are unsubstituted or substituted by $R^d$;

$R^b$ is $C_1$-$C_6$-alkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;

wherein the substituent $R^d$ is unsubstituted or substituted by $R^e$;

$R^e$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfonyl;

$R^3$ is halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-halo-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cyclic groups of $R^3$ are unsubstituted or substituted by substituents $R^a$;

$R^4$, $R^5$, $R^6$ and $R^7$ independently of one another are H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cyclic groups of $R^4$ $R^5$, $R^6$ and $R^7$ are unsubstituted or substituted by $R^a$;

or an agriculturally acceptable salt, amide, ester, or thioester of the pyrimidine compound of formula (I);

with the exception of 5-(2-bromophenyl)-2-cyclopropyl-4-methyl-pyrimidine;

5-(2-bromophenyl)-2-ethyl-4- methyl-pyrimidine; and 5-(2-bromophenyl)-2-methoxy-4- methyl-pyrimidine.

2. The pyrimidine compound of formula (I) according to claim 1, wherein $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_4$-$C_6$-haloalkynyloxy, $C_1$-$C_6$-alkylthio, or $C_3$-$C_6$-cycloalkyl wherein cycloalkyl is unsubstituted.

3. The pyrimidine compound of formula (I) according to claim 1, wherein $R^2$ $C_2$-$C_6$-alkenyl, $C_2$-$C_6$-haloalkenyl, $C_1$-$C_6$-alkoxy-$C_2$-$C_6$-alkenyl, $C_2$-$C_6$-alkynyl, $C_3$-$C_6$-cycloalkenyl, $C_3$-$C_6$-cycloalkenyl-$C_1$-$C_6$-alkyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-cycloalkenyl-$C_1$-$C_6$-alkylidenyl, $C_3$-$C_6$-hydroxycycloalkyl-$C_1$-$C_6$-alkyl, $C_3$-$C_6$-hydroxycycloalkenyl-$C_1$-$C_6$-alkyl, $C_1$-$C_6$-hydroxyalkyl, $C_3$-$C_6$-cycloalkyl-$C_2$-$C_6$-hydroxyalkylidenyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-alkyl, $C_3$-$C_6$-hydroxycycloalkyl-$C_1$-$C_6$-hydroxyalkyl, $C_2$-$C_6$-dihydroxyalkyl, $C_3$-$C_6$-cycloalkyl-$C_3$-$C_6$-dihydroxyalkylidenyl, hydroxycarbonyl-$C_2$-$C_6$-dihydroxyalkyl, $C_1$-$C_6$-alkoxycarbonyl-$C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl;

wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$;

$R^b$ is $C_1$-$C_6$-alkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;

wherein the substituent $R^d$ is unsubstituted or substituted by $R^e$;

$R^e$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfonyl.

4. The pyrimidine compound of formula (I) according to claim 1, wherein $R^3$ is halogen, CN, $NO_2$, $C_1$-$C_6$-alkoxy, or $C_3$-$C_6$-cycloalkyl;

$R^4$ is H, halogen, CN, $C_1$-$C_6$-haloalkyl, or $C_1$-$C_6$-alkoxy;

$R^5$ is H, halogen, CN, $C_1$-$C_6$-haloalkyl, or $C_1$-$C_6$-alkoxy;

$R^6$ is H, halogen, $C_1$-$C_6$-alkyl, or $C_1$-$C_6$-haloalkyl;

$R^7$ is H, halogen, CN, $C_1$-$C_6$-alkyl, or $C_1$-$C_6$-alkoxy.

5. The pyrimidine compound of formula (I) according to claim 1, wherein $R^1$ is c-$C_3H_5$;

$R^2$ is $C_2$-$C_6$-alkenyl, $C_2$-$C_6$-haloalkenyl, $C_1$-$C_6$-alkoxy-$C_2$-$C_6$-alkenyl, $C_2$-$C_6$-alkynyl, $C_3$-$C_6$-cycloalkenyl, $C_3$-$C_6$-cycloalkenyl-$C_1$-$C_6$-alkyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-cycloalkenyl-$C_1$-$C_6$-alkylidenyl, $C_3$-$C_6$-hydroxycycloalkyl-$C_1$-$C_6$-alkyl, $C_3$-$C_6$-hydroxycycloalkenyl-$C_1$-$C_6$-alkyl, $C_1$-$C_6$-hydroxyalkyl, $C_3$-$C_6$-cycloalkyl-$C_2$-$C_6$-hydroxyalkylidenyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-alkyl, $C_3$-$C_6$-hydroxycycloalkyl-$C_1$-$C_6$-hydroxyalkyl, $C_2$-$C_6$-dihydroxyalkyl, $C_3$-$C_6$-cycloalkyl-$C_3$-$C_6$-dihydroxyalkylidenyl, hydroxycarbonyl-$C_2$-$C_6$-dihydroxyalkyl, $C_1$-$C_6$-alkoxycarbonyl-$C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl;

wherein OH groups of $R^2$ are unsubstituted or substituted by $R^b$,
cyclic groups of $R^2$ are unsubstituted or substituted by $R^c$, and
acyclic aliphatic groups of $R^2$ are unsubstituted or substituted by $R^d$;

$R^b$ is $C_1$-$C_6$-alkyl, $C_1$-$C_6$-haloalkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;
wherein the substituent $R^d$ is unsubstituted or substituted by $R^e$;

$R^e$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfonyl;
$R^3$ is Cl, Br, I, $CH_3$, $CF_3$, or $CF_2H$;
$R^4$ is H;
$R^5$ is H or F;
$R^6$ is H, F, $CF_3$, Cl, or Br;
$R^7$ is H or F.

6. The pyrimidine compound of formula (I) according to claim 1 which corresponds to formula I.K,

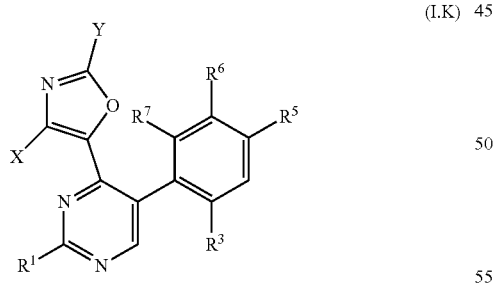

(I.K)

wherein
X and Y independently are selected from H, $CH_3$, $C_2H_5$, n-propyl, iso-propyl, iso-butyl,
n-butyl, 2-butyl, t-butyl, OH, $OCH_3$, $SCH_3$, $S(O)CH_3$, $S(O)_2CH_3$, CN, F, $C_1$, Br, I, $CH_2CF_3$, $CF_2CF_3$, $CF_2CH_3$, $CF_3$, $CF_2H$, $OCF_2H$, and $OCF_3$;
$R^1$ is c-$C_3H_5$;
$R^3$ is Cl, Br, I, $CH_3$, $CF_3$, or $CF_2H$;
$R^5$ is H or F;
$R^6$ is H, F, $CF_3$, Cl, or Br;
$R^7$ is H or F.

7. A herbicidal mixture comprising:
A) at least one compound of formula I, including agriculturally acceptable salts or derivatives of the pyrimidine compound of formula (I) having an acidic functionality,
one pyrimidine compound of formula (I),

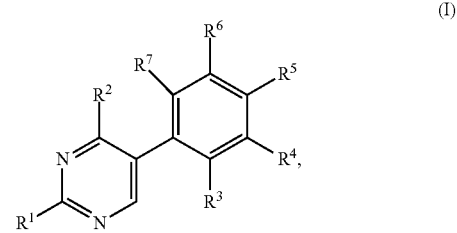

(I)

wherein:
$R^1$ is $C_1$-$C_6$-alkyl, $C_1$-$C_6$-haloalkyl, HO—$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, or 3- to 6-membered heterocyclyl;
wherein the cyclic groups of $R^1$ are unsubstituted or substituted by $R^a$;

$R^2$ is $C_1$-$C_6$-alkyl, $C_1$-$C_6$-haloalkyl, $C_2$-$C_6$-alkenyl, $C_2$-$C_6$-haloalkenyl, $C_1$-$C_6$-alkoxy-$C_2$-$C_6$-alkenyl, $C_1$-$C_6$-alkoxy-$C_2$-$C_6$-haloalkenyl, $C_1$-$C_6$-haloalkoxy-$C_2$-$C_6$-alkenyl, $C_1$-$C_6$-haloalkoxy-$C_2$-$C_6$-haloalkenyl, $C_2$-$C_6$-alkynyl, $C_2$-$C_6$-haloalkynyl, $C_1$-$C_6$-alkoxy-$C_2$-$C_6$-alkynyl, $C_1$-$C_6$-alkoxy-$C_3$-$C_6$-haloalkynyl, $C_1$-$C_6$-haloalkoxy-$C_2$-$C_6$-alkynyl, $C_1$-$C_6$-haloalkoxy-$C_3$-$C_6$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-halocycloalkyl-$C_1$-$C_6$-alkyl, $C_3$-$C_6$-halocycloalkyl-$C_1$-$C_6$-haloalkyl, $C_3$-$C_6$-cycloalkenyl-$C_1$-$C_6$-alkyl, $C_3$-$C_6$-cycloalkenyl-$C_1$-$C_6$-haloalkyl, $C_3$-$C_6$-halocycloalkenyl-$C_1$-$C_6$-alkyl, $C_3$-$C_6$-halocycloalkenyl-$C_1$-$C_6$-haloalkyl, $C_3$-$C_6$-cycloalkyl-$C_2$-$C_6$-alkenyl, $C_3$-$C_6$-cycloalkyl-$C_2$-$C_6$-haloalkenyl, $C_3$-$C_6$-halocycloalkyl-$C_2$-$C_6$-alkenyl, $C_3$-$C_6$-halocycloalkyl-$C_2$-$C_6$-haloalkenyl, $C_3$-$C_6$-cycloalkenyl-$C_2$-$C_6$-alkenyl, $C_3$-$C_6$-cycloalkenyl-$C_2$-$C_6$-haloalkenyl, $C_3$-$C_6$-halocycloalkenyl-$C_2$-$C_6$-alkenyl, $C_3$-$C_6$-halocycloalkenyl-$C_2$-$C_6$-haloalkenyl, $C_3$-$C_6$-cycloalkyl-$C_2$-$C_6$-alkynyl, $C_3$-$C_6$-cycloalkyl-$C_3$-$C_6$-haloalkynyl, $C_3$-$C_6$-halocycloalkyl-$C_2$-$C_6$-alkynyl, $C_3$-$C_6$-halocycloalkyl-$C_3$-$C_6$-haloalkynyl, $C_3$-$C_6$-cycloalkenyl-$C_2$-$C_6$-alkynyl, $C_3$-$C_6$-cycloalkenyl-$C_3$-$C_6$-haloalkynyl, $C_3$-$C_6$-halocycloalkenyl-$C_2$-$C_6$-alkynyl, $C_3$-$C_6$-halocycloalkenyl-$C_3$-$C_6$-haloalkynyl, $C_3$-$C_6$-cycloalkyl-$C_1$-$C_6$-alkylidenyl, $C_3$-$C_6$-cycloalkyl-$C_2$-$C_6$-haloalkylidenyl, $C_3$-$C_6$-halocycloalkyl-$C_1$-$C_6$-alkylidenyl, $C_3$-$C_6$-halocycloalkyl-$C_2$-$C_6$-haloalkylidenyl, $C_3$-$C_6$-cycloalkenyl-$C_1$-$C_6$-alkylidenyl, $C_3$-$C_6$-cycloalkenyl-$C_2$-$C_6$-haloalkylidenyl, $C_3$-$C_6$-halocycloalkenyl-$C_1$-$C_6$-alkylidenyl, $C_3$-$C_6$-halocycloalkenyl-$C_2$-$C_6$-haloalkylidenyl, heterocyclyl-$C_1$-$C_6$-alkylidenyl, heterocyclyl-$C_1$-$C_6$-haloalkylidenyl, $C_3$-$C_6$-hydroxycyclyl-$C_1$-$C_6$-alkyl, $C_3$-$C_6$-hydroxycycloalkyl-$C_1$-$C_6$-haloalkyl, $C_3$-$C_6$-hydroxycycloalkenyl-$C_1$-$C_6$-alkyl, $C_3$-$C_6$-hydroxycycloalkenyl-$C_1$-$C_6$-haloalkyl, $C_1$-$C_6$-hydroxyalkyl, $C_2$-$C_6$-hydroxyhaloalkyl, $C_3$-$C_6$-hydroxyalkenyl, $C_3$-$C_6$-hydroxyhaloalkenyl, $C_3$-$C_6$-hydroxyalkynyl, $C_4$-$C_6$-hydroxyhaloalkynyl, $C_3$-$C_6$-hydroxycycloalkyl, $C_3$-$C_6$-hydroxyhalocycloalkyl, $C_3$-$C_6$-hydroxycycloalkenyl, $C_3$-$C_6$-hydroxyhalocycloalkenyl, $C_3$-$C_6$-cycloalkyl-$C_1$-$C_6$-hydroxyalkyl, $C_3$-$C_6$-cycloalkyl-$C_2$-$C_6$-hydroxyhaloalkyl, $C_3$-$C_6$-halocycloalkyl-$C_1$-$C_6$-hydroxyalkyl, $C_3$-$C_6$-halocycloalkyl-$C_2$-$C_6$-hydroxyhaloalkyl, $C_3$-$C_6$-cycloalkenyl-$C_1$-$C_6$-hydroxyalkyl, $C_3$-$C_6$-cycloalkenyl-$C_2$-$C_6$-hydroxyhaloalkyl, $C_3$-$C_6$-halocycloalkenyl-$C_1$-$C_6$-hydroxyalkyl$C_3$-$C_6$-halocycloalkenyl-$C_2$-$C_6$-hydroxyhaloalkyl, $C_3$-$C_6$-cycloalkyl-$C_3$-$C_6$-hydroxyalkenyl, $C_3$-$C_6$-cycloalkyl-$C_3$-$C_6$-hydroxyhaloalkenyl, $C_3$-$C_6$-halocycloalkyl-$C_3$-$C_6$-hydroxyalkenyl, $C_3$-$C_6$-halocycloalkyl-$C_3$-$C_6$-hydroxyhaloalkenyl, $C_3$-$C_6$-cycloalkenyl-$C_3$-$C_6$-hydroxyalkenyl, $C_3$-$C_6$-cycloalkenyl-$C_3$-$C_6$-hydroxyhaloalkenyl, $C_3$-$C_6$-halocycloalkenyl-$C_3$-$C_6$-hydroxyalkenyl, $C_3$-$C_6$-halocycloalkenyl-$C_3$-$C_6$-hydroxyhaloalkenyl, $C_3$-$C_6$-cycloalkyl-$C_3$-$C_6$-hydroxyalkynyl, $C_3$-$C_6$-halocycloalkyl-$C_3$-$C_6$-hydroxyalkynyl, $C_3$-$C_6$-cycloalkenyl-$C_3$-$C_6$-hydroxyalkynyl, $C_3$-$C_6$-halocycloalkenyl-$C_3$-$C_6$-hydroxyalkynyl, $C_3$-$C_6$-cycloalkyl-$C_2$-$C_6$-hydroxyalkylidenyl, $C_3$-$C_6$-halocycloalkyl-$C_2$-$C_6$-hydroxyalkylidenyl, $C_3$-$C_6$-cycloalkenyl-$C_2$-$C_6$-hydroxyalkylidenyl, $C_3$-$C_6$-halocycloalkyl-$C_2$-$C_6$-hydroxyalkylidenyl, heterocyclyl-$C_2$-$C_6$-hydroxyalkylidenyl, hydroxy-carbonyl-$C_1$-$C_6$-hydroxyalkyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-hydroxyalkyl, $C_1$-$C_6$-haloalkoxycarbonyl-$C_1$-$C_6$-hydroxyalkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-hydroxycycloalkyl-$C_1$-$C_6$-hydroxyalkyl, $C_3$-$C_6$-hydroxycycloalkenyl-$C_1$-$C_6$-hydroxyalkyl, $C_3$-$C_6$-hydroxycycloalkyl-$C_3$-$C_6$-hydroxyalkenyl, $C_3$-$C_6$-hydroxycycloalkenyl-$C_3$-$C_6$-hydroxyalkenyl, $C_3$-$C_6$-hydroxycycloalkyl-$C_3$-$C_6$-hydroxyalkynyl, $C_3$-$C_6$-hydroxycycloalkenyl-$C_3$-$C_6$-hydroxyalkenyl, $C_2$-$C_6$-dihydroxyalkyl, $C_3$-$C_6$-dihydroxyhaloalkyl, $C_4$-$C_6$-dihydroxyalkenyl, $C_4$-$C_6$-dihydroxyhaloalkenyl, $C_4$-$C_6$-dihydroxyalkynyl, $C_6$-$C_6$-dihydroxyhaloalkynyl, $C_4$-$C_6$-dihydroxycycloalkyl, $C_4$-$C_6$-dihydroxyhalocycloalkyl, $C_4$-$C_6$-dihydroxycycloalkenyl, $C_4$-$C_6$-dihydroxyhalocycloalkenyl, $C_3$-$C_6$-cycloalkyl-$C_2$-$C_6$-dihydroxyalkyl, $C_3$-$C_6$-halocycloalkyl-$C_2$-$C_6$-dihydroxyalkyl, $C_3$-$C_6$-cycloalkenyl-$C_2$-$C_6$-dihydroxyalkyl, $C_3$-$C_6$-halocycloalkenyl-$C_2$-$C_6$-dihydroxyalkyl, $C_3$-$C_6$-cycloalkyl-$C_3$-$C_6$-dihydroxyalkenyl, $C_3$-$C_6$-halocycloalkyl-$C_3$-$C_6$-dihydroxyalkenyl, $C_3$-$C_6$-cycloalkenyl-$C_3$-$C_6$-dihydroxyalkenyl, $C_3$-$C_6$-halocycloalkenyl-$C_3$-$C_6$-dihydroxyalkenyl, $C_3$-$C_6$-cycloalkyl-$C_4$-$C_6$-dihydroxyalkynyl, $C_3$-$C_6$-halocycloalkyl-$C_4$-$C_6$-dihydroxyalkynyl, $C_3$-$C_6$-cycloalkenyl-$C_4$-$C_6$-dihydroxyalkynyl, $C_3$-$C_6$-halocycloalkyl-$C_4$-$C_6$-dihydroxyalkynyl, $C_3$-$C_6$-cycloalkyl-$C_3$-$C_6$-dihydroxyalkylidenyl, $C_3$-$C_6$-halocycloalkyl-$C_3$-$C_6$-dihydroxyalkylidenyl, heterocyclyl-$C_3$-$C_6$-dihydroxyalkylidenyl, hydroxycarbonyl-$C_2$-$C_6$-dihydroxyalkyl, hydroxycarbonyl-$C_3$-$C_6$-dihydroxyhaloalkyl, $C_1$-$C_6$-alkoxycarbonyl-$C_2$-$C_6$-dihydroxyalkyl, $C_1$-$C_6$-haloalkoxycarbonyl-$C_2$-$C_6$-dihydroxyalkyl, $C_1$-$C_6$-haloalkoxycarbonyl-$C_3$-$C_6$-dihydroxyhaloalkyl, $C_3$-$C_6$-dihydroxycycloalkyl-$C_1$-$C_6$-alkyl, $C_3$-$C_6$-dihydroxycycloalkyl-$C_1$-$C_6$-haloalkyl, $C_3$-$C_6$-dihydroxycycloalkyl-$C_2$-$C_6$-alkenyl, $C_3$-$C_6$-dihydroxycycloalkyl-$C_2$-$C_6$-haloalkenyl, $C_3$-$C_6$-dihydroxycycloalkyl-$C_2$-$C_6$-alkynyl, $C_3$-$C_6$-dihydroxycycloalkyl-$C_3$-$C_6$-haloalkynyl, $C_1$-$C_6$-alkylcarbonyl-$C_1$-$C_6$-alkyl, $C_1$-$C_6$-haloalkylcarbonyl-$C_1$-$C_6$-alkyl, $C_1$-$C_6$-alkylcarbonyl-$C_1$-$C_6$-haloalkyl, $C_1$-$C_6$-haloalkylcarbonyl-$C_1$-$C_6$-haloalkyl, hydroxycarbonyl-$C_2$-$C_6$-alkenyl, hydroxycarbonyl-$C_2$-$C_6$-haloalkenyl, $C_1$-$C_6$-alkoxycarbonyl-$C_2$-$C_6$-alkenyl, $C_1$-$C_6$-haloalkoxycarbonyl-$C_2$-$C_6$-alkenyl, $C_1$-$C_6$-alkoxycarbonyl-$C_2$-$C_6$-haloalkenyl, $C_1$-$C_6$-haloalkoxycarbonyl-$C_2$-$C_6$-haloalkenyl, hydroxycarbonyl-$C_2$-$C_6$-alkynyl, hydroxycarbonyl-$C_3$-$C_6$-haloalkynyl, $C_1$-$C_6$-alkoxycarbonyl-$C_2$-$C_6$-alkynyl, $C_1$-$C_6$-haloalkoxycarbonyl-$C_2$-$C_6$-alkynyl, $C_1$-$C_6$-alkoxycarbonyl-$C_3$-$C_6$-halo-alkynyl, $C_1$-$C_6$-haloalkoxycarbonyl-$C_3$-$C_6$-haloalkynyl, $C_1$-$C_6$-cyanoalkyl, $C_2$-$C_6$-cyanohaloalkyl, $C_1$-$C_6$-dicyanoalkyl, $C_2$-$C_6$-dicyanohaloalkyl, di(hydroxycarbonyl)-$C_1$-$C_6$-alkyl, di(hydroxycarbonyl)-$C_1$-$C_6$-haloalkyl, di($C_1$-$C_6$-alkoxycarbonyl)-$C_1$-$C_6$-alkyl, di($C_1$-$C_6$-haloalkoxycarbonyl)-$C_1$-$C_6$-alkyl, di($C_1$-$C_6$-alkoxycarbonyl)-$C_1$-$C_6$-haloalkyl, di($C_1$-$C_6$-haloalkoxycarbonyl)-$C_1$-$C_6$-haloalkyl, di($C_1$-$C_6$-alkoxyl)phosphoryl-$C_1$-$C_6$-alkyl, di($C_1$-$C_6$-haloalkoxyl)phosphoryl-$C_1$-$C_6$-alkyl, di($C_1$-$C_6$-alkoxyl)phosphoryl-$C_1$-$C_6$-haloalkyl, di($C_1$-$C_6$-haloalkoxyl)phosphoryl-$C_1$-$C_6$-haloalkyl, phosphoryl-$C_1$-$C_6$-alkyl, phosphoryl-$C_1$-$C_6$-haloalkyl, di[di($C_1$-$C_6$-alkoxyl)phosphoryl-)]$C_1$-$C_6$-alkyl, di[di($C_1$-$C_6$-haloalkoxyl)phosphoryl-)]$C_1$-$C_6$-alkyl, di[di($C_1$-$C_6$-alkoxyl)phosphoryl-)]$C_1$-$C_6$-haloalkyl, di[di($C_1$-$C_6$-haloalkoxyl)phosphoryl-)]$C_1$-$C_6$-haloalkyl, diphosphoryl-$C_1$-$C_6$-alkyl, diphosphoryl-$C_1$-$C_6$-haloalkyl, $C_1$-$C_6$-alkylthio-$C_1$-$C_6$-alkyl, $C_1$-$C_6$-haloalkylthio-$C_1$-$C_6$-alkyl, $C_1$-$C_6$-alkylthio-$C_1$-$C_6$-haloalkyl, $C_1$-$C_6$-haloalkylthio-$C_1$-$C_6$-haloalkyl, $C_1$-$C_6$-alkylsulfinly-$C_1$-$C_6$-alkyl, $C_1$-$C_6$-haloalkylsulfinly-$C_1$-$C_6$-alkyl, $C_1$-$C_6$-alkylsulfinly-$C_1$-$C_6$-haloalkyl, $C_1$-$C_6$-haloalkylsulfinly-$C_1$-$C_6$-haloalkyl, $C_1$-$C_6$-alkylsulfonyl-$C_1$-$C_6$-alkyl, $C_1$-$C_6$-haloalkylsulfonyl-$C_1$-$C_6$-alkyl, $C_1$-$C_6$-haloalkylsulfonyl-$C_1$-$C_6$-haloalkyl, phenyl, 5-, 6- or 9 membered heteroaryl, 3- to 6-membered heterocyclyl, ($C_1$-$C_6$-alkyl)carbonylaminocarbonyl, ($C_2$-$C_6$-alkenyl)carbo-nylaminocarbonyl, ($C_3$-$C_6$-alkynyl)carbonylaminocarbonyl, ($C_1$-$C_6$-haloalkyl)carbo-nylaminocarbonyl, ($C_2$-$C_6$-haloalkenyl)carbonylaminocarbonyl, ($C_3$-$C_6$-haloalkynyl)car-bonylaminocarbonyl, phenylcarbonylaminocarbonyl, ($C_3$-$C_6$-cycloalkyl)carbonylaminocarbonyl, [($C_1$-$C_6$-alkyl)amino]carbonylaminocarbonyl, or [di($C_1$-$C_6$-alkyl)amino]carbonylaminocarbonyl, heterocyclylcarbonylaminocarbonyl, heteroarylcarbonylaminocarbonyl, phenylcarbonylaminocarbonyl;

wherein OH groups of $R^2$ are unsubstituted or substituted by $R^b$;

cyclic groups of $R^2$ are unsubstituted or substituted by $R^c$; and acyclic aliphatic groups of $R^2$ are unsubstituted or substituted by $R^d$;

$R^b$ is $C_1$-$C_6$-alkyl, $C_1$-$C_6$-haloalkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;

wherein the substituent $R^d$ is unsubstituted or substituted by $R^e$;

$R^e$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfonyl;

$R^3$ is halogen, CN, $NO_2$, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-halo-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-haloalkylthio, $NH_2$, ($C_1$-$C_6$-alkyl)amino, di($C_1$-$C_6$-alkyl) amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cyclic groups of $R^3$ are unsubstituted or substituted by substituents $R^a$;

$R^4$, $R^5$, $R^6$ and $R^7$ independently of one another are H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl) oxy or phenyl;

wherein the cyclic groups of $R^4$ $R^5$, $R^6$ and $R^7$ are unsubstituted or substituted by $R^a$;

$R^a$ is halogen, CN, $NO_2$, $C_1$-$C_6$-alkoxy, or $C_1$-$C_6$-haloalkoxy;

or an agriculturally acceptable salt, amide, ester, or thioester of the pyrimidine compound of formula (I), and B) herbicides of class b1) to b15):

b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitosis inhibitors;
b10) inhibitors of the synthesis of very long chain fatty acids (VLCFA inhibitors);
b11) cellulose biosynthesis inhibitors;
b12) decoupler herbicides;
b13) auxinic herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol, and its salts and esters;

including their agriculturally acceptable salts or derivatives.

8. The composition according to claim 7, wherein the composition comprises at least one herbicide B selected from herbicides of class b1, b2, b3, b4, b5, b6, b9, b10, b13 and b14.

9. The composition according to claim 7, wherein the weight ratio of component A to component B is in the range of from 1:500 to 500:1.

10. A herbicidal composition comprising a herbicidally active amount of at least one compound of formula (I) or an agriculturally acceptable salt or derivative of the pyrimidine compound of formula (I) having an acidic functionality one pyrimidine compound of formula (I),

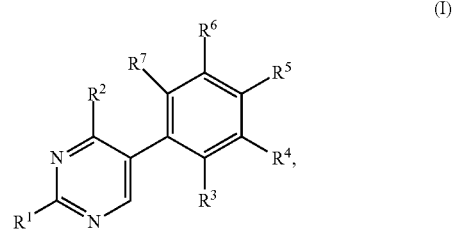

(I)

wherein:

$R^1$ is $C_1$-$C_6$-alkyl, $C_1$-$C_6$-haloalkyl, HO—$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, phenyl, or 3- to 6-membered heterocyclyl;

wherein the cyclic groups of $R^1$ are unsubstituted or substituted by $R^a$;

$R^2$ is $C_1$-$C_6$-alkyl, $C_1$-$C_6$-haloalkyl, $C_2$-$C_6$-alkenyl, $C_2$-$C_6$-haloalkenyl, $C_1$-$C_6$-alkoxy-$C_2$-$C_6$-alkenyl, $C_1$-$C_6$-alkoxy-$C_2$-$C_6$-haloalkenyl, $C_1$-$C_6$-haloalkoxy-$C_2$-$C_6$-alkenyl, $C_1$-$C_6$-haloalkoxy-$C_2$-$C_6$-haloalkenyl, $C_2$-$C_6$-alkynyl, $C_2$-$C_6$-haloalkynyl, $C_1$-$C_6$-alkoxy-$C_2$-$C_6$-alkynyl, $C_1$-$C_6$-alkoxy-$C_3$-$C_6$-haloalkynyl, $C_1$-$C_6$-haloalkoxy-$C_2$-$C_6$-alkynyl, $C_1$-$C_6$-haloalkoxy-$C_3$-$C_6$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-halocycloalkyl-$C_1$-$C_6$-alkyl, $C_3$-$C_6$-halocycloalkyl-$C_1$-$C_6$-haloalkyl, $C_3$-$C_6$-cycloalkenyl-$C_1$-$C_6$-alkyl, $C_3$-$C_6$-cycloalkenyl-$C_1$-$C_6$-haloalkyl, $C_3$-$C_6$-halocycloalkenyl-$C_1$-$C_6$-alkyl, $C_3$-$C_6$-halocycloalkenyl-$C_1$-$C_6$-haloalkyl, $C_3$-$C_6$-cycloalkyl-$C_2$-$C_6$-alkenyl, $C_3$-$C_6$-cycloalkyl-$C_2$-$C_6$-haloalkenyl, $C_3$-$C_6$-halocycloalkyl-$C_2$-$C_6$-alkenyl, $C_3$-$C_6$-halocycloalkyl-$C_2$-$C_6$-haloalkenyl, $C_3$-$C_6$-cycloalkenyl-$C_2$-$C_6$-alkenyl, $C_3$-$C_6$-cycloalkenyl-$C_2$-$C_6$-haloalkenyl, $C_3$-$C_6$-halocycloalkenyl-$C_2$-$C_6$-alkenyl, $C_3$-$C_6$-halocycloalkenyl-$C_2$-$C_6$-haloalkenyl, $C_3$-$C_6$-cycloalkyl-$C_2$-$C_6$-alkynyl, $C_3$-$C_6$-cycloalkyl-$C_3$-$C_6$-haloalkynyl, $C_3$-$C_6$-halocycloalkyl-$C_2$-$C_6$-alkynyl, $C_3$-$C_6$-halocycloalkyl-$C_3$-$C_6$-haloalkynyl, $C_3$-$C_6$-cycloalkenyl-$C_2$-$C_6$-alkynyl, $C_3$-$C_6$-cycloalkenyl-$C_3$-$C_6$-haloalkynyl, $C_3$-$C_6$-halocycloalkenyl-$C_2$-$C_6$-alkynyl, $C_3$-$C_6$-halocycloalkenyl-$C_3$-$C_6$-haloalkynyl, $C_3$-$C_6$-cycloalkyl-$C_1$-$C_6$-alkylidenyl, $C_3$-$C_6$-cycloalkyl-$C_2$-$C_6$-haloalkylidenyl, $C_3$-$C_6$-halocycloalkyl-$C_1$-$C_6$-alkylidenyl, $C_3$-$C_6$-halocycloalkyl-$C_2$-$C_6$-haloalkylidenyl, $C_3$-$C_6$-cycloalkenyl-$C_1$-$C_6$-alkylidenyl, $C_3$-$C_6$-cycloalkenyl-$C_2$-$C_6$-haloalkylidenyl, $C_3$-$C_6$-halocycloalkenyl-$C_1$-$C_6$-alkylidenyl, $C_3$-$C_6$-halocycloalkenyl-$C_2$-$C_6$-haloalkylidenyl, heterocyclyl-$C_1$-$C_6$-alkylidenyl, heterocyclyl-$C_1$-$C_6$-haloalkylidenyl, $C_3$-$C_6$-hydroxycycloalkyl-$C_1$-$C_6$-alkyl, $C_3$-$C_6$-hydroxycycloalkyl-$C_1$-$C_6$-haloalkyl, $C_3$-$C_6$-hydroxycycloalkenyl-$C_1$-$C_6$-alkyl, $C_3$-$C_6$-hydroxycycloalkenyl-$C_1$-$C_6$-haloalkyl, $C_1$-$C_6$-hydroxyalkyl, $C_2$-$C_6$-hydroxyhaloalkyl, $C_3$-$C_6$-hydroxyalkenyl, $C_3$-$C_6$-hydroxyhaloalkenyl, $C_3$-$C_6$-hydroxyalkynyl, $C_4$-$C_6$-hydroxyhaloalkynyl, $C_3$-$C_6$-hydroxycycloalkyl, $C_3$-$C_6$-hydroxyhalocycloalkyl, $C_3$-$C_6$-hydroxycycloalkenyl, $C_3$-$C_6$-hydroxyhalocycloalkenyl, $C_3$-$C_6$-cycloalkyl-$C_1$-$C_6$-hydroxyalkyl, $C_3$-$C_6$-cycloalkyl-$C_2$-$C_6$-hydroxyhaloalkyl, $C_3$-$C_6$-halocycloalkyl-$C_1$-$C_6$-hydroxyalkyl, $C_3$-$C_6$-halocycloalkyl-$C_2$-$C_6$-hydroxyhaloalkyl, $C_3$-$C_6$-cycloalkenyl-$C_1$-$C_6$-hydroxyalkyl, $C_3$-$C_6$-cycloalkenyl-$C_2$-$C_6$-hydroxyhaloalkyl, $C_3$-$C_6$-halocycloalkenyl-$C_1$-$C_6$-hydroxyhaloalkyl $C_3$-$C_6$-halocycloalkenyl-$C_2$-$C_6$-hydroxyhaloalkyl, $C_3$-$C_6$-cycloalkyl-$C_3$-$C_6$-hydroxyalkenyl, $C_3$-$C_6$-cycloalkyl-$C_3$-$C_6$-hydroxyhaloalkenyl, $C_3$-$C_6$-halocycloalkyl-$C_3$-$C_6$-hydroxyalkenyl, $C_3$-$C_6$-halocycloalkyl-$C_3$-$C_6$-hydroxyhaloalkenyl, $C_3$-$C_6$-cycloalkenyl-$C_3$-$C_6$-hydroxyalkenyl, $C_3$-$C_6$-cycloalkenyl-$C_3$-$C_6$-hydroxyhaloalkenyl, $C_3$-$C_6$-halocycloalkenyl-$C_3$-$C_6$-hydroxyalkenyl, $C_3$-$C_6$-halocycloalkenyl-$C_3$-$C_6$-hydroxyhaloalkenyl, $C_3$-$C_6$-cycloalkyl-$C_3$-$C_6$-hydroxyalkynyl, $C_3$-$C_6$-halocycloalkyl-$C_3$-$C_6$-hydroxyalkynyl, $C_3$-$C_6$-cycloalkenyl-$C_3$-$C_6$-hydroxyalkynyl, $C_3$-$C_6$-halocycloalkenyl-$C_3$-$C_6$-hydroxyalkynyl, $C_3$-$C_6$-cycloalkyl-$C_2$-$C_6$-hydroxyalkylidenyl, $C_3$-$C_6$-halocycloalkyl-$C_2$-$C_6$-hydroxyalkylidenyl, $C_3$-$C_6$-cycloalkenyl-$C_2$-$C_6$-hydroxyalkylidenyl, $C_3$-$C_6$-halocycloalkenyl-$C_2$-$C_6$-hydroxyalkylidenyl, heterocyclyl-$C_2$-$C_6$-hydroxyalkylidenyl, hydroxy-carbonyl-$C_1$-$C_6$-hydroxyalkyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-hydroxyalkyl, $C_1$-$C_6$-haloalkoxycarbonyl-$C_1$-$C_6$-hydroxyalkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-hydroxycycloalkyl-$C_1$-$C_6$-hydroxyalkyl, $C_3$-$C_6$-hydroxycycloalkenyl-$C_1$-$C_6$-hydroxyalkyl, $C_3$-$C_6$-hydroxycycloalkyl-$C_3$-$C_6$-hydroxyalkenyl, $C_3$-$C_6$-hydroxycycloalkyl-$C_3$-$C_6$-hydroxyalkenyl, $C_3$-$C_6$-hydroxycycloalkyl-$C_3$-$C_6$-hydroxyalkynyl, $C_3$-$C_6$-hydroxycycloalkenyl-$C_3$-$C_6$-hydroxyalkenyl, $C_2$-$C_6$-dihydroxyalkyl, $C_3$-$C_6$-dihydroxyhaloalkyl, $C_4$-$C_6$-dihydroxyalkenyl, $C_4$-$C_6$-dihydroxyhaloalkenyl, $C_4$-$C_6$-dihydroxyalkynyl, $C_5$-$C_6$-dihydroxyhaloalkynyl, $C_4$-$C_6$-dihydroxycycloalkyl, $C_4$-$C_6$-dihydroxyhalocycloalkyl, $C_4$-$C_6$-dihydroxycycloalkenyl, $C_4$-$C_6$-dihydroxyhalocycloalkenyl, $C_3$-$C_6$-cycloalkyl-$C_2$-$C_6$-dihydroxyalkyl, $C_3$-$C_6$-halocycloalkyl-$C_2$-$C_6$-dihydroxyalkyl, $C_3$-$C_6$-cycloalkenyl-$C_2$-$C_6$-dihydroxyalkyl, $C_3$-$C_6$-halocycloalkenyl-$C_2$-$C_6$-dihydroxyalkyl, $C_3$-$C_6$-cycloalkyl-$C_3$-$C_6$-dihydroxyalkenyl, $C_3$-$C_6$-halocycloalkyl-$C_3$-$C_6$-dihydroxyalkenyl, $C_3$-$C_6$-cycloalkenyl-$C_3$-$C_6$-dihydroxyalkenyl, $C_3$-$C_6$-halocycloalkenyl-$C_3$-$C_6$-dihydroxyalkenyl, $C_3$-$C_6$-cycloalkyl-$C_4$-$C_6$-dihydroxyalkynyl, $C_3$-$C_6$-halocycloalkyl-$C_4$-$C_6$-dihydroxyalkynyl, $C_3$-$C_6$-cycloalkenyl-$C_4$-$C_6$-dihydroxyalkynyl, $C_3$-$C_6$-halocycloalkyl-$C_4$-$C_6$-dihydroxyalkynyl, $C_3$-$C_6$-cycloalkyl-$C_3$-$C_6$-dihydroxyalkylidenyl, $C_3$-$C_6$-halocycloalkyl-$C_3$-$C_6$-dihydroxyalkylidenyl, heterocyclyl-$C_3$-$C_6$-dihydroxyalkylidenyl, hydroxycarbonyl-$C_2$-$C_6$-dihydroxyalkyl, hydroxycarbonyl-$C_3$-$C_6$-dihydroxyhaloalkyl, $C_1$-$C_6$-alkoxycarbonyl-$C_2$-$C_6$-dihydroxyalkyl, $C_1$-$C_6$-haloalkoxycarbonyl-$C_2$-$C_6$-dihydroxyalkyl, $C_1$-$C_6$-haloalkoxycarbonyl-$C_3$-$C_6$-dihydroxyhaloalkyl, $C_3$-$C_6$-dihydroxycycloalkyl-$C_1$-$C_6$-alkyl, $C_3$-$C_6$-dihydroxycycloalkyl-$C_1$-$C_6$-haloalkyl, $C_3$-$C_6$-dihydroxycycloalkyl-$C_2$-$C_6$-alkenyl, $C_3$-$C_6$-dihydroxycycloalkyl-$C_2$-$C_6$-haloalkenyl, $C_3$-$C_6$-dihydroxycycloalkyl-$C_2$-$C_6$-alkynyl, $C_3$-$C_6$-dihydroxycycloalkyl-$C_3$-$C_6$-haloalkynyl, $C_1$-$C_6$-alkylcarbonyl-$C_1$-$C_6$-alkyl, $C_1$-$C_6$-haloalkylcarbonyl-$C_1$-$C_6$-alkyl, $C_1$-$C_6$-alkylcarbonyl-$C_1$-$C_6$-haloalkyl, $C_1$-$C_6$-haloalkylcarbonyl-$C_1$-$C_6$-haloalkyl, hydroxycarbonyl-$C_2$-$C_6$-alkenyl, hydroxycarbonyl-$C_2$-$C_6$-haloalkenyl, $C_1$-$C_6$-alkoxycarbonyl-$C_2$-$C_6$-alkenyl, $C_1$-$C_6$-haloalkoxycarbonyl-$C_2$-$C_6$-alkenyl, $C_1$-$C_6$-alkoxycarbonyl-$C_2$-$C_6$-haloalkenyl, $C_1$-$C_6$-haloalkoxycarbonyl-$C_2$-$C_6$-haloalkenyl, hydroxycarbonyl-C₂-C₆-alkynyl, hydroxycarbonyl-C₃-C₆-haloalkynyl, C₁-C₆-alkoxycarbonyl-C₂-C₆-alkynyl, C₁-C₆-haloalkoxycarbonyl-C₂-C₆-alkynyl, C₁-C₆-alkoxycarbonyl-C₃-C₆-halo-alkynyl, C₁-C₆-haloalkoxycarbonyl-C₃-C₆-haloalkynyl, C₁-C₆-cyanoalkyl, C₂-C₆-cyanohaloalkyl, C₁-C₆-dicyanoalkyl, C₂-C₆-dicyanohaloalkyl, di(hydroxycarbonyl)-C₁-C₆-alkyl, di(hydroxycarbonyl)-C₁-C₆-haloalkyl, di(C₁-C₆-alkoxycarbonyl)-C₁-C₆-alkyl, di(C₁-C₆-haloalkoxycarbonyl)-C₁-C₆-alkyl, di(C₁-C₆-alkoxycarbonyl)-C₁-C₆-haloalkyl, di(C₁-C₆-haloalkoxycarbonyl)-C₁-C₆-haloalkyl, di(C₁-C₆-alkoxyl)phosphoryl-C₁-C₆-alkyl, di(C₁-C₆-haloalkoxyl)phosphoryl-C₁-C₆-alkyl, di(C₁-C₆-alkoxyl)phosphoryl-C₁-C₆-haloalkyl, di(C₁-C₆-haloalkoxyl)phosphoryl-C₁-C₆-haloalkyl, phosphoryl-C₁-C₆-alkyl, phosphoryl-C₁-C₆-haloalkyl, di[di(C₁-C₆-alkoxyl)phosphoryl-)]C₁-C₆-alkyl, di[di(C₁-C₆-haloalkoxyl)phosphoryl-)]C₁-C₆-alkyl, di[di(C₁-C₆-alkoxyl)phosphoryl-)]C₁-C₆-haloalkyl, di[di(C₁-C₆-haloalkoxyl)phosphoryl-)]C₁-C₆-haloalkyl, diphosphoryl-C₁-C₆-alkyl, diphosphoryl-C₁-C₆-haloalkyl, alkyl, C₁-C₆-haloalkylsulfinly-C₁-C₆-alkyl, C₁-C₆-haloalkylsulfinly-C₁-C₆-haloalkyl, C₁-C₆-haloalkylsulfonyl-C₁-C₆-haloalkyl, phenyl, 5-, 6- or 9 membered heteroaryl, 3- to 6-membered heterocyclyl, (C₁-C₆-alkyl)carbonylaminocarbonyl, (C₂-C₆-alkenyl)carbo-nylamino-carbonyl, (C₃-C₆-alkynyl)carbonylaminocarbonyl, (C₁-C₆-haloalkyl)carbo-nylaminocarbonyl, (C₂-C₆-haloalkenyl)carbonylaminocarbonyl, (C₃-C₆-haloalkynyl)carbonylaminocarbonyl, phenylcarbonylaminocarbonyl, (C₃-C₆-cycloalkyl)carbonylaminocarbonyl, [(C₁-C₆-alkyl)amino]carbonylaminocarbonyl, or [di(C₁-C₆-alkyl)amino]carbonylaminocarbonyl, heterocyclylcarbonylaminocarbonyl, heteroarylcarbonylaminocarbonyl, phenylcarbonylaminocarbonyl;

wherein OH groups of R² are unsubstituted or substituted by $R^b$;
cyclic groups of R² are unsubstituted or substituted by $R^c$; and
acyclic aliphatic groups of R² are unsubstituted or substituted by $R^d$;
$R^b$ is C₁-C₆-alkyl, C₃-C₆-alkenyl, C₃-C₆-haloalkenyl, C₃-C₆-alkynyl, C₃-C₆-haloalkynyl, C₃-C₆-cycloalkyl, C₃-C₆-halocycloalkyl, C₄-C₆-cycloalkenyl, C₃-C₆-halocycloalkenyl, C₁-C₆-alkoxycarbonyl-C₁-C₆-alkyl, C₁-C₆-haloalkoxycarbonyl-C₁-C₆-alkyl, C₁-C₆-alkoxycarbonyl-C₁-C₆-haloalkyl, C₁-C₆-haloalkoxycarbonyl-C₁-C₆-haloalkyl, alkylcarbonyl, C₁-C₆-haloalkylcarbonyl, hydroxycarbonyl-C₁-C₆-alkyl, hydroxycarbonyl-C₁-C₆-haloalkyl, C₁-C₆-alkyloxycarbonyl, C₁-C₆-haloalkyloxycarbonyl, C₁-C₆-alkylthiocarbonyl, C₁-C₆-haloalkylthiocarbonyl, C₁-C₆-alkylaminocarbonyl, C₁-C₆-haloalkylaminocarbonyl, C₁-C₆-dialkylaminocarbonyl, C₁-C₆-dihaloalkylaminocarbonyl, C₁-C₆-alkylsulfonyl, C₁-C₆-haloalkylsulfonyl, C₁-C₆-haloalkoxy-C₁-C₆-haloalkyl, phenyl-C₁-C₆-alkyl, or phenyl-C₁-C₆-haloalkyl;
$R^c$ is halogen, CN, NO₂, C₁-C₆-haloalkyl, OH, C₁-C₆-alkoxy, C₁-C₆-haloalkoxy, C₁-C₆-alkylsulfinyl, or C₁-C₆-alkylsulfonyl;
$R^d$ is phenyl, 5- or 6-membered heteroaryl, or 3- to 6-membered heterocyclyl;
wherein the substituent $R^d$ is unsubstituted or substituted by $R^e$;
$R^e$ is halogen, CN, NO₂, C₁-C₆-haloalkyl, OH, C₁-C₆-alkoxy, C₁-C₆-haloalkoxy, C₁-C₆-alkylsulfonyl;

R³ is halogen, CN, NO₂, C₁-C₆-alkylcarbonyl, C₂-C₆-alkenyl, C₂-C₆-haloalkenyl, C₂-C₆-alkynyl, C₂-C₆-haloalkynyl, C₁-C₆-alkoxy, C₁-C₆-halo-alkoxy, C₃-C₆-alkenyloxy, C₃-C₆-haloalkenyloxy, C₃-C₆-alkynyloxy, C₃-C₆-haloalkynyloxy, C₁-C₆-alkoxy-C₁-C₆-alkoxy, hydroxycarbonyl, C₁-C₆-alkoxycarbonyl, C₁-C₆-haloalkylthio, NH₂, (C₁-C₆-alkyl)amino, di(C₁-C₆-alkyl)amino, (C₁-C₆-alkyl)sulfinyl, (C₁-C₆-alkyl)sulfonyl, C₃-C₆-cycloalkyl, (C₃-C₆-cycloalkyl)oxy or phenyl;
wherein the cyclic groups of R³ are unsubstituted or substituted by substituents $R^a$;
R⁴, R⁵, R⁶ and R⁷ independently of one another are H, halogen, CN, NO₂, C₁-C₆-alkyl, C₁-C₆-haloalkyl, C₁-C₆-alkylcarbonyl, C₂-C₆-alkenyl, C₂-C₆-haloalkenyl, C₂-C₆-alkynyl, C₂-C₆-haloalkynyl, C₁-C₆-alkoxy, C₁-C₆-haloalkoxy, C₃-C₆-alkenyloxy, C₃-C₆-haloalkenyloxy, C₃-C₆-alkynyloxy, C₃-C₆-haloalkynyloxy, C₁-C₆-alkoxy-C₁-C₆-alkoxy, hydroxycarbonyl, C₁-C₆-alkoxycarbonyl, C₁-C₆-haloalkylthio, NH₂, (C₁-C₆-alkyl)amino, di(C₁-C₆-alkyl)amino, (C₁-C₆-alkyl)sulfinyl, (C₁-C₆-alkyl)sulfonyl, C₃-C₆-cycloalkyl, (C₃-C₆-cycloalkyl)oxy or phenyl;
wherein the cyclic groups of R⁴ R⁵, R⁶ and R⁷ are unsubstituted or substituted by $R^a$;
$R^a$ is halogen, CN, NO₂, C₁-C₆-alkoxy, or C₆-haloalkoxy;
or an agriculturally acceptable salt, amide, ester, or thioester of the pyrimidine compound of formula (I),
and at least one inert liquid and/or solid carrier and, if appropriate, at least one surface-active substance.

11. A composition comprising the composition according to claim 10, further comprising a safener.

12. A method of controlling undesired vegetation, which comprises allowing a herbicidal active amount of at least one pyrimidine compound of formula (I),

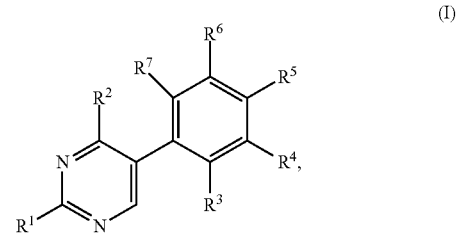

(I)

wherein:
R¹ is C₁-C₆-alkyl, C₁-C₆-haloalkyl, HO—C₁-C₆-alkyl, C₂-C₆-alkenyl, C₂-C₆-haloalkenyl, C₂-C₆-alkynyl, C₃-C₆-haloalkynyl, C₁-C₆-alkoxy-C₁-C₆-alkyl, C₁-C₆-alkoxy, C₃-C₆-alkenyloxy, C₃-C₆-haloalkenyloxy, C₃-C₆-alkynyloxy, C₃-C₆-haloalkynyloxy, C₁-C₆-haloalkoxy, C₃-C₆-cycloalkoxy, C₃-C₆-halocycloalkoxy, C₃-C₆-cycloalkenyloxy, C₃-C₆-halocycloalkenyloxy, C₁-C₆-alkylthio, C₁-C₆-haloalkylthio, (C₁-C₆-alkyl)amino, di(C₁-C₆-alkyl)amino, C₁-C₆-alkylsulfinyl, C₁-C₆-alkylsulfonyl, C₃-C₆-cycloalkyl, C₃-C₆-cycloalkenyl, C₃-C₆-halocycloalkyl, C₃-C₆-halocycloalkenyl, [1-(C₁-C₆-alkyl)]-C₃-C₆-cycloalkyl, [1-(C₂-C₆-alkenyl)]-C₃-C₆-cycloalkyl, [1-(C₂-C₆-alkynyl)]-C₃-C₆-cycloalkyl, [1-(C₁-C₆-haloalkyl)]-C₃-C₆-cycloalkyl, [1-(C₂-C₆-haloalkenyl)]-C₃-C₆-cycloalkyl, [1-(C₃-C₆-haloalkynyl)]-C₃-C₆-cycloalkyl, C₃-C₆-cycloalkyl-C₁-C₆-alkyl, C₃-C₆-cycloalkyl-C₁-C₆-haloalkyl, C₃-C₆-cycloalkyl-C₁-C₆-alkoxy, C₃-C₆-cycloalkyl-C₁-C₆-haloalkoxy, phenyl, or 3- to 6-membered heterocyclyl;

wherein the cyclic groups of $R^1$ are unsubstituted or substituted by $R^a$;

$R^2$ is $C_1$-$C_6$-alkyl, $C_1$-$C_6$-haloalkyl, $C_2$-$C_6$-alkenyl, $C_2$-$C_6$-haloalkenyl, $C_1$-$C_6$-alkoxy-$C_2$-$C_6$-alkenyl, $C_1$-$C_6$-alkoxy-$C_2$-$C_6$-haloalkenyl, $C_1$-$C_6$-haloalkoxy-$C_2$-$C_6$-alkenyl, $C_1$-$C_6$-haloalkoxy-$C_2$-$C_6$-haloalkenyl, $C_2$-$C_6$-alkynyl, $C_2$-$C_6$-haloalkynyl, $C_1$-$C_6$-alkoxy-$C_2$-$C_6$-alkynyl, $C_1$-$C_6$-alkoxy-$C_3$-$C_6$-haloalkynyl, $C_1$-$C_6$-haloalkoxy-$C_2$-$C_6$-alkynyl, $C_1$-$C_6$-haloalkoxy-$C_3$-$C_6$-haloalkynyl, $C_3$-$C_6$-cycloalkyl, $C_3$-$C_6$-halocycloalkyl, $C_3$-$C_6$-cycloalkenyl, $C_3$-$C_6$-halocycloalkenyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-halocycloalkyl-$C_1$-$C_6$-alkyl, $C_3$-$C_6$-halocycloalkyl-$C_1$-$C_6$-haloalkyl, $C_3$-$C_6$-cycloalkenyl-$C_1$-$C_6$-alkyl, $C_3$-$C_6$-cycloalkenyl-$C_1$-$C_6$-haloalkyl, $C_3$-$C_6$-halocycloalkenyl-$C_1$-$C_6$-alkyl, $C_3$-$C_6$-halocycloalkenyl-$C_1$-$C_6$-haloalkyl, $C_3$-$C_6$-cycloalkyl-$C_2$-$C_6$-alkenyl, $C_3$-$C_6$-cycloalkyl-$C_2$-$C_6$-haloalkenyl, $C_3$-$C_6$-halocycloalkyl-$C_2$-$C_6$-alkenyl, $C_3$-$C_6$-halocycloalkyl-$C_2$-$C_6$-haloalkenyl, $C_3$-$C_6$-cycloalkenyl-$C_2$-$C_6$-alkenyl, $C_3$-$C_6$-cycloalkenyl-$C_2$-$C_6$-haloalkenyl, $C_3$-$C_6$-halocycloalkenyl-$C_2$-$C_6$-alkenyl, $C_3$-$C_6$-halocycloalkenyl-$C_2$-$C_6$-haloalkenyl, $C_3$-$C_6$-cycloalkyl-$C_2$-$C_6$-alkynyl, $C_3$-$C_6$-cycloalkyl-$C_3$-$C_6$-haloalkynyl, $C_3$-$C_6$-halocycloalkyl-$C_2$-$C_6$-alkynyl, $C_3$-$C_6$-halocyclalkyl-$C_3$-$C_6$-haloalkynyl, $C_3$-$C_6$-cycloalkenyl-$C_2$-$C_6$-alkynyl, $C_3$-$C_6$-cycloalkenyl-$C_3$-$C_6$-haloalkynyl, $C_3$-$C_6$-halocycloalkenyl-$C_2$-$C_6$-alkynyl, $C_3$-$C_6$-halocyclaalkenyl-$C_3$-$C_6$-haloalkynyl, $C_3$-$C_6$-cycloalkyl-$C_1$-$C_6$-alkylidenyl, $C_3$-$C_6$-cycloalkyl-$C_2$-$C_6$-haloalkylidenyl, $C_3$-$C_6$-halocycloalkyl-$C_1$-$C_6$-alkylidenyl, $C_3$-$C_6$-halocycloalkyl-$C_2$-$C_6$-haloalkylidenyl, $C_3$-$C_6$-cycloalkenyl-$C_1$-$C_6$-alkylidenyl, $C_3$-$C_6$-cycloalkenyl-$C_2$-$C_6$-haloalkylidenyl, $C_3$-$C_6$-halocycloalkenyl-$C_1$-$C_6$-alkylidenyl, $C_3$-$C_6$-halocycloalkenyl-$C_2$-$C_6$-haloalkylidenyl, heterocyclyl-$C_1$-$C_6$-alkylidenyl, heterocyclyl-$C_1$-$C_6$-haloalkylidenyl, $C_3$-$C_6$-hydroxycycloalkyl-$C_1$-$C_6$-alkyl, $C_3$-$C_6$-hydroxycycloalkyl-$C_1$-$C_6$-haloalkyl, $C_3$-$C_6$-hydroxycycloalkenyl-$C_1$-$C_6$-alkyl, $C_3$-$C_6$-hydroxycycloalkenyl-$C_1$-$C_6$-haloalkyl, $C_1$-$C_6$-hydroxyalkyl, $C_2$-$C_6$-hydroxyhaloalkyl, $C_3$-$C_6$-hydroxyalkenyl, $C_3$-$C_6$-hydroxyhaloalkenyl, $C_3$-$C_6$-hydroxyalkynyl, $C_4$-$C_6$-hydroxyhaloalkynyl, $C_3$-$C_6$-hydroxycycloalkyl, $C_3$-$C_6$-hydroxyhalocycloalkyl, $C_3$-$C_6$-hydroxycycloalkenyl, $C_3$-$C_6$-hydroxyhalocycloalkenyl, $C_3$-$C_6$-cycloalkyl-$C_1$-$C_6$-hydroxyalkyl, $C_3$-$C_6$-cycloalkyl-$C_2$-$C_6$-hydroxyhaloalkyl, $C_3$-$C_6$-halocycloalkyl-$C_1$-$C_6$-hydroxyalkyl, $C_3$-$C_6$-halocycloalkyl-$C_2$-$C_6$-hydroxyhaloalkyl, $C_3$-$C_6$-cycloalkenyl-$C_1$-$C_6$-hydroxyalkyl, $C_3$-$C_6$-cycloalkenyl-$C_2$-$C_6$-hydroxyhaloalkyl, $C_3$-$C_6$-halocycloalkenyl-$C_1$-$C_6$-hydroxyalkyl$C_3$-$C_6$-halocycloalkenyl-$C_2$-$C_6$-hydroxyhaloalkyl, $C_3$-$C_6$-cycloalkyl-$C_3$-$C_6$-hydroxyalkenyl, $C_3$-$C_6$-cycloalkyl-$C_3$-$C_6$-hydroxyhaloalkenyl, $C_3$-$C_6$-halocycloalkyl-$C_3$-$C_6$-hydroxyalkenyl, $C_3$-$C_6$-halocycloalkyl-$C_3$-$C_6$-hydroxyhaloalkenyl, $C_3$-$C_6$-cycloalkenyl-$C_3$-$C_6$-hydroxyalkenyl, $C_3$-$C_6$-cycloalkenyl-$C_3$-$C_6$-hydroxyhaloalkenyl, $C_3$-$C_6$-halocycloalkenyl-$C_3$-$C_6$-hydroxyalkenyl, $C_3$-$C_6$-halocycloalkenyl-$C_3$-$C_6$-hydroxyhaloalkenyl, $C_3$-$C_6$-cycloalkyl-$C_3$-$C_6$-hydroxyalkynyl, $C_3$-$C_6$-cycloalkyl-$C_3$-$C_6$-hydroxyalkynyl, $C_3$-$C_6$-halocycloalkyl-$C_3$-$C_6$-hydroxyalkynyl, $C_3$-$C_6$-cycloalkyl-$C_2$-$C_6$-hydroxyalkylidenyl, $C_3$-$C_6$-halocycloalkyl-$C_2$-$C_6$-hydroxyalkylidenyl, $C_3$-$C_6$-cycloalkenyl-$C_2$-$C_6$-hydroxyalkylidenyl, $C_3$-$C_6$-halocycloalkyl-$C_2$-$C_6$-hydroxyalkylidenyl, heterocyclyl-$C_2$-$C_6$-hydroxyalkylidenyl, hydroxy-carbonyl-$C_1$-$C_6$-hydroxyalkyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-hydroxyalkyl, $C_1$-$C_6$-haloalkoxycarbonyl-$C_1$-$C_6$-hydroxyalkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkoxycarbonyl-$C_1$-$C_6$-alkyl, $C_1$-$C_6$-haloalkoxycarbonyl-$C_1$-$C_6$-alkyl, $C_3$-$C_6$-hydroxycycloalkyl-$C_1$-$C_6$-hydroxyalkyl, $C_3$-$C_6$-hydroxycycloalkenyl-$C_1$-$C_6$-hydroxyalkyl, $C_3$-$C_6$-hydroxycycloalkyl-$C_3$-$C_6$-hydroxyalkenyl, $C_3$-$C_6$-hydroxycycloalkenyl-$C_3$-$C_6$-hydroxyalkenyl, $C_3$-$C_6$-hydroxycycloalkyl-$C_3$-$C_6$-hydroxyalkynyl, $C_3$-$C_6$-hydroxycycloalkenyl-$C_3$-$C_6$-hydroxyalkenyl, $C_2$-$C_6$-dihydroxyalkyl, $C_3$-$C_6$-dihydroxyhaloalkyl, $C_4$-$C_6$-dihydroxyalkenyl, $C_4$-$C_6$-dihydroxyhaloalkenyl, $C_4$-$C_6$-dihydroxyalkynyl, $C_5$-$C_6$-dihydroxyhaloalkynyl, $C_4$-$C_6$-dihydroxycycloalkyl, $C_4$-$C_6$-dihydroxyhalocycloalkyl, $C_4$-$C_6$-dihydroxycycloalkenyl, $C_4$-$C_6$-dihydroxyhalocycloalkenyl, $C_3$-$C_6$-cycloalkyl-$C_2$-$C_6$-dihydroxyalkyl, $C_3$-$C_6$-halocycloalkyl-$C_2$-$C_6$-dihydroxyalkyl, $C_3$-$C_6$-cycloalkenyl-$C_2$-$C_6$-dihydroxyalkyl, $C_3$-$C_6$-halocycloalkenyl-$C_2$-$C_6$-dihydroxyalkyl, $C_3$-$C_6$-cycloalkyl-$C_3$-$C_6$-dihydroxyalkenyl, $C_3$-$C_6$-halocycloalkyl-$C_3$-$C_6$-dihydroxyalkenyl, $C_3$-$C_6$-cycloalkenyl-$C_3$-$C_6$-dihydroxyalkenyl, $C_3$-$C_6$-halocycloalkenyl-$C_3$-$C_6$-dihydroxyalkenyl, $C_3$-$C_6$-cycloalkyl-$C_4$-$C_6$-dihydroxyalkynyl, $C_3$-$C_6$-halocycloalkyl-$C_4$-$C_6$-dihydroxyalkynyl, $C_3$-$C_6$-cycloalkenyl-$C_4$-$C_6$-dihydroxyalkynyl, $C_3$-$C_6$-halocycloalkyl-$C_4$-$C_6$-dihydroxyalkynyl, $C_3$-$C_6$-cycloalkenyl-$C_3$-$C_6$-dihydroxyalkylidenyl, $C_3$-$C_6$-halocycloalkyl-$C_3$-$C_6$-dihydroxyalkylidenyl, heterocyclyl-$C_3$-$C_6$-dihydroxyalkylidenyl, hydroxycarbonyl-$C_2$-$C_6$-dihydroxyalkyl, hydroxycarbonyl-$C_3$-$C_6$-dihydroxyhaloalkyl, $C_1$-$C_6$-alkoxycarbonyl-$C_2$-$C_6$-dihydroxyalkyl, $C_1$-$C_6$-haloalkoxycarbonyl-$C_2$-$C_6$-dihydroxyalkyl, $C_1$-$C_6$-haloalkoxycarbonyl-$C_3$-$C_6$-dihydroxyhaloalkyl, $C_3$-$C_6$-dihydroxycycloalkyl-$C_1$-$C_6$-alkyl, $C_3$-$C_6$-dihydroxycycloalkyl-$C_1$-$C_6$-haloalkyl, $C_3$-$C_6$-dihydroxycycloalkyl-$C_2$-$C_6$-alkenyl, $C_3$-$C_6$-dihydroxycycloalkyl-$C_2$-$C_6$-haloalkenyl, $C_3$-$C_6$-dihydroxycycloalkyl-$C_2$-$C_6$-alkynyl, $C_3$-$C_6$-dihydroxycycloalkyl-$C_3$-$C_6$-haloalkynyl, $C_1$-$C_6$-alkylcarbonyl-$C_1$-$C_6$-alkyl, $C_1$-$C_6$-haloalkylcarbonyl-$C_1$-$C_6$-alkyl, $C_1$-$C_6$-alkylcarbonyl-$C_1$-$C_6$-haloalkyl, $C_1$-$C_6$-haloalkylcarbonyl-$C_1$-$C_6$-haloalkyl, hydroxycarbonyl-$C_2$-$C_6$-alkenyl, hydroxycarbonyl-$C_2$-$C_6$-haloalkenyl, $C_1$-$C_6$-alkoxycarbonyl-$C_2$-$C_6$-alkenyl, $C_1$-$C_6$-haloalkoxycarbonyl-$C_2$-$C_6$-alkenyl, $C_1$-$C_6$-alkoxycarbonyl-$C_2$-$C_6$-haloalkenyl, $C_1$-$C_6$-haloalkoxycarbonyl-$C_2$-$C_6$-haloalkenyl, hydroxycarbonyl-$C_2$-$C_6$-alkynyl, hydroxycarbonyl-$C_3$-$C_6$-haloalkynyl, $C_1$-$C_6$-alkoxycarbonyl-$C_2$-$C_6$-alkynyl, $C_1$-$C_6$-haloalkoxycarbonyl-$C_2$-$C_6$-alkynyl, $C_1$-$C_6$-alkoxycarbonyl-$C_3$-$C_6$-halo-alkynyl, $C_1$-$C_6$-haloalkoxycarbonyl-$C_3$-$C_6$-haloalkynyl, $C_1$-$C_6$-cyanoalkyl, $C_2$-$C_6$-cyanohaloalkyl, $C_1$-$C_6$-dicyanoalkyl, $C_2$-$C_6$-dicyanohaloalkyl, di(hydroxycarbonyl)-$C_1$-$C_6$-alkyl, di(hydroxycarbonyl)-$C_1$-$C_6$-haloalkyl, di($C_1$-$C_6$-alkoxycarbonyl)-$C_1$-$C_6$-alkyl, di($C_1$-$C_6$-haloalkoxycarbonyl)-$C_1$-$C_6$-alkyl, di($C_1$-$C_6$-alkoxycarbonyl)-$C_1$-$C_6$-haloalkyl, di($C_1$-$C_6$-haloalkoxycarbonyl)-$C_1$-$C_6$-haloalkyl, di($C_1$-$C_6$-alkoxyl)phosphoryl-$C_1$-$C_6$-alkyl, di($C_1$-$C_6$-haloalkoxyl)phosphoryl-$C_1$-$C_6$-alkyl, di($C_1$-$C_6$-alkoxyl)phosphoryl-$C_1$-$C_6$-haloalkyl, di($C_1$-$C_6$-haloalkoxyl)phosphoryl-$C_1$-$C_6$-haloalkyl, phosphoryl-$C_1$-$C_6$-alkyl, phosphoryl-$C_1$-$C_6$-haloalkyl, di[di($C_1$-$C_6$-alkoxyl)phosphoryl-)]$C_1$-$C_6$-alkyl, di[di($C_1$-$C_6$-haloalkoxyl)phosphoryl-)]$C_1$-$C_6$-alkyl, di[di($C_1$-$C_6$-alkoxyl)phosphoryl-)]$C_1$-$C_6$-haloalkyl, di[di($C_1$-$C_6$-haloalkoxyl)phosphoryl-)]$C_1$-$C_6$-haloalkyl, diphosphoryl-$C_1$-$C_6$-alkyl, diphosphoryl-$C_1$-$C_6$-haloalkyl, $C_1$-$C_6$-alkylthio-$C_1$-$C_6$-alkyl, $C_1$-$C_6$-haloalkylthio-$C_1$-$C_6$-alkyl, $C_1$-$C_6$-alkylthio-$C_1$-$C_6$-haloalkyl, $C_1$-$C_6$-haloalkylthio-$C_1$-$C_6$-haloalkyl, $C_1$-$C_6$-alkylsulfinly-$C_1$-$C_6$-alkyl, $C_1$-$C_6$-haloalkylsulfinly-$C_1$-$C_6$-alkyl, $C_1$-$C_6$-alkylsulfinly-$C_1$-$C_6$-haloalkyl, $C_1$-$C_6$-haloalkylsulfinly-$C_1$-$C_6$-haloalkyl, $C_1$-$C_6$-alkylsulfonyl-$C_1$-$C_6$-alkyl, $C_1$-$C_6$-haloalkylsulfonyl-$C_1$-$C_6$-haloalkyl, phenyl, 5-, 6- or 9 membered heteroaryl, 3- to 6-membered heterocyclyl, ($C_1$-$C_6$-alkyl)carbonylaminocarbonyl, ($C_2$-$C_6$-alkenyl)carbonylamino-carbonyl, ($C_3$-$C_6$-alkynyl)carbonylaminocarbonyl, ($C_1$-$C_6$-haloalkyl)carbonylaminocarbonyl, ($C_2$-$C_6$-haloalkenyl)carbonylaminocarbonyl, ($C_3$-$C_6$-haloalkynyl)carbonylaminocarbonyl, phenylcarbonylaminocarbonyl, ($C_3$-$C_6$-cycloalkyl)carbonylaminocarbonyl, [($C_1$-$C_6$-alkyl)amino]carbonylaminocarbonyl, or [di($C_1$-$C_6$-alkyl)amino]carbonylaminocarbonyl, heterocyclylcarbonylaminocarbonyl, heteroarylcarbonylaminocarbonyl, phenylcarbonylaminocarbonyl;

wherein OH groups of $R^2$ are unsubstituted or substituted by $R^b$;

cyclic groups of $R^2$ are unsubstituted or substituted by $R^c$; and acyclic aliphatic groups of $R^2$ are unsubstituted or substituted by $R^d$;

$R^b$ is $C_1$-$C_6$-alkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;

wherein the substituent $R^d$ is unsubstituted or substituted by $R^e$;

$R^e$ is halogen, CN, $NO_2$, $C_1$-$C_6$-alkyl, $C_1$-$C_6$-haloalkyl, OH, $C_1$-$C_6$-alkoxy, $C_1$-$C_6$-haloalkoxy, $C_1$-$C_6$-alkylsulfonyl;

$R^3$ is halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-halo-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cyclic groups of $R^3$ are unsubstituted or substituted by substituents $R^a$;

$R^4$, $R^5$, $R^6$ and $R^7$ independently of one another are H, halogen, CN, $NO_2$, $C_1$-$C_6$-alkyl, $C_1$-$C_6$-haloalkyl, $C_1$-$C_6$-alkylcarbonyl, $C_2$-$C_6$-alkenyl, $C_2$-$C_6$-haloalkenyl, $C_2$-$C_6$-alkynyl, $C_2$-$C_6$-haloalkynyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-alkoxy-$C_1$-$C_6$-alkoxy, hydroxycarbonyl, $C_1$-$C_6$-alkoxycarbonyl, $C_1$-$C_6$-alkylthio, $C_1$-$C_6$-haloalkylthio, $NH_2$, ($C_1$-$C_6$-alkyl)amino, di($C_1$-$C_6$-alkyl)amino, ($C_1$-$C_6$-alkyl)sulfinyl, ($C_1$-$C_6$-alkyl)sulfonyl, $C_3$-$C_6$-cycloalkyl, ($C_3$-$C_6$-cycloalkyl)oxy or phenyl;

wherein the cyclic groups of $R^4$ $R^5$, $R^6$ and $R^7$ are unsubstituted or substituted by $R^a$;

$R^a$ is halogen, CN, $NO_2$, $C_1$-$C_6$-haloalkyl, $C_1$-$C_6$-alkoxy, or $C_1$-$C_6$-haloalkoxy;

or an agriculturally acceptable salt, amide, ester, or thioester of the pyrimidine compound of formula (I), to act on plants, their environment or on seed.

13. The method of claim 12, wherein $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_4$-$C_6$-haloalkynyloxy, $C_1$-$C_6$-alkylthio, or $C_3$-$C_6$-cycloalkyl, wherein the cycloalkyl substituent is unsubstituted;

$R^2$ is $C_2$-$C_6$-alkenyl, $C_2$-$C_6$-haloalkenyl, $C_1$-$C_6$-alkoxy-$C_2$-$C_6$-alkenyl, $C_2$-$C_6$-alkynyl, $C_3$-$C_6$-cycloalkenyl, $C_3$-$C_6$-cycloalkenyl-$C_1$-$C_6$-alkyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-cycloalkenyl-$C_1$-$C_6$-alkylidenyl, $C_3$-$C_6$-hydroxycycloalkyl-$C_1$-$C_6$-alkyl, $C_3$-$C_6$-hydroxycycloalkenyl-$C_1$-$C_6$-alkyl, $C_1$-$C_6$-hydroxyalkyl, $C_3$-$C_6$-cycloalkyl-$C_2$-$C_6$-hydroxyalkylidenyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-alkyl, $C_3$-$C_6$-hydroxycycloalkyl-$C_1$-$C_6$-hydroxyalkyl, $C_2$-$C_6$-dihydroxyalkyl, $C_3$-$C_6$-cycloalkyl-$C_3$-$C_6$-dihydroxyalkylidenyl, hydroxycarbonyl-$C_2$-$C_6$-dihydroxyalkyl, $C_1$-$C_6$-alkoxycarbonyl-$C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl;

wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$;

$R^b$ is $C_1$-$C_6$-alkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;

wherein the substituent $R^d$ is unsubstituted or substituted by $R^e$;

$R^e$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfonyl;

$R^3$ is halogen, CN, $NO_2$, $C_1$-$C_6$-alkoxy or $C_3$-$C_6$-cycloalkyl;

$R^4$ is H, halogen, CN, $C_1$-$C_6$-haloalkyl or $C_1$-$C_6$-alkoxy;

$R^5$ is H, halogen, CN, $C_1$-$C_6$-haloalkyl or $C_1$-$C_6$-alkoxy;

$R^6$ is H, halogen, $C_1$-$C_6$-alkyl or $C_1$-$C_6$-haloalkyl;

$R^7$ is H, halogen, CN, $C_1$-$C_6$-alkyl or $C_1$-$C_6$-alkoxy.

14. The method of claim 12, wherein the variables $R^2$, $R^3$, $R^4$, $R^5$, $R^6$ and $R^7$ are as defined in claim 12, $R^1$ is $C_1$-$C_6$-alkyl, $C_1$-$C_6$-haloalkyl, HO—$C_1$-$C_6$-alkyl, $C_2$-$C_6$-alkenyl, $C_2$-$C_6$-haloalkenyl, $C_2$-$C_6$-alkynyl, $C_3$-$C_6$-haloalkynyl, $C_1$-$C_6$-alkoxy-$C_1$-$C_6$-alkyl, $C_1$-$C_6$-alkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_1$-$C_6$-haloalkoxy, $C_3$-$C_6$-cycloalkoxy, $C_3$-$C_6$-halocycloalkoxy, $C_3$-$C_6$-cycloalkenyloxy, $C_3$-$C_6$-halocycloalkenyloxy, $C_1$-$C_6$-alkylthio, $C_1$-$C_6$-haloalkylthio, ($C_1$-$C_6$-alkyl)amino, di($C_1$-$C_6$-alkyl)amino, $C_1$-$C_6$-alkylsulfinyl, $C_1$-$C_6$-alkylsulfonyl, $C_3$-$C_6$-cycloalkyl, $C_3$-$C_6$-cycloalkenyl, $C_3$-$C_6$-halocycloalkyl, $C_3$-$C_6$-halocycloalkenyl, [1-($C_1$-$C_6$-alkyl)]-$C_3$-$C_6$-cycloalkyl, [1-($C_2$-$C_6$-alkenyl)]-$C_3$-$C_6$-cycloalkyl, [1-($C_2$-$C_6$-alkynyl)]-$C_3$-$C_6$-cycloalkyl, [1-($C_1$-$C_6$-haloalkyl)]-$C_3$-$C_6$-cycloalkyl, [1-($C_2$-$C_6$-haloalkenyl)]-$C_3$-$C_6$-cycloalkyl, [1-($C_3$-$C_6$-haloalkynyl)]-$C_3$-$C_6$-cycloalkyl, $C_3$-$C_6$-cycloalkyl-$C_1$-$C_6$-alkyl, $C_3$-$C_6$-cycloalkyl-$C_1$-$C_6$-haloalkyl, $C_3$-$C_6$-cycloalkyl-$C_1$-$C_6$-alkoxy, $C_3$-$C_6$-cycloalkyl-$C_1$-$C_6$-haloalkoxy, or 3- to 6-membered heterocyclyl;

wherein the cyclic groups of $R^1$ are unsubstituted or substituted by $R^a$;

$R^a$ is halogen, CN, $NO_2$, $C_1$-$C_6$-alkoxy, or $C_1$-$C_6$-haloalkoxy;

including agriculturally acceptable salts, amides, esters, or thioester of the pyrimidine compound of formula (I);

with the exception of 5-(2-bromophenyl)-2-cyclopropyl-4-methyl-pyrimidine;

5-(2-bromophenyl)-2-ethyl-4- methyl-pyrimidine; and 5-(2-bromophenyl)-2-methoxy-4- methyl-pyrimidine.

15. The method of claim 12, wherein $R^1$ is $C_1$-$C_6$-alkyl, $C_1$-$C_6$-alkoxy, $C_1$-$C_6$-haloalkoxy, $C_3$-$C_6$-alkenyloxy, $C_3$-$C_6$-haloalkenyloxy, $C_3$-$C_6$-alkynyloxy, $C_4$-$C_6$-haloalkynyloxy, $C_1$-$C_6$-alkylthio, or $C_3$-$C_6$-cycloalkyl wherein cycloalkyl is unsubstituted.

16. The method of claim 12, wherein $R^2$ $C_2$-$C_6$-alkenyl, $C_2$-$C_6$-haloalkenyl, $C_1$-$C_6$-alkoxy-$C_2$-$C_6$-alkenyl, $C_2$-$C_6$-alkynyl, $C_3$-$C_6$-cycloalkenyl, $C_3$-$C_6$-cycloalkenyl-$C_1$-$C_6$-alkyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-cycloalkenyl-$C_1$-$C_6$-alkylidenyl, $C_3$-$C_6$-hydroxycycloalkyl-$C_1$-$C_6$-alkyl, $C_3$-$C_6$-hydroxycycloalkenyl-$C_1$-$C_6$-alkyl, $C_1$-$C_6$-hydroxyalkyl, $C_3$-$C_6$-cycloalkyl-$C_2$-$C_6$-hydroxyalkylidenyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-alkyl, $C_3$-$C_6$-hydroxycycloalkyl-$C_1$-$C_6$-hydroxyalkyl, $C_2$-$C_6$-dihydroxyalkyl, $C_3$-$C_6$-cycloalkyl-$C_3$-$C_6$-dihydroxyalkylidenyl, hydroxycarbonyl-$C_2$-$C_6$-dihydroxyalkyl, $C_1$-$C_6$-alkoxycarbonyl-$C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl;

wherein OH groups of $R^2$ are unsubstituted or substituted by $R^b$, cyclic groups of $R^2$ are unsubstituted or substituted by $R^c$, and acyclic aliphatic groups of $R^2$ are unsubstituted or substituted by $R^d$;

$R^b$ is $C_1$-$C_6$-alkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;

wherein the substituent $R^d$ is unsubstituted or substituted by $R^e$;

$R^e$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfonyl.

17. The method of claim 12, wherein $R^3$ is halogen, CN, $NO_2$, $C_1$-$C_6$-alkoxy, or $C_3$-$C_6$-cycloalkyl;

$R^4$ is H, halogen, CN, $C_1$-$C_6$-haloalkyl, or $C_1$-$C_6$-alkoxy;

$R^5$ is H, halogen, CN, $C_1$-$C_6$-haloalkyl, or $C_1$-$C_6$-alkoxy;

$R^6$ is H, halogen, $C_1$-$C_6$-alkyl, or $C_1$-$C_6$-haloalkyl;

$R^7$ is H, halogen, CN, $C_1$-$C_6$-alkyl, or $C_1$-$C_6$-alkoxy.

18. The method of claim 12, wherein $R^1$ is c-$C_3H_5$;

$R^2$ is $C_2$-$C_6$-alkenyl, $C_2$-$C_6$-haloalkenyl, $C_1$-$C_6$-alkoxy-$C_2$-$C_6$-alkenyl, $C_2$-$C_6$-alkynyl, $C_3$-$C_6$-cycloalkenyl, $C_3$-$C_6$-cycloalkenyl-$C_1$-$C_6$-alkyl, $C_3$-$C_6$-cycloalkyl-$C_1$-$C_6$-alkylidenyl, $C_3$-$C_6$-halocycloalkyl-$C_1$-$C_6$-alkylidenyl, $C_3$-$C_6$-cycloalkenyl-$C_1$-$C_6$-alkylidenyl, $C_3$-$C_6$-hydroxycycloalkyl-$C_1$-$C_6$-alkyl, $C_3$-$C_6$-hydroxycycloalkenyl-$C_1$-$C_6$-alkyl, $C_1$-$C_6$-hydroxyalkyl, $C_3$-$C_6$-cycloalkyl-$C_2$-$C_6$-hydroxyalkylidenyl, hydroxycarbonyl-$C_1$-$C_6$-alkyl, hydroxycarbonyl-$C_1$-$C_6$-haloalkyl, $C_1$-$C_6$-alkoxycarbonyl-$C_1$-$C_6$-alkyl, $C_3$-$C_6$-hydroxycycloalkyl-$C_1$-$C_6$-hydroxyalkyl, $C_2$-$C_6$-dihydroxyalkyl, $C_3$-$C_6$-cycloalkyl-$C_3$-$C_6$-dihydroxyalkylidenyl, hydroxycarbonyl-$C_2$-$C_6$-dihydroxyalkyl, $C_1$-$C_6$-alkoxycarbonyl-$C_2$-$C_6$-dihydroxyalkyl, $C_1$-$C_6$-dicyanoalkyl, 5- or 6-membered heteroaryl, or ($C_1$-$C_6$-alkyl)carbonylaminocarbonyl;

wherein OH groups of $R^2$ are unsubstituted or substituted by $R^b$,
cyclic groups of $R^2$ are unsubstituted or substituted by $R^c$, and
acyclic aliphatic groups of $R^2$ are unsubstituted or substituted by $R^d$;

$R^b$ is $C_1$-$C_6$-alkyl, $C_1$-$C_6$-haloalkyl, $C_3$-$C_6$-alkenyl, $C_3$-$C_6$-haloalkenyl, $C_3$-$C_6$-alkynyl, $C_3$-$C_6$-haloalkynyl, $C_3$-$C_6$-cycloalkyl, $C_3$-$C_6$-halocycloalkyl, $C_4$-$C_6$-cycloalkenyl, $C_3$-$C_6$-halocycloalkenyl, $C_1$-$C_6$-alkoxycarbonyl-$C_1$-$C_6$-alkyl, $C_1$-$C_6$-haloalkoxycarbonyl-$C_1$-$C_6$-alkyl, $C_1$-$C_6$-alkoxycarbonyl-$C_1$-$C_6$-haloalkyl, $C_1$-$C_6$-haloalkoxycarbonyl-$C_1$-$C_6$-haloalkyl, $C_1$-$C_6$-alkylcarbonyl, $C_1$-$C_6$-haloalkylcarbonyl, hydroxycarbonyl-$C_1$-$C_6$-alkyl, hydroxycarbonyl-$C_1$-$C_6$-haloalkyl, $C_1$-$C_6$-alkyloxycarbonyl, $C_1$-$C_6$-haloalkyloxycarbonyl, $C_1$-$C_6$-alkylthiocarbonyl, $C_1$-$C_6$-haloalkylthiocarbonyl, $C_1$-$C_6$-alkylaminocarbonyl, $C_1$-$C_6$-haloalkylaminocarbonyl, $C_1$-$C_6$-dialkylaminocarbonyl, $C_1$-$C_6$-dihaloalkylaminocarbonyl, $C_1$-$C_6$-alkylsulfonyl, $C_1$-$C_6$-haloalkylsulfonyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-haloalkyl, $C_1$-$C_6$-haloalkoxy-$C_1$-$C_6$-haloalkyl, phenyl-$C_1$-$C_6$-alkyl, or phenyl-$C_1$-$C_6$-haloalkyl;

$R^c$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfinyl, or $C_1$-$C_6$-alkylsulfonyl;

$R^d$ is phenyl, 5- or 6-membered heteroaryl, or 3- to 6-membered heterocyclyl;

wherein the substituent $R^d$ is unsubstituted or substituted by $R^e$;

$R^e$ is halogen, CN, $NO_2$, $C_1$-$C_6$-haloalkyl, OH, $C_1$-$C_6$-alkoxy, $C_1$-$C_6$-haloalkoxy, $C_1$-$C_6$-alkylsulfonyl;

$R^3$ is Cl, Br, I, $CH_3$, $CF_3$, or $CF_2H$;
$R^4$ is H;
$R^5$ is H or F;
$R^6$ is H, F, $CF_3$, Cl, or Br;
$R^7$ is H or F.

19. The method of claim 12, wherein the compound of formula (I) corresponds to formula I.K,

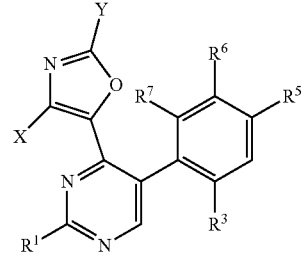

(I.K)

wherein
X and Y independently are selected from H, CHs, $C_2H_5$, n-propyl, iso-propyl, iso-butyl, n-butyl, 2-butyl, t-butyl, OH, $OCH_3$, $SCH_3$, $S(O)CH_3$, $S(O)_2CH_3$, CN, F, $C_1$, Br, I, $CH_2CF_3$, $CF_2CF_3$, $CF_2CH_3$, $CF_3$, $CF_2H$, $OCF_2H$, and $OCF_3$;

$R^1$ is c-$C_3H_5$;
$R^3$ is Cl, Br, I, CHs, $CF_3$, or $CF_2H$;
$R^5$ is H or F;
$R^6$ is H, F, $CF_3$, Cl, or Br;
$R^7$ is H or F.

20. A method of controlling undesired vegetation, which comprises allowing a herbicidal active amount of the composition of claim 10 to act on plants, their environment or on seed.

21. A method of controlling undesired vegetation, which comprises allowing a herbicidal active amount of the composition of claim 11 to act on plants, their environment or on seed.

* * * * *